(12) United States Patent
Dowdell et al.

(10) Patent No.: US 10,450,288 B2
(45) Date of Patent: Oct. 22, 2019

(54) HYDROXY FORMAMIDE DERIVATIVES AND THEIR USE

(71) Applicant: GLAXOSMITHKLINE INTELLECTUAL PROPERTY (NO.2) LIMITED, Brentford, Middlesex (GB)

(72) Inventors: Sarah E. Dowdell, King of Prussia, PA (US); Hilary Schenck Eidam, King of Prussia, PA (US); Mark Elban, King of Prussia, PA (US); Ryan Michael Fox, Collegeville, PA (US); Marlys Hammond, Erie, CO (US); Mark A. Hilfiker, King of Prussia, PA (US); Tram H. Hoang, King of Prussia, PA (US); Lara Kallander, King of Prussia, PA (US); Brian Griffin Lawhorn, King of Prussia, PA (US); Sharada Manns, King of Prussia, PA (US); Joanne Philp, King of Prussia, PA (US); David G. Washburn, King of Prussia, PA (US); Guosen Ye, King of Prussia, PA (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 15/110,776

(22) PCT Filed: Jan. 9, 2015

(86) PCT No.: PCT/IB2015/050179
§ 371 (c)(1),
(2) Date: Jul. 11, 2016

(87) PCT Pub. No.: WO2015/104684
PCT Pub. Date: Jul. 16, 2015

(65) Prior Publication Data
US 2016/0340328 A1 Nov. 24, 2016

Related U.S. Application Data

(60) Provisional application No. 61/925,848, filed on Jan. 10, 2014.

(51) Int. Cl.
| | | |
|---|---|---|
| C07D 307/12 | (2006.01) |
| C07D 307/38 | (2006.01) |
| A61K 31/341 | (2006.01) |
| C07D 307/68 | (2006.01) |
| C07D 407/04 | (2006.01) |
| C07D 307/24 | (2006.01) |
| A61K 31/4025 | (2006.01) |
| A61K 31/416 | (2006.01) |
| A61K 31/428 | (2006.01) |
| A61K 31/443 | (2006.01) |
| A61K 31/665 | (2006.01) |
| C07D 405/04 | (2006.01) |
| C07D 417/04 | (2006.01) |
| C07F 9/655 | (2006.01) |

(52) U.S. Cl.
CPC .......... *C07D 307/68* (2013.01); *A61K 31/341* (2013.01); *A61K 31/4025* (2013.01); *A61K 31/416* (2013.01); *A61K 31/428* (2013.01); *A61K 31/443* (2013.01); *A61K 31/665* (2013.01); *C07D 307/12* (2013.01); *C07D 307/24* (2013.01); *C07D 307/38* (2013.01); *C07D 405/04* (2013.01); *C07D 407/04* (2013.01); *C07D 417/04* (2013.01); *C07F 9/65515* (2013.01)

(58) Field of Classification Search
CPC .. C07D 307/68; C07D 307/24; C07D 405/04; C07D 307/12; C07D 307/38; A61K 31/341
USPC ........................................................... 514/99
See application file for complete search history.

(56) References Cited

U.S. PATENT DOCUMENTS

| | | | |
|---|---|---|---|
| 6,242,455 B1 | 6/2001 | Grams et al. |
| 6,750,202 B1 | 6/2004 | Burchardt |
| 7,442,793 B2 * | 10/2008 | Lee ....................... C07C 259/06 544/235 |
| 2003/0069291 A1 | 4/2003 | Bailey et al. |
| 2011/0237648 A1 | 9/2011 | Khvorova et al. |
| 2012/0022100 A1 | 1/2012 | Maibaum et al. |

FOREIGN PATENT DOCUMENTS

| | | |
|---|---|---|
| EP | 0854191 A2 | 7/1998 |
| EP | 1455808 B1 | 7/2007 |
| EP | 1932907 | 6/2008 |
| WO | WO1994/025477 | 11/1994 |
| WO | WO1994/028171 | 12/1994 |
| WO | WO1995/001369 | 1/1995 |
| WO | WO1995/001370 | 1/1995 |
| WO | WO1995/015974 | 6/1995 |
| WO | WO1995/016202 | 6/1995 |

(Continued)

OTHER PUBLICATIONS

Turtle E.D. et al.; "Inhibition of procollagen C-proteinase: Fibrosis and beyond", Aug. 1, 2004, Expert Opinion on Therapeutic Patents, Informa Healthcare, GB, pp. 1185-1197, XP002565735, ISN: 1354-3776, p. 1190-1194 tables 2-5 compounds 1-19.

(Continued)

*Primary Examiner* — Rita J Desai
(74) *Attorney, Agent, or Firm* — Loretta J. Sauermelch

(57) ABSTRACT

Disclosed are compounds having the formula:

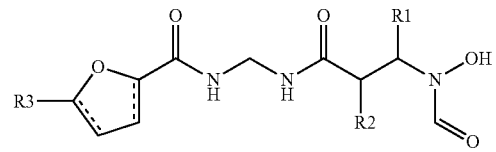

wherein R1, R2 and R3 are as defined herein, and methods of making and using the same, including use as inhibitors of BMP1, TLL1 and/or TLL2 and in treatment of diseases associated with BMP1, TLL1 and/or TLL2 activity.

40 Claims, No Drawings

(56) References Cited

FOREIGN PATENT DOCUMENTS

| WO | WO1996/002558 | 2/1996 |
|---|---|---|
| WO | WO1996/011205 | 4/1996 |
| WO | WO1997/45528 | 12/1997 |
| WO | WO1998/55862 | 12/1998 |
| WO | WO1998/058915 | 12/1998 |
| WO | WO1999/031078 | 6/1999 |
| WO | WO1999/051730 | 10/1999 |
| WO | WO 00/27377 A2 | 5/2000 |
| WO | WO 00/34313 A1 | 6/2000 |
| WO | WO2000/037436 | 6/2000 |
| WO | WO2001/016322 | 3/2001 |
| WO | WO2001/016323 | 3/2001 |
| WO | WO2001/047901 | 7/2001 |
| WO | WO2001/077342 | 10/2001 |
| WO | WO2001/095897 | 12/2001 |
| WO | WO2002/26696 | 4/2002 |
| WO | WO2002/042487 | 5/2002 |
| WO | WO2002/050046 | 6/2002 |
| WO | WO2002/079175 | 10/2002 |
| WO | WO2002/079200 | 10/2002 |
| WO | WO2003/002528 | 1/2003 |
| WO | WO2003/007980 | 1/2003 |
| WO | WO2003/037877 | 5/2003 |
| WO | WO2003/086448 | 10/2003 |
| WO | WO2003/094904 | 11/2003 |
| WO | WO2004/024092 | 3/2004 |
| WO | WO2004/024890 | 3/2004 |
| WO | WO 2004/052919 A2 | 6/2004 |
| WO | WO2004/108130 | 12/2004 |
| WO | WO2005/005456 | 1/2005 |
| WO | WO2005/065396 | 7/2005 |
| WO | WO2006/057951 | 6/2006 |
| WO | WO2006/067114 | 6/2006 |
| WO | WO2006/078717 | 7/2006 |
| WO | WO2006/098758 | 9/2006 |
| WO | WO2007/006858 | 1/2007 |
| WO | WO2007/024705 | 3/2007 |
| WO | WO2007/024715 | 3/2007 |
| WO | WO2007/060132 | 5/2007 |
| WO | WO2008/011193 | 1/2008 |
| WO | WO2008/024188 | 2/2008 |
| WO | WO2008/024767 | 2/2008 |
| WO | WO2009/097893 | 8/2009 |
| WO | WO2010/033246 | 3/2010 |
| WO | WO2010/033247 | 3/2010 |
| WO | WO2010/033248 | 3/2010 |
| WO | WO2010/059861 | 5/2010 |
| WO | WO2011/069149 | 6/2011 |
| WO | WO2013/163479 | 10/2013 |
| WO | WO2017/006295 | 1/2017 |
| WO | WO2017/006296 | 1/2017 |

OTHER PUBLICATIONS

Bataller, et al., Liver Fibrosis. The Journal of Clinical Investigation, 115:209-218 2005.
Chakraborty, et al., Emerging Therapeutic Interventions for Idiopathic Pulmonary Fibrosis. Expert Opinion on Investigational Drugs, (2014) 23(7): 893-910.
Chen, et al., The Scar-in-a-Jar: Studying Potential Antifibrotic Compounds from the Epigenetic to Extracellular Level in a Single Well. British Journal of Pharmacology (2009), 158, 1196-1209.
Cho, S., Identification and In Vivo Functional Characterization of Novel Compound Heterozygous BMP1 Variants in Osteogenesis Imperfecta. Human Mutation 36: 191-195, 2015.
Cvetjeticanin, B. et al., Possible Target for Preventing Fibrotic Scar Formation Following Acute Myocardial Infarction. Medical Hypotheses 83 (2014) 656-658.
Dankwardt, et al., Solid-Phase Synthesis of Di- and Tripeptidic Hydroxamic Acids as Inhibitors of Procollagen C-proteinase. Bioorganic & Medicinal Chemistry Letters 10 (2000) 2513-2516.
Eckes, B., et al., Molecular and Cellular Basis of Scleroderma. J Mol Med (2014) 92:913-924.
Fernández-Klett, F. et al., The Fibrotic Scar in Neurological Disorders. Brain Pathology 24 (2014) 404-413.
Fish, et al., Potent and Selective Nonpeptidic Inhibitors of Procollagen C-Proteinase. J. Med. Chem. 2007, 50, 3442-3456.
Fukagawa, M. et al., Embryonic Expression of Mouse Bone Morphogenetic Protein-1 (BMP-1), which is Related to the *Drosophila* Dorsoventral Gene Tolloid and Encodes a Putative Astacin Metalloendopeptidase. Dev. Biol. 163, 175-183 (1994).
Gamo, et al.,Thousands of Chemical Starting Points for Antimalarial Lead Identification. Nature, vol. 465 May 20, 2010 305-312.
Ge et al., Developmental Roles of the BMP1/TLD Metalloproteinases. Birth Defects Res. (2006), 78: 47-68.
Ge, et al., BMP1 Controls TGFβ1 Activation via Cleavage of Latent TGFβ-binding Protein. The Journal of Cell Biology, vol. 175, No. 1 Oct 9, 2006 111-120.
Gonzalez, et al., New Directions in the Assessment and Treatment of Hypertensive Heart Disease. Curr. Opin. Nephrol. Hypertens. 2005, 14:428-434.
Greenspan D., Biosynthetic Processing of Collagen Molecules. Topics in Current Chemistry; (2005) 247:149-183.
Grgurevic, et al., Circulating Bone Morphogenetic Protein 1-3 Isoform Increases Renal Fibrosis. J. Am. Soc. Nephrol. 21: 681-692, 2011.
Habig, et al., Efficient Elimination of Nonstoichiometric Enzyme Inhibitors from HTS Hit Lists. Journal of Biomolecular Screening 14(6); 2009: 679-689.
He, et al., Exogenously Administered Secreted Frizzled Related Protein 2(Sfrp2) Reduces Fibrosis and Improves Cardiac Function in a Rat Model of Myocardial Infarction. 21110-21115 PNAS Dec. 7, 2010 vol. 107 No. 49.
Ho, et al., Myocardial Fibrosis as an Early Manifestation of Hypertrophic Cardiomyopathy. The New England Journal of Medicine 2010; 363: 552-563.
Hopkins, et al., The Bone Morphogenetic Protein 1/Tolloid-like Metalloproteinases. Matrix Biology 26 (2007) 508-523.
Ishiyama, et al., Iridium-catalyzed C—H borylation of arenes and heteroarenes:1-chloro-3-iodo-5-(4,4,5,5-tetramethyl-1,3,2-dioxaborolan-2-yl) benzene and 2-(4,4,5,5-tetrarnethyl-1,3,2-dioxaborolan-2-yl)indole (2-(3-Chloro-5-iodophenyl)-4,4,5,5-tetramethyl-1,3,2-dioxaborolane) (2-(4,4,5,5-Tetramethyl-1,3,2-dioxaborolan-2-yl)-1H-indole). Organic Syntheses, vol. 82 p. 126-133 (2005).
Janitz et al., Three Alternatively Spliced Variants of the Gene Coding for the Human Bone Morphogenetic Protein-1. J Mol Med (1998) 76:141-146.
Kessler et al., Bone Morphogenetic Protein-1: The Type I Procollagen C-Proteinase. Science 271, 360-362 (1996).
Klingler, et al., The Role of Fibrosis in Duchenne Muscular Dystrophy. Acta Myologica, 2012; XXXI: p. 184-195.
Kostin, et al., Structural Correlate of Atrial Fibrillation in Human Patients. Cardiovascular Research 54 (2002) 361-379.
Lee, S., Regulation of Muscle Mass by Myostatin. Annu. Rev. Cell Dev. Biol. 2004. 20: 61-86.
Lee, S., Genetic analysis of the role of proteolysis in the activation of latent myostatin. PloS one (2008), 3(2), e1628, 1-7.
Li et al., The C-Proteinase That Processes Procollagens to Fibrillar Collagens Is Identical to the Protein Previously Identified as Bone Morphogenic Protein-1. Proc. Natl. Acad. Sci. USA vol. 93; pp. 5127-5130, May 1996 Cell Biology.
Liu, Y., Cellular and Molecular Mechanisms of Renal Fibrosis. Nature Reviews Nephrology 7, 684-696 (2011).
Lopez, et al., Role of Lysyl Oxidase in Myocardial Fibrosis: from Basic Science to Clinical Aspects. Am. J. Physiol. Heart Circ. Physiol. 299: H1-H9, 2010.
Lopez, et al., Circulating Biomarkers of Collagen Metabolism in Cardiac Diseases. Circulation, 2010; 21: 1645-1654.
Lopez, et al., Identification of a Potential Cardiac Antifibrotic Mechanism of Torasemide in Patients with Chronic Heart Failure. Journal of the American College of Cardiology, vol. 50, No. 9, 2007, 859-867.
Malecaze, F., et al., Upregulation of Bone Morphogenetic Protein-1/Mammalian Tolloid and Procollagen C-Proteinase Enhancer-1 in Corneal Scarring. Investigative Opthalmology and Visual Science 2014; 55: 6712-6721.

(56) References Cited

OTHER PUBLICATIONS

McLaughlin, et al.; Management of Pulmonary Arterial Hypertension. J. Am. Coll. Card. 2015; 65: 1976-1997.
Meier, et al., Emerging New Drugs for Scar Reduction. Expert Opin. Emerging Drugs (2006) 11(1): 39-47.
Molitoris, B., Therapeutic Translation in Acute Kidney Injury: the Epithelial/endothelial Axis. The Journal of Clinical Investigation, 2014; 124(6): 2355-2363.
Ovens, et al., Design and Synthesis of Acidic Dipeptide Hydroxamate Inhibitors of Procollagen C-proteinase. Journal of Peptide Science 6: 489-495 (2000).
Rimar, D. et al., Lysyl Oxidase Is a Potential Biomarker of Fibrosis in Systemic Sclerosis. Arthritis & Rheumatology, vol. 66, No. 3, Mar. 2014, pp. 726-730.
Salazar, et al., Fibrotic Response of Tissue Remodeling in COPD. Lung (2011) 189: 101-109.
See, F., et al., Fibrosis as a Therapeutic Target Post-Myocardial Infarction. Current Pharmaceutical Design, 2005, 11, 477-487.
Serrano, et al., Regulation and Dysregulation of Fibrosis in Skeletal Muscle. Experimental Cell Research 316 (2010) 3050-3058.
Shoulders, et al., Collagen Structure and Stability. Annu. Rev. Biochem. 2009 78: 929-958.
Sun, Y.M., et al., Recent Advances in Understanding the Biochemical and Molecular Mechanism of Diabetic Nephropathy. Biochemical and Biophysical Research Communications 433 (2013) 359-361.
Syx, D, et al., Defective Proteolytic Processing of Fibrillar Procollagens and Prodecorin Due to Biallelic BMP1 Mutations Results in a Severe, Progressive Form of Osteogenesis Imperfecta. Journal of Bone and Mineral Research, vol. 30, No. 8, Aug. 2015, pp. 1445-1456.
Takahara, K., et al., Bone Morphogenetic Protein-1 and Mammalian Tolloid Homolome (mTld) Are Encoded by Alternatively Spliced Transcripts Which Are Differentially Expressed in Some Tissues. The Journal of Biological Chemistry, vol. 269, No. 51, Issue of Dec. 23, pp. 32572-32578, 1994.
Tovar-Vidales, et al., Transforming Growth Factor-$\beta$2 Induces Expression of Biologically Active Bone Morphogenetic Protein-1 in Human Trabecular Meshwork Cells. Invest. Ophthalmol. Vis. Sci. 2013; 54: 4741-4748.
Uzel, et al., Multiple Bone Morphogenetic Protein 1-related Mammalian Metalloproteinases Process Pro-lysyl Oxidase at the Correct Physiological Site and Control Lysyl Oxidase Activation in Mouse Embryo Fibroblast Cultures. The Journal of Biological Chemistry, vol. 276, No. 25, Issue of Jun. 22, pp. 22537-22543, 2001.
Van der Weer, W. et al., Potential Cellular and Molecular Causes of Hypertrophic Scar Formation. Burns 35 (2009) 15-29.
Venkatachalam, M.A. et al., Acute Kidney Injury: A Springboard for Progression in Chronic Kidney Disease. Am J Physiol Renal Physiol 298: F1078—F1094, 2010.
Wolfman, et al., Activation of Latent Myostatin by the BMP-1/tolloid Family of Metalloproteinases. 15842-15846 PNAS Dec. 23, 2003 vol. 100 No. 26.
Wozney et al., Novel Regulators of Bone Formation: Molecular Clones and Activities. Science vol. 242 1528-1534 (1988).
Wu, X., et al., miR-194 Suppresses Metastasis of Non-small Cell Lung Cancer through Regulating Expression of BMP1 and $p27^{kiP1}$. Oncogene (2014) 33, 1506-1514.
Yazawa, et al., A New Formylation Reagent: 4-formyl-2-methyl-1, 3, 4-thiadiazolin-5-thione. Tetrahedron Letters, vol. 26, No. 31, pp. 3703-3706, 1985.

\* cited by examiner

HYDROXY FORMAMIDE DERIVATIVES AND THEIR USE

This application is a 371 of International Application No. PCT/IB2015/050179, filed Jan. 9, 2015, which claims the benefit of U.S. Provisional Application No. 61/925,848, filed Jan. 10, 2014, which is incorporated herein in its entirety.

FIELD OF THE INVENTION

The present invention relates to compounds that inhibit BMP1 (also known as BMP-1, bone morphogenic protein 1, bone morphogenetic protein 1, procollagen C-proteinase, and procollagen C-endopeptidase), Tolloid-like 1 (TLL1) and/or Tolloid-like 2 (TLL2) metalloproteases, inclusive of isoforms, in particular multiple isoforms encoded by RNA splice variants, and methods of making and using the same. Specifically, the present invention relates to reverse hydroxamate compounds as BMP1, TLL1 and/or TLL2 inhibitors.

BACKGROUND OF THE INVENTION

Fibrous collagens are integral parts of the extracellular matrix that support tissue integrity and maintain the cellular microenvironment for normal physiological functions. Collagens I-III, the major isoforms of the fibrous collagen protein family, are synthesized as procollagen precursors containing N-terminal and C-terminal propeptides. The procollagens are post-translationally modified by proline hydroxylation, and secreted into the peri-vascular space for further processing. N-terminal propeptides of the collagens are subsequently cleaved by proteinases of the ADAMTS (A Distintegrin And Metalloproteinase with ThromboSpondin repeats) family, while the C-terminal propeptides are processed by the Tolloid family of metalloproteases, which include BMP1, TLL1 and TLL2 (Hopkins, D. R. et al., Matrix Biology, 2007, 26, 508-523). The cleavage of both N-terminal and C-terminal propeptides allows further maturation of the collagen, leading to cross-linking at lysine residues and formation of insoluble fibrillar structures (Shoulders, M. D. et al., Annual Review of Biochemistry, 2009, 78, 929-958).

Whereas the BMP1, TLL1 and TLL2 proteins are encoded by separate genes, this family also includes isoforms of BMP1, including multiple isoforms of BMP1 that result from alternative splicing of the same gene product (see e.g., Takahara, K., et al., The Journal of Biological Chemistry, 1994, 269. 32572-32578; and Cvetjeticanin, B. et al., Medical Hypotheses, 2014, 83, 656-658). The originally discovered form of BMP1 is designated BMP-1-1 or BMP1-1. Other BMP1 isoforms encoded by splice variant RNA transcripts have been described at the transcriptional level and designated with sequential suffixes, e.g., as BMP-1-2, BMP-1-3, BMP-1-4, BMP-1-5, BMP-1-6, and BMP-1-7 (see, e.g., Wozney et al., Science (1988), 242: 1528-1534; Kessler et al., Science, (1996) 271: 360-362; Li et al., Proc. Natl. Acad. Sci. USA (1996), 93: 5127-5130; Janitz et al., J. Mol. Med. (1998), 76: 141-146; Takahara et al., J. Biol. Chem. (1994), 269: 32572-32578; and Ge and Greenspan, Birth Defect Res. (2006), 78: 47-68).

A number of BMP1 isoforms have also been confirmed at the protein level as circulating in the blood of patients with various diseases and in healthy humans (see, e.g., International Patent publication Nos. WO2008/011193 A2 and WO2013/163479 A1, and Grgurevic et al., J. Am. Soc. Nephrol. (2011), 21:681-692. In addition, the role of BMP1 in processing procollagen leading to fibrosis and scar tissue in a variety of diseases as well as the discovery of blood profiles comprising individual BMP1 isoforms in patients with various diseases has made BMP1 an attractive target for developing new therapies (see, e.g. WO2008/011193 A2; WO2013/163479 A1; Grgurevic et al., J. Am. Soc. Nephrol. (2011), 21:681-692, Cvetjeticanin, B. et al., Medical Hypotheses, 2014, 83, 656-658; and Turtle et al., Expert Opin. Ther. Patents (2004), 14(8):1185-1197).

Excessive production of extracellular matrix (ECM) proteins, including collagen, can lead to fibrotic pathologies in various organs or tissues that may be associated with increased tissue rigidity, parenchymal replacement, aberrant electrical conductance, sclerotic wound healing (e.g. infarction and burns), and/or abnormal cell-cell interactions. For example, increased fibrosis and collagen production are consistently observed in patients with acute and chronic cardiac diseases, e.g., heart failure, arrhythmias, hypertrophic cardiomyopathy, and myocardial infarction (Lopez, B. et al., Circulation, 2010, 121, 1645-1654; Ho, C. Y., et al., New England Journal of Medicine, 2010, 363, 552-563; Kostin, S. et al., Cardiovascular Research, 2002, 54, 361-379; See, F., et al., Current Pharmaceutical Design, 2005, 11, 477-487; Cvetjeticanin, B. et al. Medical Hypotheses, 2014, 83, 656-658), chronic obstructive pulmonary disease ("COPD") (Salazar, L. M., et al., Lung, 2011, 189, 101-109), liver cirrhosis and nonalcoholic steatohepatitis ("NASH") (Bataller, R., et al., Journal of Clinical Investigation, 2005, 115, 209-218), idiopathic pulmonary fibrosis (Chakraborty, S, et al., Expert Opin Investig Drugs, 2014, 23, 893-910), collagen vascular diseases, e.g. systemic lupus erythematosus, rheumatoid arhthritis and scleroderma (Eckes, B., et al., J Mol Med, 2014, 92, 913-924), muscular dystrophies (e.g., Serrano, A. C., et al., Experimental Cell Research, 2010, 316, 3050-3058; Klingler, W., et al., Acta Myoligica, XXXI, 2012, 184-195), chronic kidney disease (Liu, Y., Nature Reviews Nephrology, 2011, 7, 684-696), acute kidney injury (Molitoris, B., The Journal of clinical Investigation, 2014, 124, 2355-2363; Venkatachalam, M. A. et al., Am J Physiol Renal Physiol 298: F1078-F1094, 2010), diabetic nephropathy (Sun, Y. M., et a., Biochemical and Biophysical Research Communications, 2013, 433, 359-361), keloids, wound healing, adhesions, hypertrophic and other scarring associated with, e.g. burns, surgery and other trauma (Meier K., et al., Expert Opinion on Emerging Drugs, 2006, 11, 39-47; Malecaze, F., et al., Investigative Opthalmology and Visual Science, 2014, 55, 6712-6721; van der Weer, W. et al., Burns, 2009, 35, 15-29), stroke, multiple sclerosis and spinal cord injury (Fernandez-Klett, F. and Piller, J. Brain Pathology, 2014, 24, 404-13; Rimar, D. et al., Arthritis & Rheumatology, Vol. 66, No. 3, March 2014, 726-730). Therefore, reducing excessive collagen production and maturation by targeting the BMP1, TLL1 and/or TLL2 pathway(s) can be an effective therapeutic strategy for treating fibrotic pathologies such as these diseases. This is supported by recent published studies using pharmacological agents that inhibit BMP1, TLL1 and/or TLL2 activity in cardiac and kidney disease models in small animals (Grgurevic, L., et al., Journal of the AmericanSociety of Nephrology, 2011, 21, 681-692; He, W., et al., Proceedings of the National Academy of Sciences, 2010, 107, 21110-21115; Cvetjeticanin, B. et al., Medical Hypotheses, 2014, 83, 656-658; International Patent publication Nos. WO2008/011193 A2 and WO2013/163479 A1).

The Tolloid family of metalloproteases (BMP1, TLL1 and TLL2) has additional substrates beyond collagens that may also contribute to its role in promoting ECM protein production. For example, the pro-form of lysyl oxidase 1

(LOX1) has been shown to be a substrate of BMP1, and cleavage by BMP1 enhances the LOX enzyme activity and thereby induces collagen cross-linking (Uzel, M. I., et al., Journal of Biological Chemistry, 2001, 276, 22537-22543). Thus, BMP1 also has a role in the development of pathological tissue stiffness via this mechanism, for example in glaucoma (Tovar-Vidales, T., et al., Investigative Ophthalmology & Visual Science, 2013, 54, 4741-4748) and in diastolic dysfunction in the heart (López, B., et al., American Journal of Physiology—Heart and Circulatory Physiology, 2010, 299, H1-H9). TGF-beta binding protein (LTBP) has also been shown to be cleaved by BMP1, allowing enhanced TGF-beta action to induce further collagen production (Ge, G., et al., Journal of Cell Biology, 2006, 175, 111-120). Regulation of TGF-beta by BMP1 may also play roles in other pathologies, such as control of cancer cell metastasis and invasion (Wu, X., et al. Oncogene, 2014, 33, 1506-1514). Similarly, BMP1, TLL1 and/or TLL2 also activate a broader range of other TGF-beta like molecules, such as BMPs 2 and 4, by proteolytically processing interacting proteins (Hopkins, D. R. et al., Matrix Biology, 2007, 26, 508-523). The combined actions of BMP1 and its various substrates suggest that BMP1, TLL1 and TLL2 are key regulators of tissue ECM production/maturation and that the members of the tolloid family of metalloproteases are particularly effective targets for anti-fibrosis therapeutic intervention.

BMP1, TLL1 and TLL2 may also affect other biological pathways via additional substrate processing. In particular, they may affect muscle biology via promoting activation of myostatin. Myostatin is a hormone that negatively regulates muscle growth (Lee, S. J., 2004, Annual Review of Cell & Developmental Biology, 20, 61-86). BMP1 has been demonstrated to cleave an inhibitory pro-peptide of myostatin and thus enhance myostatin activity (Wolfman N. M., et al., Proceedings of the National Academy of Sciences, 2003, 100, 15842-15846). Knockout of TLL2 in mice demonstrated enhanced muscle mass, thereby providing support for the connection between tolloid metalloprotease and myostatin (Lee, S. J., PLoS one, 2008, 3, e1628). An inhibitor of BMP1, TLL1 and/or TLL2 could therefore be beneficial in diseases where muscle function or muscle mass is diminished, including muscular dystrophy, sarcopenia, and cachexia associated with, e.g., heart failure, CKD, COPD, cancer or old age.

Taken together, the biology of BMP1, TLL1 and TLL2 lends strong support for their key roles in collagen processing, assembly and cross-linking, leading to the formation of a fibrillar collagen network that maintains tissue integrity and proper cellular microenvironment. This family of proteins may also play important roles in the etiology of fibrotic conditions, for example in the heart, lung, skeletal muscle, kidney, liver, skin, vasculature, nervous system, and eye, and inhibitors of these metalloproteases may provide broad benefits as anti-fibrotic agents for the treatment of diseases associated with fibrosis, such as myocardial infarction, heart failure, cardiac arrhythmias, hypertrophic cardiomyopathy, chronic kidney disease (CKD), post-acute kidney injury, diabetic nephropathy, delayed graft function post-transplantation, chronic obstructive pulmonary disease (COPD), idiopathic pulmonary fibrosis (IPF), liver cirrhosis, non-alcoholic steatohepatitis (NASH), muscular dystrophies (e.g., Duchenne, Becker, limb-girdle, congenital, facioscapulohumeral, myotonic, oculopharyngeal, distal, and Emery-Dreifuss), glaucoma, corneal scarring, keloids, wound healing, adhesions, hypertrophic scarring, other scarring, e.g. associated with burns, surgery or other trauma, stroke, collagen vascular diseases such as systemic lupus erythematosus, rheumatoid arthritis and scleroderma, spinal cord injury and multiple sclerosis. Furthermore, BMP1, TLL1 and TLL2 inhibitors may have additional therapeutic applications in muscular disease based on their impact on myostatin biology, in particular muscular dystrophies (e.g., Duchenne, Becker, limb-girdle, congenital, facioscapulohumeral, myotonic, oculopharyngeal, distal, and Emery-Dreifuss), sarcopenia, and cachexia associated with, e.g., heart failure, CKD, COPD, cancer or old age.

SUMMARY OF THE INVENTION

In one aspect, the present invention relates to compounds of Formula (I):

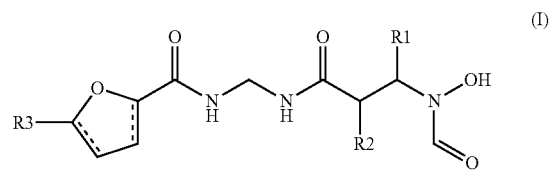

wherein:

R1 is selected from the group consisting of H, ($C_1$-$C_4$) straight chain alkyl, and ($C_1$-$C_4$) straight chain alkyl substituted with a hydroxy group;

R2 is selected from H, ($C_1$-$C_{11}$)alkyl, ($C_1$-$C_3$)alkyl-($C_3$-$C_6$) cycloalkyl, ($C_1$-$C_3$)alkyl-phenyl, ($C_1$-$C_3$)alkyl-naphthyl and ($C_1$-$C_3$)alkyl-heterocyclyl, wherein heterocyclyl is a monocyclic ring having 5-6 ring atoms wherein 1-2 of the ring atoms are selected from nitrogen, oxygen and sulfur, and wherein said ($C_1$-$C_{11}$)alkyl, cycloalkyl, phenyl, naphthyl and heterocyclyl may be optionally substituted with 1-2 groups independently selected from ($C_1$-$C_4$)alkyl, ($C_1$-$C_4$) alkoxy, halo, and cyano; and R3 is selected from:

a) phenyl, optionally substituted with 1-3 groups independently selected from:

($C_1$-$C_6$)alkyl, optionally substituted with 1-3 groups independently selected from: fluoro (e.g., —$CF_3$); —$CO_2H$; —P(O)$R^fR^g$; NR$^a$R$^b$ wherein R$^a$ is selected from H and ($C_1$-$C_4$)alkyl and R$^b$ is selected from ($C_1$-$C_4$)alkyl substituted with —$CO_2H$ or —P(O)$R^fR^g$, and —C(O)NR$^a$R$^b$ wherein R$^a$ and R$^b$ are independently selected from H and ($C_1$-$C_4$)alkyl, wherein the ($C_1$-$C_4$)alkyl is optionally substituted with 1-3 groups independently selected from hydroxy, —$CO_2H$, —C(O)O($C_1$-$C_4$)alkyl and —P(O)$R^fR^g$;

cyclopropyl, optionally substituted with 1 —$CO_2H$;

—C(O)NR$^a$R$^b$ wherein R$^a$ and R$^b$ are independently selected from H and ($C_1$-$C_4$)alkyl, wherein the ($C_1$-$C_4$)alkyl is optionally substituted with 1-3 groups independently selected from hydroxy, —$CO_2H$, —C(O)O($C_1$-$C_4$)alkyl, —P(O)$R^fR^g$, NR$^c$R$^d$ and N$^+$R$^c$R$^d$R$^e$;

($C_1$-$C_6$)alkoxy, optionally substituted with 1-3 substituents independently selected from halo, hydroxy, —$CO_2H$, ($C_3$-$C_6$)cycloalkyl, C(O)NH$_2$ and pyrrolidinyl;

($C_3$-$C_6$)cycloalkoxy, optionally substituted with 1-3 substituents independently selected from halo, hydroxy, and —$CO_2H$;

—NR$^a$R$^b$ wherein R$^a$ and R$^b$ are independently selected from H and ($C_1$-$C_4$)alkyl, wherein the ($C_1$-$C_4$)alkyl is optionally substituted with 1-3 groups independently selected from oxo and —$CO_2H$;

—SR$^a$ wherein R$^a$ is selected from H and (C$_1$-C$_4$)alkyl; —CO$_2$H; —C(NOH)NH$_2$, cyano; —C(O)O(C$_1$-C$_4$)alkyl; —C(O)CO$_2$H; —P(O)R$^f$R$^g$; —OP(O)R$^f$R$^g$; halo; hydroxy; nitro; —NHSO$_2$(C$_1$-C$_2$)alkyl; —SO$_3$H; —SO$_2$(C$_1$-C$_2$)alkyl; —SO$_2$NR$^c$R$^d$; —SO$_2$NHC(O)(C$_1$-C$_2$)alkyl; and —B(OH)$_2$; and b) heteroaryl, optionally substituted with 1-2 groups independently selected from: (C$_1$-C$_4$)alkyl, (C$_1$-C$_4$)alkoxy, oxo, —CO$_2$H, —P(O)R$^f$R$^g$, and —OP(O)R$^f$R$^g$;

wherein in each occurrence: R$^c$, R$^d$ and R$^e$ are independently selected from H and (C$_1$-C$_2$)alkyl; and R$^f$ and R$^g$ are independently selected from hydroxy, (C$_1$-C$_2$)alkyl and (C$_1$-C$_2$)alkoxy;

and salts, particularly pharmaceutically acceptable salts, thereof.

This invention is also directed to compounds of Formula (I) as represented above, wherein:

R1 is selected from H, (C$_1$-C$_4$) straight chain alkyl, and (C$_1$-C$_4$) straight chain alkyl substituted with a hydroxy group;

R2 is selected from H, (C$_1$-C$_{11}$)alkyl, (C$_1$-C$_3$)alkyl-(C$_3$-C$_6$)cycloalkyl, (C$_1$-C$_3$)alkyl-phenyl and (C$_1$-C$_3$)alkyl-heterocyclyl, wherein heterocyclyl is a monocyclic ring having 5-6 ring atoms wherein 1-2 of the ring atoms are selected from nitrogen, oxygen and sulfur, and wherein said (C$_1$-C$_{11}$)alkyl, cycloalkyl, phenyl and heterocyclyl may be optionally substituted with 1-2 groups independently selected from (C$_1$-C$_4$)alkyl, (C$_1$-C$_4$)alkoxy, halo, and cyano; and R3 is selected from:

a) phenyl, optionally substituted with 1-3 groups independently selected from:

(C$_1$-C$_6$)alkyl, optionally substituted with 1-3 groups independently selected from: fluoro (e.g., —CF$_3$); —CO$_2$H; —P(O)R$^f$R$^g$; and —C(O)NR$^a$R$^b$ wherein R$^a$ and R$^b$ are independently selected from H and (C$_1$-C$_4$)alkyl, wherein the (C$_1$-C$_4$)alkyl is optionally substituted with 1-3 groups independently selected from hydroxy, —CO$_2$H, —C(O)O(C$_1$-C$_4$)alkyl and —P(O)R$^f$R$^g$;

cyclopropyl, optionally substituted with 1 —CO$_2$H;

—C(O)NR$^a$R$^b$ wherein R$^a$ and R$^b$ are independently selected from H and (C$_1$-C$_4$)alkyl, wherein the (C$_1$-C$_4$)alkyl is optionally substituted with 1-3 groups independently selected from hydroxy, —CO$_2$H, —C(O)O(C$_1$-C$_4$)alkyl, —P(O)R$^f$R$^g$, NR$^c$R$^d$ and N$^+$R$^c$R$^d$R$^e$;

(C$_1$-C$_6$)alkoxy, optionally substituted with 1-3 substituents independently selected from halo, hydroxy, —CO$_2$H, (C$_3$-C$_6$)cycloalkyl and pyrrolidinyl;

(C$_3$-C$_6$)cycloalkoxy, optionally substituted with 1-3 substituents independently selected from halo, hydroxy, and —CO$_2$H;

—NR$^a$R$^b$ wherein R$^a$ and R$^b$ are independently selected from H and (C$_1$-C$_4$)alkyl, wherein the (C$_1$-C$_4$)alkyl is optionally substituted with 1-3 groups independently selected from oxo and —CO$_2$H;

—SR$^a$ wherein R$^a$ is selected from H and (C$_1$-C$_4$)alkyl; —CO$_2$H; —C(NOH)NH$_2$, cyano; —C(O)O(C$_1$-C$_4$)alkyl; —C(O)CO$_2$H; —P(O)R$^f$R$^g$; —OP(O)R$^f$R$^g$; halo; hydroxy; nitro; —NHSO$_2$(C$_1$-C$_2$)alkyl; —SO$_3$H; —SO$_2$(C$_1$-C$_2$)alkyl; —SO$_2$NR$^c$R$^d$; —SO$_2$NHC(O)(C$_1$-C$_2$)alkyl; and —B(OH)$_2$; and b) heteroaryl, optionally substituted with 1-2 groups independently selected from:

(C$_1$-C$_4$)alkyl, (C$_1$-C$_4$)alkoxy, oxo, —CO$_2$H, —P(O)R$^f$R$^g$, and —OP(O)R$^f$R$^g$;

wherein in each occurrence: R$^c$, R$^d$ and R$^e$ are independently selected from H and (C$_1$-C$_2$)alkyl; and R$^f$ and R$^g$ are independently selected from hydroxy, (C$_1$-C$_2$)alkyl and (C$_1$-C$_2$)alkoxy;

and salts, particularly pharmaceutically acceptable salts, thereof.

The compounds according to Formula (I), or salts, particularly pharmaceutically acceptable salts, thereof, are inhibitors of BMP1, TLL1 and/or TLL2.

Accordingly, the present invention is also directed to a method of inhibiting BMP1, TLL1 and/or TLL2 which method comprises contacting a biological material comprising the protein(s) with a compound according to Formula (I), or a salt, particularly a pharmaceutically acceptable salt, thereof.

The invention is further directed to a method of treating a disease associated with BMP1, TLL1 and/or TLL2 activity in a subject (e.g., a human or other mammal, particularly a human) in need thereof, including for example treatment of a disease where inhibition of BMP1, TLL1 and/or TLL2 is of therapeutic benefit, which comprises administering to the subject a therapeutically effective amount of a compound according to Formula (I), or a salt thereof, particularly a pharmaceutically acceptable salt thereof. This invention also provides a compound of Formula (I), or a salt thereof, particularly a pharmaceutically acceptable salt thereof, for use in therapy, e.g. as an active therapeutic substance in the treatment of a disease associated with BMP1, TLL1 and/or TLL2 activity. The invention also provides for the use of a compound of Formula (I), or a salt thereof, particularly a pharmaceutically acceptable salt thereof, in the manufacture of a medicament for use in the treatment of a disease associated with BMP1, TLL1 and/or TLL2 activity. The present invention is further directed to a pharmaceutical composition comprising a compound according to Formula (I), or a salt thereof, particularly a pharmaceutically acceptable salt thereof, and one or more pharmaceutically acceptable excipients. Particularly, this invention is directed to a pharmaceutical composition for the treatment of a disease associated with BMP1, TLL1 and/or TLL2 activity, where the composition comprises a compound according to Formula (I), or a salt thereof, particularly a pharmaceutically acceptable salt thereof, and one or more pharmaceutically acceptable excipients.

In some embodiments, the disease associated with BMP1, TLL1 and/or TLL2 activity is selected from those associated with pathological fibrotic conditions in body organs or tissues, e.g., such conditions of the: heart (e.g., myocardial infarction ("MI"), heart failure (e.g., heart failure with reduced ejection fraction, heart failure with preserved ejection fraction), cardiac arrhythmias (e.g., atrial fibrillation), hypertrophic cardiomyopathy), lung (e.g. chronic obstructive pulmonary disease ("COPD"), idiopathic pulmonary fibrosis ("IPF")), kidney (e.g. diabetic nephropathy, post-acute kidney injury, chronic kidney disease ("CKD"), delayed graft function post-transplantation), liver (e.g. liver cirrhosis, non-alcoholic steatohepatitis ("NASH")), eye (e.g. glaucoma, corneal scarring), skeletal muscle (e.g. muscular dystrophies, including Duchenne, Becker, limb-girdle, congenital, facioscapulohumeral, myotonic, oculopharyngeal, distal, and Emery-Dreifuss), skin (e.g. keloids, wound healing, adhesions, hypertrophic scarring and other scarring, e.g., associated with burns, surgery or other trauma), the vasculature (e.g. stroke, and collagen vascular diseases such as systemic lupus erythematosus, rheumatoid arthritis and scleroderma), and the nervous system (e.g. spinal cord injury, multiple sclerosis). In some embodiments, the disease associated with BMP1, TLL1 and/or TLL2 activity is selected from muscular diseases characterized by reduced muscle function and/or mass, e.g., muscular dystrophy (e.g., Duchenne, Becker, limb-girdle, congenital, facioscapulohumeral, myotonic, oculopharyngeal, distal, and Emery-Dreifuss), sarcopenia, and cachexia associated with, e.g., heart failure, CKD, COPD, cancer, or old age.

Other aspects of the present invention will be understood in light of this disclosure.

DETAILED DESCRIPTION OF THE INVENTION

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

As used herein, the term "alkyl" represents a saturated hydrocarbon moiety which, unless otherwise stated, may be straight or branched. The terms "$C_1$-$C_2$ alkyl", "$C_1$-$C_3$ alkyl", "$C_1$-$C_4$ alkyl", "$C_1$-$C_6$ alkyl", and "$C_1$-$C_{11}$ alkyl" refer to an alkyl group or moiety containing 1-2, 1-3, 1-4, 1-6, or 1-11 carbon atoms respectively. Exemplary alkyls include, but are not limited to methyl (Me), ethyl (Et), n-propyl, isopropyl, n-butyl, s-butyl, isobutyl, t-butyl, pentyl (also known as n-pentyl), and 2-ethylbutyl, as well as hexyl, heptyl, octyl, nonyl, decyl and undecyl, including the branched isomers of these groups.

As used herein, the term "cycloalkyl" refers to a non-aromatic, saturated, cyclic hydrocarbon ring moiety. The term "($C_3$-$C_6$)cycloalkyl" refers to a non-aromatic cyclic hydrocarbon ring moiety having three to six ring carbon atoms. Exemplary "($C_3$-$C_6$)cycloalkyl" groups include cyclopropyl, cyclobutyl, cyclopentyl, and cyclohexyl.

"Alkoxy" refers to an alkyl radical attached through an oxygen linking atom. The terms "($C_1$-$C_4$)alkoxy" and "($C_1$-$C_6$)alkoxy" refer to a straight- or branched-chain hydrocarbon radical containing 1-4 or 1-6 carbon atoms respectively, attached through an oxygen linking atom. "($C_1$-$C_4$)alkoxy" and "($C_1$-$C_6$)alkoxy" may be alternatively designated as —O($C_1$-$C_4$ alkyl) and —O($C_1$-$C_6$ alkyl) respectively. Exemplary alkoxy groups include, but are not limited to, methoxy, ethoxy, n-propoxy, isopropoxy, n-butoxy, s-butoxy, isobutoxy, t-butoxy, pentoxy, and hexoxy, including the branched isomers of these groups.

"Cycloalkoxy" refers to a cycloalkyl radical attached through an oxygen linking atom. The term "($C_3$-$C_6$)cycloalkoxy" refers to a cycloalkyl radical having 3 to 6 ring carbon atoms, attached through an oxygen linking atom. "($C_3$-$C_6$)cycloalkoxy" may be alternatively designated as —O($C_3$-$C_6$)cycloalkyl. Exemplary cycloalkoxy groups include cyclopropyloxy, cyclobutyloxy, cyclpentyloxy, and cyclohexyloxy.

A heterocyclic (alternatively referred to as heterocyclyl) group or moiety is a mono- or bi-cyclic group or moiety having as ring members atoms of at least two different elements (carbon and one or more of nitrogen, oxygen and/or sulfur). The ring(s) may be saturated or partially unsaturated (non-aromatic) or fully unsaturated (aromatic). Heterocyclic encompasses heterocycloalkyl and heteroaryl. For example, heterocyclyl may be a cyclic group or moiety having 5-10 ring atoms (i.e. "5-10 membered") wherein 1-4 of the ring atoms are heteroatoms selected from nitrogen, oxygen and sulfur, e.g., a monocyclic ring having 5-6 ring atoms wherein 1-2 of the ring atoms are heteroatoms selected from nitrogen, oxygen and sulfur, or a bicyclic ring having 9-10 ring atoms wherein 1-4 of the ring atoms are heteroatoms selected from nitrogen, oxygen and sulfur.

"Heterocycloalkyl" represents a group or moiety which is a non-aromatic, monocyclic radical, which is saturated or partially unsaturated, having 5-6 ring atoms wherein 1-2 of the ring atoms are heteroatoms selected from nitrogen, oxygen and sulfur. Illustrative examples of heterocycloalkyl groups include, but are not limited to, piperidyl (or piperidinyl), piperazinyl, morpholinyl, tetrahydrofuryl (or tetrahydrofuranyl), tetrahydropyranyl, tetrahydrothienyl, and thiomorpholinyl, including the various position isomers of the foregoing moieties.

"Heteroaryl" refers to a mono- or bi-cyclic group or moiety wherein at least one ring is aromatic, having 5-10 ring atoms wherein 1-4 of the ring atoms are heteroatoms selected from nitrogen, oxygen and sulfur. In bicyclic heteroaryl, at least one ring is aromatic and the other ring may be aromatic, or saturated or unsaturated non-aromatic, and at least one ring is heterocyclic and the other ring may be heterocyclic or carbocyclic. Thus, this term encompasses but is not limited to bicyclic heterocyclic compounds containing at least one aromatic carbocyclic or heterocylic ring moiety, e.g., a phenyl ring moiety fused to a heterocycloalkyl ring moiety. Illustrative examples of heteroaryls include, but are not limited to, thienyl, pyrrolyl, imidazolyl, pyrazolyl, furyl (or furanyl), isothiazolyl, isoxazolyl, oxazolyl, oxadiazolyl, thiazolyl, pyridyl (or pyridinyl), pyrazinyl, pyrimidinyl, pyridazinyl, triazinyl, triazolyl, tetrazolyl, indazolyl, benzothienyl, benzofuranyl, benzothiazolyl, benzimidazolyl, benzoxazolyl, benzoxadiazolyl, benzothiadiazolyl, benzotriazolyl, 2,3-dihydrobenzoisothiazolyl, and 1,1-dioxido-2,3-dihydrobenzoisothiazolyl (e.g., 1,1-dioxido-2,3-dihydrobenzo[d]isothiazolyl), including the various position isomers of the foregoing moieties.

In some embodiments, compounds of the invention comprise a 5-membered or 6-membered monocyclic heteroaryl group comprising at least one nitrogen ring atom, e.g., such groups as particularly disclosed herein. Selected 5-membered heteroaryl groups contain one nitrogen, and optionally contain one oxygen ring atom or 1, 2 or 3 additional nitrogen ring atoms. Selected 6-membered heteroaryl groups contain 1, 2, or 3 nitrogen ring heteroatoms.

In other embodiments, compounds of the invention comprise a 9-membered or 10-membered bicyclic heteroaryl group, e.g. such groups as particularly disclosed herein. Selected 9-10 membered heteroaryl groups contain one nitrogen, oxygen or sulfur ring heteroatom, and optionally contain 1, 2, or 3 additional nitrogen ring atoms.

It is to be understood that the terms heterocyclic, heteroaryl, and heterocycloalkyl are intended to encompass stable heterocyclic groups where a ring nitrogen heteroatom is optionally oxidized (e.g., heterocyclic groups containing an N-oxide, e.g., pyridine-N-oxide), or where a ring sulfur heteroatom is optionally oxidized (e.g., heterocyclic groups containing sulfones or sulfoxide moieties, e.g., tetrahydrothienyl-1-oxide [a tetrahydrothienyl sulfoxide], tetrahydrothienyl-1,1-dioxide [a tetrahydrothienyl sulfone], or 1,1-dioxido-2,3-dihydrobenzoisothiazolyl [e.g., 1,1-dioxido-2,3-dihydrobenzo[d]isothiazolyl]).

When the term "alkyl" is used in combination with other groups, e.g., "($C_1$-$C_3$)alkyl-($C_3$-$C_6$)cycloalkyl", "($C_1$-$C_3$) alkyl-phenyl" and "($C_1$-$C_3$)alkyl-heterocyclyl", the alkyl moiety is intended to encompass a divalent straight or branched-chain hydrocarbon radical and the cycloalkyl, phenyl, and heterocyclyl moieties are as defined herein. For example, in "($C_1$-$C_3$)alkyl-phenyl" the ($C_1$-$C_3$)alkyl moiety thereof is a divalent straight or branched-chain carbon radical linked to the aryl group phenyl, and is represented by the bonding arrangement present in a benzyl group (—$CH_2$-phenyl). Particular examples of such groups include (cyclopentyl)methyl, 2-phenylethyl, 3-phenylpropyl, and 2-naphthylethyl.

"Oxo" represents a double-bonded oxygen moiety; for example, if attached directly to a carbon atom forms a carbonyl moiety (C=O). The terms "halogen" and "halo" represent chloro, fluoro, bromo or iodo substituents. "Hydroxy" or "hydroxyl" is intended to mean the radical —OH. "Cyano" means the radical —CN. "Nitro" means the radical —$NO_2$.

Where a numerical range is indicated, e.g., a carbon number range or a heteroatom number range, the range is intended to encompass particular embodiments corresponding to the particular integers within the range, and well as any range of integers within the most broadly stated range.

As used herein, the terms "compound(s) of the invention" or "compound(s) of this invention" mean a compound of Formula (I), as defined above (including more particular embodiments), in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemihydrates)), and mixtures of various forms.

Accordingly, included within the present invention are compounds of Formulas (I), as defined herein (including more particular embodiments), in any salt or non-salt form and any physical form thereof, and mixtures of various forms. While such are included within the present invention, it will be understood that the compounds of Formulas (I), as defined herein, in any salt or non-salt form, and in any physical form thereof, may have varying levels of activity, different bioavailabilities and different handling properties for formulation purposes.

As used herein, the term "optionally substituted" indicates that a group, ring or moiety (such as an alkyl, cycloalkyl, alkoxy, cycloalkoxy, heterocycloalkyl, phenyl, heteroaryl, carbocyclic or heterocyclic group, ring or moiety) may be unsubstituted, or the group, ring or moiety may be substituted with one or more substituent(s) as defined. In the case where more than one group, ring or moiety may be substituted with a number of alternative substituent(s), the selected substituent(s) for each group, ring or moiety may be the same or different, i.e. the substituent(s) are selected independently for each group, ring or moiety. In the case where more than one substituent is selected from a number of possible substituents, those substituents may be the same or different, i.e. the substituents are selected independently.

As used herein, the terms "a" and "an" are intended to include one or more of the indicated moiety, unless otherwise indicated.

As used herein, "BMP1, TLL1 and/or TLL2" encompasses one or more of BMP1, TLL1 and TLL2, including isoforms thereof (including particularly isoforms encoded by RNA splice variants). Thus, for example, as used herein BMP1 may include one or more of the isoforms BMP-1-1, BMP-1-2, BMP-1-3, BMP-1-4, BMP-1-5, BMP-1-6, and BMP-1-7.

All references/publications are hereby incorporated by reference into this disclosure in their entirety.

In one aspect, the present invention is directed to a compound of Formula (I):

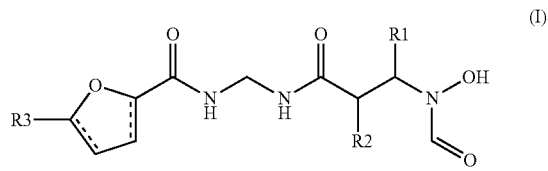

or a salt thereof,
wherein:
R1 is selected from the group consisting of H, ($C_1$-$C_4$) straight chain alkyl, and ($C_1$-$C_4$) straight chain alkyl substituted with a hydroxy group;
R2 is selected from H, ($C_1$-$C_{11}$)alkyl, ($C_1$-$C_3$)alkyl-($C_3$-$C_6$) cycloalkyl, ($C_1$-$C_3$)alkyl-phenyl, ($C_1$-$C_3$)alkyl-naphthyl and ($C_1$-$C_3$)alkyl-heterocyclyl, wherein heterocyclyl is a monocyclic ring having 5-6 ring atoms wherein 1-2 of the ring atoms are selected from nitrogen, oxygen and sulfur, and wherein said ($C_1$-$C_{11}$)alkyl, cycloalkyl, phenyl, naphthyl and heterocyclyl may be optionally substituted with 1-2 groups independently selected from ($C_1$-$C_4$)alkyl, ($C_1$-$C_4$) alkoxy, halo, and cyano; and
R3 is selected from:
c) phenyl, optionally substituted with 1-3 groups independently selected from:
($C_1$-$C_6$)alkyl, optionally substituted with 1-3 groups independently selected from: fluoro (e.g., —$CF_3$); —$CO_2H$; —P(O)$R^fR^g$; N$R^aR^b$ wherein $R^a$ is selected from H and ($C_1$-$C_4$)alkyl and $R^b$ is selected from ($C_1$-$C_4$)alkyl substituted with —$CO_2H$ or —P(O)$R^fR^g$, and —C(O)N$R^aR^b$ wherein $R^a$ and $R^b$ are independently selected from H and ($C_1$-$C_4$)alkyl, wherein the ($C_1$-$C_4$)alkyl is optionally substituted with 1-3 groups independently selected from hydroxy, —$CO_2H$, —C(O)O($C_1$-$C_4$)alkyl and —P(O)$R^fR^g$;
cyclopropyl, optionally substituted with 1 —$CO_2H$;
—C(O)N$R^aR^b$ wherein $R^a$ and $R^b$ are independently selected from H and ($C_1$-$C_4$)alkyl, wherein the ($C_1$-$C_4$)alkyl is optionally substituted with 1-3 groups independently selected from hydroxy, —$CO_2H$, —C(O)O($C_1$-$C_4$)alkyl, —P(O)$R^fR^g$, N$R^aR^d$ and $N^+R^cR^dR^e$;
($C_1$-$C_6$)alkoxy, optionally substituted with 1-3 substituents independently selected from halo, hydroxy, —$CO_2H$, ($C_3$-$C_6$)cycloalkyl, C(O)$NH_2$ and pyrrolidinyl;
($C_3$-$C_6$)cycloalkoxy, optionally substituted with 1-3 substituents independently selected from halo, hydroxy, and —$CO_2H$;
—N$R^aR^b$ wherein $R^a$ and $R^b$ are independently selected from H and ($C_1$-$C_4$)alkyl, wherein the ($C_1$-$C_4$)alkyl is optionally substituted with 1-3 groups independently selected from oxo and —$CO_2H$;
—S$R^a$ wherein $R^a$ is selected from H and ($C_1$-$C_4$)alkyl;
—$CO_2H$; —C(NOH)$NH_2$, cyano; —C(O)O($C_1$-$C_4$)alkyl; —C(O)$CO_2H$; —P(O)$R^fR^g$; —OP(O)$R^fR^g$; halo; hydroxy; nitro; —NHS$O_2$($C_1$-$C_2$)alkyl; —$SO_3H$; —$SO_2$($C_1$-$C_2$)alkyl; —$SO_2$N$R^cR^d$; —$SO_2$NHC(O)($C_1$-$C_2$)alkyl; and —B(OH)$_2$; and
d) heteroaryl, optionally substituted with 1-2 groups independently selected from: ($C_1$-$C_4$)alkyl, ($C_1$-$C_4$)alkoxy, oxo, —$CO_2H$, —P(O)$R^fR^g$, and —OP(O)$R^fR^g$;
wherein in each occurrence: $R^c$, $R^d$ and $R^e$ are independently selected from H and ($C_1$-$C_2$)alkyl; and R$^f$ and R$^g$ are independently selected from hydroxy, (C$_1$-C$_2$)alkyl and (C$_1$-C$_2$)alkoxy.

In some embodiments of the compound of Formula (I):
R1 is selected from the group consisting of H, (C$_1$-C$_4$) straight chain alkyl, and (C$_1$-C$_4$) straight chain alkyl substituted with a hydroxy group;
R2 is selected from H, (C$_1$-C$_{11}$)alkyl, (C$_1$-C$_3$)alkyl-(C$_3$-C$_6$)cycloalkyl, (C$_1$-C$_3$)alkyl-phenyl, and (C$_1$-C$_3$)alkyl-heterocyclyl, wherein heterocyclyl is a monocyclic ring having 5-6 ring atoms wherein 1-2 of the ring atoms are selected from nitrogen, oxygen and sulfur, and wherein said (C$_1$-C$_{11}$)alkyl, cycloalkyl, phenyl, and heterocyclyl may be optionally substituted with 1-2 groups independently selected from (C$_1$-C$_4$)alkyl, (C$_1$-C$_4$)alkoxy, halo, and cyano; and
R3 is selected from:

a) phenyl, optionally substituted with 1-3 groups independently selected from:
(C$_1$-C$_6$)alkyl, optionally substituted with 1-3 groups independently selected from: fluoro (e.g., —CF$_3$); —CO$_2$H; —P(O)R$^f$R$^g$; and —C(O)NR$^a$R$^b$ wherein R$^a$ and R$^b$ are independently selected from H and (C$_1$-C$_4$)alkyl, wherein the (C$_1$-C$_4$)alkyl is optionally substituted with 1-3 groups independently selected from hydroxy, —CO$_2$H, —C(O)O(C$_1$-C$_4$)alkyl and —P(O)R$^f$R$^g$;
cyclopropyl, optionally substituted with 1 —CO$_2$H;
—C(O)NR$^a$R$^b$ wherein R$^a$ and R$^b$ are independently selected from H and (C$_1$-C$_4$)alkyl, wherein the (C$_1$-C$_4$)alkyl is optionally substituted with 1-3 groups independently selected from hydroxy, —CO$_2$H, —C(O)O(C$_1$-C$_4$)alkyl, —P(O)R$^f$R$^g$, NR$^c$R$^d$ and N$^+$R$^c$R$^d$R$^e$;
(C$_1$-C$_6$)alkoxy, optionally substituted with 1-3 substituents independently selected from halo, hydroxy, —CO$_2$H, (C$_3$-C$_6$)cycloalkyl, and pyrrolidinyl;
(C$_3$-C$_6$)cycloalkoxy, optionally substituted with 1-3 substituents independently selected from halo, hydroxy, and —CO$_2$H;
—NR$^a$R$^b$ wherein R$^a$ and R$^b$ are independently selected from H and (C$_1$-C$_4$)alkyl, wherein the (C$_1$-C$_4$)alkyl is optionally substituted with 1-3 groups independently selected from oxo and —CO$_2$H;
—SR$^a$ wherein R$^a$ is selected from H and (C$_1$-C$_4$)alkyl;
—CO$_2$H; —C(NOH)NH$_2$, cyano; —C(O)O(C$_1$-C$_4$)alkyl; —C(O)CO$_2$H; —P(O)R$^f$R$^g$; —OP(O)R$^f$R$^g$; halo; hydroxy; nitro; —NHSO$_2$(C$_1$-C$_2$)alkyl; —SO$_3$H; —SO$_2$(C$_1$-C$_2$)alkyl; —SO$_2$NR$^c$R$^d$; —SO$_2$NHC(O)(C$_1$-C$_2$)alkyl; and —B(OH)$_2$; and b) heteroaryl, optionally substituted with 1-2 groups independently selected from: (C$_1$-C$_4$)alkyl, (C$_1$-C$_4$)alkoxy, oxo, —CO$_2$H, —P(O)R$^f$R$^g$, and —OP(O)R$^f$R$^g$;
wherein in each occurrence: R$^c$, R$^d$ and R$^e$ are independently selected from H and (C$_1$-C$_2$)alkyl; and
R$^f$ and R$^g$ are independently selected from hydroxy, (C$_1$-C$_2$)alkyl and (C$_1$-C$_2$)alkoxy.

In some embodiments, the compound according to Formula (I) has the Formula (I)(a):

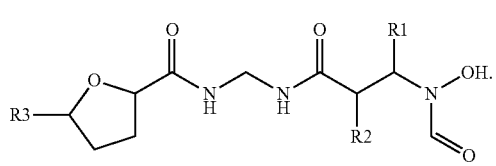

(I)(a)

In other embodiments, the compound according to Formula (I) has the Formula (I)(b):

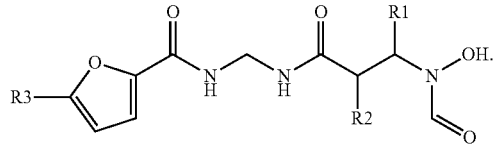

(I)(b)

In some embodiments of the compounds of the invention (e.g. compounds of Formula (I)), R1 is H, methyl, ethyl, or —CH$_2$OH; in more particular embodiments H, ethyl or —CH$_2$OH, more particularly H or ethyl and especially ethyl. In some embodiments, R1 is (C$_1$-C$_4$) straight chain alkyl substituted with one hydroxy group.

In some embodiments of the compounds of the invention (e.g. compounds of Formula (I)), R2 is H, n-pentyl, 2-ethylbutyl, (cyclopentyl)methyl, benzyl, 2-phenylethyl, or 3-phenylpropyl (in more particular embodiments n-pentyl, (cyclopentyl)methyl, 2-phenylethyl, or 3-phenylpropyl, even more particularly n-pentyl), where such groups are optionally substituted as defined above in accordance with Formula (I). In some embodiments of the compounds of the invention (e.g. compounds of Formula (I)), R2 is 2-naphthylethyl, optionally substituted as defined above in accordance with Formula (I). In some embodiments such groups are unsubstituted. In some embodiments, R2 is n-pentyl.

In some embodiments of the compounds of the invention (e.g. compounds of Formula (I)), R1 and R2 have (R) stereochemistry.

In some embodiments of the compounds of the invention (e.g. compounds of Formula (I)), R3 is phenyl, pyridyl, pyridazinyl, pyrimidinyl, oxazolyl, tetrazolyl, pyrazolyl, indazolyl, or 1,1-dioxido-2,3-dihydrobenzo[d]isothiazolyl (in more particular embodiments, phenyl, pyridyl, indazolyl, or 1,1-dioxido-2,3-dihydrobenzo[d]isothiazolyl), including the various position isomers thereof, where such groups are optionally substituted as defined above in accordance with Formula (I), including more particular embodiments of Formula (I).

In more particular embodiments, R3 is phenyl optionally substituted in accordance with the definition of Formula (I), including more particular embodiments of Formula (I). In more particular embodiments of compounds of the invention (e.g. compounds of Formula (I)), R3 is 3,4- or 3,5-disubstituted phenyl wherein the substituent groups are selected in accordance with the definition of Formula (I), including more particular embodiments of Formula (I). In some embodiments, R3 is phenyl substituted with ethoxy in the 3-position and —P(O)(OH)$_2$ or —CO$_2$H in the 4- or 5-position (said positions relative to the point of attachment of the phenyl ring to the remainder of the compound of Formula (I)). In some embodiments, R3 is phenyl substituted with ethoxy in the 3-position —OCH$_2$CO$_2$H, or —C(O)NHCH(CO$_2$H)(CH$_2$CO$_2$H) in the 4- or 5-position (said positions relative to the point of attachment of the phenyl ring to the remainder of the compound of Formula (I)).

In some embodiments of the compounds of the invention (e.g. a compound of Formula (I)), R3 is phenyl substituted with 1-3 groups selected from: —OCH$_3$, —OC$_2$H$_5$, —OC$_3$H$_7$, —OCH(CH$_3$)$_2$, —OCF$_3$, —OCHF$_2$, —OCH$_2$CF$_3$, —OCH$_2$CHF$_2$, —OC$_2$H$_4$-pyrrolidine, —OCH$_2$CO$_2$H, —OCH$_2$C(O)NH$_2$, —CO$_2$H, —CH$_3$, cyclopropane-1-carboxylic acid, —CH$_2$CO$_2$H, —C(CH$_3$)$_2$CO$_2$H, —CH(CH$_3$)CO$_2$H, —CF$_2$CO$_2$H, —CH$_2$C(O)NHCH(CO$_2$H)(CH$_2$CO$_2$H), —CH$_2$P(O)(OH)$_2$, —CH$_2$N(CH$_3$)

(CH₂CO₂H), —CH₂NHCH₂P(O)(OH)₂, —C(NH₂)(NOH), cyano, nitro, hydroxy, —SO₂NH₂, —SO₂N(CH₃)₂, —SO₂NH(CH₃), —SO₂CH₃, —SO₂NHC(O)C₂H₅, —SCH₃, —SC₂H₅, —C(O)OCH₃, —C(O)OC(CH₃)₃, —C(O)NHCH₃, —C(O)NH(C₂H₄NH₂), —C(O)NHC₂H₄N⁺(CH₃)₃, —C(O)NHCH(CO₂H)(CH₂CO₂H), —C(O)NHCH(CO₂H)(C₂H₄CO₂H), —C(O)NHCH₂CO₂H, —C(O)N(CH₂CO₂H)₂, —C(O)NHCH₂P(O)(OH)₂, —C(O)NHC(CH₂OH)₃, fluoro, —NH₂, —N(CH₃)₂, —P(O)(CH₃)(OC₂H₅), —P(O)(OCH₃)₂, —P(O)(CH₃)(OH), —P(O)(OH)(OCH₃), and —P(O)(OH)₂. In some embodiments, R3 is phenyl substituted with 1-3 groups selected from: —OC₂H₅, hydroxy, —CO₂H, —OCH₂CO₂H, —P(O)(OH)₂, —C(O)NHCH(CO₂H)(CH₂CO₂H) and —C(O)NHCH₂P(O)(OH)₂.

In some embodiments of the compounds of the invention (e.g. a compound of Formula (I)), R3 is optionally substituted pyridyl, pyridazinyl, pyrimidinyl, oxazolyl, tetrazolyl, pyrazolyl, indazolyl, or 1,1-dioxido-2,3-dihydrobenzo[d]isothiazolyl. In some embodiments, R3 is optionally substituted pyridyl, indazolyl, or 1,1-dioxido-2,3-dihydrobenzo[d]isothiazolyl (including particularly pyridin-3-yl, pyridin-2-yl, 1,1-dioxido-2,3-dihydrobenzo[d]isothiazol-6-yl, and indazol-6-yl). In these embodiments such R3 groups may be optionally substituted as defined in accordance with Formula (I), including more particular embodiments of Formula (I). In some embodiments, such R3 groups are substituted with 1-2 groups independently selected from: —OCH₃, —OC₂H₅, —OC₃H₇, —OCH(CH₃)₂, —CO₂H, —CH₃, —P(O)(CH₃)(OC₂H₅), —P(O)(OCH₃)₂, —P(O)(CH₃)(OH), —P(O)(OH)(OCH₃), and —P(O)(OH)₂. In some embodiments, such R3 groups are substituted with 1-2 groups independently selected from: —OCH₃, —CH₃, and —CO₂H.

Accordingly, a compound of the invention includes a compound of Formula (I), or a salt thereof, particularly a pharmaceutically acceptable salt thereof. Representative compounds of this invention include the specific compounds described herein, e.g., the compounds of the Examples, as well as any free acid/base forms, salt forms, and alternative salt forms thereof (particularly pharmaceutically acceptable salt or alternative salt forms thereof), as applicable.

Accordingly, in some embodiments the compound of the invention is a compound selected from the group consisting of:

2-ethoxy-4-(5-((((R)-2-((R)-1-(N-hydroxyformamido)propyl)heptanamido)methyl)carbamoyl)furan-2-yl)benzoic acid (R)—N-((3-cyclopentyl-2-((N-hydroxyformamido)methyl)propanamido)methyl)-5-phenylfuran-2-carboxamide (R)—N-((2-((N-hydroxyformamido)methyl)-5-phenylpentanamido)methyl)-5-phenylfuran-2-carboxamide (R)—N-((2-((N-hydroxyformamido)methyl)-4-phenylbutanamido)methyl)-5-phenylfuran-2-carboxamide (R)—N-((2-((N-hydroxyformamido)methyl)heptanamido)methyl)-5-phenylfuran-2-carboxamide (R)—N-((2-((N-hydroxyformamido)methyl)heptanamido)methyl)-5-(2-methoxyphenyl)furan-2-carboxamide (R)—N-((2-((N-hydroxyformamido)methyl)heptanamido)methyl)-5-(3-methoxyphenyl)furan-2-carboxamide (R)-5-(3-cyanophenyl)-N-((2-((N-hydroxyformamido)methyl)heptanamido)methyl)furan-2-carboxamide (R)—N-((2-((N-hydroxyformamido)methyl)heptanamido)methyl)-5-(2-hydroxyphenyl)furan-2-carboxamide (R)—N-((2-((N-hydroxyformamido)methyl)heptanamido)methyl)-5-(5-methoxypyridin-3-yl)furan-2-carboxamide (R)-5-(4-cyanophenyl)-N-((2-((N-hydroxyformamido)methyl)heptanamido)methyl)furan-2-carboxamide (R)—N-((2-((N-hydroxyformamido)methyl)heptanamido)methyl)-5-(3-sulfamoylphenyl)furan-2-carboxamide (R)—N-((2-((N-hydroxyformamido)methyl)heptanamido)methyl)-5-(3-(trifluoromethoxy)phenyl)furan-2-carboxamide (R)-5-(3-ethoxyphenyl)-N-((2-((N-hydroxyformamido)methyl)heptanamido)methyl)furan-2-carboxamide (R)—N-((2-((N-hydroxyformamido)methyl)heptanamido)methyl)-5-(6-methoxypyridin-2-yl)furan-2-carboxamide (R)-methyl 3-(5-(((2-((N-hydroxyformamido)methyl)heptanamido)methyl)carbamoyl)furan-2-yl)benzoate (R)-5-(4-fluoro-3-methoxyphenyl)-N-((2-((N-hydroxyformamido)methyl)heptanamido)methyl)furan-2-carboxamide (R)—N-((2-((N-hydroxyformamido)methyl)heptanamido)methyl)-5-(4-methoxypyridin-2-yl)furan-2-carboxamide (R)—N-((2-((N-hydroxyformamido)methyl)heptanamido)methyl)-5-(3-(methylcarbamoyl)phenyl)furan-2-carboxamide (R)—N-((2-((N-hydroxyformamido)methyl)-4-phenylbutanamido)methyl)-5-(3-(methylsulfonyl)phenyl)furan-2-carboxamide (R)-5-(3-(N,N-dimethylsulfamoyl)phenyl)-N-((2-((N-hydroxyformamido)methyl)heptanamido)methyl)furan-2-carboxamide (R)—N-((2-((N-hydroxyformamido)methyl)heptanamido)methyl)-5-(3-(N-methylsulfamoyl)phenyl)furan-2-carboxamide (R)—N-((2-((N-hydroxyformamido)methyl)heptanamido)methyl)-5-(3-(2,2,2-trifluoroethoxy)phenyl)furan-2-carboxamide N—(((R)-2-((R)-1-(N-hydroxyformamido)propyl)heptanamido)methyl)-5-phenylfuran-2-carboxamide (R)—N-((2-((N-hydroxyformamido)methyl)heptanamido)methyl)-5-(3-isopropoxyphenyl)furan-2-carboxamide (R)-methyl 3-ethoxy-5-(5-(((2-((N-hydroxyformamido)methyl)heptanamido)methyl)carbamoyl)furan-2-yl)benzoate (R)-5-(3-(dimethylamino)phenyl)-N-((2-((N-hydroxyformamido)methyl)heptanamido)methyl)furan-2-carboxamide (R)—N-((2-((N-hydroxyformamido)methyl)heptanamido)methyl)-5-(3-(N-propionylsulfamoyl)phenyl)furan-2-carboxamide (R)-3-(5-(((2-((N-hydroxyformamido)methyl)heptanamido)methyl)carbamoyl)furan-2-yl)-5-methoxybenzoic acid (R)-3-ethoxy-5-(5-(((2-((N-hydroxyformamido)methyl)heptanamido)methyl)carbamoyl)furan-2-yl)benzoic acid ethyl (3-(5-((((R)-2-((N-hydroxyformamido)methyl)heptanamido)methyl)carbamoyl)furan-2-yl)phenyl)(methyl)phosphinate N—(((R)-2-((S)-2-hydroxy-1-(N-hydroxyformamido)ethyl)heptanamido)methyl)-5-phenylfuran-2-carboxamide (R)-5-(3-((2-aminoethyl)carbamoyl)-5-methoxyphenyl)-N-((2-((N-hydroxyformamido)methyl)heptanamido)methyl)furan-2-carboxamide (R)-5-(3-((2-aminoethyl)carbamoyl)-5-ethoxyphenyl)-N-((2-((N-hydroxyformamido)methyl)heptanamido)methyl)furan-2-carboxamide (R)-5-(3-(difluoromethoxy)phenyl)-N-((2-((N-hydroxyformamido)methyl)heptanamido)methyl)furan-2-carboxamide (R)-dimethyl (3-(5-(((2-((N-hydroxyformamido)methyl)heptanamido)methyl)carbamoyl)furan-2-yl)phenyl)phosphonate (R)-5-(1,1-dioxido-2,3-dihydrobenzo[d]isothiazol-6-yl)-N-((2-((N-hydroxyformamido)methyl)heptanamido)methyl)furan-2-carboxamide (R)—N-((2-((N-hydroxyformamido)methyl)heptanamido)methyl)-5-(3-(2-(pyrrolidin-1-yl)ethoxy)phenyl)furan-2-carboxamide 3-ethoxy-5-(5-((((R)-2-((R)-1-(N-hydroxyformamido)propyl)heptanamido)methyl)carbamoyl)furan-2-yl)benzoic acid 5-(3-((2-aminoethyl)carbamoyl)-5-ethoxyphenyl)-N—(((R)-2-((R)-1-(N-hydroxyformamido)propyl)heptanamido)methyl)furan-2-carboxamide 2-(2-ethoxy-4-(5-((((R)-2-((R)-1-(N-hydroxyformamido)propyl)heptanamido)methyl)carbamoyl)furan-2-yl)phenyl)acetic acid 2-(4-(5-((((R)-2-((R)-1-(N-hydroxyformamido)propyl)heptanamido)methyl)carbamoyl)furan-2-yl)phenyl)acetic acid 2-(4-(5-((((R)-2-((R)-1-(N-hydroxyformamido)propyl)heptanamido)methyl)carbamoyl)furan-2-yl)phenyl)-2-methylpropanoic acid 1-(4-(5-((((R)-2-((R)-1-(N-hydroxyformamido)propyl)heptanamido)methyl)carbamoyl)furan-2-yl)phenyl)cyclopropanecarboxylic acid (S)-5-(tert-butoxy)-4-(3-ethoxy-5-(5-((((R)-2-((R)-1-(N-hydroxyformamido)propyl)heptanamido)methyl)carbamoyl)furan-2-yl)benzamido)-5-oxopentanoic acid 5-(5-((((R)-2-((R)-1-(N-hydroxyformamido)propyl)heptanamido)methyl)carbamoyl)furan-2-yl)nicotinic acid (S)-4-(tert-butoxy)-3-(3-ethoxy-5-(5-((((R)-2-((R)-1-(N-hydroxyformamido)propyl)heptanamido)methyl)carbamoyl)furan-2-yl)benzamido)-4-oxobutanoic acid (S)-dimethyl 2-(3-ethoxy-5-(5-((((R)-2-((R)-1-(N-hydroxyformamido)propyl)heptanamido)methyl)carbamoyl)furan-2-yl)benzamido)pentanedioate 2-(3-ethoxy-5-(5-((((R)-2-((R)-1-(N-hydroxyformamido)propyl)heptanamido)methyl)carbamoyl)furan-2-yl)phenyl)-2,2-difluoroacetic acid dimethyl (3-ethoxy-5-(5-((((R)-2-((R)-1-(N-hydroxyformamido)propyl)heptanamido)methyl)carbamoyl)furan-2-yl)phenyl)phosphonate (R)-methyl 2-fluoro-5-(5-(((2-((N-hydroxyformamido)methyl)heptanamido)methyl)carbamoyl)furan-2-yl)benzoate (R)-5-(3,5-dimethoxyphenyl)-N-((2-((N-hydroxyformamido)methyl)heptanamido)methyl)furan-2-carboxamide (R)-5-(2,5-dimethoxyphenyl)-N-((2-((N-hydroxyformamido)methyl)heptanamido)methyl)furan-2-carboxamide (R)-5-(5-(((2-((N-hydroxyformamido)methyl)heptanamido)methyl)carbamoyl)furan-2-yl)-2-methylbenzoic acid (R)-3-(5-(((2-((N-hydroxyformamido)methyl)heptanamido)methyl)carbamoyl)furan-2-yl)-2-methoxybenzoic acid (R)-5-(5-(((2-((N-hydroxyformamido)methyl)heptanamido)methyl)carbamoyl)furan-2-yl)-2-methoxybenzoic acid (R)-methyl 2-(5-(((2-((N-hydroxyformamido)methyl)heptanamido)methyl)carbamoyl)furan-2-yl)benzoate (R)-methyl 4-(5-(((2-((N-hydroxyformamido)methyl)heptanamido)methyl)carbamoyl)furan-2-yl)benzoate (R)-2-fluoro-3-(5-(((2-((N-hydroxyformamido)methyl)heptanamido)methyl)carbamoyl)furan-2-yl)benzoic acid (R)-2-(3-(5-(((2-((N-hydroxyformamido)methyl)heptanamido)methyl)carbamoyl)furan-2-yl)phenyl)acetic acid (R)-3-(5-(((2-((N-hydroxyformamido)methyl)heptanamido)methyl)carbamoyl)furan-2-yl)-2-methylbenzoic acid (R)-2-hydroxy-5-(5-(((2-((N-hydroxyformamido)methyl)heptanamido)methyl)carbamoyl)furan-2-yl)benzoic acid (R)-tert-butyl 3-(5-(((2-((N-hydroxyformamido)methyl)heptanamido)methyl)carbamoyl)furan-2-yl)benzoate (R)-2-amino-5-(5-(((2-((N-hydroxyformamido)methyl)heptanamido)methyl)carbamoyl)furan-2-yl)benzoic acid 2-(3-ethoxy-5-(5-((((R)-2-((R)-1-(N-hydroxyformamido)propyl)heptanamido)methyl)carbamoyl)furan-2-yl)benzamido)-N,N,N-trimethylethanaminium hydroxide 5-(5-((((R)-2-((R)-1-(N-hydroxyformamido)propyl)heptanamido)methyl)carbamoyl)furan-2-yl)-2-methoxybenzoic acid 2-(3-(5-((((R)-2-((R)-1-(N-hydroxyformamido)propyl)heptanamido)methyl)carbamoyl)furan-2-yl)phenyl)-2-methylpropanoic acid 5-(5-((((R)-2-((R)-1-(N-hydroxyformamido)propyl)heptanamido)methyl)carbamoyl)furan-2-yl)-2-methylbenzoic acid N—(((R)-2-((R)-1-(N-hydroxyformamido)propyl)heptanamido)methyl)-5-(3-propoxyphenyl)furan-2-carboxamide 2-(2-fluoro-5-(5-((((R)-2-((R)-1-(N-hydroxyformamido)propyl)heptanamido)methyl)carbamoyl)furan-2-yl)phenyl)acetic acid 4-(5-((((R)-2-((R)-1-(N-hydroxyformamido)propyl)heptanamido)methyl)carbamoyl)furan-2-yl)benzoic acid 2-(3-ethoxy-5-(5-((((R)-2-((R)-1-(N-hydroxyformamido)propyl)heptanamido)methyl)carbamoyl)furan-2-yl)phenyl)acetic acid 5-(3-ethoxy-5-hydroxyphenyl)-N—(((R)-2-((R)-1-(N-hydroxyformamido)propyl)heptanamido)methyl)furan-2-carboxamide (S)-2-(2-ethoxy-4-(5-((((R)-2-((R)-1-(N-hydroxyformamido)propyl)heptanamido)methyl)carbamoyl)furan-2-yl)benzamido)succinic acid (S)-2-(2-(2-ethoxy-4-(5-((((R)-2-((R)-1-(N-hydroxyformamido)propyl)heptanamido)methyl)carbamoyl)furan-2-yl)phenyl)acetamido)succinic acid 2-(3-(5-((((R)-2-((N-hydroxyformamido)methyl)heptanamido)methyl)carbamoyl)furan-2-yl)phenyl)propanoic acid (S)-2-(3-ethoxy-5-(5-((((R)-2-((R)-1-(N-hydroxyformamido)propyl)heptanamido)methyl)carbamoyl)furan-2-yl)benzamido)succinic acid (R)-2,6-difluoro-3-(5-(((2-((N-hydroxyformamido)methyl)heptanamido)methyl)carbamoyl)furan-2-yl)benzoic acid 3-ethoxy-5-(5-(((3-(N-hydroxyformamido)propanamido)methyl)carbamoyl)furan-2-yl)benzoic acid 1-(3-(5-((((R)-2-((R)-1-(N-hydroxyformamido)propyl)heptanamido)methyl)carbamoyl)furan-2-yl)phenyl)cyclopropanecarboxylic acid 5-ethoxy-2-hydroxy-3-(5-((((R)-2-((R)-1-(N-hydroxyformamido)propyl)heptanamido)methyl)carbamoyl)furan-2-yl)benzoic acid 3-(5-((((R)-2-((R)-1-(N-hydroxyformamido)propyl)heptanamido)methyl)carbamoyl)furan-2-yl)-5-propoxybenzoic acid (S)-2-(3-(5-((((R)-2-((R)-1-(N-hydroxyformamido)propyl)heptanamido)methyl)carbamoyl)furan-2-yl)benzamido)succinic acid (R)-2-(3-ethoxy-5-(5-((((R)-2-((R)-1-(N-hydroxyformamido)propyl)heptanamido)methyl)carbamoyl)furan-2-yl)benzamido)succinic acid 2-(3-ethoxy-5-(5-((((R)-2-((R)-1-(N-hydroxyformamido)propyl)heptanamido)methyl)carbamoyl)furan-2-yl)benzamido)acetic acid 2,2'-((2-ethoxy-4-(5-((((R)-2-((R)-1-(N-hydroxyformamido)propyl)heptanamido)methyl)carbamoyl)furan-2-yl)benzoyl)azanediyl)diacetic acid 2,2'-((3-ethoxy-5-(5-((((R)-2-((R)-1-(N-hydroxyformamido)propyl)heptanamido)methyl)carbamoyl)furan-2-yl)benzoyl)azanediyl)diacetic acid
5-(3-((1,3-dihydroxy-2-(hydroxymethyl)propan-2-yl)carbamoyl)-5-ethoxyphenyl)-N—(((R)-2-((R)-1-(N-hydroxyformamido)propyl)heptanamido)methyl)furan-2-carboxamide
(R)-3-(5-(((2-((N-hydroxyformamido)methyl)heptanamido)methyl)carbamoyl)furan-2-yl)benzoic acid
(R)-2-(5-(((2-((N-hydroxyformamido)methyl)heptanamido)methyl)carbamoyl)furan-2-yl)benzoic acid
(R)-2-fluoro-5-(5-(((2-((N-hydroxyformamido)methyl)heptanamido)methyl)carbamoyl)furan-2-yl)benzoic acid
(R)-4-(5-(((2-((N-hydroxyformamido)methyl)heptanamido)methyl)carbamoyl)furan-2-yl)benzoic acid
(S)-2-(3-ethoxy-5-(5-((((R)-2-((R)-1-(N-hydroxyformamido)propyl)heptanamido)methyl)carbamoyl)furan-2-yl)benzamido)pentanedioic acid
(3-(5-((((R)-2-((N-hydroxyformamido)methyl)heptanamido)methyl)carbamoyl)furan-2-yl)phenyl)(methyl)phosphinic acid
methyl hydrogen (3-(5-((((R)-2-((N-hydroxyformamido)methyl)heptanamido)methyl)carbamoyl)furan-2-yl)phenyl)phosphonate
(3-ethoxy-5-(5-((((R)-2-((R)-1-(N-hydroxyformamido)propyl)heptanamido)methyl)carbamoyl)furan-2-yl)phenyl)phosphonic acid
(3-ethoxy-5-(5-((((R)-2-((R)-1-(N-hydroxyformamido)propyl)heptanamido)methyl)carbamoyl)tetrahydrofuran-2-yl)phenyl)phosphonic acid
(2-ethoxy-4-(5-((((R)-2-((R)-1-(N-hydroxyformamido)propyl)heptanamido)methyl)carbamoyl)furan-2-yl)phenyl)phosphonic acid
(3-ethoxy-5-(5-((((R)-2-((R)-1-(N-hydroxyformamido)propyl)heptanamido)methyl)carbamoyl)furan-2-yl)benzyl)phosphonic acid
((3-ethoxy-5-(5-((((R)-2-((R)-1-(N-hydroxyformamido)propyl)heptanamido)methyl)carbamoyl)furan-2-yl)benzamido)methyl)phosphonic acid
methyl hydrogen (3-ethoxy-5-(5-((((R)-2-((R)-1-(N-hydroxyformamido)propyl)heptanamido)methyl)carbamoyl)furan-2-yl)phenyl)phosphonate
(R)-5-(3-(2,2-difluoroethoxy)phenyl)-N-((2-((N-hydroxyformamido)methyl)heptanamido)methyl)furan-2-carboxamide
(R)-5-(3-(ethylthio)phenyl)-N-((2-((N-hydroxyformamido)methyl)heptanamido)methyl)furan-2-carboxamide
(R)—N-((2-((N-hydroxyformamido)methyl)heptanamido)methyl)-5-(3-(methylthio)phenyl)furan-2-carboxamide
(R)—N-((2-((N-hydroxyformamido)methyl)heptanamido)methyl)-5-(3-nitrophenyl)furan-2-carboxamide
(R)—N-((2-((N-hydroxyformamido)methyl)heptanamido)methyl)-5-(1-methyl-1H-indazol-6-yl)furan-2-carboxamide
(R)—N-((2-((N-hydroxyformamido)methyl)heptanamido)methyl)-5-(2-methyl-2H-indazol-6-yl)furan-2-carboxamide
(R)-(3-(5-(((2-((N-hydroxyformamido)methyl)heptanamido)methyl)carbamoyl)furan-2-yl)phenyl)phosphonic acid
5-(3-((Z)—N'-hydroxycarbamimidoyl)phenyl)-N—(((R)-2-((R)-1-(N-hydroxyformamido)propyl)heptanamido)methyl)furan-2-carboxamide and
N—(((R)-2-((R)-1-(N-hydroxyformamido)propyl)heptanamido)methyl)-5-phenyltetrahydrofuran-2-carboxamide;
or a salt thereof (in more particular embodiments, a pharmaceutically acceptable salt thereof).

In some embodiments the compound of the invention is a compound selected from the group consisting of:
(3-ethoxy-2-fluoro-5-(5-((((R)-2-((R)-1-(N-hydroxyformamido)propyl)heptanamido)methyl)carbamoyl)furan-2-yl)benzoic acid
3-hydroxy-5-(5-((((R)-2-((R)-1-(N-hydroxyformamido)propyl)heptanamido)methyl)carbamoyl)furan-2-yl)benzoic acid
3-(carboxymethoxy)-5-(5-((((R)-2-((R)-1-(N-hydroxyformamido)propyl)heptanamido)methyl)carbamoyl)furan-2-yl)benzoic acid
2-(carboxymethyl)-4-(5-((((R)-2-((R)-1-(N-hydroxyformamido)propyl)heptanamido)methyl)carbamoyl)furan-2-yl)benzoic acid
5-ethoxy-2-hydroxy-3-(5-((((2R,3R)-3-(N-hydroxyformamido)-2-phenethylpentanamido)methyl)carbamoyl)furan-2-yl)benzoic acid
(S)-2-(2-ethoxy-4-(5-((((2R,3R)-3-(N-hydroxyformamido)-2-(2-(naphthalen-2-yl)ethyl)pentanamido)methyl)carbamoyl)furan-2-yl)benzamido)succinic acid
5-(carboxymethoxy)-3-(5-((((2R,3R)-2-(2,4-difluorophenethyl)-3-(N-hydroxyformamido)pentanamido)methyl)carbamoyl)furan-2-yl)-2-hydroxybenzoic acid
(S)-2-(4-(5-((((R)-2-((R)-1-(N-hydroxyformamido)propyl)heptanamido)methyl)carbamoyl)furan-2-yl)benzamido)succinic acid
(S)-2-(4-(5-((((R)-2-((R)-1-(N-hydroxyformamido)propyl)heptanamido)methyl)carbamoyl)furan-2-yl)-2-methylbenzamido)succinic acid
5-(carboxymethoxy)-2-hydroxy-3-(5-((((R)-2-((R)-1-(N-hydroxyformamido)propyl)heptanamido)methyl)carbamoyl)furan-2-yl)benzoic acid
2,2'-((3-(5-((((2R,3R)-2-(2,4-difluorophenethyl)-3-(N-hydroxyformamido)pentanamido)methyl)carbamoyl)furan-2-yl)-5-ethoxybenzoyl)azanediyl)diacetic acid
(S)-2-(4-(5-((((2R,3R)-2-(2,4-difluorophenethyl)-3-(N-hydroxyformamido)pentanamido)methyl)carbamoyl)furan-2-yl)-2-ethoxybenzamido)succinic acid
2,2'-((2-ethoxy-4-(5-((((2R,3R)-3-(N-hydroxyformamido)-2-phenethylpentanamido)methyl)carbamoyl)furan-2-yl)benzoyl)azanediyl)diacetic acid
(S)-2-(3-(carboxymethoxy)-5-(5-((((R)-2-((R)-1-(N-hydroxyformamido)propyl)heptanamido)methyl)carbamoyl)furan-2-yl)benzamido)succinic acid
(S)-2-(2-(carboxymethoxy)-4-(5-((((R)-2-((R)-1-(N-hydroxyformamido)propyl)heptanamido)methyl)carbamoyl)furan-2-yl)benzamido)succinic acid
(S)-2-(2-ethoxy-4-(5-((((2R,3R)-3-(N-hydroxyformamido)-2-phenethylpentanamido)methyl)carbamoyl)furan-2-yl)benzamido)succinic acid
2-ethoxy-6-hydroxy-4-(5-((((R)-2-((R)-1-(N-hydroxyformamido)propyl)heptanamido)methyl)carbamoyl)furan-2-yl)benzoic acid
4-(5-((((R)-2-((R)-1-(N-hydroxyformamido)propyl)heptanamido)methyl)carbamoyl)furan-2-yl)phthalic acid
2-((3-ethoxy-5-(5-((((R)-2-((R)-1-(N-hydroxyformamido)propyl)heptanamido)methyl)carbamoyl)furan-2-yl)benzyl)(methyl)amino)acetic acid
3-(2-amino-2-oxoethoxy)-5-(5-((((R)-2-((R)-1-(N-hydroxyformamido)propyl)heptanamido)methyl)carbamoyl)furan-2-yl)benzoic acid
(R)-2-(2-ethoxy-4-(5-((((R)-2-((R)-1-(N-hydroxyformamido)propyl)heptanamido)methyl)carbamoyl)furan-2-yl)benzamido)succinic acid
((R)-2-(4-(5-((((R)-2-((R)-1-(N-hydroxyformamido)propyl)heptanamido)methyl)carbamoyl)furan-2-yl)benzamido)succinic acid (S)-2-(4-(5-((((R)-2-((R)-1-(N-hydroxyformamido)propyl)
heptanamido)methyl)carbamoyl)furan-2-yl)benzamido)
pentanedioic acid
(S)-2-(2-ethoxy-4-(5-((((R)-2-((R)-1-(N-hydroxyformamido)propyl)heptanamido)methyl)carbamoyl)furan-2-yl)
benzamido)pentanedioic acid
2,2'-((4-(5-((((R)-2-((R)-1-(N-hydroxyformamido)propyl)
heptanamido)methyl)carbamoyl)furan-2-yl)benzoyl)
azanediyl)diacetic acid
(((3-ethoxy-5-(5-((((R)-2-((R)-1-(N-hydroxyformamido)
propyl)heptanamido)methyl)carbamoyl)furan-2-yl)benzyl)amino)methyl)phosphonic acid,
(3-hydroxy-5-(5-((((R)-2-((R)-1-(N-hydroxyformamido)
propyl)heptanamido)methyl)carbamoyl)furan-2-yl)phenyl)phosphonic acid
((2-ethoxy-4-(5-((((R)-2-((R)-1-(N-hydroxyformamido)
propyl)heptanamido)methyl)carbamoyl)furan-2-yl)benzamido)methyl)phosphonic acid
(3-ethoxy-5-(5-((((2R,3R)-3-(N-hydroxyformamido)-2-
phenethylpentanamido)methyl)carbamoyl)furan-2-yl)
phenyl)phosphonic acid
(3-ethoxy-5-(5-((((2R,3R)-3-(N-hydroxyformamido)-2-(2-
(naphthalen-2-yl)ethyl)pentanamido)methyl)carbamoyl)
furan-2-yl)phenyl)phosphonic acid
((2-hydroxy-4-(5-((((R)-2-((R)-1-(N-hydroxyformamido)
propyl)heptanamido)methyl)carbamoyl)furan-2-yl)benzamido)methyl)phosphonic acid
((4-(5-((((R)-2-((R)-1-(N-hydroxyformamido)propyl)heptanamido)methyl)carbamoyl)furan-2-yl)benzamido)
methyl)phosphonic acid
((4-(5-((((R)-2-((R)-1-(N-hydroxyformamido)propyl)heptanamido)methyl)carbamoyl)furan-2-yl)-2-methylbenzamido)methyl)phosphonic acid
2-(3-(5-((((R)-2-((R)-1-(N-hydroxyformamido)propyl)heptanamido)methyl)carbamoyl)furan-2-yl)-5-phosphonophenoxy)acetic acid and
2-hydroxy-4-(5-((((R)-2-((R)-1-(N-hydroxyformamido)propyl)heptanamido)methyl)carbamoyl)furan-2-yl)benzoic acid;
or a salt thereof (in more particular embodiments a pharmaceutically acceptable salt thereof).

In some embodiments the compound of the invention is a compound selected from the group consisting of:
2-ethoxy-4-(5-((((R)-2-((R)-1-(N-hydroxyformamido)propyl)heptanamido)methyl)carbamoyl)furan-2-yl)benzoic acid
3-ethoxy-5-(5-((((R)-2-((R)-1-(N-hydroxyformamido)propyl)heptanamido)methyl)carbamoyl)furan-2-yl)benzoic acid
(S)-2-(2-ethoxy-4-(5-((((R)-2-((R)-1-(N-hydroxyformamido)propyl)heptanamido)methyl)carbamoyl)furan-2-yl)
benzamido)succinic acid
(S)-2-(3-ethoxy-5-(5-((((R)-2-((R)-1-(N-hydroxyformamido)propyl)heptanamido)methyl)carbamoyl)furan-2-yl)
benzamido)succinic acid
5-ethoxy-2-hydroxy-3-(5-((((R)-2-((R)-1-(N-hydroxyformamido)propyl)heptanamido)methyl)carbamoyl)furan-2-yl)benzoic acid
(3-ethoxy-5-(5-((((R)-2-((R)-1-(N-hydroxyformamido)propyl)heptanamido)methyl)carbamoyl)furan-2-yl)phenyl)
phosphonic acid
(2-ethoxy-4-(5-((((R)-2-((R)-1-(N-hydroxyformamido)propyl)heptanamido)methyl)carbamoyl)furan-2-yl)phenyl)
phosphonic acid
3-(carboxymethoxy)-5-(5-((((R)-2-((R)-1-(N-hydroxyformamido)propyl)heptanamido)methyl)carbamoyl)furan-2-yl)benzoic acid
(S)-2-(4-(5-((((R)-2-((R)-1-(N-hydroxyformamido)propyl)
heptanamido)methyl)carbamoyl)furan-2-yl)benzamido)
succinic acid
(S)-2-(2-(carboxymethoxy)-4-(5-((((R)-2-((R)-1-(N-hydroxyformamido)propyl)heptanamido)methyl)carbamoyl)furan-2-yl)benzamido)succinic acid
4-(5-((((R)-2-((R)-1-(N-hydroxyformamido)propyl)heptanamido)methyl)carbamoyl)furan-2-yl)phthalic acid
(3-hydroxy-5-(5-((((R)-2-((R)-1-(N-hydroxyformamido)
propyl)heptanamido)methyl)carbamoyl)furan-2-yl)phenyl)phosphonic acid
((2-ethoxy-4-(5-((((R)-2-((R)-1-(N-hydroxyformamido)
propyl)heptanamido)methyl)carbamoyl)furan-2-yl)benzamido)methyl)phosphonic acid and
(3-ethoxy-5-(5-((((2R,3R)-3-(N-hydroxyformamido)-2-
phenethylpentanamido)methyl)carbamoyl)furan-2-yl)
phenyl)phosphonic acid;
or a salt thereof (in more particular embodiments a pharmaceutically acceptable salt thereof).

In some embodiments, the compound of the invention is (3-ethoxy-5-(5-((((R)-2-((R)-1-(N-hydroxyformamido)propyl)heptanamido)methyl)carbamoyl)furan-2-yl)phenyl) phosphonic acid. In some embodiments, the compound of the invention is a salt (e.g., pharmaceutically acceptable salt) of (3-ethoxy-5-(5-((((R)-2-((R)-1-(N-hydroxyformamido) propyl)heptanamido)methyl)carbamoyl)furan-2-yl)phenyl) phosphonic acid.

In some embodiments, the compound of the invention is (S)-2-(2-ethoxy-4-(5-((((R)-2-((R)-1-(N-hydroxyformamido)propyl)heptanamido)methyl)carbamoyl)furan-2-yl) benzamido)succinic acid. In some embodiments, the compound of the invention is a salt (e.g., a pharmaceutically acceptable salt) of (S)-2-(2-ethoxy-4-(5-((((R)-2-((R)-1-(N-hydroxyformamido)propyl)heptanamido)methyl)carbamoyl)furan-2-yl)benzamido)succinic acid.

In some embodiments, the compound of the invention is (S)-2-(2-(carboxymethoxy)-4-(5-((((R)-2-((R)-1-(N-hydroxyformamido)propyl)heptanamido)methyl)carbamoyl) furan-2-yl)benzamido)succinic acid. In some embodiments, the compound of the invention is a salt (e.g., a pharmaceutically acceptable salt) of (S)-2-(2-(carboxymethoxy)-4-(5-((((R)-2-((R)-1-(N-hydroxyformamido)propyl)heptanamido)methyl)carbamoyl)furan-2-yl)benzamido)succinic acid.

In some embodiments, the invention is directed to a method of inhibiting BMP1, TLL1 and/or TLL2 comprising contacting a biological material comprising the protein(s) with a compound of the invention. In some embodiments the contact is made in-vitro, and the biological material is, e.g., cell culture or cellular tissue. In other embodiments, the contact is made in-vivo.

In other embodiments, the invention is directed to a method of treating a disease associated with BMP1, TLL1 and/or TLL2 activity in a subject (e.g., a human or other mammal) in need thereof, comprising administering to the subject a therapeutically effective amount of a compound of the invention (particularly a compound of Formula (I) or a pharmaceutically acceptable salt thereof). The invention is still further directed to the use of a compound of the invention or a pharmaceutical composition comprising a compound of the invention (particularly a compound of Formula (I) or a pharmaceutically acceptable salt thereof) to treat a disease associated with BMP1, TLL1 and/or TLL2 activity. The invention is further directed to a compound of the invention ((particularly a compound of Formula (I) or a pharmaceutically acceptable salt thereof) for use in therapy, particularly as an active therapeutic substance in the treatment of a disease associated with BMP1, TLL1 and/or TLL2 activity. The invention is further directed to the use of a compound of the invention (particularly a compound of Formula (I) or a pharmaceutically acceptable salt thereof) in the manufacture of a medicament for use in treating a disease associated with BMP1, TLL1 and/or TLL2 activity.

In some embodiments, the disease associated with BMP1, TLL1 and/or TLL2 activity is selected from those associated with pathological fibrotic conditions in body organs or tissues, e.g., such conditions of the heart, lung, kidney, liver, eye, skeletal muscle, skin, the vasculature, and the nervous system, e.g., myocardial infarction ("MI"), heart failure (e.g., heart failure with reduced ejection fraction, heart failure with preserved ejection fraction), cardiac arrhythmias (e.g., atrial fibrillation), hypertrophic cardiomyopathy, chronic obstructive pulmonary disease ("COPD"), idiopathic pulmonary fibrosis ("IPF"), diabetic nephropathy, post-acute kidney injury, chronic kidney disease ("CKD"), delayed graft function post-transplantation, liver cirrhosis, non-alcoholic steatohepatitis ("NASH"), glaucoma, corneal scarring, muscular dystrophies (including Duchenne, Becker, limb-girdle, congenital, facioscapulohumeral, myotonic, oculopharyngeal, distal, and Emery-Dreifuss), keloids, wound healing, adhesions, hypertrophic scarring and other scarring, e.g., associated with burns, surgery or other trauma, stroke, collagen vascular diseases (such as systemic lupus erythematosus, rheumatoid arthritis and scleroderma), spinal cord injury, and multiple sclerosis.

In some embodiments, the disease associated with BMP1, TLL1 and/or TLL2 activity is selected from muscular diseases characterized by reduced muscle function and/or mass, e.g., muscular dystrophy (e.g., Duchenne, Becker, limb-girdle, congenital, facioscapulohumeral, myotonic, oculopharyngeal, distal, and Emery-Dreifuss), sarcopenia, and cachexia associated with, e.g., heart failure, CKD, COPD, cancer, or old age.

The compounds according to Formula (I) may contain one or more asymmetric center(s) (also referred to as a chiral center(s)) and may, therefore, exist as individual enantiomers, diastereomers, or other stereoisomeric forms, or as mixtures thereof. Chiral centers, such as a chiral carbon, sulfur or phosphorus, may also be present in the compounds of this invention. Where the stereochemistry of a chiral center present in a compound of this invention (e.g., compound name or in any chemical structure illustrated herein) is not specified, the compound, compound name, or structure is intended to encompass all individual stereoisomers and all mixtures thereof. Thus, compounds according to Formula (I) containing one or more chiral center(s) may be present as racemic mixtures, enantiomerically enriched mixtures, or as enantiomerically pure individual stereoisomers.

Individual stereoisomers of a compound according to Formula (I) which contain one or more asymmetric center(s) may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

It is to be understood that a solid form of a compound of the invention may exist in crystalline forms, non-crystalline forms or a mixture thereof. Such crystalline forms may also exhibit polymorphism (i.e. the capacity to occur in different crystalline forms). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Because of their potential use in medicine, the salts of the compounds of Formula (I) are preferably pharmaceutically acceptable salts. Suitable pharmaceutically acceptable salts include those described by Berge, S. M. et al., Journal of Pharmaceutical Sciences, 1977, 66, 1-19.

When a compound of the invention is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like, or with a pyranosidyl acid, such as glucuronic acid or galacturonic acid, or with an alpha-hydroxy acid, such as citric acid or tartaric acid, or with an amino acid, such as aspartic acid or glutamic acid, or with an aromatic acid, such as benzoic acid or cinnamic acid, or with a sulfonic acid, such as p-toluenesulfonic acid, methanesulfonic acid, ethanesulfonic acid or the like.

Suitable acid addition salts include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfite, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, dinitrobenzoate, hydroxybenzoate, methoxybenzoate, phthalate, phenylacetate, phenylpropionate, phenylbutrate, lactate, γ-hydroxybutyrate, mandelate, and sulfonates, such as xylenesulfonate, propanesulfonate, naphthalene-1-sulfonate and naphthalene-2-sulfonate.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, tertiary or quaternary), an alkali metal or alkaline earth metal hydroxide, alkoxide (e.g. $(C_{1-4})$ alkoxide), alkyl ester (e.g., $(C_{1-4})$alkyl ester, e.g. acetate), or the like. Illustrative examples of suitable salts include organic salts derived from amino acids such as glycine, lysine, and arginine, ammonia, primary, secondary, tertiary, and quaternary amines, cyclic amines, and amino sugars, e.g., 2-amino-2-deoxysugars, such as N-methyl-D-glucamine, diethylamine, isopropylamine, trimethylamine, ethylene diamine, dicyclohexylamine, ethanolamine, choline, piperidine, morpholine, piperazine, Tris (also known as THAM, or tris(hydroxymethyl)aminomethane), 2-amino-2-hydroxymethyl-propane-1,3-diol, and 2-amino-2-(hydroxymethyl)-1,3-propanediol), meglumine (also known as 1-Deoxy-1-(methylamino)-D-glucitol), galactosamine, glucosamine, and N-acetylglucosamine, as well as inorganic salts derived from sodium, calcium, potassium, magnesium, manganese, iron, copper, zinc, aluminum, and lithium (e.g., hydroxides, $(C_{1-4})$alkoxides, and $(C_{1-4})$alkyl esters of such alkali and alkaline earth metals).

Treatment of a compound of Formula (I) containing a free acid with an inorganic or organic base, or containing a free base with an acid, to form a salt of the compound of Formula (I) may be done by methods known in the art. For example, the free acid may be admixed with a suitable solvent (e.g. in which the free acid is soluble) and treated with the base, with stirring, and optionally with heating and/or temperature cycling. Analogously, for a compound of Formula (I) containing a free base, the free base may be admixed with a suitable solvent (e.g. in which the free base is soluble) and treated with the acid, with stirring, and optionally with heating and/or temperature cycling. Certain of the compounds of the invention may form salts with one or more equivalents of an acid (if the compound contains a basic moiety) or a base (if the compound contains an acidic moiety). The present invention includes within its scope all possible stoichiometric and non-stoichiometric salt forms.

Compounds of the invention having both a basic and acidic moiety may be in the form of zwitterions, acid-addition salts of the basic moiety or base salts of the acidic moiety.

This invention also provides for the conversion of one pharmaceutically acceptable salt of a compound of this invention into another pharmaceutically acceptable salt of a compound of this invention.

In some embodiments, the compound of the invention is a salt, e.g., a pharmaceutically acceptable salt, of (3-ethoxy-5-(5-((((R)-2-((R)-1-(N-hydroxyformamido)propyl)heptanamido)methyl)carbamoyl)furan-2-yl)phenyl)phosphonic acid. In some embodiments, the compound of the invention is a meglumine salt, Tris salt, or calcium salt of (3-ethoxy-5-(5-((((R)-2-((R)-1-(N-hydroxyformamido)propyl)heptanamido)methyl)carbamoyl)furan-2-yl)phenyl)phosphonic acid, including all possible stoichiometric and non-stoichiometric forms of such salts.

In some embodiments, the compound of the invention is a salt, e.g., a pharmaceutically acceptable salt, of (S)-2-(2-ethoxy-4-(5-((((R)-2-((R)-1-(N-hydroxyformamido)propyl)heptanamido)methyl)carbamoyl)furan-2-yl)benzamido)succinic acid.

In some embodiments, the compound of the invention is a salt, e.g., a pharmaceutically acceptable salt, of (S)-2-(2-(carboxymethoxy)-4-(5-((((R)-2-((R)-1-(N-hydroxyformamido)propyl)heptanamido)methyl)carbamoyl)furan-2-yl)benzamido)succinic acid.

The compounds of Formula (I) and salts (including pharmaceutically acceptable salts) thereof may be in the form of a solvate. For solvates of the compounds of Formula (I), including solvates of salts of the compounds of Formula (I), that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethylsulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Solvates include stoichiometric solvates as well as compositions containing variable amounts of the incorporated solvent(s), e.g. a hydrate includes stoichiometric hydrates and compositions containing variable amounts of water. The invention includes all such solvates, particularly hydrates. It is to be understood that the term "a salt, particularly a pharmaceutically acceptable salt, thereof, or solvate thereof" and the like in reference to a compound of Formula (I) encompasses a salt of a compound of Formula (I), a pharmaceutically acceptable salt of a compound of Formula (I), a solvate of a compound of Formula (I), a solvate of a salt of a compound of Formula (I), and a solvate of a pharmaceutically acceptable salt of a compound of Formula (I) (for example, where water is the incorporated solvent, said solvates are hydrates).

Because the compounds of the invention, particularly compounds of Formula (I), and pharmaceutically acceptable salts thereof, or a solvate (e.g., hydrate) thereof, are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

General Methods of Preparation:

The compounds of Formula (I) may be obtained by using synthetic procedures illustrated in the Schemes below or by drawing on the knowledge of a skilled organic chemist. The syntheses provided in these Schemes are applicable for producing compounds of the invention having a variety of different R1, R2 and R3 groups employing appropriate precursors. Those skilled in the art will appreciate that in the preparation of compounds of the invention (e.g., compounds of Formula (I), salts thereof, and/or solvates thereof) it may be necessary and/or desirable to protect one or more sensitive groups in the molecule or the appropriate intermediate to prevent undesirable side reactions. Suitable protecting groups for use according to the present invention are well know to those skilled in the art and may be used in a conventional manner. See for example, "Protective groups in organic synthesis" by T. W. Green and P. G. M Wuts (Wiley & Sons, 1991) or "Protecting Groups" by P. J. Kocienski (Georg Thieme Verlag, 1994). Subsequent deprotection, where needed, affords compounds of the nature generally disclosed. While the Schemes are shown with compounds of Formula (I), they are illustrative of processes that may be used to make the compounds of the invention.

Compound names were generated using the software naming program Chem Draw Ultra v12.0 available from Perkin Elmer, 940 Winter Street, Waltham, Mass., 02451, USA. (http://www.perkinelmer.com/).

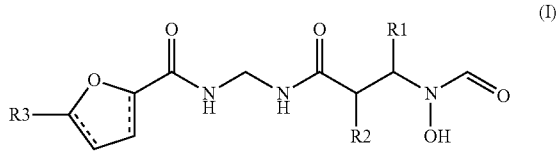

In a general process, compounds of Formula (I) may be prepared according to reaction Schemes 1, 2 or 3:

Scheme 1

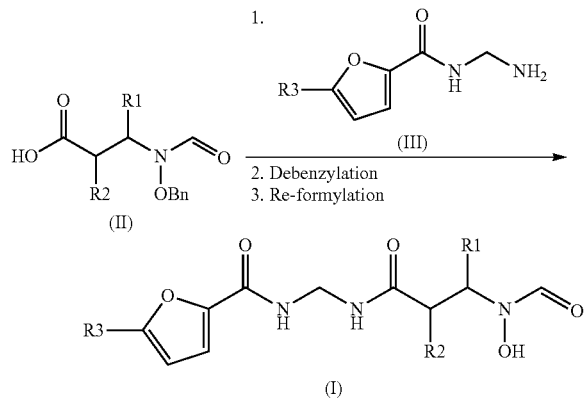

1. React (II) and (III) in the presence of an amide coupling reagent (e.g. EDC/HOBT, HATU or HBTU) in the presence of a base (e.g. triethylamine or DIPEA) in a solvent such as DCM, DMF or THF either at room temperature or at an elevated temperature such as 50° C. 2. Debenzylation may be achieved via hydrogenation using a catalyst such as Pd/C and a hydrogen source (e.g. hydrogen gas or ammonium formate) at atmospheric pressure and temperature. Alternatively deprotection may be achieved using $BCl_3$ in a solvent such as DCM at 0° C. to room temperature. 3. If required, re-formylation may be achieved utilizing a pre-mixed solution of CDI/formic acid in a solvent such as DCM at room temperature. Alternatively re-formylation may be achieved via reaction with 5-methyl-2-thioxo-1,3,4-thiadiazole-3 (2H)-carbaldehyde (Yazawa, H., et al., Tetrahedron Letters, 1985, 26(31), 3703-6) in a solvent such as DCM at room temperature. As appreciated by those skilled in the art the order of the synthetic steps may be varied or omitted if unnecessary.

Scheme 2

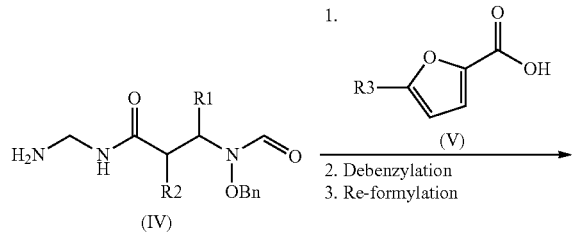

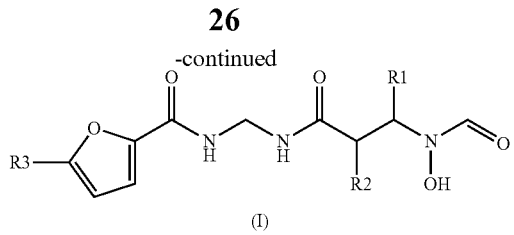

1. React (IV) and (V) in the presence of an amide coupling reagent (e.g. EDC/HOBT, HATU or HBTU) in the presence of a base (e.g. triethylamine, DIPEA or NMO) in a solvent such as DCM or DMF at room temperature or at an elevated temperature such as 50° C. 2.-3. Debenzylation and re-formylation (if required) may be achieved as described in Step 2 and Step 3 of Scheme 1. As appreciated by those skilled in the art the order of the synthetic steps may be varied or omitted if unnecessary.

Scheme 3

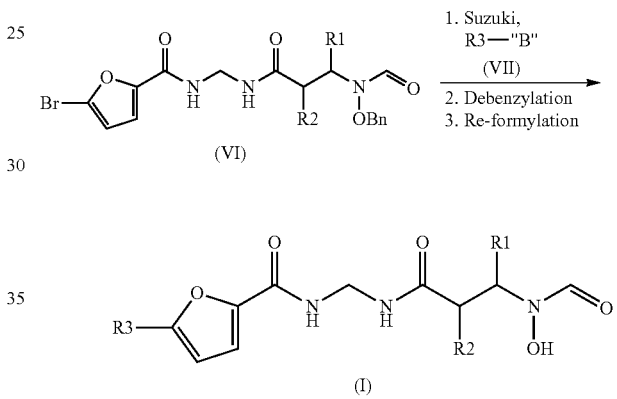

1. React (VI) with the appropriate boronic acid or boronate ester (R3-"B") derivative (VII) in the presence of a catalyst (e.g. $Pd(PPh_3)_4$ or $Pd(dppf)Cl_2$) in the presence of an inorganic base (e.g. potassium carbonate or aqueous sodium carbonate) in a suitable solvent (e.g. 1,4-dioxane or DME/water) at elevated temperature (50-150° C.) under microwave irradiation or by classical heating. 2.-3. Debenzylation and re-formylation (if required) may be achieved as described in Step 2 and Step 3 of Scheme 1. As appreciated by those skilled in the art the order of the synthetic steps may be varied or omitted if unnecessary.

In a general process, compounds of Formula (I) wherein R3 contains a carboxylic acid (e.g., Formula (Ia)), phosphonic acid (e.g., Formula (Ib)) or phosphinic acid (e.g., Formula (Ic)) may be prepared according to Schemes 1, 2, 3 or as outlined in Scheme 4 from their corresponding ester functionalities (VIIIa), (VIIIb) and (VIIIc). The transformations in Scheme 4 are illustrated with a phenyl ring R3 however Scheme 4 applies analogously to preparation of corresponding molecules of Formula (Ia-c) with all embodiments of R3 disclosed herein (including, e.g., where R3 is heteroaryl and/or optionally further substituted).

Scheme 4

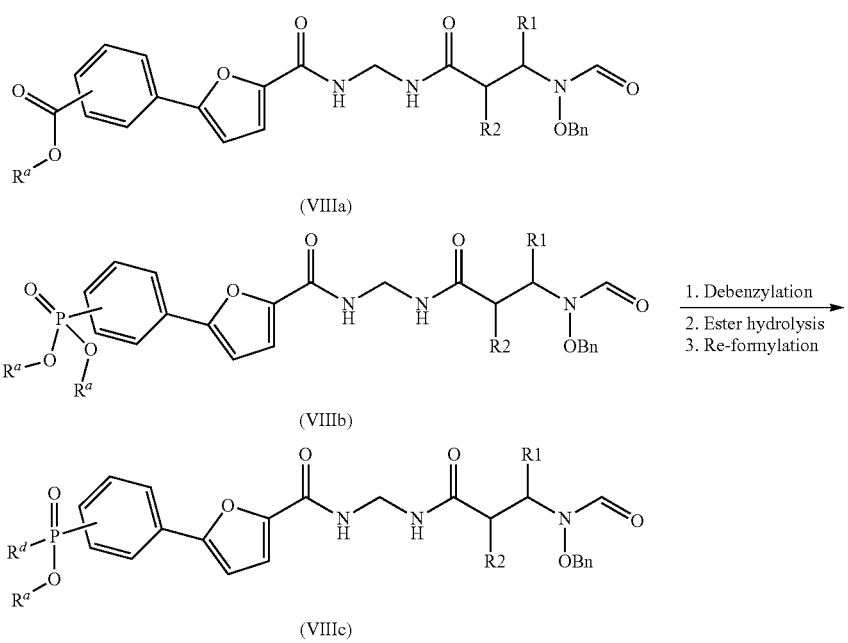

1. Debenzylation may be achieved as described in Step 2 of Scheme 1. 2. Ester hydrolysis may be achieved by reaction with lithium hydroxide in a suitable solvent such as a THF/water mixture or alcoholic solvent (e.g. ethanol or methanol/water mixture). For compounds of Formula (VIIIb) and (VIIIc), hydrolysis may be alternatively achieved by reaction with TMS-Br in a suitable solvent such as DCM at 0° C. to room temperature. 3. If required, re-formylation can be achieved as described in Step 3 of Scheme 1. As appreciated by those skilled in the art the order of the synthetic steps may be varied or omitted if unnecessary.

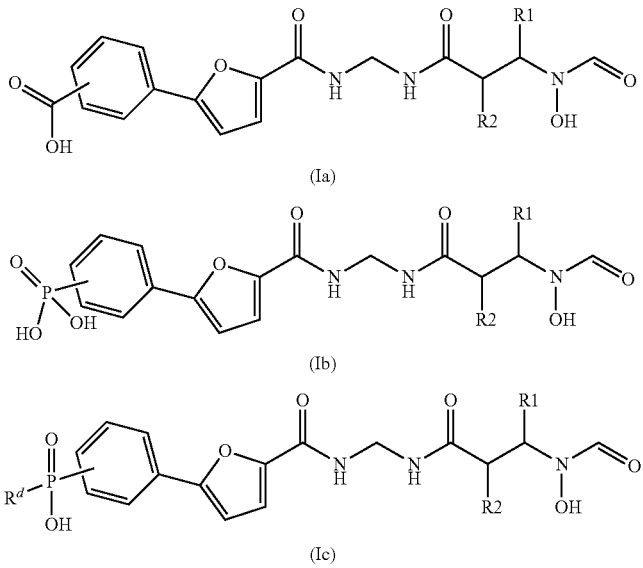

In a general process, compounds of Formula (I) wherein R3 contains an amide (e.g., Formula (1d)) may be prepared according to Scheme 1, 2, 3 or may be prepared according to reaction Scheme 5. The transformations in Scheme 5 are illustrated with a phenyl ring R3 however Scheme 5 applies analogously to preparation of corresponding molecules of Formula (1d) with all embodiments of R3 disclosed herein (including, e.g., where R3 is heteroaryl and/or optionally further substituted).

Scheme 5

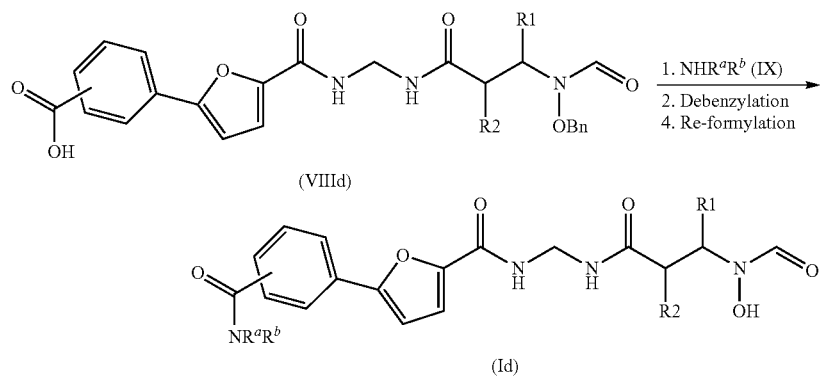

1. React a compound of Formula (VIIId) and the appropriate amine NHR$^a$R$^b$ (IX) in the presence of an amide coupling reagent (e.g. EDC/HOBT, HATU, HBTU or T3P®) in the presence of a base (e.g. triethylamine, DIPEA or NMO) in a solvent such as DCM or DMF at room temperature. 2.-3. Debenzylation and re-formylation (if required) may be achieved as described in Step 2 and Step 3 of Scheme 1. As appreciated by those skilled in the art the order of the synthetic steps may be varied or omitted if unnecessary.

In a general process, compounds of Formula (I) wherein R3 contains an acyl sulphonamide (e.g., Formula (Ie)) may be prepared from compounds of Formula (VIIIe) wherein R3 contains a primary sulphonamide according to reaction Scheme 6. The transformations in Scheme 6 are illustrated with a phenyl ring R3 however Scheme 6 applies analogously to preparation of corresponding molecules of Formula (Ie) with all embodiments of R3 disclosed herein (including, e.g., where R3 is heteroaryl and/or optionally further substituted).

Scheme 6

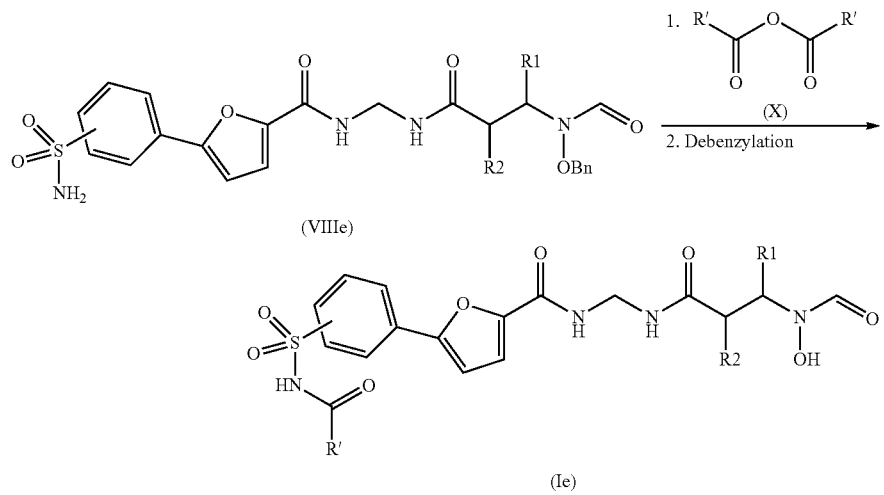

1. React a compound of Formula (VIIIe) with the appropriately substituted symmetrical anhydride (X) wherein R' is selected from C$_{1-2}$ alkyl in the presence of a base such as triethylamine in a suitable solvent such as DCM at elevated temperature, such as 50° C.

2. Debenzylation may be achieved as described in Step 2 of Scheme 1.

In a general process, compounds of Formula (I) wherein R3 contains an amide oxime (e.g., Formula (Ig)) may be prepared from compounds of Formula (If) wherein R3 contains a nitrile according to reaction Scheme 7. The transformation in Scheme 7 is illustrated with a phenyl ring R3 however Scheme 7 applies analogously to preparation of corresponding molecules of Formula (Ig) with all embodiments of R3 disclosed herein (including, e.g., where R3 is heteroaryl and/or optionally further substituted).

Scheme 7

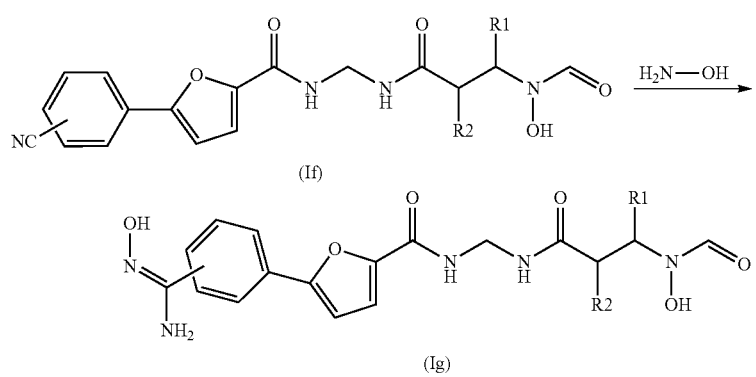

React a compound of Formula (If) with hydroxylamine in a suitable solvent such as ethanol at an elevated temperature such as 75° C.

In a general process, compounds of Formula (I) wherein R2 contains a nitrile functionality (e.g., Formula (Ih)) may be prepared from compounds of Formula (VIIIf) wherein R2 contains a bromide (Formula (VIIIf)) according to reaction Scheme 8. The transformations in Scheme 8 are illustrated with a propyl R2 however Scheme 8 applies analogously to preparation of corresponding molecules of Formula (1 h) with all embodiments of R2 disclosed herein, including $(C_1-C_{11})$alkyl, $(C_1-C_3)$alkyl-$(C_3-C_6)$cycloalkyl, $(C_1-C_3)$alkyl-phenyl and $(C_1-C_3)$alkyl-heterocyclyl and/or optionally further substituted.

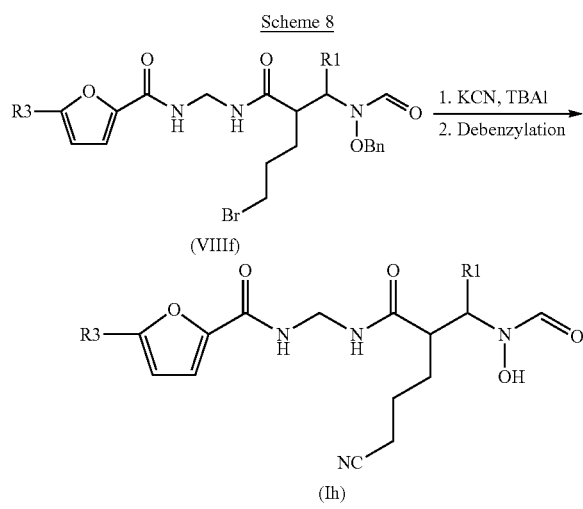

1. React with potassium cyanide in the presence of catalytic TBAI in a suitable solvent such as acetonitrile at elevated temperature such as 80° C. 2. Debenzylation may be achieved as described in Step 2 of Scheme 1.

With regard to the above Schemes 1-8:

Compounds of Formula (II) may be prepared according to Schemes 9-14.

Compounds of Formula (III) may be prepared according to Schemes 15-17.

Compounds of formula (IV) may be prepared according to Scheme 18.

Compounds of Formula (VI) may be prepared according to Scheme 1 or 2 where the R3 of (III) or (V) is replaced by a bromide and by omitting the debenzylation step.

Compounds of Formula (VIIIa-c), (VIIId), and (VIIIe), and corresponding compounds with other R3; and compounds of Formula (VIIIf) and corresponding compounds with other R2, may be prepared according to Scheme 1, 2 or 3 by omitting the debenzylation step.

Compounds of Formula (If) and corresponding compounds with other R3 may be prepared according to Schemes 1, 2 or 3.

Compounds of Formula (V), (VII), and (X) may be sourced commercially or may be prepared by methods known in the literature or by processes known to those skilled in the art.

Compounds of Formula (IX) are commercially available.

In a general process, compounds of Formula (II), wherein R1 is H, may be prepared according to the following reaction Schemes 9, 10, 11 or 14. In a general process, compounds of Formula (II) may be alternatively prepared according to the following reaction Schemes 12 or 13.

Scheme 9

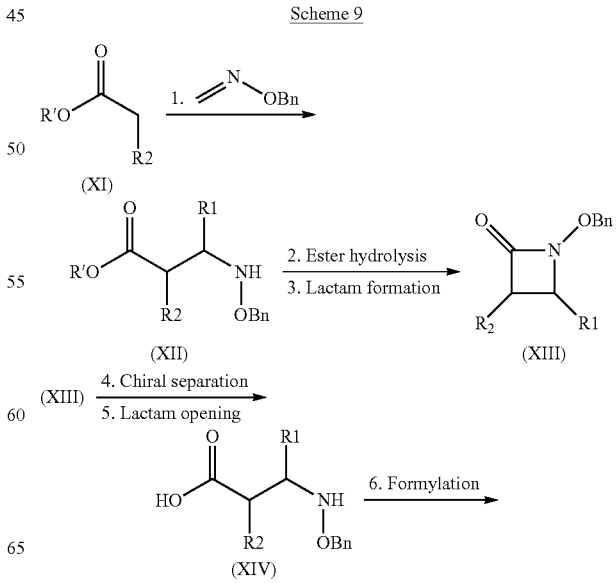

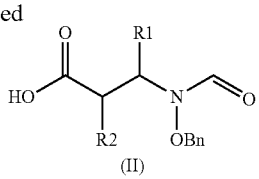

1. React formaldehyde O-benzyl oxime with a pre-mixed solution of NaI and TMS-Cl or TMS-OTf and then treat with a base such as triethylamine and a compound of Formula (XI) in a suitable solvent such as acetonitrile or DCM. 2. In instances where R' is not H but selected from $C_{1-2}$ alkyl, ester hydrolysis can be achieved by reaction with lithium hydroxide in a suitable solvent such as an ethanol/water mixture. 3. Lactam formation may be achieved by reaction with phosphoryl trichloride in the presence of a base such as 2,6-dimethylpyridine in a suitable solvent such as toluene at an elevated temperature, such as at 50° C. 4. Chiral separation may be conducted at this stage using techniques known to those skilled in the art. 5. Lactam ring opening may be achieved by reaction with lithium hydroxide in a suitable solvent such as a THF/water mixture. 6. Formylation may be achieved as described in Step 3 of Scheme 1. As appreciated by those skilled in the art synthetic steps may be omitted if unnecessary.

Scheme 10

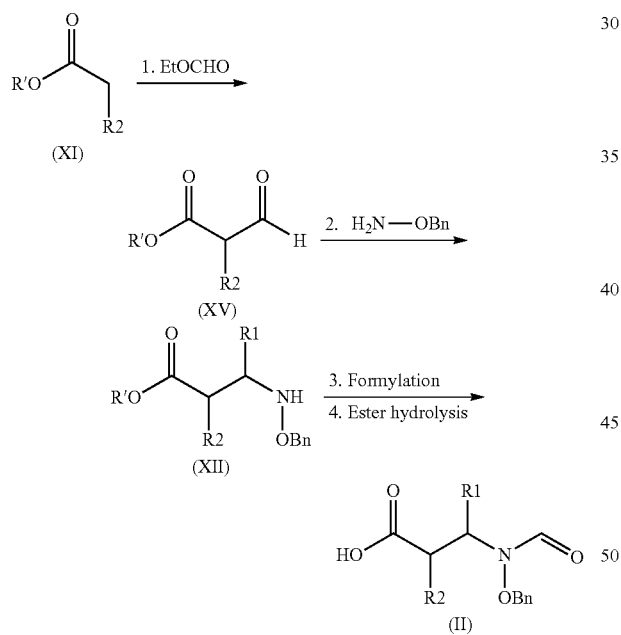

1. React a compound of Formula (XI) with a base such as LDA followed by reaction with ethyl formate in a suitable solvent such as THF at −78° C. to 0° C. 2. Conduct a reductive amination with O-benzylhydroxylamine hydrochloride in the presence of a reducing agent such as sodium triacetoxyborohydride in suitable solvent system such as a DCM/acetic acid mixture. 3. Formylation may be achieved utilizing a mixture of CDI/formic acid in a solvent such as DCM at room temperature. 4. Ester hydrolysis may be achieved by reaction with lithium hydroxide in a suitable solvent such as a THF/methanol/water mixture. As appreciated by those skilled in the art the order of the synthetic steps may be varied.

Scheme 11

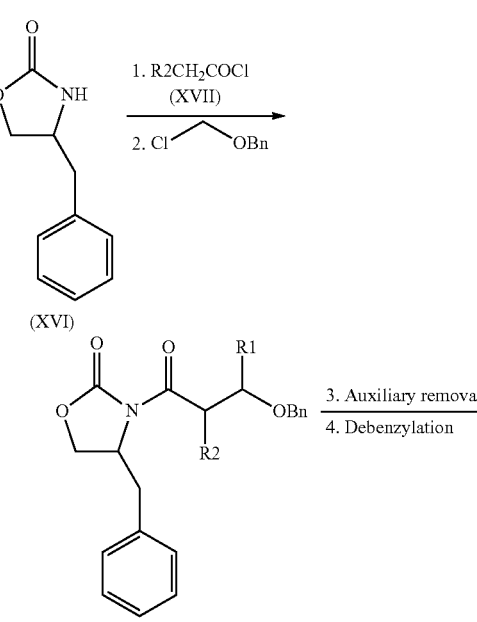

1. React the appropriate enantiomer of (XVI) with a base such as butyl lithium followed by the appropriate acyl chloride (XVII) in a suitable solvent such as THF at −78° C. to 0° C. 2. React with $TiCl_4$ in the presence of a suitable base such as DIPEA in a suitable solvent such as DCM followed by reaction with ((chloromethoxy)methyl)benzene. 3. React with hydrogen peroxide and lithium hydroxide in a suitable solvent such as a mixture of THF and water at 0° C. 4. Debenzylation may be achieved via hydrogenation using Pd/C catalyst and a hydrogen source (e.g. hydrogen gas or ammonium formate) at room temperature. 5. React with O-benzylhydroxylamine hydrochloride in the presence of a coupling agent such as EDC and DMAP in a suitable solvent such as DCM. 6. Lactam formation may be achieved by reaction with DIAD and triphenylphosphine in a suitable solvent such as THF. 7. Lactam ring opening may be achieved by reaction with lithium hydroxide in a suitable solvent such as a methanol/water mixture. 8. Formylation may be achieved utilizing a mixture of CDI/formic acid in a solvent such as DCM at room temperature.

fonyl chloride using a suitable base such as pyridine as the solvent. 5. React with tetrabutylammonium hydroxide in a suitable solvent such as 2-methyl tetrahydrofuran. 6. Formylation may be achieved utilizing a mixture of CDI/formic acid in a solvent such as DCM at room temperature.

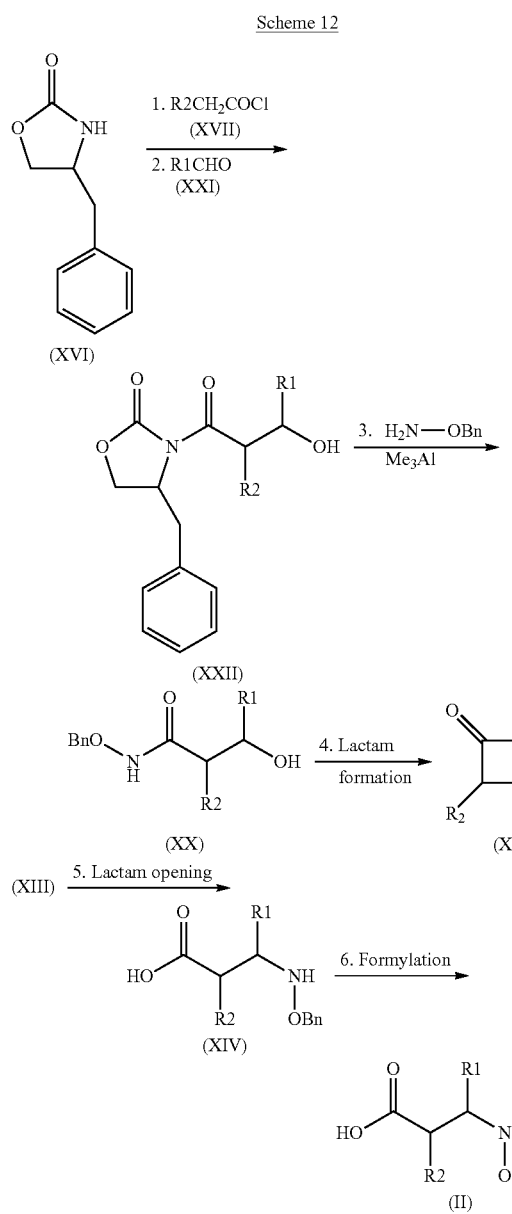

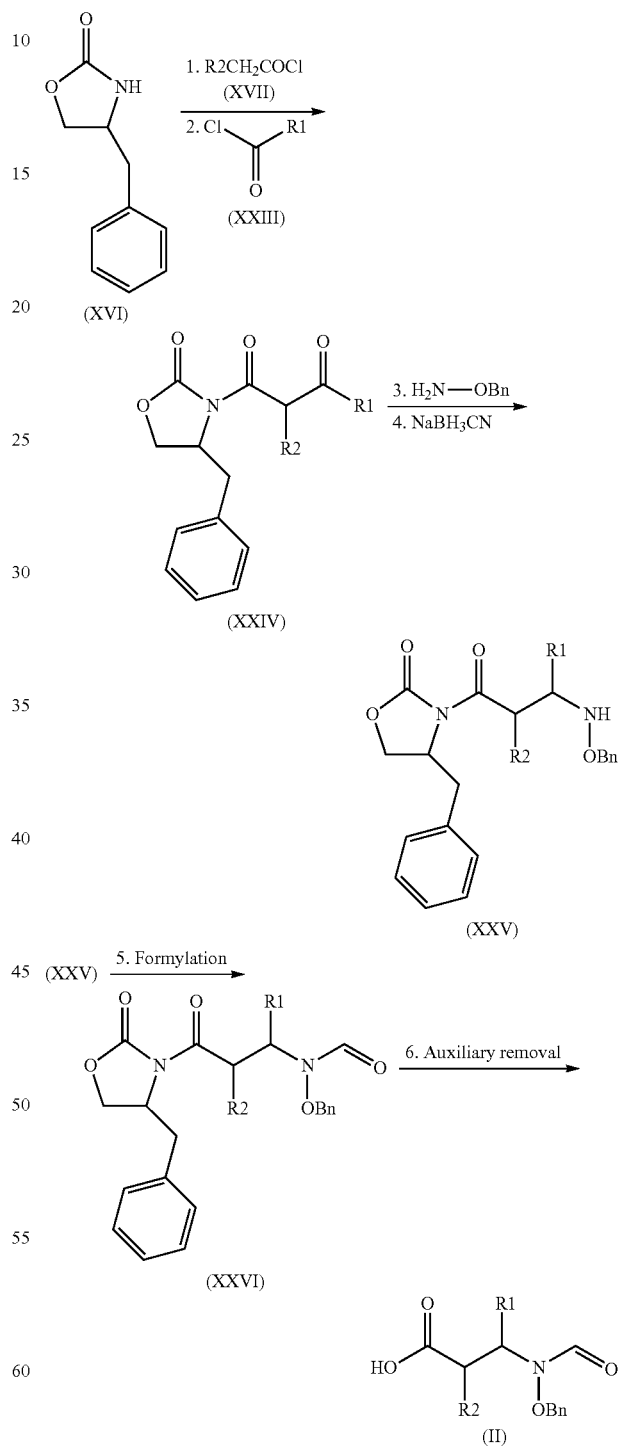

1. React the appropriate enantiomer of (XVI) with a base such as butyl lithium followed by the appropriate acyl chloride (XVII) in a suitable solvent such as THF. 2. React with TiCl$_4$ in the presence of a suitable base such as DIPEA with a suitable additive such as NMP in a suitable solvent such as DCM followed by reaction with the appropriate aldehyde (XXI). 3. React with O-benzylhydroxylamine hydrochloride in a suitable solvent such as THF in the presence of trimethylaluminium. 4. React with methanesul- 1. React the appropriate enantiomer of (XVI) with a base such as butyl lithium followed by the appropriate acyl chloride (XVII) in a suitable solvent such as THF. 2. React with a suitable base such as NaHMDS in a suitable solvent such as THF at −78° C. followed by the appropriate acyl chloride (MID. 3. React with O-benzylhydroxylamine hydrochloride in the presence of sodium acetate in a suitable solvent such as methanol. 4. React with sodium cyanoborohydride in a suitable solvent mixture such as dichloroethane and acetic acid. 5. Formylation may be achieved utilizing a mixture of CDI/formic acid in a solvent such as DCM at room temperature. 6. React with hydrogen peroxide and lithium hydroxide in a suitable solvent such as a mixture of methanol and water at 0° C.

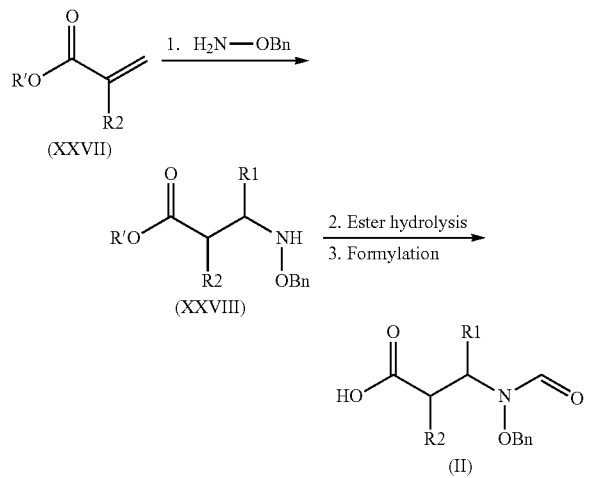

1. React a compound of Formula (XXVII), wherein R' is $C_{1-2}$ alkyl, with O-benzylhydroxylamine hydrochloride in the presence of (a) a suitable base such as triethylamine in a suitable solvent such as ethanol, or (b) MgBr$_2$ in a suitable solvent such as methanol at an elevated temperature such as 100° C. 2. Ester hydrolysis may be achieved by reaction with lithium hydroxide in a suitable solvent such as a THF/water mixture. 3. Formylation may be achieved utilizing a mixture of CDI/formic acid in a solvent such as DCM at room temperature.

With regard to the above Schemes 9-14, compounds of Formula (XI), (XVI), (XVII), (XXI), (XXIII), and (XXVII) are commercially available or may be prepared by methods known in the literature or by processes known to those skilled in the art.

In a general process, compounds of Formula (III) may be prepared according to reaction Scheme 15, 16 or 17:

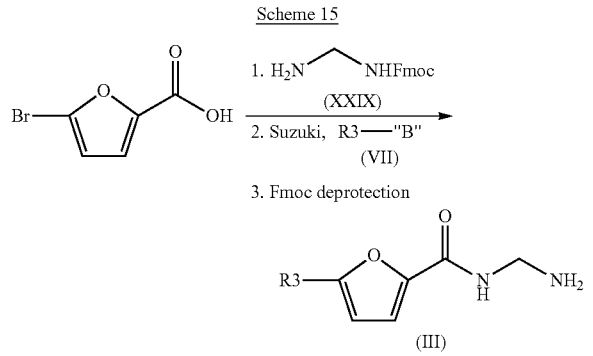

1. React 5-bromofuran-2-carboxylic acid with (XXIX) in the presence of a coupling reagent such as HATU in the presence of a base such as DIPEA in a suitable solvent such as DCM. 2. React with the appropriate boronic acid or boronate ester (R3-"B") derivative (VII) in the presence of a catalyst (e.g. Pd(dppf)Cl$_2$) in the presence of an inorganic base (e.g aqueous sodium carbonate) in a suitable solvent such as 1,4-dioxane or DME at an elevated temperature such as 100-105° C. under microwave irradiation. 3. Fmoc deprotection may be achieved by reaction with a secondary amine such as piperidine, or pyrollidine in a suitable solvent such as DCM or acetonitrile. As appreciated by those skilled in the art the order of the synthetic steps may be varied.

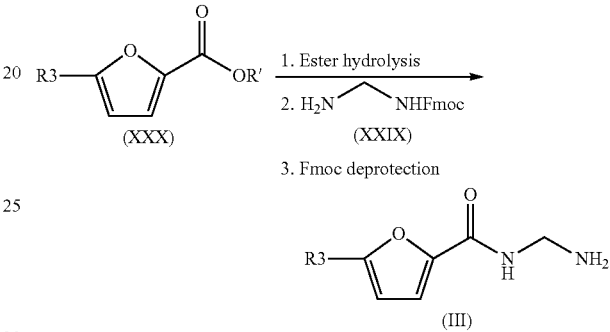

1. In instances where R' is not H but selected from $C_{1-2}$ alkyl, ester hydrolysis may be achieved by reaction of a compound of Formula (XXX) with lithium hydroxide in a suitable solvent such as a mixture of methanol and water. 2. Amide formation may be achieved by reaction with oxalyl chloride in a suitable solvent such as DMF at room temperature followed by reaction with a compound of Formula (XXIX) in the presence of a base such as DIPEA in a suitable solvent such as DCM. Alternatively, amide formation may be achieved by reaction (XXIX) in the presence of a coupling reagent such as HATU in the presence of a base such as DIPEA in a suitable solvent such as DCM. 3. Fmoc deprotection may be achieved by reaction with a secondary amine such as pyrollidine or morpholine in a suitable solvent such as DCM or acetonitrile.

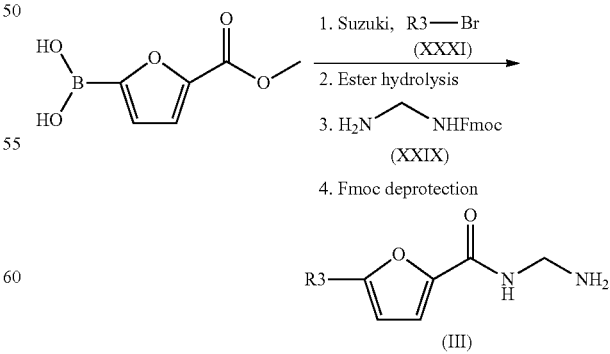

1. React (5-(methoxycarbonyl)furan-2-yl)boronic acid with the appropriate bromide, R$^3$—Br (XXXI), in the presence of a catalyst (e.g. Pd(dppf)Cl$_2$) in the presence of an inorganic base (e.g. aqueous sodium carbonate) in a suitable solvent (e.g. 1,4-dioxane) at elevated temperature (e.g. 100° C.) under microwave irradiation. 2. Ester hydrolysis may be achieved by reaction with lithium hydroxide in a suitable solvent such as a THF/water mixture at room temperature. 3. React with (XXIX) in the presence of a coupling reagent such as HBTU in the presence of a base such as DIPEA in a suitable solvent such as DMF at room temperature. 4. Fmoc deprotection may be achieved by reaction with a secondary amine such as piperidine, or pyrollidine in a suitable solvent such as DCM or acetonitrile.

In a general process, compounds of Formula (IV) may be prepared according to reaction Scheme 18.

Scheme 18

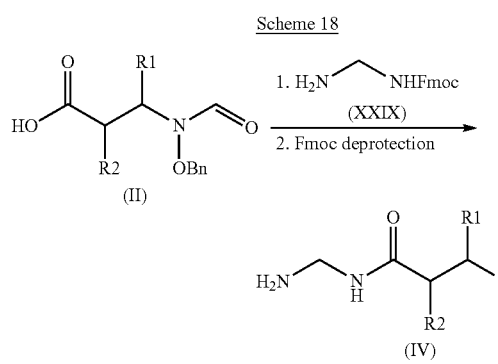

1. React compound of Formula (II) with (XXIX) in the presence of a coupling reagent such as HATU in the presence of a base such as DIPEA in a suitable solvent such as DMF at room temperature. 2. Fmoc deprotection may be achieved by reaction with a secondary amine such as morpholine in a suitable solvent such as acetonitrile.

With regard to the above Schemes 15-18:

Compound (XXIX) may be prepared by processes known to those skilled in the art.

Compounds of Formula (VII) and (XXX) are commercially available, may be prepared by methods known in the literature or by processes known to those skilled in the art.

Compounds of Formula (XXXI) may be sourced commercially or prepared by methods known to those skilled in the art.

In a general process, compounds of Formula (XXXII) may be prepared according to reaction Scheme 19.

Scheme 19

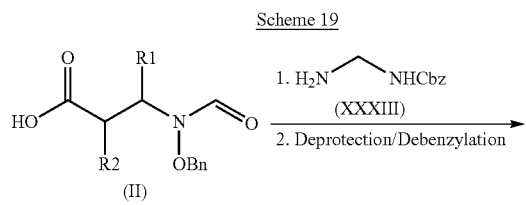

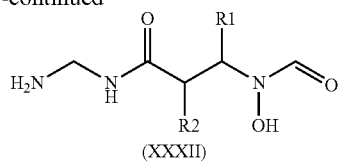

1. React compound of Formula (II) with (XXXIII) in the presence of a coupling reagent such as HATU in the presence of a base such as DIPEA in a suitable solvent such as DMF at room temperature. 2. Deprotection of the Cbz group and debenzylation may be achieved under similar conditions described in Step 2 of Scheme 1 to yield the amine (XXXII).

In a general process, compounds of Formula I) may be prepared according to reaction Scheme 20.

Scheme 20

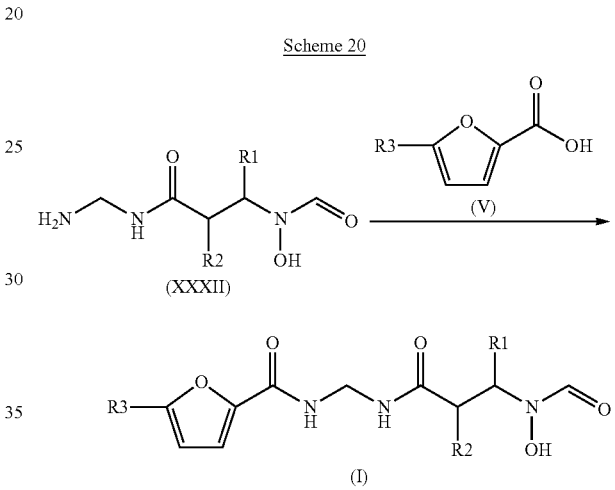

React (XXXII) and (V) in the presence of an amide coupling reagent (e.g. EDC/HOBT, HATU or HBTU) in the presence of a base (e.g. triethylamine, DIPEA or NMO) in a solvent such as DCM or DMF in the presence of TMSCl at room temperature or at an elevated temperature such as 50° C. to yield the final product (I).

In a general process, compounds of Formula (I) wherein R3 contains a phenol (e.g., Formula (Ii) may be prepared from compounds of Formula (XXXIV) wherein R3 contains a benzylether according to reaction Scheme 21. The transformation in Scheme 21 is illustrated with a phenyl ring R3 however Scheme 21 applies analogously to preparation of corresponding molecules of Formula (Ii) with all embodiments of R3 disclosed herein (including, e.g., where R3 is heteroaryl and/or optionally further substituted).

Scheme 21

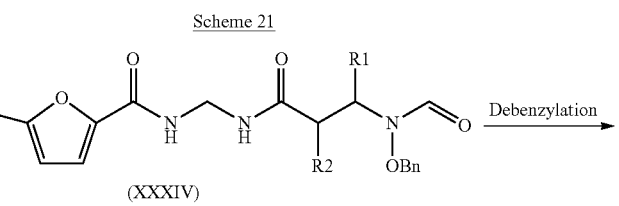

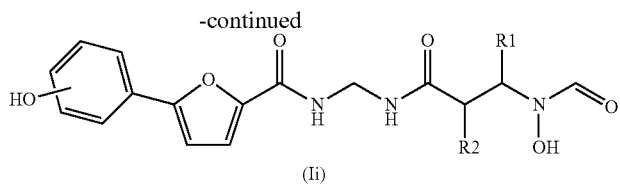

React a compound of Formula (XXXIV) under debenzylation conditions similar to those described in Step 2 of Scheme 1 to yield the phenol (Ii).

In a general process, compounds of Formula (I) wherein R3 contains an amide (e.g., Formula (ID may be prepared from compounds of Formula (XXXV) wherein R3 contains a phenol according to reaction Scheme 22. The transformation in Scheme 22 is illustrated with a phenyl ring R3 however Scheme 22 applies analogously to preparation of corresponding molecules of Formula (ID with all embodiments of R3 disclosed herein (including, e.g., where R3 is heteroaryl and/or optionally further substituted).

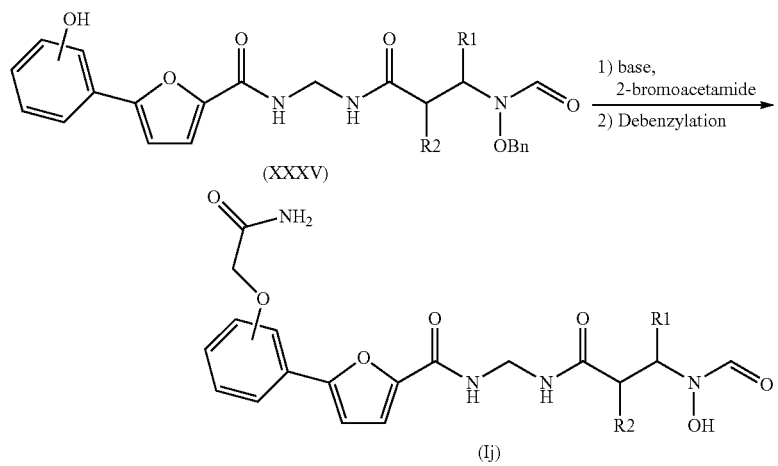

1. React compound of Formula (XXXV) with an alkyl bromide such as 2-bromoacetamide in the presence of a base such as $K_2CO_3$ in a suitable solvent such as $CH_3CN$ at elevated temperatures such as 80° C. 2. Debenzylation may be achieved under similar conditions described in Step 2 of Scheme 1 to yield the product (ID.

Further details for the preparation of compounds of the invention are found in the Intermediates and Examples section hereinafter.

Use of Compounds of the Invention:

The compounds of this invention are inhibitors of BMP1, TLL1 and/or TLL2 activity, and may be particularly useful for treatment of diseases associated with BMP1, TLL1 and/or TLL2 activity, including for example treatment of diseases where inhibition of BMP1, TLL1 and/or TLL2 is of therapeutic benefit. For example, compounds of the invention may be particularly useful for treatment of diseases where inhibition of tissue ECM (extracellular matrix) production and/or maturation would be beneficial, or where inhibition of myostatin activity would be beneficial.

In some embodiments, the disease associated with BMP1, TLL1 and/or TLL2 activity is selected from diseases associated with pathological fibrotic conditions in body organs or tissues, e.g., such conditions of the:

heart (e.g., myocardial infarction ("MI"), heart failure (e.g., heart failure with reduced ejection fraction, heart failure with preserved ejection fraction), cardiac arrhythmias (e.g., atrial fibrillation), hypertrophic cardiomyopathy), lung (e.g. chronic obstructive pulmonary disease ("COPD"), idiopathic pulmonary fibrosis ("IPF")), kidney (e.g. diabetic nephropathy, post-acute kidney injury, chronic kidney disease ("CKD"), delayed graft function post-transplantation), liver (e.g. liver cirrhosis, non-alcoholic steatohepatitis ("NASH")), eye (e.g. glaucoma, corneal scarring), skeletal muscle (e.g. muscular dystrophies, including Duchenne, Becker, limb-girdle, congenital, facioscapulohumeral, myotonic, oculopharyngeal, distal, and Emery-Dreifuss), skin (e.g. keloids, wound healing, adhesions, hypertrophic scarring and other scarring, e.g., associated with burns, surgery or other trauma), the vasculature (e.g. stroke, and collagen vascular diseases such as systemic lupus erythematosus, rheumatoid arthritis and scleroderma), and the nervous system (e.g. spinal cord injury, multiple sclerosis).

In some embodiments, the disease associated with BMP1, TLL1 and/or TLL2 activity is selected from muscular diseases characterized by reduced muscle function and/or mass, e.g., muscular dystrophy (e.g., Duchenne, Becker, limb-girdle, congenital, facioscapulohumeral, myotonic, oculopharyngeal, distal, and Emery-Dreifuss), sarcopenia, and cachexia associated with, e.g., heart failure, CKD, COPD, cancer, or old age.

Accordingly, this invention provides a method of treating a disease associated with BMP1, TLL1 and/or TLL2 activity in a subject in need thereof (e.g. a human or other mammal, particularly a human), for example the diseases recited herein, comprising administering to the subject a therapeutically effective amount of a compound of Formula (I), or a salt thereof, particularly a pharmaceutically acceptable salt thereof.

In some embodiments, a compound of the invention is administered post-MI (i.e. to a subject who has suffered an MI), e.g. to treat fibrosis associated with myocardial infarction. In some embodiments, a compound of the invention is administered post-MI, e.g. to prevent fibrosis associated with myocardial infarction.

In some embodiments, the method of treating comprises administering a specific compound described herein, e.g., a compound of the Examples, or any free acid/base form, salt form, or alternative salt form (particularly pharmaceutically acceptable salts or alternative pharmaceutically acceptable salt forms) thereof, as applicable.

In some embodiments, the method of treating comprises administering (3-ethoxy-5-(5-((((R)-2-((R)-1-(N-hydroxyformamido)propyl)heptanamido)methyl)carbamoyl)furan-2-yl)phenyl)phosphonic acid. In some embodiments, the method of treating comprises administering a pharmaceutically acceptable salt of (3-ethoxy-5-(5-((((R)-2-((R)-1-(N-hydroxyformamido)propyl)heptanamido)methyl)carbamoyl)furan-2-yl)phenyl)phosphonic acid. In some embodiments, the method of treating comprises administering a meglumine salt, Tris salt, or calcium salt of (3-ethoxy-5-(5-((((R)-2-((R)-1-(N-hydroxyformamido)propyl)heptanamido)methyl)carbamoyl)furan-2-yl)phenyl)phosphonic acid.

In some embodiments, the method of treating comprises administering (S)-2-(2-ethoxy-4-(5-((((R)-2-((R)-1-(N-hydroxyformamido)propyl)heptanamido)methyl)carbamoyl)furan-2-yl)benzamido)succinic acid. In some embodiments, the method of treating comprises administering a pharmaceutically acceptable salt of (S)-2-(2-ethoxy-4-(5-((((R)-2-((R)-1-(N-hydroxyformamido)propyl)heptanamido)methyl)carbamoyl)furan-2-yl)benzamido)succinic acid.

In some embodiments, the method of treating comprises administering (S)-2-(2-(carboxymethoxy)-4-(5-((((R)-2-((R)-1-(N-hydroxyformamido)propyl)heptanamido)methyl)carbamoyl)furan-2-yl)benzamido)succinic acid. In some embodiments, the method of treating comprises administering a pharmaceutically acceptable salt of (S)-2-(2-(carboxymethoxy)-4-(5-((((R)-2-((R)-1-(N-hydroxyformamido)propyl)heptanamido)methyl)carbamoyl)furan-2-yl)benzamido)succinic acid.

This invention also provides a compound of Formula (I), or a salt thereof, particularly a pharmaceutically acceptable salt thereof, for use in therapy. This invention specifically provides for the use of a compound of Formula (I), or a pharmaceutically acceptable salt thereof, as an active therapeutic substance in the treatment of a disease associated with BMP1, TLL1 and/or TLL2 activity, for example the diseases recited herein.

In some embodiments, the compound for use in therapy, e.g. for use in the treatment of a disease associated with BMP1, TLL1 and/or TLL2 activity, is a specific compound described herein, e.g., a compound of the Examples, or any free acid/base form, salt form, or alternative salt form (particularly pharmaceutically acceptable salts or alternative pharmaceutically acceptable salt forms) thereof, as applicable.

In some embodiments, the compound for use in therapy is (3-ethoxy-5-(5-((((R)-2-((R)-1-(N-hydroxyformamido)propyl)heptanamido)methyl)carbamoyl)furan-2-yl)phenyl)phosphonic acid. In some embodiments, the compound for use in therapy is a pharmaceutically acceptable salt of (3-ethoxy-5-(5-((((R)-2-((R)-1-(N-hydroxyformamido)propyl)heptanamido)methyl)carbamoyl)furan-2-yl)phenyl)phosphonic acid. In some embodiments, the compound for use in therapy is a meglumine salt, Tris salt, or calcium salt of (3-ethoxy-5-(5-((((R)-2-((R)-1-(N-hydroxyformamido)propyl)heptanamido)methyl)carbamoyl)furan-2-yl)phenyl)phosphonic acid.

In some embodiments, the compound for use in therapy is (S)-2-(2-ethoxy-4-(5-((((R)-2-((R)-1-(N-hydroxyformamido)propyl)heptanamido)methyl)carbamoyl)furan-2-yl)benzamido)succinic acid. In some embodiments, the compound for use in therapy is a pharmaceutically acceptable salt of (S)-2-(2-ethoxy-4-(5-((((R)-2-((R)-1-(N-hydroxyformamido)propyl)heptanamido)methyl)carbamoyl)furan-2-yl)benzamido)succinic acid.

In some embodiments, the compound for use in therapy is (S)-2-(2-(carboxymethoxy)-4-(5-((((R)-2-((R)-1-(N-hydroxyformamido)propyl)heptanamido)methyl)carbamoyl)furan-2-yl)benzamido)succinic acid. In some embodiments, the compound for use in therapy is a pharmaceutically acceptable salt of (S)-2-(2-(carboxymethoxy)-4-(5-((((R)-2-((R)-1-(N-hydroxyformamido)propyl)heptanamido)methyl)carbamoyl)furan-2-yl)benzamido)succinic acid.

The invention also provides for the use of a compound of Formula (I), or a salt thereof, particularly a pharmaceutically acceptable salt thereof, in the manufacture of a medicament for use in the treatment of a disease associated with BMP1, TLL1 and/or TLL2 activity, for example the diseases recited herein.

In some embodiments, the invention provides for the use of a specific compound described herein, e.g., a compound of the Examples, or any free acid/base form, salt form, or alternative salt form (particularly pharmaceutically acceptable salts or alternative pharmaceutically acceptable salt forms) thereof, as applicable, in the manufacture of a medicament for use in the treatment of a disease associated with BMP1, TLL1 and/or TLL2 activity.

In some embodiments, the invention provides for the use of (3-ethoxy-5-(5-((((R)-2-((R)-1-(N-hydroxyformamido)propyl)heptanamido)methyl)carbamoyl)furan-2-yl)phenyl)phosphonic acid, in the manufacture of a medicament for use in the treatment of a disease associated with BMP1, TLL1 and/or TLL2 activity. In some embodiments, the invention provides for the use of a pharmaceutically acceptable salt of (3-ethoxy-5-(5-((((R)-2-((R)-1-(N-hydroxyformamido)propyl)heptanamido)methyl)carbamoyl)furan-2-yl)phenyl)phosphonic acid, in the manufacture of a medicament for use in the treatment of a disease associated with BMP1, TLL1 and/or TLL2 activity. In some embodiments, the invention provides for the use of a meglumine salt, Tris salt, or calcium salt of (3-ethoxy-5-(5-((((R)-2-((R)-1-(N-hydroxyformamido)propyl)heptanamido)methyl)carbamoyl)furan-2-yl)phenyl)phosphonic acid, in the manufacture of a medicament for use in the treatment of a disease associated with BMP1, TLL1 and/or TLL2 activity.

In some embodiments, the invention provides for the use of (S)-2-(2-ethoxy-4-(5-((((R)-2-((R)-1-(N-hydroxyformamido)propyl)heptanamido)methyl)carbamoyl)furan-2-yl)benzamido)succinic acid, in the manufacture of a medicament for use in the treatment of a disease associated with BMP1, TLL1 and/or TLL2 activity. In some embodiments, the invention provides for the use of a pharmaceutically acceptable salt of (S)-2-(2-ethoxy-4-(5-((((R)-2-((R)-1-(N-hydroxyformamido)propyl)heptanamido)methyl)carbamoyl)furan-2-yl)benzamido)succinic acid, in the manufacture of a medicament for use in the treatment of a disease associated with BMP1, TLL1 and/or TLL2 activity.

In some embodiments, the invention provides for the use (S)-2-(2-(carboxymethoxy)-4-(5-((((R)-2-((R)-1-(N-hydroxyformamido)propyl)heptanamido)methyl)carbamoyl)furan-2-yl)benzamido)succinic acid, in the manufacture of a medicament for use in the treatment of a disease associated with BMP1, TLL1 and/or TLL2 activity. In some embodiments, the invention provides for the use of a pharmaceutically acceptable salt of (S)-2-(2-(carboxymethoxy)-4-(5-((((R)-2-((R)-1-(N-hydroxyformamido)propyl)heptanamido)methyl)carbamoyl)furan-2-yl)benzamido) succinic acid, in the manufacture of a medicament for use in the treatment of a disease associated with BMP1, TLL1 and/or TLL2 activity.

Treatment of a disease associated with BMP1, TLL1 and/or TLL2 activity may be achieved using a compound of this invention as a monotherapy, or in dual or multiple combination therapy. For example, the compounds of this invention may be administered in combination with one or more therapeutically active agents selected from the group consisting of: anticoagulants, angiotensin-converting-enzyme (ACE) inhibitors, angiotensin II receptor blockers (ARBs), beta("β")-blockers, aldosterone antagonists, diuretics, vasodilators, cholesterol-lowering drugs (e.g., statins, fibrates, niacin, resins), statins, platelet antagonists, anti-arrhythmics, calcium channel blockers, erythropoiesis-stimulating agents (ESAs), iron, beta agonists, inhaled or oral steroids, anticholinergics, theophylline, PDE4 inhibitors, antibiotics, other antifibrotic agents, PDE5 inhibitors, immune modulators, neprilysin inhibitors, and *digitalis* preparations, e.g., any such agents as are known in the art, and combinations thereof. Particular therapeutic agents in these classes include those in the United States Pharmacopeia (USP). It will be understood that a particular active agent may fall within one or more of the foregoing classes. Such agents may be administered in therapeutically effective amounts, e.g., as is known in the art, or lesser or greater amounts than known in the art provided that the amount administered is therapeutically effective.

For example, treatment of cardiac diseases may include administration of one or more agents selected from the group: anticoagulants, ACE inhibitors, ARBs, β-blockers, aldosterone antagonists, diuretics, vasodilators (e.g. nitrates), cholesterol lowering drugs (e.g., statins, fibrates, niacin, resins), platelet antagonists, anti-arrhythmics, calcium channel blockers, neprilysin inhibitors, *digitalis* preparations, and combinations thereof. In particular embodiments, treatment of atrial fibrillation, heart failure, or hypertrophic cardiomyopathy may comprise administration of one or more such agents.

As another example, treatment of CKD may include administration of one or more agents selected from ESAs, iron, ACE inhibitors, ARBs, β-blockers, diuretics, calcium channel blockers, statins, and combinations thereof.

In other exemplary embodiments, treatment of COPD may include administration of one or more agents selected from the group: beta agonists, inhaled or oral steroids, anticholinergics, theophylline, PDE4 inhibitors, antibiotics, and combinations thereof.

For example, idiopathic pulmonary fibrosis may include administration of one or more agents selected from the group: antifibrotics, PDE5 inhibitors, immune modulators, and combinations thereof.

Particular examples of other therapeutically active agents which may be used in combination with one or more compounds of the invention, for example to treat cardiac diseases, include:

anticoagulants such as: dalteparin (FRAGMIN), danaparoid (ORGARAN), enoxaparin (LOVENOX), heparin, tinzaparin (INNOHEP), warfarin (COUMADIN), alteplase, aspirin, ardeparin, fondaparinux, lepirudin, desirudin, bivalirudin, urokinase, rivaroxaban, apixaban, dabigatran, argatroban;

ACE inhibitors such as benazepril (LOTENSIN), captopril (CAPOTEN), enalapril (VASOTEC), fosinopril (MONOPRIL), lisinopril (PRINIVIL, ZESTRIL), moexipril (UNIVASC), perindopril (ACEON), quinapril (ACCUPRIL), Ramipril (ALTACE), trandolapril (MAVIK), imidapril;

ARBs such as candesartan (ATACAND), eprosartan (TEVETEN), irbesartan (AVAPRO), losartan (COZAAR), telmisartan (MICARDIS), valsartan (DIOVAN), olmesartan, azilsartan;

beta-blockers such as acebutolol (SECTRAL), atenolol (TENORMIN), betaxolol (KERLONE), bisoprolol/hydrochlorothiazide (ZIAC), bisoprolol (ZEBETA), carteolol (CARTROL), metoprolol (LOPRESSOR, TOPROL XL), nadolol (CORGARD), propranolol (INDERAL), sotalol (BETAPACE), timolol (BLOCADREN);

aldosterone antagonists such as spironolactone, eplerenone, Canrenone (canrenoate potassium), Prorenone (prorenoate potassium), Mexrenone (mexrenoate potassium);

diuretics such as amiloride (MIDAMOR), bumetanide (BUMEX), chlorothiazide (DIURIL), chlorthalidone (HYGROTON), furosemide (LASIX), hydro-chlorothiazide (ESIDRIX, HYDRODIURIL), indapamide (LOZOL), spironolactone (ALDACTONE), metolazone, torsemide, triamterene;

vasodilators such as nitroglycerin, isosorbide dinitrate (ISORDIL), isosorbide mononitrate, nesiritide (NATRECOR), hydralazine (APRESOLINE)

cholesterol-lowering drugs, e.g., statins, such as atorvastatin, fluvastatin, lovastatin, pitavastatin, pravastatin, rosuvastatin, simvastatin, including combination products, such as ADVICOR (lovastatin/niacin extended-release), SIMCOR (simvastatin/niacin extended-release), and VYTORIN (simvastatin/ezetimibe); nicotinic acid (niacin), fibrates such as gemfibrozil (LOPID), fenofibrate (TRICOR, FIBRICOR), clofibrate;

platelet antagonists such as aspirin, ticlopidine, clopidogrel (PLAVIX), dipyridamole;

anti-arrhythmics such as quinidine, procainamide, disopyramide, lidocaine, phenytoin, mexiletine, tocainide, encainide, flecainide, propafenone, moricizine, carvedilol, propranolol, esmolol, timolol, metoprolol, atenolol, bisoprolol, amiodarone, sotalol, ibutilide, dofetilide, dronedarone, verapamil, diltiazem, adenosine, digoxin, magnesium sulfate;

calcium channel blockers, such as amlodipine (NORVASC, LOTREL), bepridil (VASCOR), diltiazem (CARDIZEM, TIAZAC), felodipine (PLENDIL), nifedipine (ADALAT, PROCARDIA), nimodipine (NIMOTOP), nisoldipine (SULAR), verapamil (CALAN, ISOPTIN, VERELAN), isradipine, nicardipine;

neprilysin inhibitors such as sacubitril, including, e.g., a combination of sacubitril and valsartan, such as LCZ696;

*digitalis* preparations such as digoxin, digitoxin.

Combination therapy includes administration of the therapeutically active agents in separate dosage forms or together in a single dosage form. Combination therapy may involve simultaneous administration or separate administration of the therapeutically active agents, which may be substantially simultaneous or substantially separate administration. Typically, combination therapy will involve administration of each agent such that therapeutically effective amounts of each agent are present in the subject's body in at least an overlapping period.

In some embodiments, combination therapy comprises administering a specific compound described herein, e.g., a compound of the Examples, or any free acid/base form, salt form, or alternative salt form (particularly pharmaceutically acceptable salts or alternative pharmaceutically acceptable salt forms) thereof, as applicable, and one or more additional therapeutically active agents.

In some embodiments, combination therapy comprises administering (3-ethoxy-5-(5-((((R)-2-((R)-1-(N-hydroxyformamido)propyl)heptanamido)methyl)carbamoyl)furan-2-yl)phenyl)phosphonic acid, and one or more additional therapeutically active agents. In some embodiments, combination therapy comprises administering a pharmaceutically acceptable salt of (3-ethoxy-5-(5-((((R)-2-((R)-1-(N-hydroxyformamido)propyl)heptanamido)methyl)carbamoyl)furan-2-yl)phenyl)phosphonic acid, and one or more additional therapeutically active agents. In some embodiments, combination therapy comprises administering a meglumine salt, Tris salt, or calcium salt of (3-ethoxy-5-(5-((((R)-2-((R)-1-(N-hydroxyformamido)propyl)heptanamido)methyl)carbamoyl)furan-2-yl)phenyl)phosphonic acid, and one or more additional therapeutically active agents.

In some embodiments, combination therapy comprises administering (S)-2-(2-ethoxy-4-(5-((((R)-2-((R)-1-(N-hydroxyformamido)propyl)heptanamido)methyl)carbamoyl)furan-2-yl)benzamido)succinic acid, and one or more additional therapeutically active agents. In some embodiments, combination therapy comprises administering a pharmaceutically acceptable salt of (S)-2-(2-ethoxy-4-(5-((((R)-2-((R)-1-(N-hydroxyformamido)propyl)heptanamido)methyl)carbamoyl)furan-2-yl)benzamido)succinic acid, and one or more additional therapeutically active agents.

In some embodiments, combination therapy comprises administering (S)-2-(2-(carboxymethoxy)-4-(5-((((R)-2-((R)-1-(N-hydroxyformamido)propyl)heptanamido)methyl)carbamoyl)furan-2-yl)benzamido)succinic acid, and one or more additional therapeutically active agents. In some embodiments, combination therapy comprises administering a pharmaceutically acceptable salt of (S)-2-(2-(carboxymethoxy)-4-(5-((((R)-2-((R)-1-(N-hydroxyformamido)propyl)heptanamido)methyl)carbamoyl)furan-2-yl)benzamido)succinic acid, and one or more additional therapeutically active agents.

Accordingly, the present invention provides a composition comprising a) a compound of formula (I) or a pharmaceutically acceptable salt thereof and b) a combination partner. As used herein, suitable combination partners include one or more other therapeutically active agents such as those described above by classification or more particularly.

The present invention further provides a method for treating a disease associated with BMP1, TLL1 and/or TLL2 activity in a subject (e.g. a human or other mammal, particularly a human) in need thereof comprising administering to said subject a therapeutically effective amount of a) a compound of formula (I) or a pharmaceutically acceptable salt thereof and b) a combination partner. The individual components of the combination may be administered either sequentially or simultaneously in separate or combined pharmaceutical formulations by any convenient route.

The invention further provides a combination of a) a compound of formula (I) or a pharmaceutically acceptable salt thereof and b) a combination partner.

In the compositions, methods and combinations of the invention comprising a combination partner, suitable combination partners include other therapeutically active agents such as described above by classification or more particularly.

In some embodiments of the compositions, methods and combinations of the inventions comprising a combination partner, the compound of formula (I) or a pharmaceutically acceptable salt thereof is a specific compound described herein, e.g., a compound of the Examples, or any free acid/base form, pharmaceutically acceptable salt form or alternative pharmaceutically acceptable salt form thereof, as applicable; in various more particular embodiments the compound of formula (I) or a pharmaceutically acceptable salt thereof is (3-ethoxy-5-(5-((((R)-2-((R)-1-(N-hydroxyformamido)propyl)heptanamido)methyl)carbamoyl)furan-2-yl)phenyl)phosphonic acid, a pharmaceutically acceptable salt thereof, or a meglumine salt, Tris salt, or calcium salt thereof; in other various more particular embodiments the compound of formula (I) or a pharmaceutically acceptable salt thereof is (S)-2-(2-ethoxy-4-(5-((((R)-2-((R)-1-(N-hydroxyformamido)propyl)heptanamido)methyl)carbamoyl)furan-2-yl)benzamido)succinic acid, or a pharmaceutically acceptable salt thereof; in other various more particular embodiments the compound of formula (I) or a pharmaceutically acceptable salt thereof is (S)-2-(2-(carboxymethoxy)-4-(5-((((R)-2-((R)-1-(N-hydroxyformamido)propyl)heptanamido)methyl)carbamoyl)furan-2-yl)benzamido) succinic acid, or a pharmaceutically acceptable salt thereof.

A "therapeutically effective amount" is intended to mean that amount of a compound that, when administered to a subject in need of such treatment, is sufficient to effect treatment, as defined herein. Thus, for example, a therapeutically effective amount of a compound of the invention, e.g. a compound of Formula (I) or a pharmaceutically acceptable salt thereof, is a quantity of such agent that, when administered to a subject (e.g., human) in need thereof, is sufficient to modulate or inhibit the activity of BMP1, TLL1 and/or TLL2 such that a disease condition which is mediated or inhibited by that activity is reduced, alleviated or prevented. The amount of a given compound that will correspond to such an amount will vary depending upon factors such as the particular compound (e.g., the potency (pIC$_{50}$) and the biological half-life of the particular compound), disease condition and its severity, and the identity (e.g., age, size and weight) of the subject in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the subject in need of treatment (e.g., weight), the particular compound and its properties (e.g., pharmaceutical characteristics), disease and its severity and the specific composition and method being used, but can nevertheless be determined by one of skill in the art.

In some embodiments, 0.1 mg to 1000 mg (e.g., 0.1-500 mg, or 0.1-100 mg) of a compound of the invention, particularly a compound of Formula (I) or a pharmaceutically acceptable salt thereof, is administered at a frequency of twice a day, once a day, once a week, or frequencies therebetween. In some embodiments, a compound of the invention, particularly a compound of Formula (I) or a pharmaceutically acceptable salt thereof, is administered sub-cutaneously in an amount of less than 100 mg per dose (e.g., 0.1-<100 mg per dose).

"Treat", "treating" or "treatment" is intended to mean at least the mitigation of a disease in a subject. The methods of treatment for mitigation of a disease include the use of the compounds in this invention in any conventionally acceptable manner, for example for prevention, retardation, prophylaxis, therapy, improvement or cure of a disease. Thus, treatment may involve at least the mitigation of one or more symptoms of a disease. Specific diseases that may be particularly susceptible to treatment using a compound of this invention include those described herein.

The compounds of the invention may be administered by any suitable route of administration, including both systemic administration and topical administration. Systemic administration includes oral administration, parenteral administration, transdermal administration, rectal administration, and administration by inhalation. Oral administration includes enteral (digestive tract) and buccal or sublingual administration. Parenteral administration refers to routes of administration other than enteral, transdermal, or by inhalation, and is typically by injection or infusion into tissue or blood. Parenteral administration includes intravenous, intramuscular, subcutaneous, intradermal, and transdermal implant injection or infusion. Inhalation refers to administration into the subject's lungs whether inhaled through the mouth or through the nasal passages. Topical administration includes application to the skin.

For use in therapy, the compounds of the invention will be normally, but not necessarily, formulated into a pharmaceutical composition prior to administration to a subject. Accordingly, the invention also is directed to pharmaceutical compositions comprising a compound of the invention, particularly a compound of Formula (I) or a pharmaceutically acceptable salt thereof, and one or more pharmaceutically acceptable excipients.

The pharmaceutical compositions of the invention may be prepared and packaged in bulk form wherein an effective amount of a compound of the invention can be extracted and then given to the subject such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), or a salt, particularly a pharmaceutically acceptable salt, thereof). When prepared in unit dosage form, the pharmaceutical compositions may contain from 0.1 mg to 1000 mg (e.g., 0.1-500 mg, or 0.1-100 mg) of a compound of this invention.

The pharmaceutical composition may include one or more compounds of the invention and/or one or more pharmaceutically acceptable excipients. The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds, e.g., the therapeutically active agents described above by classification or more particularly.

In some embodiments, the pharmaceutical composition comprises a) 0.01-100 mg of a compound of formula (I) or a pharmaceutically acceptable salt thereof and b) 0.001-900 mg of one or more pharmaceutically acceptable excipients.

In some embodiments, the pharmaceutical composition comprises a) 0.01-100 mg/mL of a compound of formula (I) or a pharmaceutically acceptable salt thereof and b) 0.001-900 mg/mL of one or more pharmaceutically acceptable excipients.

In some embodiments, the pharmaceutical composition comprises a specific compound described herein, e.g., a compound of the Examples, or any free acid/base form, pharmaceutically acceptable salt form, or alternative pharmaceutically acceptable salt form thereof, as applicable.

In some embodiments, the pharmaceutical composition comprises (3-ethoxy-5-(5-((((R)-2-((R)-1-(N-hydroxyformamido)propyl)heptanamido)methyl)carbamoyl)furan-2-yl)phenyl)phosphonic acid, and one or more pharmaceutically acceptable excipients. In some embodiments, the pharmaceutical composition comprises a pharmaceutically acceptable salt of (3-ethoxy-5-(5-((((R)-2-((R)-1-(N-hydroxyformamido)propyl)heptanamido)methyl)carbamoyl) furan-2-yl)phenyl)phosphonic acid, and one or more pharmaceutically acceptable excipients. In some embodiments, the pharmaceutical composition comprises a meglumine salt, Tris salt, or calcium salt of (3-ethoxy-5-(5-((((R)-2-((R)-1-(N-hydroxyformamido)propyl)heptanamido)methyl) carbamoyl)furan-2-yl)phenyl)phosphonic acid, and one or more pharmaceutically acceptable excipients.

In some embodiments, the pharmaceutical composition comprises (S)-2-(2-ethoxy-4-(5-((((R)-2-((R)-1-(N-hydroxyformamido)propyl)heptanamido)methyl)carbamoyl) furan-2-yl)benzamido)succinic acid, and one or more pharmaceutically acceptable excipients. In some embodiments, the pharmaceutical composition comprises a pharmaceutically acceptable salt of (S)-2-(2-ethoxy-4-(5-((((R)-2-((R)-1-(N-hydroxyformamido)propyl)heptanamido)methyl)carbamoyl)furan-2-yl)benzamido)succinic acid, and one or more pharmaceutically acceptable excipients.

In some embodiments, the pharmaceutical composition comprises (S)-2-(2-(carboxymethoxy)-4-(5-((((R)-2-((R)-1-(N-hydroxyformamido)propyl)heptanamido)methyl)carbamoyl)furan-2-yl)benzamido)succinic acid, and one or more pharmaceutically acceptable excipients. In some embodiments, the pharmaceutical composition comprises a pharmaceutically acceptable salt of (S)-2-(2-(carboxymethoxy)-4-(5-((((R)-2-((R)-1-(N-hydroxyformamido) propyl)heptanamido)methyl)carbamoyl)furan-2-yl)benzamido)succinic acid, and one or more pharmaceutically acceptable excipients.

As used herein, "pharmaceutically acceptable excipient" means a material, composition or vehicle other than a pharmaceutical active ingredient(s) intended for treating a disease (e.g., a compound of the invention). Pharmaceutically acceptable excipients are involved in providing a property or function useful to a pharmaceutical composition, for example an excipient may be involved in modifying physical, sensory, stability, or pharmaco-kinetic properties of the composition, for example in giving form or consistency to the composition, in bulking up the active ingredient (e.g. for convenient and accurate dispensation), in enhancing therapy (e.g. facilitating drug absorption or solubility, or other pharmacokinetic properties), in the manufacturing process (e.g. as a handling or processing aid), in stabilizing the composition, or in enhancing subject compliance (e.g., enhancing palatability or appearance of the composition). Each excipient must be compatible with the other ingredients of the pharmaceutical composition when commingled such that interactions which would substantially reduce the efficacy of the compound of the invention (or any other active ingredient, if present) when administered to a subject and interactions which would result in pharmaceutical compositions that are sufficiently high purity to render it pharmaceutically acceptable.

The compounds of the invention and the pharmaceutically acceptable excipient or excipients will typically be formulated into a dosage form adapted for administration to the subject by the desired route of administration. Conventional dosage forms include those adapted for (1) oral administration such as tablets, capsules, caplets, pills, lozenges, troches, powders, syrups, elixirs, suspensions, solutions, emulsions, sachets, and cachets; (2) parenteral administration such as sterile solutions, suspensions, lyophiles, microparticles, nanocarriers, implants, preformed implants and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, gels, dermal patches, and transdermal patches or sprays.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to: facilitate the production of uniform dosage forms, to facilitate the production of stable dosage forms, to facilitate the carrying or transporting the compound or compounds of the invention once administered to the subject from one organ, or portion of the body, to another organ, or portion of the body, and/or to enhance subject compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, carriers, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press), including current and past editions.

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler, and optionally a binder, disintegrant, and/or lubricant. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). Suitable disintegrants include crospovidone, sodium starch glycolate, croscarmelose, alginic acid, and sodium carboxymethyl cellulose. Suitable lubricants include stearic acid, magnesium stearate, calcium stearate, and talc.

In another aspect, the invention is directed to a parenteral formulation, e.g., in-situ gels, microspheres, nanospheres, nanosuspensions, or lyophilized products to control the release of a compound following subcutaneous administration, comprising a compound of the invention, a surfactant and/or a polymeric carrier and/or a solubilising excipient and/or an excipient to control osmolality. Suitable surfactants include polysorbates, polyvinyl alcohol, polyvinyl pyrrolidone and combinations thereof. Suitable polymeric carriers include polyethylene glycol, polymethacrylate, ethylene vinyl acetate copolymer, polyglactin, polyoxyethylene fatty acid esters, poly(lactic-co-glycolic acid), poly (epsilon-caprolactone), poly(p-dioxanone), poly(anhydride esters) and combinations thereof. Suitable solubilising excipients include n-methyl pyrollidone, polyethoxylated castor oil (e.g., CREMOPHOR such as CREMOPHOR EL), polysorbates, Solutol® (Macrogol 15 Hydroxystearate Ph. Eur; Polyoxyl 15 Hydroxystearate USP), ethanol and combinations thereof. Suitable excipients to control osmolality (and in the case of lyophiles, to bulk the lyophilized material) include mannitol, sucrose, glycine, and polyvinyl pyrrolidone.

In-situ gels can be prepared by solubilising a compound of the invention in solvent phase and water-insoluble polymeric carrier(s). The solution is then sterilized, e.g., by gamma irradiation.

Nanosuspensions can be prepared by combining a compound of the invention, a surfactant, a polymeric carrier and an excipient to control osmolality in aqueous phase, then bead milling or microfluidising the combination in aqueous phase to deliver particles of the compound between 100 nm to less than 1 µm. The nanosuspension is sterilized, e.g., by utilizing terminal heat sterilization or gamma irradiation techniques.

Microspheres and nanospheres can be prepared by various methods known in the art including water/oil/water emulsion methods, solvent/oil/water emulsion methods, oil/water emulsion methods, organic phase separation or melt extrusion/cryomilling techniques which involve inclusion of the compound of the invention and polymer(s) to control drug delivery. The particles are delivered to less than 100 µm for microspheres and between 100 nm to less than 1 µm for nanospheres. The microspheres and nanospheres can go through further processing, including lyophilization, and require sterilization, e.g., through gamma irradiation.

A lyophilized product may suitably include a compound of the invention in a concentration of from 0.01-100 mg/mL, a surfactant, a polymeric carrier, and a solubilizing excipient. General conditions to provide a lyophilized product involve forming a solution of the product ingredients, reducing the solution below the glass transition, providing differential pressure to pull off aqueous and/or solvent phase, and slowly increasing temperature to form a lyophilized cake.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the following experimental descriptions, the following abbreviations may be used:

| Abbreviation | Meaning |
| --- | --- |
| AcOH | acetic acid |
| aq. | aqueous |
| $BBr_3$ | boron tribromide |
| $BCl_3$ | boron trichloride |
| $BH_3$ | borane |
| Bn | benzyl |
| brine | saturated aqueous sodium chloride |
| BuLi | butyl lithium |
| CDI | carbonyldiimidazole |
| $CH_2Cl_2$ | methylene chloride |
| $CH_3CN$ | acetonitrile |
| $COCl_2$ | oxalyl chloride |
| DCC | dicyclohexylcarbodiimide |
| DCM | methylene chloride |
| DEAD | Diethyl azodicarboxylate |
| DEAP | diethyl aminopyridine |
| DIAD | diisopropyl azodicarboxylate |
| DIPEA | N,N-diisopropylethylamine |
| DMAP | 4-dimethylaminopyridine |
| DMF | N,N-dimethylformamide |
| DME | dimethoxyethane |
| DMSO | dimethylsulfoxide |
| EDC | 1-[3-(dimethylamino)propyl]-3-ethylcarbodiimide hydrochloride |
| Et | ethyl |
| $Et_3N$ (also TEA) | triethylamine |
| $Et_2O$ | diethyl ether |
| EtOAc | ethyl acetate |
| EtOH | ethanol |
| Fmoc | fluorenylmethyloxycarbonyl |
| h | hour(s) |
| $H_2$ | hydrogen |
| $H_2O_2$ | hydrogen peroxide |
| $H_2O$ | water |
| $H_2SO_4$ | sulfuric acid |
| HATU | (O-(7-azabenzotriazol-1-yl)-N,N,N',N'-tetramethyluronium hexafluorophosphate) |
| HBTU | 2-(1H-benzo[d][1,2,3]triazol-1-yl)-1,1,3,3-tetramethylisouronium hexafluorophosphate(V) |
| HCl | hydrochloric acid |
| $HCO_2H$ | formic acid |
| HOBt | 1-hydroxybenzotriazole |
| HPLC | high performance liquid chromatography |
| $I_2$ | Iodine |
| JLR | jacketed lab reactor |
| $K_2CO_3$ | potassium carbonate |
| $KHSO_4$ | potassium hydrogen sulfate |
| KOAc | potassium acetate |
| LAH | Lithium aluminum hydride |
| LCMS | liquid chromatography-mass spectroscopy |
| LDA | lithium diisopropyl amide |
| LiOH | lithium hydroxide |
| LHMDS | lithium bis(trimethylsilyl)amide |
| Me | methyl |
| MeOH | methanol |
| $MgBr_2$ | magnesium bromide |
| $MgSO_4$ | magnesium sulfate |
| min | minute(s) |
| MS | mass spectrum |
| MTBE | Methyl tert-butyl ether |
| µw | microwave |
| $N_2$ | nitrogen |
| $Na(CN)BH_3$ | sodium cyanoborohydride |
| NaCl | sodium chloride |
| $Na_2CO_3$ | sodium carbonate |
| $NaHCO_3$ | sodium bicarbonate |
| NaHMDS | sodium bis(trimethylsilyl)amide |
| $NaHSO_3$ | sodium bisulfite |
| NaH | sodium hydride |
| NaI | sodium iodide |
| NaOH | sodium hydroxide |
| $Na_2SO_3$ | sodium sulfite |
| $Na_2SO_4$ | sodium sulfate |
| $NH_4Cl$ | ammonium chloride |
| $HCO_2 \cdot NH_4$ | ammonium formate |
| $NH_4OH$ | ammonium hydroxide |
| NMO | 4-methylmorpholine N-oxide |
| NMP | N-methyl-2-pyrrolidone |
| Pd/C | palladium on carbon |
| $PdCl_2(dbpf)$ | 1,1'-bis(di-tert-butylphosphino)ferrocene dichloropalladium |
| $Pd(dppf)Cl_2$/ $PdCl_2(dppf)$ | [1,1'-bis(diphenylphosphino)ferrocene] dichloropalladium(II) |
| $Pd(Ph_3)_4$ | tetrakis(triphenylphosphine)palladium(0) |
| $Pd(OAc)_2$ | palladium acetate |
| $Pd(OH)_2$ | palladium hydroxide |
| Ph | phenyl |
| PL $HCO_3$ MP | macroporus polystyrene supported carbonate |
| $POCl_3$ | phosphoryl chloride |
| PTFE | polytetrafluoroethylene |
| rt | room temperature |
| sat. | saturated |
| SFC | supercritical fluid chromatography |
| Si | silica |
| SPE | solid phase extraction |
| T3P ® | propylphosphonic anhydride |
| TBAF | tetrabutylammonium fluoride |
| TBAI | tetrabutylammonium iodide |
| TBDMSCl | tert-butyldimethylsilyl chloride |
| TBME | tert-butylmethyl ether |
| TFA | trifluoroacetic acid |
| THF | tetrahydrofuran |
| $TiCl_4$ | titanium tetrachloride |
| TMS—Br | trimethylsilyl bromide |
| TMS—Cl | trimethylsilyl chloride |
| TMS—OTf | trimethylsilyl triflate |
| tR | retention time |
| UPLC | ultra performance liquid chromatography |

Intermediate 1: (R)-2-((N-(benzyloxy)formamido)methyl)heptanoic acid

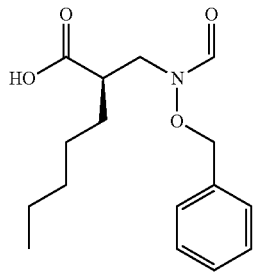 [SMILES: CCCCC[C@H](CN(C=O)OCc1ccccc1)C(=O)O]

Step 1: formaldehyde O-benzyl oxime

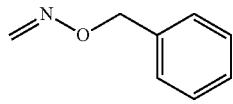

A suspension of O-benzylhydroxylamine, hydrochloride (308 g, 1930 mmol) in t-butylmethyl ether (1800 ml) was added to a solution of sodium hydroxide (93 g, 2316 mmol) in water (570 ml) via an addition funnel. The funnel was rinsed with water (15 ml) and the reaction stirred for 10 minutes. Formaldehyde (37% wt in water, 150 ml, 2015 mmol) was then added via an addition funnel slowly over ~20 minutes. The funnel was rinsed with water (15 ml) and the reaction mixture was stirred at 25° C. for 3 hours. The layers were then separated and the organic phase washed with 0.2 N HCl (480 ml), 5% NaHCO$_3$ solution (300 ml), and 10% brine solution (480 ml). The organics were separated and concentrated to give the title compound as a colorless oil (247 g, 90% yield). MS (m/z) 136.1 (M+H$^+$)

Step 2: 2-(((benzyloxy)amino)methyl)heptanoic acid

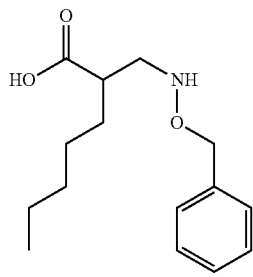 [SMILES: CCCCCC(CNOCc1ccccc1)C(=O)O]

Acetonitrile (1250 ml) and sodium iodide (931 g, 6213 mmol) were charged to a 6 l reactor vessel under nitrogen at room temperature. The mixture was stirred vigorously for 10 minutes and chlorotrimethylsilane (790 ml, 6224 mmol) was then added. After stirring at room temperature for 15 minutes, the reaction was cooled to 15° C. Triethylamine (870 ml, 6242 mmol) was added. Heptanoic acid (264 ml, 1864 mmol) was then added slowly, maintaining the temperature below 35° C. The addition funnel was rinsed with CH$_3$CN (50 ml). The mixture was stirred at room temperature for 15 minutes and formaldehyde O-benzyl oxime (247 g, 1827 mmol) was added. The addition funnel was rinsed with CH$_3$CN (120 ml). The reaction was stirred at room temperature for 17 hours. The reaction mixture was then cooled to 12° C. and quenched with a freshly prepared solution of sodium thiosulfate (491 g, 3107 mmol) in water (2250 ml) maintaining the temperature below 30° C. The reaction was stirred for 20 minutes and the pH of the reaction was then adjusted with 6N HCl (330 ml, 1980 mmol) to pH ~4. After stirring for 10 minutes EtOAc (500 ml) was added. The mixture was stirred for 5 minutes and then the layers were separated. The aqueous layer was back extracted with EtOAc (1750 ml). The combined organic solutions were washed with water (2×1250 ml) and 5% brine (1250 ml) and then separated and concentrated to give 620 g of the crude product as a yellow oil. The crude residue was preabsorbed on silica and purified by flash chromatography (ISCO Torrent, 1.5 kg RediSep column, 1-5% CH$_2$Cl$_2$/MeOH (6 runs)) to give three batches of the title compound as a colorless oil (176 g, 35% yield), as a white solid (206 g, 41% yield) and as a colorless oil (8 g, 2% yield). MS (m/z) 266.1 (M+H$^+$)

Step 3: 1-(benzyloxy)-3-pentylazetidin-2-one

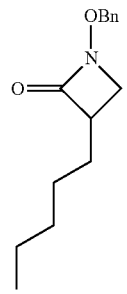 [SMILES: CCCCCC1CN(OCc2ccccc2)C1=O]

A 6 l reactor was charged with toluene (1750 ml) and 2,6-dimethylpyridine (232 ml, 1990 mmol) under a stream of nitrogen. Phosphoryl trichloride (99 ml, 1061 mmol) was added and the mixture was heated to 50° C. A solution of 2-(((benzyloxy)amino)methyl)heptanoic acid (176 g, 663 mmol) in toluene (1050 ml) was added over 40 minutes while maintaining the temperature below 55° C. The addition funnel was rinsed with toluene (100 ml). The reaction mixture was then stirred at 50° C. for 1 hour. The reaction mixture was then cooled to 20° C. and then drained. The reactor was rinsed with toluene (400 ml) and combined with the reaction mixture. The reactor was then charged with water (1600 ml) and Na$_2$CO$_3$ (239 g, 2255 mmol). The reaction mixture was slowly added to the Na$_2$CO$_3$ solution while maintaining the temperature below 35° C. The addition vessel was rinsed with toluene (400 ml). The biphasic mixture was stirred at 35° C. for 30 minutes. The layers were left to separate, and the aqueous layer was drained. The organic phase was held at 3° C. overnight and warmed up to 35° C. the next morning before proceeding with the workup. The organic phase was washed sequentially with a mixed solution of concentrated HCl (123 ml) and 10% brine (1400 ml) to prevent emulsion formation, 10% brine solution (900 ml), 5% NaHCO$_3$ solution (900 ml) stirring for 10 minutes and then 10% brine solution (900 ml). The organic phase was separated and concentrated to give the crude product as a yellow oil. The crude residue was preabsorbed on silica and purified by flash chromatography (ISCO Torrent 1.5 kg RediSep column, CH$_2$Cl$_2$/MeOH 0-5%) to afford the title compound as a yellow oil. (87 g, 52% yield). MS (m/z) 248.1 (M+H$^+$)

Step 4: (R)-1-(benzyloxy)-3-pentylazetidin-2-one

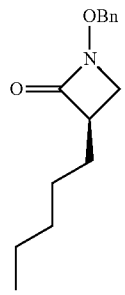 [SMILES: CCCCC[C@@H]1CN(OCc2ccccc2)C1=O]

1-(benzyloxy)-3-pentylazetidin-2-one (220 g, 889 mmol) was subjected to chiral separation utilizing a SFC-70 Thar prep system. (Chiralpak AS-H column at room temperature, 15% isopropanol, 50 g/min, 5 minute run time at a concentration of 250 mg/ml). Concentration of the appropriate fractions yielded two batches of the title compound (13.5 g, 6.01% yield, >96% ee) and (87 g, 38.8% yield, 96% ee). MS (m/z) 248.1 (M+H$^+$)

Step 5: (R)-2-(((benzyloxy)amino)methyl)heptanoic acid

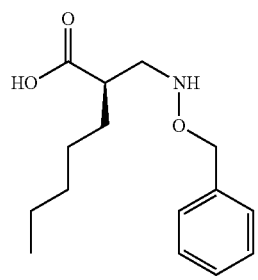 [SMILES: CCCCC[C@H](CNOCc1ccccc1)C(=O)O]

To a suspension of (R)-1-(benzyloxy)-3-pentylazetidin-2-one (10 g, 40.4 mmol) in tetrahydrofuran (108 ml) and water (53.9 ml) was added a freshly prepared solution of lithium hydroxide (4.84 g, 202 mmol) in water (53.9 ml) in a dropwise fashion. The reaction was then stirred at room temperature for 18 hours. The reaction was then cooled to −5° C. and 1 M HCl was added dropwise until pH 5 was obtained. The reaction was extracted twice with ethyl acetate and the combined organics washed with brine, dried and concentrated to give the title compound as a thick clear oil which was used without further purification or characterization.

Step 6: (R)-2-((N-(benzyloxy)formamido)methyl)heptanoic acid

Formic acid (4.65 ml, 121 mmol) was added dropwise to a solution of CDI (19.67 g, 121 mmol) in dichloromethane (79 ml) and stirred at room temperature for 45 minutes. A solution of (R)-2-(((benzyloxy)amino)methyl)heptanoic acid (10.73 g, 40.4 mmol) in dichloromethane (79 ml) was then added and the reaction stirred at room temperature for 2 hours. The reaction was partitioned with 1 M HCl and the organic was collected via hydrophobic frit and concentrated to give a thick yellow oil which was dissolved in the minimum amount of DCM and passed through a Si plug (250 g Silica, DCM, 50:50 DCM: ether and ether in 250 ml fractions). Concentration of the cleanest fractions yielded the title compound as a clear oil (3.65 g, 97% ee). Concentration of additional fractions yielded 8 g of an orange oil which was purified by flash chromatography (ISCO Companion, 120 g, 15-100% ethyl acetate/hexanes) to give additional batches of the title compound as an orange oil (2.38 g, 97% ee and 1.38 g, 97% ee). MS (m/z) 294.1 (M+H$^+$)

Intermediate 2: (R)-3-(N-(benzyloxy)formamido)-2-(cyclopentylmethyl)propanoic acid

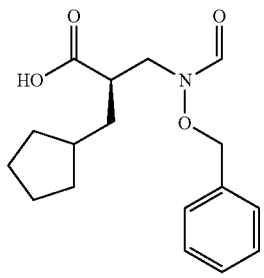 [SMILES: O=CN(C[C@@H](CC1CCCC1)C(=O)O)OCc1ccccc1]

Intermediate 2 may be prepared according to procedures detailed for Intermediate A in WO2009061879, page 55.

Intermediate 3: 3-(N-(benzyloxy)formamido)propanoic acid

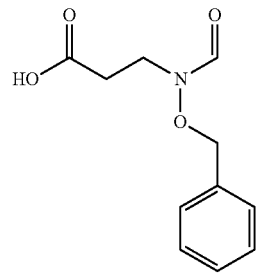 [SMILES: O=CN(CCC(=O)O)OCc1ccccc1]

Step 1: ethyl 3-((benzyloxy)amino)propanoate

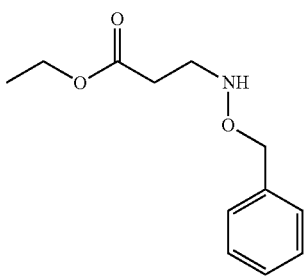 [SMILES: CCOC(=O)CCNOCc1ccccc1]

A solution of ethyl acrylate (13.67 ml, 125 mmol) in ethanol (150 ml) was cooled to −78° C. A solution of O-benzylhydroxylamine, hydrochloride (10.0 g, 62.7 mmol)

and triethylamine (10.48 ml, 75 mmol) in ethanol (150 ml) was added dropwise via addition funnel. The reaction mixture was allowed to warm to room temperature and stirred for 24 hours. The reaction was then concentrated and the residue purified via flash chromatography (ISCO Combi-flash Rf, 330 g column, 0-100% ethyl acetate/hexanes) to give two batches of the title compound (4.67 g, 33% yield) and (6.27 g, 45% yield). MS (m/z) 224.1 (M+H$^+$).

Step 2: 3-((benzyloxy)amino)propanoic acid

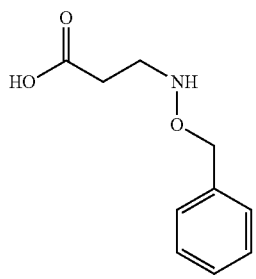 [SMILES: O=C(O)CCNOCc1ccccc1]

Ethyl 3-((benzyloxy)amino)propanoate (6.27 g, 28.1 mmol, 44.8% yield) was dissolved in ethanol (100 ml) and water (25 ml) and lithium hydroxide (3.00 g, 125 mmol) was added. The reaction mixture was stirred at room temperature for 2 hours. The ethanol was removed in vacuo and the mixture extracted with DCM. The aqueous was adjusted to ~pH 3 via addition of 6 N HCl and extracted with EtOAc (2×50 ml). The ethyl acetate layer was passed through a phase separator, concentrated and dried under vacuum over 4 days to give the title compound (609 mg). The aqueous layer was concentrated and combined with the aqueous layer isolated from a second hydrolysis reaction (4.67 g scale, conducted utilizing the same procedure) and extracted with ethyl acetate (4×50 ml). The ethyl acetate layer was passed through a phase separator, concentrated and dried under house vacuum overnight to give the title compound (6.91 g). The combined batches of the title compound were then triturated with ether/DCM. The solid was washed with ether, collected and dried under vacuum overnight to give the title compound (720 mg). The filtrate and residual solid from the trituration were recombined to give an additional batch of the title compound as a yellow oil (5.17 g, 70% purity) which was used without further purification. MS (m/z) 196.0 (M+H$^+$).

Step 3: 3-(N-(benzyloxy)formamido)propanoic acid

To a solution of CDI (1.50 g mg, 9.23 mmol) in dichloromethane (20 ml) was added formic acid (0.35 ml, 9.23 mmol) dropwise. The reaction mixture was stirred at room temperature for 1 hour. A solution of 3-((benzyloxy)amino) propanoic acid (721 mg, 3.69 mmol) in dichloromethane (5 ml) was then added dropwise. The reaction mixture was stirred at room temperature for 3 hours. The reaction was then cooled in a water bath and 1 N HCl (15 ml) added. The layers were separated and the organic layer washed with water, collected via hydrophobic frit and concentrated to give the title compound (570 mg, 69% yield) which was dried under vacuum overnight and used without further purification. MS (m/z) 224.0 (M+H$^+$).

Intermediate 4: 4-phenylbutanoyl chloride

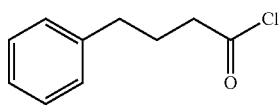 [SMILES: O=C(Cl)CCCc1ccccc1]

Oxalyl chloride (6 ml, 68.5 mmol) was added to a solution of 4-phenylbutanoic acid (7 g, 42.6 mmol) in dichloromethane (207 ml) and a few drops of DMF at 0° C. The reaction was allowed to warm to room temperature overnight then concentrated to give the title compound as a yellow oil which was used without further purification or characterization.

INTERMEDIATE 5 was prepared from 5-phenylpentanoic acid by methods analogous to that described for Intermediate 4.

| # | Name | Structure | MS (m/z) (M + H$^+$) |
|---|------|-----------|----------------------|
| 5 | 5-phenyl-pentanoyl chloride | 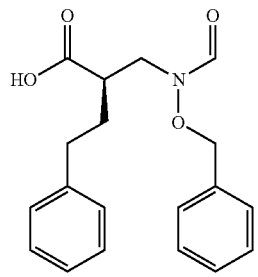 [SMILES: O=CN(C[C@@H](CCc1ccccc1)C(=O)O)OCc1ccccc1] | used without further purification or characterization |

Intermediate 6: (R)-2-((N-(benzyloxy)formamido) methyl)-4-phenylbutanoic acid

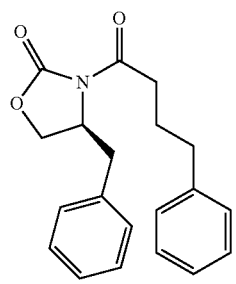 [SMILES: O=C(CCCc1ccccc1)N1C(=O)OC[C@@H]1Cc1ccccc1]

Step 1: (S)-4-benzyl-3-(4-phenylbutanoyl)oxazolidin-2-one

N-butyllithium (2.7 M in heptanes, 16.73 ml, 45.2 mmol) was added dropwise to a solution of (S)-4-benzyloxazolidin-2-one (7.28 g, 41.1 mmol) in tetrahydrofuran (91 ml) at −78° C. under N$_2$. After stirring for 30 minutes at −78° C., 4-phenylbutanoyl chloride (7.5 g, 41.1 mmol) was added and the reaction was stirred at −78° C. for 1.5 hours and then at 0° C. for 2 hours. Aqueous NH₄Cl (150 ml) was then added and the mixture extracted with EtOAc (2×). The combined organic layers were dried over Na₂SO₄ and concentrated to give the title compound as white crystals (13.15 g, 99% yield). MS (m/z) 324.2 (M+H⁺).

Step 2: (S)-4-benzyl-3-((R)-2-((benzyloxy)methyl)-4-phenylbutanoyl)oxazolidin-2-one

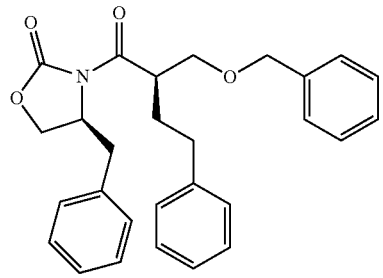 [SMILES: O=C1OC[C@H](Cc2ccccc2)N1C(=O)[C@H](CCc1ccccc1)COCc1ccccc1]

DIPEA (8.28 ml, 47.4 mmol) was added dropwise to a solution of (S)-4-benzyl-3-(4-phenylbutanoyl)oxazolidin-2-one (13.94 g, 43.1 mmol) and TiCl₄ (4.99 ml, 45.3 mmol) in dichloromethane (122 ml) at 0° C. After stirring at 0° C. for 1.5 hours ((chloromethoxy)methyl)benzene (11.99 ml, 86 mmol) was added and the reaction was stirred at 0° C. for 3 hours. The reaction was then quenched with H₂O (150 ml), extracted with DCM (2×) and the organics dried over MgSO₄ and concentrated. The residue was purified via flash chromatography (ISCO, 320 g column, hexanes: 5 minutes; 0-10% hexanes/EtOAc: 15 minutes; 10-30%: EtOAc/DCM: 5 minutes) to give the title compound as a clear oil (14.65 g, 77% yield). MS (m/z) 444.2 (M+H⁺).

Step 3: (R)-2-((benzyloxy)methyl)-4-phenylbutanoic acid

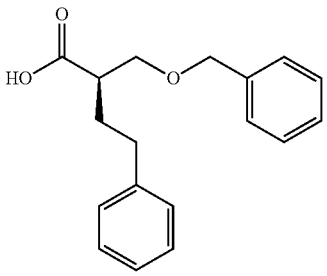 [SMILES: O=C(O)[C@H](CCc1ccccc1)COCc1ccccc1]

A mixture of (S)-4-benzyl-3-((R)-2-((benzyloxy)methyl)-4-phenylbutanoyl)oxazolidin-2-one (14.65 g, 33.0 mmol) in tetrahydrofuran (78 ml) and water (25.9 ml) was treated with hydrogen peroxide (30% in H₂O, 27.0 ml, 264 mmol) followed by lithium hydroxide (1.58 g, 66.1 mmol) at 0° C. The reaction was allowed to warm to room temperature overnight. The THF was removed under reduced pressure and the residue was extracted with DCM. The DCM layer was washed with H₂O (2×). The combined aqueous layers were then acidified to pH 3 via addition of with 6N HCl and then extracted with EtOAc (4×). The combined ethyl acetate extracts were dried over Na₂SO₄ and concentrated to give the title compound as a clear oil (9.5 g). MS (m/z) 267.1 (M−17⁺).

Step 4: (R)-2-(hydroxymethyl)-4-phenylbutanoic acid

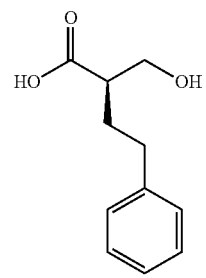 [SMILES: O=C(O)[C@@H](CO)CCc1ccccc1]

A solution of (R)-2-((benzyloxy)methyl)-4-phenylbutanoic acid (9.5 g, 33.4 mmol) in ethanol (130 ml) was added to Pd/C (2.94 g, 2.76 mmol) under N₂ and the reaction was subjected to hydrogenation in a Parr shaker at ~35 psi at room temperature overnight. The reaction was then filtered through a pad of Celite® and the filtrate concentrated to give the title compound as a clear oil (6.65 g). MS (m/z) 177.1 (M−17⁺).

Step 5: (R)—N-(benzyloxy)-2-(hydroxymethyl)-4-phenylbutanamide

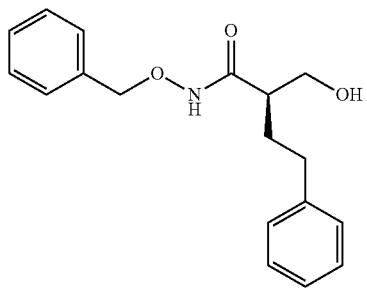 [SMILES: O=C(NOCc1ccccc1)[C@@H](CO)CCc1ccccc1]

EDC (6.56 g, 34.2 mmol) was added to a solution of (R)-2-(hydroxymethyl)-4-phenylbutanoic acid (6.65 g, 34.2 mmol), O-benzylhydroxylamine hydrochloride (5.46 g, 34.2 mmol), and DMAP (8.37 g, 68.5 mmol) in dichloromethane (143 ml) at 0° C. and the reaction was allowed to warm to room temperature overnight. 1 N HCl (55 ml) was then added and the reaction was extracted with DCM (2×) dried over Na₂SO₄ and concentrated to give the title compound as a white solid (9.52 g, 93% yield). MS (m/z) 300.1 (M+H⁺).

Step 6: (R)-1-(benzyloxy)-3-phenethylazetidin-2-one

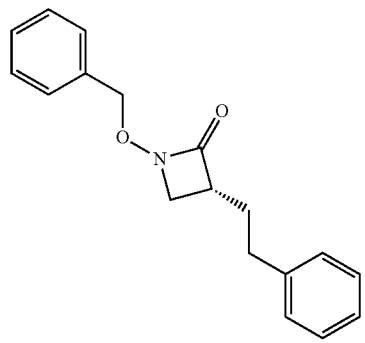 [SMILES: O=C1[C@H](CCc2ccccc2)CN1OCc1ccccc1]

DIAD (7.42 ml, 38.2 mmol) was added to a solution of (R)—N-(benzyloxy)-2-(hydroxymethyl)-4-phenylbutanamide (9.52 g, 31.8 mmol) and triphenylphosphine (10.01 g, 38.2 mmol) in tetrahydrofuran (200 ml) at 0° C. and the reaction was allowed to warm to room temperature over 3.5 hours. Water (100 ml) was then added and the reaction was extracted with DCM (2×). The organics were separated, dried over MgSO$_4$ and concentrated. The residue was triturated with Et$_2$O (3×) and the solid removed by filtration. The filtrate was concentrated and purified via flash chromatography (ISCO, 220 g column, 0-20% EtOAc/hexanes: 15 minutes, 20% EtOAc/hexanes: 10 minutes) to give the title compound as a clear oil (5.06 g, 57% yield). MS (m/z) 282.1 (M+H$^+$).

Step 7: (R)-2-(((benzyloxy)amino)methyl)-4-phenylbutanoic acid

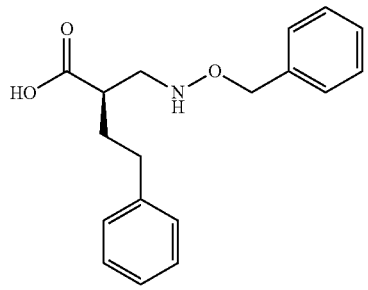 [SMILES: O=C(O)[C@H](CCc1ccccc1)CNOCc1ccccc1]

(R)-1-(benzyloxy)-3-phenethylazetidin-2-one (5.06 g, 17.97 mmol) in tetrahydrofuran (54 ml), methanol (18 ml) and water (18 ml) was treated with lithium hydroxide (4.30 g, 180 mmol) at room temperature for 1.5 days. The volatiles were removed under reduced pressure and the residue was acidified to ~pH 5-6 via addition of 6 N HCl. The mixture was extracted with EtOAc (2×), dried over Na$_2$SO$_4$ and concentrated to give the title compound as a clear oil (5.7 g). MS (m/z) 300.1 (M+H$^+$).

Step 8: (R)-2-((N-(benzyloxy)formamido)methyl)-4-phenylbutanoic acid

Formic acid (1.5 ml, 39.1 mmol) was added dropwise to a solution of CDI (6.3 g, 38.9 mmol) in dichloromethane (320 ml) and the reaction was stirred for 40 minutes before a solution of (R)-2-(((benzyloxy)amino)methyl)-4-phenylbutanoic acid (5 g, 16.70 mmol) in dichloromethane (40 ml) was added dropwise. The reaction was stirred at room temperature for 2 hours and then washed quickly with 1 N HCl. The organic layer was washed with H$_2$O, dried over Na$_2$SO$_4$ and concentrated to give the title compound as a sticky yellow oil (5.8 g). MS (m/z) 328.1 (M+H$^+$).

Intermediate 7: (R)-2-((N-(benzyloxy)formamido)methyl)-5-phenylpentanoic acid

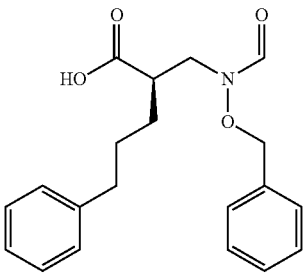 [SMILES: O=CN(C[C@@H](CCCc1ccccc1)C(=O)O)OCc1ccccc1]

Intermediate 7 was prepared from 5-phenylpentanoyl chloride by methods analogous to that described for Intermediate 6.

| Step | Name | MS (m/z) |
| --- | --- | --- |
| 1 | (S)-4-benzyl-3-(5-phenylpentanoyl)oxazolidin-2-one | 338.2 (M + H$^+$) |
| 2 | (S)-4-benzyl-3-((R)-2-((benzyloxy)methyl)-5-phenylpentanoyl)oxazolidin-2-one | 458.2 (M + H$^+$) |
| 3 | (R)-2-((benzyloxy)methyl)-5-phenylpentanoic acid | 281.1 (M − 17$^+$) |
| 4 | (R)-2-(hydroxymethyl)-5-phenylpentanoic acid | 191.1 (M − 17$^+$) |
| 5 | (R)-N-(benzyloxy)-2-(hydroxymethyl)-5-phenylpentanamide | 314.2 (M + H$^+$) |
| 6 | (R)-1-(benzyloxy)-3-(3-phenylpropyl)azetidin-2-one | 296.1 (M + H$^+$) |
| 7 | (R)-2-(((benzyloxy)amino)methyl)-5-phenylpentanoic acid | 314.2 (M + H$^+$) |
| 8 | (R)-2-((N-(benzyloxy)formamido)methyl)-5-phenylpentanoic acid | 342.2 (M + H$^+$) |

Intermediate 8: (R)-2-((R)-1-(N-(benzyloxy)formamido)propyl)heptanoic acid

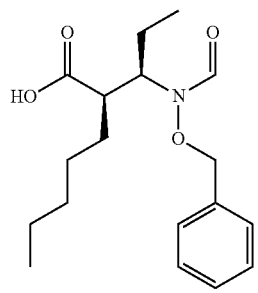 [SMILES: CCCCC[C@@H](C(=O)O)[C@@H](CC)N(C=O)OCc1ccccc1]

Step 1: (R)-4-benzyl-3-heptanoyloxazolidin-2-one

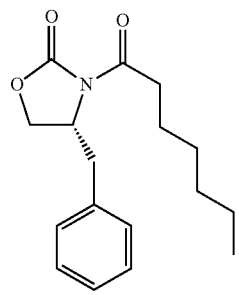 [SMILES: CCCCCCC(=O)N1C(=O)OC[C@H]1Cc1ccccc1]

(R)-4-benzyloxazolidin-2-one (9.95 g, 56.2 mmol) was dissolved in dry tetrahydrofuran (100 ml) and the mixture cooled in a dry-ice acetone bath. BuLi (2.7 M in hexanes, 20.80 ml, 56.2 mmol) was added over 5 minutes under nitrogen resulting in a color change to dark yellow. The color was titrated out by addition of HCl in dioxane, then re-treated with enough BuLi to turn the mixture slightly yellow. Heptanoyl chloride (8.87 ml, 57.3 mmol) was then added. The mixture was stirred for ~30 minutes and then additional heptanoyl chloride (3 ml) was added. The reaction was then quenched by slow addition of water (10 ml). Solid formation was noted, additional water was added to obtain a solution. EtOAc (300 ml) was added and the layers separated. The organic was washed with sat. aq sodium carbonate then dried over sodium sulfate, filtered and concentrated. The residue was dissolved in heptane, and then concentrated to a thick oil. The residue was dissolved in heptane (100 ml) and the mixture cooled in an acetone/dry ice bath with stirring. The resultant precipitate was collected by filtration and dried under vacuum overnight to give the title compound as a white solid (15.1 g, 93% yield).

Step 2: (R)-4-benzyl-3-((R)-2-((S)-1-hydroxypropyl)heptanoyl)oxazolidin-2-one

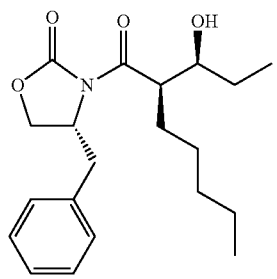 [SMILES: CCCCC[C@@H](C(=O)N1C(=O)OC[C@H]1Cc1ccccc1)[C@@H](O)CC]

To a solution of (R)-4-benzyl-3-heptanoyloxazolidin-2-one (15 g, 51.8 mmol) in DCM (300 ml) under $N_2$ in a ice-acetone bath was added $TiCl_4$ (6.00 ml, 54.4 mmol). DIPEA (9.96 ml, 57.0 mmol) was then slowly added followed by NMP (9.98 ml, 104 mmol) and the mixture stirred for 15 minutes. Propionaldehyde (7 ml, 95 mmol) was then added and the reaction stirred for 1.5 hours. The reaction was then quenched by addition of a solution of AcOH in DCM (15 ml of a 50:50 mix by volume). Aqueous Rochelles salt was added followed by aq HCl (50% v/v) to dissolve any solids. The layers were then separated and the aqueous extracted with additional DCM. The combined organics were treated with aq $NaHSO_3$ for 30 minutes then the layers allowed to settle in a separation funnel overnight. The organic was then separated and filtered through a plug of silica (~3 cm). The filtrates were combined, concentrated and dried under vacuum to give the title compound (19 g, 87% yield) which was used without further purification.

Step 3: (R)—N-(benzyloxy)-2-((S)-1-hydroxypropyl)heptanamide

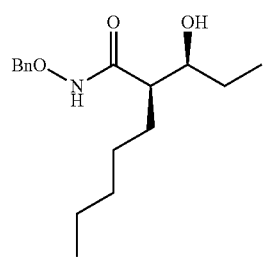 [SMILES: CCCCC[C@@H](C(=O)NOCc1ccccc1)[C@@H](O)CC]

THF was boiled out of a 2 l JLR and the reactor purged with $N_2$ whilst cooling to room temperature. O-benzylhydroxylamine, hydrochloride (15.96 g, 100 mmol) was added and the vessel purged with $N_2$. THF (800 ml) was then added and the mixture cooled to 0° C. Trimethylaluminum (50 ml, 2 M in toluene, 100 mmol) was then added slowly. The white slurry was stirred for 15 minutes to obtain a clear solution. A solution of (R)-4-benzyl-3-((R)-2-((S)-1-hydroxypropyl)heptanoyl)oxazolidin-2-one (18 g, 51.8 mmol) in THF (200 ml) was then added over 5 minutes via cannula and the mixture stirred for 1.5 hours at 0° C. The reaction mixture was warmed to 5° C. Separately, O-benzylhydroxylamine, hydrochloride (5 g, 31 mmol) was dissolved in THF (100 ml) and treated with trimethylaluminum (17 ml, 2 M in toluene, 34 mmol) at 0° C. The mixture was stirred until a solution was obtained and then added to primary reaction via cannula. The reaction was then quenched by the addition of sat.aq $KHSO_4$. A HCl solution (500 ml water, 500 ml conc HCl) was added and the layers separated. The organics were reduced in volume and re-combined with the aqueous, the volatiles were removed via rotovap and a white precipitate formed. The solids were collected by filtration and washed with 10% HCl then water. The filter cake was then washed with toluene (2×100 ml) and air dried to give the title compound (10.65 g, 70% yield). MS (m/z) 294.3 $(M+H^+)$.

Step 4: (3R,4R)-1-(benzyloxy)-4-ethyl-3-pentylazetidin-2-one

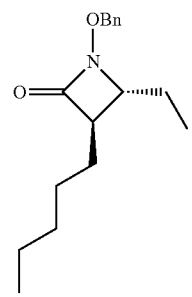 [SMILES: CCCCC[C@H]1C(=O)N(OCc2ccccc2)[C@@H]1CC]

(R)—N-(benzyloxy)-2-((S)-1-hydroxypropyl)heptanamide (4.61 g, 15.7 mmol) was dissolved in pyridine (14 ml) and cooled in an ice bath. Methanesulfonyl chloride (2.45 ml, 31.4 mmol) was then added dropwise maintaining the internal temperature below 10° C. The reaction was then stirred for 2 hours. The reaction was diluted by the addition of TBME (23 ml) and 1 M HCl (46 ml) was added while cooling was applied. The layers were separated and the organic was washed with 1 M HCl (23 ml), sat. aq NaHCO₃ (9 ml) and brine (9 ml) and then concentrated to minimum volume then dissolved in acetone (46 ml). K₂CO₃ (6.51 g, 47.1 mmol) was added and the reaction heated at 50° C. for 1 hour. The reaction was then cooled to room temperature and filtered. The flask and filter cake were rinsed with acetone (2×23 ml). The filtrate was concentrated give the title compound (4.26 g).

Step 5: (R)-2-((R)-1-((benzyloxy)amino)propyl) heptanoic acid

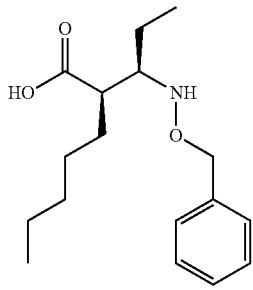 [SMILES: CCCCC[C@@H](C(=O)O)[C@@H](CC)NOCc1ccccc1]

(3R,4R)-1-(benzyloxy)-4-ethyl-3-pentylazetidin-2-one (356 g, 1.27 mol) was dissolved in 2-methyltetrahydrofuran (3560 ml). Tetrabutylammonium hydroxide (40% aqueous solution, 1245 ml, 1.90 mol) was added. The reaction was heated to 50° C. for 2 hours and then cooled to room temperature. The reaction was diluted with water (1780 ml) and acidified with 6 M HCl (338 ml) to pH 3-4. The phases were separated and the organic phase was concentrated down to 5 volumes (1780 ml) and was used without further purification MS (m/z) 322 (M+H⁺).

Step 6: (R)-2-((R)-1-(N-(benzyloxy)formamido) propyl)heptanoic acid

Carbonyldiimidazole (822 g, 5.07 mol) was suspended in 2-methyltetrahydrofuran (5340 ml) and cooled to 0° C. Formic acid (88%, 276 ml, 6.33 mol) was added dropwise via addition funnel. The reaction was stirred at 5° C. for 10 minutes and then warmed to room temperature for an additional 30 minutes. The reaction was cooled back to 5° C. and (R)-2-((R)-1-((benzyloxy)amino)propyl)heptanoic acid in 2-methyltetrahydrofuran (1780 ml solution from previous step) was added. The reaction was warmed to room temperature and stirred for 40 minutes. In a separate vessel, carbonyldiimidazole (279 g, 1.72 mol) was suspended in 2-methyltetrahydrofuran (1500 ml) and cooled to 0° C. Formic acid, (88%, 93.8 ml, 2.16 mol) was added dropwise via addition funnel and stirred at 5° C. for 10 minutes and then warmed to room temperature for an additional 30 minutes. This mixture was then added dropwise via addition funnel to the original reaction at 5° C. The reaction was warmed to room temperature and stirred for 60 minutes. The reaction was then cooled to 10° C. and quenched by addition of NaOH (4 M, 2122 ml) to pH 9. The phases were separated and the organic phase was washed with a 1:1 mixture (v/v) of 6 M HCl and saturated aqueous brine (4561 ml). The phases were separated and the organic phase was concentrated to 3.5 volumes (1246 ml) to give the title compound as a 30% by weight solution in 2-methyltetrahydrofuran (1.15 kg, equates to 346 g of crude title product).

Steps 2 and 3 were repeated on 365 g scale to provide a second batch of the title compound as a 36% by weight solution in 2-methyltetrahydrofuran (1.09 kg, equates to 363 g of crude title product) and on 20 g scale to provide the title compound as a 30% by weight solution in 2-methyltetrahydrofuran (66 g, equates to 19.8 g of crude title product).

The 30% by weight solution of crude title compound in 2-methyltetrahydrofuran (1.15 kg, 346 g crude) was concentrated, azeotroped three times with hexanes and then diluted with hexanes (2500 ml). The solution was seeded with crystals obtained from a previous SFC purification. Nitrogen was then passed over the solution with stirring overnight. The resulting crystalline material was broken up, diluted with hexanes and stirred at room temperature for 30 minutes then filtered to give the title compound as a light yellow crystalline solid (275 g).

The 36% (1.09 kg, 363 g crude) and 30% (66.04 g, 19.8 g crude) by weight solutions of crude title compound were concentrated, azeotroped three times with methanol and combined with the filtrate from the initial 30% by weight batch. The residue was diluted with methanol to a concentration of 200 mg/ml and purified by SFC (Thar SFC-70, DEAP column, 5 µM, 30×250 mm, i.d., eluting with 35% isocratic methanol co-solvent, 60 g/min, 7 minute run) to give the title compound as a yellow oil. The oil was diluted with hexanes (2500 ml) and the solution seeded with crystals obtained from previous isolates. Nitrogen was passed over the solution with stirring overnight. The resulting crystalline material was broken up, diluted with hexanes, and stirred at room temperature for 30 minutes then filtered to give the title compound as a light yellow crystalline solid (360 g). MS (m/z) 322.0 (M+H⁺).

Intermediate 9: (R)-2-((S)-2-(benzyloxy)-1-(N-(benzyloxy)formamido)ethyl)heptanoic acid

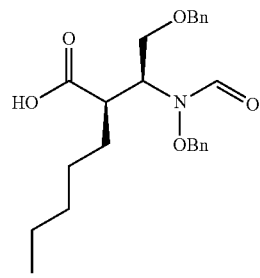 [SMILES: CCCCC[C@@H](C(=O)O)[C@@H](COCc1ccccc1)N(C=O)OCc1ccccc1]

Step 1: (S)-4-benzyl-3-heptanoyloxazolidin-2-one

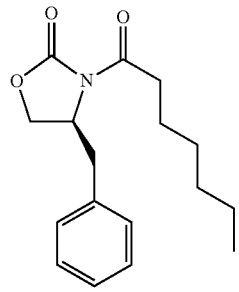 [SMILES: CCCCCCC(=O)N1C(=O)OC[C@@H]1Cc1ccccc1]

To a solution of (S)-4-benzyloxazolidin-2-one (5.0 g, 28.2 mmol) in dry THF (60 ml) at −78° C. was added dropwise n-BuLi (11.28 ml, 2.5 M in Hexane, 28.2 mmol). After stirring for 30 minutes at −78° C., the reaction mixture was then treated with heptanoyl chloride (4.34 ml, 28.2 mmol). The reaction mixture was allowed to warm to room temperature and stirred overnight. The reaction was then quenched with saturated aqueous NH$_4$Cl solution and extracted with ethyl acetate. The combined organic layers were washed with brine, dried over Na$_2$SO$_4$, filtered and concentrated under reduced pressure. The residue was purified by flash chromatography (1-20% EtOAc/cyclohexane) to give the title compound (7.5 g, 51% yield). MS (m/z) 290.1 (M+H$^+$).

Step 2: (R)-1-((S)-4-benzyl-2-oxooxazolidin-3-yl)-4-(benzyloxy)-2-pentylbutane-1,3-dione

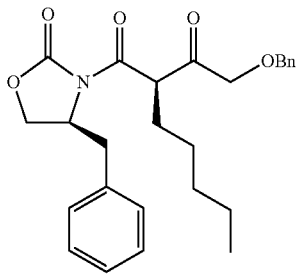 [SMILES: CCCCC[C@H](C(=O)COCc1ccccc1)C(=O)N1C(=O)OC[C@@H]1Cc1ccccc1]

Sodium bis(trimethylsilyl)amide (29.02 ml, 1 M in THF) was added dropwise to a stirred solution of (S)-4-benzyl-3-heptanoyloxazolidin-2-one (7.0 g, 24.2 mmol) in THF (150 ml) at −78° C. After addition was complete the mixture was allowed to stir at −78° C. for 30 minutes then 1-(benzyloxy)-3-chloropropan-2-one (5.72 ml, 36.3 mmol) was added. The reaction mixture was stirred at −78° C. for 1 hour then quenched with saturated ammonium chloride solution (200 ml). The mixture was warmed to room temperature and extracted with EtOAc (2×250 ml). The combined organic phases were washed with brine (200 ml), dried over sodium sulphate and evaporated under reduced pressure. The residue was purified by flash chromatography (SNAP 340 g column, 5-15% EtOAc/cyclohexane) to give the title compound as a colorless oil (5.43 g, containing ~40% (S)-4-benzyl-3-heptanoyloxazolidin-2-one) which was used without further purification. MS (m/z) 460.0 (M+23$^+$).

Step 3: (S)-4-benzyl-3-((R)-2-(2-(benzyloxy)-1-((benzyloxy)imino)ethyl)heptanoyl)oxazolidin-2-one

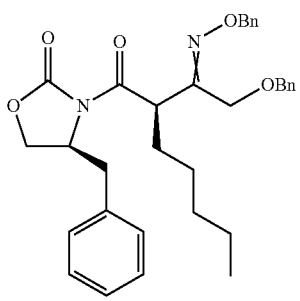 [SMILES: CCCCC[C@@H](C(=O)N1C(=O)OC[C@@H]1Cc1ccccc1)C(COCc1ccccc1)=NOCc1ccccc1]

Sodium acetate (2.04 g, 24.8 mmol) was added to a stirred solution of (R)-1-((S)-4-benzyl-2-oxooxazolidin-3-yl)-4-(benzyloxy)-2-pentylbutane-1,3-dione (5.43 g, 12.4 mmol) in MeOH (100 ml) followed by O-benzylhydroxylamine hydrochloride (3.96 g, 24.8 mmol) and the mixture stirred at room temperature for 18 hours. The reaction mixture was evaporated under reduced pressure and the residue was partitioned between water (200 ml) and EtOAc (300 ml). The phases were separated and the organic washed with sodium hydrogen carbonate solution (100 ml) and brine (100 ml), dried over sodium sulphate and evaporated under reduced pressure. The residue was purified by flash chromatography (SNAP 340 g column, 5-10% EtOAc/cyclohexane) to give the title compound as a colorless oil which solidified on standing (5.06 g). MS (m/z) 565.1 (M+23).

Step 4: (4S)-4-benzyl-3-((2R)-2-(2-(benzyloxy)-1-((benzyloxy)amino)ethyl)heptanoyl)oxazolidin-2-one

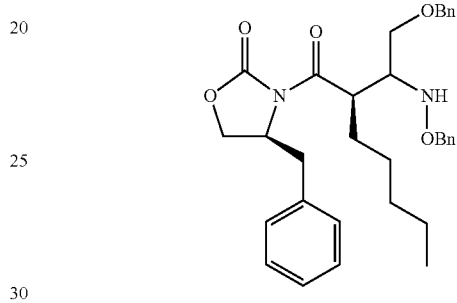

Sodium cyanoborohydride (2.18 g, 34.5 mmol) was added portionwise over a period of 1 hour to a stirred solution of (S)-4-benzyl-3-((R)-2-(2-(benzyloxy)-1-((benzyloxy)imino)ethyl)heptanoyl)oxazolidin-2-one (4.72 g, 8.7 mmol) in dichloroethane (60 ml) and acetic acid (20 ml) at 0° C. After addition the mixture was allowed to stir for 1 hour. Further sodium cyanoborohydride (1.09 g, 17.3 mmol) was added portionwise at 0° C. and the reaction stirred for 2 hours. The reaction mixture was evaporated under reduced pressure and the residue was treated with water (300 ml) and adjusted to pH 9 by addition of 2 M NaOH solution. The aqueous was extracted with EtOAc (1×200 ml, 1×100 ml). The combined organic phases were washed with sodium hydrogen carbonate solution (200 ml) and brine (100 ml), dried over sodium sulphate and evaporated under reduced pressure. The residue was purified by flash chromatography (SNAP 340 g column, 5-10% EtOAc/cyclohexane) to give the title compound as a ~3:1 mixture of diastereoisomers as a colorless oil (4.48 g). MS (m/z) 545.1 (M+H$^+$).

Step 5: N-((2S,3R)-3-((S)-4-benzyl-2-oxooxazolidine-3-carbonyl)-1-(benzyloxy)octan-2-yl)-N-(benzyloxy)formamide

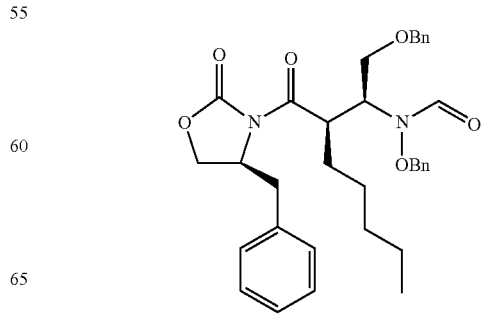

Formic acid (0.46 ml, 12.3 mmol) was added dropwise to a suspension of CDI (1.99 g, 12.3 mmol) in dichloromethane (75 ml) at 0° C. After addition was complete the mixture was allowed to warm to room temperature and stirred for 30 minutes to give a clear solution. This mixture was then added to a solution of (4S)-4-benzyl-3-((2R)-2-(2-(benzyloxy)-1-((benzyloxy)amino)ethyl)heptanoyl)oxazolidin-2-one (4.47 g, 8.2 mmol) in dichloromethane (25 ml) at 0° C. and the resulting mixture was stirred at 0° C. for 30 minutes then at room temperature overnight. The reaction mixture was warmed to 40° C. for 4 hours but no further conversion was observed. In a separate flask formic acid (0.23 ml, 5 mmol) was added dropwise to a suspension of CDI (0.99 g, 5 mmol) in dichloromethane (25 ml) and this mixture was stirred for 30 minutes then added to the main reaction mixture. The reaction was stirred for a further 2 hours at 40° C. The reaction mixture was then diluted with EtOAc (500 ml) and washed with pH 3 buffer solution (300 ml), sodium bicarbonate solution (300 ml), and brine (300 ml). The organic phase was dried over sodium sulphate and evaporated under reduced pressure. The residue was purified by flash chromatography (SNAP 340 g column, 5-30% EtOAc/cyclohexane). Impure fractions from this column were purified by flash chromatography (SNAP 25 g column, 10-20% EtOAc/cyclohexane). Combination of the appropriate fractions from both columns were concentrated to give the title compound as a white solid (0.68 g). MS (m/z) 573.1 (M+H$^+$).

Step 6: (R)-2-((S)-2-(benzyloxy)-1-(N-(benzyloxy)formamido)ethyl)heptanoic acid

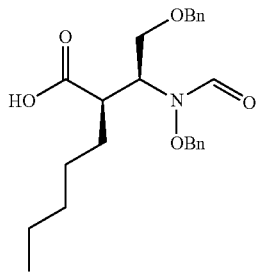

A solution of N-((2S,3R)-3-((S)-4-benzyl-2-oxooxazolidine-3-carbonyl)-1-(benzyloxy)octan-2-yl)-N-(benzyloxy)formamide (680 mg, 1.2 mmol) in a 3:1 mixture of THF (15 ml) and H$_2$O (5 ml) was treated with H$_2$O$_2$ (30%, 0.55 ml, 4.8 mmol) followed by LiOH (75 mg, 1.8 mmol) at 0° C. The resulting mixture was allowed to warm to room temperature and stirred overnight. The reaction mixture was quenched with aqueous sodium sulphite solution, diluted with pH 3 buffer (50 ml) and brought to pH 3 by addition of 1 M HCl solution. The aqueous phase was then extracted with EtOAc (2×50 ml) and the combined organic phases were washed with brine (30 ml), dried over sodium sulphate and evaporated under reduced pressure. The residue was purified by flash chromatography (SNAP 50 g column, 1-4% MeOH in a 25:75 mixture of EtOAc/dichloromethane) to give impure product which was then purified by Isolute NH$_2$ cartridge (2 g, eluted with 30% EtOAc/dichloromethane and then 30% EtOAc in dichloromethane+1% formic acid) to give the title compound (383 mg) as a colorless oil. MS (m/z) 414.1 (M+H$^+$).

Intermediate 10: (9H-fluoren-9-yl)methyl (aminomethyl)carbamate, trifluoroacetic acid salt

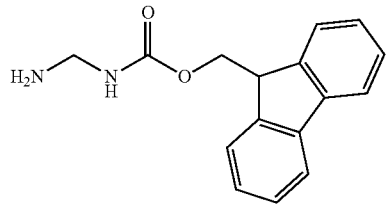 [SMILES: NCNC(=O)OCC1c2ccccc2-c2ccccc21]

Step 1: (9H-fluoren-9-yl)methyl (2-amino-2-oxoethyl)carbamate

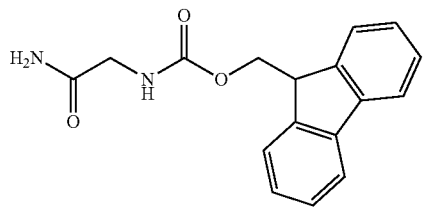 [SMILES: NC(=O)CNC(=O)OCC1c2ccccc2-c2ccccc21]

A mixture of 2-aminoacetamide, hydrochloride (231 g, 2.09 mol) in DCM (4 l) at 0° C. was treated with DIPEA (1.1 l, 6.27 mol) and then portionwise with (9H-fluoren-9-yl) methyl carbonochloridate (541 g, 2.09 mol). This mixture was stirred for 1 hour and was warmed to room temperature and then treated with water (2 l). The white precipitate was collected by filtration, then washed thoroughly with water, DCM, water and Et$_2$O and then air dried to give the title compound (618 g, 80% yield) as a white solid. MS (m/z) 297.0 (M+H$^+$).

Step 2: (9H-fluoren-9-yl)methyl (aminomethyl)carbamate, trifluoroacetic acid salt

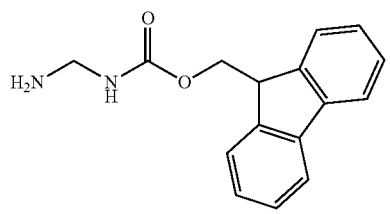 [SMILES: NCNC(=O)OCC1c2ccccc2-c2ccccc21]

To a solution of [bis(trifluoroacetoxy)iodo]benzene (109 g, 253 mmol), water (800 ml), and THF (800 ml) was added (9H-fluoren-9-yl)methyl (2-amino-2-oxoethyl)carbamate (50 g, 169 mmol) and the mixture was stirred with an overhead stirrer for 60 minutes. Diethyl ether (1 l) and hexane (250 ml) were added and the layers were separated. The aqueous layer was washed with diethyl ether (600 ml). The organics were collected and concentrated to 350 ml of total volume, hexanes (600 ml) was then added with stirring. The mixture was stirred for an additional 1.5 hours then the precipitate was collected via filtration to yield the title compound as an off white solid (32.8 g, 51% yield). MS (m/z) 269.1 (M+H$^+$).

Intermediate 11: (R)—N-(aminomethyl)-2-((N-(benzyloxy)formamido)methyl)heptanamide

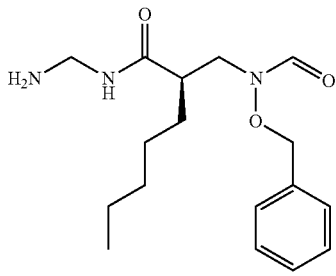 [SMILES: CCCCC[C@H](CN(C=O)OCc1ccccc1)C(=O)NCN]

Step 1: (R)-(9H-fluoren-9-yl)methyl ((2-((N-(benzyloxy)formamido)methyl)heptanamido)methyl)carbamate

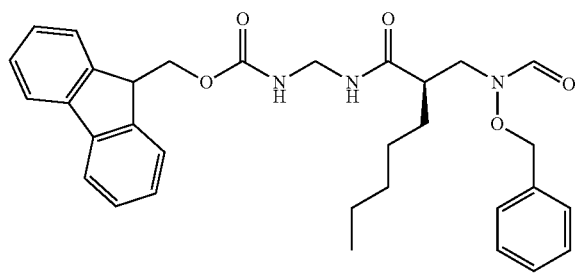 [SMILES: CCCCC[C@H](CN(C=O)OCc1ccccc1)C(=O)NCNC(=O)OCC1c2ccccc2-c2ccccc21]

(R)-2-((N-(benzyloxy)formamido)methyl)heptanoic acid (1.13 g, 3.84 mmol) was dissolved in N,N-dimethylformamide (10.79 ml) and treated with HATU (1.46 g, 3.84 mmol). 9H-fluoren-9-yl)methyl (aminomethyl)carbamate, hydrochloride (1.17 g, 3.84 mmol) was added followed by DIPEA (2.01 ml, 11.52 mmol). The reaction was allowed to stir at room temperature for 18 hours. The reaction was then diluted with EtOAc (100 ml) and water (50 ml). The layers were separated, and the aqueous layer was washed with EtOAc (50 ml). The combined organics were washed with brine (1×20 ml), dried over MgSO₄, filtered, and concentrated. The residue was purified by flash chromatography (120 g silica gel column, 30% EtOAc/hexanes: 10 minutes, 30-50% EtOAc/hexanes: 3 minutes, 50% EtOAc/hexanes: 15 minutes) to yield the title compound as a white solid (1.4 g, 67.1% yield). MS (m/z) 544.3 (M+H$^+$).

Step 2: (R)—N-(aminomethyl)-2-((N-(benzyloxy)formamido)methyl)heptanamide

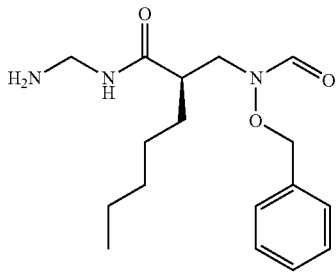 [SMILES: CCCCC[C@H](CN(C=O)OCc1ccccc1)C(=O)NCN]

(R)-(9H-fluoren-9-yl)methyl((2-((N-(benzyloxy)formamido)methyl)heptanamido)methyl)carbamate (1.4 g, 2.6 mmol) was suspended in acetonitrile (12 ml) and treated at room temperature with morpholine (6 ml, 68.9 mmol). The reaction was allowed to stir at room temperature for 2 hours. The reaction was then filtered, washing with ether. The combined filtrates were concentrated and the residue was purified by flash chromatography (40 g column, 100% DCM: 5 minutes, 0-10% MeOH/DCM: 12 minutes, 10% MeOH/DCM: 5 minutes) to yield the title compound as a clear, colorless oil (663 mg, 80% yield).

Intermediate 12: (R)—N-(aminomethyl)-2-((N-hydroxyformamido)methyl)heptanamide

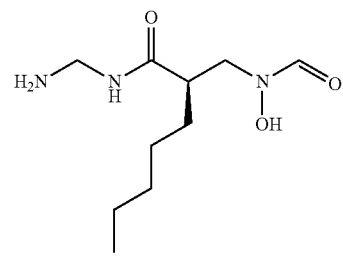 [SMILES: CCCCC[C@H](CN(O)C=O)C(=O)NCN]

To a solution of (R)—N-(aminomethyl)-2-((N-(benzyloxy)formamido)methyl)heptanamide (55 mg, 0.17 mmol) in EtOH (10 ml) was added Pd/C (10% wt, Degussa wet, 30 mg). The reaction mixture was hydrogenated at room temperature for 30 minutes. The catalyst was filtered off and washed with EtOH. The filtrate was concentrated under reduced pressure to give the title compound as a grey solid (40 mg, 80% purity) which was used without further purification.

Intermediate 13: N-(aminomethyl)-5-bromofuran-2-carboxamide

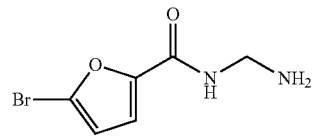

Step 1: (9H-fluoren-9-yl)methyl ((5-bromofuran-2-carboxamido)methyl)carbamate

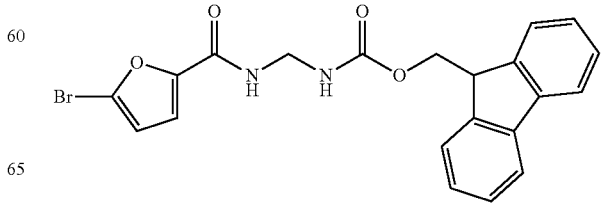

To a suspension of 5-bromofuran-2-carboxylic acid (25 g, 131 mmol) in DCM (367 ml) was added HATU (54.7 g, 144 mmol) followed by DIPEA (68.5 ml, 392 mmol) then (9H-fluoren-9-yl)methyl (aminomethyl)carbamate, trifluoroacetic acid salt (50 g, 131 mmol). The reaction mixture was stirred at room temperature for ~10 minutes. The precipitate was then collected via filtration to yield the title compound as an off white solid (40.8 g, 64% yield). Additional precipitates could be obtained from the filtrate to yield additional batches of the title compound (8.8 g, 12% yield and 1.1 g, 2% yield). MS (m/z) 443.0 (M+2$^+$).

Step 2: N-(aminomethyl)-5-bromofuran-2-carboxamide

A suspension of (9H-fluoren-9-yl)methyl((5-bromofuran-2-carboxamido)methyl)carbamate (46.5 g, 84 mmol) in acetonitrile (198 ml) was treated with piperidine (83 ml, 843 mmol) and stirred at room temperature. After ~10 minutes, a thick precipitate formed and the reaction mixture was filtered. The filtrate was concentrated and the residue suspended in acetonitrile (100 ml) and filtered. The filtrate was collected and concentrated and the residue was suspended in DCM (100 ml) and a white precipitate formed. The precipitate was collected by filtration to give the title compound (10.6 g, 57% yield). MS (m/z) 191.9 (M−28$^+$). The filtrates were combined, concentrated, and purified by flash chromatography (ISCO Combiflash, 330 g column, 0-20% methanol in DCM). Concentration of the appropriate fractions yielded a yellow solid (12.4 g) which was then suspended in DCM and filtered to yield an additional batch of the title compound as a white solid (2.83 g, 15% yield). MS (m/z) 191.9 (M−28$^+$).

Intermediate 14: N-(aminomethyl)-5-(3-(2,2,2-trifluoroethoxy)phenyl)furan-2-carboxamide

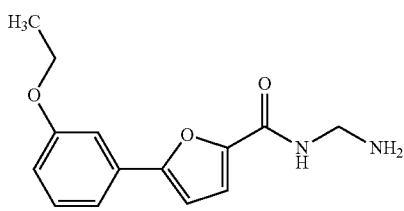 [SMILES: CCOc1cccc(-c2ccc(C(=O)NCN)o2)c1]

Step 1: (9H-fluoren-9-yl)methyl ((5-(3-(2,2,2-trifluoroethoxy)phenyl)furan-2-carboxamido)methyl)carbamate

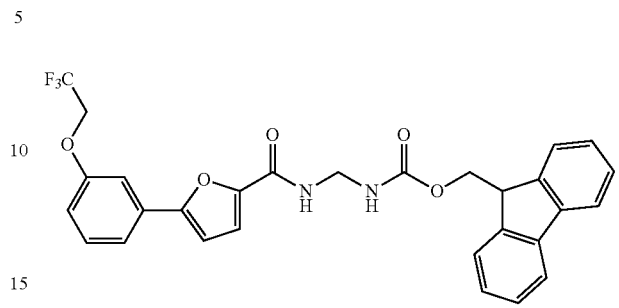

PdCl$_2$(dppf)-CH$_2$Cl$_2$ adduct (278 mg, 0.34 mmol) was added to a microwave vial containing sodium carbonate (1 M, 6.80 ml, 6.80 mmol) 1,2-dimethoxyethane (12 ml), (3-(2,2,2-trifluoroethoxy)phenyl)boronic acid (598 mg, 2.72 mmol), and (9H-fluoren-9-yl)methyl ((5-bromofuran-2-carboxamido)methyl)carbamate (1000 mg, 2.27 mmol) and the reaction irradiated at 105° C. for 5 minutes in a Biotage Initiator. The reaction was poured into brine and the mixture extracted with EtOAc. The organics were collected, dried over Na$_2$SO$_4$, filtered, concentrated, and purified by column chromatography (1-1.5% MeOH/DCM). Concentration of the appropriate fractions yielded material which was then triturated with ether to give the title compound as an off-white solid (700 mg, 58% yield). MS (m/z) 537.1 (M+H$^+$).

Step 2: N-(aminomethyl)-5-(3-(2,2,2-trifluoroethoxy)phenyl)furan-2-carboxamide

Pyrrolidine (2.16 ml, 26.1 mmol) was added to a mixture of (9H-fluoren-9-yl)methyl ((5-(3-(2,2,2-trifluoroethoxy)phenyl)furan-2-carboxamido)methyl)carbamate (700 mg, 1.31 mmol) in acetonitrile (5 ml) and the reaction was stirred for 2 hours. The reaction was concentrated and the residue was purified by flash chromatography (1-5% MeOH/CH$_2$Cl$_2$) to give the title compound (350 mg, 85% yield). MS (m/z) 315.0 (M+H$^+$).

INTERMEDIATE 15 was prepared from (9H-fluoren-9-yl)methyl ((5-bromofuran-2-carboxamido)methyl)carbamate and (3-(methylsulfonyl)phenyl)boronic acid by methods analogous to that described for Intermediate 14.

| # | Name | Structure | MS (m/z) | Name Step 1 | MS (m/z) (M + H$^+$) Step 1 |
|---|------|-----------|----------|-------------|------------------------------|
| 15 | N-(aminomethyl)-5-(3-(methylsulfonyl)phenyl)furan-2-carboxamide | 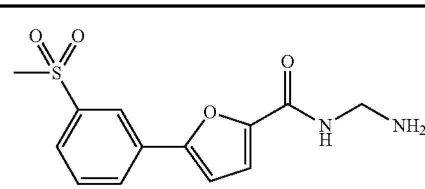 | 560.1 (2M − 28$^+$) | (9H-fluoren-9-yl)methyl ((5-(3-(methylsulfonyl)phenyl)furan-2-carboxamido)methyl)carbamate | 517.1 |

Intermediate 16: N-(aminomethyl)-5-(3-(2-(pyrrolidin-1-yl)ethoxy)phenyl)furan-2-carboxamide

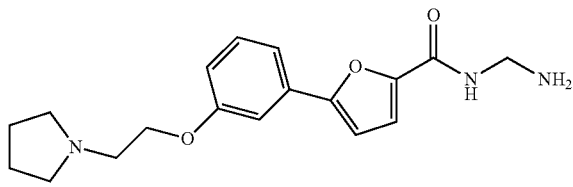 [SMILES: NCNC(=O)c1ccc(-c2cccc(OCCN3CCCC3)c2)o1]

Step 1: methyl 5-(3-(2-(pyrrolidin-1-yl)ethoxy)phenyl)furan-2-carboxylate

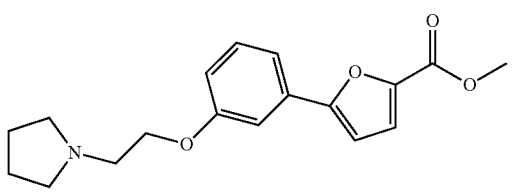 [SMILES: COC(=O)c1ccc(-c2cccc(OCCN3CCCC3)c2)o1]

A mixture of 1-(2-(3-bromophenoxy)ethyl)pyrrolidine, hydrochloride (0.71 ml, 1.96 mmol), (5-(methoxycarbonyl)furan-2-yl)boronic acid (0.40 g, 2.35 mmol), PdCl$_2$(dppf)-CH$_2$Cl$_2$ adduct (0.16 g, 0.20 mmol) and sodium carbonate (1 M, 5.5 ml, 5.50 mmol) in 1,4-dioxane (3.57 ml) was irradiated for 5 minutes at 100° C. The reaction was extracted with DCM (3×). The organic extracts were passed through a phase separator and concentrated. The residue was purified by flash chromatography (ISCO, 40 g column, 0-100% EtOAc/DCM: 15 minutes, 100% EtOAc: 15 minutes) to give the title compound as a thick yellow oil (331 mg, 54% yield). MS (m/z) 316.2 (M+H$^+$).

Step 2: 5-(3-(2-(pyrrolidin-1-yl)ethoxy)phenyl)furan-2-carboxylic acid

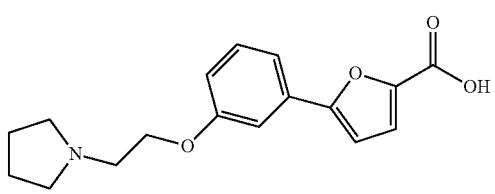 [SMILES: O=C(O)c1ccc(-c2cccc(OCCN3CCCC3)c2)o1]

Methyl 5-(3-(2-(pyrrolidin-1-yl)ethoxy)phenyl)furan-2-carboxylate (331 mg, 1.05 mmol) in methanol (6.56 ml) and water (3.94 ml) was treated with lithium hydroxide (101 mg, 4.20 mmol) at room temperature for 4 hours. The volatiles were removed and the residue was acidified to ~pH 4 by the addition of 1 N HCl. The mixture was extracted with EtOAc (2×). The aqueous layer was concentrated to give the title compound as a brown solid (316 mg, 99% yield). MS (m/z) 302.1 (M+H+).

Step 3: N-(aminomethyl)-5-(3-(2-(pyrrolidin-1-yl)ethoxy)phenyl)furan-2-carboxamide A solution of (9H-fluoren-9-yl)methyl (aminomethyl)carbamate, trifluoroacetic acid salt (381 mg, 1 mmol), 5-(3-(2-(pyrrolidin-1-yl)ethoxy)phenyl)furan-2-carboxylic acid (300 mg, 1 mmol), HBTU (453 mg, 1.2 mmol), DIPEA (0.52 ml, 3 mmol) in N,N-dimethylformamide (5 ml) was stirred at room temperature overnight. Water was then added and the reaction was stirred for 30 minutes. The grey precipitate was collected by filtration, washed with water and air dried. The solid was suspended in acetonitrile (4 ml) and treated with pyrrolidine (2.47 ml, 29.9 mmol) for 1 hour. The reaction was concentrated and the residue purified via flash chromatography (ISCO, 40 g silica gel column, 0-5% MeOH/DCM: 10 minutes, 5% MeOH/DCM: 10 minutes, 5-15% MeOH/DCM: 5 minutes, 15% MeOH/DCM: 7 minutes, 20% MeOH (+0.1% TEA)/DCM: 30 minutes) to give the title compound (110 mg, 34% yield). MS (m/z) 330.1 (M+H$^+$).

Intermediate 17: N-(aminomethyl)-5-phenylfuran-2-carboxamide

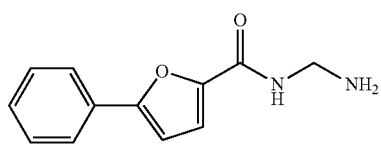 [SMILES: NCNC(=O)c1ccc(-c2ccccc2)o1]

Step 1: 5-phenylfuran-2-carbonyl chloride

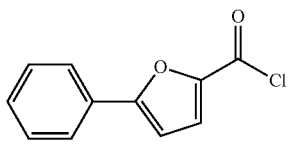 [SMILES: O=C(Cl)c1ccc(-c2ccccc2)o1]

A mixture of 5-phenylfuran-2-carboxylic acid (16 g, 85 mmol) in dichloromethane (300 ml) at 25° C. was treated with DMF (0.07 ml, 0.85 mmol) and then oxalyl chloride (11.16 ml, 128 mmol) and stirred overnight before being concentrated to give the title compound as a pale yellow solid (17.6 g, 100% yield). MS (m/z) 206.9 (M)$^+$

Step 2: (9H-fluoren-9-yl)methyl ((5-phenylfuran-2-carboxamido)methyl)carbamate

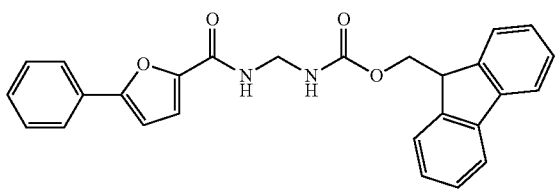 [SMILES: O=C(NCNC(=O)c1ccc(-c2ccccc2)o1)OCC1c2ccccc2-c2ccccc21]

To a mixture of 5-phenylfuran-2-carbonyl chloride (17.6 g, 85 mmol) in dichloromethane (300 ml) at 25° C. was added (9H-fluoren-9-yl)methyl (aminomethyl)carbamate, trifluoroacetic acid salt (35.8 g, 94 mmol) followed by DIPEA (59.5 ml, 341 mmol) and the reaction stirred for 15 minutes before being treated with water and extracted with CH$_2$Cl$_2$. The organic extract was concentrated to give a tan solid, which was triturated with water and Et₂O and then air dried to give the title compound as a tan solid (33 g, 88% yield). MS (m/z) 439.1 (M+H⁺).

Step 3:
N-(aminomethyl)-5-phenylfuran-2-carboxamide

A mixture of (9H-fluoren-9-yl)methyl ((5-phenylfuran-2-carboxamido)methyl)carbamate (35 g, 80 mmol) in acetonitrile (300 ml) at 25° C. was treated with morpholine (160 ml, 1836 mmol) and stirred for 2 hours before being filtered, washing with acetonitrile. The filtrate was concentrated and the residue was purified by flash chromatography (2-10% MeOH/CH₂Cl₂) to give pure product. Impure product was also isolated and purified by flash chromatography (2-5% MeOH/CH₂Cl₂). Combination of the pure batches yielded a brown oil which was dissolved in CH₂Cl₂ and concentrated under reduced pressure, then placed under high vacuum for 20 hours, then under a stream of nitrogen for 24 hours to give the title compound as a brown oil (13.2 g, 69% yield). MS (m/z) 188.1 (M–28⁺).

Intermediate 18:
(5-(methoxycarbonyl)furan-2-yl)boronic acid

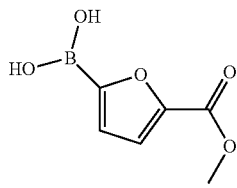

Isopropylmagnesium chloride (2 M in THF) (14.36 ml, 28.7 mmol) was added to a solution of 2,2'-oxybis(N,N-dimethylethanamine) (5.47 ml, 28.7 mmol) in tetrahydrofuran (130 ml) at 15° C. After stirring for 25 minutes, methyl 5-bromofuran-2-carboxylate (3.27 g, 15.95 mmol) was added and the reaction was stirred at room temperature for 35 minutes. The reaction was cooled to 0° C. in an ice bath and trimethyl borate (8.91 ml, 80 mmol) was added and the reaction stirred at 0° C. for 10 minutes and then quenched with 1 N HCl to ~pH 6 and then with 6 N HCl until ~pH 2. The mixture was extracted with EtOAc (2×). The organic layers were dried over Na₂SO₄ filtered and concentrated. The resultant brown solid was triturated with hexanes/EtOAc to give the title compound as a beige solid (2.15 g, 79% yield). MS (m/z) 171.1 (M+H⁺).

Intermediate 19: ((R)—N-((2-((N-(benzyloxy)formamido)methyl)heptanamido)methyl)-5-bromofuran-2-carboxamide

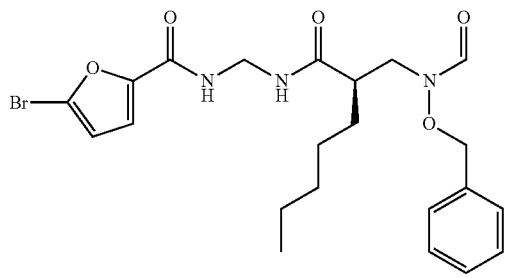 [SMILES: CCCCC[C@H](CN(C=O)OCc1ccccc1)C(=O)NCNC(=O)c1ccc(Br)o1]

A solution of N-(aminomethyl)-5-bromofuran-2-carboxamide (0.75 g, 3.4 mmol) in DCM (4.8 ml) was added to a suspension of (R)-2-((N-(benzyloxy)formamido)methyl) heptanoic acid (1 g, 3.41 mmol), EDC (0.72 g, 3.75 mmol) and DIPEA (1.79 ml, 10.23 mmol) in DCM (4.8 ml). After stirring overnight, the reaction mixture was diluted with water and the organics were collected via hydrophobic frit and concentrated. The residue was then dissolved in the minimum amount of DCM and purified by flash chromatography (20 g Si SPE, eluted with DCM, 50:50 DCM: ether, ether), concentration of the appropriate fractions yielded the title compound as a white solid (1.03 g, 61% yield). MS (m/z) 496.0 (M+2⁺).

Intermediate 20: N—(((R)-2-((R)-1-(N-(benzyloxy) formamido)propyl)heptanamido)methyl)-5-bromo-furan-2-carboxamide

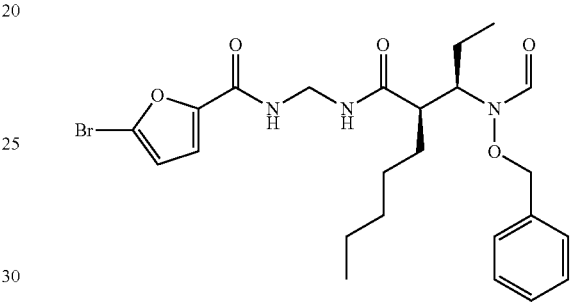

(R)-2-((R)-1-(N-(benzyloxy)formamido)propyl)heptanoic acid (8.26 ml, 22.1 mmol) was dissolved in N,N-dimethylformamide (91 ml) and treated with N-(aminomethyl)-5-bromofuran-2-carboxamide (4.84 g, 22.1 mmol), HBTU (8.80 g, 23.2 mmol) and DIPEA (11.57 ml, 66.3 mmol). The reaction mixture was stirred at room temperature for 4 hours. The reaction was then diluted with water and EtOAc. The layers were separated, and the organics were washed with brine, concentrated and the residue purified by flash chromatography (ISCO, 330 g column, 0-100% EtOAc/hexanes over 30 minutes) to give the title compound as a white foam (9.9 g, 86% yield). MS (m/z) 522.2 (M⁺).

Intermediate 21: N-((3-(N-(benzyloxy)formamido) propanamido)methyl)-5-bromofuran-2-carboxamide

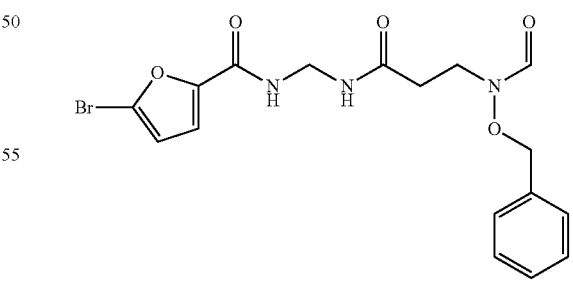

A mixture of N-(aminomethyl)-5-bromofuran-2-carboxamide, hydrochloride (200 mg, 0.78 mmol), 3-(N-(benzyloxy)formamido)propanoic acid (0.19 ml, 0.78 mmol), EDC (300 mg, 1.57 mmol), HOBT (144 mg, 0.94 mmol), and N-methylmorpholine (0.26 ml, 2.35 mmol) in dichloromethane (4 ml) was stirred at room temperature overnight. 1 N HCl (10 ml) and DCM (5 ml) were then added and the mixture stirred for 20 minutes. The layers were then separated and the organic passed through a phase separator and concentrated. The residue was purified by flash chromatography (ISCO Combiflash Rf, 25 g column, 0-100% ethyl acetate/dichloromethane) to give the title compound (295 mg, 89% yield) which was dried under vacuum overnight and then used without further purification. MS (m/z) 424.0 (M$^+$).

Intermediate 22: ethyl 3-bromo-5-ethoxy-2-hydroxybenzoate

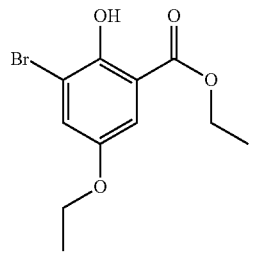 [SMILES: CCOC(=O)c1cc(OCC)cc(Br)c1O]

Step 1: ethyl 5-ethoxy-2-hydroxybenzoate

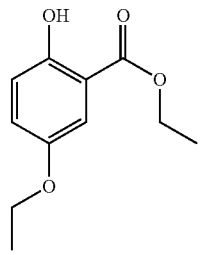

A mixture of 5-ethoxy-2-hydroxybenzoic acid (3.2 g, 17.6 mmol) in EtOH (35 ml), toluene (11 ml) and c.H$_2$SO$_4$ (0.88 ml) was heated at reflux for 12 hours. The reaction was then concentrated. The solid was dissolved in EtOAC (100 ml), washed with sat. NaHCO$_3$ dried (MgSO$_4$) and concentrated to give the title compound as a white solid (2.75 g).

Step 2: ethyl 3-bromo-5-ethoxy-2-hydroxybenzoate

Ethyl 5-ethoxy-2-hydroxybenzoate (500 mg, 2.4 mmol) was dissolved in glacial acetic acid (2.5 ml) and treated with sodium acetate (213 mg, 2.6 ml) and the mixture cooled in an ice bath. The mixture was then removed from the ice bath and a solution of bromine (125 μl, 2.45 mmol) in acetic acid (1 ml) was added dropwise. The reaction was stirred at room temperature for 1 hour and then concentrated. Water (20 ml) and sat. aq. NaHCO$_3$ solution (50 ml) were then added and the mixture extracted with ethyl acetate (50 ml). The reaction was repeated under the same conditions on a 2 g scale and the combined ethyl acetate extracts were dried over MgSO$_4$ and concentrated. The residue was crystallized from hexanes to give the title compound as a pink solid (2 g).

Intermediate 23: methyl 3-bromo-5-propoxybenzoate

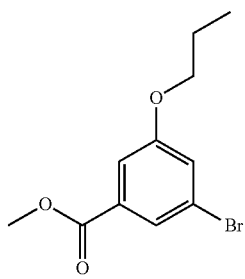

A mixture of methyl 3-bromo-5-hydroxybenzoate (200 mg, 0.87 mmol) and K$_2$CO$_3$ (598 mg, 4.33 mmol) in acetonitrile (8.54 ml) was treated with 1-iodopropane (0.12 ml, 1.21 mmol) and the reaction mixture heated to 70° C. overnight. The reaction was cooled to room temperature and then filtered. The filtrate was concentrated and the residue partitioned between DCM (10 ml) and water (5 ml). The organic phase was passed through a hydrophobic frit and concentrated to give the title compound (203 mg, 86% yield). MS (m/z) 274.9 (M+2$^+$).

Intermediate 24: ethyl 4-bromo-2-ethoxybenzoate

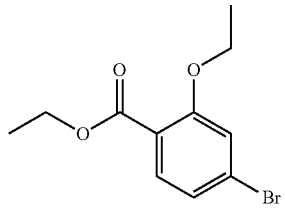

Iodoethane (17.20 ml, 213 mmol) was added dropwise to a mixture of 4-bromo-2-hydroxybenzoic acid (22 g, 101 mmol) and potassium carbonate (70.1 g, 507 mmol) in acetonitrile (659 ml) and the reaction mixture heated to 80° C. After 3.5 hours DMF (300 ml) was added. The temperature was lowered to 50° C. and the reaction stirred overnight. The reaction mixture was then cooled to room temperature and combined with another reaction conducted on a 5 g scale using the same conditions (except the 5 g scale reaction was stirred overnight at 40° C.), and filtered. The volatiles were removed in vacuo and ethyl acetate (500 ml) added. The organic layer was washed twice with water, separated and concentrated to give the title compound (34 g, 100% yield). MS (m/z) 273.0 (M+H$^+$).

Intermediate 25: methyl 2-(3-bromophenyl)propanoate

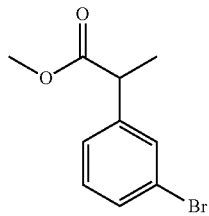

2-(3-bromophenyl)propanoic acid (1 g, 4.36 mmol) was dissolved in methanol (50 ml) and conc. $H_2SO_4$ (0.1 ml) was added and the solution stirred over the weekend. The reaction was then neutralized by the addition of aq. $NaHCO_3$ and concentrated. The residue was partitioned between water and ethyl acetate. The organic phase was separated, dried over $Na_2SO_4$, filtered and concentrated under reduced pressure to give the title compound (996 mg, 94% yield). MS (m/z) 243.0 ($M^+$).

Intermediate 26: methyl 4-bromo-2-ethoxybenzoate

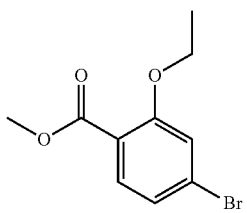

Iodoethane (6.12 ml, 76 mmol) was added dropwise to a mixture of methyl 4-bromo-2-hydroxybenzoate (5 g, 21.6 mmol) and potassium carbonate (8.97 g, 64.9 mmol) in N,N-dimethylformamide (80 ml) and the reaction mixture stirred at room temperature overnight. The mixture was then filtered, diluted with EtOAc and the organic layer washed twice with water. The organic layer was separated and then concentrated to give the title compound (5.61 g, 100% yield). MS (m/z) 261.0 ($M+2^+$).

Intermediate 27: 4-bromo-2-ethoxybenzoic acid

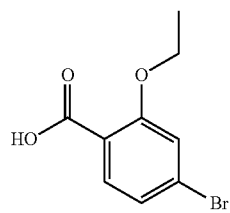

To a mixture of methyl 4-bromo-2-ethoxybenzoate (5.6 g, 21.6 mmol) in ethanol (25 ml) and tetrahydrofuran (25 ml) was added NaOH (2 M, 10.25 ml, 20.5 mmol) and the reaction stirred for 2 hours. Similarly, to a mixture of ethyl 4-bromo-2-ethoxybenzoate (33.9 g, 124 mmol) in ethanol (146 ml) and tetrahydrofuran (146 ml) was added NaOH (2 M, 62.1 ml, 124 mmol) and the reaction stirred at room temperature for 2 hours. The two reactions were then combined for workup, the volatiles were removed in vacuo and the residual aqueous extracted with DCM. The aqueous layer was then adjusted to ~pH 4 via addition of 6 N HCl. The mixture was then stirred and the light yellow solid collected by filtration, washed with water and air dried to give the title compound (33 g, 92% yield) which was used without further purification. MS (m/z) 513.0 (2M+23).

Intermediate 28: 4-bromo-1-(chloromethyl)-2-ethoxybenzene

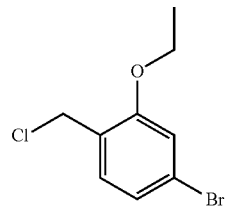

Step 1: (4-bromo-2-ethoxyphenyl)methanol

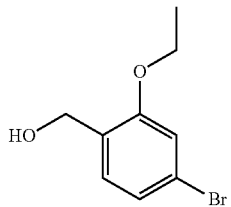

To a 250 ml flask was added 4-bromo-2-ethoxybenzoic acid (10.25 g, 41.8 mmol) and tetrahydrofuran (50 ml). The solution was cooled to 0° C. in an ice-bath and then $BH_3$.THF (1 M, 46.0 ml, 46.0 mmol) was added dropwise over ~15 minutes while keeping the temperature below 20° C. The reaction mixture was then stirred for 5 hours at room temperature and then carefully added to a saturated aq. $K_2CO_3$ solution (50 ml). The suspension was diluted with water (100 ml) and the THF layer separated and concentrated. The aqueous layer was extracted with EtOAc (3×). The residue from the concentrated THF layer was combined with the organic layer which was washed with brine and then dried ($Na_2SO_4$), filtered and concentrated to give the title compound as a yellow solid (9.68 g). MS (m/z) 213.0 ($M-17^+$).

Step 2: 4-bromo-1-(chloromethyl)-2-ethoxybenzene

To a 100 ml flask was added (4-bromo-2-ethoxyphenyl) methanol (9.68 g, 41.9 mmol) and thionyl chloride (13.76 ml, 189 mmol). The solution was heated to reflux for 15 minutes and then cooled to room temperature. The reaction was then concentrated and the residue dissolved in EtOAc, washed with saturated aq. $NaHCO_3$ and the layers separated. The aqueous layer was extracted with additional EtOAc and the combined organics were dried ($Na_2SO_4$), filtered and concentrated to give the title compound as a yellow solid (9.8 g). MS (m/z) 212.2 (fragment corresponding to loss of chlorine).

INTERMEDIATE 29 was prepared from 3-bromo-5-ethoxybenzoic acid by methods analogous to those described for Intermediate 28.

| # | Name | Structure | MS (m/z) (M + H⁺) | Name Step 1 | Step 1 MS (m/z) (M + H⁺) |
|---|------|-----------|-------------------|-------------|--------------------------|
| 29 | 1-bromo-3-(chloromethyl)-5-ethoxybenzene | 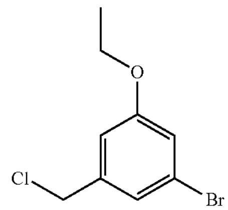 | | (3-bromo-5-ethoxyphenyl)Methanol | |

Intermediate 30: 2-(4-bromo-2-ethoxyphenyl)acetic acid

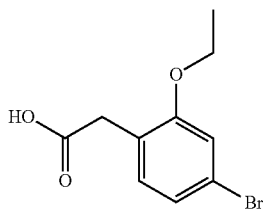

Step 1: 2-(4-bromo-2-ethoxyphenyl)acetonitrile

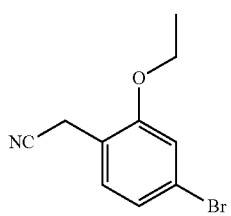

To a 100 ml flask was added 4-bromo-1-(chloromethyl)-2-ethoxybenzene (6.01 ml, 39.3 mmol), N,N-dimethylformamide (33.3 ml) and sodium cyanide (2.18 g, 43.2 mmol). The solution was stirred at room temperature overnight under nitrogen. The reaction was then diluted by the addition of NH₄Cl and EtOAc. The biphasic solution was diluted with water, the EtOAc layer separated and the aqueous extracted with additional EtOAc. The combined organic layers were washed with brine (2×), dried (Na₂SO₄), filtered and concentrated to give the title compound as a dark oil (9.4 g) which was used without further purification or characterization.

Step 2: 2-(4-bromo-2-ethoxyphenyl)acetic acid

To a 250 ml flask was added 2-(4-bromo-2-ethoxyphenyl)acetonitrile (5.79 ml, 39.3 mmol) followed by a solution of NaOH (11.5 g, 288 mmol) dissolved in water (140 ml). The reaction was heated to reflux for 5 hours, then cooled to room temperature and stirred for 7 hours. The reaction was extracted with DCM, and while stirring rapidly was acidified via addition of 6 N HCl. The resulting suspension was stirred at room temperature for 15 minutes and then filtered. The solids were dried under reduced pressure to give the title compound as a light yellow solid (8.9 g). MS (m/z) 278.0 (M+18⁺).

INTERMEDIATE 31 was prepared from 3-bromo-5-ethoxybenzoic acid by methods analogous to those described for Intermediate 30.

| # | Name | Structure | MS (m/z) | Name Step 1 | MS (m/z) (M + H⁺) Step 1 |
|---|------|-----------|----------|-------------|---------------------------|
| 31 | 2-(3-bromo-5-ethoxyphenyl)acetic acid | 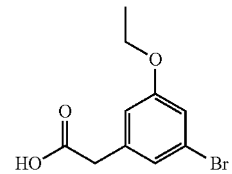 | 261.0 (M + 2⁺) | 2-(3-bromo-5-ethoxyphenyl)acetonitrile | |

Intermediate 32: dimethyl (3-bromo-5-ethoxyphenyl)phosphonate

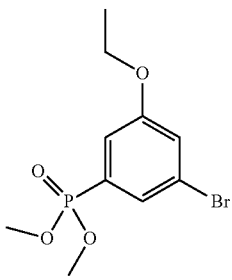 [SMILES: CCOc1cc(Br)cc(P(=O)(OC)OC)c1]

Step 1: 1-bromo-3-ethoxy-5-iodobenzene

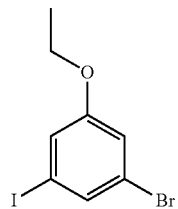

To a 250 ml flask was added CH₃CN (158 ml), 3-bromo-5-iodophenol (12.1 g, 40.5 mmol), potassium carbonate (28.0 g, 202 mmol), and iodoethane (3.60 ml, 44.5 mmol). The mixture was heated to 80° C. overnight and then cooled to room temperature. The reaction was filtered and the solids washed with CH₃CN. The filtrate was concentrated and the residue was stirred with hexanes, then filtered and the solid washed with hexanes. The hexanes was concentrated to give the title compound as a yellow oil (13.2 g, 100% yield). MS (m/z) 328.9 (M+2⁺).

Step 2: dimethyl (3-bromo-5-ethoxyphenyl)phosphonate

To a 250 ml flask was added 1-bromo-3-ethoxy-5-iodobenzene (13.24 g, 40.5 mmol), Pd(OAc)₂ (0.91 g, 4.05 mmol) and trimethyl phosphate (10.77 ml, 92 mmol). The reaction was heated to 105° C. for 1 h. Additional Pd(OAc)₂ (0.91 g, 4.05 mmol) was added. After an additional 1.5 h, Pd(OAc)₂ (0.91 g, 4.05 mmol) was added along with trimethyl phosphite (4.79 ml, 40.5 mmol) and the reaction temperature increased to ~110° C. Additional trimethyl phosphite (5.98 ml, 50.63 mmol) was added and the reaction observed to go to completion in 1 hour. The reaction was cooled to room temperature, diluted with Et₂O and then filtered. The filtrate was concentrated, and the residue stirred with hexanes. The hexanes was decanted and the process repeated twice with additional hexanes. The combined hexanes decants were washed with water, dried over Na₂SO₄, filtered and concentrated to give the title compound as an orange oil. (7.56 g, 60% yield). MS (m/z) 309.0 (M⁺).

Intermediate 33: Dimethyl (3-bromophenyl)phosphonate

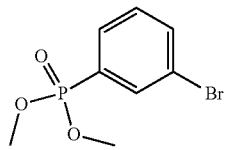

A mixture of 1-bromo-3-iodobenzene (5 g, 17.70 mmol), trimethyl phosphite (2.19 ml, 18.55 mmol) and palladium acetate (0.31 g, 1.38 mmol) was stirred in a sealed vial at 90° C. overnight. Further trimethyl phosphite (1.4 ml, 11.86 mmol) was added and the reaction heated for an additional 5 hours. After cooling, diethyl ether was added and the black mixture was filtered over Celite®. The solvent was evaporated and the residue was purified by flash chromatography (Biotage SP1, SNAP silica column, 0-10% methanol/DCM) to give the title compound (4.68 g, 99.8% yield). MS (m/z) 266.8 (M+H⁺).

Intermediate 34: dimethyl (4-bromo-2-ethoxyphenyl)phosphonate

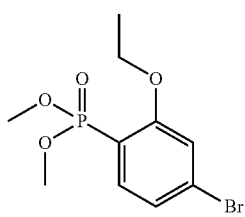 [SMILES: CCOc1cc(Br)ccc1P(=O)(OC)OC]

Step 1: 4-bromo-2-ethoxy-1-iodobenzene

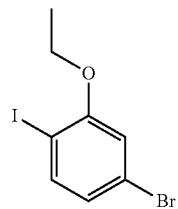

To a solution of 4-bromo-2-ethoxyaniline (8.78 g, 40.6 mmol) in acetonitrile (105 ml) at ° C. was added dropwise a solution of I₂ (20.63 g, 81 mmol) and tert-butyl nitrite (5.79 ml, 48.8 mmol) in acetonitrile (400 ml) over 30 minutes and the reaction stirred for 1.5 hours. The mixture was then quenched with aqueous Na₂SO₃ while maintaining the temperature below 10° C. and then extracted with hexanes (3×500 ml). The combined hexane extracts were dried (MgSO₄), filtered and concentrated. The residue was purified by flash chromatography (ISCO, 330 g column, 0-5% EtOAc/hexanes over 30 minutes) to give the title compound as a clear oil (6 g, 45% yield). MS (m/z) 327.2 (M+H⁺).

Step 2: dimethyl (4-bromo-2-ethoxyphenyl)phosphonate

To a 50 ml flask was added 4-bromo-2-ethoxy-1-iodobenzene (6 g, 18.35 mmol), Pd(OAc)₂ (1.03 g, 4.59 mmol) and trimethyl phosphite (3.69 ml, 31.2 mmol). The mixture was heated to 90° C. After 1 hour, additional Pd(OAc)₂ (1.03 g, 4.59 mmol) was added along with trimethyl phosphite (1.08 ml, 9.2 mmol). The temperature was increased to 105° C. and the reaction stirred at this temperature for 2.25 hour. The reaction mixture was cooled to room temperature, Et₂O was then added and the reaction was filtered through a plug of Celite®, washing with ethyl acetate. The filtrate was concentrated and the residue purified by flash chromatography (ISCO, 120 g column, 0-100% EtOAc in DCM over 30 minutes) to give the title compound as a light orange oil (5.1 g, 90% yield) which was used without further purification. MS (m/z) 311.0 (M+2⁺).

Intermediate 35: dimethyl 3-bromo-5-ethoxybenzylphosphonate

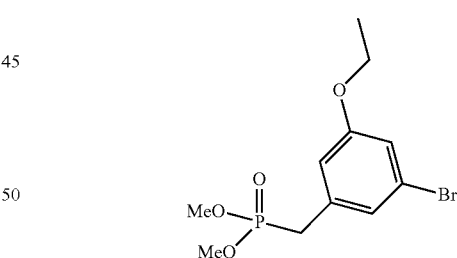

NaH (0.08 g, 2.1 mmol) was added to a solution of dimethyl phosphonate (0.23 g, 2.1 mmol) in DMF (5 ml) at 0° C. The reaction was stirred for 20 minutes, and then a solution of 1-bromo-3-(chloromethyl)-5-ethoxybenzene (0.5 g, 2 mmol) in DMF (2 ml) was added. The reaction was heated to 80° C. for 1 hour. The reaction mixture was then poured into water. The layers were separated and the aqueous layer extracted with EtOAc (3×15 ml). The organic layer was washed with brine, dried (Na₂SO₄), filtered and concentrated. The residue was purified by flash chromatography (ISCO, 25 g column, 0-5% MeOH/DCM: 15 minutes, 5-10%: 10 minutes) to give the title compound (0.25 g, 80% yield). MS (m/z) 325.0 (M+2⁺).

Intermediate 36: methyl 1-(3-bromophenyl)cyclopropanecarboxylate

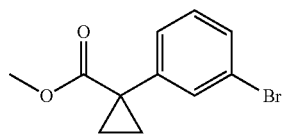

A mixture of 1-(3-bromophenyl)cyclopropanecarboxylic acid (250 mg, 1.037 mmol) and $K_2CO_3$ (717 mg, 5.18 mmol) in acetonitrile (10.3 ml) was treated with iodomethane (0.08 ml, 1.24 mmol) and the reaction mixture heated at 50° C. overnight. The reaction mixture was filtered and the filtrate concentrated. The residue was partitioned between DCM (10 ml) and water (5 ml). The organic was collected via hydrophobic frit and concentrated, the residue was placed under vacuum overnight to give the title compound (168 mg, 64% yield). MS (m/z) 256.9 (M+2$^+$).

Intermediate 37: 3-bromo-5-ethoxyphenol

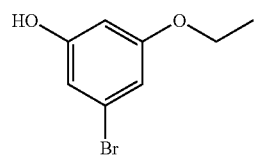

Step 1: 5-bromobenzene-1,3-diol

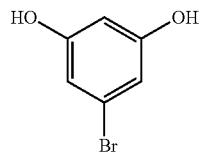

To a mixture of 1-bromo-3,5-dimethoxybenzene (15 g, 69.1 mmol) in dichloromethane (500 ml) at 0° C. was added BBr$_3$ (14.37 ml, 152 mmol) dropwise over 5 minutes at 0° C. The reaction mixture was allowed to warm to room temperature and stirred for 5 hours. The reaction was then cooled to 0° C. and BBr$_3$ (7.2 ml, 76 mmol) added dropwise. The reaction mixture was allowed to warm up to room temperature and stirred overnight. The reaction was again cooled to 0° C. and BBr$_3$ (3.6 ml, 38 mmol) added dropwise. The reaction mixture was allowed to warm up to room temperature and stirred for 4 hours. The mixture was then poured slowly onto ice. When the ice melted, DCM (200 ml) was added and the layers separated. The aqueous was extracted with EtOAc (500 ml) and the layers separated. The combined organics were passed through a through a hydrophobic frit and concentrated. The residue was purified via flash chromatography (ISCO Combiflash Rf, 220 g column, 0-100% ethyl acetate/hexanes) to give the title compound as a yellow oil (19.5 g, 70% purity). MS (m/z) 189.0 (M$^+$).

Step 2: 3-bromo-5-ethoxyphenol

To a solution of 5-bromobenzene-1,3-diol (19.5 g, 69.1 mmol) in acetonitrile (200 ml) was added potassium carbonate (11.46 g, 83 mmol). Iodoethane (5.58 ml, 69.1 mmol) was then added dropwise to the reaction and the mixture stirred at 70° C. for 3 hours. The reaction mixture was cooled to room temperature and filtered. The filtrate was concentrated and the residue dissolved in DCM (250 ml) and washed with water. The organic was passed through a phase separator and concentrated. The residue was purified via flash chromatography (ISCO Combiflash Rf, 220 g column, 0-100% ethyl acetate/hexanes) to give the title compound as a clear oil (6.2 g, 41% yield). MS (m/z) 219.0 (M+2$^+$).

Intermediate 38: 2-(3-bromo-5-ethoxyphenyl)-2,2-difluoroacetic acid

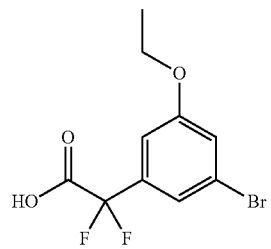 [SMILES: CCOc1cc(Br)cc(C(F)(F)C(=O)O)c1]

Step 1: ethyl 2-(3-bromo-5-ethoxyphenyl)-2,2-difluoroacetate

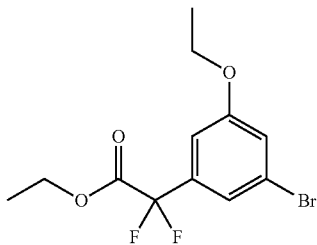 [SMILES: CCOC(=O)C(F)(F)c1cc(Br)cc(OCC)c1]

Ethyl 2-bromo-2,2-difluoroacetate (0.87 g, 4.28 mmol) was added to a suspension of copper (0.54 g, 8.56 mmol) in DMSO (7.14 ml) under N$_2$ and the reaction stirred for 1 hour at room temperature. 1-bromo-3-ethoxy-5-iodobenzene (0.7 g, 2.14 mmol) was added and the reaction was heated at 60° C. overnight. The reaction was then quenched by addition of sat. NH$_4$Cl, extracted with DCM (2×) dried over Na$_2$SO$_4$ and concentrated. The residue was purified by flash chromatography (ISCO, 80 g column, 100% hexanes: 4 minutes, 0-30% DCM/hexanes: 15 minutes) to give the title compound as a clear oil (540 mg, 78% yield). MS (m/z) 296.1 (fragment corresponding to acid).

Step 2: 2-(3-bromo-5-ethoxyphenyl)-2,2-difluoroacetic acid

A solution of ethyl 2-(3-bromo-5-ethoxyphenyl)-2,2-difluoroacetate (0.6 g, 1.86 mmol) in methanol (3.5 ml) and THF (3.5 ml) was treated with sodium hydroxide (1.02 ml, 2.04 mmol) for 1.5 hours. The solvents were removed under reduced pressure and the residue was acidified with 6 N HCl. The mixture was extracted with EtOAc, washed with brine, dried over Na$_2$SO$_4$ and concentrated to give the title compound as a white solid (533 mg, 97% yield). MS (m/z) 294.8 (M+H$^+$).

Intermediate 39: 2-ethoxy-4-(4,4,5,5-tetramethyl-1,3,2-dioxaborolan-2-yl)benzoic acid

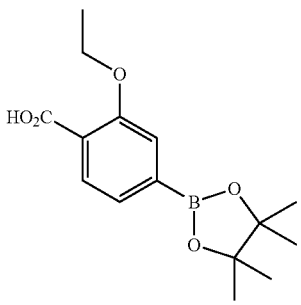 [SMILES: CCOc1cc(B2OC(C)(C)C(C)(C)O2)ccc1C(=O)O]

PdCl$_2$(dppf)-CH$_2$Cl$_2$ adduct (0.53 g, 0.64 mmol was added to a mixture of 4-bromo-2-ethoxybenzoic acid (3.15 g, 12.85 mmol), bis(pinacolato)diboron (4.90 g, 19.28 mmol), and potassium acetate (6.31 g, 64.3 mmol) in 1,4-dioxane (51.4 ml) and the reaction heated at 100° C. for 4 hours. The reaction was then diluted with EtOAc and washed with NaOH (2 N, 50 ml). The layers were separated and the organic washed with water (2×50 ml). The aqueous layer was then acidified to pH 4 via addition of 6 N HCl and extracted with ethyl acetate. The EtOAc was concentrated to give a brown oil which was purified by flash chromatography (ISCO Rf, 120 g column, 0-100% EtOAc/DCM) to give the title compound as an off white solid (2.5 g, 67% yield). MS (m/z) 211.1 (fragment corresponding to mass of boronic acid).

INTERMEDIATES 40-55 were prepared from the indicated bromide by methods analogous to those described for Intermediate 39.

| # | Name | Structure | MS (m/z) | Bromide |
|---|------|-----------|----------|---------|
| 40 | methyl 2-(3-(4,4,5,5-tetramethyl-1,3,2-dioxaborolan-2-yl)phenyl)propanoate | 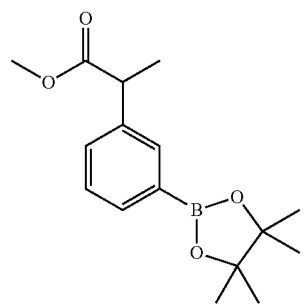 | 291.1 (M + H$^+$) | methyl 2-(3-bromophenyl)propanoate |
| 41 | 2-methyl-3-(4,4,5,5-tetramethyl-1,3,2-dioxaborolan-2-yl)benzoic acid | 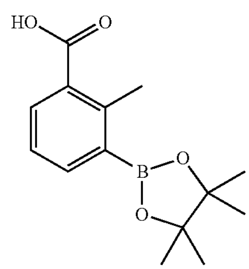 [SMILES: Cc1c(B2OC(C)(C)C(C)(C)O2)cccc1C(=O)O] | 263.1 (M + H$^+$) | 3-bromo-2-methylbenzoic acid |
| 42 | 2-amino-5-(4,4,5,5-tetramethyl-1,3,2-dioxaborolan-2-yl)benzoic acid | 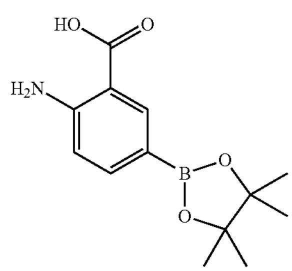 [SMILES: CC1(C)OB(c2ccc(N)c(C(=O)O)c2)OC1(C)C] | 264.1 (M + H$^+$) | 2-amino-5-bromobenzoic acid |
| 43 | 2-hydroxy-5-(4,4,5,5-tetramethyl-1,3,2-dioxaborolan-2-yl)benzoic acid | 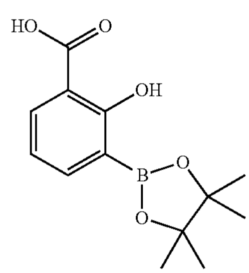 [SMILES: CC1(C)OB(c2cccc(C(=O)O)c2O)OC1(C)C] | 265.1 (M + H$^+$) | 5-bromo-2-hydroxybenzoic acid |

-continued

| # | Name | Structure | MS (m/z) | Bromide |
|---|------|-----------|----------|---------|
| 44 | 2-(3-(difluoromethoxy)phenyl)-4,4,5,5-tetramethyl-1,3,2-dioxaborolane | 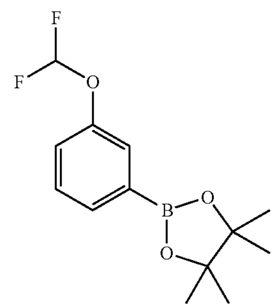 [SMILES: CC1(C)OB(c2cccc(OC(F)F)c2)OC1(C)C] | 271.1 (M + H⁺) | 1-bromo-3-(difluoromethoxy)benzene |
| 45 | ethyl 5-ethoxy-2-hydroxy-3-(4,4,5,5-tetramethyl-1,3,2-dioxaborolan-2-yl)benzoate | 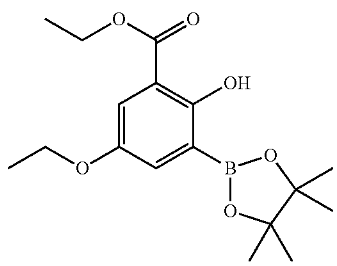 [SMILES: CCOC(=O)c1cc(OCC)cc(B2OC(C)(C)C(C)(C)O2)c1O] | 337.1 (M + H⁺) | ethyl 3-bromo-5-ethoxy-2-hydroxybenzoate |
| 46 | methyl 3-propoxy-5-(4,4,5,5-tetramethyl-1,3,2-dioxaborolan-2-yl)benzoate | 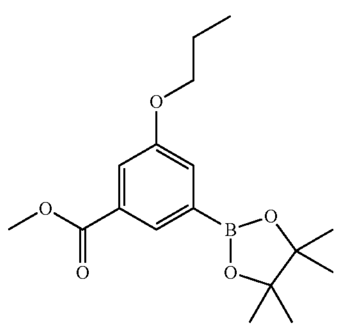 | 321.1 (M + H⁺) | methyl 3-bromo-5-propoxybenzoate |
| 47 | 2-(2-fluoro-5-(4,4,5,5-tetramethyl-1,3,2-dioxaborolan-2-yl)phenyl)acetic acid | 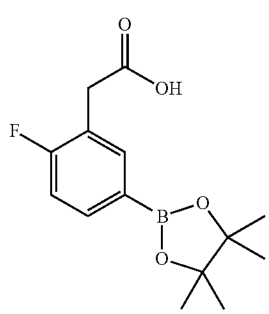 [SMILES: CC1(C)OB(c2ccc(F)c(CC(=O)O)c2)OC1(C)C] | 281.1 (M + H⁺) | 2-(5-bromo-2-fluorophenyl)acetic acid |
| 48 | 2-(3-ethoxy-5-(4,4,5,5-tetramethyl-1,3,2-dioxaborolan-2-yl)phenyl)acetic acid | 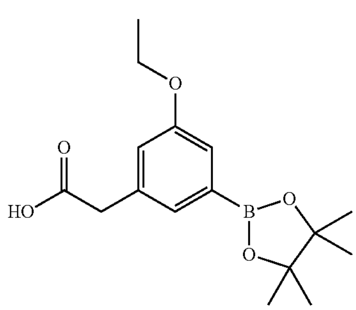 [SMILES: CCOc1cc(CC(=O)O)cc(B2OC(C)(C)C(C)(C)O2)c1] | | 2-(3-bromo-5-ethoxyphenyl)acetic acid |

-continued

| # | Name | Structure | MS (m/z) | Bromide |
|---|------|-----------|----------|---------|
| 49 | dimethyl 3-ethoxy-5-(4,4,5,5-tetramethyl-1,3,2-dioxaborolan-2-yl)benzylphosphonate | 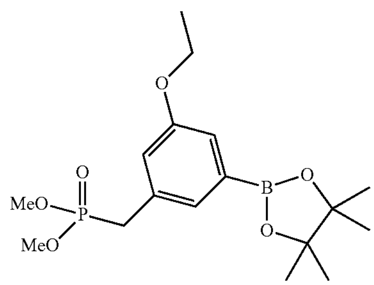 | 317.1 (M + H+) | dimethyl 3-bromo-5-ethoxybenzyl-phosphonate |
| 50 | methyl 1-(3-(4,4,5,5-tetramethyl-1,3,2-dioxaborolan-2-yl)phenyl)cyclopropane-carboxylate | 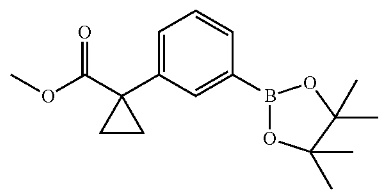 | 303.1 (M + H+) | methyl 1-(3-bromophenyl)cyclopropane-carboxylate |
| 51 | 3-ethoxy-5-(4,4,5,5-tetramethyl-1,3,2-dioxaborolan-2-yl)phenol | 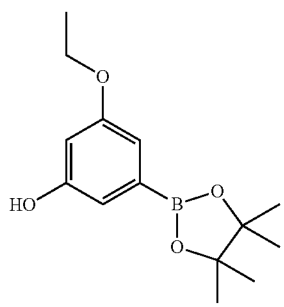 [SMILES: CCOc1cc(O)cc(B2OC(C)(C)C(C)(C)O2)c1] | 265.2 (M + H+) | 3-bromo-5-ethoxyphenol |
| 52 | 2-(2-ethoxy-4-(4,4,5,5-tetramethyl-1,3,2-dioxaborolan-2-yl)phenyl)acetic acid | 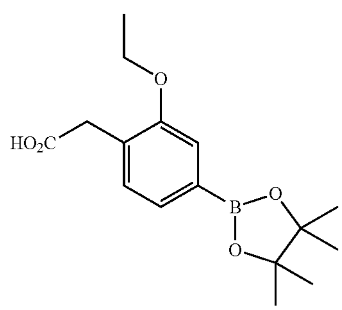 [SMILES: CCOc1cc(B2OC(C)(C)C(C)(C)O2)ccc1CC(=O)O] | | 2-(4-bromo-2-ethoxyphenyl)acetic acid |
| 53 | 2-(3-ethoxy-5-(4,4,5,5-tetramethyl-1,3,2-dioxaborolan-2-yl)phenyl)-2,2-difluoroacetic acid | 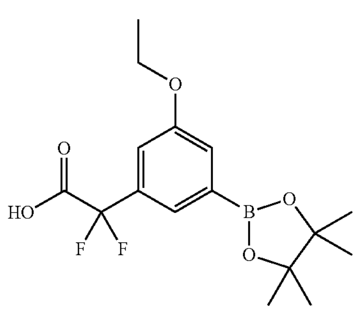 [SMILES: CCOc1cc(B2OC(C)(C)C(C)(C)O2)cc(C(F)(F)C(=O)O)c1] | 360.0 (M + 18+) | 2-(3-bromo-5-ethoxyphenyl)-2,2-difluoroacetic acid |

Intermediate 54: dimethyl (3-ethoxy-5-(4,4,5,5-tetramethyl-1,3,2-dioxaborolan-2-yl)phenyl)phosphonate

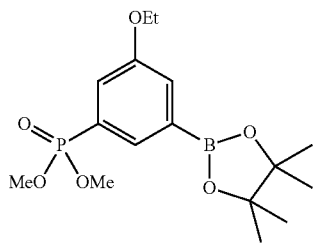 [SMILES: CCOc1cc(B2OC(C)(C)C(C)(C)O2)cc(P(=O)(OC)OC)c1]

PdCl$_2$(dppf)-CH$_2$Cl$_2$ adduct (1.00 g, 1.22 mmol) was added to a mixture of dimethyl (3-bromo-5-ethoxyphenyl)phosphonate (7.56 g, 24.46 mmol), bis(pinacolato)diboron (9.32 g, 36.7 mmol), and potassium acetate (9.60 g, 98 mmol) in 1,4-dioxane (48.9 ml) and the reaction heated at 105° C. for 3 hours. The reaction was then cooled to room temperature and diluted by the addition of Et$_2$O and water. The mixture was stirred for 5 minutes and then the layers were separated. The aqueous layer was extracted with additional ether. The combined ether extracts were filtered and concentrated to give a dark residue. Hexanes was added to the residue and the solution stirred for 5 minutes. The hexanes was decanted off and the process repeated twice more. The combined hexanes decants were dried over Na$_2$SO$_4$, filtered and concentrated to give an orange oil which was purified by flash chromatography (ISCO, 330 g column, 0-100% EtOAc/DCM over 20 minutes and then 0-20% MeOH/DCM over 20 minutes) to give the title compound as an orange oil (6.5 g, 60% yield) that crystallized on standing. MS (m/z) 275.1 (mass of boronic acid).

Intermediate 55: dimethyl (2-ethoxy-4-(4,4,5,5-tetramethyl-1,3,2-dioxaborolan-2-yl)phenyl)phosphonate

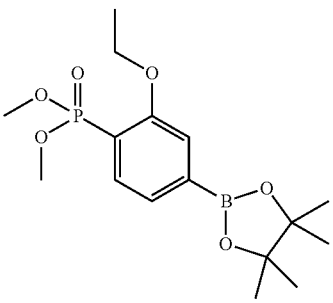

To a mixture of dimethyl (4-bromo-2-ethoxyphenyl)phosphonate (5 g, 16.18 mmol), bis(pinacolato)diboron (6.16 g, 24.26 mmol), and potassium acetate (7.94 g, 81 mmol) in 1,4-dioxane (48 ml) was added PdCl$_2$(dppf)-CH$_2$Cl$_2$ adduct (0.66 g, 0.81 mmol) and the reaction heated at 105° C. for 3.5 hours. The reaction was diluted with EtOAc, cooled to room temperature with stirring and then filtered over Celite®. The filtrate was concentrated and the residue purified via flash chromatography (ISCO Rf, 220 g column, 0-100% EtOAc/DCM over 25 minutes, 0-20% MeOH/DCM over 15 minutes) to give 3.4 g of a dark material. Et$_2$O was added to the mixture resulting in precipitation of solids. The ether was decanted and concentrated to give 2.2 g of a dark oil which was purified via flash chromatography (ISCO, 80 g column, 0-20% MeOH/DCM over 30 minutes) to give the title compound (1.4 g, 24% yield). The remaining solids were dissolved in EtOAc and then concentrated to give 1.2 g of a black residue which was purified via flash chromatography (ISCO, 80 g column, 0-20% MeOH/DCM over 30 minutes) to give an additional batch of the title compound (1.2 g). MS (m/z) 275.1 (mass of boronic acid).

Intermediate 56: (S)-dimethyl 2-(2-ethoxy-4-(4,4,5,5-tetramethyl-1,3,2-dioxaborolan-2-yl)benzamido)succinate

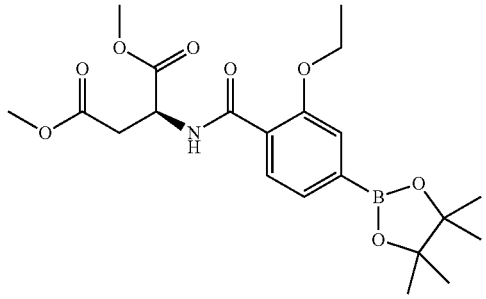

To a mixture of 2-ethoxy-4-(4,4,5,5-tetramethyl-1,3,2-dioxaborolan-2-yl)benzoic acid (500 mg, 1.71 mmol) and (S)-dimethyl 2-aminosuccinate, hydrochloride (406 mg, 2.05 mmol) in dichloromethane (5.95 ml) was added DIPEA (0.90 ml, 5.13 mmol) and added HATU (781 mg, 2.05 mmol). The reaction mixture was stirred at room temperature for 2 hours. The reaction was washed with water and the layers separated. The DCM layer was concentrated and the residue was purified via flash chromatography (ISCO Combiflash Rf, 80 g column, 20-100% ethyl acetate/hexanes) to yield the title compound as a light yellow solid (638 mg, 86% yield). MS (m/z) 436.2 (M+H$^+$).

INTERMEDIATES 57 and 58 were prepared from (S)-dimethyl 2-aminosuccinate, hydrochloride and the indicated acid by methods analogous to those described for Intermediate 56.

| # | Name | Structure | MS (m/z) (M + H$^+$) | Acid |
|---|---|---|---|---|
| 57 | S)-dimethyl 2-(3-ethoxy-5-(4,4,5,5-tetramethyl-1,3,2-dioxaborolan-2-yl)benzamido)succinate | 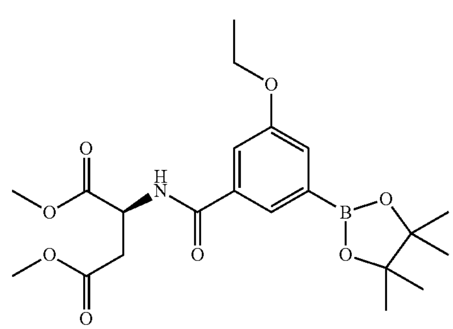 | 436.1 | 3-ethoxy-5-(4,4,5,5-tetramethyl-1,3,2-dioxaborolan-2-yl)benzoic acid |

| # | Name | Structure | MS (m/z) (M + H+) | Acid |
|---|------|-----------|---------------------|------|
| 58 | (S)-dimethyl 2-(2-(2-ethoxy-4-(4,4,5,5-tetramethyl-1,3,2-dioxaborolan-2-yl)phenyl)acetamido)succinate | 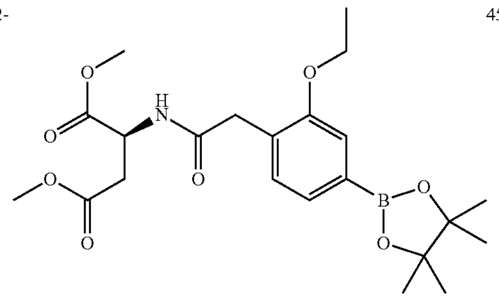 | 450.2 | 2-(2-ethoxy-4-(4,4,5,5-tetramethyl-1,3,2-dioxaborolan-2-yl)phenyl)acetic acid |

Intermediate 59: 5-(3-(ethoxy(methyl)phosphoryl)phenyl)furan-2-carboxylic acid

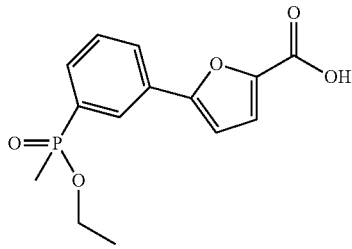 [SMILES: CCOP(C)(=O)c1cccc(-c2ccc(C(=O)O)o2)c1]

Step 1: ethyl (3-bromophenyl)phosphinate

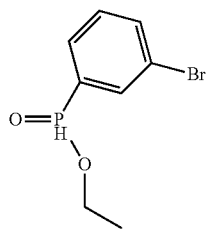

n-BuLi (2.65 ml, 1.6 M in hexanes, 4.24 mmol) was added dropwise to a solution of 1,3-dibromobenzene (0.51 ml. 4.24 mmol) in THF (15 ml) at −78° C. After stirring for 30 minutes at −78° C. the reaction mixture was cannulated into a stirred solution of diethyl chlorophosphite (0.61 ml, 8.48 mmol) in THF (5 ml) at −78° C. The reaction mixture was stirred −78° C. for 1 hour then quenched with saturated aqueous NH$_4$Cl solution (20 ml). The reaction mixture was extracted with EtOAc (100 ml). The organic layer was washed with brine (25 ml), dried over Na$_2$SO$_4$, filtered and concentrated under reduced pressure. The residue was purified by flash chromatography (50 g SNAP silica column, 20-100% EtOAc/cyclohexane) to give the title compound as a colorless oil (420 mg, 40% yield). MS (m/z) 250.8 (M+H+).

Step 2: ethyl (3-bromophenyl)(methyl)phosphinate

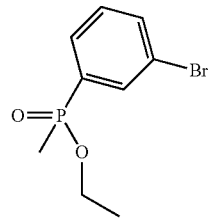

A solution of ethyl (3-bromophenyl)phosphinate (0.41 g, 1.64 mmol) in THF (5 ml) was cooled to −78° C. and deoxygenated by stirring under vacuum for 5 minutes. The flask was then back-filled with nitrogen and LHMDS (1.64 ml, 1.0 M in hexanes, 1.64 mmol) was added dropwise. After stirring for 10 minutes at −78° C., iodomethane (107 μl, 1.72 mmol) was added and the reaction mixture stirred at −78° C. for 1 hour and then allowed to warm to room temperature. The reaction mixture was quenched with saturated aqueous NH$_4$Cl solution (10 ml) and brine (10 ml) and extracted with EtOAc (40 ml). The organic layer was dried over Na$_2$SO$_4$, filtered and concentrated under reduced pressure. The residue was purified by flash chromatography (25 g SNAP silica column, 50-100% EtOAc/cyclohexanes) to give the title compound as a colorless oil (268 mg, 62% yield). MS (m/z) 264.9 (M+H+).

Step 3: 5-(3-(ethoxy(methyl)phosphoryl)phenyl)furan-2-carboxylic acid

A flask charged with DME, water and EtOH was degassed with N$_2$ for 5 minutes. Ethyl (3-bromophenyl)(methyl)phosphinate (263 mg, 1.00 mmol), monobasic potassium phosphate (136 mg, 1.00 mmol), tribasic potassium phosphate (212 mg. 1.00 mmol) and 5-boronofuran-2-carboxylic acid (203 mg, 1.30 mmol) were then added. The reaction was degassed with N$_2$ and PdCl$_2$(dbpf) (24 mg, 0.05 mmol) then added. The reaction was then stirred at room temperature for 2 hours. Further PdCl$_2$(dbpf) (24 mg, 0.05 mmol) was added and the reaction stirred overnight. The organics were evaporated and the mixture then diluted with pH 3 buffer solution (50 ml) and brine (50 ml) and extracted with EtOAc (3×50 ml) and dichloromethane (2×50 ml). The combined organic phases were dried over Na$_2$SO$_4$, filtered and evaporated under reduced pressure. The residue was purified by flash chromatography (30 g SNAP C$_{18}$ column, 0-30% CH$_3$CN in water modified with 0.1% formic acid). Fractions containing product were partially evaporated to remove the CH$_3$CN then saturated with solid NaCl and extracted with dichloromethane (3×50 ml). The combined organic phases were dried over Na$_2$SO$_4$, filtered and evaporated under reduced pressure to give the title compound as a light brown gum (164 mg, 56% yield). MS (m/z) 295.0 (M+H$^+$).

Intermediate 60: 5-(3-(dimethoxyphosphoryl)phenyl)furan-2-carboxylic acid

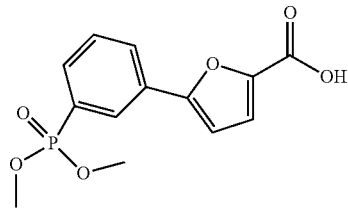 [SMILES: COP(=O)(OC)c1cccc(-c2ccc(C(=O)O)o2)c1]

Step 1: methyl 5-(3-(dimethoxyphosphoryl)phenyl)furan-2-carboxylate

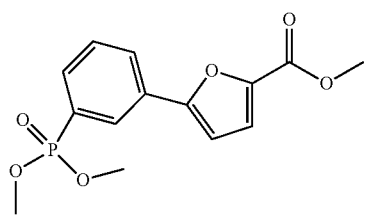 [SMILES: COC(=O)c1ccc(-c2cccc(P(=O)(OC)OC)c2)o1]

A mixture of (5-(methoxycarbonyl)furan-2-yl)boronic acid (1.5 g, 5.66 mmol, prepared according to Ishiyama, T., et al., Organic Synthesis, 2005, 82, 126-133, dimethyl (3-bromophenyl)phosphonate (1.25 g, 7.36 mmol), monobasic potassium phosphate (0.77 g, 5.66 mmol), tribasic potassium phosphate (1.2 g, 0.57 mmol) and 1,1'-Bis(di-tert-butylphosphino)ferrocene palladium (134 mg, 0.28 mmol) in DME (25 ml) and water (18.5 ml) was degassed with N$_2$ for 10 minutes and then stirred at room temperature overnight. The solvent was evaporated, the mixture was then diluted with DCM, washed with water, brine, dried over Na$_2$SO$_4$ and filtered. The solvent was evaporated and the residue was purified by flash chromatography (Biotage SP1, SNAP silica column, 50-75% EtOAc/cyclohexanes) to give the title compound as an orange oil (1.06 g, 60% yield). MS (m/z) 311.0 (M+H$^+$).

Step 2: 5-(3-(dimethoxyphosphoryl)phenyl)furan-2-carboxylic acid

A solution of methyl 5-(3-(dimethoxyphosphoryl)phenyl)furan-2-carboxylate (1.06 g, 3.42 mmol) in MeOH (13 ml) and water (4 ml) at room temperature was treated with LiOH monohydrate (155 mg, 3.76 mmol) and stirred overnight. Additional LiOH monohydrate was added (60 mg, 1.46 mmol) and the reaction stirred for 4 hours. The reaction mixture was evaporated, the residue was taken up into Et$_2$O and acidified with 1N HCl to pH 2. The aqueous was extracted with Et$_2$O (3×). The combined organics were washed with brine, dried over Na$_2$SO$_4$, filtered and concentrated to dryness. The residue was purified by flash chromatography (Biotage SP1, SNAP silica column, 0-5% MeOH+5% AcOH/DCM) to yield the title compound (0.66 g, 65% yield). MS (m/z) 297.0 (M+H$^+$).

Intermediate 61: 5-(3-phosphonophenyl)furan-2-carboxylic acid

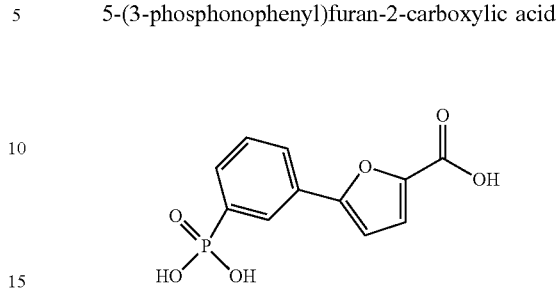

To a stirred solution of 5-(3-(dimethoxyphosphoryl)phenyl)furan-2-carboxylic acid (22 mg, 0.07 mmol) in dichloromethane (1.0 ml) was added bromotrimethyl silane (0.1 ml, 0.74 mmol) and the reaction mixture was stirred at room temperature for 1 hour. The reaction was quenched with 1 M NaOH solution (1 ml) and diluted with water (2 ml) and dichloromethane (5 ml). The organic phase was discarded and the aqueous phase was acidified to pH 1 via addition of 3 M HCl solution. The aqueous phase was then saturated with solid NaCl and dichloromethane (5 ml) added, resulting in emulsion formation. Addition of EtOAc (15 ml) and a few drops of MeOH failed to resolve the emulsion. The emulsion was filtered and the solid collected to give the title compound as a white solid (14 mg, 71 5 yield). MS (m/z) 269.0 (M+H$^+$).

Intermediate 62: 5-(1,1-dioxido-2,3-dihydrobenzo[d]isothiazol-6-yl)furan-2-carboxylic acid

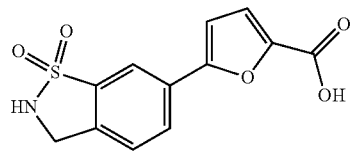 [SMILES: O=C(O)c1ccc(-c2ccc3c(c2)S(=O)(=O)NC3)o1]

Step 1: methyl 5-(1,1-dioxido-2,3-dihydrobenzo[d]isothiazol-6-yl)furan-2-carboxylate

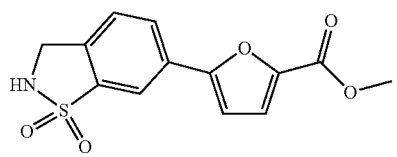 [SMILES: COC(=O)c1ccc(-c2ccc3c(c2)S(=O)(=O)NC3)o1]

A mixture of 6-bromo-2,3-dihydrobenzo[d]isothiazole 1,1-dioxide (300 mg, 1.21 mmol), (5-(methoxycarbonyl)furan-2-yl)boronic acid (267 mg, 1.57 mmol, prepared according to Ishiyama, T., et al., Organic Synthesis, 2005, 82, 126-133, monobasic potassium phosphate (164 mg, 1.21 mmol), tribasic potassium phosphate (256 mg, 1.21 mmol) and 1,1'-Bis(di-tert-butylphosphino)ferrocene palladium (29 mg, 0.06 mmol) in DME (5.5 ml), water (4 ml) and EtOH (1.4 ml) was degassed with N$_2$ for 10 minutes. The reaction was then stirred at room temperature for 5 hours. The reaction was diluted with DCM, washed with water, brine, dried over Na₂SO₄, filtered and the solvent evaporated. The residue was purified by flash chromatography (Biotage SP1, SNAP silica column, 25-50% EtOAc/cyclohexanes) to give the title compound (230 mg, 65% yield). MS (m/z) 293.9 (M+H⁺).

Step 2: 5-(1,1-dioxido-2,3-dihydrobenzo[d]isothiazol-6-yl)furan-2-carboxylic acid A solution of methyl 5-(1,1-dioxido-2,3-dihydrobenzo[d]isothiazol-6-yl)furan-2-carboxylate (230 mg, 0.78 mmol) in MeOH (8 ml) and water (2 ml) was treated with LiOH monohydrate (39 mg, 0.940 mmol) and stirred at room temperature for 5 hours. The reaction was concentrated and the residue taken into Et₂O and acidified to pH 2 via addition of 1 N HCl. The aqueous was extracted with Et₂O (3×). The combined organics were washed with brine, dried over Na₂SO₄, filtered and concentrated to give the title compound (210 mg, 97% yield). MS (m/z) 280.1 (M+H⁺).

Intermediate 63: 6-(((tert-butyldimethylsilyl)oxy)methyl)-2,2,3,3,9,9,10,10-octamethyl-4,8-dioxa-3,9-disilaundecan-6-amine

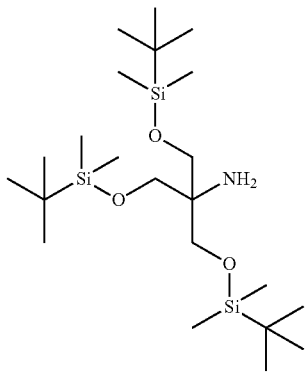 [SMILES: CC(C)(C)[Si](C)(C)OCC(N)(CO[Si](C)(C)C(C)(C)C)CO[Si](C)(C)C(C)(C)C]

A mixture of 2-amino-2-(hydroxymethyl)propane-1,3-diol (100 mg, 0.83 mmol), TBDMSCl (622 mg, 4.13 mmol) and imidazole (562 mg, 8.26 mmol) in N,N-dimethylformamide (0.5 ml) was stirred at room temperature overnight. The reaction was then reduced in volume and diluted with EtOAc (5 ml) and washed with water (3×10 ml). The organic layer was separated, passed through a phase separator and concentrated to give the title compound (491 mg) which was used without further purification.

Intermediate 64: (R)—N-((2-((N-(benzyloxy)formamido)methyl)heptanamido)methyl)-5-phenylfuran-2-carboxamide

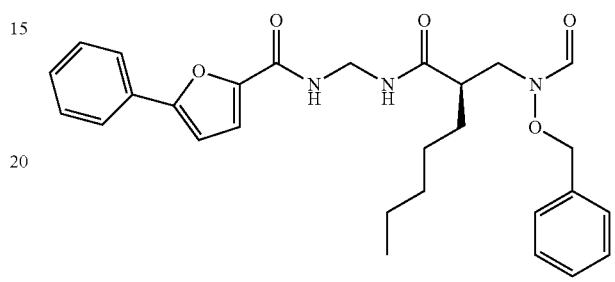

A mixture of N-(aminomethyl)-5-phenylfuran-2-carboxamide (1.62 g, 7.50 mmol), (R)-2-((N-(benzyloxy)formamido)methyl)heptanoic acid (2 g, 6.82 mmol), HOBt (1.15 g, 7.50 mmol), and Et₃N (2.85 ml, 20.45 mmol) in N,N-dimethylformamide (40 ml) was treated with EDC (1.44 g, 7.50 mmol) and stirred at 25° C. for 4 hours before being quenched with the addition of water and extracted with EtOAc. The organic extracts were washed with 1 N HCl, saturated aq. NaHCO₃, brine and then dried (sodium sulfate), and concentrated. The was subjected to flash chromatography (50-100% EtOAc/hexanes, sample loaded as a CH₂Cl₂ solution) to give a colorless oil, which crystallized upon addition of Et₂O. The solid was collected by filtration, washed with Et₂O, and dried to give the title compound (1.5 g, 41% yield) as a white solid. MS (m/z) 492.2 (M+H⁺).

INTERMEDIATE 65 was prepared from N-(aminomethyl)-5-phenylfuran-2-carboxamide and the indicated acid by methods analogous to those described for Intermediate 64 utilizing DIPEA as the base instead of Et₃N.

| # | Name | Structure | MS (m/z) (M + H⁺) | Acid |
|---|------|-----------|-------------------|------|
| 65 | N-(((R)-2-((S)-1-(N-(benzyloxy)formamido)-2-hydroxyethyl)heptanamido)methyl)-5-phenylfuran-2-carboxamide | 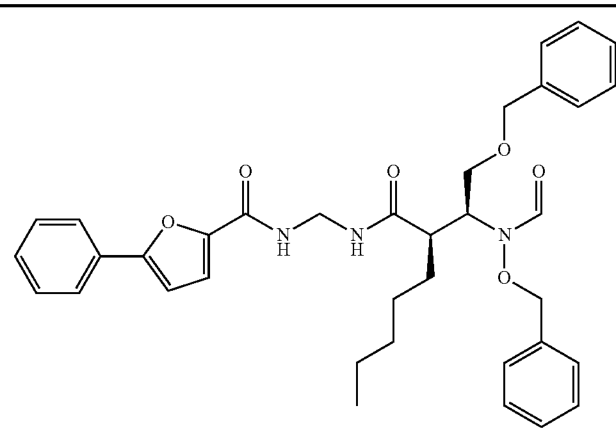 | 612.1 | (R)-2-((S)-2-(benzyloxy)-1-(N-(benzyloxy)formamido)ethyl)heptanoic acid |

INTERMEDIATES 66-68 were prepared from N-(aminomethyl)-5-phenylfuran-2-carboxamide and the indicated acid by methods analogous to those described for Intermediate 64 using DIPEA as the base instead of Et$_3$N and conducting the reaction at 50° C. instead of at room temperature. Intermediates 67 and 68 used THF as solvent instead of DMF.

A solution of N-(aminomethyl)-5-(3-(methylsulfonyl)phenyl)furan-2-carboxamide (0.11 g, 0.36 mmol), (R)-2-((N-(benzyloxy)formamido)methyl)-4-phenylbutanoic acid (0.12 g, 0.36 mmol), HATU (0.16 g, 0.43 mmol), and DIPEA (0.19 ml, 1.07 mmol) in N,N-dimethylformamide (2 ml) was stirred at room temperature overnight. Water was

| | Name | Structure | MS (m/z) (M + H$^+$) | Acid |
|---|---|---|---|---|
| 66 | (R)-N-((3-(N-(benzyloxy)formamido)-2-(cyclopentylmethyl)propanamido)methyl)-5-phenylfuran-2-carboxamide | 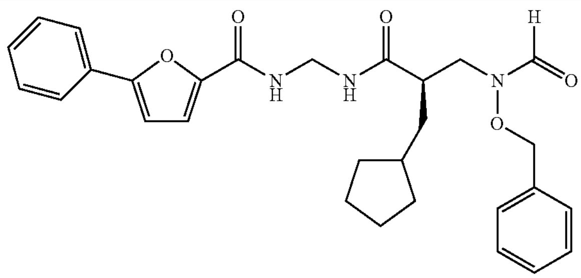 [SMILES: O=CN(C[C@@H](CC1CCCC1)C(=O)NCNC(=O)c1ccc(-c2ccccc2)o1)OCc1ccccc1] | 504.0 | (R)-3-(N-(benzyloxy)formamido)-2-(cyclopentylmethyl)propanoic acid |
| 67 | (R)-N-((2-((N-(benzyloxy)formamido)methyl)-4-phenylbutanamido)methyl)-5-phenylfuran-2-carboxamide | 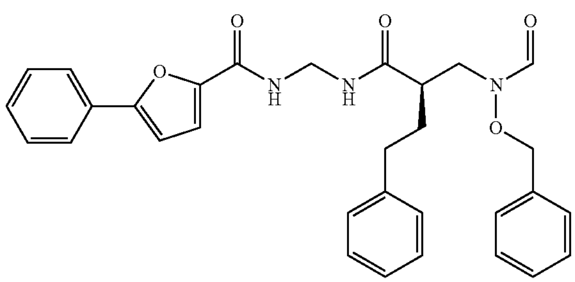 [SMILES: O=CN(C[C@@H](CCc1ccccc1)C(=O)NCNC(=O)c1ccc(-c2ccccc2)o1)OCc1ccccc1] | 526.2 | (R)-2-((N-(benzyloxy)formamido)methyl)-4-phenylbutanoic acid |
| 68 | (R)-N-((2-((N-(benzyloxy)formamido)methyl)-5-phenylpentanamido)methyl)-5-phenylfuran-2-carboxamide | 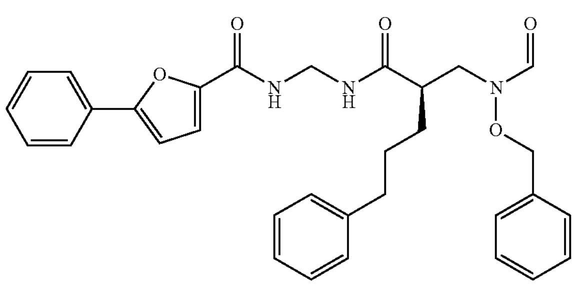 [SMILES: O=CN(C[C@@H](CCCc1ccccc1)C(=O)NCNC(=O)c1ccc(-c2ccccc2)o1)OCc1ccccc1] | 540.3 | (R)-2-((N-(benzyloxy)formamido)methyl)-5-phenylpentanoic acid |

Intermediate 69: (R)—N-((2-((N-(benzyloxy)formamido)methyl)-4-phenylbutanamido)methyl)-5-(3-(methylsulfonyl)phenyl)furan-2-carboxamide

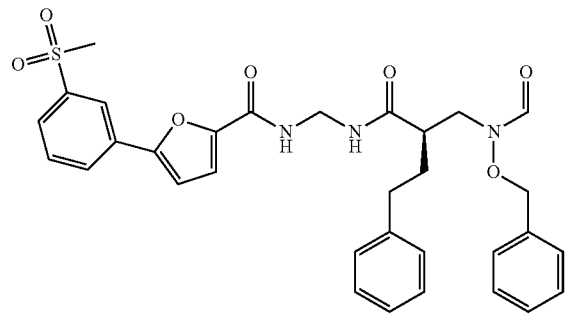 [SMILES: CS(=O)(=O)c1cccc(-c2ccc(C(=O)NCNC(=O)[C@H](CCc3ccccc3)CN(C=O)OCc3ccccc3)o2)c1]

added and the reaction was extracted twice with EtOAc. The combined organic extracts were washed with water (3×), dried over Na$_2$SO$_4$, filtered and concentrated. The residue was purified via flash chromatography (ISCO, 24 g silica column, 0-60% EtOAc/DCM: 15 minutes, 60% EtOAc: 6 minutes, 60-100% EtOAc/DCM: 5 minutes, 100% EtOAc: 5 minutes) to give the title compound as a sticky white solid (0.143 g, 66.4% yield). MS (m/z) 604.2 (M+H$^+$).

INTERMEDIATE 70 was prepared from N-(aminomethyl)-5-(3-(2,2,2-trifluoroethoxy)phenyl)furan-2-carboxamide and the indicated acid by methods analogous to those described for Intermediate 69.

| # | Name | Structure | MS (m/z) (M + H⁺) | Acid |
|---|---|---|---|---|
| 70 | (R)-N-((2-((N-(benzyloxy)formamido)methyl)heptanamido)methyl)-5-(3-(2,2,2-trifluoroethoxy)phenyl)furan-2-carboxamide | 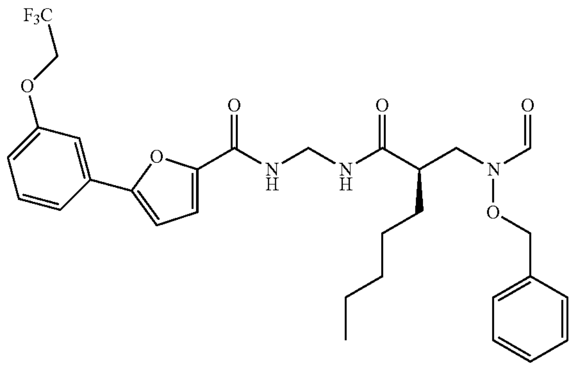 [SMILES: CCCCC[C@H](CN(C=O)OCc1ccccc1)C(=O)NCNC(=O)c1ccc(-c2cccc(OCC(F)(F)F)c2)o1] | 590.2 | (R)-2-((N-(benzyloxy)formamido)methyl)heptanoic acid |

INTERMEDIATE 71 was prepared from N-(aminomethyl)-5-(3-(2-(pyrrolidin-1-yl)ethoxy)phenyl)furan-2-carboxamide and the indicated acid by methods analogous to those described for Intermediate 69 utilizing HBTU as the coupling reagent instead of HATU and DCM as the solvent instead of DMF.

| # | Name | Structure | MS (m/z) (M + H⁺) | Acid |
|---|---|---|---|---|
| 71 | (R)-N-((2-((N-(benzyloxy)formamido)methyl)heptanamido)methyl)-5-(3-(2-(pyrrolidin-1-yl)ethoxy)phenyl)furan-2-carboxamide | 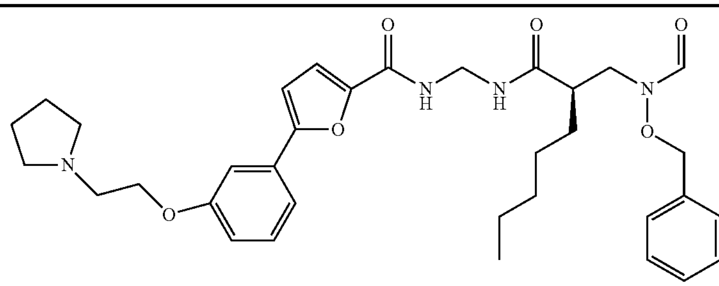 | 605.4 | (R)-2-((N-(benzyloxy)formamido)methyl)heptanoic acid |

INTERMEDIATE 72 was prepared from N-(aminomethyl)-5-phenylfuran-2-carboxamide and the indicated acid by methods analogous to those described for Intermediate 69 utilizing HBTU as the coupling reagent instead of HATU.

| # | Name | Structure | MS (m/z) (M + H⁺) | Acid |
|---|---|---|---|---|
| 72 | N-(((R)-2-((R)-1-(N-(benzyloxy)formamido)propyl)heptanamido)methyl)-5-phenylfuran-2-carboxamide | 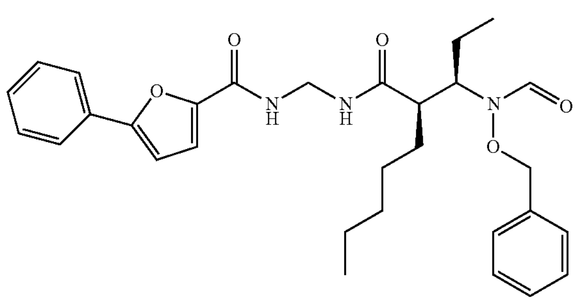 [SMILES: CCCCC[C@@H](C(=O)NCNC(=O)c1ccc(-c2ccccc2)o1)[C@@H](CC)N(C=O)OCc1ccccc1] | 520.3 | (R)-2-((R)-1-(N-(benzyloxy)formamido)propyl)heptanoic acid |

Intermediate 73: (R)—N-((2-((N-(benzyloxy)formamido)methyl)heptanamido)methyl)-5-(4-methoxypyridin-2-yl)furan-2-carboxamide

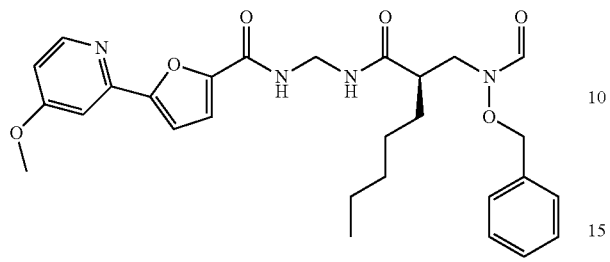

(R)—N-(aminomethyl)-2-((N-(benzyloxy)formamido)methyl)heptanamide (0.1 g, 0.31 mmol) in dichloromethane (1 ml) was added to a solution of 5-(4-methoxypyridin-2-yl)furan-2-carboxylic acid (0.07 g, 0.31 mmol), HATU (0.13 g, 0.34 mmol), and DIPEA (0.16 ml, 0.93 mmol) in N,N-dimethylformamide (1 ml) and the reaction was stirred at room temperature overnight. The reaction was then extracted with EtOAc (2×). The combined organic extracts were washed with water, dried over $Na_2SO_4$ and concentrated. The residue was treated with a pre-mixed solution of CDI (0.04 g, 0.23 mmol) and formic acid (0.01 ml, 0.31 mmol) in DCM (2 ml), and the reaction was stirred at room temperature overnight. The reaction was washed with 1N HCl, and then with water, dried over $Na_2SO_4$ and concentrated. The residue was purified by reverse phase HPLC (Waters, Sunfire $C_{18}$ OBD column, 20-60% $CH_3CN$/water (+0.1% TFA), 16 minute gradient). The fractions containing desired product were combined and neutralized with sat. $NaHCO_3$, extracted with DCM, dried over $Na_2SO_4$ and concentrated to give the title compound as a thick oil (57 mg, 35% yield). MS (m/z) 523.2 (M+H$^+$).

Intermediate 74: ethyl (3-(5-((((R)-2-((N-(benzyloxy)formamido)methyl)heptanamido)methyl)carbamoyl)furan-2-yl)phenyl)(methyl)phosphinate

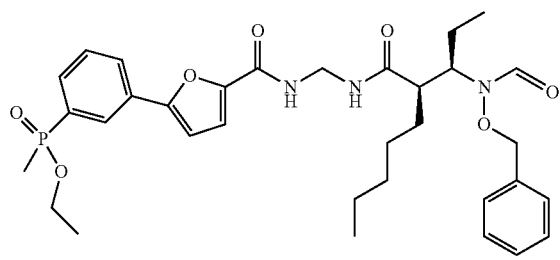 [SMILES: CCCCC[C@@H](C(=O)NCNC(=O)c1ccc(-c2cccc(P(C)(=O)OCC)c2)o1)[C@@H](CC)N(C=O)OCc1ccccc1]

To a mixture of 5-(3-(ethoxy(methyl)phosphoryl)phenyl)furan-2-carboxylic acid (160 mg, 0.54 mmol), DIPEA (0.19 ml, 1.09 mmol), HOBt (96 mg, 0.71 mmol) and (R)—N-(aminomethyl)-2-((N-(benzyloxy)formamido)methyl)heptanamide (175 mg, 0.54 mmol) in DCM (5 ml) was added EDC (135 mg, 0.71 mmol). The reaction mixture was stirred overnight. The reaction mixture was then diluted with EtOAc (50 ml), washed with saturated $NaHCO_3$ solution (50 ml) and brine (25 ml), dried over $Na_2SO_4$, filtered and concentrated under reduced pressure. The residue was dissolved in DCM (5 ml) and treated with a solution of CDI (31 mg, 0.19 mmol) and formic acid (8 μl) in DCM (2 ml) that had been pre-stirred for 30 minutes at room temperature. The reaction was stirred for 1 hour. The reaction was then diluted with EtOAc (50 ml) and washed with pH 3 buffer solution (50 ml), saturated $NaHCO_3$ solution (50 ml) and brine (25 ml). The organics were dried over $Na_2SO_4$, filtered and concentrated under reduced pressure. The residue was purified by flash chromatography (25 g SNAP column, 0-15% MeOH/EtOAc) to give the title compound as a pale yellow foam (274 mg, 84% yield). MS (m/z) 598.1 (M+H$^+$).

Intermediate 75: (R)-dimethyl (3-(5-(((2-((N-(benzyloxy)formamido)methyl)heptanamido)methyl)carbamoyl)furan-2-yl)phenyl)phosphonate

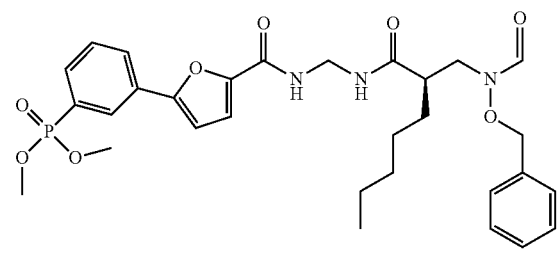 [SMILES: CCCCC[C@H](CN(C=O)OCc1ccccc1)C(=O)NCNC(=O)c1ccc(-c2cccc(P(=O)(OC)OC)c2)o1]

Step 1: (R)-dimethyl (3-(5-(((2-((N-(benzyloxy)formamido)methyl)heptanamido)methyl) carbamoyl)furan-2-yl)phenyl)phosphonate and (R)-dimethyl (3-(5-(((2-(((benzyloxy)amino)methyl)heptanamido)methyl)carbamoyl)furan-2-yl)phenyl)phosphonate

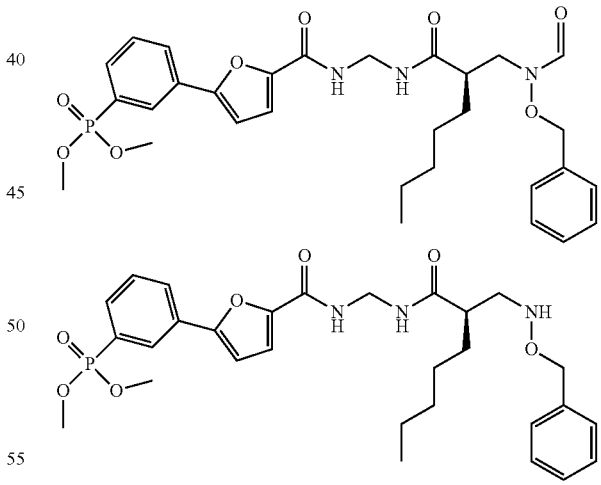

To a mixture of 5-(3-(dimethoxyphosphoryl)phenyl)furan-2-carboxylic acid (0.20 g, 0.68 mmol), DIPEA (0.22 ml, 1.24 mmol), HOBt (0.10 g, 0.75 mmol) and EDC (0.16 g, 0.81 mmol) in DCM (4 ml) under nitrogen was added dropwise a solution of (R)—N-(aminomethyl)-2-((N-(benzyloxy)formamido)methyl)heptanamide (0.20 g, 0.62 mmol) in DCM (4 ml) and the reaction stirred for 1 hour. Additional (R)—N-(aminomethyl)-2-((N-(benzyloxy)formamido)methyl) heptanamide (0.05 g, 0.16 mmol in 1 ml of DCM) was added and the reaction stirred at room temperature overnight. The reaction was then diluted with DCM, washed with saturated NaHCO₃ solution, brine, dried over Na₂SO₄, filtered and concentrated to afford a mixture of the title compounds (440 mg) which was used without further purification. MS (m/z) 600.0 (M+H⁺) and 572.3 (M+H⁺).

Step 2: (R)-dimethyl (3-(5-(((2-((N-(benzyloxy)formamido)methyl)heptanamido)methyl)carbamoyl)furan-2-yl)phenyl)phosphonate To a suspension of CDI (40 mg, 0.25 mmol) in DCM (3 ml) at 0° C. was added formic acid (12 μl, 0.31 mmol). The solution was stirred at room temperature for 20 minutes then added dropwise to a solution of (R)-dimethyl (3-(5-(((2-((N-(benzyloxy)formamido)methyl)heptanamido)methyl)carbamoyl)furan-2-yl)phenyl)phosphonate and (R)-dimethyl (3-(5-(((2-(((benzyloxy)amino)methyl)heptanamido)methyl)carbamoyl)furan-2-yl)phenyl)phosphonate (440 mg) in DCM (6 ml) at 0° C. The reaction was stirred at room temperature for 6 hours. The reaction was then diluted with DCM and quenched by addition of NaHCO₃. The organic phase was separated via hydrophobic frit and concentrated. The residue was purified by flash chromatography (SNAP silica column, 0-6% methanol/DCM) to give the title compound (310 mg). MS (m/z) 600.2 (M+H⁺).

Intermediate 76: (R)—N-((2-((N-(benzyloxy)formamido)methyl)heptanamido)methyl)-5-(1,1-dioxido-2,3-dihydrobenzo[d]isothiazol-6-yl)furan-2-carboxamide

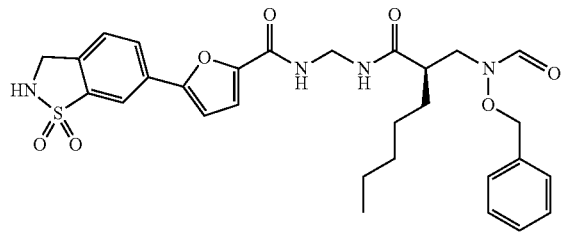

Step 1: (R)—N-((2-(((benzyloxy)amino)methyl)heptanamido)methyl)-5-(1,1-dioxido-2,3-dihydrobenzo[d]isothiazol-6-yl)furan-2-carboxamide and (R)—N-((2-((N-(benzyloxy)formamido)methyl)heptanamido)methyl)-5-(1,1-dioxido-2,3-dihydrobenzo[d]isothiazol-6-yl)furan-2-carboxamide

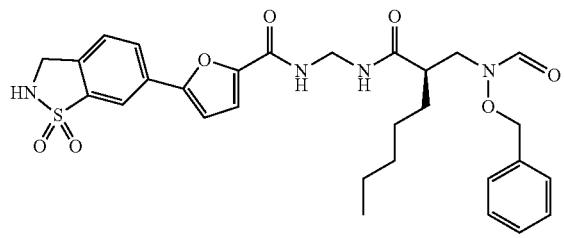 [SMILES: CCCCC[C@H](CN(C=O)OCc1ccccc1)C(=O)NCNC(=O)c1ccc(-c2ccc3c(c2)S(=O)(=O)NC3)o1]

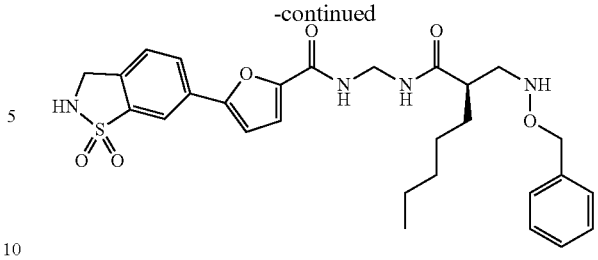

To a mixture 5-(1,1-dioxido-2,3-dihydrobenzo[d]isothiazol-6-yl)furan-2-carboxylic acid (210 mg, 0.75 mmol), DIPEA (0.26 ml, 1.5 mmol), HOBt (122 mg, 0.9 mmol) and EDC.HCl (172 mg, 0.9 mmol) in dichloromethane (4 ml) under nitrogen was added dropwise a solution of (R)—N-(aminomethyl)-2-((N-(benzyloxy)formamido)methyl)heptanamide (240 mg, 0.75 mmol) in DCM (4 ml). After 1 hour, additional (R)—N-(aminomethyl)-2-((N-(benzyloxy)formamido)methyl) heptanamide (50 mg, 0.16 mmol) dissolved in DCM (1 ml) was added and the reaction mixture was stirred at room temperature overnight. The reaction mixture was diluted with DCM and the layers separated. The organic was washed with saturated NaHCO₃ solution and brine, dried over Na₂SO₄ and concentrated under reduced pressure to give a mixture of the title compounds (400 mg) which was used without further purification. MS (m/z) 583.0 (M+H⁺) and 555.0 (M+H⁺).

Step 2: (R)—N-((2-((N-(benzyloxy)formamido)methyl)heptanamido)methyl)-5-(1,1-dioxido-2,3-dihydrobenzo[d]isothiazol-6-yl)furan-2-carboxamide To a suspension of CDI (36 mg, 0.22 mmol) in DCM (2 ml) at 0° C. was added formic acid (9 μl) and the solution was stirred at room temperature for 20 minutes then added dropwise to a solution of (R)—N-((2-(((benzyloxy)amino)methyl)heptanamido)methyl)-5-(1,1-dioxido-2,3-dihydrobenzo[d]isothiazol-6-yl)furan-2-carboxamide and (R)—N-((2-((N-(benzyloxy)formamido)methyl)heptanamido)methyl)-5-(1,1-dioxido-2,3-dihydrobenzo[d]isothiazol-6-yl)furan-2-carboxamide (400 mg) in DCM (6 ml) at 0° C. The reaction was then warmed to room temperature and stirred for 2 hours. The reaction was then diluted with DCM and quenched by addition of sat aq. NaHCO₃. The organic phase was separated via hydrophobic frit and concentrated. The residue was purified by flash chromatography (SNAP silica cartridge, 0-5% MeOH/DCM) to give the title compound (80 mg). MS (m/z) 583.2 (M+H⁺).

Intermediate 77: (R)—N-((2-((N-(benzyloxy)formamido)methyl)heptanamido)methyl)-5-(2-methoxyphenyl)furan-2-carboxamide

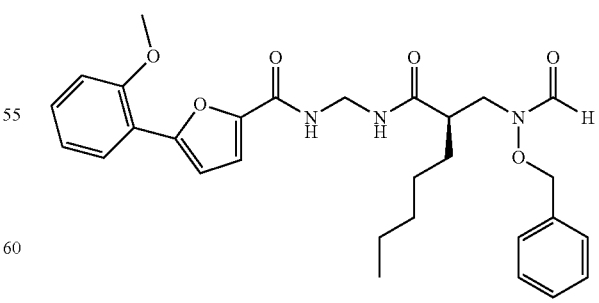

To a microwave vial charged with 1,2-dimethoxyethane (1 ml), water (0.1 ml), (R)—N-((2-((N-(benzyloxy)formamido)methyl)heptanamido)methyl)-5-bromofuran-2-carboxamide (150 mg, 0.30 mmol), K₂CO₃ (84 mg, 0.61 mmol), and (2-methoxyphenyl)boronic acid (69.2 mg, 0.46 mmol) was added Tetrakis (35.1 mg, 0.03 mmol) and the vial irradiated at 150° C. for 30 minutes in a microwave reactor (Biotage Initiator). The reaction was then poured into water and the mixture extracted with EtOAc. The organic was collected, dried (Na$_2$SO$_4$), filtered, concentrated, and the residue purified by flash chromatography (50% EtOAc/hexanes) to give the title compound (80 mg, 51% yield). MS (m/z) 522.2 (M+H$^+$).

Intermediate 78: (R)-methyl 3-(5-(((2-((N-(benzyloxy)formamido)methyl)heptanamido)methyl)carbamoyl)furan-2-yl)benzoate

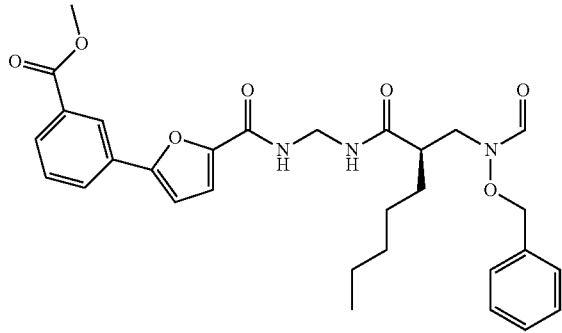 [SMILES: CCCCC[C@H](CN(C=O)OCc1ccccc1)C(=O)NCNC(=O)c1ccc(-c2cccc(C(=O)OC)c2)o1]

To a microwave reaction vessel charged with (R)—N-((2-((N-(benzyloxy)formamido)methyl)heptanamido)methyl)-5-bromofuran-2-carboxamide (150 mg, 0.30 mmol) and (3-(methoxycarbonyl)phenyl)boronic acid (65.5 mg, 0.36 mmol) and 1,4-dioxane (1.75 ml), was added PdCl$_2$(dppf)-CH$_2$Cl$_2$ adduct (24.78 mg, 0.03 mmol) and sodium carbonate (1M, 0.91 ml, 0.91 mmol). The reaction vessel was sealed and irradiated in a microwave reactor (Biotage Initiator) for 5 minutes at 100° C. The reaction mixture was concentrated and the residue purified by flash chromatography (ISCO Combiflash, 24 g column, 0-60% EtOAc/DCM, over 15 minutes) to yield the title compound (167 mg, 60% yield). (MS (m/z) 550.3 (M+H$^+$).

INTERMEDIATES 79-118 were prepared from ((R)—N-((2-((N-(benzyloxy)formamido)methyl)heptanamido)methyl)-5-bromofuran-2-carboxamide and the indicated boronic acid or boronate by methods analogous to those described for Intermediate 78.

| # | Name | Structure | MS (m/z) (M + H$^+$) | Boronic acid/Boronate |
|---|------|-----------|----------------------|------------------------|
| 79 | (R)-methyl 3-(5-(((2-((N-(benzyloxy)formamido)methyl)heptanamido)methyl)carbamoyl)furan-2-yl)-5-ethoxy-benzoate | 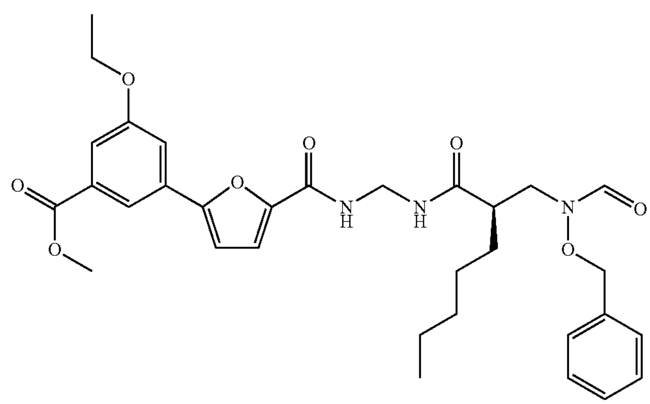 [SMILES: CCCCC[C@H](CN(C=O)OCc1ccccc1)C(=O)NCNC(=O)c1ccc(-c2cc(OCC)cc(C(=O)OC)c2)o1] | 594.2 | methyl 3-ethoxy-5-(4,4,5,5-tetramethyl-1,3,2-dioxaborolan-2-yl)benzoate |
| 80 | (R)-N-((2-((N-(benzyloxy)formamido)methyl)heptanamido)methyl)-5-(3-(dimethylamino)phenyl)furan-2-carboxamide | 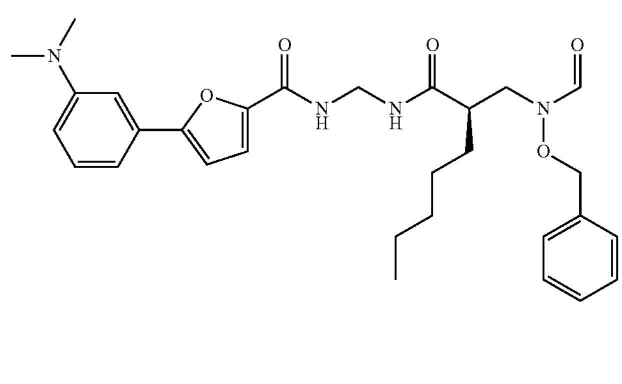 [SMILES: CCCCC[C@H](CN(C=O)OCc1ccccc1)C(=O)NCNC(=O)c1ccc(-c2cccc(N(C)C)c2)o1] | 535.2 | (3-(dimethylamino)phenyl)boronic acid |

-continued

| # | Name | Structure | MS (m/z) (M + H+) | Boronic acid/Boronate |
|---|---|---|---|---|
| 81 | (R)-N-((2-((N-(benzyloxy)formamido)methyl)heptanamido)methyl)-5-(3-(methylcarbamoyl)phenyl)furan-2-carboxamide | 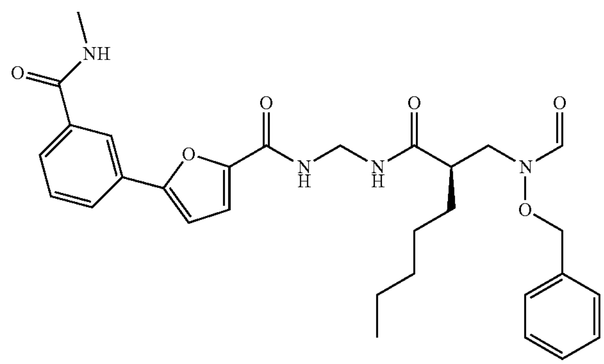 [SMILES: CCCCC[C@H](CN(C=O)OCc1ccccc1)C(=O)NCNC(=O)c1ccc(-c2cccc(C(=O)NC)c2)o1] | 549.3 | (3-(methylcarbamoyl)phenyl)boronic acid |
| 82 | (R)-N-((2-((N-(benzyloxy)formamido)methyl)heptanamido)methyl)-5-(3-(N,N-dimethylsulfamoyl)phenyl)furan-2-carboxamide | 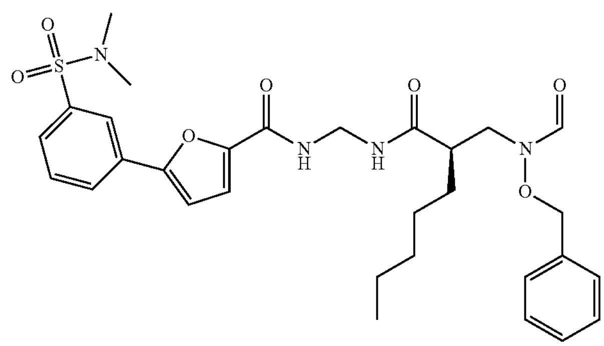 [SMILES: CCCCC[C@H](CN(C=O)OCc1ccccc1)C(=O)NCNC(=O)c1ccc(-c2cccc(S(=O)(=O)N(C)C)c2)o1] | 599.2 | (3-(N,N-dimethylsulfamoyl)phenyl)boronic acid |
| 83 | (R)-N-((2-((N-(benzyloxy)formamido)methyl)heptanamido)methyl)-5-(3-(N-methylsulfamoyl)phenyl)furan-2-carboxamide | 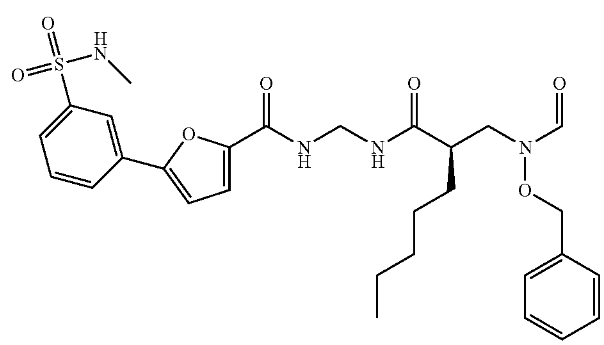 [SMILES: CCCCC[C@H](CN(C=O)OCc1ccccc1)C(=O)NCNC(=O)c1ccc(-c2cccc(S(=O)(=O)NC)c2)o1] | 585.3 | (3-(N-methylsulfamoyl)phenyl)boronic acid |
| 84 | (R)-N-((2-((N-(benzyloxy)formamido)methyl)heptanamido)methyl)-5-(3-(trifluoromethoxy)phenyl)furan-2-carboxamide | 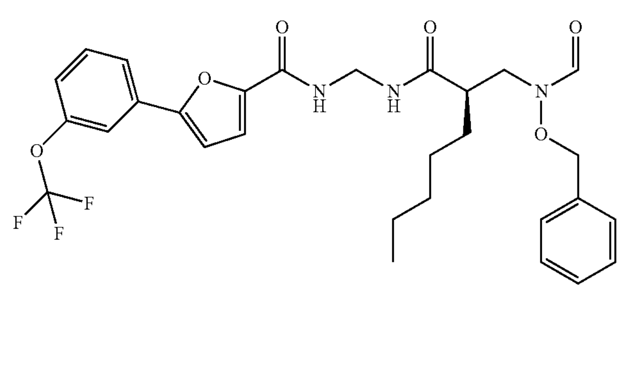 [SMILES: CCCCC[C@H](CN(C=O)OCc1ccccc1)C(=O)NCNC(=O)c1ccc(-c2cccc(OC(F)(F)F)c2)o1] | 576.2 | (3-(trifluoromethoxy)phenyl)boronic acid |

| # | Name | Structure | MS (m/z) (M + H+) | Boronic acid/Boronate |
|---|---|---|---|---|
| 85 | (R)-N-((2-((N-(benzyloxy)formamido)methyl)heptanamido)methyl)-5-(3-ethoxyphenyl)furan-2-carboxamide | 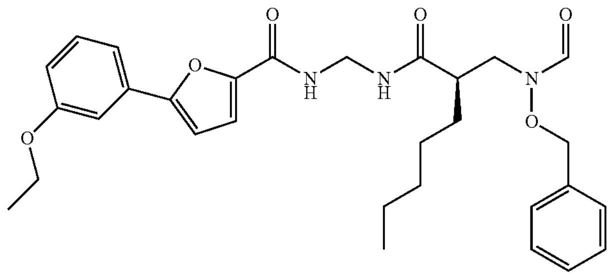 [SMILES: CCCCC[C@H](CN(C=O)OCc1ccccc1)C(=O)NCNC(=O)c1ccc(-c2cccc(OCC)c2)o1] | 536.3 | (3-ethoxyphenyl) boronic acid |
| 86 | (R)-N-((2-((N-(benzyloxy)formamido)methyl)heptanamido)methyl)-5-(3-isopropoxyphenyl)furan-2-carboxamide | 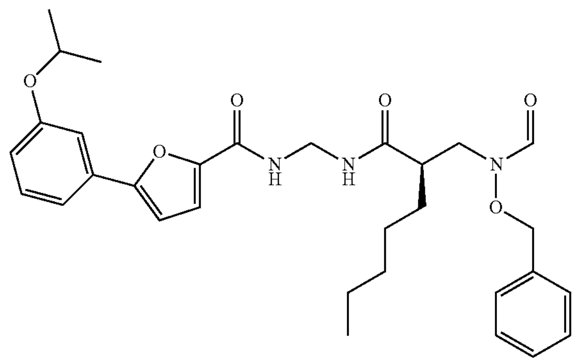 [SMILES: CCCCC[C@H](CN(C=O)OCc1ccccc1)C(=O)NCNC(=O)c1ccc(-c2cccc(OC(C)C)c2)o1] | 550.3 | (3-isopropoxyphenyl) boronic acid |
| 87 | (R)-N-((2-((N-(benzyloxy)formamido)methyl)heptanamido)methyl)-5-(2-hydroxyphenyl)furan-2-carboxamide | 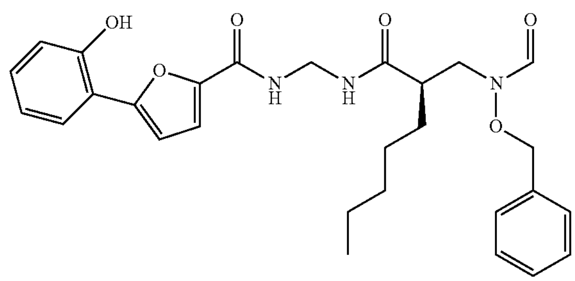 [SMILES: CCCCC[C@H](CN(C=O)OCc1ccccc1)C(=O)NCNC(=O)c1ccc(-c2ccccc2O)o1] | 508.2 | (2-hydroxyphenyl) boronic acid |
| 88 | (R)-N-((2-((N-(benzyloxy)formamido)methyl)heptanamido)methyl)-5-(3-cyanophenyl)furan-2-carboxamide | 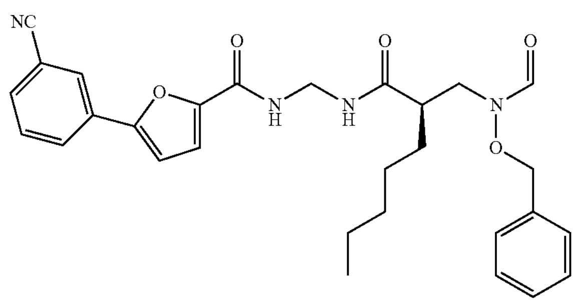 [SMILES: CCCCC[C@H](CN(C=O)OCc1ccccc1)C(=O)NCNC(=O)c1ccc(-c2cccc(C#N)c2)o1] | 517.2 | (3-cyanophenyl) boronic acid |
| 89 | (R)-N-((2-((N-(benzyloxy)formamido)methyl)heptanamido)methyl)-5-(3-sulfamoylphenyl)furan-2-carboxamide | 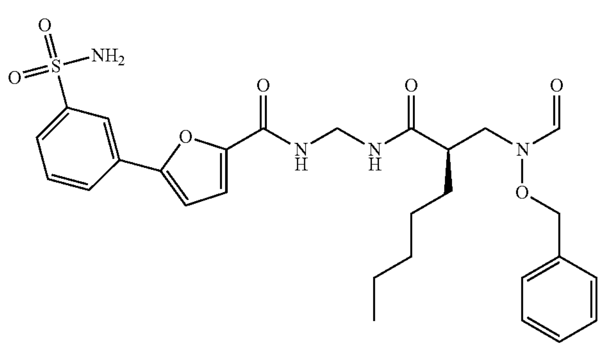 [SMILES: CCCCC[C@H](CN(C=O)OCc1ccccc1)C(=O)NCNC(=O)c1ccc(-c2cccc(S(N)(=O)=O)c2)o1] | 571.2 | (3-sulfamoylphenyl) boronic acid |

-continued

| # | Name | Structure | MS (m/z) (M + H⁺) | Boronic acid/Boronate |
|---|---|---|---|---|
| 90 | (R)-N-((2-((N-(benzyloxy)formamido)methyl)heptanamido)methyl)-5-(4-cyanophenyl)furan-2-carboxamide | 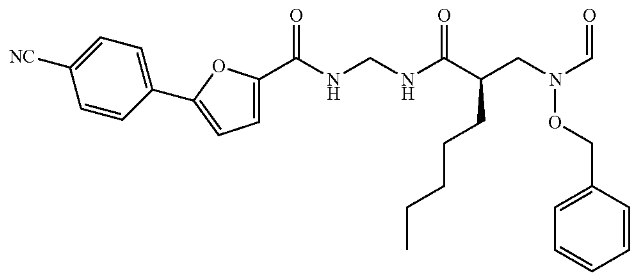 [SMILES: CCCCC[C@H](CN(C=O)OCc1ccccc1)C(=O)NCNC(=O)c1ccc(-c2ccc(C#N)cc2)o1] | 517.3 | (4-cyanophenyl) boronic acid |
| 91 | (R)-N-((2-((N-(benzyloxy)formamido)methyl)heptanamido)methyl)-5-(4-fluoro-3-methoxyphenyl)furan-2-carboxamide | 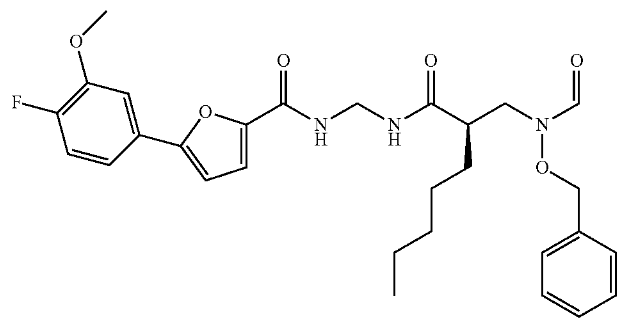 [SMILES: CCCCC[C@H](CN(C=O)OCc1ccccc1)C(=O)NCNC(=O)c1ccc(-c2ccc(F)c(OC)c2)o1] | 540.3 | (4-fluoro-3-methoxyphenyl) boronic acid |
| 92 | (R)-N-((2-((N-(benzyloxy)formamido)methyl)heptanamido)methyl)-5-(6-methoxypyridin-2-yl)furan-2-carboxamide | 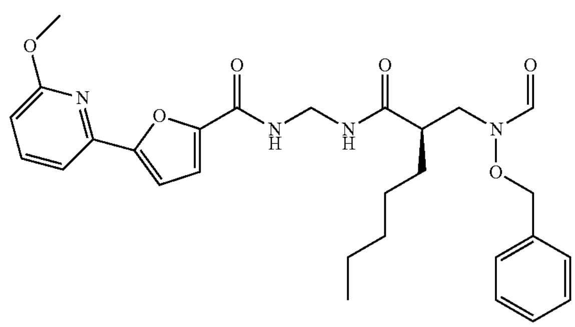 [SMILES: CCCCC[C@H](CN(C=O)OCc1ccccc1)C(=O)NCNC(=O)c1ccc(-c2cccc(OC)n2)o1] | 523.3 | (6-methoxypyridin-2-yl) boronic acid |
| 93 | (R)-3-(5-(((2-((N-(benzyloxy)formamido)methyl)heptanamido)methyl)carbamoyl)furan-2-yl)-5-methoxybenzoic acid | 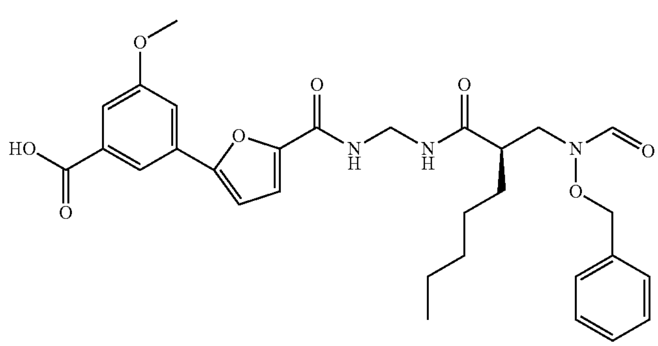 [SMILES: CCCCC[C@H](CN(C=O)OCc1ccccc1)C(=O)NCNC(=O)c1ccc(-c2cc(OC)cc(C(=O)O)c2)o1] | 566.2 | 3-borono-5-methoxybenzoic acid |

-continued

| # | Name | Structure | MS (m/z) (M + H+) | Boronic acid/Boronate |
|---|---|---|---|---|
| 94 | (R)-N-((2-((N-(benzyloxy)formamido)methyl)heptanamido)methyl)-5-(5-methoxypyridin-3-yl)furan-2-carboxamide | 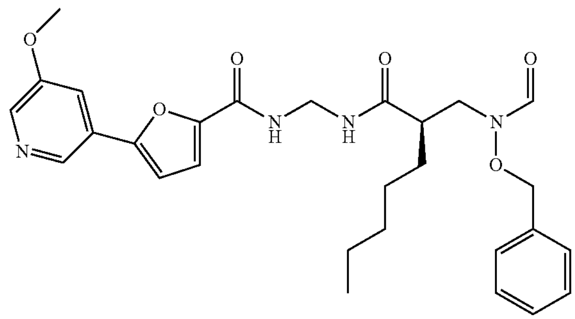 [SMILES: CCCCC[C@H](CN(C=O)OCc1ccccc1)C(=O)NCNC(=O)c1ccc(-c2cncc(OC)c2)o1] | 523.2 | 3-methoxy-5-(4,4,5,5-tetramethyl-1,3,2-dioxaborolan-2-yl)pyridine |
| 95 | (R)-N-((2-((N-(benzyloxy)formamido)methyl)heptanamido)methyl)-5-(3-methoxyphenyl)furan-2-carboxamide | 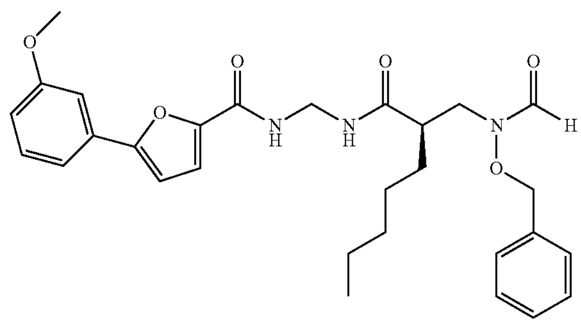 [SMILES: CCCCC[C@H](CN(C=O)OCc1ccccc1)C(=O)NCNC(=O)c1ccc(-c2cccc(OC)c2)o1] | 522.3 | (3-methoxyphenyl)boronic acid |
| 96 | R)-methyl 5-(5-(((2-((N-(benzyloxy)formamido)methyl)heptanamido)methyl)carbamoyl)furan-2-yl)-2-fluorobenzoate | 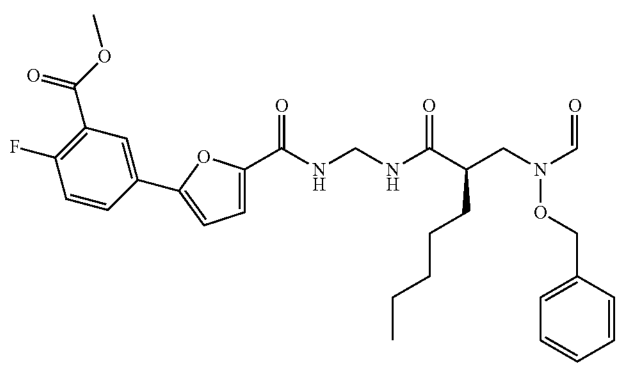 [SMILES: CCCCC[C@H](CN(C=O)OCc1ccccc1)C(=O)NCNC(=O)c1ccc(-c2ccc(F)c(C(=O)OC)c2)o1] | 568.2 | (4-fluoro-3-(methoxycarbonyl)phenyl)boronic acid |
| 97 | (R)-methyl 2-(5-(((2-((N-(benzyloxy)formamido)methyl)heptanamido)methyl)carbamoyl)furan-2-yl)benzoate | 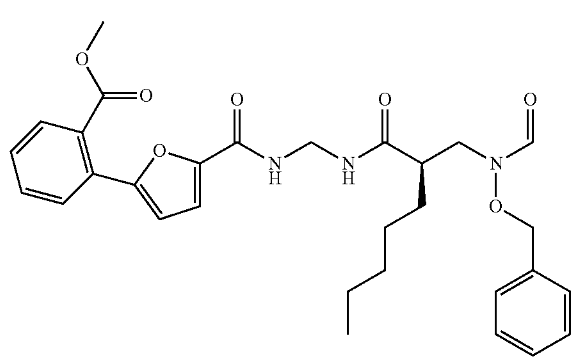 [SMILES: CCCCC[C@H](CN(C=O)OCc1ccccc1)C(=O)NCNC(=O)c1ccc(-c2ccccc2C(=O)OC)o1] | 550.2 | (2-(methoxycarbonyl)phenyl)boronic acid |

-continued

| # | Name | Structure | MS (m/z) (M + H+) | Boronic acid/Boronate |
|---|---|---|---|---|
| 98 | (R)-N-((2-((N-(benzyloxy)formamido)methyl)heptanamido)methyl)-5-(2,5-dimethoxyphenyl)furan-2-carboxamide | 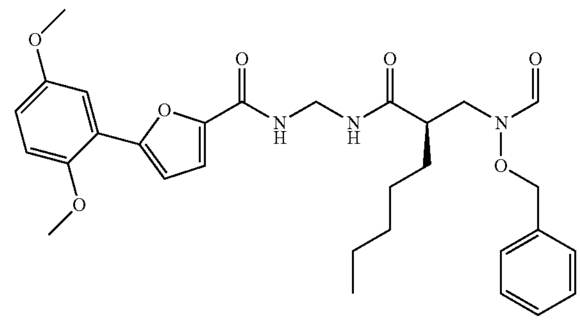 [SMILES: CCCCC[C@H](CN(C=O)OCc1ccccc1)C(=O)NCNC(=O)c1ccc(-c2cc(OC)ccc2OC)o1] | 552.2 | (2,5-dimethoxyphenyl)boronic acid |
| 99 | (R)-N-((2-((N-(benzyloxy)formamido)methyl)heptanamido)methyl)-5-(3,5-dimethoxyphenyl)furan-2-carboxamide | 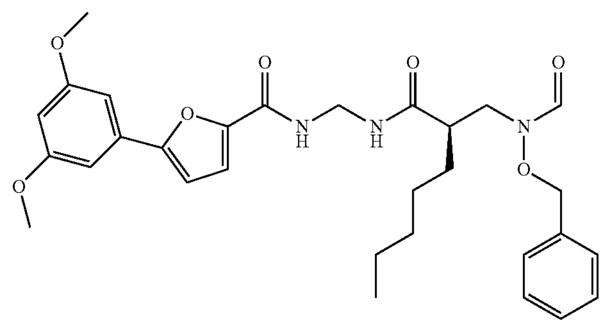 [SMILES: CCCCC[C@H](CN(C=O)OCc1ccccc1)C(=O)NCNC(=O)c1ccc(-c2cc(OC)cc(OC)c2)o1] | 552.2 | (3,5-dimethoxyphenyl)boronic acid |
| 100 | (R)-2-(3-(5-(((2-((N-(benzyloxy)formamido)methyl)heptanamido)methyl)carbamoyl)furan-2-yl)phenyl)acetic acid | 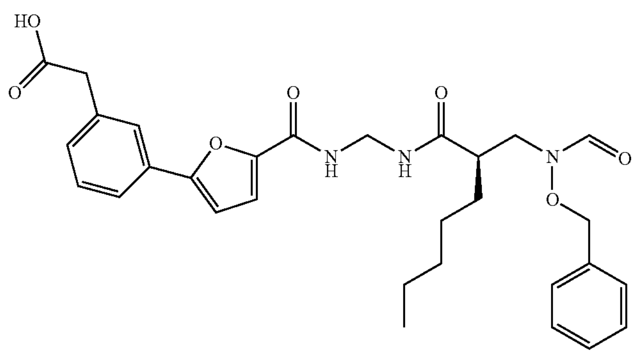 [SMILES: CCCCC[C@H](CN(C=O)OCc1ccccc1)C(=O)NCNC(=O)c1ccc(-c2cccc(CC(=O)O)c2)o1] | 550.2 | 2-(3-boronophenyl)acetic acid |
| 101 | (R)-5-(5-(((2-((N-(benzyloxy)formamido)methyl)heptanamido)methyl)carbamoyl)furan-2-yl)-2-methylbenzoic acid | 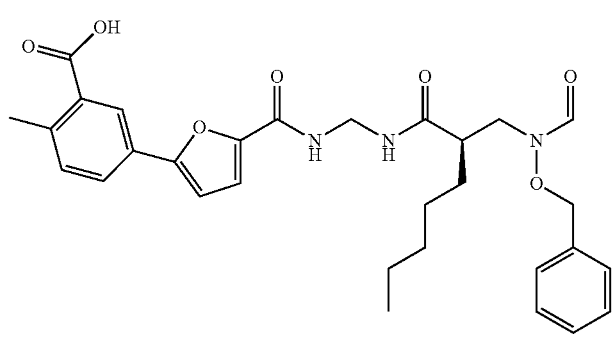 [SMILES: CCCCC[C@H](CN(C=O)OCc1ccccc1)C(=O)NCNC(=O)c1ccc(-c2ccc(C)c(C(=O)O)c2)o1] | 550.2 | 5-borono-2-methylbenzoic acid |

-continued

| # | Name | Structure | MS (m/z) (M + H+) | Boronic acid/Boronate |
|---|---|---|---|---|
| 102 | (R)-3-(5-(((2-((N-(benzyloxy)formamido)methyl)heptanamido)methyl)carbamoyl)furan-2-yl)-2-fluoro-benzoic acid | 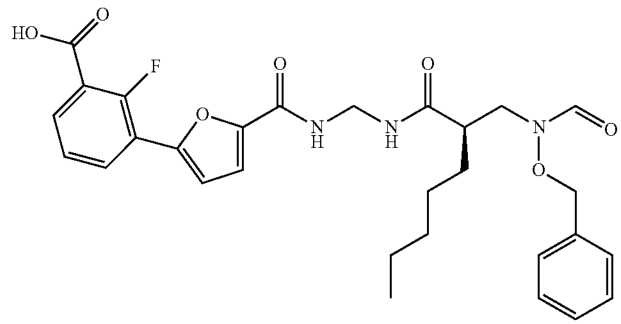 | 554.2 | 3-borono-2-fluoro-benzoic acid |
| 103 | (R)-5-(5-(((2-((N-(benzyloxy)formamido)methyl)heptanamido)methyl)carbamoyl)furan-2-yl)-2-methoxy-benzoic acid | 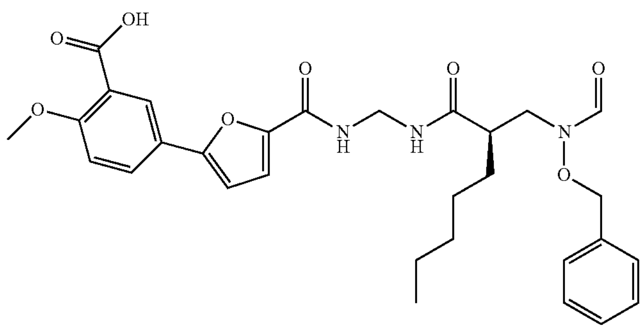 [SMILES: CCCCC[C@H](CN(C=O)OCc1ccccc1)C(=O)NCNC(=O)c1ccc(-c2ccc(OC)c(C(=O)O)c2)o1] | 566.2 | 5-borono-2-methoxy-benzoic acid |
| 104 | (R)-3-(5-(((2-((N-(benzyloxy)formamido)methyl)heptanamido)methyl)carbamoyl)furan-2-yl)-2-methoxy-benzoic acid | 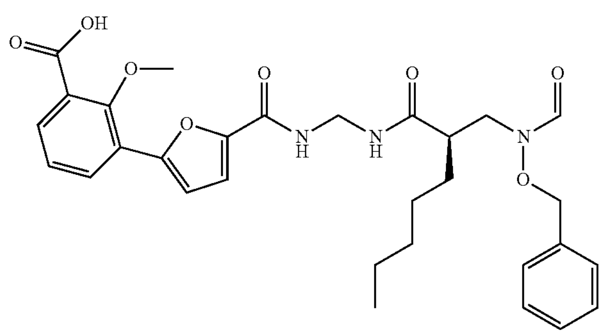 [SMILES: CCCCC[C@H](CN(C=O)OCc1ccccc1)C(=O)NCNC(=O)c1ccc(-c2cccc(C(=O)O)c2OC)o1] | 566.2 | 3-borono-2-methoxy-benzoic acid |
| 105 | (R)-methyl 4-(5-(((2-((N-(benzyloxy)formamido)methyl)heptanamido)methyl)carbamoyl)furan-2-yl)benzoate | 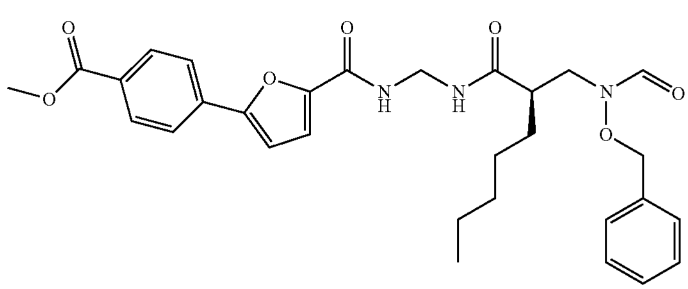 [SMILES: CCCCC[C@H](CN(C=O)OCc1ccccc1)C(=O)NCNC(=O)c1ccc(-c2ccc(C(=O)OC)cc2)o1] | 550.2 | methyl 4-(4,4,5,5-tetramethyl-1,3,2-dioxaborolan-2-yl)benzoate |

| # | Name | Structure | MS (m/z) (M + H+) | Boronic acid/Boronate |
|---|---|---|---|---|
| 106 | (R)-3-(5-(((2-((N-(benzyloxy)formamido)methyl)heptanamido)methyl)carbamoyl)furan-2-yl)-2-methyl-benzoic acid | 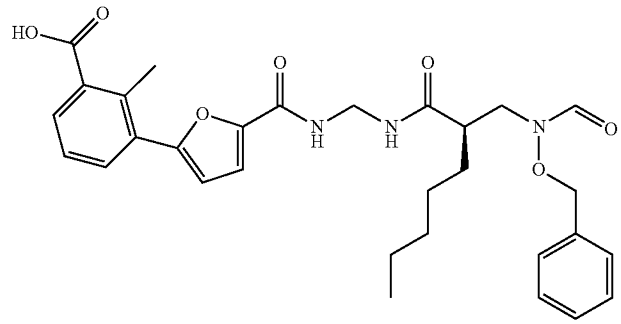 [SMILES: CCCCC[C@H](CN(C=O)OCc1ccccc1)C(=O)NCNC(=O)c1ccc(-c2cccc(C(=O)O)c2C)o1] | 550.2 | 2-methyl-3-(4,4,5,5-tetramethyl-1,3,2-dioxaborolan-2-yl)benzoic acid |
| 107 | (R)-tert-butyl 3-(5-(((2-((N-(benzyloxy)formamido)methyl)heptanamido)methyl)carbamoyl)furan-2-yl)benzoate | 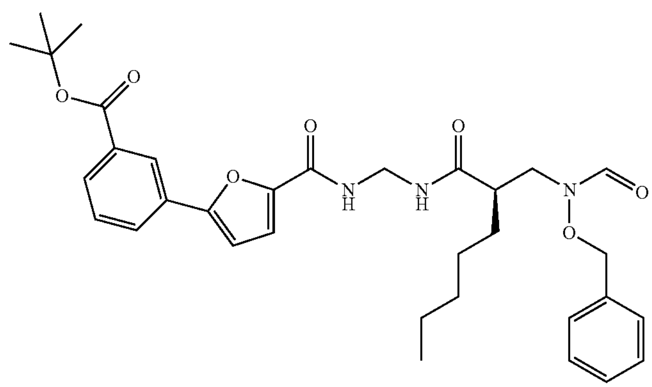 [SMILES: CCCCC[C@H](CN(C=O)OCc1ccccc1)C(=O)NCNC(=O)c1ccc(-c2cccc(C(=O)OC(C)(C)C)c2)o1] | 592.3 | (3-(tert-butoxycarbonyl)phenyl)boronic acid |
| 108 | (R)-2-amino-5-(5-(((2-((N-(benzyloxy)formamido)methyl)heptanamido)methyl)carbamoyl)furan-2-yl)benzoic acid | 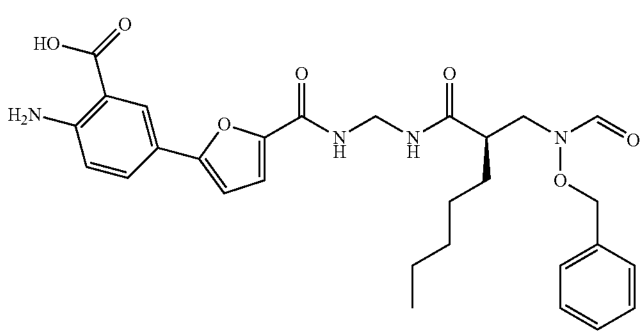 [SMILES: CCCCC[C@H](CN(C=O)OCc1ccccc1)C(=O)NCNC(=O)c1ccc(-c2ccc(N)c(C(=O)O)c2)o1] | 551.2 | 2-amino-5-(4,4,5,5-tetramethyl-1,3,2-dioxaborolan-2-yl)benzoic acid |
| 109 | (R)-5-(5-(((2-((N-(benzyloxy)formamido)methyl)heptanamido)methyl)carbamoyl)furan-2-yl)-2-hydroxy-benzoic acid | 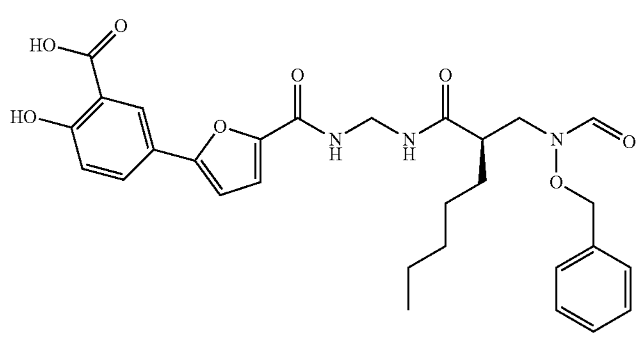 [SMILES: CCCCC[C@H](CN(C=O)OCc1ccccc1)C(=O)NCNC(=O)c1ccc(-c2ccc(O)c(C(=O)O)c2)o1] | 552.2 | 2-hydroxy-5-(4,4,5,5-tetramethyl-1,3,2-dioxaborolan-2-yl)benzoic acid |

-continued

| # | Name | Structure | MS (m/z) (M + H+) | Boronic acid/Boronate |
|---|------|-----------|-------------------|----------------------|
| 110 | (R)-methyl 3-(5-(((2-((N-(benzyloxy)formamido)methyl)heptanamido)methyl)carbamoyl)furan-2-yl)benzoate | 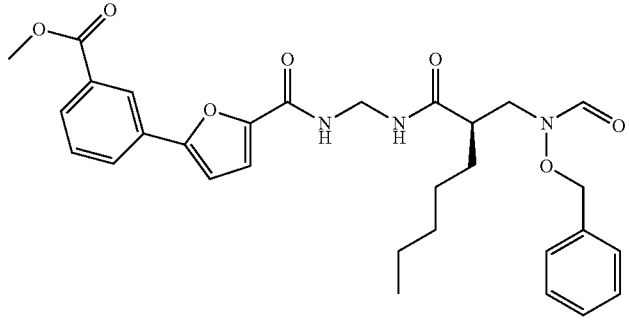 [SMILES: CCCCC[C@H](CN(C=O)OCc1ccccc1)C(=O)NCNC(=O)c1ccc(-c2cccc(C(=O)OC)c2)o1] | 550.2 | (3-(methoxycarbonyl)phenyl)boronic acid |
| 111 | methyl 2-(3-(5-((((R)-2-((N-(benzyloxy)formamido)methyl)heptanamido)methyl)carbamoyl)furan-2-yl)phenyl)propanoate | 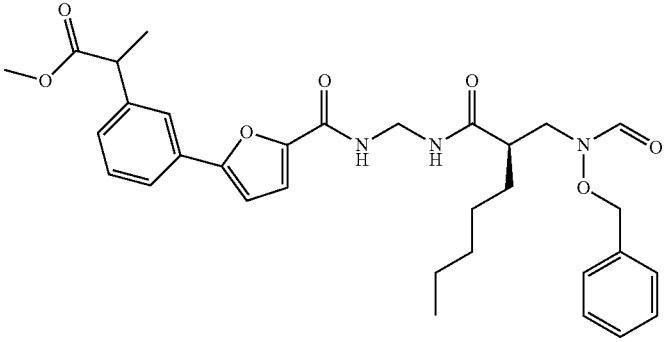 [SMILES: CCCCC[C@H](CN(C=O)OCc1ccccc1)C(=O)NCNC(=O)c1ccc(-c2cccc(C(C)C(=O)OC)c2)o1] | 578.3 | methyl 2-(3-(4,4,5,5-tetramethyl-1,3,2-dioxaborolan-2-yl)phenyl)propanoate |
| 112 | (R)-methyl 3-(5-(((2-((N-(benzyloxy)formamido)methyl)heptanamido)methyl)carbamoyl)furan-2-yl)-2,6-difluorobenzoate | 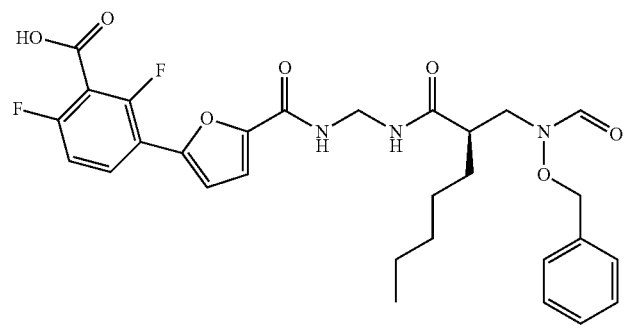 [SMILES: CCCCC[C@H](CN(C=O)OCc1ccccc1)C(=O)NCNC(=O)c1ccc(-c2ccc(F)c(C(=O)O)c2F)o1] | 586.2 | (2,4-difluoro-3-(methoxycarbonyl)phenyl)boronic acid |
| 113 | (R)-N-((2-((N-(benzyloxy)formamido)methyl)heptanamido)methyl)-5-(3-nitrophenyl)furan-2-carboxamide | 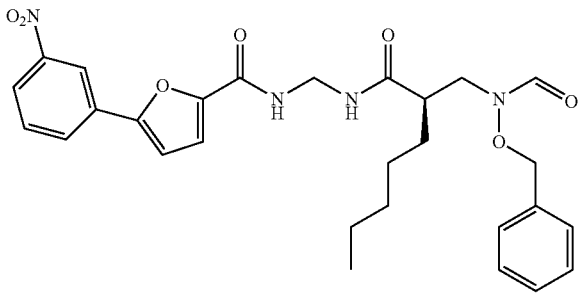 [SMILES: CCCCC[C@H](CN(C=O)OCc1ccccc1)C(=O)NCNC(=O)c1ccc(-c2cccc([N+](=O)[O-])c2)o1] | 537.2 | (3-nitrophenyl)boronic acid |

-continued

| # | Name | Structure | MS (m/z) (M + H+) | Boronic acid/Boronate |
|---|---|---|---|---|
| 114 | (R)-N-((2-((N-(benzyloxy)formamido)methyl)heptanamido)methyl)-5-(3-(2,2-difluoroethoxy)phenyl)furan-2-carboxamide | 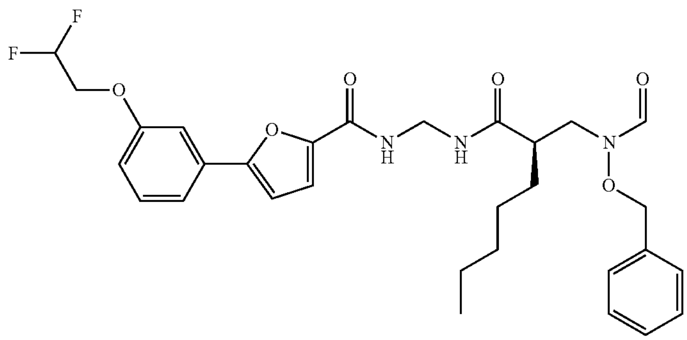 [SMILES: CCCCC[C@H](CN(C=O)OCc1ccccc1)C(=O)NCNC(=O)c1ccc(-c2cccc(OCC(F)F)c2)o1] | 572.2 | 2-(3-(2,2-difluoroethoxy)phenyl)-4,4,5,5-tetramethyl-1,3,2-dioxaborolane |
| 115 | (R)-N-((2-((N-(benzyloxy)formamido)methyl)heptanamido)methyl)-5-(3-(ethylthio)phenyl)furan-2-carboxamide | 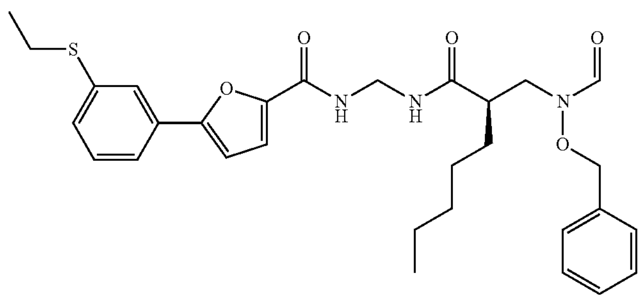 [SMILES: CCCCC[C@H](CN(C=O)OCc1ccccc1)C(=O)NCNC(=O)c1ccc(-c2cccc(SCC)c2)o1] | 552.2 | (3-(ethylthio)phenyl)boronic acid |
| 116 | (R)-N-((2-((N-(benzyloxy)formamido)methyl)heptanamido)methyl)-5-(3-(methylthio)phenyl)furan-2-carboxamide | 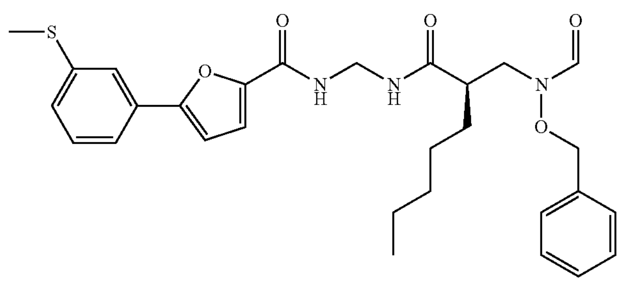 [SMILES: CCCCC[C@H](CN(C=O)OCc1ccccc1)C(=O)NCNC(=O)c1ccc(-c2cccc(SC)c2)o1] | 538.2 | (3-(methylthio)phenyl)boronic acid |
| 117 | (R)-N-((2-((N-(benzyloxy)formamido)methyl)heptanamido)methyl)-5-(1-methyl-1H-indazol-6-yl)furan-2-carboxamide | 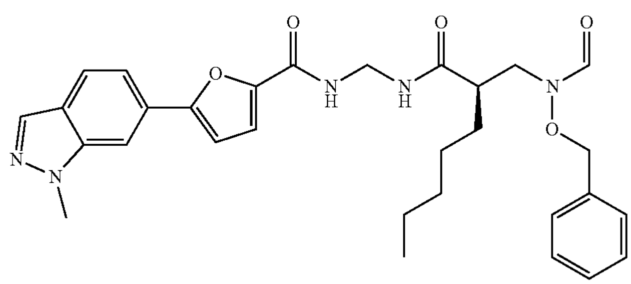 [SMILES: CCCCC[C@H](CN(C=O)OCc1ccccc1)C(=O)NCNC(=O)c1ccc(-c2ccc3cnn(C)c3c2)o1] | 546.2 | (1-methyl-1H-indazol-6-yl)boronic acid |
| 118 | (R)-N-((2-((N-(benzyloxy)formamido)methyl)heptanamido)methyl)-5-(2-methyl-2H-indazol-6-yl)furan-2-carboxamide | 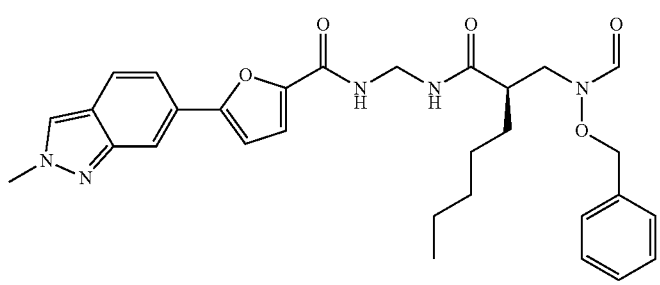 [SMILES: CCCCC[C@H](CN(C=O)OCc1ccccc1)C(=O)NCNC(=O)c1ccc(-c2ccc3cn(C)nc3c2)o1] | 546.2 | (2-methyl-2H-indazol-6-yl)boronic acid |

INTERMEDIATE 119 was prepared from ((R)—N-((2-((N-(benzyloxy)formamido)methyl)heptanamido)methyl)-5-bromofuran-2-carboxamide using the indicated boronate by methods analogous to those described in Intermediate 78 irradiating for 35 minutes at 110° C., 15 minutes at 115° C. and then 15 minutes at 120° C.

| #   | Name | Structure | MS (m/z) (M + H+) | Boronate |
| --- | --- | --- | --- | --- |
| 119 | (R)-N-((2-((N-(benzyloxy)formamido)methyl)heptanamido)methyl)-5-(3-(difluoromethoxy)phenyl)furan-2-carboxamide | 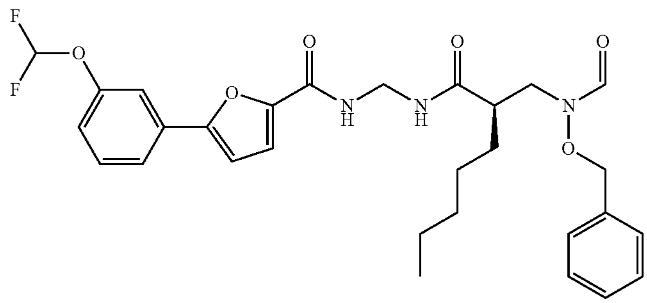 [SMILES: CCCCC[C@H](CN(C=O)OCc1ccccc1)C(=O)NCNC(=O)c1ccc(-c2cccc(OC(F)F)c2)o1] | 558.3 | 2-(3-(difluoromethoxy)phenyl)-4,4,5,5-tetramethyl-1,3,2-dioxaborolane |

INTERMEDIATES 120-131 were prepared from N—(((R)-2-((R)-1-(N-(benzyloxy)formamido)propyl)heptanamido)methyl)-5-bromofuran-2-carboxamide and the indicated boronate by methods analogous to those described for Intermediate 78.

| #   | Name | Structure | MS (m/z) (M + H+) | Boronate |
| --- | --- | --- | --- | --- |
| 120 | ethyl 3-(5-((((R)-2-((R)-1-(N-(benzyloxy)formamido)propyl)heptanamido)methyl)carbamoyl)furan-2-yl)-5-ethoxy-2-hydroxybenzoate | 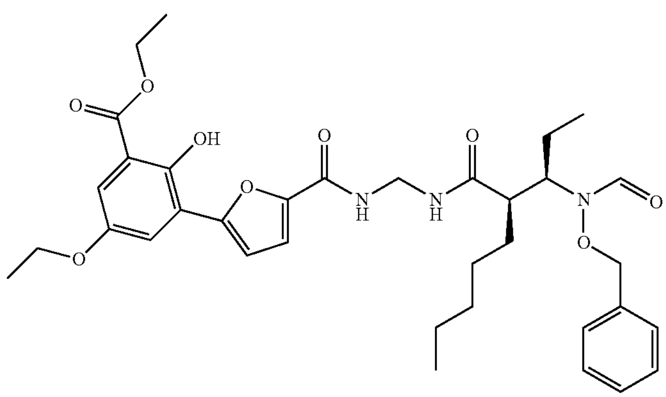 [SMILES: CCCCC[C@@H](C(=O)NCNC(=O)c1ccc(-c2cc(OCC)cc(C(=O)OCC)c2O)o1)[C@@H](CC)N(C=O)OCc1ccccc1] | 652.2 | ethyl 5-ethoxy-2-hydroxy-3-(4,4,5,5-tetramethyl-1,3,2-dioxaborolan-2-yl)benzoate |
| 121 | methyl 3-(5-((((R)-2-((R)-1-(N-(benzyloxy)formamido)propyl)heptanamido)methyl)carbamoyl)furan-2-yl)-5-propoxybenzoate | 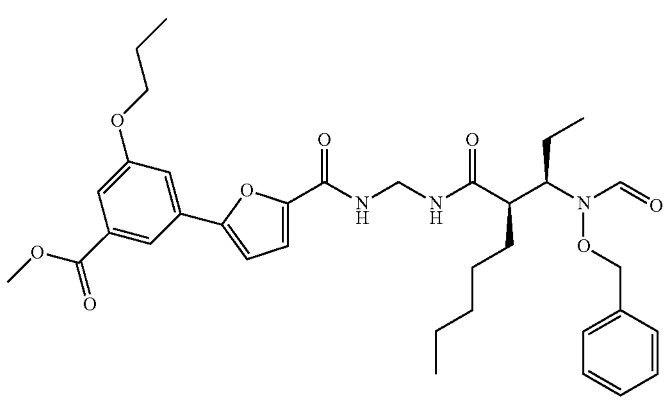 [SMILES: CCCCC[C@@H](C(=O)NCNC(=O)c1ccc(-c2cc(OCCC)cc(C(=O)OC)c2)o1)[C@@H](CC)N(C=O)OCc1ccccc1] | 636.3 | methyl 3-propoxy-5-(4,4,5,5-tetramethyl-1,3,2-dioxaborolan-2-yl)benzoate |

-continued

| # | Name | Structure | MS (m/z) (M + H⁺) | Boronate |
|---|------|-----------|-------------------|----------|
| 122 | 5-(5-((((R)-2-((R)-1-(N-(benzyloxy)formamido)propyl)heptanamido)methyl)carbamoyl)furan-2-yl)-2-methylbenzoic acid | 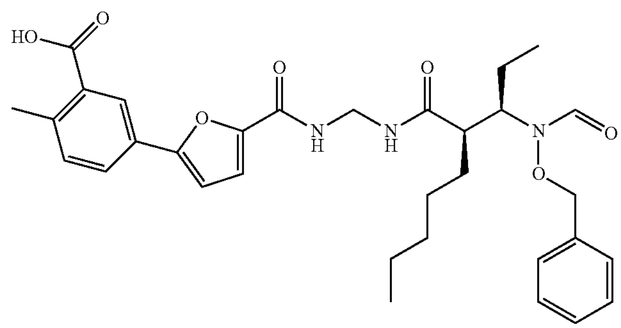 [SMILES: CCCCC[C@@H](C(=O)NCNC(=O)c1ccc(-c2ccc(C)c(C(=O)O)c2)o1)[C@@H](CC)N(C=O)OCc1ccccc1] | 578.3 | 5-borono-2-methylbenzoic acid |
| 123 | N-(((R)-2-((R)-1-(N-(benzyloxy)formamido)propyl)heptanamido)methyl)-5-(3-propoxyphenyl)furan-2-carboxamide | 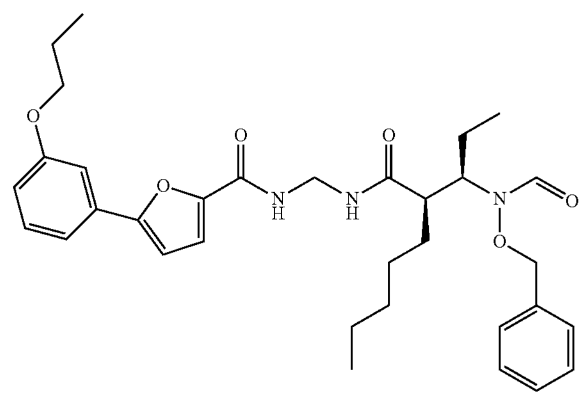 [SMILES: CCCCC[C@@H](C(=O)NCNC(=O)c1ccc(-c2cccc(OCCC)c2)o1)[C@@H](CC)N(C=O)OCc1ccccc1] | 578.3 | (3-propoxyphenyl)boronic acid |
| 124 | 2-(5-(5-((((R)-2-((R)-1-(N-(benzyloxy)formamido)propyl)heptanamido)methyl)carbamoyl)furan-2-yl)-2-fluorophenyl)acetic acid | 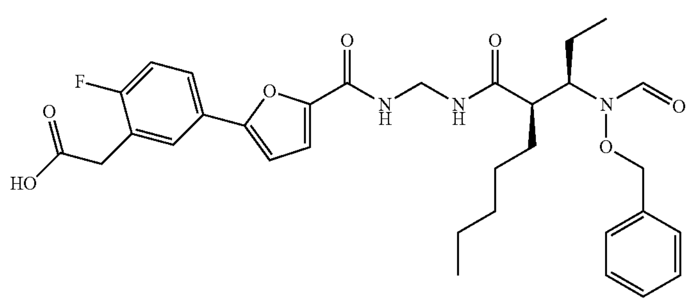 [SMILES: CCCCC[C@@H](C(=O)NCNC(=O)c1ccc(-c2ccc(F)c(CC(=O)O)c2)o1)[C@@H](CC)N(C=O)OCc1ccccc1] | 596.3 | 2-(2-fluoro-5-(4,4,5,5-tetramethyl-1,3,2-dioxaborolan-2-yl)phenyl)acetic acid |
| 125 | 4-(5-((((R)-2-((R)-1-(N-(benzyloxy)formamido)propyl)heptanamido)methyl)carbamoyl)furan-2-yl)benzoic acid | 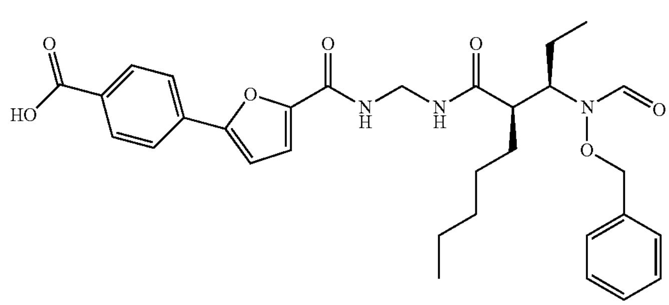 [SMILES: CCCCC[C@@H](C(=O)NCNC(=O)c1ccc(-c2ccc(C(=O)O)cc2)o1)[C@@H](CC)N(C=O)OCc1ccccc1] | 564.3 | 4-boronobenzoic acid |

| # | Name | Structure | MS (m/z) (M + H+) | Boronate |
|---|---|---|---|---|
| 126 | 2-(3-(5-((((R)-2-((R)-1-(N-(benzyloxy)formamido)propyl)heptanamido)methyl)carbamoyl)furan-2-yl)-5-ethoxyphenyl) acetic acid | 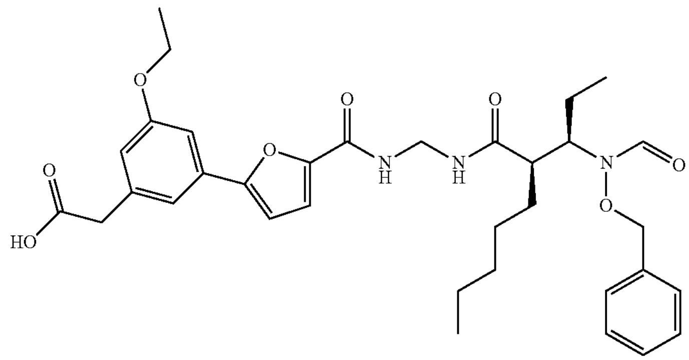 [SMILES: CCCCC[C@@H](C(=O)NCNC(=O)c1ccc(-c2cc(CC(=O)O)cc(OCC)c2)o1)[C@@H](CC)N(C=O)OCc1ccccc1] | 532.3 | 2-(3-ethoxy-5-(4,4,5,5-tetramethyl-1,3,2-dioxaborolan-2-yl)phenyl) acetic acid |
| 127 | 3-(5-((((R)-2-((R)-1-(N-(benzyloxy)formamido)propyl)heptananamido)methyl)carbamoyl)furan-2-yl) benzoic acid | 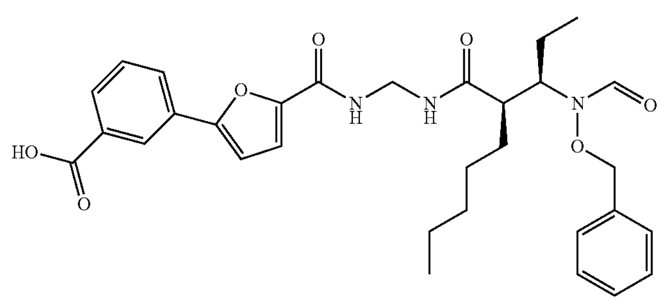 [SMILES: CCCCC[C@@H](C(=O)NCNC(=O)c1ccc(-c2cccc(C(=O)O)c2)o1)[C@@H](CC)N(C=O)OCc1ccccc1] | 564.3 | 3-boronobenzoic acid |
| 128 | (S)-dimethyl 2-(3-(5-((((R)-2-((R)-1-(N-(benzyloxy)formamido)propyl)heptanamido)methyl)carbamoyl)furan-2-yl)-5-ethoxybenzamido) succinate | 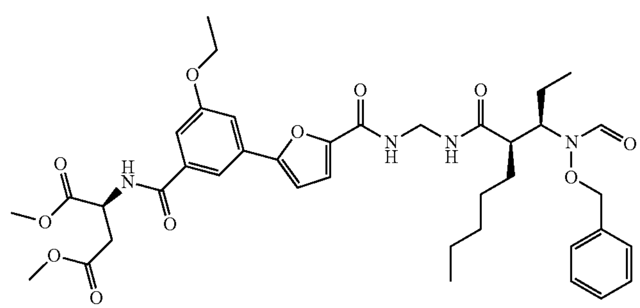 [SMILES: CCCCC[C@@H](C(=O)NCNC(=O)c1ccc(-c2cc(OCC)cc(C(=O)N[C@@H](CC(=O)OC)C(=O)OC)c2)o1)[C@@H](CC)N(C=O)OCc1ccccc1] | 751.3 | (S)-dimethyl 2-(3-ethoxy-5-(4,4,5,5-tetramethyl-1,3,2-dioxaborolan-2-yl)benzamido) succinate |
| 129 | methyl 1-(3-(5-((((R)-2-((R)-1-(N-(benzyloxy)formamido)propyl)heptanamido)methyl)carbamoyl)furan-2-yl)phenyl) cyclopropanecarboxylate | 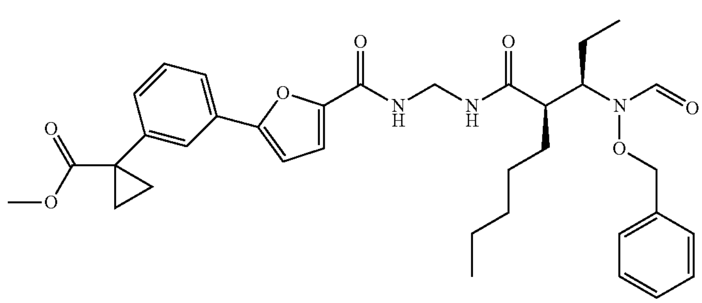 [SMILES: CCCCC[C@@H](C(=O)NCNC(=O)c1ccc(-c2cccc(C3(C(=O)OC)CC3)c2)o1)[C@@H](CC)N(C=O)OCc1ccccc1] | 618.3 | methyl 1-(3-(4,4,5,5-tetramethyl-1,3,2-dioxaborolan-2-yl)phenyl) cyclopropanecarboxylate |

| # | Name | Structure | MS (m/z) (M + H+) | Boronate |
|---|---|---|---|---|
| 130 | 5-(5-((((R)-2-((R)-1-(N-(benzyloxy)formamido)propyl)heptanamido)methyl)carbamoyl)furan-2-yl)-2-methoxybenzoic acid | 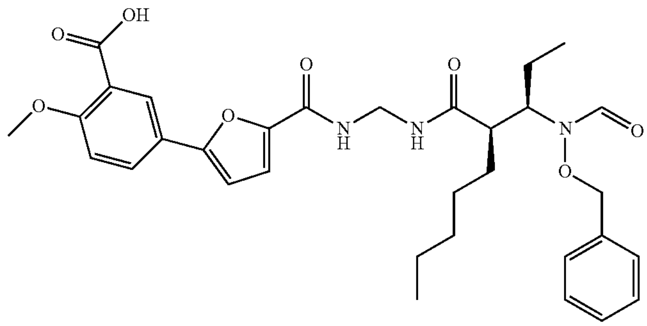 [SMILES: CCCCC[C@@H](C(=O)NCNC(=O)c1ccc(-c2ccc(OC)c(C(=O)O)c2)o1)[C@@H](CC)N(C=O)OCc1ccccc1] | 594.2 | 5-borono-2-methoxy-benzoic acid |
| 131 | 2-(3-(5-((((R)-2-((R)-1-(N-(benzyloxy)formamido)propyl)heptanamido)methyl)carbamoyl)furan-2-yl)phenyl)-2-methylpropanoic acid | 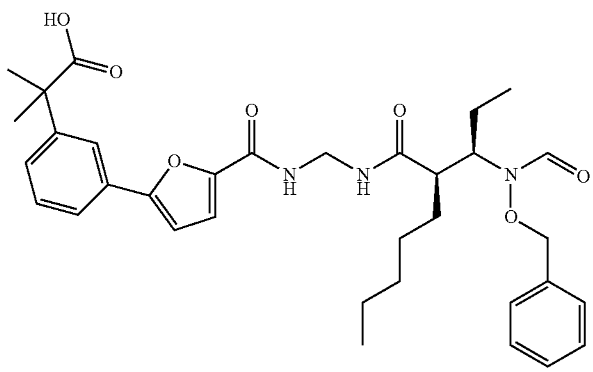 [SMILES: CCCCC[C@@H](C(=O)NCNC(=O)c1ccc(-c2cccc(C(C)(C)C(=O)O)c2)o1)[C@@H](CC)N(C=O)OCc1ccccc1] | 606.3 | 2-(3-boronophenyl)-2-methyl-propanoic acid |

INTERMEDIATE 132 was prepared from N-((3-(N-(benzyloxy)formamido)propanamido)methyl)-5-bromofuran-2-carboxamide and the indicated boronate by methods analogous to those described for Intermediate 78.

| # | Name | Structure | MS (m/z) (M + H+) | Boronate |
|---|---|---|---|---|
| 132 | methyl 3-(5-(((3-(N-(benzyloxy)formamido)propanamido)methyl)carbamoyl)furan-2-yl)-5-ethoxybenzoate | 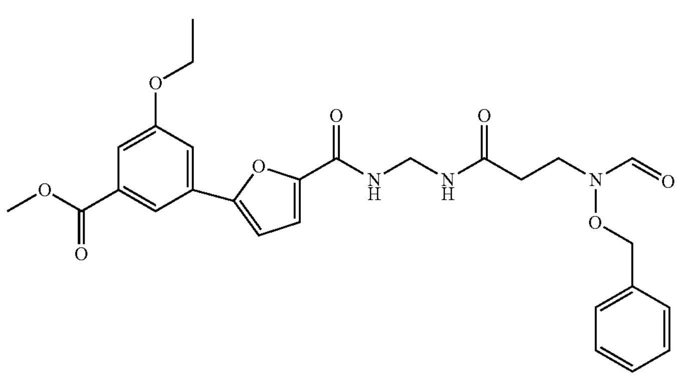 [SMILES: CCOc1cc(C(=O)OC)cc(-c2ccc(C(=O)NCNC(=O)CCN(C=O)OCc3ccccc3)o2)c1] | 524.1 | methyl 3-ethoxy-5-(4,4,5,5-tetramethyl-1,3,2-dioxaborolan-2-yl)benzoate |

Intermediate 133: (R)-3-(5-(((2-((N-(benzyloxy)formamido)methyl)heptanamido)methyl)carbamoyl)furan-2-yl)-5-methoxybenzoic acid

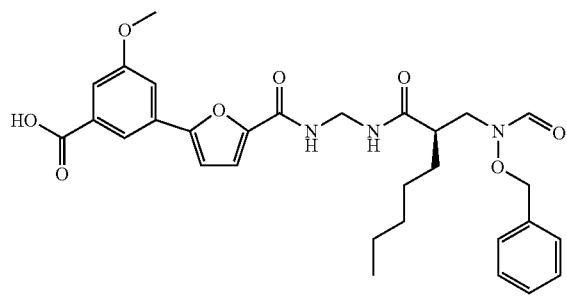 [SMILES: CCCCC[C@H](CN(C=O)OCc1ccccc1)C(=O)NCNC(=O)c1ccc(-c2cc(OC)cc(C(=O)O)c2)o1]

Step 1: (R)-3-(5-(((2-((N-hydroxyformamido)methyl)heptanamido)methyl)carbamoyl)furan-2-yl)-5-methoxybenzoic acid and (R)-3-(5-(((2-(((benzyloxy)amino)methyl)heptanamido)methyl)carbamoyl)furan-2-yl)-5-methoxybenzoic acid

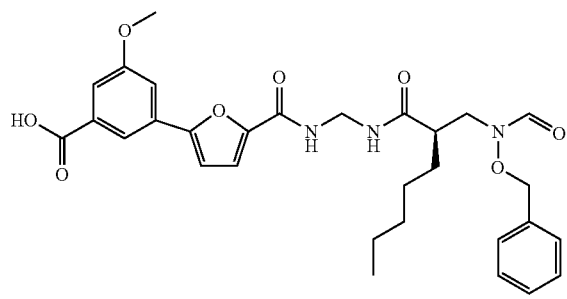

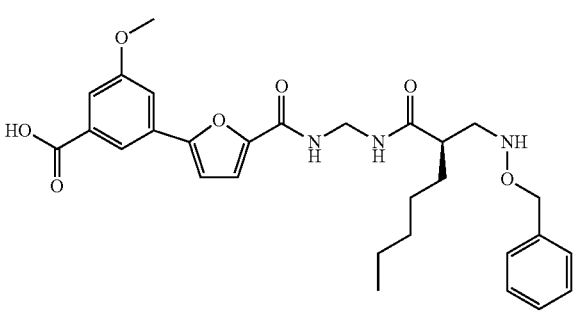

A mixture of 3-borono-5-methoxybenzoic acid (404 mg, 2.06 mmol), (R)—N-((2-((N-(benzyloxy)formamido)methyl)heptanamido)methyl)-5-bromofuran-2-carboxamide (850 mg, 1.72 mmol), PdCl$_2$(dppf)-CH$_2$Cl$_2$ adduct (140 mg, 0.17 mmol) and Na$_2$CO$_3$ (1 M, 5.16 ml, 5.16 mmol) in 1,4-dioxane (4.5 ml) was irradiated in a microwave for 5 minutes at 100° C. Water and DCM were added to the reaction mixture and the pH adjusted to 5 by the addition of 1 M HCl. The DCM layer was collected and the aqueous extracted with ethyl acetate. The combined organics were concentrated and the residue purified by flash chromatography (ISCO CombiFlash, 40 g silica column, 0-20% MeOH/DCM) to yield a beige solid which was purified by flash chromatography (20 g Si SPE, DCM, diethyl ether, ethyl acetate, acetone and 10% MeOH/DCM) to give a mixture of the title compounds (531 mg). MS (m/z) 566.2 (M+H$^+$) and 538.2 (M+H$^+$).

Step 2: (R)-3-(5-(((2-((N-(benzyloxy)formamido)methyl)heptanamido)methyl)carbamoyl)furan-2-yl)-5-methoxybenzoic acid 5-methyl-2-thioxo-1,3,4-thiadiazole-3(2H)-carbaldehyde (e.g., Yazawa, H., et al., Tetrahedron Letters, 1985, 26 (31), 3703-3706) (31.9 mg, 0.20 mmol) was added to a solution of ((R)-3-(5-(((2-((N-(benzyloxy)formamido)methyl)heptanamido)methyl)carbamoyl)furan-2-yl)-5-methoxybenzoic acid and (R)-3-(5-(((2-(((benzyloxy)amino)methyl)heptanamido)methyl)carbamoyl)furan-2-yl)-5-methoxybenzoic acid (530 mg, 0.80 mmol) in dichloromethane (2 ml) and the reaction stirred at room temperature for 45 minutes. The reaction mixture was concentrated, the residue dissolved in the minimum amount of DCM and purified by flash chromatography (10 g Si SPE, DCM, diethyl ether, ethyl acetate, acetone and 10% MeOH/DCM) to give the title compound as an off white solid (482 mg). MS (m/z) 566.2 (M+H$^+$).

Intermediate 134: 4-(5-(((((R)-2-((R)-1-(N-(benzyloxy)formamido)propyl)heptanamido)methyl)carbamoyl)furan-2-yl)-2-ethoxybenzoic acid

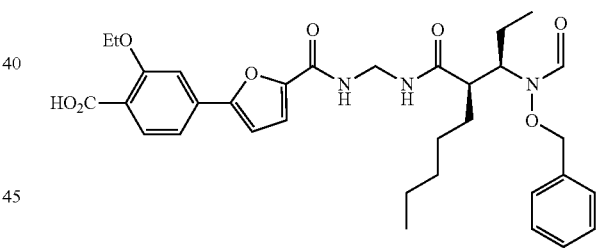

A mixture of 2-ethoxy-4-(4,4,5,5-tetramethyl-1,3,2-dioxaborolan-2-yl)benzoic acid (151 mg, 0.52 mmol), N—(((R)-2-((R)-1-(N-(benzyloxy)formamido)propyl)heptanamido)methyl)-5-bromofuran-2-carboxamide (250 mg, 0.47 mmol), PdCl$_2$(dppf)-CH$_2$Cl$_2$ adduct (28.7 mg, 0.04 mmol) and Na$_2$CO$_3$ (1 M in water, 1.4 ml, 1.4 mmol) in 1,4-dioxane (3.6 ml) was stirred at 70° C. for 60 mins. The reaction was then cooled to room temperature and slowly diluted with water (5 ml) and DCM (5 ml) and acidified via addition of HCl. The layers were separated and the DCM layer filtered and then concentrated to give the title compound as a yellow solid. MS (m/z) 608.3 (M+H$^+$).

INTERMEDIATES 135-146 were prepared from N—(((R)-2-((R)-1-(N-(benzyloxy)formamido)propyl)heptanamido)methyl)-5-bromofuran-2-carboxamide and the indicated boronic acid or boronate by methods analogous to those described for Intermediate 134.

| # | Name | Structure |
|---|------|-----------|
| 135 | 5-(5-((((R)-2-((R)-1-(N-(benzyloxy)formamido)propyl)heptanamido)methyl)carbamoyl)furan-2-yl)nicotinic acid | 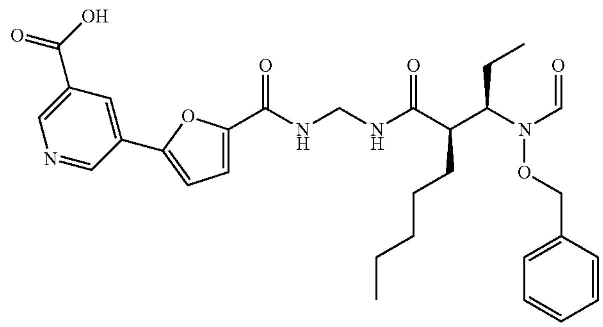 [SMILES: CCCCC[C@@H](C(=O)NCNC(=O)c1ccc(-c2cncc(C(=O)O)c2)o1)[C@@H](CC)N(C=O)OCc1ccccc1] |
| 136 | (S)-dimethyl 2-(4-(5-((((R)-2-((R)-1-(N-(benzyloxy)formamido)propyl)heptanamido)methyl)carbamoyl)furan-2-yl)-2-ethoxybenzamido)succinate | 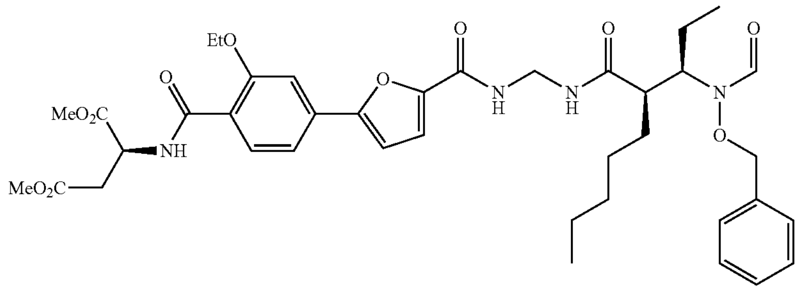 [SMILES: CCCCC[C@@H](C(=O)NCNC(=O)c1ccc(-c2ccc(C(=O)N[C@@H](CC(=O)OC)C(=O)OC)c(OCC)c2)o1)[C@@H](CC)N(C=O)OCc1ccccc1] |
| 137 | (S)-dimethyl 2-(2-(4-(5-((((R)-2-((R)-1-(N-(benzyloxy)formamido)propyl)heptanamido)methyl)carbamoyl)furan-2-yl)-2-ethoxyphenyl)acetamido)succinate | 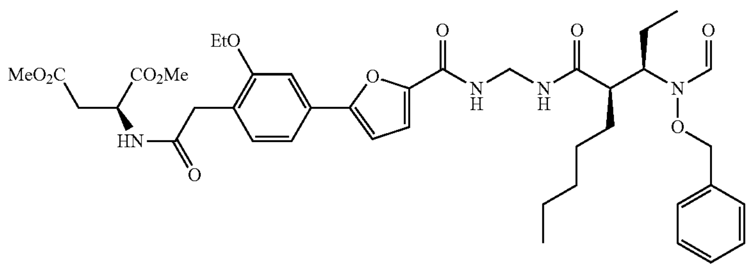 [SMILES: CCCCC[C@@H](C(=O)NCNC(=O)c1ccc(-c2ccc(CC(=O)N[C@@H](CC(=O)OC)C(=O)OC)c(OCC)c2)o1)[C@@H](CC)N(C=O)OCc1ccccc1] |
| 138 | methyl-3-(5-((((R)-2-((R)-1-(N-(benzyloxy)formamido)propyl)heptanamido)methyl)carbamoyl)furan-2-yl)-5-ethoxybenzoate | 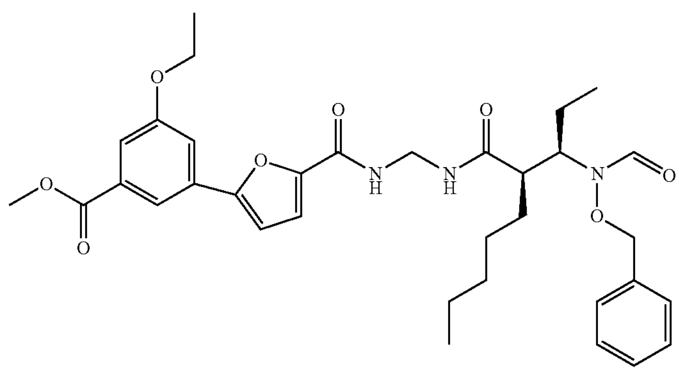 [SMILES: CCCCC[C@@H](C(=O)NCNC(=O)c1ccc(-c2cc(OCC)cc(C(=O)OC)c2)o1)[C@@H](CC)N(C=O)OCc1ccccc1] |
| 139 | N-(((R)-2-((R)-1-(N-(benzyloxy)formamido)propyl)heptanamido)methyl)-5-(3-ethoxy-5-hydroxyphenyl)furan-2-carboxamide | 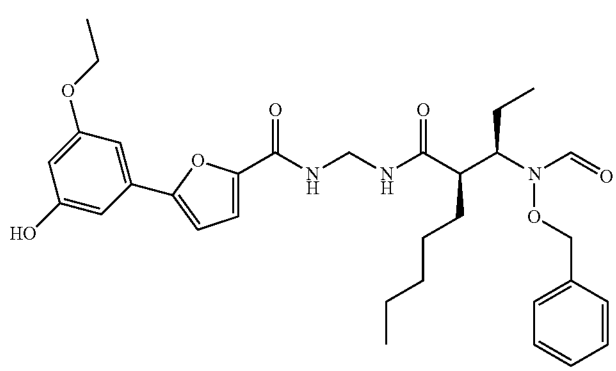 [SMILES: CCCCC[C@@H](C(=O)NCNC(=O)c1ccc(-c2cc(O)cc(OCC)c2)o1)[C@@H](CC)N(C=O)OCc1ccccc1] |

| | | |
|---|---|---|
| 140 | 2-(4-(5-((((R)-2-((R)-1-(N-(benzyloxy)formamido)propyl)heptanamido)methyl)carbamaoyl)furan-2-yl)-2-ethoxyphenyl)acetic acid | 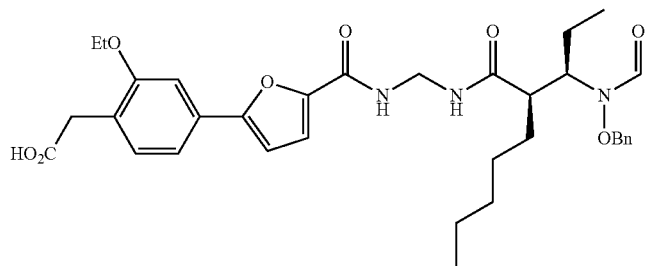 |
| 141 | 2-(4-(5-((((R)-2-((R)-1-(N-(benzyloxy)formamido)propyl)heptanamido)methyl)carbamoyl)furan-2-yl)phenyl)acetic acid | 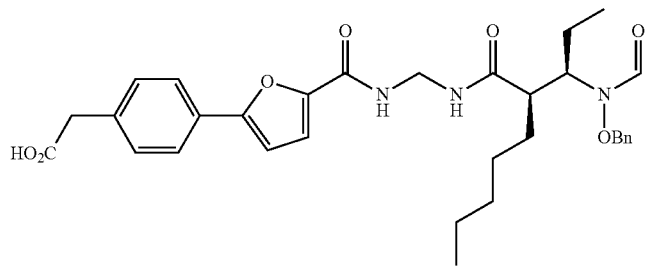 [SMILES: CCCCC[C@@H](C(=O)NCNC(=O)c1ccc(-c2ccc(CC(=O)O)cc2)o1)[C@@H](CC)N(C=O)OCc1ccccc1] |
| 142 | 2-(4-(5-((((R)-2-((R)-1-(N-(benzyloxy)formamido)propyl)heptanamido)methyl)carbamoyl)furan-2-yl)phenyl)-2-methylpropanoic acid | 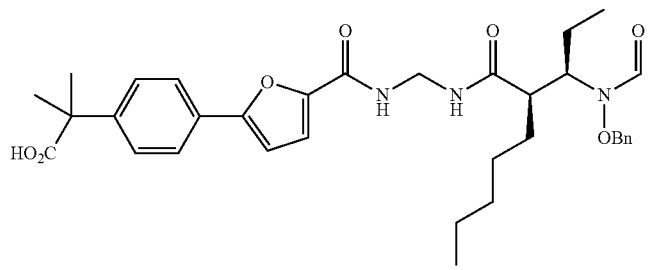 [SMILES: CCCCC[C@@H](C(=O)NCNC(=O)c1ccc(-c2ccc(C(C)(C)C(=O)O)cc2)o1)[C@@H](CC)N(C=O)OCc1ccccc1] |
| 143 | 1-(4-(5-((((R)-2-((R)-1-(N-(benzyloxy)formamido)propyl)heptanamido)methyl)carbamoyl)furan-2-yl)phenyl)cyclopropanecarboxylic acid | 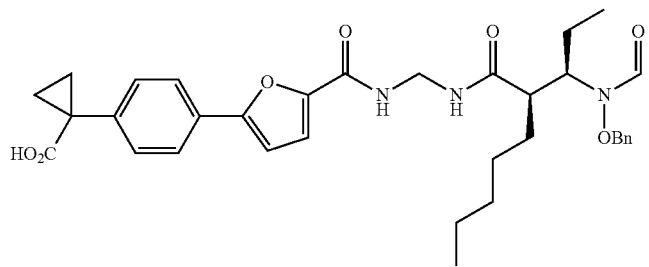 [SMILES: CCCCC[C@@H](C(=O)NCNC(=O)c1ccc(-c2ccc(C3(C(=O)O)CC3)cc2)o1)[C@@H](CC)N(C=O)OCc1ccccc1] |
| 144 | 2-(3-(5-((((R)-2-((R)-1-(N-(benzyloxy)formamido)propyl)heptanamido)methyl)carbamaoyl)furan-2-yl)-5-ethoxyphenyl)-2,2-difluoroacetic acid | 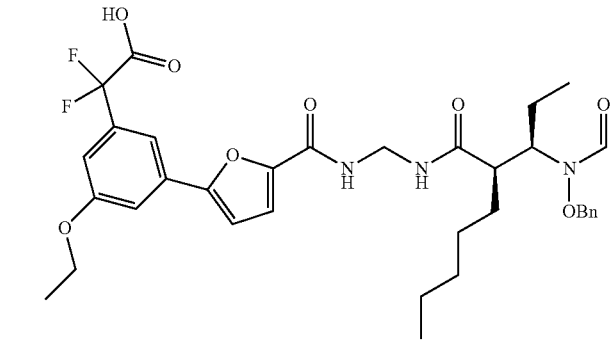 |

-continued

| # | | | MS (m/z) (M + H⁺) | Boronoic Acid/Boronate |
|---|---|---|---|---|
| 145 | dimethyl 3-(5-((((R)-2-((R)-1-(N-(benzyloxy)formamido)propyl)heptanamido)methyl)carbamoyl)furan-2-yl)-5-ethoxybenzylphosphonate |  | | |
| 135 | | | 565.2 | 5-borononicotinic acid |
| 136 | | | 751.4 | (S)-dimethyl 2-(2-ethoxy-4-(4,4,5,5-tetramethyl-1,3,2-dioxaborolan-2-yl)benzamido)succinate |
| 137 | | | 765.3 | (S)-dimethyl 2-(2-(2-ethoxy-4-(4,4,5,5-tetramethyl-1,3,2-dioxaborolan-2-yl)phenyl)acetamido)succinate |
| 138 | | | 622.3 | 3-ethoxy-5-(4,4,5,5-tetramethyl-1,3,2-dioxaborolan-2-yl)benzoate |
| 139 | | | 580.4 | 3-ethoxy-5-(4,4,5,5-tetramethyl-1,3,2-dioxaborolan-2-yl)phenol |
| 140 | | | 622.3 | 2-(2-ethoxy-4-(4,4,5,5-tetramethyl-1,3,2-dioxaborolan-2-yl)phenyl)acetic acid |
| 141 | | | 578.3 | 2-(4-(4,4,5,5-tetramethyl-1,3,2-dioxaborolan-2-yl)phenyl)acetic acid |
| 142 | | | 606.3 | 2-(4-boronophenyl)-2-methylpropanoic acid |
| 143 | | | 604.3 | 1-(4-boronophenyl)cyclopropanecarboxylic acid |
| 144 | | | 658.0 | 2-(3-ethoxy-5-(4,4,5,5-tetramethyl-1,3,2-dioxaborolan-2-yl)phenyl)-2,2-difluoroacetic acid |
| 145 | | | 686.3 | dimethyl 3-ethoxy-5-(4,4,5,5-tetramethyl-1,3,2-dioxaborolan-2-yl)benzylphosphonate |

INTERMEDIATE 146 was prepared from (R)—N-((2-((N-(benzyloxy)formamido)methyl)heptanamido)methyl)-5-bromofuran-2-carboxamide and the indicated boronate by methods analogous to those described for Intermediate 134.

| # | Name | Structure | MS (m/z) (M + H⁺) | Boronate |
|---|---|---|---|---|
| 146 | (R)-methyl 3-(5-(((2-((N-(benzyloxy)formamido)methyl)heptanamido)methyl)carbamoyl)furan-2-yl)-5-ethoxybenzoate | 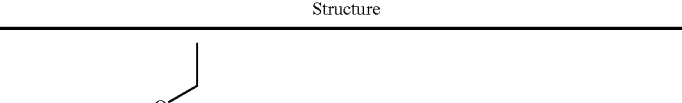 | 594.2 | methyl 3-ethoxy-5-(4,4,5,5-tetramethyl-1,3,2-dioxaborolan-2-yl)benzoate |

Intermediate 147: dimethyl (4-(5-((((R)-2-((R)-1-(N-(benzyloxy)formamido)propyl)heptanamido)methyl)carbamoyl)furan-2-yl)-2-ethoxyphenyl)phosphonate

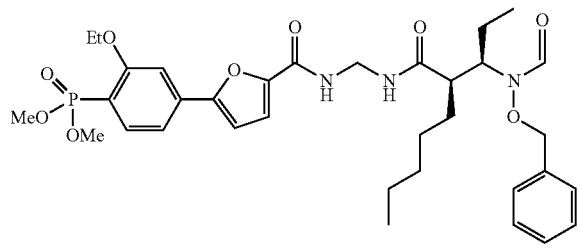 [SMILES: CCCCC[C@@H](C(=O)NCNC(=O)c1ccc(-c2ccc(P(=O)(OC)OC)c(OCC)c2)o1)[C@@H](CC)N(C=O)OCc1ccccc1]

A mixture of dimethyl (2-ethoxy-4-(4,4,5,5-tetramethyl-1,3,2-dioxaborolan-2-yl)phenyl) phosphonate (409 mg, 1.15 mmol), N—(((R)-2-((R)-1-(N-(benzyloxy)formamido)propyl)heptanamido)methyl)-5-bromofuran-2-carboxamide (500 mg, 0.96 mmol), $PdCl_2(dppf)$-$CH_2Cl_2$ adduct (19.6 mg, 0.02 mmol) and $Na_2CO_3$ (1 M in water, 2.87 ml, 2.87 mmol) in 1,4-dioxane (6.7 ml) was stirred at 50° C. for 30 minutes. The reaction was then cooled to room temperature and slowly diluted with water and DCM. The layers were separated and the aqueous layer extracted twice with DCM. The combined DCM extracts were combined and concentrated. The residue was purified by flash chromatography (ISCO, 120 g silica column, 0-10% MeOH/DCM over 30 minutes) to give the title compound (600 mg, 93% yield). MS (m/z) 672.3 (M+H$^+$).

Intermediate 148: dimethyl (3-(5-((((R)-2-((R)-1-(N-(benzyloxy)formamido)propyl)heptanamido)methyl)carbamoyl)furan-2-yl)-5-ethoxyphenyl)phosphonate

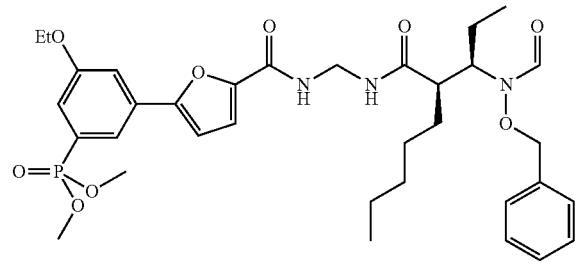 [SMILES: CCCCC[C@@H](C(=O)NCNC(=O)c1ccc(-c2cc(OCC)cc(P(=O)(OC)OC)c2)o1)[C@@H](CC)N(C=O)OCc1ccccc1]

A mixture of dimethyl (3-ethoxy-5-(4,4,5,5-tetramethyl-1,3,2-dioxaborolan-2-yl)phenyl)phosphonate (6.44 g, 14.65 mmol), N—(((R)-2-((R)-1-(N-(benzyloxy)formamido)propyl)heptanamido)methyl)-5-bromofuran-2-carboxamide (6.95 g, 13.30 mmol), $PdCl_2(dppf)$-$CH_2Cl_2$ adduct (0.38 g, 0.47 mmol) and $Na_2CO_3$ (1 M in water, 39.9 ml, 39.9 mmol) in 1,4-dioxane (93 ml) was stirred at 50° C. for 60 minutes. The reaction was then cooled to room temperature and slowly diluted with $Et_2O$ and water. The layers were separated and the aqueous layer extracted twice with $Et_2O$. The combined ether extracts were dried over $Na_2SO_4$, filtered and concentrated to give a dark residue. To this residue was added $Et_2O$ (until it became cloudy), the solution was stirred and additional ether was added (~200 ml). After 10 minutes, the slurry was filtered. The filtrate was concentrated to give ~3 g of impure material. The gray solids were azeotroped with DCM to give 7.8 g of a gray material.

The 3 g of material obtained from the filtrate was purified via flash chromatography (ISCO, 330 g column, 0-10% MeOH/DCM over 30 minutes) to give 1.6 g of the desired product containing some impurities. To this residue was added $Et_2O$ (until it became cloudy), the solution was stirred and additional ether was added (~200 ml). After 10 minutes, the slurry was filtered. The filtrate was purified by reverse phase HPLC (Waters, Sunfire, 30×150 mm, 30-80% $CH_3CN$/water (+0.1% TFA) over 14 minutes). Fractions containing product were diluted with EtOAc and water. The water was extracted a total of 3 times and the combined extracts were concentrated to give the title compound as an off white solid (0.4 g, 5% yield).

The gray solid (7.8 g) was purified by flash chromatography (ISCO, 220 g, 0-10% MeOH/DCM over 30 minutes), fractions containing product were combined with the solids obtained from the 1.6 g crystallization and the material azeotroped with EtOAc (3×). The resulting solids were then suspended in EtOAc (~100 ml) and the mixture heated to 60° C. then allowed to cool to room temperature with stirring, which was continued overnight. The slurry was then cooled to 0° C. and the solids collected by filtration, washed with hexanes and dried to give the desired product as a light gray solid. The filtrate was concentrated to dryness and re-crystalized from $Et_2O$ and combined with the light gray solid from the EtOAc crystallization to give an additional batch of the title compound (7.25 g, 81% yield). The filter funnel from the ether filtration was washed with DCM and the filtrate concentrated to give an additional batch of the title compound (0.9 g, 10% yield). MS (m/z) 672.3 (M+H$^+$).

Intermediate 149: 3-(5-((((R)-2-((R)-1-(N-(benzyloxy)formamido)propyl)heptanamido)methyl)carbamoyl)furan-2-yl)-5-ethoxybenzoic acid

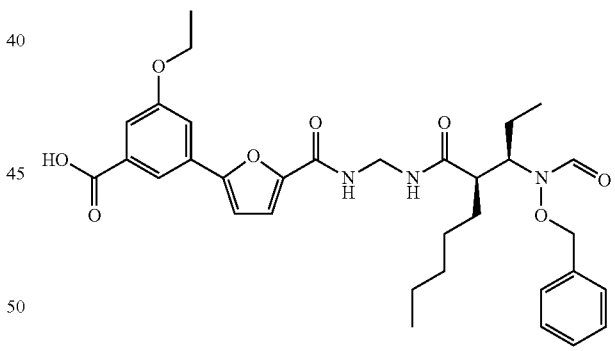

Lithium hydroxide hydrate (26.3 mg, 0.627 mmol) was added to a solution of methyl 3-(5-((((R)-2-((R)-1-(N-(benzyloxy)formamido)propyl)heptanamido)methyl)carbamoyl)furan-2-yl)-5-ethoxybenzoate (260 mg, 0.314 mmol) in water (0.84 ml) and tetrahydrofuran (3.35 ml) and stirred at room temperature for 18 hours. The reaction was diluted with a small amount of $CH_3CN$, filtered, and purified via reverse phase HPLC (Waters, XBridge Prep Shield RP $C_{18}$ 5 μm OBD 30×150 mm column, 20-60% $CH_3CN$/water+ 0.1% $NH_4OH$ over 14 minutes). Fractions containing product were combined, diluted with water, acidified by the addition of HCl and extracted with DCM. The DCM was passed through a phase separator and concentrated to give the title compound (162 mg, 85% yield). MS (m/z) 608.3 (M+H$^+$).

151

Intermediate 150: (R)-3-(5-(((2-((N-(benzyloxy)formamido)methyl)heptanamido)methyl)carbamoyl)furan-2-yl)-5-ethoxybenzoic acid

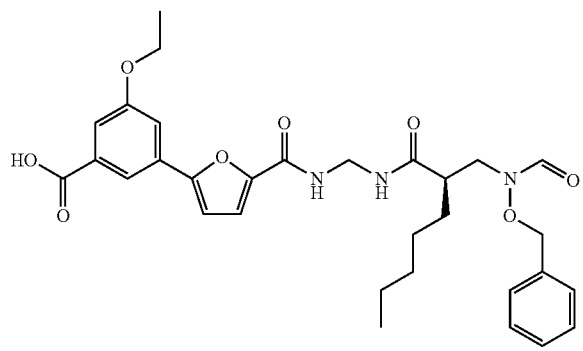 [SMILES: CCCCC[C@H](CN(C=O)OCc1ccccc1)C(=O)NCNC(=O)c1ccc(-c2cc(OCC)cc(C(=O)O)c2)o1]

Step 1: (R)-3-(5-(((2-((N-(benzyloxy)formamido)methyl)heptanamido)methyl)carbamoyl)furan-2-yl)-5-ethoxybenzoic acid and (R)-3-(5-(((2-(((benzyloxy)amino)methyl)heptanamido)methyl)carbamoyl)furan-2-yl)-5-ethoxybenzoic acid

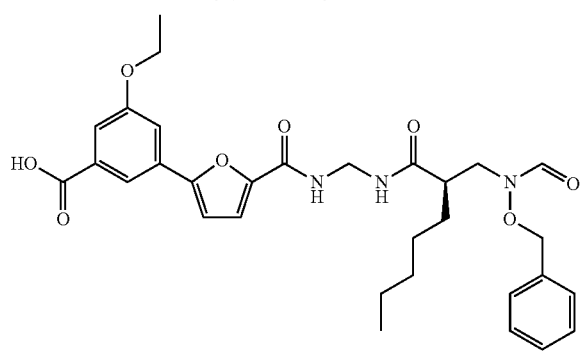 [SMILES: CCCCC[C@H](CN(C=O)OCc1ccccc1)C(=O)NCNC(=O)c1ccc(-c2cc(OCC)cc(C(=O)O)c2)o1]

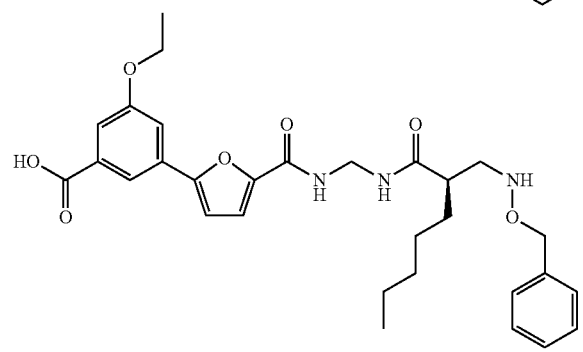

152

(R)-methyl 3-(5-(((2-((N-(benzyloxy)formamido)methyl)heptanamido)methyl)carbamoyl)furan-2-yl)-5-ethoxybenzoate (572 mg, 0.87 mmol), was dissolved in methanol (2.5 ml) and tetrahydrofuran (2.5 ml) and sodium hydroxide (2 M, 2.17 ml, 4.34 mmol) was added and the reaction stirred at room temperature for 30 minutes. The reaction mixture was then concentrated and the residue adjusted to pH 5 via addition of 1 M HCl and extracted with EtOAc (2×) and DCM (1×). The combined organic layers were concentrated to give a mixture of the title compounds as a pale yellow solid (424 mg). MS (m/z) 580.3 (M+H$^+$) and 552.3 (M+H$^+$).

Step 2: (R)-3-(5-(((2-((N-(benzyloxy)formamido)methyl)heptanamido)methyl)carbamoyl)furan-2-yl)-5-ethoxybenzoic acid

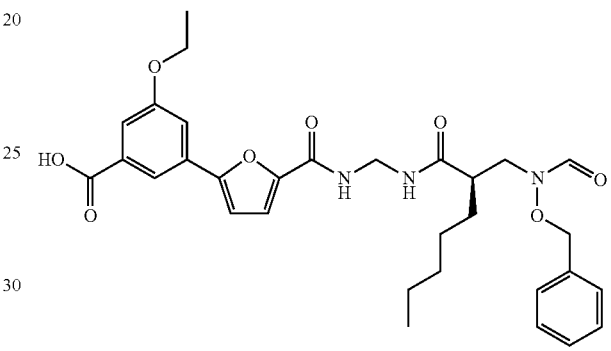

5-methyl-2-thioxo-1,3,4-thiadiazole-3(2H)-carbaldehyde (103 mg, 0.646 mmol) was added to a solution of (R)-3-(5-(((2-((N-(benzyloxy)formamido)methyl)heptanamido)methyl)carbamoyl)furan-2-yl)-5-ethoxybenzoic acid and (R)-3-(5-(((2-(((benzyloxy)amino)methyl)heptanamido)methyl)carbamoyl)furan-2-yl)-5-ethoxybenzoic acid (312 mg, 0.538 mmol) in dichloromethane (4 ml) and the reaction stirred at room temperature for 1 hour. The reaction mixture was concentrated and the residue purified by flash chromatography (10 g Si SPE, DCM, diethyl ether, ethyl acetate, acetone and 10% MeOH/DCM) to yield the title compound as an off white solid (402 mg, 80% yield). MS (m/z) 580.2 (M+H$^+$).

Intermediate 151: (S)-dimethyl 2-(3-(5-((((R)-2-((R)-1-(N-(benzyloxy)formamido)propyl)heptanamido)methyl)carbamoyl)furan-2-yl)benzamido)succinate

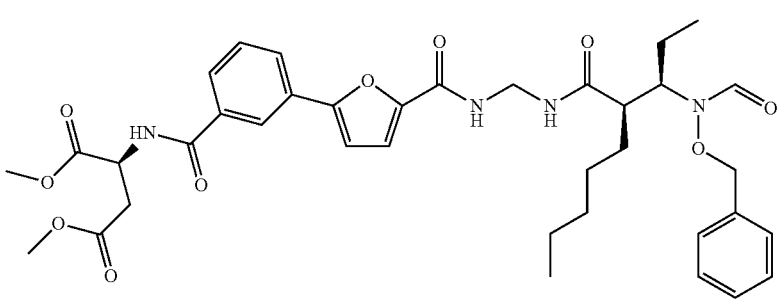 [SMILES: CCCCC[C@@H](C(=O)NCNC(=O)c1ccc(-c2cccc(C(=O)N[C@@H](CC(=O)OC)C(=O)OC)c2)o1)[C@@H](CC)N(C=O)OCc1ccccc1]

To a mixture of (S)-dimethyl 2-aminosuccinate, hydrochloride (56.1 mg, 0.28 mmol), 3-(5-((((R)-2-((R)-1-(N-(benzyloxy)formamido)propyl)heptanamido)methyl)carbamoyl)furan-2-yl)benzoic acid (160 mg, 0.28 mmol) and triethylamine (0.12 ml, 0.85 mmol) in dichloromethane (2.38 ml) was added T3P® (50% wt in EtOAc, 0.34 ml, 0.57 mmol) and the reaction stirred for 2 hours at room temperature. The reaction was then diluted by the addition of DCM (7 ml) and water (5 ml). The layers were separated and the organic washed with water (5 ml), additional water (20 ml) was added to the emulsion that formed. The organic was then collected via hydrophobic frit and concentrated. The residue was purified via flash chromatography (ISCO Combiflash Rf, 25 g, column, 20-100% ethyl acetate/hexanes) to give the title compound (98 mg, 49% yield). MS (m/z) 707.3 (M+H$^+$).

INTERMEDIATE 152 was prepared from 3-(5-((((R)-2-((R)-1-(N-(benzyloxy)formamido)propyl)heptanamido)methyl)carbamoyl)furan-2-yl)-5-ethoxybenzoic acid and the indicated amine by methods analogous to those described for Intermediate 151.

| # | Name | Structure | MS (m/z) (M + H$^+$) | Amine |
|---|------|-----------|---------------------|-------|
| 152 | (R)-dimethyl 2-(3-(5-((((R)-2-((R)-1-(N-(benzyloxy)formamido)propyl)heptanamido)methyl)carbamoyl)furan-2-yl)-5-ethoxybenzamido)succinate | 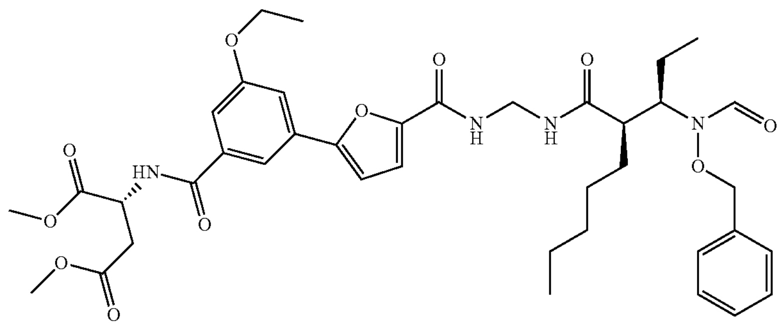 [SMILES: CCCCC[C@@H](C(=O)NCNC(=O)c1ccc(-c2cc(OCC)cc(C(=O)N[C@H](CC(=O)OC)C(=O)OC)c2)o1)[C@@H](CC)N(C=O)OCc1ccccc1] | 751.3 | (R)-dimethyl 2-aminosuccinate, hydrochloride |

INTERMEDIATE 153 was prepared from 4-(5-((((R)-2-((R)-1-(N-(benzyloxy)formamido)propyl)heptanamido)methyl)carbamoyl)furan-2-yl)-2-ethoxybenzoic acid and the indicated amine by methods analogous to those described for Intermediate 151.

| # | Name | Structure | MS (m/z) (M + H$^+$) | Amine |
|---|------|-----------|---------------------|-------|
| 153 | dimethyl 2,2'-((4-(5-((((R)-2-((R)-1-(N-(benzyloxy)formamido)propyl)heptanamido)methyl)carbamoyl)furan-2-yl)-2-ethoxybenzoyl)azanediyl)diacetate | 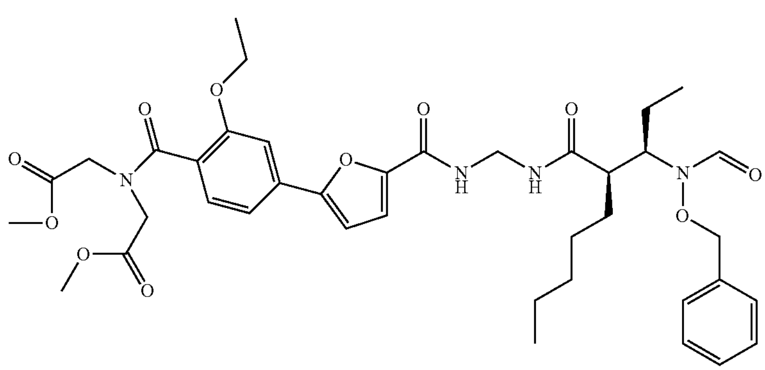 [SMILES: CCCCC[C@@H](C(=O)NCNC(=O)c1ccc(-c2ccc(C(=O)N(CC(=O)OC)CC(=O)OC)c(OCC)c2)o1)[C@@H](CC)N(C=O)OCc1ccccc1] | 751.4 | dimethyl 2,2'-azanediyldiacetate |

Intermediate 154: methyl 2-(3-(5-((((R)-2-((R)-1-(N-(benzyloxy)formamido)propyl)heptanamido)methyl)carbamoyl)furan-2-yl)-5-ethoxybenzamido)acetate

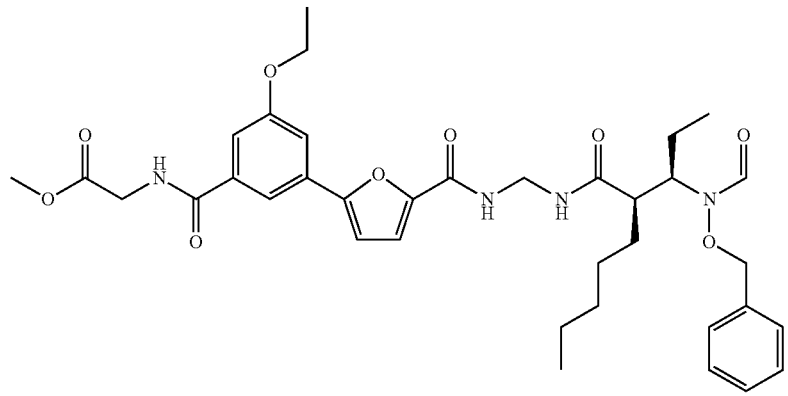 [SMILES: CCCCC[C@@H](C(=O)NCNC(=O)c1ccc(-c2cc(OCC)cc(C(=O)NCC(=O)OC)c2)o1)[C@@H](CC)N(C=O)OCc1ccccc1]

To a solution of 3-(5-((((R)-2-((R)-1-(N-(benzyloxy)formamido)propyl)heptanamido)methyl)carbamoyl)furan-2-yl)-5-ethoxybenzoic acid (185 mg, 0.30 mmol), glycine methyl ester hydrochloride (38.2 mg, 0.30 mmol) and HATU (133 mg, 0.35 mmol) in dichloromethane (1.55 ml) was added DIPEA (0.17 ml, 0.94 mmol) and the reaction stirred at room temperature for 1 hr 15 minutes. The reaction was then concentrated and water (10 ml) and DCM (10 ml) were added to the residue. The organic was collected via hydrophobic frit and concentrated. The residue was purified via flash chromatography (ISCO Combiflash Rf, 25 g column, 20-100% ethyl acetate/hexanes) to give the title compound (83.6 mg, 41% yield). MS (m/z) 679.3 (M+H⁺).

INTERMEDIATES 155-158 were prepared from 3-(5-((((R)-2-((R)-1-(N-(benzyloxy)formamido)propyl)heptanamido)methyl)carbamoyl)furan-2-yl)-5-ethoxybenzoic acid and the indicated amine by methods analogous to those detailed for Intermediate 154.

| # | Name | Structure |
|---|------|-----------|
| 155 | dimethyl 2,2'-((3-(5-((((R)-2-((R)-1-(N-(benzyloxy)formamido)propyl)heptanamido)methyl)carbamoyl)furan-2-yl)-5-ethoxybenzoyl)azanediyl)diacetate | 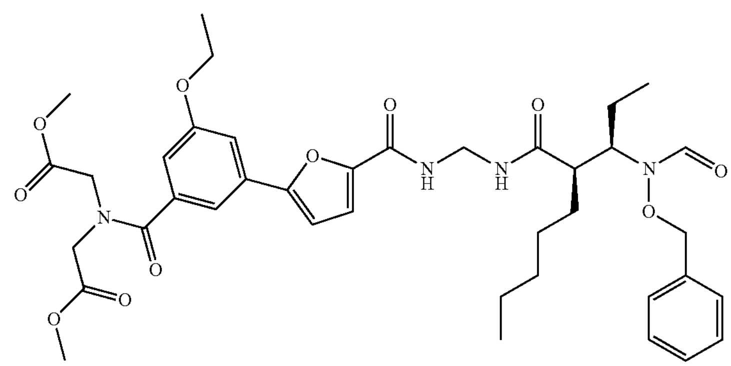 [SMILES: CCCCC[C@@H](C(=O)NCNC(=O)c1ccc(-c2cc(OCC)cc(C(=O)N(CC(=O)OC)CC(=O)OC)c2)o1)[C@@H](CC)N(C=O)OCc1ccccc1] |
| 156 | 2-(3-5-((((R)-2-((R)-1-(N-(benzyloxy)formamido)propyl)heptanamido)methyl)carbamoyl)furan-2-yl)-5-ethoxybenzamido)-N,N,N-trimethylethanaminium | 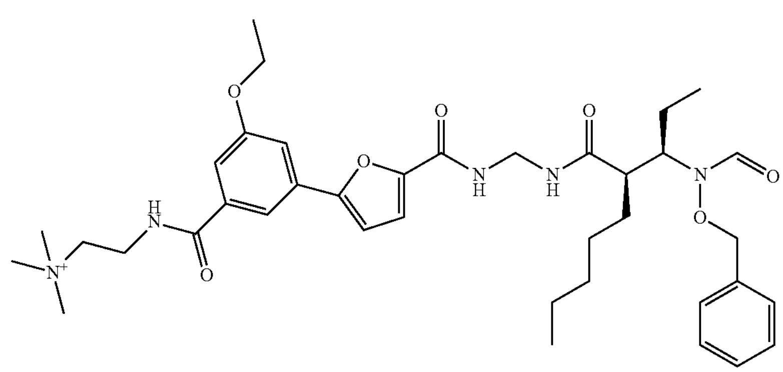 [SMILES: CCCCC[C@@H](C(=O)NCNC(=O)c1ccc(-c2cc(OCC)cc(C(=O)NCC[N+](C)(C)C)c2)o1)[C@@H](CC)N(C=O)OCc1ccccc1] |

| # | Name | Structure |
|---|---|---|
| 157 | N-(((R)-2-((R)-1-(N-(benzyloxy)formamido)propyl)heptanamido)methyl)-5-(3-ethoxy-5-((6-(hydroxymethyl)-2,2,3,3,9,9,10,10-octamethyl-4,8-dioxa-3,9-disilaundecan-6-yl)carbamoyl)phenyl)furan-2-carboxamide | 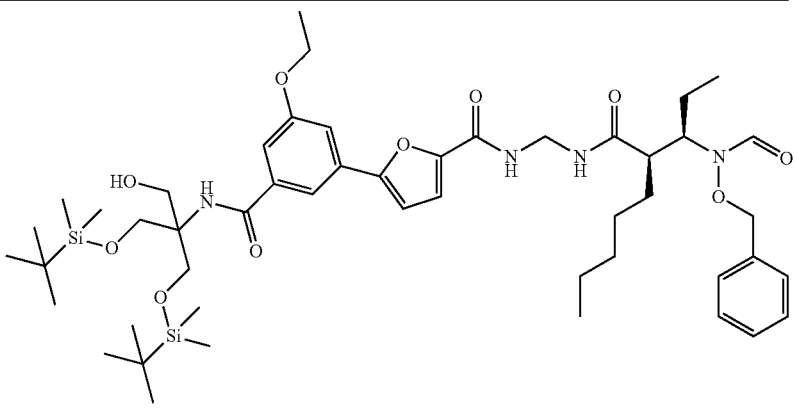 |
| 158 | diethyl ((3-(5-((((R)-2-((R)-1-(N-(benzyloxy)formamido)propyl)heptanamido)methyl)carbamoyl)furan-2-yl)-5-ethoxybenzamido)methyl)phosphonate | 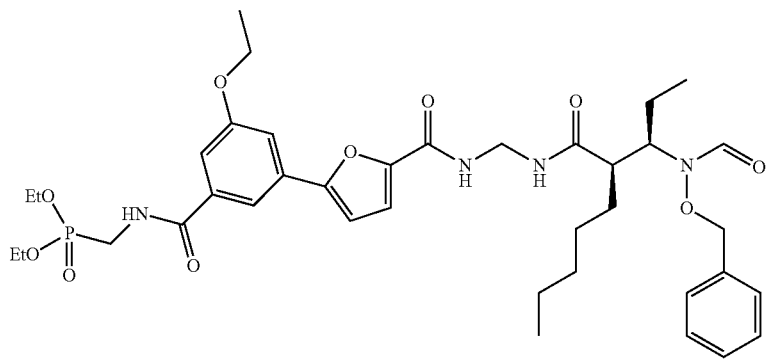 [SMILES: CCCCC[C@@H](C(=O)NCNC(=O)c1ccc(-c2cc(OCC)cc(C(=O)NCP(=O)(OCC)OCC)c2)o1)[C@@H](CC)N(C=O)OCc1ccccc1] |

| # | MS (m/z) | Amine |
|---|---|---|
| 155 | | dimethyl 2,2'-azanediyldiacetate, hydrochloride |
| 156 | 692.3 (M+) | 2-amino-N,N,N-trimethylethanaminium, chloride•hydrochloride |
| 157 | 940.5 (M + H⁺) | 6-(((tertbutyldimethylsilyl)oxy)methyl)-2,2,3,3,9,9,10,10-octamethyl-4,8-dioxa-3,9-disilaundecan-6-amine |
| 158 | 757.3 (M + H⁺) | diethyl(aminomethyl)phosphonate |

INTERMEDIATES 159-161 were prepared from benzyl (2-aminoethyl)carbamate, hydrochloride and the indicated acid by methods analogous to those described for Intermediate 154. Intermediates 159 and 161 used DMF as solvent instead of DCM.

| # | Name | Structure |
|---|---|---|
| 159 | (R)-benzyl 2-(3-(5-(((2-(N-(benzyloxy)formamido)methyl)heptanamido)methyl)carbamoyl)furan-2-yl)-5-methoxybenzamido)ethyl)carbamate | 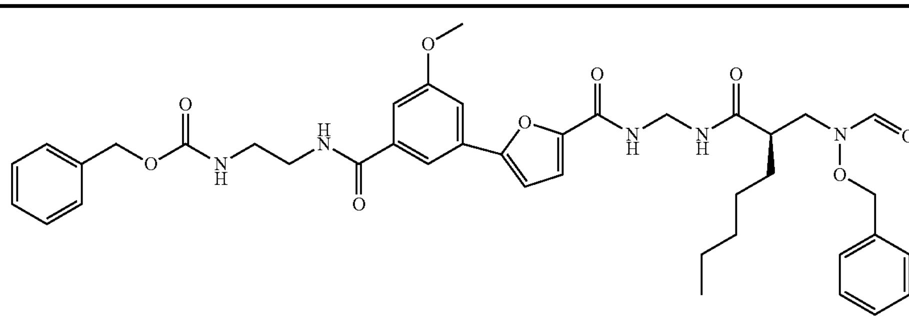 |

| 160 | (R)-benzyl (2-(3-(5-(((2-((N-benzyloxy)formamido)methyl)heptanamido)methyl)carbamoyl)furan-2-yl)-5-ethoxybenzamido)ethyl)carbamate | 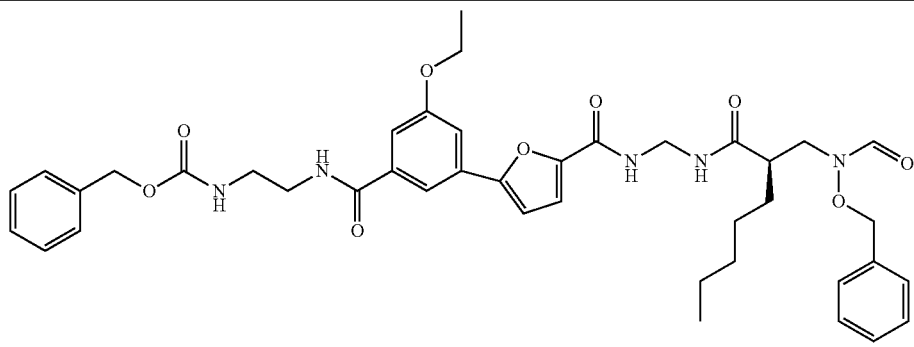 |

| 161 | benzyl (2-(3-(5-((((R)-2-((R)-1-(N-(benzyloxy)formamido)propyl)heptanamido)methyl)carbamoyl)furan-2-yl)-5-ethoxybenzamido)ethyl)carbamate | 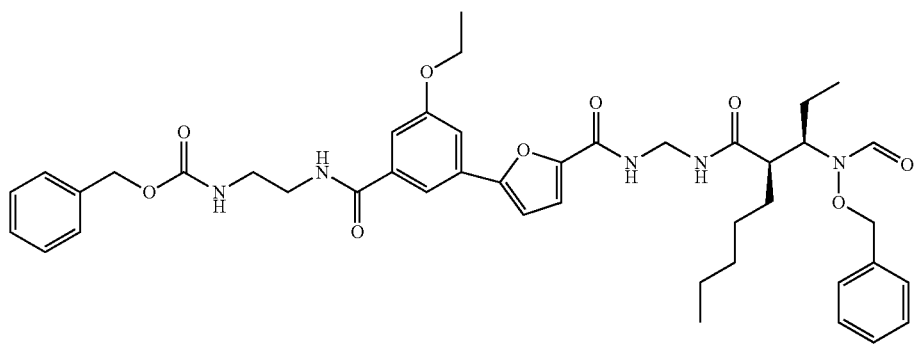 [SMILES: CCCCC[C@@H](C(=O)NCNC(=O)c1ccc(-c2cc(OCC)cc(C(=O)NCCNC(=O)OCc3ccccc3)c2)o1)[C@@H](CC)N(C=O)OCc1ccccc1] |

| # | MS (m/z) (M + H⁺) | Acid |
|---|---|---|
| 159 | 742.3 | (R)-3-(5-(((2-((N-(benzyloxy)formamido)methyl)heptanamido)methyl)carbamoyl)furan-2-yl)-5-methoxybenzoic acid |
| 160 | 756.3 | (R)-3-(5-(((2-((N-(benzyloxy)formamido)methyl)heptanamido)methyl)carbamoyl)furan-2-yl)-5-ethoxy-benzoic acid |
| 161 | 784.3 | 3-(5-((((R)-2-((R)-1-(N-(benzyloxy)formamido)propyl)heptanamido)methyl)carbamoyl)furan-2-yl)-5-ethoxybenzoic acid |

INTERMEDIATES 162-164 were prepared from 3-(5-(((((R)-2-((R)-1-(N-(benzyloxy)formamido)propyl)heptanamido)methyl)carbamoyl)furan-2-yl)-5-ethoxybenzoic acid and the indicated amine by methods analogous to those detailed for Intermediate 154 utilizing triethylamine as the base instead of DIPEA.

| Name | Structure | MS (m/z) (M + H⁺) | Amine |
|---|---|---|---|
| 162 (S)-5-benzyl 1-tert-butyl 2-(3-(5-((((R)-2-((R)-1-(N-(benzyloxy)formamido)propyl)heptanamido)methyl)carbamoyl)furan-2-yl)-5-ethoxybenzamido)pentanedioate | | 883.5 | (S)-5-benzyl 1-tert-butyl 2-aminopentanedioate, hydrochloride |
| 163 (S)-4-benzyl 1-tert-butyl 2-(3-(5-((((R)-2-((R)-1-(N-(benzyloxy)formamido)propyl)heptanamido)methyl)carbamoyl)furan-2-yl)-5-ethoxybenzamido)succinate | | 869.3 | (S)-4-benzyl 1-tert-butyl 2-aminosuccinate, hydrochloride |
| 164 (S)-dimethyl 2-(3-(5-((((R)-2-((R)-1-(N-(benzyloxy)formamido)propyl)heptanamido)methyl)carbamoyl)furan-2-yl)-5-ethoxybenzamido)pentanedioate | | 765.3 | (S)-dimethyl 2-aminopentanedioate, hydrochloride |

Intermediate 165: (R)—N-((2-((N-(benzyloxy)formamido)methyl)heptanamido)methyl)-5-(3-(N-propionylsulfamoyl) phenyl)furan-2-carboxamide

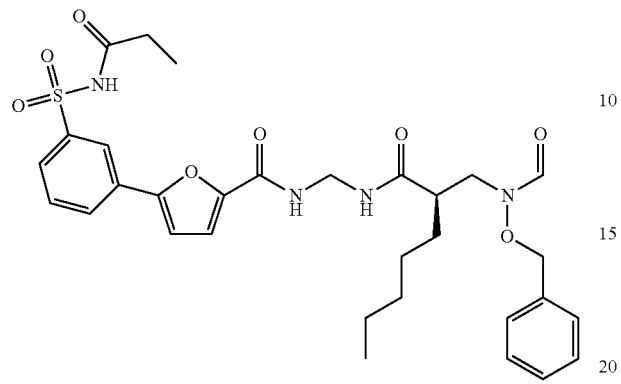

(R)—N-((2-((N-(benzyloxy)formamido)methyl)heptanamido)methyl)-5-(3-sulfamoylphenyl)furan-2-carboxamide (103 mg, 0.180 mmol) in DCM (723 µl) was treated with triethylamine (75 µl, 0.541 mmol) for 20 minutes. Propionic anhydride (69.4 µl, 0.541 mmol) was added and the reaction was heated to 50° C. overnight. The reaction was then cooled to room temp and ice added. The reaction was then extracted with DCM, the organic layer was passed through a phase separator and concentrated. The residue was purified by flash chromatography (ISCO, 24 g silica gel column. 0-100% EtOAc/DCM: 10 minutes, 100% EtOAc: 20 minutes) to give the title compound as a sticky solid (59 mg, 52.2% yield). MS (m/z) 627.3 (M+H$^+$).

Intermediate 166: (2R,3R)-3-(N-(benzyloxy)formamido)-2-phenethylpentanoic acid

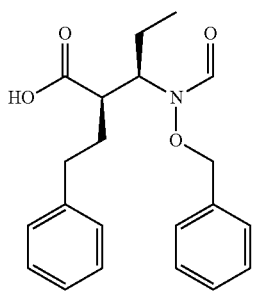 [SMILES: CC[C@H]([C@@H](CCc1ccccc1)C(=O)O)N(C=O)OCc1ccccc1]

Intermediate 166 was prepared from 4-phenylbutanoyl chloride by methods analogous to that described for Intermediate 8.

| Step | Name | MS (m/z) |
|---|---|---|
| 1 | (R)-4-benzyl-3-(4-phenylbutanoyl)oxazolidin-2-one | 324.1 |
| 2 | (R)-4-benzyl-3-((2R,3S)-3-hydroxy-2-phenethylpentanoyl)oxazolidin-2-one | 382.1 |
| 3 | (2R,3S)-N-(benzyloxy)-3-hydroxy-2-phenethylpentanamide | 328.1 |
| 4 | (3R,4R)-1-(benzyloxy)-4-ethyl-3-phenethylazetidin-2-one | 310.1 |
| 5 | (2R,3R)-3-((benzyloxy)amino)-2-phenethylpentanoic acid | 328.1 |
| 6 | (2R,3R)-3-(N-(benzyloxy)formamido)-2-phenethylpentanoic acid | 356.1 |

Intermediate 167: (2R,3R)-3-(N-(benzyloxy)formamido)-2-(2-(naphthalen-2-yl)ethyl)pentanoic acid

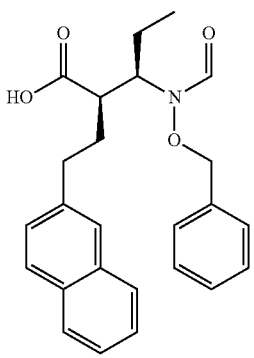 [SMILES: CC[C@H]([C@@H](CCc1ccc2ccccc2c1)C(=O)O)N(C=O)OCc1ccccc1]

Intermediate 167 was prepared from 4-(naphthalen-2-yl)butanoyl chloride by methods analogous to that described for Intermediate 8, except for Step 4' which is outlined below.

Step 4': (3R,4R)-1-(benzyloxy)-4-ethyl-3-(2-(naphthalen-2-yl)ethyl)azetidin-2-one To a cooled solution at 0° C. of (2R,3S)—N-(benzyloxy)-3-hydroxy-2-(2-(naphthalen-2-yl)ethyl)pentanamide (20 g, 28.1 mmol) in tetrahydrofuran (THF) (150 ml) was added triphenylphosphine (8.84 g, 33.7 mmol) and DEAD (5.34 mL, 33.7 mmol). The reaction stirred for 2 hours allowing to warm to RT. The reaction was monitored by TLC (SiO$_2$). Upon completion water (80 ml) was added to the reaction mixture and extracted with ethyl acetate (2×150 ml). The combined organic layers were washed with water (150 ml) and concentrated in-vacuo to afford a yellow oil. The residue was purified by flash column chromatography (10% EtOAc/Hexanes) to give the title compound (7 g, 55% yield). MS (m/z) 360.2 (M+H$^+$).

| Step | Name | MS (m/z) |
|---|---|---|
| 1 | (R)-4-benzyl-3-(4-(naphthalen-2-yl)butanoyl)oxazolidin-2-one | 374.1 |
| 2 | (R)-4-benzyl-3-((2S,3S)-3-hydroxy-2-(2-(naphthalen-2-yl)ethyl)pentanoyl)oxazolidin-2-one | N/A |
| 3 | (2R,3S)-N-(benzyloxy)-3-hydroxy-2-(2-(naphthalen-2-yl)ethyl)pentanamide | 378.3 |
| 4* | (3R,4R)-1-(benzyloxy)-4-ethyl-3-(2-(naphthalen-2-yl)ethyl)azetidin-2-one | 360.2 |
| 5 | (2R,3R)-3-((benzyloxy)amino)-2-(2-(naphthalen-2-yl)ethyl)pentanoic acid | N/A |
| 6 | 2R,3R)-3-(N-(benzyloxy)formamido)-2-(2-(naphthalen-2-yl)ethyl)pentanoic acid | 406.1 |

Intermediate 168: (2R,3R)-3-(N-(benzyloxy)formamido)-2-(2,4-difluorophenethyl)pentanoic acid

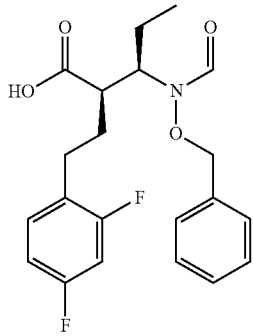 [SMILES: CC[C@H]([C@@H](CCc1ccc(F)cc1F)C(=O)O)N(C=O)OCc1ccccc1]

Intermediate 168 was prepared from 4-(2,4-difluorophenyl)butanoyl chloride by methods analogous to that described for Intermediate 167.

| Step | Name | MS (m/z) |
|---|---|---|
| 1 | (R)-4-benzyl-3-(4-(2,4-difluorophenyl)butanoyl)oxazolidin-2-one | 360.3 |
| 2 | (R)-4-benzyl-3-((2S,3S)-2-(2,4-difluorophenethyl)-3-hydroxypentanoyl)oxazolidin-2-one | 417.9 |
| 3 | (2R,3S)-N-(benzyloxy)-2-(2,4-difluorophenethyl)-3-hydroxypentanamide | 363.9 |
| 4 | (3R,4R)-1-(benzyloxy)-3-(2,4-difluorophenethyl)-4-ethylazetidin-2-one | 346.1 |
| 5 | (2R,3R)-3-((benzyloxy)amino)-2-(2,4-difluorophenethyl)pentanoic acid | 364.2 |
| 6 | (2R,3R)-3-(N-(benzyloxy)formamido)-2-(2,4-difluorophenethyl)pentanoic acid | 392.2 |

Intermediate 169: N-(((2R,3R)-3-(N-(benzyloxy)formamido)-2-phenethylpentanamido)methyl)-5-bromofuran-2-carboxamide

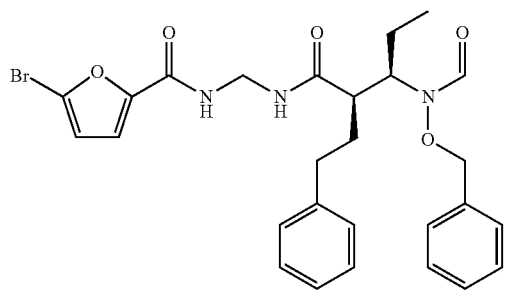 [SMILES: CC[C@H]([C@@H](CCc1ccccc1)C(=O)NCNC(=O)c1ccc(Br)o1)N(C=O)OCc1ccccc1]

N-(aminomethyl)-5-bromofuran-2-carboxamide (0.600 g, 2.74 mmol) was added to a solution of (2R,3R)-3-(N-(benzyloxy)formamido)-2-phenethylpentanoic acid (0.97 g, 2.74 mmol), HATU (1.15 g, 3.01 mmol) and DIPEA (1.44 ml, 8.22 mmol) in DCM (12.26 ml). The reaction mixture was stirred at room temperature for 15 minutes. The reaction was then diluted with water. The layers were separated and the organic was passed through a hydrophobic frit, concentrated and the residue purified by flash chromatography (ISCO Companion, 40 g column, 20-80% ethylacetate/hexanes). The residue was dissolved in DCM and partitioned with water and stirred for 3 hours. The layers were separated and the organic was passed through a hydrophobic frit and concentrated to give the title compound as a white solid (1.23 g, 72.6% yield). MS (m/z) 558.1 (M+).

Intermediate 170: N-(((2R,3R)-3-(N-(benzyloxy)formamido)-2-(2,4-difluorophenethyl)pentanamido)methyl)-5-bromofuran-2-carboxamide

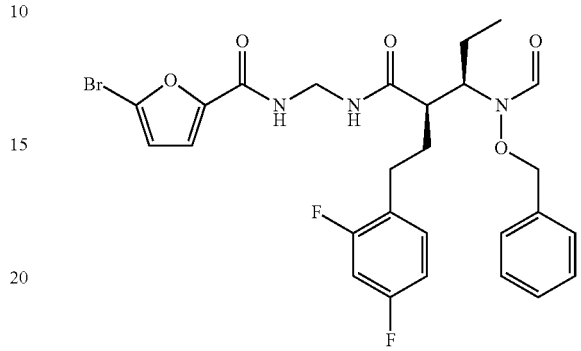

(2R,3R)-3-(N-(benzyloxy)formamido)-2-(2,4-difluorophenethyl)pentanoic acid (3.00 g, 7.67 mmol), N-(aminomethyl)-5-bromofuran-2-carboxamide (1.68 g, 7.67 mmol), EDC (2.06 g, 10.74 mmol), 1-hydroxybenzotriazole hydrate (1.64 g, 10.74 mmol) and 4-methylmorpholine (3.37 ml, 30.7 mmol) were dissolved in DMF (40 ml). The reaction mixture was stirred for 2 hours at 25° C. The reaction was then diluted with water and EtOAc. The layers were separated and the organics were washed with water three times, dried, concentrated and the residue purified by flash chromatography (ISCO, 80 g column, 0-40% hexanes/EtOAc) to give the title compound as a colorless oil (4.37 g, 91% yield). MS (m/z) 594.1 (M+).

Intermediate 171: N-(((2R,3R)-3-(N-(benzyloxy)formamido)-2-(2-(naphthalen-2-yl)ethyl)pentanamido)methyl)-5-bromofuran-2-carboxamide

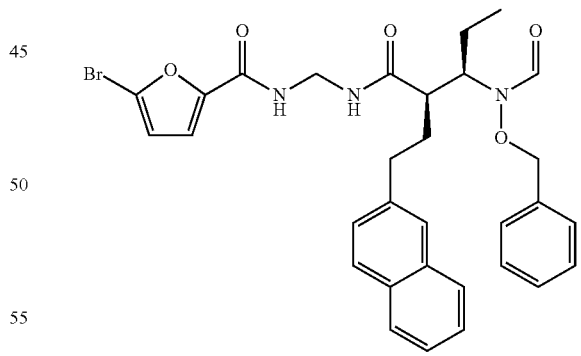

(2R,3R)-3-(N-(benzyloxy)formamido)-2-(2-(naphthalen-2-yl)ethyl)pentanoic acid (3.56 g, 8.79 mmol), N-(aminomethyl)-5-bromofuran-2-carboxamide (2.75 g, 8.79 mmol), EDC (2.190 g, 11.43 mmol) and HOBt (1.750 g, 11.43 mmol) were dissolved in DCM (60 ml) with N-methylmorpholine (3.86 ml, 35.2 mmol). The reaction mixture was stirred at 25° C. for 2.5 hours. A gummy residue formed on the edges of the flask, and the solution was decanted away from the gummy residue. The solution was diluted with water (60 ml) and DCM (50 ml) and stirred for 30 minutes.

The layers were separated, and the organics were washed with brine and passed through a hydrophobic frit. The gummy residue was dissolved in MeOH and filtered. The filtrate was combined with the organic layer from the solution work up, concentrated and the residue purified by flash chromatography (ISCO Combiflash Rf, 80 g column, 0 to 100% Ethyl Acetate/hexanes over 40 minutes) to give the title compound as a yellow oil (2.28 g, 29.9% yield). MS (m/z) 606.3 (M+).

Intermediate 172: diethyl (((3-bromo-5-ethoxybenzyl)amino)methyl)phosphonate

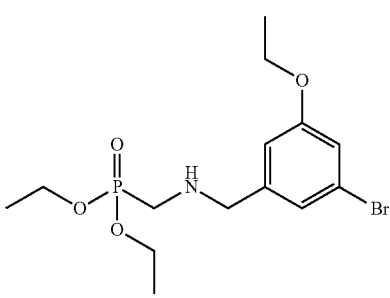 [SMILES: CCOc1cc(Br)cc(CNCP(=O)(OCC)OCC)c1]

Step 1: (3-bromo-5-ethoxyphenyl)methanol

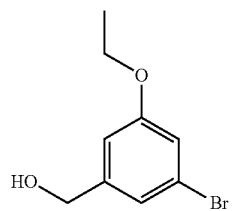

To a solution of methyl 3-bromo-5-ethoxybenzoate (5.6 g, 21.6 mmol) in toluene (108 ml) was added LAH (1.6 g, 43.2 mmol) upon which the reaction mixture was heated to 65° C. for 3 hours. 1N HCl was added slowly after cooling the reaction mixture in an ice bath. A slurry was formed. EtOAc was added and the layers were separated. The aq. layer was extracted with EtOAc (2×100 ml). The organics were washed with brine, dried over Na$_2$SO$_4$, filtered and concentrated to afford the title product as a colorless oil. MS (m/z) 230.9 (M+H+).

Step 2: 1-bromo-3-(bromomethyl)-5-ethoxybenzene

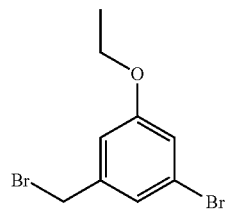

(3-bromo-5-ethoxyphenyl)methanol (4.6 g, 20 mmol) was dissolved in Et$_2$O (100 ml) and cooled to 0° C. before the addition of phosphorous tribromide (2.1 ml, 22 mmol). The mixture was allowed to stir at rt overnight. It was then poured into an ice water: ether solution. The aq. layer was extracted with ether (3×50 ml). The combined organic layers were dried over Na$_2$SO$_4$, filtered and concentrated. The resultant residue was purified via flash column chromatography (0-15% EtOAc/hexanes) to afford the title compound as colorless oil (4.52 g, 71% yield). MS (m/z) 293.0 (M+H+).

Step 3: diethyl (((3-bromo-5-ethoxybenzyl)amino)methyl)phosphonate

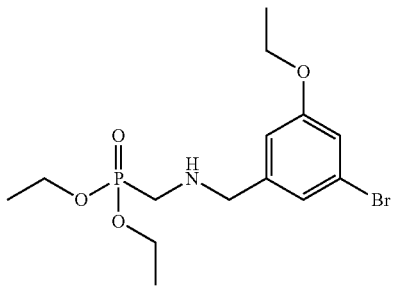 [SMILES: CCOc1cc(Br)cc(CNCP(=O)(OCC)OCC)c1]

A solution of diethyl(aminomethyl)phosphonate, oxalic acid salt (1.1 g, 4.3 mmol), and TEA (1.35 ml, 9.7 mmol) was stirred in DMF (5 ml) for 15 minutes, upon which 1-bromo-3-(bromomethyl)-5-ethoxybenzene (1.14 g, 3.9 mmol) in DMF (1 mL) was added to the reaction mixture and stirred for 18 hours at rt. The reaction was poured into water and extracted into EtOAc (3×50 ml). The combined organic layers were washed with water, brine, and dried over Na$_2$SO$_4$, filtered and concentrated. The resultant residue was purified by flash column chromatography (0-10% MeOH/EtOAc) to afford the title compound as a white solid (0.755 g, 51% yield). MS (m/z) 380.1 (M+H+).

INTERMEDIATE 173 was prepared from the indicated amine by methods analogous to those described for Intermediate 172.

| # | Name | Structure | MS (m/z) (M + H+) | Amine |
|---|---|---|---|---|
| 173 | methyl 2-((3-bromo-5-ethoxybenzyl)methyl)amino)acetate | 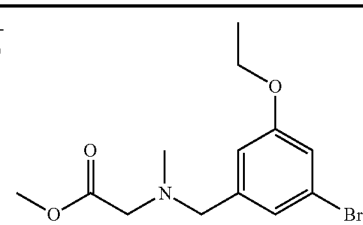 | 364.1 | methyl 2-(methylamino)acetate |

Intermediate 174: dimethyl (3-(benzyloxy)-5-bromophenyl)phosphonate

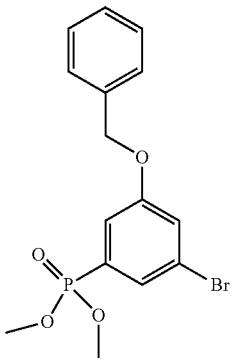 [SMILES: COP(=O)(OC)c1cc(Br)cc(OCc2ccccc2)c1]

Step 1: 1-(benzyloxy)-3-bromo-5-iodobenzene

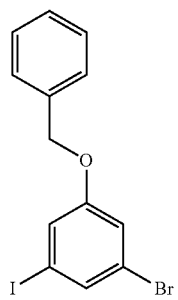 [SMILES: Brc1cc(I)cc(OCc2ccccc2)c1]

To a solution of 3-bromo-5-iodophenol (1.5 g, 5 mmol) in DMF (10 ml) was added K₂CO₃ (0.83 g, 6 mmol). The reaction mixture was then heated at 50° C. for 30 minutes before the addition of KI (0.08 g, 0.5 mmol) and (bromomethyl)benzene (0.93 g, 5.4 mmol). The reaction continued to stir for 18 hours at 65° C. The mixture was poured into water and extracted with EtOAc (3×100 ml). The combined organic layers were washed with water (3×50 ml), brine, dried over Na₂SO₄, filtered and concentrated in vacuo. The resultant residue was purified via flash column chromatography (0-10% EtOAc:Hexane) to afford the title compound as a yellow oil (1.3 g, 50% yield). MS (m/z) 391.3 (M+H⁺).

Step 2: dimethyl (3-(benzyloxy)-5-bromophenyl)phosphonate

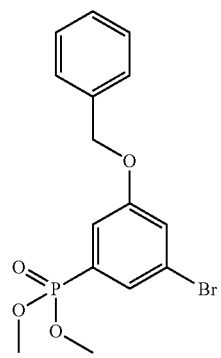 [SMILES: COP(=O)(OC)c1cc(Br)cc(OCc2ccccc2)c1]

To a solution of dimethyl (3-(benzyloxy)-5-bromophenyl) phosphonate (1.39 g, 3.57. mmol) in 1,4-dioxane (16 ml) were added trimethyl phosphite (0.99 g, 8.04 mmol) and diacetoxypalladium (0.12 g, 0.54 mmol). The reaction was heated at 105° C. for 5 hours. The reaction was monitored via LCMS to show the reaction was complete. The reaction mixture was filtered, concentrated and purified by flash column chromatography (0-5% MeOH/DCM) to afford the title compound as a white solid (1.0 g, 75% yield). MS (m/z) 371.9 (M+H⁺).

Intermediate 175: (S)-dimethyl 2-(4-bromo-2-methylbenzamido)succinate

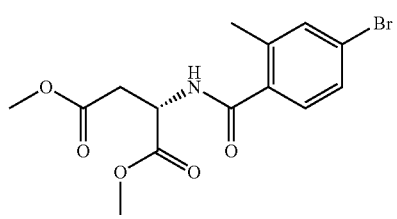 [SMILES: COC(=O)C[C@H](NC(=O)c1ccc(Br)cc1C)C(=O)OC]

To a solution containing (S)-dimethyl 2-aminosuccinate hydrochloride (5.51 g, 27.9 mmol) and 4-bromo-2-methylbenzoic acid (5 g, 23.25 mmol) in N,N-dimethylformamide (100 ml) was added HATU (10.61 g, 27.9 mmol) followed by DIPEA (12.18 ml, 69.8 mmol). The reaction stirred for 18 hours. The reaction mixture was diluted with NH₄Cl aq. solution, extracted with ethyl ether (3×100 ml), dried over MgSO₄, filtered and concentrated onto SiO₂. Purification via flash column chromatography (0-50% EtOAc/Hexanes) afforded the titled compound as a colorless solid (6.0 g, 74% yield). MS (m/z) 360.0 (M+H⁺).

Intermediate 176: methyl 3-bromo-2-hydroxy-5-(2-methoxy-2-oxoethoxy)benzoate

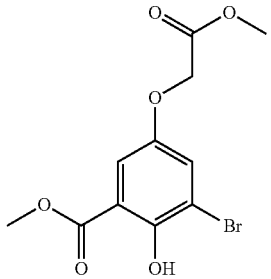

Step 1: methyl 2-hydroxy-5-(2-methoxy-2-oxoethoxy)benzoate

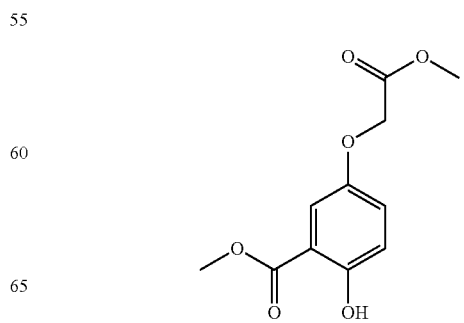

To a solution containing methyl 2,5-dihydroxybenzoate (25 g, 149 mmol) in acetone (600 ml) was added potassium carbonate (41.1 g, 297 mmol) followed by methyl 2-bromoacetate (14.07 mL, 149 mmol). The reaction was stirred for 18 hours at 55° C. The mixture was filtered, concentrated and redissolved in DCM, then washed with water and brine. The organic phase was separated and passed through a hydrophobic frit, concentrated onto SiO$_2$ and purified by flash chromatography (Isco, 120 g column, 0-2% EtOAc/DCM) to afford the title compound as a colorless solid (16.2 g, 45.2% yield). MS (m/z) 242.0 (M+H$^+$).

Step 2: methyl 3-bromo-2-hydroxy-5-(2-methoxy-2-oxoethoxy)benzoate

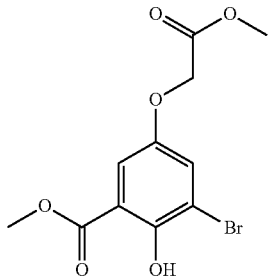

To a solution containing methyl 2-hydroxy-5-(2-methoxy-2-oxoethoxy)benzoate (5 g, 20.82 mmol) in acetic acid (50 mL) was added bromine (1.180 mL, 22.90 mmol) and the mixture stirred for 5 hours. Additional bromine (0.590 mL, 11.45 mmol) was added and the reaction stirred for 18 hours. The reaction mixture was poured into water upon which precipitation was formed. The precipitate was collected via filtration of the mixture. The solid was dissolved in DCM and concentrated onto SiO$_2$. Purification by flash chromatography (Isco, 40 g column, 0-30% EtOAc/hexane) afforded the title product as a yellow oil (4.0 g, 63% yield). MS (m/z) 320.9 (M+H$^+$).

Intermediate 177: (S)-dimethyl 2-(3-bromo-5-(2-methoxy-2-oxoethoxy)benzamido)succinate

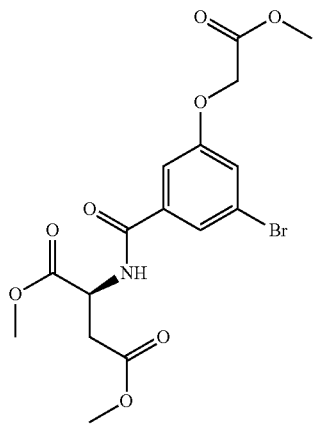 [SMILES: COC(=O)COc1cc(Br)cc(C(=O)N[C@@H](CC(=O)OC)C(=O)OC)c1]

Step 1: (S)-dimethyl 2-(3-bromo-5-hydroxybenzamido)succinate

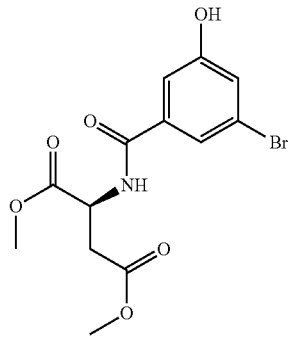 [SMILES: COC(=O)C[C@H](NC(=O)c1cc(O)cc(Br)c1)C(=O)OC]

To a solution containing (S)-dimethyl 2-aminosuccinate hydrochloride (5.46 g, 27.6 mmol) and 3-bromo-5-hydroxybenzoic acid (5 g, 23.04 mmol) in N,N-dimethylformamide (100 ml) was added DIPEA (12.07 ml, 69.1 mmol) followed by HATU (10.51 g, 27.6 mmol). The reaction was stirred for 18 hours. The reaction mixture was diluted with NH$_4$Cl aq. soln., extracted with ethyl ether (3×50 mL), dried over MgSO$_4$, filtered and concentrated onto SiO$_2$. Purification by flash chromatography (Isco, 80 g column, 0-50% EtOAc/hexanes) afforded the title compound as a colorless glass (6.0 g, 79% yield). MS (m/z) 361.9 (M+H$^+$).

Step 2: (S)-dimethyl 2-(3-bromo-5-(2-methoxy-2-oxoethoxy)benzamido)succinate

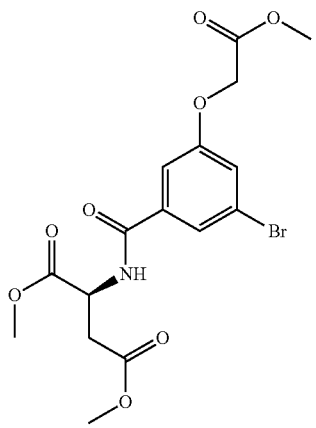 [SMILES: COC(=O)COc1cc(Br)cc(C(=O)N[C@@H](CC(=O)OC)C(=O)OC)c1]

To a solution of (S)-dimethyl 2-(3-bromo-5-hydroxybenzamido)succinate (6.54 g, 18.16 mmol) in acetone (65 mL) was added potassium carbonate (5.02 g, 36.3 mmol) and methyl 2-bromoacetate (1.891 ml, 19.97 mmol). The reaction stirred for 18 hours. The reaction was diluted with water and extracted with EtOAc (3×100 ml). The organic layers were collected, dried over MgSO$_4$, filtered and concentrated onto SiO$_2$. Purification by flash chromatography (Isco, 80 g column, 0-70% EtOAc/hexanes) afforded the title compound as a colorless glass (7.3 g, 93% yield). MS (m/z) 432.0 (M+H$^+$).

Intermediate 178: (S)-dimethyl 2-(4-bromo-2-(2-methoxy-2oxoethoxy)benzamido)succinate

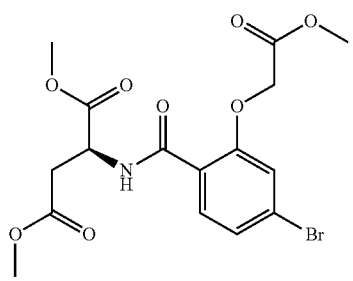 [SMILES: COC(=O)COc1cc(Br)ccc1C(=O)N[C@@H](CC(=O)OC)C(=O)OC]

Step 1: (S)-dimethyl 2-(4-bromo-2-hydroxybenzamido)succinate

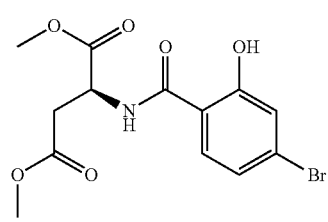 [SMILES: COC(=O)C[C@H](NC(=O)c1ccc(Br)cc1O)C(=O)OC]

To a solution of (S)-dimethyl 2-aminosuccinate hydrochloride (5.46 g, 27.6 mmol) and 4-bromo-2-hydroxybenzoic acid (5 g, 23.04 mmol) in N,N-dimethylformamide (50 ml) was added DIPEA (12.07 ml, 69.1 mmol) followed by 1H-benzo[d][1,2,3]triazol-1-ol (3.74 g, 27.6 mmol) and EDC (5.30 g, 27.6 mmol). The reaction mixture was stirred for 18 hours. The reaction mixture was diluted with NH$_4$Cl aq. soln. and extracted with ethyl ether (3×50 ml). The organics were collected, dried over MgSO$_4$, filtered and concentrated onto SiO$_2$. Purification by flash chromatography (Isco, 80 g column, 0-50% EtOAc/hexanes) afforded the title compound as a yellow glass (3.1 g, 37.2% yield). MS (m/z) 362.0 (M+H$^+$).

Step 2: (S)-dimethyl 2-(4-bromo-2-(2-methoxy-2oxoethoxy)benzamido)succinate

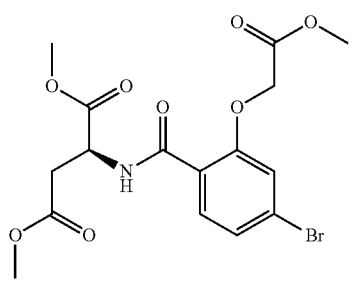 [SMILES: COC(=O)COc1cc(Br)ccc1C(=O)N[C@@H](CC(=O)OC)C(=O)OC]

To a solution containing (S)-dimethyl 2-(4-bromo-2-hydroxybenzamido)succinate (3.09 g, 8.58 mmol) in acetone (40 ml) was added methyl 2-bromoacetate (0.893 ml, 9.44 mmol) and potassium carbonate (2.371 g, 17.16 mmol). The reaction mixture was stirred for 3 hours. The reaction was diluted with water and extracted with EtOAc (3×50 ml). The combined organic layers were dried over MgSO$_4$, filtered and concentrated onto SiO$_2$. Purification by flash chromatography (Isco, 40 g column, 0-70% ethyl EtOAc/hexanes) afforded the title compound as a colorless glass (3.5 g, 95% yield). MS (m/z) 434.1 (M+H$^+$).

Intermediate 179: methyl 5-bromo-3-ethoxy-2-fluorobenzoate

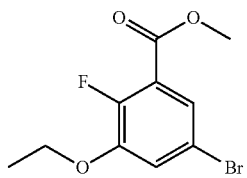

Step 1: 5-bromo-1-ethoxy-2-fluoro-3-methylbenzene

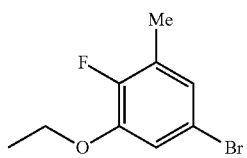

5-bromo-2-fluoro-3-methylphenol (2 g, 9.75 mmol) was dissolved in tetrahydrofuran (31.6 ml) and treated at RT with sodium hydride (0.429 g, 10.73 mmol). The reaction mixture was stirred for 30 minutes and then treated with iodoethane (0.867 ml, 10.73 mmol). The reaction was heated to 55° C. for 3 days. The reaction mixture was then cooled to RT, quenched with sat. aq. ammonium chloride solution, and allowed to stir for 15 minutes. The layers were separated and the aqueous layer was extracted with EtOAc (3×50 ml). The combined organic layers were dried over MgSO$_4$, filtered, and concentrated. The resultant oil was purified via flash column chromatography (10% EtOAc/hexanes). The desired fractions were combined and concentrated to afford the title compound (77 mg, 34% yield). MS (m/z) 230.1 (M+H$^+$).

Step 2: 5-bromo-3-ethoxy-2-fluorobenzoic acid

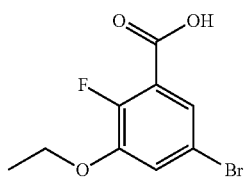

5-bromo-1-ethoxy-2-fluoro-3-methylbenzene (777 mg, 3.33 mmol) was dissolved in pyridine (3334 µl) and water (3334 µl) and treated with potassium permanganate (2213 mg, 14.00 mmol) at 90° C. for 18 hours. The reaction was cooled to rt, filtered through celite, and acidified to pH<4. A white precipitate formed which was collected via filtration. The white solid was dissolved in EtOAc, dried over MgSO$_4$, filtered, and concentrated to afford the title compound as a white solid (132 mg, 15% yield). The product was used directly in the next reaction without further purification.

Step 3: methyl 5-bromo-3-ethoxy-2-fluorobenzoate

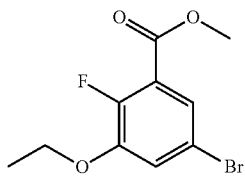

5-bromo-3-ethoxy-2-fluorobenzoic acid (132 mg, 0.50 mmol) was dissolved in acetonitrile (2.5 ml), treated with potassium carbonate (208 mg, 1.51 mmol), and heated to 80° C. for 18 hours. The reaction was cooled to RT, diluted with ether, and filtered through celite. The residual solid was washed with ether, and the filtrates were combined and purified via flash column chromatography (10-20% EtOAc/Hexanes) to afford the title compound as a white solid (103 mg, 74% yield). MS (m/z) 276.9 (M+H$^+$).

Intermediate 180: (R)-dimethyl 2-(4-bromo-2-ethoxybenzamido)succinate

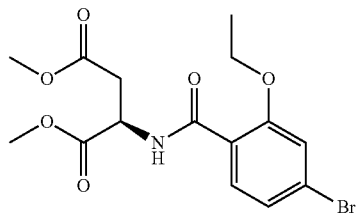 [SMILES: CCOc1cc(Br)ccc1C(=O)N[C@H](CC(=O)OC)C(=O)OC]

2,4,6-tripropyl-1,3,5,2,4,6-trioxatriphosphinane 2,4,6-trioxide (3.39 ml, 5.69 mmol) was added to a suspension of (R)-dimethyl 2-aminosuccinate (0.61 g, 3.79 mmol), 4-bromo-2-ethoxybenzoic acid (0.93 g, 3.79 mmol) and triethylamine (1.59 ml, 11.38 mmol) in DCM (15 ml) at 25° C. After 2 hours, the reaction was diluted with DCM and washed with water, 1N HCl and saturated NaHCO$_3$ solution. The organic layer was separated, concentrated and purified via flash column chromatography (12 g column, 0-30% EtOAC:EtOH 3:1/Hexanes) to obtain the title compound as a white solid (0.56 g, 34.2% yield). MS (m/z) 388.0 (M+H$^+$).

Intermediate 181: methyl 2-(3-bromo-5-(dimethoxyphosphoryl)phenoxy)acetate

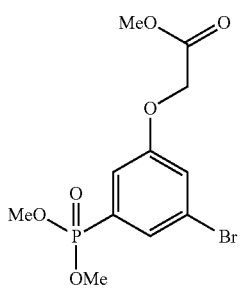 [SMILES: COC(=O)COc1cc(Br)cc(P(=O)(OC)OC)c1]

Step 1: methyl 2-(3-bromo-5-iodophenoxy)acetate

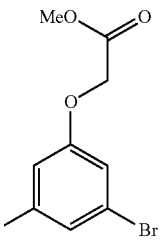

To a round bottom flask equipped with a teflon stir bar was added 3-bromo-5-iodophenol (2.06 g, 6.89 mmol), methyl 2-bromoacetate (0.979 ml, 10.34 mmol), acetonitrile (15.0 ml), and K$_2$CO$_3$ (4.76 g, 34.5 mmol). A water cooled-condenser, attached to a N$_2$ outlet was attached to the flask and the reaction heated to 80° C. The reaction was cooled to room temperature and quenched with water (40 ml). The solution was extracted with EtOAc (2×40 ml). The combined organic layers were washed with brine, dried over Na$_2$SO$_4$, filtered, and concentrated to afford the titled compound (2.0 g, 78% yield crude). MS (m/z) 372.7 (M+H$^+$).

Step 2: methyl 2-(3-bromo-5-(dimethoxyphosphoryl)phenoxy)acetate

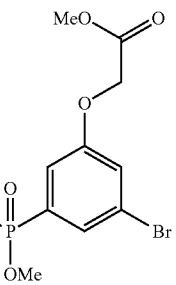

To a round bottomed flask equipped with a teflon stir bar was added methyl 2-(3-bromo-5-iodophenoxy)acetate (2.0 g, 5.39 mmol), trimethyl phosphite (1.4 ml, 13.47 mmol), 1,4-dioxane (12.77 ml), and Pd(OAc)$_2$ (0.242 g, 1.08 mmol). A water cooled condenser with a N$_2$ outlet was attached to the top of the flask and the reaction heated to reflux for 18 hours. The reaction was poured into water and extracted with EtOAc (3×50 ml). The combined organic layers were washed with water, brine, then dried over sodium sulfate, filtered and concentrated. The resultant orange residue was purified by flash chromatography (ISCO, 80 g, 0% to 10% MeOH/DCM) to afford the titled compound as a yellow solid (2.3 g, 109% yield). MS (m/z) 354.9 (M+H$^+$).

Intermediate 182: methyl 3-bromo-5-(2-methoxy-2-oxoethoxy)benzoate

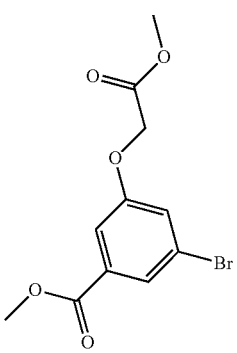 [SMILES: COC(=O)COc1cc(Br)cc(C(=O)OC)c1]

To a solution of methyl 3-bromo-5-hydroxybenzoate (34 g, 147 mmol), K₂CO₃ (61 g, 441 mmol), in N,N-Dimethylformamide (DMF) (340 mL) was added methyl 2-bromoacetate (22.5 g, 147 mmol). The reaction stirred at RT under nitrogen for 2 hours upon which the reaction was poured into ice water. A white precipitate formed which was filtered, washed with water, and dried to afford the title compound as a white solid (36 g, 81% yield) MS (m/z) 304.2 (M+H⁺).

Intermediate 183: diethyl ((4-bromo-2-ethoxybenzamido)methyl)phosphonate

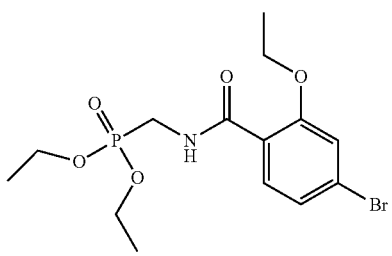 [SMILES: CCOc1cc(Br)ccc1C(=O)NCP(=O)(OCC)OCC]

4-bromo-2-ethoxybenzoic acid (3 g, 12.24 mmol), EDC (2.82 g, 14.69 mmol), diethyl(aminomethyl)phosphonate, oxalic acid salt (3.15 g, 12.24 mmol), 1-hydroxy-7-azabenzotriazole (2.0 g, 14.69 mmol) and N-methylmorpholine (5.38 ml, 49.0 mmol) were dissolved in DCM (76 ml). The reaction mixture was stirred at room temperature for 1 hour. The reaction was then concentrated and the residue purified by flash chromatography (ISCO, 120 g column, 0-100% ethyl acetate/hexanes over 45 minutes) to give the title compound as an off white solid (3.0 g, 62.2% yield). MS (m/z) 395.9 (M⁺).

Intermediate 184: dimethyl 2,2'-((4-bromo-2-ethoxybenzoyl)azanediyl)diacetate

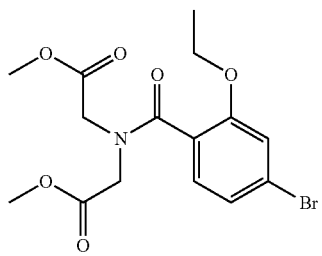 [SMILES: CCOc1cc(Br)ccc1C(=O)N(CC(=O)OC)CC(=O)OC]

4-bromo-2-ethoxybenzoic acid (0.5 g, 2.040 mmol), dimethyl 2,2'-azanediyldiacetate (0.33 g, 2.040 mmol), EDC (0.39 g, 2.040 mmol), 1-hydroxy-7-azabenzotriazole (0.31 g, 2.04 mmol) and N-methylmorpholine (0.22 ml, 2.04 mmol) were dissolved in DMF. The reaction mixture was stirred at room temperature for 18 hours. The reaction was then poured into water and diluted with ethyl acetate (50 ml). The layers were separated and the aqueous layer was washed twice with DCM (50 ml each). The layers were separated, and the organic layers were combined, washed with brine, dried over sodium sulfate, filtered and concentrated. The residue was purified by flash chromatography (ISCO, 0-50% ethyl acetate/hexanes) to give the title compound (0.64 g, 81% yield). MS (m/z) 390.3 (M⁺).

Intermediate 185: (S)-dimethyl 2-(4-bromo-2-ethoxybenzamido)succinate

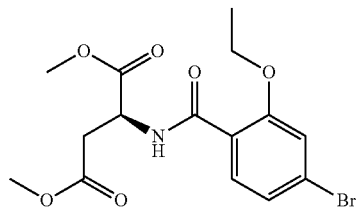 [SMILES: CCOc1cc(Br)ccc1C(=O)N[C@@H](CC(=O)OC)C(=O)OC]

T3P, 50% wt in EtOAc (150 ml, 252 mmol) was added dropwise (in 1 hr 10 minutes) to a suspension of 4-bromo-2-ethoxybenzoic acid (43.27 g, 177 mmol), (S)-dimethyl 2-aminosuccinate, hydrochloride (36.6 g, 185 mmol), and triethylamine (73.8 ml, 530 mmol) in DCM (420 ml) in a water bath to prevent warming. After addition completed, the reaction mixture was stirred at room temperature for 2 hours. The reaction was then diluted with DCM and water. The layers were separated and the organics washed with 1N HCl and then sat. NaHCO₃. The layers were separated, the organic layer was dried over MgSO₄, concentrated and the residue split in half and purified by flash chromatography (ISCO, 330 g column, 0-50% EtOAc/hexanes) to obtain the title compound as a yellow oil (62.7 g, 91% yield). MS (m/z) 390.0 (M⁺).

Intermediate 186: (S)-dimethyl 2-(4-bromobenzamido)succinate

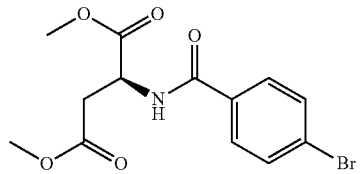 [SMILES: COC(=O)C[C@H](NC(=O)c1ccc(Br)cc1)C(=O)OC]

2,4,6-tripropyl-1,3,5,2,4,6-trioxatriphosphinane 2,4,6-trioxide (4.40 ml, 7.39 mmol) was added to a suspension of (S)-dimethyl 2-aminosuccinate (1.0 g, 4.92 mmol), 4-bromobenzoic acid (1.0 g, 4.92 mmol) and TEA (2.06 ml, 14.77 mmol) in DCM (10 ml) in a water bath to prevent warming. The reaction mixture was stirred for 2 hours at 25° C. The reaction was diluted with DCM and water. The layers were separated and the organic layer was washed with 1N HCl and then saturated NaHCO₃ solution, dried, and concentrated to obtain the title compound as a white solid (1.67 g, 98% yield). MS (m/z) 344.0 (M⁺).

Intermediate 187: methyl 4-bromo-2-ethoxy-6-hydroxybenzoate

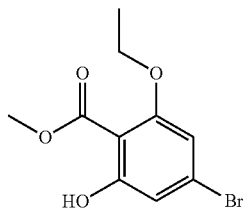

Methyl 4-bromo-2-ethoxybenzoate (3.0 g, 11.58 mmol), potassium persulfate (3.44 g, 12.74 mmol), and dichloro(p-cymene)ruthenium(II) dimer (177 mg, 0.29 mmol) were combined in TFA (20.26 ml) and trifluoroacetic anhydride (8.68 ml). The reaction mixture was stirred overnight at 80° C. under nitrogen. The reaction was cooled to room temperature and added dropwise to a solution of 10% sodium carbonate cooled to 0° C. The neutral solution was warmed to room temperature and diluted with DCM (200 ml). The layers were separated and the aqueous layer was back extracted twice more with DCM (200 ml). The combined organics were dried over sodium sulfate, filtered, concentrated half-way and the residue was purified by flash chromatography (ISCO, 5-50% EtOAc/Hexanes over 35 minutes) to obtain the title compound as a white solid (250 mg, 7.85% yield).

INTERMEDIATES 188-200 were prepared from the indicated bromide in general by methods analogous to those described for Intermediate 55. Reaction times vary from 3.5 hours to 12 hours.

| # | Name | Structure | MS (m/z) | Bromide |
|---|------|-----------|----------|---------|
| 188 | diethyl (((3-ethoxy-5-(4,4,5,5-tetramethyl-1,3,2-dioxaborolan-2-yl)benzyl)amino)methyl)phosphonate | 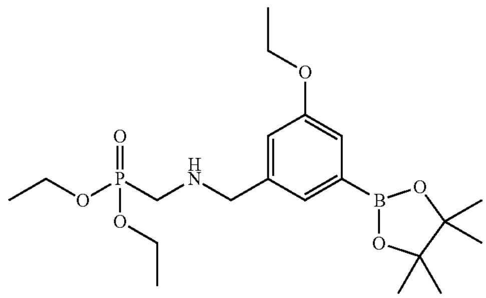 [SMILES: CCOc1cc(CNCP(=O)(OCC)OCC)cc(B2OC(C)(C)C(C)(C)O2)c1] | 428.1 | diethyl (((3-bromo-5-ethoxybenzyl)amino)methyl)phosphonate |
| 189 | dimethyl (3-(benzyloxy)-5-(4,4,5,5-tetramethyl-1,3,2-dioxaborolan-2-yl)phenyl)phosphonate | 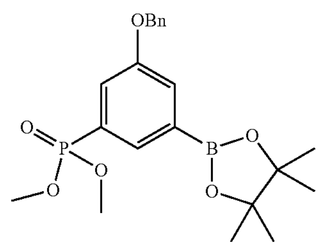 | 419.1 | dimethyl (3-(benzyloxy)-5-bromophenyl)phosphonate |
| 190** | methyl 2-(2-methoxy-2-oxoethyl)-4-(4,4,5,5-tetramethyl-1,3,2-dioxaborolan-2-yl)benzoate | 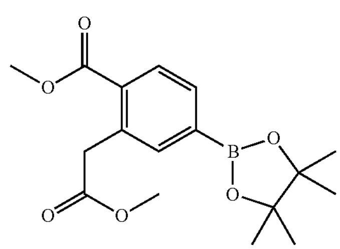 | 335.1 | methyl 4-bromo-2-(2-methoxy-2-oxoethyl)benzoate |
| 191 | (S)-dimethyl 2-(2-methyl-4-(4,4,5,5-tetramethyl-1,3,2-dioxaborolan-2-yl)benzamido)succinate | 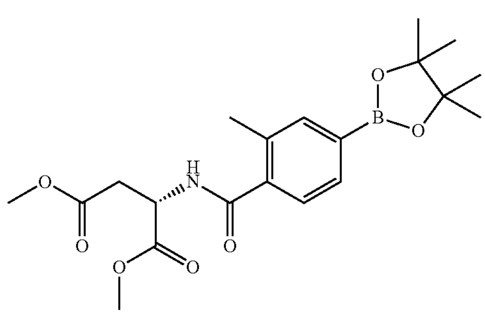 | 406.4 | (S)-dimethyl 2-(4-bromo-2-methylbenzamido)succinate |

-continued

| # | Name | Structure | MS (m/z) | Bromide |
|---|---|---|---|---|
| 192 | methyl 2-hydroxy-5-(2-methoxy-2-oxoethoxy)-3-(4,4,5,5-tetramethyl-1,3,2-dioxaborolan-2-yl)benzoate | 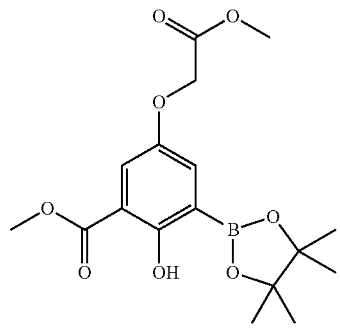 | 367.1 | methyl 3-bromo-2-hydroxy-5-(2-methoxy-2-oxoethoxy)benzoate |
| 193 | methyl 2-hydroxy-5-(2-methoxy-2-oxoethoxy)-3-(4,4,5,5-tetramethyl-1,3,2-dioxaborolan-2-yl)benzoate | 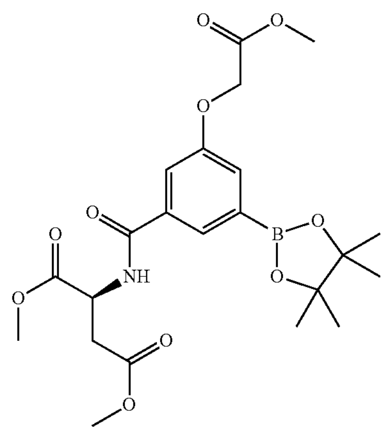 [SMILES: COC(=O)COc1cc(B2OC(C)(C)C(C)(C)O2)cc(C(=O)N[C@@H](CC(=O)OC)C(=O)OC)c1] | 480.2 | (S)-dimethyl 2-(3-bromo-5-(2-methoxy-2-oxoethoxy)benzamido)succinate |
| 194 | (S)-dimethyl 2-(2-(2-methoxy-2-oxoethoxy)-4-(4,4,5,5-tetramethyl-1,3,2-dioxaborolan-2-yl)benzamido)succinate | 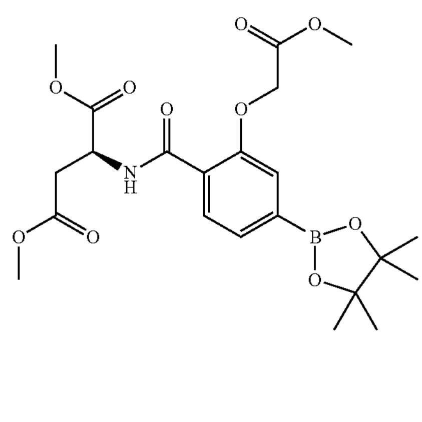 [SMILES: COC(=O)COc1cc(B2OC(C)(C)C(C)(C)O2)ccc1C(=O)N[C@@H](CC(=O)OC)C(=O)OC] | 480.2 | (S)-dimethyl 2-(4-bromo-2-(2-methoxy-2-oxoethoxy)benzamido)succinate |
| 195 | methyl 2-((3-ethoxy-5-(4,4,5,5-tetramethyl-1,3,2-dioxaborolan-2-yl)benzyl)(methyl)amino)acetate | 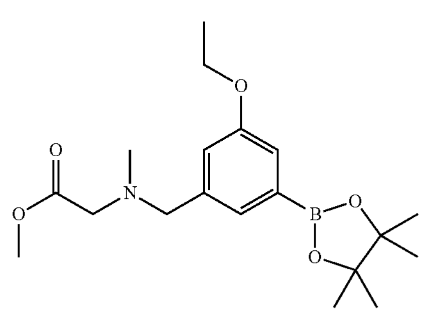 | 364.1 | methyl 2-((3-bromo-5-ethoxybenzyl)(methyl)amino)acetate |

-continued

| # | Name | Structure | MS (m/z) | Bromide |
|---|---|---|---|---|
| 196 | methyl 3-ethoxy-2-fluoro-5-(4,4,5,5-tetramethyl-1,3,2-dioxaborolan-2-yl)benzoate | 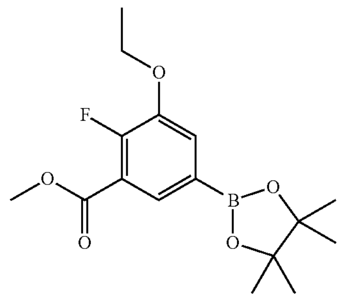 | 325.1 | methyl 5-bromo-3-ethoxy-2-fluorobenzoate |
| 197 | (R)-(4-((1,4-dimethoxy-1,4-dioxobutan-2-yl)carbamoyl)-3-ethoxyphenyl)boronic acid | 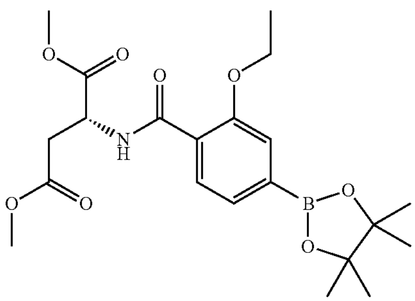 | 436.2 | (R)-dimethyl 2-(4-bromo-2-ethoxybenzamido)succinate |
| 198 | methyl 2-(3-(dimethoxyphosphoryl)-5-(4,4,5,5-tetramethyl-1,3,2-dioxaborolan-2-yl)phenoxy)acetate | 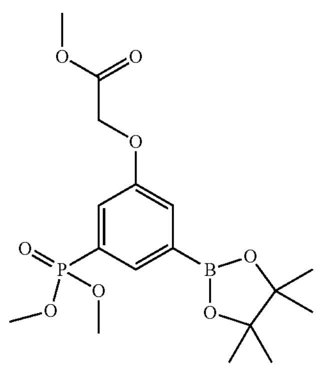 | 401.1 | methyl 2-(3-bromo-5-(dimethoxyphosphoryl)phenoxy)acetate |
| 199** | methyl 2-hydroxy-4-(4,4,5,5-tetramethyl-1,3,2-dioxaborolan-2-yl)benzoate | 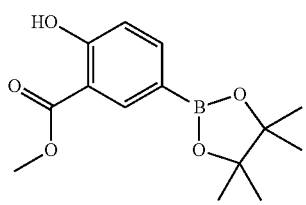 | 279.0 | methyl 4-bromo-2-hydroxybenzoate |
| 200 | methyl 3-(2-methoxy-2-oxoethoxy)-5-(4,4,5,5-tetramethyl-1,3,2-dioxaborolan-2-yl)benzoate | 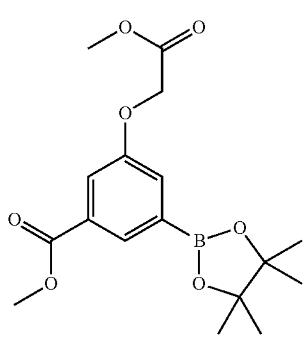 [SMILES: COC(=O)COc1cc(B2OC(C)(C)C(C)(C)O2)cc(C(=O)OC)c1] | 351.2 | methyl 3-bromo-5-(2-methoxy-2-oxoethoxy)benzoate |

**Reaction performed in Biotage microwave reactor for 30 minutes versus thermally.

INTERMEDIATE 201 was prepared from (S)-dimethyl 2-aminosuccinate, hydrochloride and the indicated acid by methods analogous to those described for Intermediate 56.

| # | Name | Structure | MS (m/z) (M + H+) | Acid |
|---|---|---|---|---|
| 201 | (S)-dimethyl 2-(3-(4,4,5,5-tetramethyl-1,3,2-dioxaborolan-2-yl)benzamido)succinate | 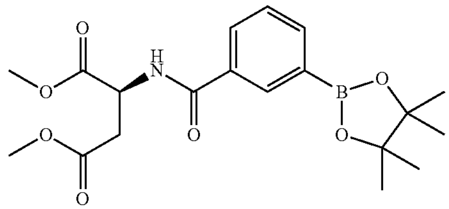 | 392.4 | 3-(4,4,5,5-tetramethyl-1,3,2-dioxaborolan-2-yl)benzoic acid |

Intermediate 202: Dimethyl 2,2'-((3-ethoxy-5-(4,4,5,5-tetramethyl-1,3,2-dioxaborolan-2-yl)benzoyl)azanediyl)diacetate

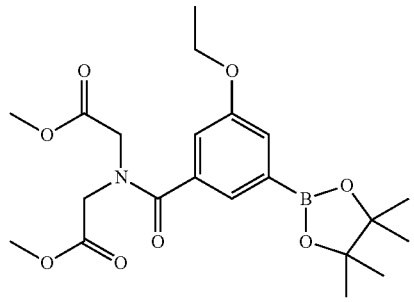

3-ethoxy-5-(4,4,5,5-tetramethyl-1,3,2-dioxaborolan-2-yl) benzoic acid (350 mg, 1.198 mmol), dimethyl 2,2'-azanediyldiaceate, hydrochloride (237 mg, 1.2 mmol), EDC (276 mg, 1.438 mmol), 1-hydroxy-7-azabenzotriazole (196 mg, 1.44 mmol) and N-methylmorpholine (527 µl, 4.79 mmol) were dissolved in DMF (7.46 ml). The reaction mixture was stirred at room temperature for 18 hours. The reaction was poured slowly into cold stirring water and diluted with ethyl acetate. The layers were separated and the aqueous layer was back extracted twice more with ethyl acetate. The combined organics were washed with brine, dried over sodium sulfate, filtered, concentrated and the residue purified by flash chromatography (ISCO, 12 g column, 10-70% EtOAc/Hexanes over 15 min) to obtain the title compound as a colorless oil (216 mg, 41.4% yield). MS (m/z) 436.3 (M+).

Intermediate 203: (S)-Dimethyl 2-(4-(4,4,5,5-tetramethyl-1,3,2-dioxaborolan-2-yl)benzamido)succinate

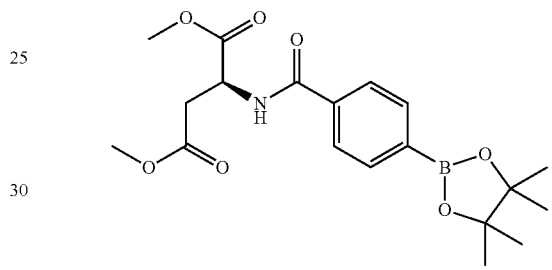

(S)-dimethyl 2-(4-bromobenzamido)succinate (1.67 g, 4.85 mmol) was dissolved in 1,4-dioxane (24.26 ml) and followed by addition of bis(pinacolato)diboron (1.51 g, 5.82 mmol), PdCl₂(dppf)-CH₂Cl₂ adduct (0.16 g, 0.19 mmol) and potassium acetate (1.91 g, 19.41 mmol). The reaction mixture was heated to 100° C. overnight. The reaction was diluted with EtOAc and water and then filtered. The layers of the filtrate were separated and the aqueous layer was back extracted with EtOAc three times. The combined organics were dried and concentrated to obtain the title compound as a black oil (0.53 g, 28% yield). MS (m/z) 392.1 (M+).

INTERMEDIATES 204-208 were prepared from N—(((R)-2-((R)-1-(N-(benzyloxy)formamido)propyl)heptanamido)methyl)-5-bromofuran-2-carboxamide and the indicated boronate by methods analogous to those described for Intermediate 78.

| # | Name | Structure | MS (m/z) (M + H+) | Boronate |
|---|---|---|---|---|
| 204 | methyl 4-(5-((((R)-2-((R)-1-(N-(benzyloxy)formamido)propyl)heptanamido)methyl)carbamoyl)furan-2-yl)-2-(2-methoxy-2-oxoethyl)benzoate | 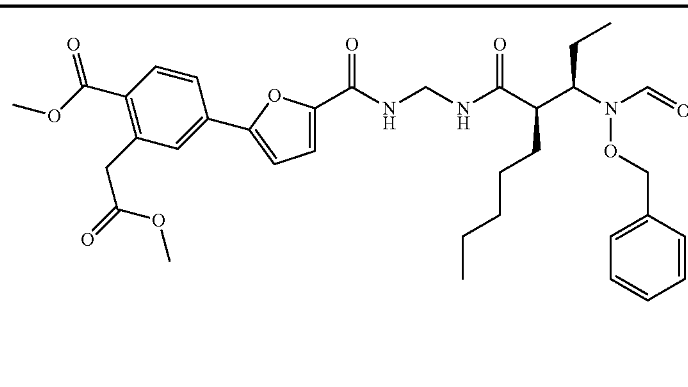 | 650.2 | methyl 2-(2-methoxy-2-oxoethyl)-4-(4,4,5,5-tetramethyl-1,3,2-dioxaborolan-2-yl)benzoate |

-continued

| # | Name | Structure | MS (m/z) (M + H⁺) | Boronate |
|---|------|-----------|-------------------|----------|
| 205 | dimethyl 4-(5-((((R)-2-((R)-1-(N-(benzyloxy)formamido)propyl)heptanamido)methyl)carbamoyl)furan-2-yl)phthalate | 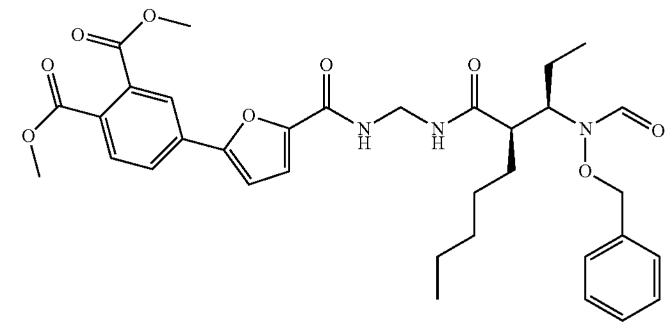 [SMILES: CCCCC[C@@H](C(=O)NCNC(=O)c1ccc(-c2ccc(C(=O)OC)c(C(=O)OC)c2)o1)[C@@H](CC)N(C=O)OCc1ccccc1] | 634.2 | (3,4-bis(methoxycarbonyl)phenyl)boronic acid |
| 206 | methyl 3-(5-((((R)-2-((R)-1-(N-(benzyloxy)formamido)propyl)heptanamido)methyl)carbamoyl)furan-2-yl)-5-hydroxybenzoate | 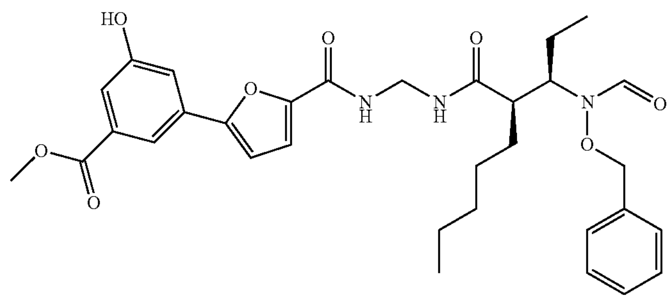 [SMILES: CCCCC[C@@H](C(=O)NCNC(=O)c1ccc(-c2cc(O)cc(C(=O)OC)c2)o1)[C@@H](CC)N(C=O)OCc1ccccc1] | 594.2 | methyl 3-hydroxy-5-(4,4,5,5-tetramethyl-1,3,2-dioxaborolan-2-yl)benzoate |
| 207 | methyl 2-(3-(5-((((R)-2-((R)-1-(N-(benzyloxy)formamido)propyl)heptanamido)methyl)carbamoyl)furan-2-yl)-5-(dimethoxyphosphoryl)phenoxy)acetate | 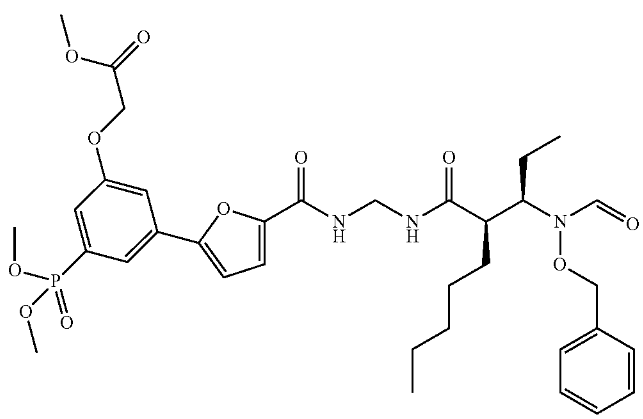 [SMILES: CCCCC[C@@H](C(=O)NCNC(=O)c1ccc(-c2cc(OCC(=O)OC)cc(P(=O)(OC)OC)c2)o1)[C@@H](CC)N(C=O)OCc1ccccc1] | 716.2 | methyl 2-(3-(dimethoxyphosphoryl)-5-(4,4,5,5-tetramethyl-1,3,2-dioxaborolan-2-yl)phenoxy)acetate |
| 208 | methyl 4-(5-((((R)-2-((R)-1-(N-(benzyloxy)formamido)propyl)heptanamido)methyl)carbamoyl)furan-2-yl)-2-hydroxybenzoate | 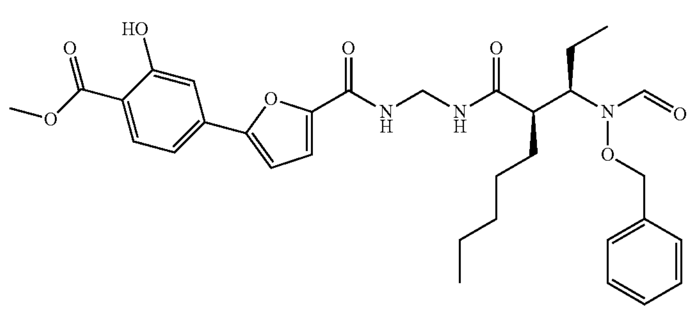 [SMILES: CCCCC[C@@H](C(=O)NCNC(=O)c1ccc(-c2ccc(C(=O)OC)c(O)c2)o1)[C@@H](CC)N(C=O)OCc1ccccc1] | 594.2 | methyl 2-hydroxy-4-(4,4,5,5-tetramethyl-1,3,2-dioxaborolan-2-yl)benzoate |

INTERMEDIATES 209-218 were prepared from N—(((R)-2-((R)-1-(N-(benzyloxy)formamido)propyl)heptanamido)methyl)-5-bromofuran-2-carboxamide and the indicated boronate by methods analogous to those described for Intermediate 147.

| # | Name | Structure | MS (m/z) (M + H+) | Boronate |
|---|------|-----------|-------------------|----------|
| 209 | diethyl (((3-(5-((((R)-2-((R)-1-(N-(benzyloxy)formamido)propyl)heptanamido)methyl)carbamoyl)furan-2-yl)-5-ethoxybenzyl)amino)methyl)phosphonate | 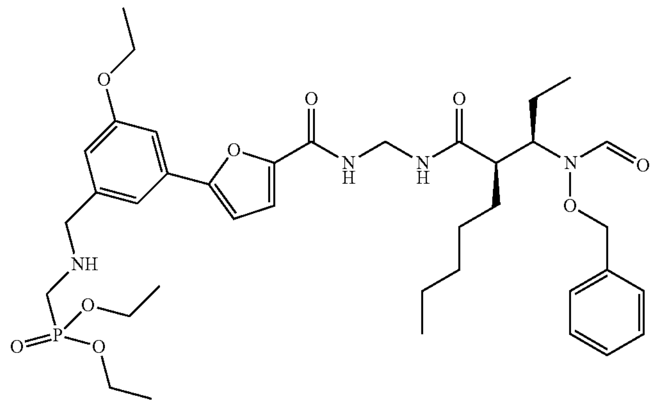 [SMILES: CCCCC[C@@H](C(=O)NCNC(=O)c1ccc(-c2cc(CNCP(=O)(OCC)OCC)cc(OCC)c2)o1)[C@@H](CC)N(C=O)OCc1ccccc1] | 743.2 | diethyl (((3-ethoxy-5-(4,4,5,5-tetramethyl-1,3,2-dioxaborolan-2-yl)benzyl)amino)methyl) phosphonate |
| 210 | dimethyl (3-(benzyloxy)-5-(5-((((R)-2-((R)-1-(N-(benzyloxy)formamido)propyl)heptanamido)methyl)carbamoyl)furan-2-yl)phenyl)phosphonate | 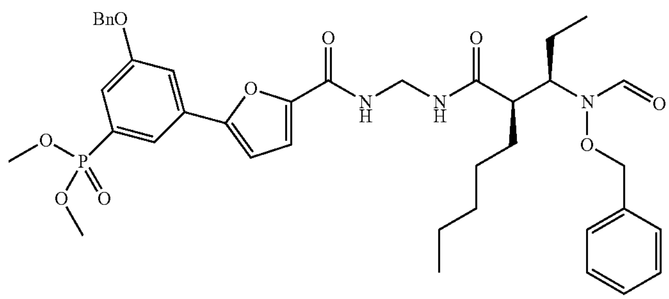 [SMILES: CCCCC[C@@H](C(=O)NCNC(=O)c1ccc(-c2cc(OCc3ccccc3)cc(P(=O)(OC)OC)c2)o1)[C@@H](CC)N(C=O)OCc1ccccc1] | N/A | dimethyl (3-(benzyloxy)-5-(4,4,5,5-tetramethyl-1,3,2-dioxaborolan-2-yl)phenyl) phosphonate |
| 211 | (S)-dimethyl 2-(4-(5-((((R)-2-((R)-1-(N-(benzyloxy)formamido)propyl)heptanamido)methyl)carbamoyl)furan-2-yl)benzamido)succinate | 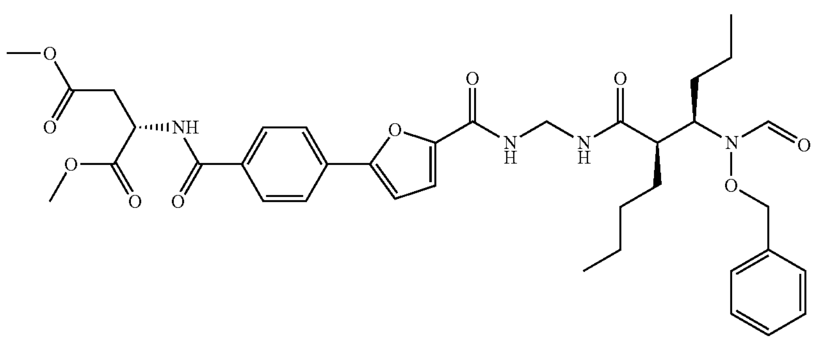 [SMILES: CCCC[C@@H](C(=O)NCNC(=O)c1ccc(-c2ccc(C(=O)N[C@@H](CC(=O)OC)C(=O)OC)cc2)o1)[C@@H](CCC)N(C=O)OCc1ccccc1] | 707.4 | (S)-dimethyl 2-(4-(4,4,5,5-tetramethyl-1,3,2-dioxaborolan-2-yl)benzamido) succinate |
| 212 | (S)-dimethyl 2-(4-(5-((((R)-2-((R)-1-(N-(benzyloxy)formamido)propyl)heptanamido)methyl)carbamoyl)furan-2-yl)-2-methylbenzamido)succinate | 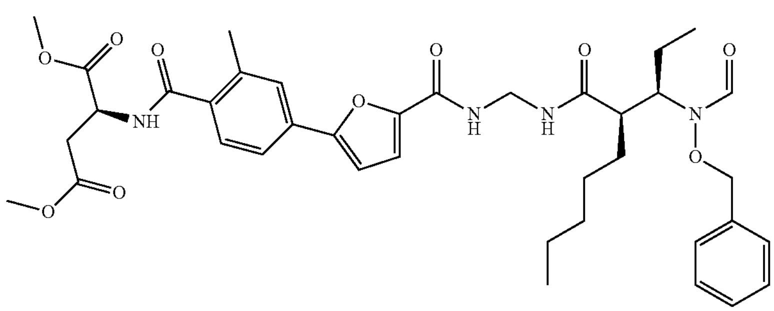 [SMILES: CCCCC[C@@H](C(=O)NCNC(=O)c1ccc(-c2ccc(C(=O)N[C@@H](CC(=O)OC)C(=O)OC)c(C)c2)o1)[C@@H](CC)N(C=O)OCc1ccccc1] | 721.2 | (S)-dimethyl 2-(2-methyl-4-(4,4,5,5-tetramethyl-1,3,2-dioxaborolan-2-yl)benzamido) succinate |

-continued

| # | Name | Structure | MS (m/z) (M + H+) | Boronate |
|---|---|---|---|---|
| 213 | methyl 3-(5-((((R)-2-((R)-1-(N-(benzyloxy)formamido)propyl)heptanamido)methyl)carbamoyl)furan-2-yl)-2-hydroxy-5-(2-methoxy-2-oxoethoxy)benzoate | 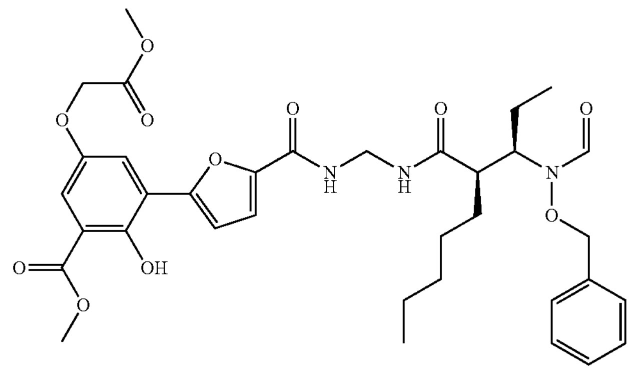 [SMILES: CCCCC[C@@H](C(=O)NCNC(=O)c1ccc(-c2cc(OCC(=O)OC)cc(C(=O)OC)c2O)o1)[C@@H](CC)N(C=O)OCc1ccccc1] | 682.3 | methyl 2-hydroxy-5-(2-methoxy-2-oxoethoxy)-3-(4,4,5,5-tetramethyl-1,3,2-dioxaborolan-2-yl)benzoate |
| 214 | (S)-dimethyl 2-(3-(5-((((R)-2-((R)-1-(N-(benzyloxy)formamido)propyl)heptanamido)methyl)carbamoyl)furan-2-yl)-5-(2-methoxy-2-oxoethoxy)benzamido)succinate | 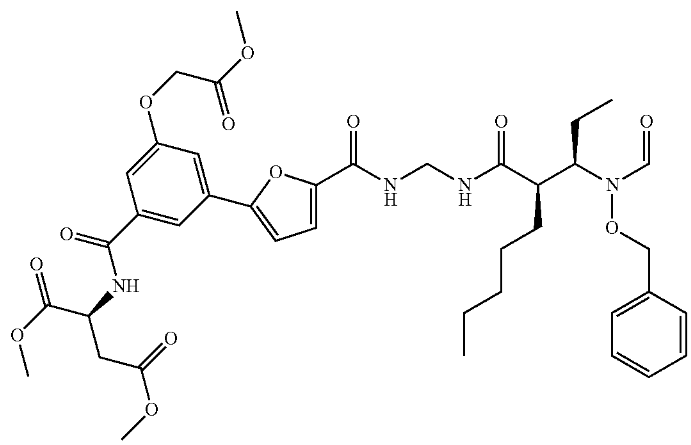 [SMILES: CCCCC[C@@H](C(=O)NCNC(=O)c1ccc(-c2cc(OCC(=O)OC)cc(C(=O)N[C@@H](CC(=O)OC)C(=O)OC)c2)o1)[C@@H](CC)N(C=O)OCc1ccccc1] | 795.3 | methyl 2-hydroxy-5-(2-methoxy-2-oxoethoxy)-3-(4,4,5,5-tetramethyl-1,3,2-dioxaborolan-2-yl)benzoate |
| 215 | (S)-dimethyl 2-(4-(5-((((R)-2-((R)-1-(N-(benzyloxy)formamido)propyl)heptanamido)methyl)carbamoyl)furan-2-yl)-2-(2-methoxy-2-oxoethoxy)benzamido)succinate | 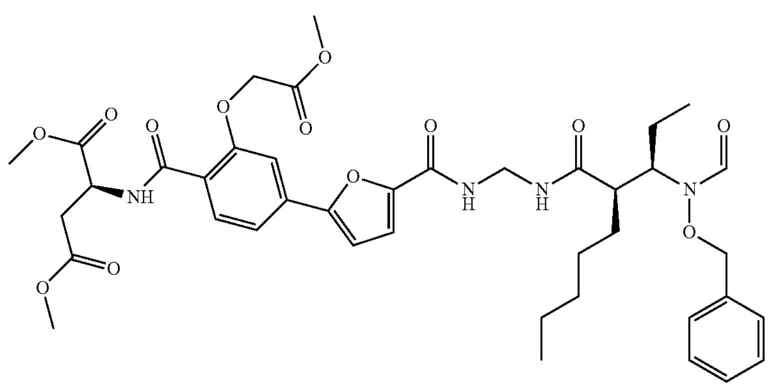 [SMILES: CCCCC[C@@H](C(=O)NCNC(=O)c1ccc(-c2ccc(C(=O)N[C@@H](CC(=O)OC)C(=O)OC)c(OCC(=O)OC)c2)o1)[C@@H](CC)N(C=O)OCc1ccccc1] | 795.3 | (S)-dimethyl 2-(2-(2-methoxy-2-oxoethoxy)-4-(4,4,5,5-tetramethyl-1,3,2-dioxaborolan-2-yl)benzamido)succinate |
| 216 | methyl 2-((3-(5-((((R)-2-((R)-1-(N-(benzyloxy)formamido)propyl)heptanamido)methyl)carbamoyl)furan-2-yl)-5-ethoxybenzyl)(methyl)amino)acetate | 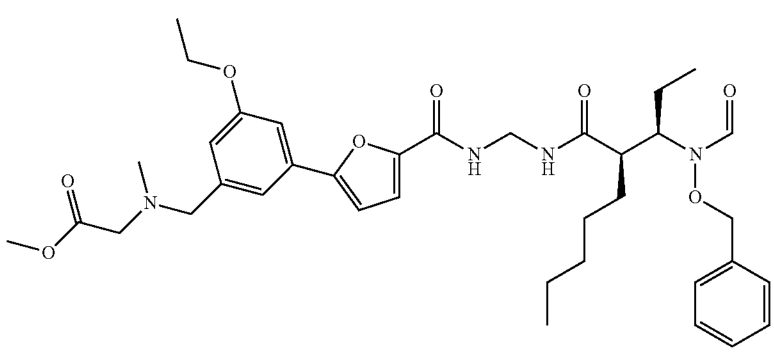 [SMILES: CCCCC[C@@H](C(=O)NCNC(=O)c1ccc(-c2cc(CN(C)CC(=O)OC)cc(OCC)c2)o1)[C@@H](CC)N(C=O)OCc1ccccc1] | 679.2 | methyl 2-((3-ethoxy-5-(4,4,5,5,-tetramethyl-1,3,2-dioxaborolan-2-yl)benzyl)(methyl)amino)acetate |

| # | Name | Structure | MS (m/z) (M + H+) | Boronate |
|---|---|---|---|---|
| 217 | methyl 5-(5-((((R)-2-((R)-1-(N-(benzyloxy)formamido)propyl)heptanamido)methyl)carbamoyl)furan-2-yl)-3-ethoxy-2-fluorobenzoate | 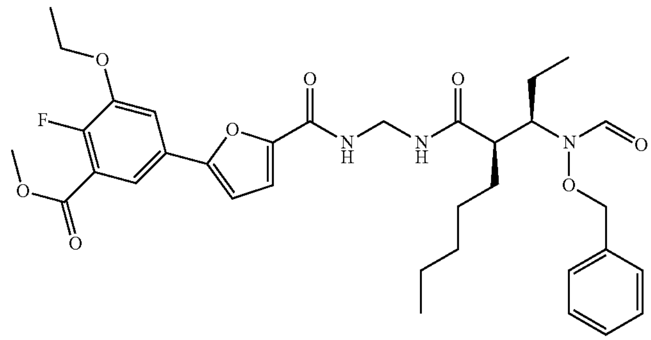 [SMILES: CCCCC[C@@H](C(=O)NCNC(=O)c1ccc(-c2cc(OCC)c(F)c(C(=O)OC)c2)o1)[C@@H](CC)N(C=O)OCc1ccccc1] | 640.3 | methyl 3-ethoxy-2-fluoro-5-(4,4,5,5-tetramethyl-1,3,2-dioxaborolan-2-yl)benzoate |
| 218 | (R)-dimethyl 2-(4-(5-((((R)-2-((R)-1-(N-(benzyloxy)formamido)propyl)heptanamido)methyl)carbamoyl)furan-2-yl)-2-ethoxybenzamido)succinate | 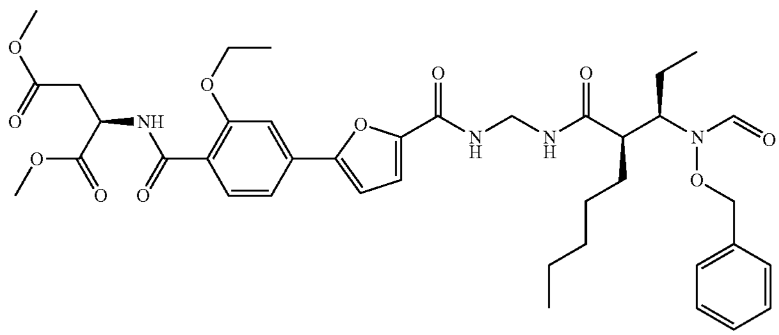 [SMILES: CCCCC[C@@H](C(=O)NCNC(=O)c1ccc(-c2ccc(C(=O)N[C@H](CC(=O)OC)C(=O)OC)c(OCC)c2)o1)[C@@H](CC)N(C=O)OCc1ccccc1] | 752.4 | (R)-(4-((1,4-dimethoxy-1,4-dioxobutan-2-yl)carbamoyl)-3-ethoxyphenyl)boronic acid |

Intermediate 219 was prepared from N-(((2R,3R)-3-(N-(benzyloxy)formamido)-2-phenethylpentanamido)methyl)-5-bromofuran-2-carboxamide and the indicated boronate by methods analogous to those described for Intermediate 147.

| # | Name | Structure | MS (m/z) (M + H+) | Boronate |
|---|---|---|---|---|
| 219 | dimethyl (3-(5-((((2R,3R)-3-(N-(benzyloxy)formamido)-2-phenethylpentanamido)methyl)carbamoyl)furan-2-yl)-5-ethoxyphenyl) phosphonate | 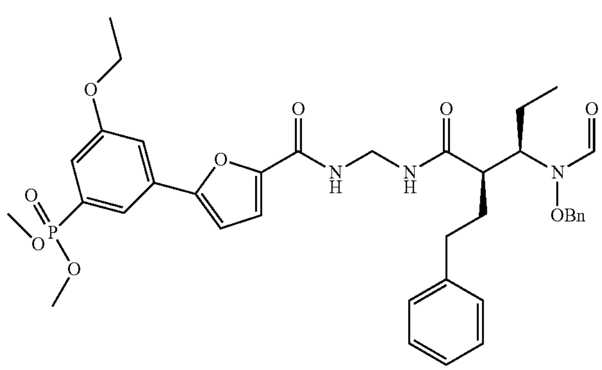 | 706.4 | dimethyl (3-ethoxy-5-(4,4,5,5-tetramethyl-1,3,2-dioxaborolan-2-yl)phenyl) phosphonate |

INTERMEDIATES 220-223 were prepared from N-(((2R,3R)-3-(N-(benzyloxy)formamido)-2-(2,4-difluorophenethyl)pentanamido)methyl)-5-bromofuran-2-carboxamide and the indicated boronate by methods analogous to those described for Intermediate 147.

| # | Name | Structure | MS (m/z) (M + H⁺) | Boronate |
|---|------|-----------|-------------------|----------|
| 220 | methyl 3-(5-((((2R,3R)-3-(N-benzyloxy)formamido)-2-(2,4-difluorophenethyl)pentanamido)methyl)carbamoyl)furan-2-yl)-2-hydroxy-5-(2-methoxy-2-oxoethoxy)benzoate | 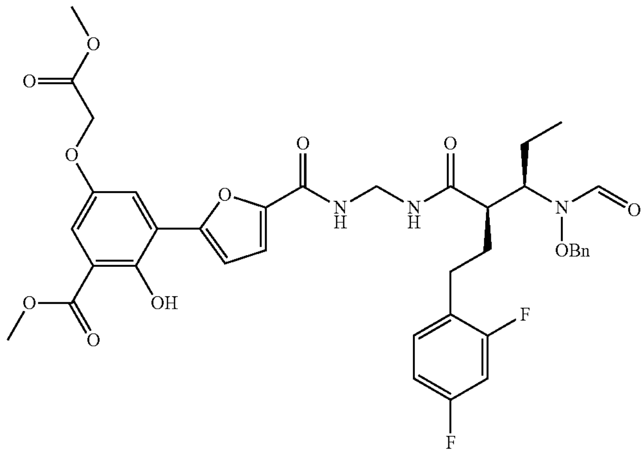 [SMILES: CC[C@H]([C@@H](CCc1ccc(F)cc1F)C(=O)NCNC(=O)c1ccc(-c2cc(OCC(=O)OC)cc(C(=O)OC)c2O)o1)N(C=O)OCc1ccccc1] | 752.4 | (2-hydroxy-5-(2-methoxy-2-oxoethoxy)-3-(methoxycarbonyl)phenyl)boronic acid |
| 221 | dimethyl 2,2'-((3-(5-((((2R,3R)-3-(N-(benzyloxy)formamido)-2-(2,4-difluorophenethyl)pentanamido)methyl)carbamoyl)furan-2-yl)-5-ethoxybenzoyl)azanediyl)diacetate | 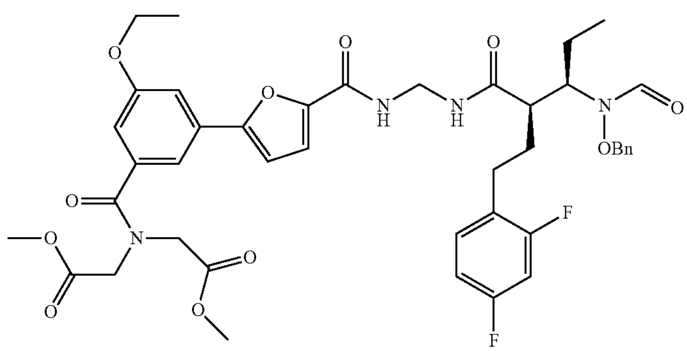 [SMILES: CCOc1cc(C(=O)N(CC(=O)OC)CC(=O)OC)cc(-c2ccc(C(=O)NCNC(=O)[C@H](CCc3ccc(F)cc3F)[C@@H](CC)N(C=O)OCc3ccccc3)o2)c1] | 821.3 | dimethyl 2,2'-((3-ethoxy-5-(4,4,5,5-tetramethyl-1,3,2-dioxaborolan-2-yl)benzoyl)azanediyl)diacetate |
| 222 | (S)-dimethyl 2-(4-(5-((((2R,3R)-3-(N-(benzyloxy)formamido)-2-(2,4-difluorophenethyl)pentanamido)methyl)carbamoyl)furan-2-yl)-2-ethoxybenzamido)succinate | 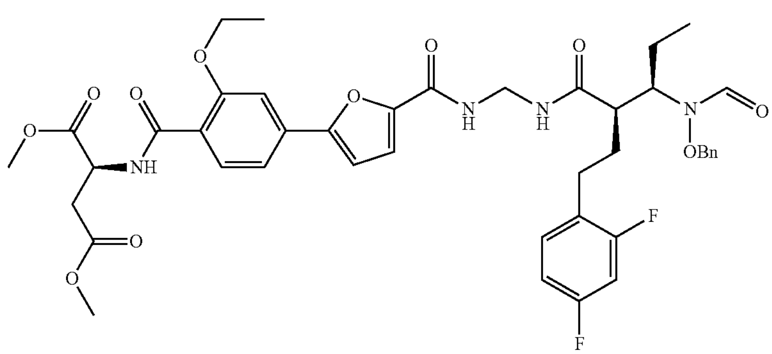 [SMILES: CCOc1cc(-c2ccc(C(=O)NCNC(=O)[C@H](CCc3ccc(F)cc3F)[C@@H](CC)N(C=O)OCc3ccccc3)o2)ccc1C(=O)N[C@@H](CC(=O)OC)C(=O)OC] | 821.3 | (S)-dimethyl 2-(2-ethoxy-4-(4,4,5,5-tetramethyl-1,3,2-dioxaborolan-2-yl)benzamido)succinate |

| # | Name | Structure | MS (m/z) (M + H⁺) | Boronate |
|---|---|---|---|---|
| 223 | methyl 3-(5-((((2R,3R)-3-(N-(benzyloxy)formamido)-2-(2,4-difluorophenethyl)pentanamido)methyl)carbamoyl)furan-2-yl)-5-(2-methoxy-2-oxoethoxy)benzoate | 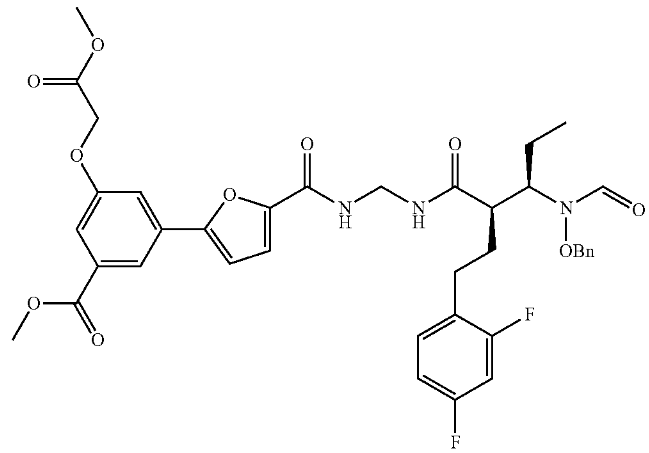 [SMILES: CC[C@H]([C@@H](CCc1ccc(F)cc1F)C(=O)NCNC(=O)c1ccc(-c2cc(OCC(=O)OC)cc(C(=O)OC)c2)o1)N(C=O)OCc1ccccc1] | 736.3 | methyl 3-(2-methoxy-2-oxoethoxy)-5-(4,4,5,5-tetramethyl-1,3,2-dioxaborolan-2-yl)benzoate |

INTERMEDIATES 224-225 were prepared from N-(((2R,3R)-3-(N-(benzyloxy)formamido)-2-(2-(naphthalen-2-yl)ethyl)pentanamido)methyl)-5-bromofuran-2-carboxamide and the indicated boronate by methods analogous to those described for Intermediate 147.

| # | Name | Structure | MS (m/z) (M + H⁺) | Boronate |
|---|---|---|---|---|
| 224 | dimethyl (3-(5-((((2R,3R)-3-(N-(benzyloxy)formamido)-2-(2-(naphthalen-2-yl)ethyl)pentanamido)methyl)carbamoyl)furan-2-yl)-5-ethoxyphenyl)phosphonate | 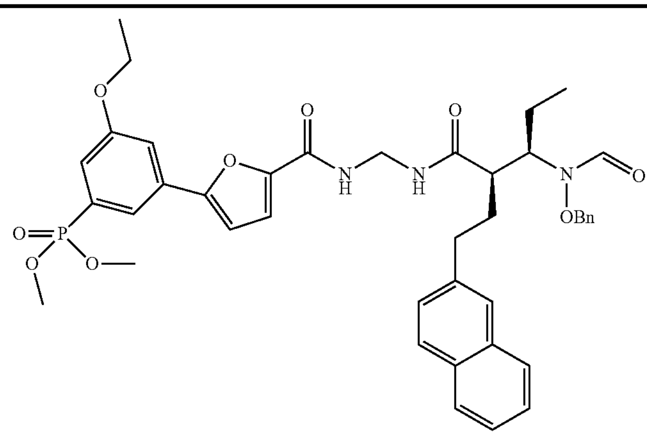 | 756.3 | dimethyl (3-ethoxy-5-(4,4,5,5-tetramethyl-1,3,2-dioxaborolan-2-yl)phenyl)phosphonate |
| 225 | (S)-dimethyl 2-(4-(5-((((2R,3R)-3-(N-(benzyloxy)formamido)-2-(2-(naphthalen-2-yl)ethyl)pentanamido)methyl)carbamoyl)furan-2-yl)-2-ethoxybenzamido)succinate | 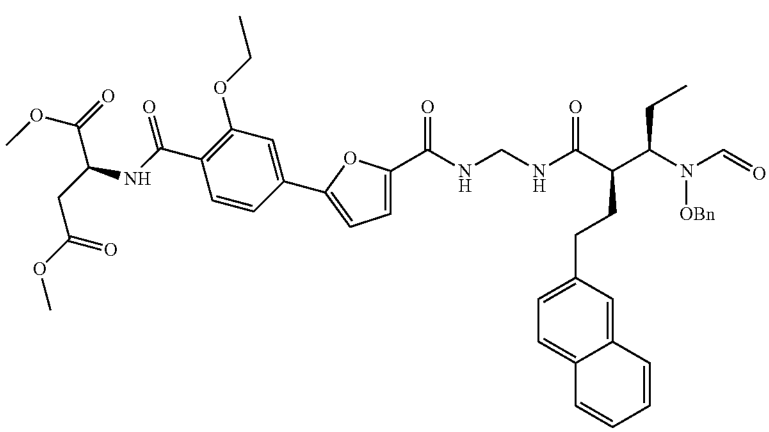 [SMILES: CCOc1cc(-c2ccc(C(=O)NCNC(=O)[C@H](CCc3ccc4ccccc4c3)[C@@H](CC)N(C=O)OCc3ccccc3)o2)ccc1C(=O)N[C@@H](CC(=O)OC)C(=O)OC] | 835.4 | (S)-dimethyl 2-(2-ethoxy-4-(4,4,5,5-tetramethyl-1,3,2-dioxaborolan-2-yl)benzamido)succinate |

Intermediate 226: methyl 3-(2-amino-2-oxoethoxy)-5-(5-((((R)-2-((R)-1-(N-(benzyloxy)formamido)propyl)heptanamido)methyl)carbamoyl)furan-2-yl)benzoate

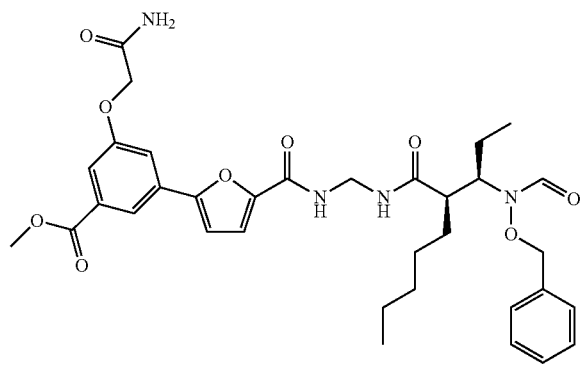 [SMILES: CCCCC[C@@H](C(=O)NCNC(=O)c1ccc(-c2cc(OCC(N)=O)cc(C(=O)OC)c2)o1)[C@@H](CC)N(C=O)OCc1ccccc1]

A mixture of methyl 3-(5-((((R)-2-((R)-1-(N-(benzyloxy)formamido)propyl)heptanamido)methyl)carbamoyl)furan-2-yl)-5-hydroxybenzoate (0.25 g, 0.42 mmol), 2-bromoacetamide (0.116 g, 0.842 mmol), and $K_2CO_3$ (0.29 g, 2.106 mmol) in acetonitrile (1.50 ml) was heated at 80° C. for 1 hour. The reaction was then cooled to RT and concentrated in-vacuo. The residue was partitioned between $H_2O$ and EtOAc and the organic layer was separated. The organic layer was washed with brine, dried over $MgSO_4$, filtered, and concentrated under vacuum to afford a white solid. The solid was purified by flash column chromotography (20-100% EtOAc:Hexane) to afford the titled compound. (0.22 g, 80% yield) as white solid. MS (m/z) 651.2 (M+H+).

Intermediate 227 was prepared from N—(((R)-2-((R)-1-(N-(benzyloxy)formamido)propyl)heptanamido)methyl)-5-bromofuran-2-carboxamide and the indicated bromide by the methods analogous to those described for Intermediate 226.

| # | Name | Structure | MS (m/z) (M + H+) | Bromide |
|---|------|-----------|-------------------|---------|
| 227 | methyl 3-(5-((((R)-2-((R)-1-(N-(benzyloxy)formamido)propyl)heptanamido)methyl)carbamoyl)furan-2-yl)-5-(2-methoxy-2-oxoethoxy)benzoate | 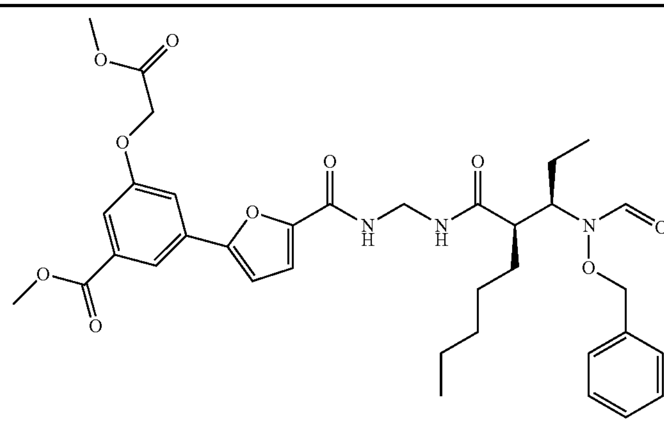 | 666.3 | methyl 1-bromoacetate |

Intermediate 228: diethyl ((4-(5-((((R)-2-((R)-1-(N-(benzyloxy)formamido)propyl)heptanamido)methyl)carbamoyl)furan-2-yl)-2-ethoxybenzamido)methyl)phosphonate

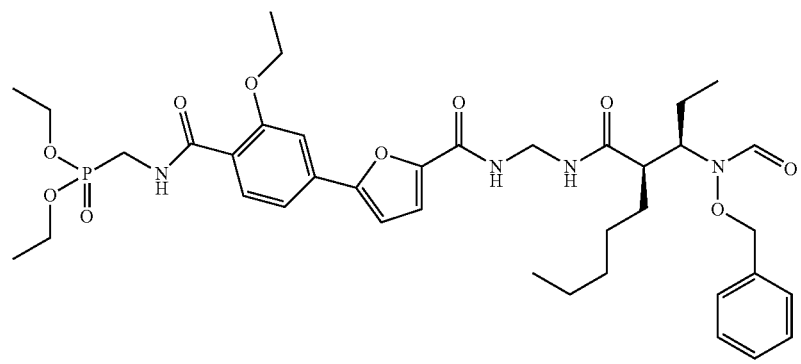 [SMILES: CCCCC[C@@H](C(=O)NCNC(=O)c1ccc(-c2ccc(C(=O)NCP(=O)(OCC)OCC)c(OCC)c2)o1)[C@@H](CC)N(C=O)OCc1ccccc1]

A solution of diethyl ((4-bromo-2-ethoxybenzamido)methyl)phosphonate (1.8 g, 4.57 mmol), 4,4,4',4',5,5,5',5'-octamethyl-2,2'-bi-1,3,2-dioxaborolane (1.39 g, 5.48 mmol), potassium acetate (1.79 g, 18.26 mmol), and PdCl$_2$(dppf)-CH$_2$Cl$_2$ (0.15 g, 0.18 mmol) refluxed in 1,4-dioxane (11.42 ml) for 15 hour under nitrogen with a condensor. The reaction was cooled to RT and to the solution was added N—(((R)-2-((R)-1-(N-(benzyloxy)formamido)propyl)heptanamido)methyl)-5-bromofuran-2-carboxamide (2.39 g, 4.57 mmol), PdCl$_2$(dppf)-CH$_2$Cl$_2$ adduct (0.37 g, 0.46 mmol), and 2M Na$_2$CO$_3$ (11.42 ml). The reaction stirred at 50° C. for 1 hour equipped with a condensor. The reaction was cooled to RT, poured into water and extracted into EtOAc (4×100 ml). The combined organic layers were collected, washed with brine, dried over sodium sulfate and decolorizing carbon, filtered thru a plug of celite and concentrated to an orange residue. The residue was redissolved in DCM and purified via flash column chromatography (120 g column, 0-10% MeOH/EtoAc over 45 minutes) to afford an off-white solid as the title compound (2.0 g, 58% yield). MS (m/z) 757.2 (M+H+).

INTERMEDIATE 229 was prepared from N—(((R)-2-((R)-1-(N-(benzyloxy)formamido)propyl)heptanamido)methyl)-5-bromofuran-2-carboxamide and the indicated bromide by the methods analogous to those described for Intermediate 228.

| # | Name | Structure | MS (m/z) (M + H$^+$) | Bromide |
|---|---|---|---|---|
| 229 | methyl 4-(5-((((R)-2-((R)-1-(N-(benzyloxy)formamido)propyl)heptanamido)methyl)carbamoyl)furan-2-yl)-2-ethoxy-6-hydroxybenzoate | 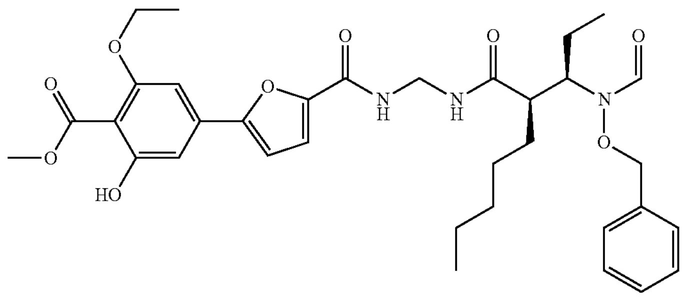 [SMILES: CCCCC[C@@H](C(=O)NCNC(=O)c1ccc(-c2cc(O)c(C(=O)OC)c(OCC)c2)o1)[C@@H](CC)N(C=O)OCc1ccccc1] | 638.2 | methyl 4-bromo-2-ethoxy-6-hydroxybenzoate |

INTERMEDIATES 230-232 were prepared from N-(((2R,3R)-3-(N-(benzyloxy)formamido)-2-phenethylpentanamido)methyl)-5-bromofuran-2-carboxamide and the indicated bromide by the methods analogous to those described for Intermediate 228.

| # | Name | Structure | MS (m/z) (M + H$^+$) | Bromide |
|---|---|---|---|---|
| 230 | ethyl 3-(5-((((2R,3R)-3-(N-(benzyloxy)formamido)-2-phenethylpentanamido)methyl)carbamoyl)furan-2-yl)-5-ethoxy-2-hydroxybenzoate | 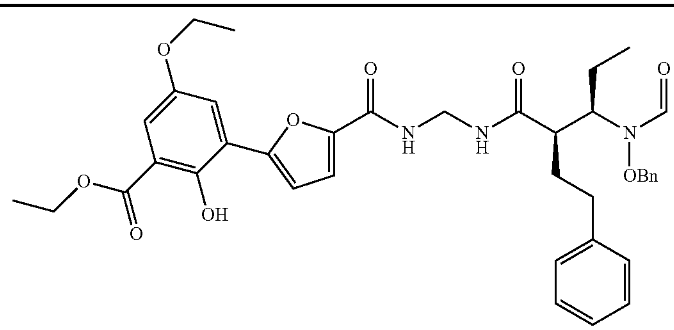 | 686.8 | bromo-5-ethoxy-2-hydroxybenzoate |
| 231 | dimethyl 2,2'-((4-(5-((((2R,3R)-3-(N-benzyloxy)formamido)-2-phenethylpentanamido)methyl)carbamoyl)furan-2-yl)-2-ethoxybenzoyl)azanediyl)diacetate | 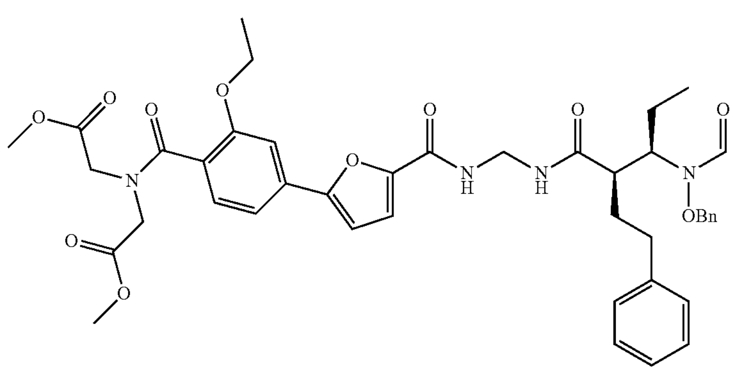 [SMILES: CCOc1cc(-c2ccc(C(=O)NCNC(=O)[C@H](CCc3ccccc3)[C@@H](CC)N(C=O)OCc3ccccc3)o2)ccc1C(=O)N(CC(=O)OC)CC(=O)OC] | 785.7 | (dimethyl 2,2'-((4-bromo-2-ethoxybenzoyl)azanediyl)diacetate |

| # | Name | Structure | MS (m/z) (M + H+) | Bromide |
|---|------|-----------|-------------------|---------|
| 232 | (S)-dimethyl 2-(4-(5-((((2R,3R)-3-(N-(benzyloxy)forma-mido)-2-phenthylpentan-amido)methyl)car-bamoyl)furan-2-yl)-2-ethoxybenzamido)succinate | 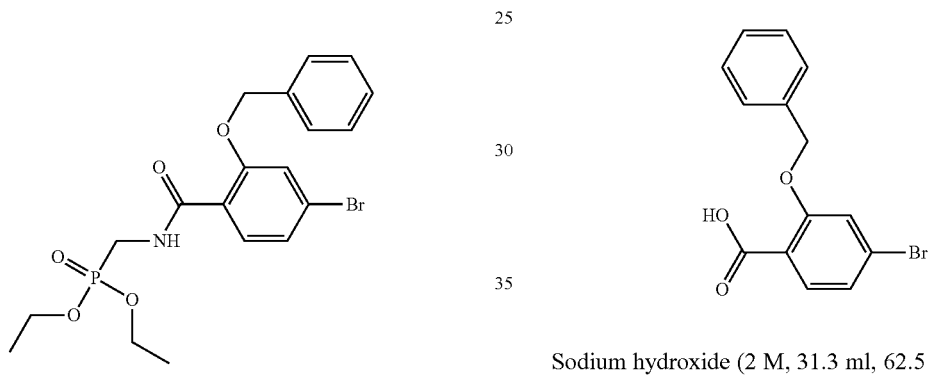 | 785.4 | (S)-dimethyl-2-(4-bromo-2-ethoxybenzami-do)succinate |

Intermediate 233: diethyl ((2-(benzyloxy)-4-bromobenzamido)methyl)phosphonate

Step 2: 2-(benzyloxy)-4-bromobenzoic acid

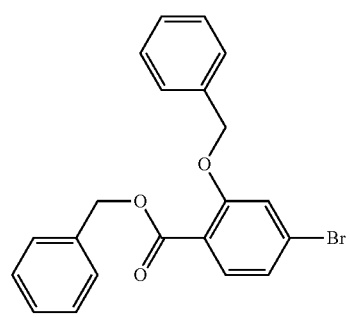 [SMILES: O=C(OCc1ccccc1)c1ccc(Br)cc1OCc1ccccc1]

Sodium hydroxide (2 M, 31.3 ml, 62.5 mmol) was added to a stirring solution of benzyl 2-(benzyloxy)-4-bromobenzoate (8.28 g, 20.84 mmol) in MeOH (20.84 ml) and THF (20.84 ml). The resulting mixture was stirred at 50° C. for 2 hr and concentrated to an aqueous mixture. The mixture was neutralized with HCl (3.47 ml, 20.84 mmol) and then concentrated to dryness. The concentrate was triturated with a 1% MeOH/EtOAc solution to give the title compound (8.73 g, 28.4 mmol, 136% yield). MS (m/z) 306.9 (M+H)+

Step 1: benzyl 2-(benzyloxy)-4-bromobenzoate

Step 3: diethyl ((2-(benzyloxy)-4-bromobenzamido)methyl)phosphonate

Diethyl (aminomethyl)phosphonate oxalate (2.51 g, 9.77 mmol) was free based using a Silicycle carbonate cartridge eluting with MeOH. After the solution was concentrated to dryness, it was combined with DMF (24.42 ml), 2-(benzyloxy)-4-bromobenzoic acid (1.50 g, 4.88 mmol), EDC (1.40 g, 7.33 mmol) and HOAt (0.80 g, 5.86 mmol) at RT. Next, N-methylmorpholine (1.611 ml, 14.65 mmol) was added to this mixture and it was stirred for 18 hr at RT. Water was added, and the organics were extracted with EtOAc (3×). The combined organic phase was washed with brine (3×), dried over MgSO4, filtered, concentrated and purified by flash chromatography (0-5% MeOH/EtOAc) to afford the title compound (1.55 g, 3.36 mmol, 68.9% yield) as a colorless solid. MS (m/z) 456.1 (M+H)+

Benzyl bromide (6.03 ml, 50.7 mmol) was added to a mixture of 4-bromo-2-hydroxybenzoic acid (5.00 g, 23.04 mmol) and potassium carbonate (10.51 g, 76 mmol) in DMF (23.04 ml). The mixture was stirred at room temperature for 2 days. Water and EtOAc were added and the organic layer was washed with brine (3×). The combined aqueous layer was extracted with EtOAc and the organics were combined and dried over MgSO4, filtered, concentrated and purified by flash chromatography (0-40% EtOAc/Hex) to give the title compound (8.24 g, 90% yield). MS (m/z) 397.0 (M+H)+

Intermediate 234: diethyl ((4-bromobenzamido)methyl)phosphonate

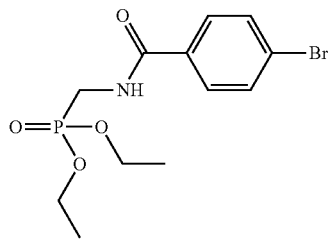 [SMILES: CCOP(=O)(CNC(=O)c1ccc(Br)cc1)OCC]

Step 1: 4-bromo-N-(hydroxymethyl)benzamide

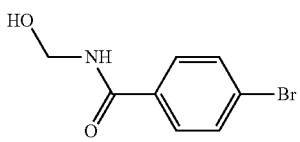

Formaldehyde (24.79 ml, 333 mmol) was added to a stirring mixture of 4-bromobenzamide (4.00 g, 20.00 mmol) and potassium carbonate (0.50 g, 3.62 mmol) in methanol (40.0 ml). The resulting mixture was stirred at RT for 2 days. SiO$_2$ was then added to the reaction mixture, the mixture was concentrated to dryness, and purified by flash chromatography (0-10% MeOH/DCM) to afford the title compound (2.5 g, 10.8 mmol, 54.0% yield). MS (m/z) 251.9 (M+Na)$^+$

Step 2: diethyl ((4-bromobenzamido)methyl)phosphonate

Phosphorus trichloride (0.64 ml, 7.28 mmol) and triethyl phosphite (19.01 ml, 109 mmol) were added to a N$_2$ flushed round bottom flask equipped with a reflux condenser. 4-bromo-N-(hydroxymethyl)benzamide (2.50 g, 10.87 mmol) was added portion-wise to the reaction mixture and the mixture stirred at 65° C. for 1 hr. The resulting mixture was evaporated and recrystallized from ether to afford the title compound (2.65 g, 7.49 mmol, 68.9% yield) as a colorless solid. MS (m/z) 350.0 (M+H)$^+$

Intermediate 235: diethyl ((4-bromo-2-methylbenzamido)methyl)phosphonate

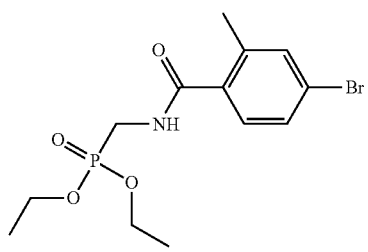 [SMILES: CCOP(=O)(CNC(=O)c1ccc(Br)cc1C)OCC]

Diethyl (aminomethyl)phosphonate oxalate (2.39 g, 9.30 mmol) was free based using a Silicycle carbonate cartridge eluting with MeOH. After the solution was concentrated to dryness, it was combined with DMF (23.25 ml), EDC (1.34 g, 6.98 mmol), and HOAt (0.76 g, 5.58 mmol) and 4-bromo-2-methylbenzoic acid (1.00 g, 4.65 mmol) at RT. Next, N-methylmorpholine (1.53 ml, 13.95 mmol) was added to the stirring mixture and it was stirred for 18 hr at RT. Water was added and the organics were extracted with EtOAc (3×). The combined organic phase was washed with brine (3×), dried over MgSO$_4$, filtered, and concentrated. Purification using ISCO Rf (0-5% MeOH/EtOAc) afforded the title compound (1.62 g, 4.40 mmol, 95% yield) as a colorless solid. MS (m/z) 364.0 (M+H)$^+$

Intermediate 236: (R)-dimethyl 2-(4-bromobenzamido)succinate

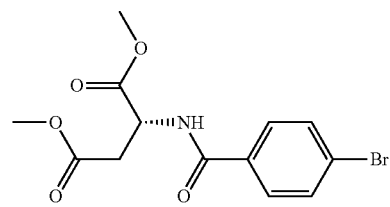 [SMILES: COC(=O)C[C@@H](NC(=O)c1ccc(Br)cc1)C(=O)OC]

HATU (10.55 g, 27.8 mmol) was added to a stirring mixture of 4-bromobenzoic acid (4.65 g, 23.13 mmol) and (R)-dimethyl 2-aminosuccinate hydrochloride (5.49 g, 27.8 mmol) in DMF (46.3 ml) at RT. Triethylamine (9.67 ml, 69.4 mmol) was then added and the mixture was stirred for 18 h. EtOAc and brine were added and the organic phase was washed with brine (2×), and then the combined aqueous layers were back extracted with EtOAc (1×). The combined organic phase was dried over MgSO$_4$, filtered, concentrated, and purified by flash chromatography (0-60% EtOAc/Hexanes) to afford the title compound (7.66 g, 22.02 mmol, 95% yield). MS (m/z) 344.0 (M+H)$^+$

Intermediate 237: (S)-dimethyl 2-(4-bromobenzamido)pentanedioate

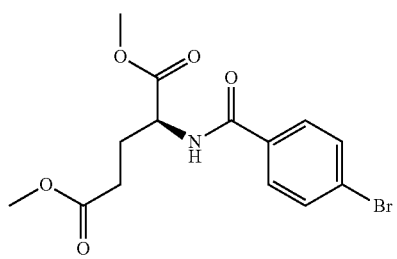 [SMILES: COC(=O)CC[C@H](NC(=O)c1ccc(Br)cc1)C(=O)OC]

To a solution containing (S)-dimethyl 2-aminopentanedioate, hydrochloride (4.63 g, 21.89 mmol) and 4-bromobenzoic acid (4.0 g, 19.90 mmol) in DMF (75 ml) was added HATU (7.45 g, 19.59 mmol) followed by DIPEA (8.55 ml, 49.0 mmol). The reaction was stirred for 18 hr and then was diluted with NH$_4$Cl aq. solution, extracted with ethyl ether, dried over MgSO$_4$, filtered and concentrated onto SiO$_2$. Purification by flash chromatography (0-50% ethyl acetate/hexanes) afforded the title compound (4.01 g, 11.2 mmol, 56%) as a colorless solid. MS (m/z) 357.9 (M+H)$^+$

Intermediate 238: (S)-dimethyl 2-(4-bromo-2-ethoxybenzamido)pentanedioate

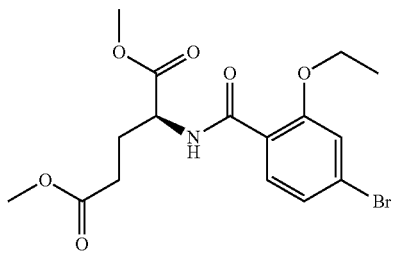 [SMILES: CCOc1cc(Br)ccc1C(=O)N[C@@H](CCC(=O)OC)C(=O)OC]

To a solution containing (S)-dimethyl 2-aminopentanedioate, hydrochloride (3.80 g, 17.95 mmol) and 4-bromo-2-ethoxybenzoic acid (4.0 g, 16.32 mmol) in DMF (75 ml) was added HATU (7.45 g, 19.59 mmol) followed by DIPEA (8.55 ml, 49.0 mmol). The reaction was stirred for 18 hr and then was diluted with NH$_4$Cl aq. solution, extracted with ethyl ether, dried over MgSO$_4$, filtered and concentrated onto SiO$_2$. Purification by flash chromatography (0-50% ethyl acetate/hexanes) afforded the title compound (5.33 g, 13.3 mmol, 81% yield) as a colorless solid. MS (m/z) 402.1 (M+H)$^+$

Intermediate 239: (4-(bis(2-methoxy-2-oxoethyl)carbamoyl)phenyl)boronic acid

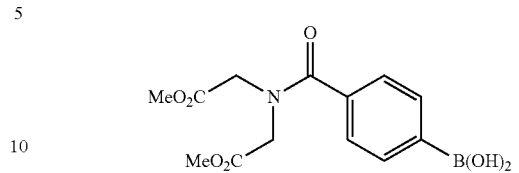

To a mixture of 4-boronobenzoic acid (0.10 g, 0.603 mmol) and DMF (1.21 ml) at 0° C. was added HATU (0.25 g, 0.66 mmol) and DIPEA (0.316 ml, 1.81 mmol). The mixture stirred for 30 min, then dimethyl 2,2'-azanediyldiacetate, hydrochloride (0.155 g, 0.78 mmol) was added. The reaction stirred for 72 hours. The reaction was diluted with 1N HCl and extracted with EtOAc (4×). The organic layers were combined, passed through a phase separator, concentrated, and purified via flash chromatography (ISCO, 12 g silica column, 0-40% MeOH:EtOAc) to give the title compound (0.143 g, 66.4% yield). MS (m/z) 310.0 (M+H$^+$).

INTERMEDIATES 240-245 were prepared from the indicated bromide in general by methods analogous to those described for Intermediate 55. Reactions were heated to 90° C. and reaction times vary from 12 hours to 18 hours.

| # | Name | Structure | MS (m/z) | Bromide |
|---|------|-----------|----------|---------|
| 240 | diethyl ((2-methyl-4-(4,4,5,5-tetramethyl-1,3,2-dioxaborolan-2-yl)benzamido)methyl)phosphonate | 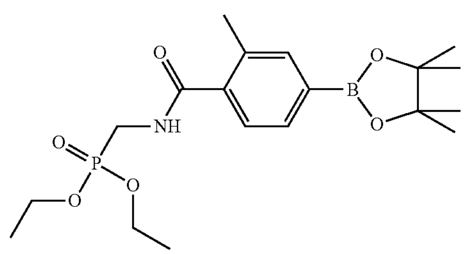 [SMILES: CCOP(=O)(CNC(=O)c1ccc(B2OC(C)(C)C(C)(C)O2)cc1C)OCC] | 412.2 | diethyl ((4-bromo-2-methylbenzamido)methyl)phosphonate |
| 241 | (R)-dimethyl 2-(4-(4,4,5,5-tetramethyl-1,3,2-dioxaborolan-2-yl)benzamido)succinate | 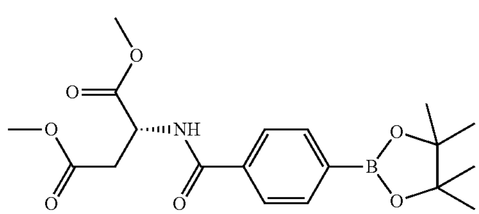 | 392.2 | (R)-dimethyl 2-(4-bromobenzamido)succinate |
| 242 | (S)-dimethyl 2-(4-(4,4,5,5-tetramethyl-1,3,2-dioxaborolan-2-yl)benzamido)pentanedioate | 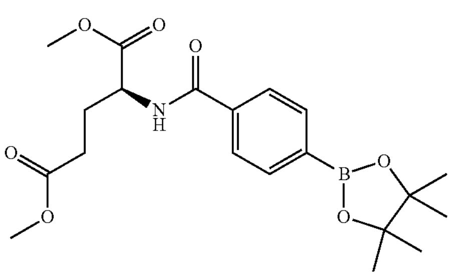 [SMILES: COC(=O)CC[C@H](NC(=O)c1ccc(B2OC(C)(C)C(C)(C)O2)cc1)C(=O)OC] | 406.4 | (S)-dimethyl 2-(4-bromobenzamido)pentanedioate |

| # | Name | Structure | MS (m/z) | Bromide |
|---|---|---|---|---|
| 243 | (S)-dimethyl 2-(2-ethoxy-4-(4,4,5,5-tetramethyl-1,3,2-dioxaborolan-2-yl)benzamido)pentanedioate | 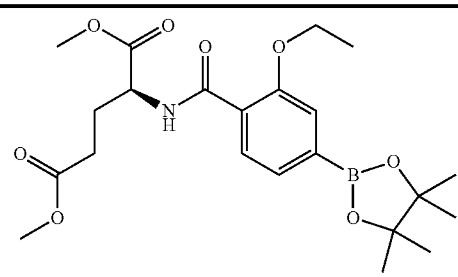 | 450.1 | (S)-dimethyl 2-(4-bromo-2-ethoxybenzamido)pentanedioate |
| 244 | diethyl ((2-(benzyloxy)-4-(4,4,5,5-tetramethyl-1,3,2-dioxaborolan-2-yl)benzamido)methyl)phosphonate | 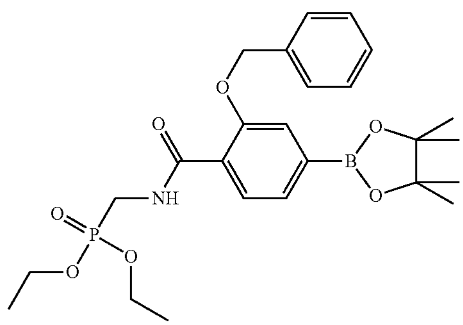 [SMILES: CCOP(=O)(CNC(=O)c1ccc(B2OC(C)(C)C(C)(C)O2)cc1OCc1ccccc1)OCC] | 504.3 | diethyl ((2-(benzyloxy)-4-bromobenzamido)methyl)phosphonate |
| 245 | diethyl ((4-(4,4,5,5-tetramethyl-1,3,2-dioxaborolan-2-yl)benzamido)methyl)phosphonate | 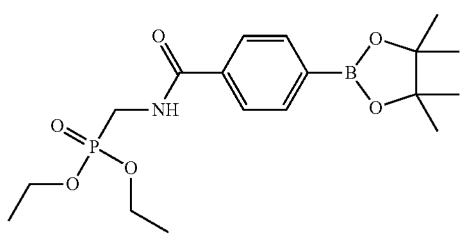 [SMILES: CCOP(=O)(CNC(=O)c1ccc(B2OC(C)(C)C(C)(C)O2)cc1)OCC] | 398.1 | diethyl ((4-bromobenzamido)methyl)phosphonate |

INTERMEDIATES 246-252 were prepared from N—(((R)-2-((R)-1-(N-(benzyloxy)formamido)propyl)heptanamido)methyl)-5-bromofuran-2-carboxamide and the indicated boronate by methods analogous to those described for Intermediate 147. For Intermediates 246-250 and 252, reaction times vary from 2 hours to 4 hours. For Intermediate 251 the reaction was heated to 80° C. and reaction time was 5 minutes.

| # | Name | Structure | MS (m/z) (M + H⁺) | Boronate |
|---|---|---|---|---|
| 246 | diethyl ((4-(5-((((R)-2-((R)-1-(N-(benzyloxy)formamido)propyl)heptanamido)methyl)carbamoyl)furan-2-yl)benzamido)methyl)phosphonate | 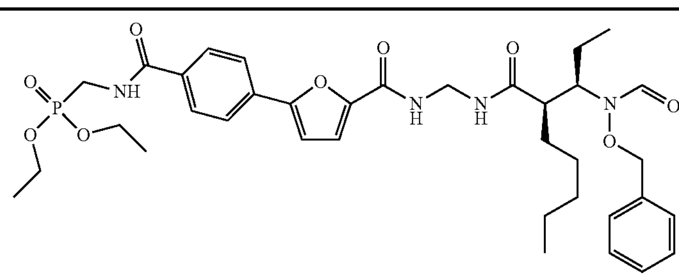 | 713.4 | diethyl ((4-(4,4,5,5-tetramethyl-1,3,2-dioxaborolan-2-yl)benzamido)methyl)phosphonate |

| # | Name | Structure | MS (m/z) (M + H+) | Boronate |
|---|------|-----------|-------------------|----------|
| 247 | diethyl ((4-(5-((((R)-2-((R)-1-(N-(benzyloxy)formamido)propyl)heptanamido)methyl)carbamoyl)furan-2-yl)-2-methylbenzamido)methyl) phosphonate | 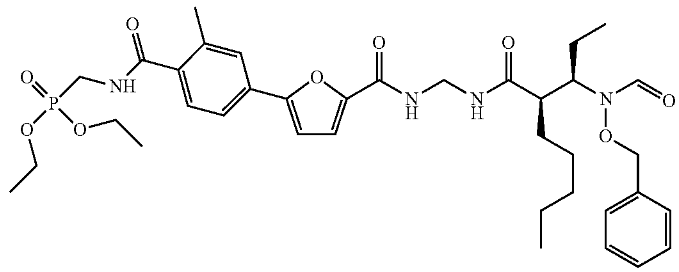 [SMILES: CCCCC[C@@H](C(=O)NCNC(=O)c1ccc(-c2ccc(C(=O)NCP(=O)(OCC)OCC)c(C)c2)o1)[C@@H](CC)N(C=O)OCc1ccccc1] | 727.4 | diethyl ((2-methyl-4-(4,4,5,5-tetramethyl-1,3,2-dioxaborolan-2-yl)benzamido)methyl) phosphonate |
| 248 | (R)-dimethyl 2-(4-(5-((((R)-2-((R)-1-(N-(benzyloxy)formamido)propyl)heptanamido)methyl)carbamoyl)furan-2-yl)benzamido) succinate | 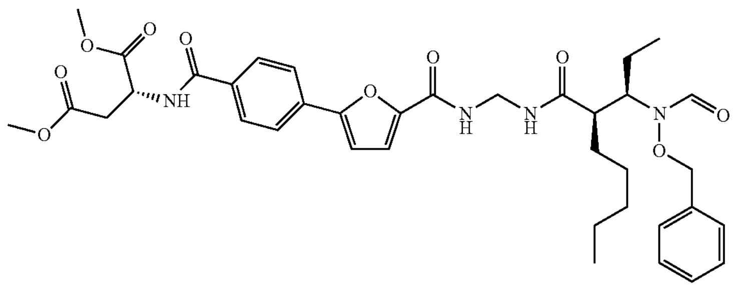 [SMILES: CCCCC[C@@H](C(=O)NCNC(=O)c1ccc(-c2ccc(C(=O)N[C@H](CC(=O)OC)C(=O)OC)cc2)o1)[C@@H](CC)N(C=O)OCc1ccccc1] | 707.3 | (R)-dimethyl 2-(4-(4,4,5,5-tetramethyl-1,3,2-dioxaborolan-2-yl)benzamido) succinate |
| 249 | (S)-dimethyl 2-(4-(5-((((R)-2-((R)-1-(N-(benzyloxy)formamido)propyl)heptanamido)methyl)carbamoyl)furan-2-yl)benzamido) pentanedioate | 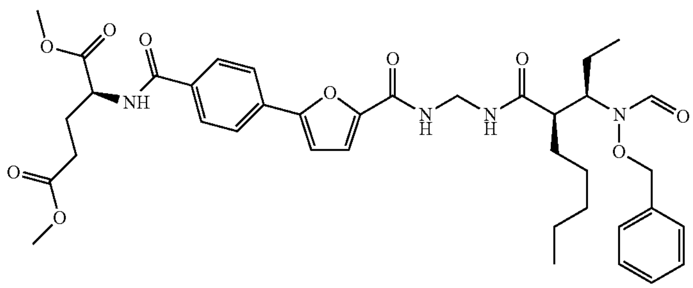 [SMILES: CCCCC[C@@H](C(=O)NCNC(=O)c1ccc(-c2ccc(C(=O)N[C@@H](CCC(=O)OC)C(=O)OC)cc2)o1)[C@@H](CC)N(C=O)OCc1ccccc1] | 721.5 | (S)-dimethyl 2-(4-(4,4,5,5-tetramethyl-1,3,2-dioxaborolan-2-yl)benzamido) pentanedioate |
| 250 | (S)-dimethyl 2-(4-(5-((((R)-2-((R)-1-(N-(benzyloxy)formamido)propyl)heptanamido)methyl)carbamoyl)furan-2-yl)-2-ethoxybenzamido) pentanedioate | 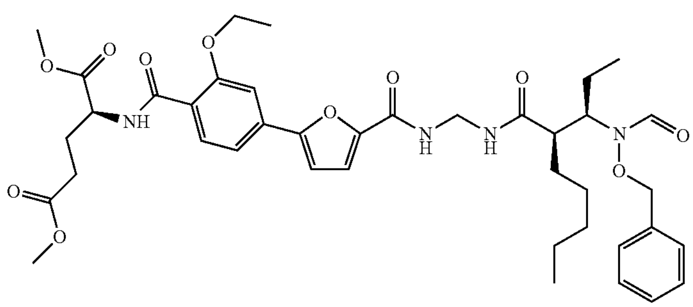 [SMILES: CCCCC[C@@H](C(=O)NCNC(=O)c1ccc(-c2ccc(C(=O)N[C@@H](CCC(=O)OC)C(=O)OC)c(OCC)c2)o1)[C@@H](CC)N(C=O)OCc1ccccc1] | 765.7 | (S)-dimethyl 2-(2-ethoxy-4-(4,4,5,5-tetramethyl-1,3,2-dioxaborolan-2-yl)benzamido) pentanedioate |
| 251 | dimethyl 2,2'-((4-(5-((((R)-2-((R)-1-(N-(benzyloxy)formamido)propyl)heptanamido)methyl)carbamoyl)furan-2-yl)benzoyl)azanediyl) diacetate | 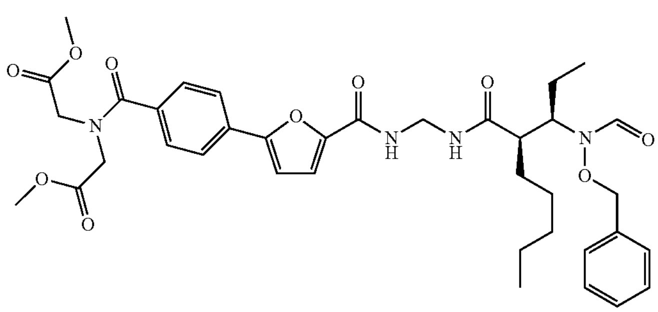 [SMILES: CCCCC[C@@H](C(=O)NCNC(=O)c1ccc(-c2ccc(C(=O)N(CC(=O)OC)CC(=O)OC)cc2)o1)[C@@H](CC)N(C=O)OCc1ccccc1] | 707.3 | (4-(bis(2-methoxy-2-oxoethyl)carbamoyl)phenyl) boronic acid |

| # | Name | Structure | MS (m/z) (M + H+) | Boronate |
|---|---|---|---|---|
| 252 | diethyl ((2-(benzyloxy)-4-(5-((((R)-2-((R)-1-(N-(benzyloxy)formamido)propyl)heptanamido)methyl)carbamoyl)furan-2-yl)benzamido)methyl)phosphonate | 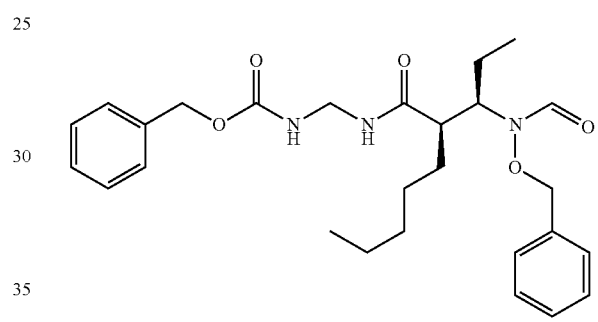 | 819.4 | diethyl ((2-(benzyloxy)-4-(4,4,5,5-tetramethyl-1,3,2-dioxaborolan-2-yl)benzamido)methyl)phosphonate |

Intermediate 253: (R)—N-(aminomethyl)-2-((R)-1-(N-hydroxyformamido)propyl)heptanamide

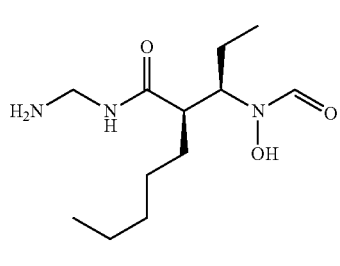 [SMILES: CCCCC[C@@H](C(=O)NCN)[C@@H](CC)N(O)C=O]

Step 1: benzyl (aminomethyl)carbamate, trifluoroacetic acid salt

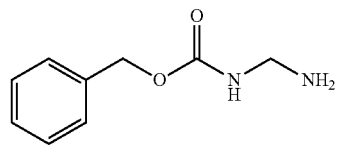 [SMILES: NCNC(=O)OCc1ccccc1]

To a 4 neck, 2-L round bottom flask under nitrogen, benzyl (2-amino-2-oxoethyl)carbamate (300 g, 1442 mmol) and DCM (8400 ml) were charged, followed by water (26 ml). To the reaction mixture, PIFA (682 g, 1586 mmol) was added and the mixture was maintained at 23° C. for 1 hour. Seeding material of product (2 wt %) was added and the reaction mixture was maintained for an additional 1 hour. The mixture was cooled to 18-20° C. for 1 hour and then the suspension was filtered and washed with 20% DCM:n-heptane (3000 ml) and then air dried to give the title compound (389 g, 91% yield) as a white solid.

Step 2: benzyl (((R)-2-((R)-1-(N-(benzyloxy)formamido)propyl)heptanamido)methyl)carbamate To a 4 neck round bottom flask (R)-2-((R)-1-(N-(benzyloxy)formamido)propyl)heptanoic acid (190 g, 592 mmol) and acetonitrile (1900 ml) were charged, followed by triethylamine (175 ml, 1256 mmol). The reaction mixture was cooled to 0-5° C. and HATU (247 g, 650 mmol) was added. The reaction mixture was warmed to 23° C. and maintained for 1 hour to form the HATU-acid adduct. In a separate round bottom flask, combined benzyl (aminomethyl)carbamate, trifluoroacetic acid salt (365 g, 1184 mmol) and acetonitrile (3800 ml) and cooled to 10-15° C. Triethylamine (963 ml, 6909 mmol) was added slowly to the reaction mixture. The prepared HATU-acid adduct mixture was then added to the benzyl (aminomethyl)carbamate solution. The combined mixture was warmed to 23° C. and maintained for 1 hour. The reaction mixture was concentrated under reduced pressure. MTBE (3420 ml) and water (2375 ml) were added to the residue and stirred for 15 minutes. The layers were separated and the organic layer was passed through 60-120 silica gel. The filtrate was concentrated under reduced pressure and the residue was diluted with MTBE (950 ml) and cooled to 0-5° C. The slurry was maintained for 1 hour and filtered to obtain title compound (170 g, 65% yield) as a white solid.

Step 3: (R)—N-(aminomethyl)-2-((R)-1-(N-hydroxyformamido)propyl)heptanamide

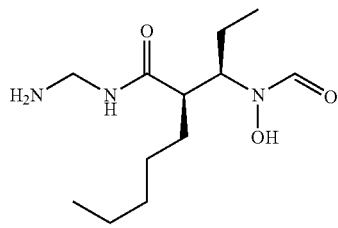

To a 5 L pressure reaction vessel, benzyl (((R)-2-((R)-1-(N-(benzyloxy)formamido)propyl)heptanamido)methyl)carbamate (180 g, 372 mmol) and ethanol (3600 ml) were charged. Palladium on carbon, 10 wt % (18 g, 16.9 mmol) was added and the reaction vessel was purged with nitrogen and degassed. The reaction mixture was pressurized with 5.0 kg/cm² hydrogen gas at 20-25° C. for 4 hours. The mixture was then filtered through celite and the celite plug was washed with ethanol (900 ml). The filtrate was concentrated under reduced pressure at 40-45° C. The crude product was slurried with n-heptane (900 ml), filtered, and dried at 35-40° C. for 6 hours to obtain the title compound (89 g, 90% yield) as a white solid.

Intermediate 254: 5-(3-(dimethoxyphosphoryl)-5-ethoxyphenyl)furan-2-carboxylic acid

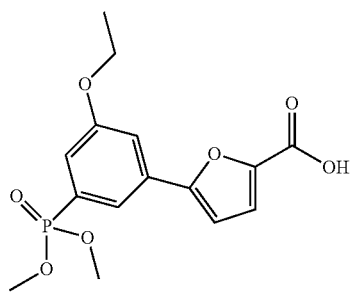 [SMILES: CCOc1cc(-c2ccc(C(=O)O)o2)cc(P(=O)(OC)OC)c1]

To a 500 ml round bottom flask was added dimethyl (3-ethoxy-5-(4,4,5,5-tetramethyl-1,3,2-dioxaborolan-2-yl)phenyl)phosphonate (5.0 g, 14.04 mmol) in toluene (35 ml) and 5-bromo-2-furoic acid (2.68 g, 14.03 mmol), followed by THF (30 ml) and water (35 ml). Sodium bicarbonate (3.5 g, 41.7 mmol) was added to the reaction mixture and the mixture was purged with nitrogen. Pd(Ph₃)₄ (0.32 g, 0.28 mmol) was added and the reaction mixture was heated to 60-70° C. for 5 hours. The reaction was cooled to 45-50° C. and concentrated under reduced vacuum. The residue was diluted with water (25 ml) and ethyl acetate (25 ml). The layers were separated and the aqueous layer was adjusted to pH 3.0-3.5 using 1N HCl. The suspension was filtered and washed with water (25 ml). The crude solid was purified by flash chromatography (100% EtOAc followed by 2-5% MeOH/DCM). The pure fractions were combined and concentrated under reduced pressure to give the title compound (5.5 g, 61%) as a brown solid.

Example 1

2-ethoxy-4-(5-((((R)-2-((R)-1-(N-hydroxyformamido)propyl)heptanamido)methyl)carbamoyl)furan-2-yl)benzoic acid

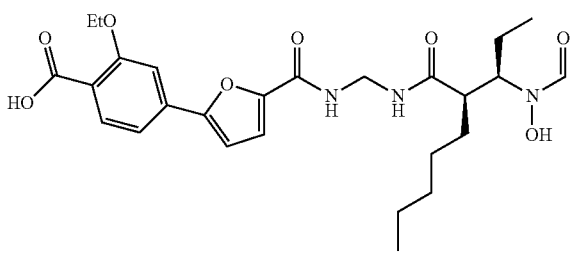 [SMILES: CCCCC[C@@H](C(=O)NCNC(=O)c1ccc(-c2ccc(C(=O)O)c(OCC)c2)o1)[C@@H](CC)N(O)C=O]

4-(5-((((R)-2-((R)-1-(N-(benzyloxy)formamido)propyl)heptanamido)methyl)carbamoyl)furan-2-yl)-2-ethoxybenzoic acid (285 mg, 0.47 mmol), was dissolved in ethanol and the reaction flushed with nitrogen. Pd/C (125 mg, 0.12 mmol) was then added and the reaction placed under hydrogen atmosphere (balloon) and stirred for 5.5 hours. The reaction was then filtered through a PTFE frit and the filtrate concentrated. The residue was dissolved in methanol and purified by reverse phase HPLC (Waters, XBridge Prep-Shield RP C₁₈, 5 μM, 30×150 mm, 10-50% CH₃CN/water+ 0.1% NH₄OH over 14 minutes). Fractions containing product were combined, made slightly acidic and extracted with DCM and then EtOAc. The combined organic extracts were concentrated to give the title compound as an off white solid (115 mg, 47% yield).

Examples 2-49 were prepared from the indicated intermediate by methods analogous to those described for Example 1. For Examples 5, 16, 21, 22, 25, 26, 27, 29, 30, 33, 34, 35, 40, 47 and 48 methanol was used as the solvent instead of ethanol. For Examples 12 and 46 a mixture of methanol and ethanol was used as the solvent instead of ethanol. For Example 45 a mixture of DCM and methanol was used as the solvent instead of ethanol.

| Ex. | Name | Structure | Intermediate |
|---|---|---|---|
| 2 | (R)-N-((3-cyclopentyl-2-((N-hydroxyformamido)methyl)propanamido)methyl)-5-phenylfuran-2-carboxamide | 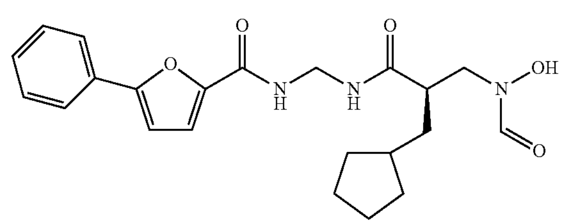 [SMILES: O=CN(O)C[C@@H](CC1CCCC1)C(=O)NCNC(=O)c1ccc(-c2ccccc2)o1] | R)-N-((3-(N-(benzyloxy)formamido)-2-(cyclopentylmethyl)propanamido)methyl)-5-phenylfuran-2-carboxamide |

-continued

| Ex. | Name | Structure | Intermediate |
|---|---|---|---|
| 3 | (R)-N-((2-((N-hydroxyformamido)methyl)-5-phenylpentanamido)methyl)-5-phenylfuran-2-carboxamide | 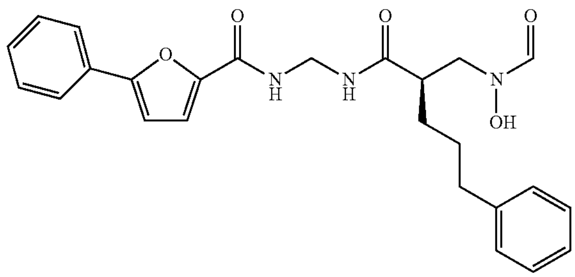 [SMILES: O=CN(O)C[C@@H](CCCc1ccccc1)C(=O)NCNC(=O)c1ccc(-c2ccccc2)o1] | (R)-N-((2-((N-(benzyloxy)formamido)methyl)-5-phenylpentanamido)methyl)-5-phenylfuran-2-carboxamide |
| 4 | (R)-N-((2-((N-hydroxyformamido)methyl)-4-phenylbutanamido)methyl)-5-phenylfuran-2-carboxamide | 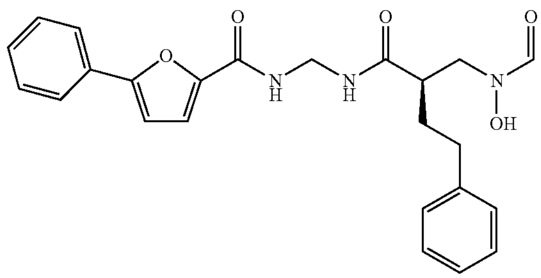 [SMILES: O=CN(O)C[C@@H](CCc1ccccc1)C(=O)NCNC(=O)c1ccc(-c2ccccc2)o1] | (R)-N-((2-((N-(benzyloxy)formamido)methyl)-4-phenylbutanamido)methyl)-5-phenylfuran-2-carboxamide |
| 5 | (R)-N-((2-((N-hydroxyformamido)methyl)heptanamido)methyl)-5-phenylfuran-2-carboxamide | 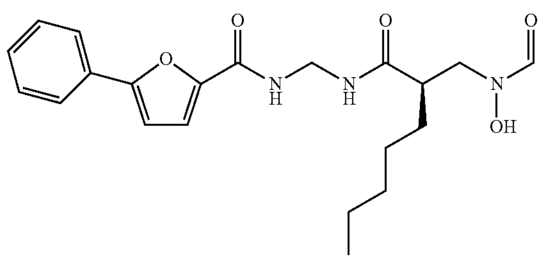 [SMILES: CCCCC[C@H](CN(O)C=O)C(=O)NCNC(=O)c1ccc(-c2ccccc2)o1] | (R)-N-((2-((N-(benzyloxy)formamido)methyl)heptanamido)methyl)-5-phenylfuran-2-carboxamide |
| 6 | (R)-N-((2-((N-hydroxyformamido)methyl)heptanamido)methyl)-5-(2-methoxyphenyl)furan-2-carboxamide | 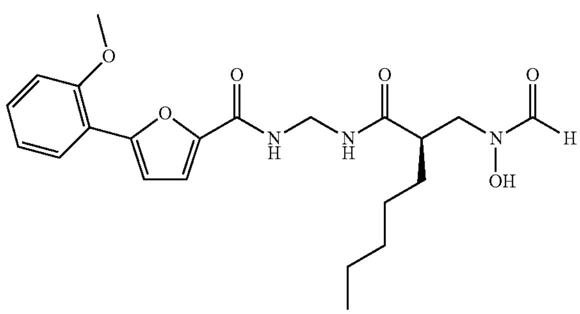 [SMILES: CCCCC[C@H](CN(O)C=O)C(=O)NCNC(=O)c1ccc(-c2ccccc2OC)o1] | (R)-N-((2-((N-(benzyloxy)formamido)methyl)heptanamido)methyl)-5-(2-methoxyphenyl)furan-2-carboxamide |
| 7 | (R)-N-((2-((N-hydroxyformamido)methyl)heptanamido)methyl)-5-(3-methoxyphenyl)furan-2-carboxamide | 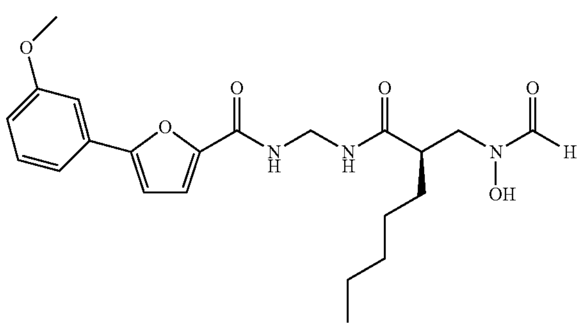 [SMILES: CCCCC[C@H](CN(O)C=O)C(=O)NCNC(=O)c1ccc(-c2cccc(OC)c2)o1] | (R)-N-((2-((N-(benzyloxy)formamido)methyl)heptanamido)methyl)-5-(3-methoxyphenyl)furan-2-carboxamide |

-continued

| Ex. | Name | Structure | Intermediate |
|---|---|---|---|
| 8 | (R)-5-(3-cyanophenyl)-N-((2-((N-hydroxyformamido)methyl)heptanamido)methyl)furan-2-carboxamide | 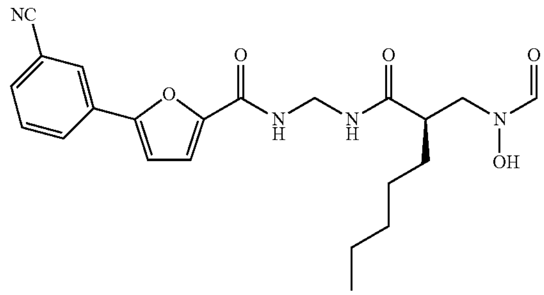 [SMILES: CCCCC[C@H](CN(O)C=O)C(=O)NCNC(=O)c1ccc(-c2cccc(C#N)c2)o1] | (R)-N-((2-((N-(benzyloxy)formamido)methyl)heptanamido)methyl)-5-(3-cyanophenyl)furan-2-carboxamide |
| 9 | (R)-N-((2-((N-hydroxyformamido)methyl)heptanamido)methyl)-5-(2-hydroxyphenyl)furan-2-carboxamide | 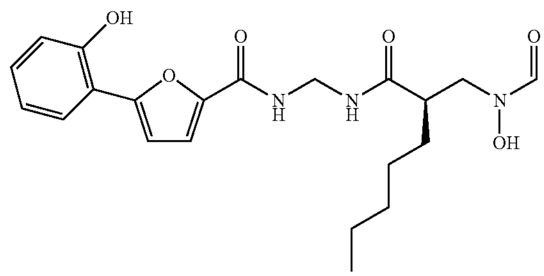 [SMILES: CCCCC[C@H](CN(O)C=O)C(=O)NCNC(=O)c1ccc(-c2ccccc2O)o1] | (R)-N-((2-((N-(benzyloxy)formamido)methyl)heptanamido)methyl)-5-(2-hydroxyphenyl)furan-2-carboxamide |
| 10 | (R)-N-((2-((N-hydroxyformamido)methyl)heptanamido)methyl)-5-(5-methoxypyridin-3-yl)furan-2-carboxamide | 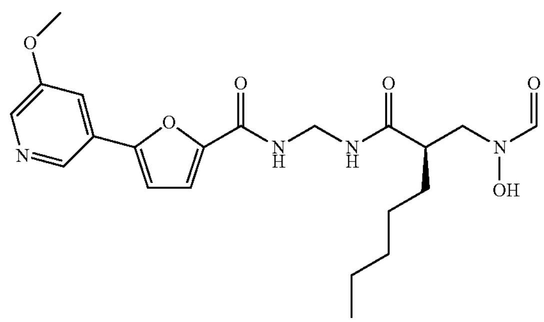 [SMILES: CCCCC[C@H](CN(O)C=O)C(=O)NCNC(=O)c1ccc(-c2cncc(OC)c2)o1] | (R)-N-((2-((N-(benzyloxy)formamido)methyl)heptanamido)methyl)-5-(5-methoxypyridin-3-yl)furan-2-carboxamide |
| 11 | (R)-5-(4-cyanophenyl)-N-((2-((N-hydroxyformamido)methyl)heptanamido)methyl)furan-2-carboxamide | 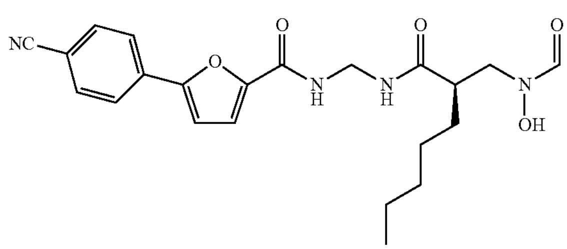 [SMILES: CCCCC[C@H](CN(O)C=O)C(=O)NCNC(=O)c1ccc(-c2ccc(C#N)cc2)o1] | (R)-N-((2-((N-(benzyloxy)formamido)methyl)heptanamido)methyl)-5-(4-cyanophenyl)furan-2-carboxamide |
| 12 | (R)-N-((2-((N-hydroxyformamido)methyl)heptanamido)methyl)-5-(3-sulfamoylphenyl)furan-2-carboxamide | 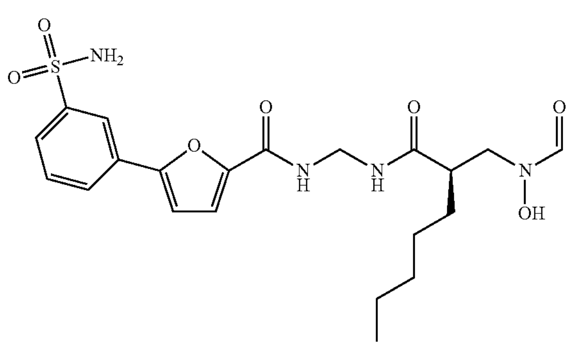 [SMILES: CCCCC[C@H](CN(O)C=O)C(=O)NCNC(=O)c1ccc(-c2cccc(S(N)(=O)=O)c2)o1] | (R)-N-((2-((N-(benzyloxy)formamido)methyl)heptanamido)methyl)-5-(3-sulfamoylphenyl)furan-2-carboxamide |

-continued

| Ex. | Name | Structure | Intermediate |
|---|---|---|---|
| 13 | (R)-N-((2-((N-hydroxyformamido)methyl)heptanamido)methyl)-5-(3-(trifluoromethoxy)phenyl)furan-2-carboxamide | 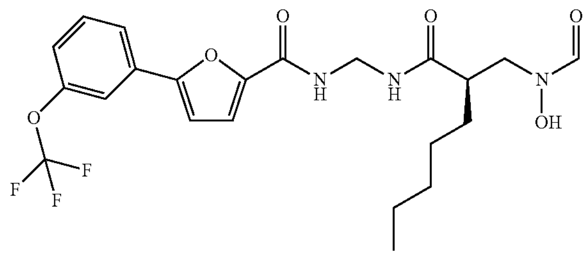 [SMILES: CCCCC[C@H](CN(O)C=O)C(=O)NCNC(=O)c1ccc(-c2cccc(OC(F)(F)F)c2)o1] | (R)-N-((2-((N-(benzyloxy)formamido)methyl)heptanamido)methyl)-5-(3-(trifluoromethoxy)phenyl)furan-2- |
| 14 | (R)-5-(3-ethoxyphenyl)-N-((2-((N-hydroxyformamido)methyl)heptanamido)methyl)furan-2-carboxamide | 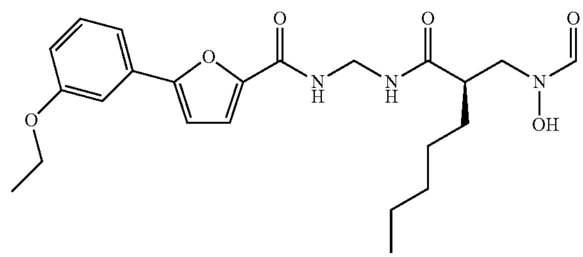 [SMILES: CCCCC[C@H](CN(O)C=O)C(=O)NCNC(=O)c1ccc(-c2cccc(OCC)c2)o1] | (R)-N-((2-((N-(benzyloxy)formamido)methyl)heptanamido)methyl)-5-(3-ethoxyphenyl)furan-2-carboxamide |
| 15 | (R)-N-((2-((N-hydroxyformamido)methyl)heptanamido)methyl)-5-(6-methoxypyridin-2-yl)furan-2-carboxamide | 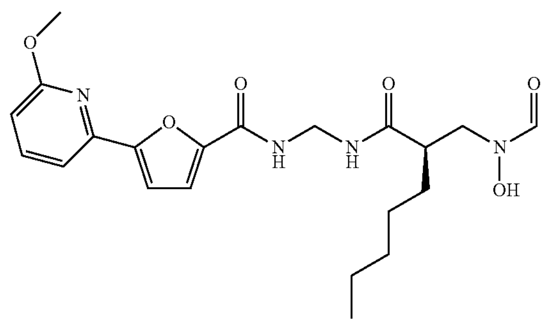 [SMILES: CCCCC[C@H](CN(O)C=O)C(=O)NCNC(=O)c1ccc(-c2cccc(OC)n2)o1] | (R)-N-((2-((N-(benzyloxy)formamido)methyl)heptanamido)methyl)-5-(6-methoxypyridin-2-yl)furan-2-carboxamide |
| 16 | (R)-methyl 3-(5-(((2-((N-hydroxyformamido)methyl)heptanamido)methyl)carbamoyl)furan-2-yl)benzoate | 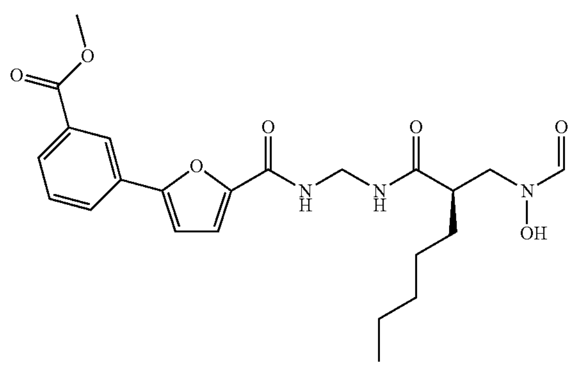 [SMILES: CCCCC[C@H](CN(O)C=O)C(=O)NCNC(=O)c1ccc(-c2cccc(C(=O)OC)c2)o1] | (R)-methyl 3-(5-(((2-((N-(benzyloxy)formamido)methyl)heptanamido)methyl)carbamoyl)furan-2-yl)benzoate |
| 17 | (R)-5-(4-fluoro-3-methoxyphenyl)-N-((2-((N-hydroxyformamido)methyl)heptanamido)methyl)furan-2-carboxamide | 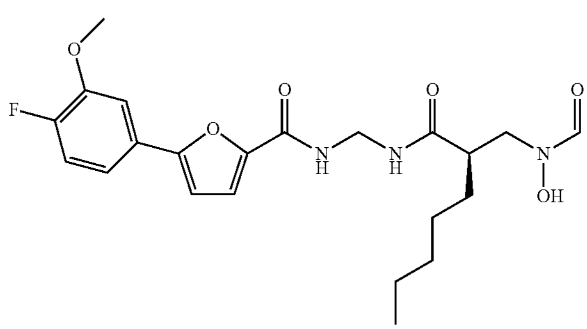 [SMILES: CCCCC[C@H](CN(O)C=O)C(=O)NCNC(=O)c1ccc(-c2ccc(F)c(OC)c2)o1] | (R)-N-((2-((N-(benzyloxy)formamido)methyl)heptanamido)methyl)-5-(4-fluoro-3-methoxyphenyl)furan-2-carboxamide |

| Ex. | Name | Structure | Intermediate |
|---|---|---|---|
| 18 | (R)-N-((2-((N-hydroxyformamido)methyl)heptanamido)methyl)-5-(4-methoxypyridin-2-yl)furan-2-carboxamide | 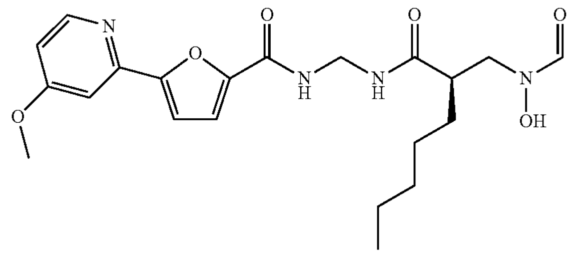 [SMILES: CCCCC[C@H](CN(O)C=O)C(=O)NCNC(=O)c1ccc(-c2cc(OC)ccn2)o1] | (R)-N-((2-((N-(benzyloxy)formamido)methyl)heptanamido)methyl)-5-(4-methoxypyridin-2-yl)furan-2-carboxamide |
| 19 | (R)-N-((2-((N-hydroxyformamido)methyl)heptanamido)methyl)-5-(3-(methylcarbamoyl)phenyl)furan-2-carboxamide | 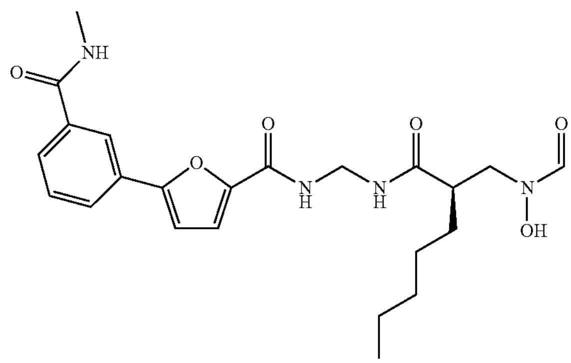 [SMILES: CCCCC[C@H](CN(O)C=O)C(=O)NCNC(=O)c1ccc(-c2cccc(C(=O)NC)c2)o1] | (R)-N-((2-((N-(benzyloxy)formamido)methyl)heptanamido)methyl)-5-(3-(methylcarbamoyl)phenyl)furan-2-carboxamide |
| 20 | (R)-N-((2-((N-hydroxyformamido)methyl)-4-phenylbutanamido)methyl)-5-(3-(methylsulfonyl)phenyl)furan-2-carboxamide | 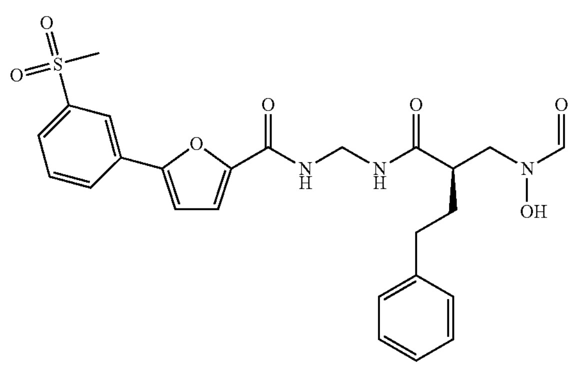 [SMILES: CS(=O)(=O)c1cccc(-c2ccc(C(=O)NCNC(=O)[C@H](CCc3ccccc3)CN(O)C=O)o2)c1] | (R)-N-((2-((N-(benzyloxy)formamido)methyl)-4-phenylbutanamido)methyl)-5-(3-(methylsulfonyl)phenyl)furan-2-carboxamide |
| 21 | (R)-5-(3-(N,N-dimethylsulfamoyl)phenyl)-N-((2-((N-hydroxyformamido)methyl)heptanamido)methyl)furan-2-carboxamide | 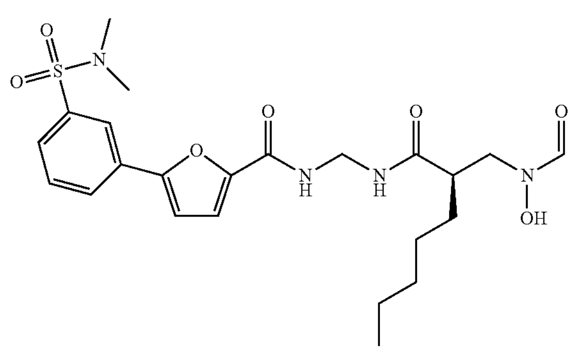 [SMILES: CCCCC[C@H](CN(O)C=O)C(=O)NCNC(=O)c1ccc(-c2cccc(S(=O)(=O)N(C)C)c2)o1] | (R)-N-((2-((N-(benzyloxy)formamido)methyl)heptanamido)methyl)-5-(3-(N,N-dimethylsulfamoyl)phenyl)furan-2-carboxamide |

-continued

| Ex. | Name | Structure | Intermediate |
|---|---|---|---|
| 22 | (R)-N-((2-((N-hydroxyformamido)methyl)heptanamido)methyl)-5-(3-(N-methylsulfamoyl)phenyl)furan-2-carboxamide | 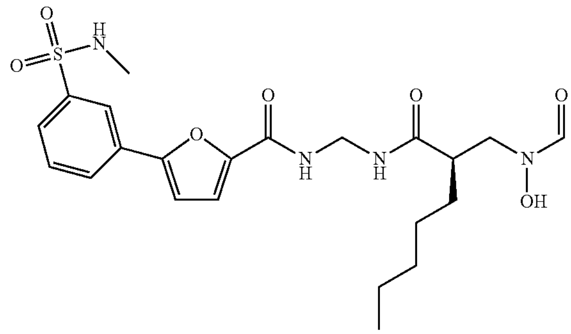 [SMILES: CCCCC[C@H](CN(O)C=O)C(=O)NCNC(=O)c1ccc(-c2cccc(S(=O)(=O)NC)c2)o1] | (R)-N-((2-((N-(benzyloxy)formamido)methyl)heptanamido)methyl)-5-(3-(N-methylsulfamoyl)phenyl)furan-2-carboxamide |
| 23 | (R)-N-((2-((N-hydroxyformamido)methyl)heptanamido)methyl)-5-(3-(2,2,2-trifluoroethoxy)phenyl)furan-2-carboxamide | 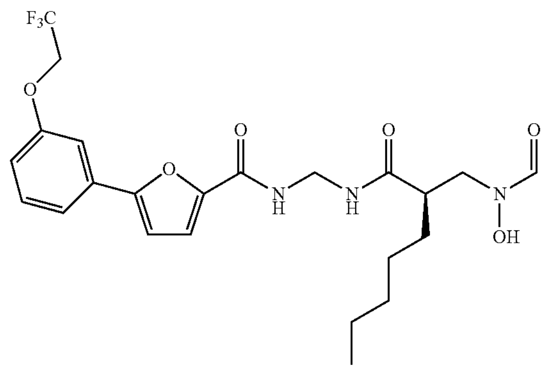 [SMILES: CCCCC[C@H](CN(O)C=O)C(=O)NCNC(=O)c1ccc(-c2cccc(OCC(F)(F)F)c2)o1] | (R)-N-((2-((N-(benzyloxy)formamido)methyl)heptanamido)methyl)-5-(3-(2,2,2-trifluoroethoxy)phenyl)furan-2-carboxamide |
| 24 | N-(((R)-2-((R)-1-(N-hydroxyformamido)propyl)heptanamido)methyl)-5-phenylfuran-2-carboxamide | 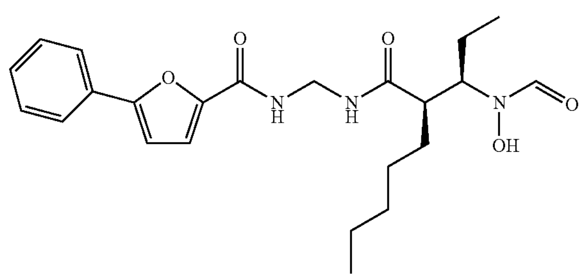 [SMILES: CCCCC[C@@H](C(=O)NCNC(=O)c1ccc(-c2ccccc2)o1)[C@@H](CC)N(O)C=O] | N-(((R)-2-((R)-1-(N-(benzyloxy)formamido)propyl)heptanamido)methyl)-5-phenylfuran-2-carboxamide |
| 25 | (R)-N-((2-((N-hydroxyformamido)methyl)heptanamido)methyl)-5-(3-isopropoxyphenyl)furan-2-carboxamide | 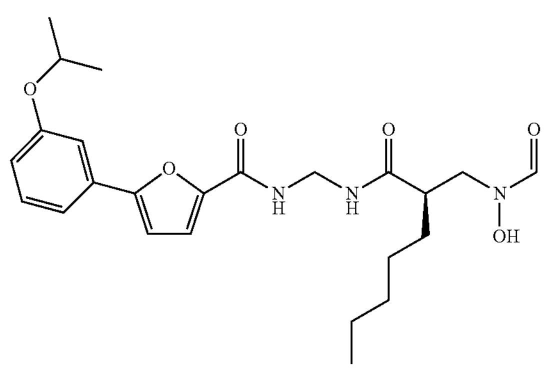 [SMILES: CCCCC[C@H](CN(O)C=O)C(=O)NCNC(=O)c1ccc(-c2cccc(OC(C)C)c2)o1] | (R)-N-((2-((N-(benzyloxy)formamido)methyl)heptanamido)methyl)-5-(3-isopropoxyphenyl)furan-2-carboxamide |

-continued

| Ex. | Name | Structure | Intermediate |
|---|---|---|---|
| 26 | (R)-methyl 3-(5-(((2-(5-(((2-((N-hydroxyformamido)methyl)heptanamido)methyl)carbamoyl)furan-2-yl)benzoate | 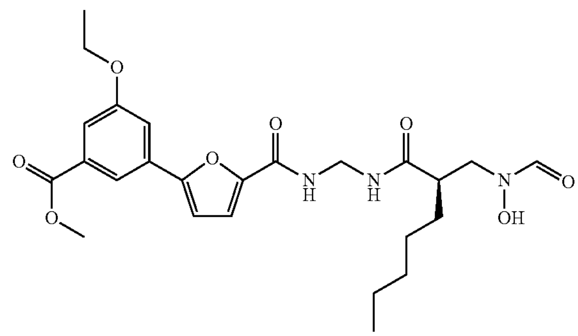 [SMILES: CCCCC[C@H](CN(O)C=O)C(=O)NCNC(=O)c1ccc(-c2cc(OCC)cc(C(=O)OC)c2)o1] | (R)-methyl 3-ethoxy-5-(((2-((N-(benzyloxy)formamido)methyl)heptanamido)methyl)carbamoyl)furan-2-yl)-5-ethoxybenzoate |
| 27 | (R)-5-(3-(dimethylamino)phenyl)-N-((2-((N-hydroxyformamido)methyl)heptanamido)methyl)furan-2-carboxamide | 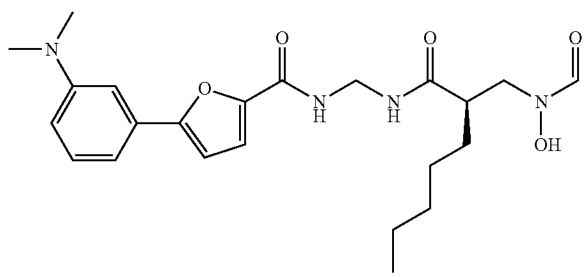 [SMILES: CCCCC[C@H](CN(O)C=O)C(=O)NCNC(=O)c1ccc(-c2cccc(N(C)C)c2)o1] | (R)-N-((2-((N-(benzyloxy)formamido)methyl)heptanamido)methyl)-5-(3-(dimethylamino)phenyl)furan-2-carboxamide |
| 28 | (R)-N-((2-((N-hydroxyformamido)methyl)heptanamido)methyl)-5-(3-(N-propionylsulfamoyl)phenyl)furan-2-carboxamide | 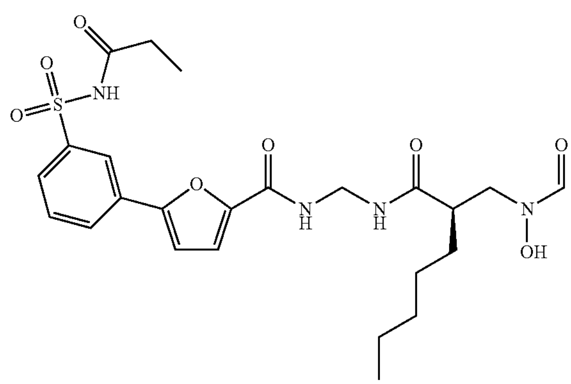 [SMILES: CCCCC[C@H](CN(O)C=O)C(=O)NCNC(=O)c1ccc(-c2cccc(S(=O)(=O)NC(=O)CC)c2)o1] | (R)-N-((2-((N-(benzyloxy)formamido)methyl)heptanamido)methyl)-5-(3-(N-propionylsulfamoyl)phenyl)furan-2-carboxamide |
| 29 | (R)-3-(5-(((2-((N-hydroxyformamido)methyl)heptanamido)methyl)carbamoyl)furan-2-yl)-5-methoxybenzoic acid | 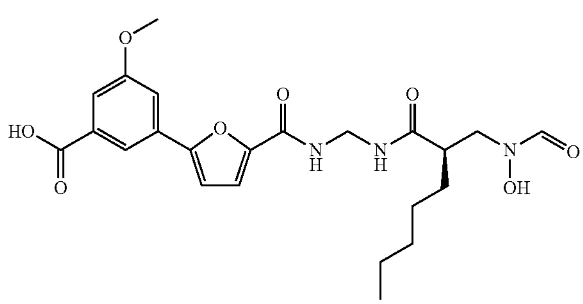 [SMILES: CCCCC[C@H](CN(O)C=O)C(=O)NCNC(=O)c1ccc(-c2cc(OC)cc(C(=O)O)c2)o1] | (R)-3-(5-(((2-((N-(benzyloxy)formamido)methyl)heptanamido)methyl)carbamoyl)furan-2-yl)-5-methoxybenzoic acid |

-continued

| Ex. | Name | Structure | Intermediate |
|---|---|---|---|
| 30 | (R)-3-ethoxy-5-(5-(((2-((N-hydroxyformamido)methyl)heptanamido)methyl)carbamoyl)furan-2-yl)benzoic acid | 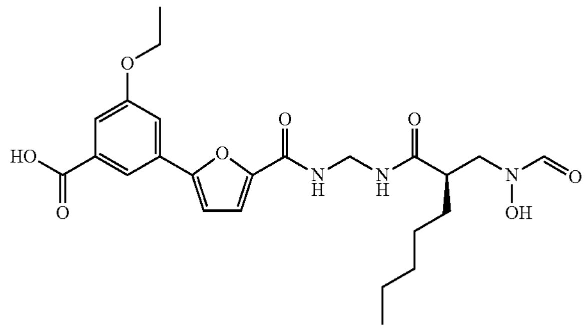 [SMILES: CCCCC[C@H](CN(O)C=O)C(=O)NCNC(=O)c1ccc(-c2cc(OCC)cc(C(=O)O)c2)o1] | (R)-3-(5-(((2-((N-(benzyloxy)formamido)methyl)heptanamido)methyl)carbamoyl)furan-2-yl)-5-ethoxybenzoic acid |
| 31 | ethyl (3-(5-((((R)-2-((N-hydroxyformamido)methyl)heptanamido)methyl)carbamoyl)furan-2-yl)phenyl)(methyl)phosphinate | 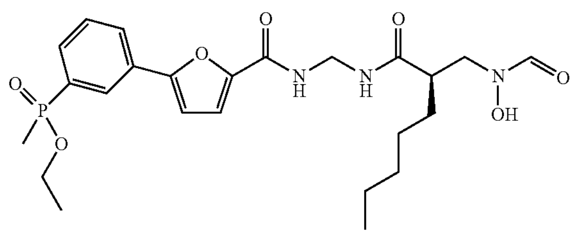 [SMILES: CCCCC[C@H](CN(O)C=O)C(=O)NCNC(=O)c1ccc(-c2cccc(P(C)(=O)OCC)c2)o1] | ethyl (3-(5-((((R)-2-((N-hydroxyformamido)methyl)heptanamido)methyl)carbamoyl)furan-2-yl)phenyl)(methyl)phosphinate |
| 32 | N-(((R)-2-((S)-2-hydroxy-1-(N-hydroxyformamido)ethyl)heptanamido)methyl)-5-phenylfuran-2-carboxamide | 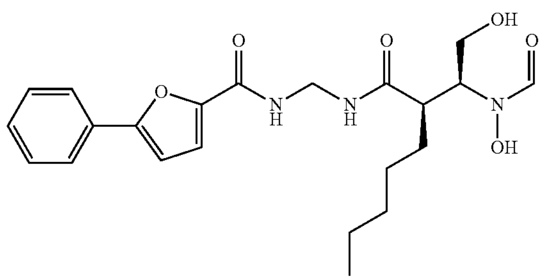 [SMILES: CCCCC[C@@H](C(=O)NCNC(=O)c1ccc(-c2ccccc2)o1)[C@@H](CO)N(O)C=O] | N-(((R)-2-((S)-2-(benzyloxy)-1-(N-(benzyloxy)formamido)ethyl)heptanamido)methyl)-5-phenylfuran-2-carboxamide |
| 33 | (R)-5-(3-((2-aminoethyl)carbamoyl)-5-methoxyphenyl)-N-((2-((N-hydroxyformamido)methyl)heptanamido)methyl)furan-2-carboxamide | 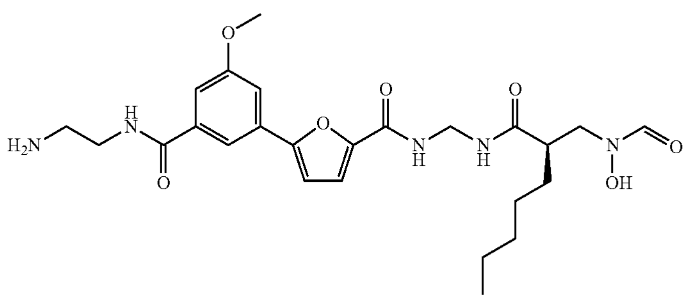 [SMILES: CCCCC[C@H](CN(O)C=O)C(=O)NCNC(=O)c1ccc(-c2cc(OC)cc(C(=O)NCCN)c2)o1] | (R)-benzyl (2-(3-(5-(((2-((N-(benzyloxy)formamido)methyl)heptanamido)methyl)carbamoyl)furan-2-yl)-5-methoxybenzamido)ethyl)carbamate |
| 34 | (R)-5-(3-((2-aminoethyl)carbamoyl)-5-ethoxyphenyl)-N-((2-((N-hydroxyformamido)methyl)heptanamido)methyl)furan-2-carboxamide | 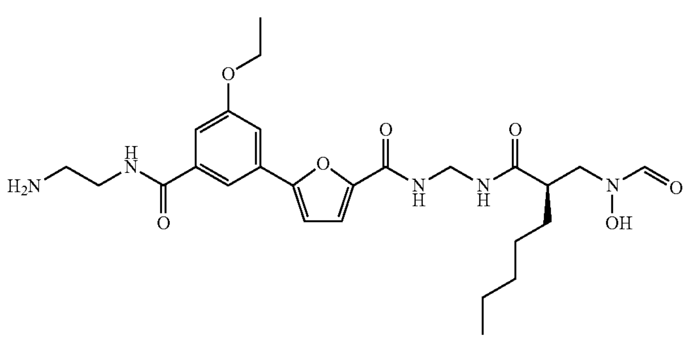 [SMILES: CCCCC[C@H](CN(O)C=O)C(=O)NCNC(=O)c1ccc(-c2cc(OCC)cc(C(=O)NCCN)c2)o1] | (R)-benzyl (2-(3-(5-(((2-((N-(benzyloxy)formamido)methyl)heptanamido)methyl)carbamoyl)furan-2-yl)-5-ethoxbenzamido)ethyl)carbamate |

-continued

| Ex. | Name | Structure | Intermediate |
|---|---|---|---|
| 35 | (R)-5-(3-(difluoromethoxy)phenyl)-N-((2-((N hydroxyformamido)methyl)heptanamido)methyl) furan-2-carboxamide | 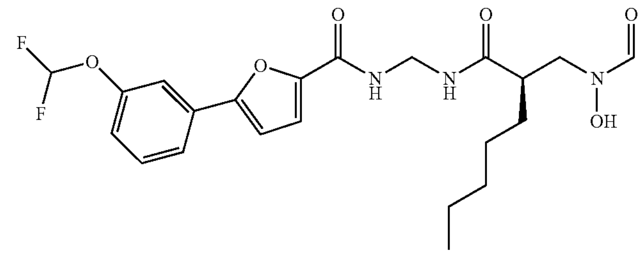 [SMILES: CCCCC[C@H](CN(O)C=O)C(=O)NCNC(=O)c1ccc(-c2cccc(OC(F)F)c2)o1] | (R)-N-((2-((N-(benzyloxy)formamido)methyl)heptanamido)methyl)-5-(3-difluoromethoxy)phenyl)furan-2-carboxamide |
| 36 | (R)-dimethyl (3-(5-(((2-((N-hydroxyformamido)methyl)heptanamido)methyl)carbamoyl)furan-2-yl)phenyl)phosphonate | 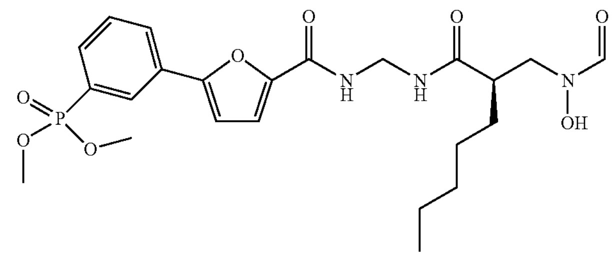 [SMILES: CCCCC[C@H](CN(O)C=O)C(=O)NCNC(=O)c1ccc(-c2cccc(P(=O)(OC)OC)c2)o1] | (R)-dimethyl (3-(5-(((2-((N-(benzyloxy)formamido)methyl)heptanamido)methyl)carbamoyl)furan-2-yl)phenyl)phosphonate |
| 37 | (R)-5-(1,1-dioxido-2,3-dihydrobenzo[d]isothiazol-6-yl)-N-((2-((N-hydroxyformamido)methyl)heptanamido)methyl)furan-2-carboxamide | 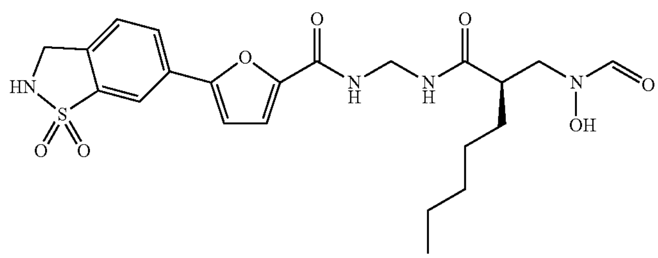 [SMILES: CCCCC[C@H](CN(O)C=O)C(=O)NCNC(=O)c1ccc(-c2ccc3c(c2)S(=O)(=O)NC3)o1] | (R)-N-((2-((N-(benzyloxy)formamido)methyl)heptanamido)methyl)-5-(1,1-dioxido-2,3-dihydrobenzo[d]isothiazol-6-yl)furan-2-carboxamide |
| 38 | R)-N-((2-((N-hydroxyformamido)methyl)heptanamido)methyl)-5-(3-(2-(pyrrolidin-1-yl)ethoxy)phenyl)furan-2-carboxamide | 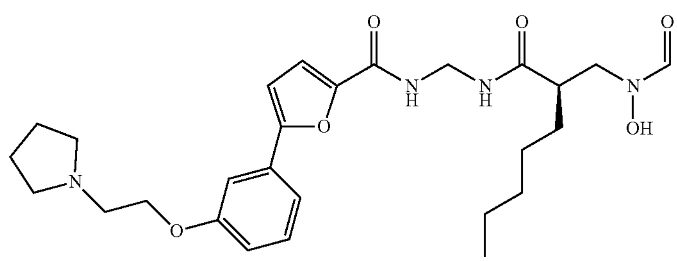 [SMILES: CCCCC[C@H](CN(O)C=O)C(=O)NCNC(=O)c1ccc(-c2cccc(OCCN3CCCC3)c2)o1] | (R)-N-((2-((N-(benzyloxy)formamido)methyl)heptanamido)methyl)-5-(3-(2-(pyrrolidin-1-yl)ethoxy)phenyl)furan-2-carboxamide |
| 39 | 3-ethoxy-5-(5-((((R)-2-((R)-1-(N-hydroxyformamido)propyl)heptanamido)methyl)carbamoyl) furan-2-yl)benzoic acid | 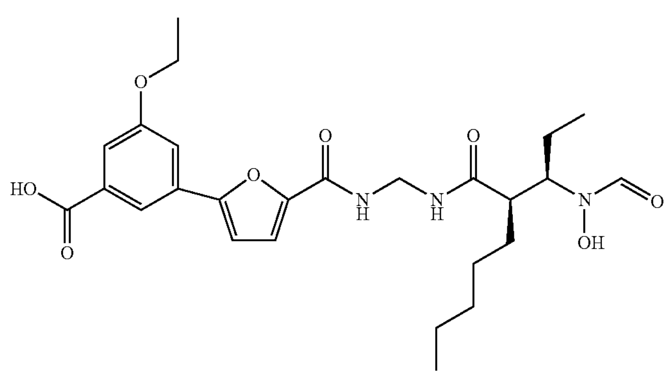 [SMILES: CCCCC[C@@H](C(=O)NCNC(=O)c1ccc(-c2cc(OCC)cc(C(=O)O)c2)o1)[C@@H](CC)N(O)C=O] | 3-(5-((((R)-2-((R)-1-(N-(benzyloxy)formamido)propyl)heptanamido)methyl)carbamoyl)furan-2-yl)-5-ethoxybenzoic acid |

-continued

| Ex. | Name | Structure | Intermediate |
|---|---|---|---|
| 40 | 5-(3-((2-aminoethyl)carbamoyl)-5-ethoxyphenyl)-N-(((R)-2-((R)-1-(N-hydroxyformamido)propyl)heptanamido)methyl)furan-2-carboxamide | 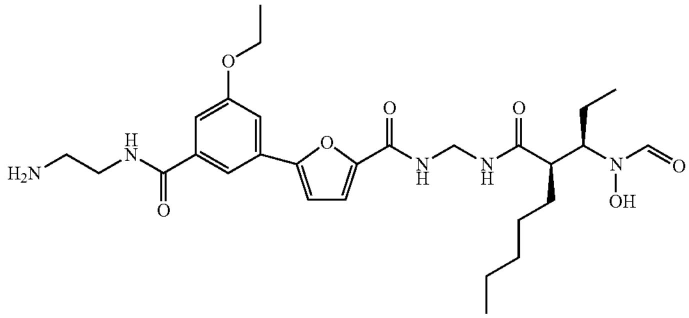 [SMILES: CCCCC[C@@H](C(=O)NCNC(=O)c1ccc(-c2cc(OCC)cc(C(=O)NCCN)c2)o1)[C@@H](CC)N(O)C=O] | benzyl (2-(3-(5-((((R)-2-((R)-1-(N-(benzyloxy)formamido)propyl)heptanamido)methyl)carbamoyl)furan-2-yl)-5-ethoxybenzamido)ethyl)carbamate |
| 41 | 2-(2-ethoxy-4-(5-((((R)-2-((R)-1-(N-hydroxyformamido)propyl)heptanamido)methyl)carbamoyl)furan-2-yl)phenyl)acetic acid | 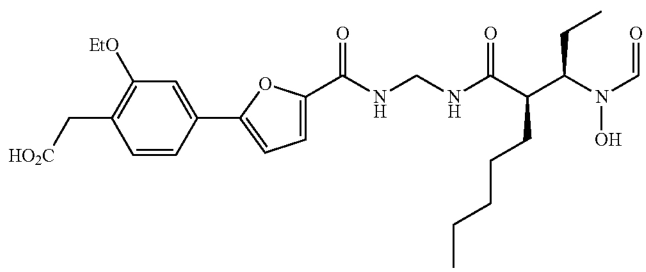 [SMILES: CCCCC[C@@H](C(=O)NCNC(=O)c1ccc(-c2ccc(CC(=O)O)c(OCC)c2)o1)[C@@H](CC)N(O)C=O] | 2-(4-(5-((((R)-2-((R)-1-(N-(benzyloxy)formamido)propyl)heptanamido)methyl)carbamoyl)furan-2-yl)-2-ethoxyphenyl)acetic acid |
| 42 | 2-(4-(5-((((R)-2-((R)-1-(N-hydroxyformamido)propyl)heptanamido)methyl)carbamoyl)furan-2-yl)phenyl)acetic acid | 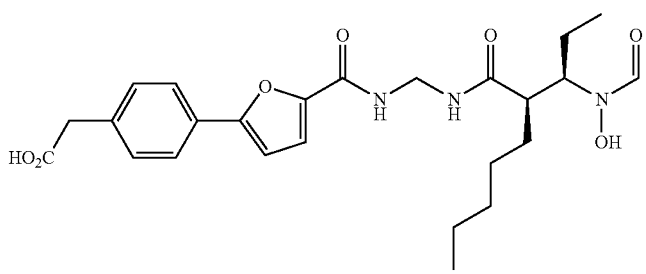 [SMILES: CCCCC[C@@H](C(=O)NCNC(=O)c1ccc(-c2ccc(CC(=O)O)cc2)o1)[C@@H](CC)N(O)C=O] | 2-(4-(5-((((R)-2-((R)-1-(N-(benzyloxy)formamido)propyl)heptanamido)methyl)carbamoyl)furan-2-yl)phenyl)acetic acid |
| 43 | 2-(4-(5-((((R)-2-((R)-1-(N-hydroxyformamido)propyl)heptanamido)methyl)carbamoyl)furan-2-yl)phenyl)-2-methylpropanoic acid | 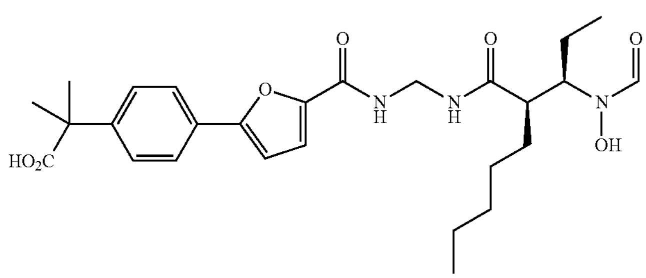 [SMILES: CCCCC[C@@H](C(=O)NCNC(=O)c1ccc(-c2ccc(C(C)(C)C(=O)O)cc2)o1)[C@@H](CC)N(O)C=O] | 2-(4-(5-((((R)-2-((R)-1-(N-(benzyloxy)formamido)propyl)heptanamido)methyl)carbamoyl)furan-2-yl)phenyl)-2-methylpropanoic acid |
| 44 | 1-(4-(5-((((R)-2-((R)-1-(N-hydroxyformamido)propyl)heptanamido)methyl)carbamoyl)furan-2-yl)phenyl)cyclopropanecarboxylic acid | 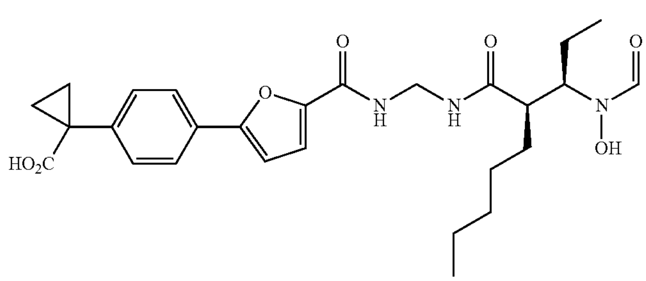 | 1-(4-(5-((((R)-2-((R)-1-(N-(benzyloxy)formamido)propyl)heptanamido)methyl)carbamoyl)furan-2-yl)phenyl)cyclopropanecarboxylic acid |

-continued

| Ex. | Name | Structure | Intermediate |
|---|---|---|---|
| 45 | (S)-5-(tert-butoxy)-4-(3-ethoxy-5-(5-((((R)-2-((R)-1-(N-hydroxyformamido)propyl)heptanamido)methyl)carbamoyl)furan-2-yl)benzamido)-5-oxopentanoic acid | 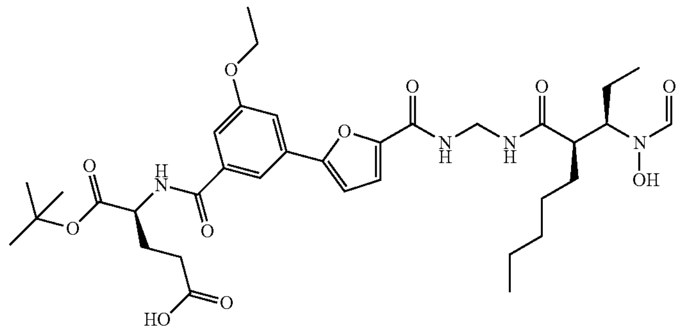 [SMILES: CCCCC[C@@H](C(=O)NCNC(=O)c1ccc(-c2cc(OCC)cc(C(=O)N[C@@H](CCC(=O)O)C(=O)OC(C)(C)C)c2)o1)[C@@H](CC)N(O)C=O] | (S)-5-benzyl 1-tert-butyl 2-(3-(5-((((R)-2-((R)-1-(N-(benzyloxy)formamido)propyl)heptanamido)methyl)carbamoyl)furan-2-yl)-5-ethoxybenzamido)pentanedioate |
| 46 | 5-(5-((((R)-2-((R)-1-(N-hydroxyformamido)propyl)heptanamido)methyl)carbamoyl)furan-2-yl)nicotinic acid | 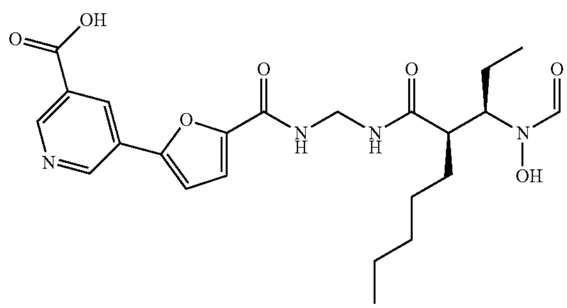 [SMILES: CCCCC[C@@H](C(=O)NCNC(=O)c1ccc(-c2cncc(C(=O)O)c2)o1)[C@@H](CC)N(O)C=O] | 5-(5-((((R)-2-((R)-1-(N-(benzyloxy)formamido)propyl)heptanamido)methyl)carbamoyl)furan-2-yl)nicotinic acid |
| 47 | (S)-4-(tert-butoxy)-3-(3-ethoxy-5-(5-((((R)-2-((R)-1-(N-hydroxyformamido)propyl)heptanamido)methyl)carbamoyl)furan-2-yl)benzamido)-4-oxobutanoic acid | 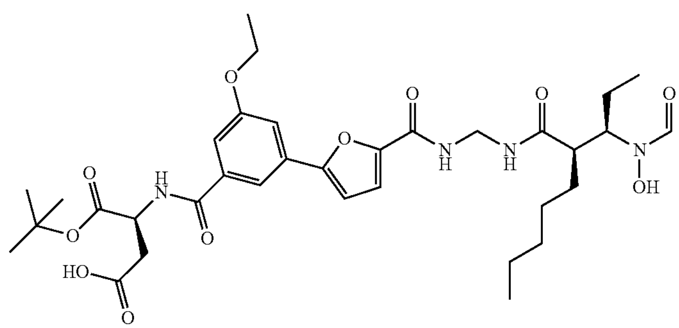 [SMILES: CCCCC[C@@H](C(=O)NCNC(=O)c1ccc(-c2cc(OCC)cc(C(=O)N[C@@H](CC(=O)O)C(=O)OC(C)(C)C)c2)o1)[C@@H](CC)N(O)C=O] | (S)-4-benzyl 1-tert-butyl 2-(3-(5-((((R)-2-((R)-1-(N-(benzyloxy)formamido)propyl)heptanamido)methyl)carbamoyl)furan-2-yl)-5-ethoxybenzamido)succinate |
| 48 | (S)-dimethyl 2-(3-ethoxy-5-(5-((((R)-2-((R)-1-(N-hydroxyformamido)propyl)heptanamido)methyl)carbamoyl)furan-2-yl)benzamido)pentanedioate | 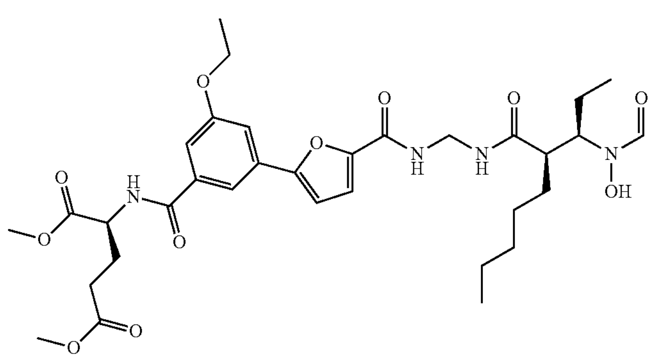 [SMILES: CCCCC[C@@H](C(=O)NCNC(=O)c1ccc(-c2cc(OCC)cc(C(=O)N[C@@H](CCC(=O)OC)C(=O)OC)c2)o1)[C@@H](CC)N(O)C=O] | (S)-dimethyl 2-(3-(5-((((R)-2-((R)-1-(N-(benzyloxy)formamido)propyl)heptanamido)methyl)carbamoyl)furan-2-yl)-5-ethoxybenzamido)pentanedioate |

| Ex. | Name | Structure | Intermediate |
|---|---|---|---|
| 49 | 2-(3-ethoxy-5-(5-((((R)-2-((R)-1-(N-hydroxyformamido)propyl)heptanamido)methyl)carbamoyl)furan-2-yl)phenyl)-2,2-difluoroacetic acid | 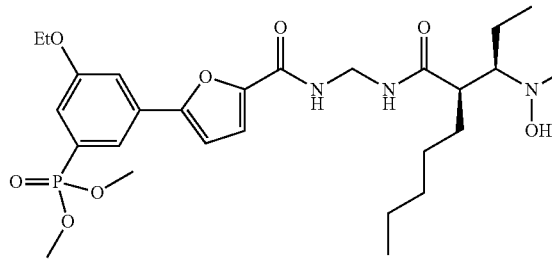 | 2-(3-(5-((((R)-2-((R)-1-(N-(benzyloxy)formamido)propyl)heptanamido)methyl)carbamoyl)furan-2-yl)-5-ethoxyphenyl)-2,2-difluoroacetic acid |

Example 50 dimethyl (3-ethoxy-5-(5-((((R)-2-((R)-1-(N-hydroxyformamido)propyl)heptanamido)methyl)carbamoyl)furan-2-yl)phenyl)phosphonate Dimethyl (3-(5-((((R)-2-((R)-1-(N-(benzyloxy)formamido)propyl)heptanamido)methyl)carbamoyl)furan-2-yl)-5-ethoxyphenyl)phosphonate (900 mg, 1.27 mmol), was dissolved in ethanol (2.5 ml) and flushed with nitrogen. Pd/C (271 mg, 0.26 mmol) was then added followed by methanol (2.5 ml) and the reaction placed under hydrogen atmosphere (balloon). The mixture was stirred at room temperature for 3.5 hours and then filtered through Celite®, washing with MeOH. The filtrate was concentrated and the residue was purified by flash chromatography (ISCO, 80 g column, 0-20% MeOH/DCM over 30 minutes) to give the title compound as an off white solid (645 mg, 87% yield).

Example 51

(R)-methyl 2-fluoro-5-(5-(((2-((N-hydroxyformamido)methyl)heptanamido)methyl)carbamoyl)furan-2-yl)benzoate Dichloromethane (0.25 ml) was added to a nitrogen purged flask containing Pd/C (8.23 mg, 7.73 μmol) followed by a solution of (R)-methyl 2-(5-(((2-((N-(benzyloxy)formamido)methyl)heptanamido)methyl)carbamoyl)furan-2-yl)benzoate (85 mg, 0.16 mmol) in methanol (2 ml) and ammonium formate (48.8 mg, 0.77 mmol). The reaction was stirred at room temperature for 4 hours then filtered through a plug of Celite® which was washed with methanol (10 ml) and the filtrate collected and concentrated. The residue was purified via flash chromatography (ISCO Combiflash Rf, 25 g column, 0-15% methanol/DCM) to give the title compound (51 mg, 66% yield).

Examples 52-73 were prepared from the indicated intermediate by methods analogous to those described for Example 51. Purification methods may vary.

| Ex. | Name | Structure | Intermediate |
|---|---|---|---|
| 52 | (R)-5-(3,5-dimethoxyphenyl)-N-((2-((N-hydroxyformamido)methyl)heptanamido)methyl)furan-2-carboxamide | 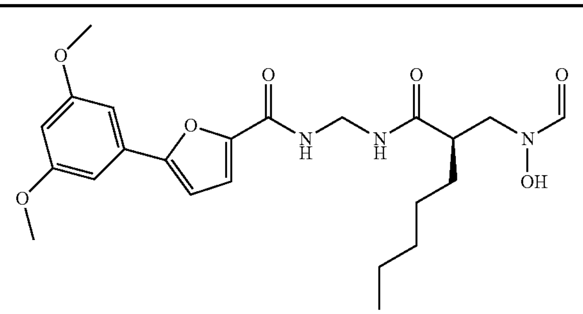 | (R)-N-((2-((N-(benzyloxy)formamido)methyl)heptanamido)methyl)-5-(3,5-dimethoxyphenyl)furan-2-carboxamide |

| Ex. | Name | Structure | Intermediate |
|---|---|---|---|
| 53 | (R)-5-(2,5-dimethoxyphenyl)-N-((2-((N-hydroxyformamido)methyl)heptanamido)methyl)furan-2-carboxamide | 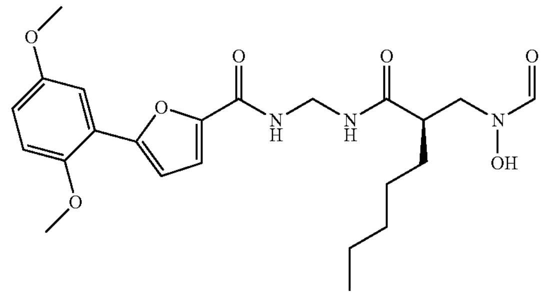 [SMILES: CCCCC[C@H](CN(O)C=O)C(=O)NCNC(=O)c1ccc(-c2cc(OC)ccc2OC)o1] | (R)-N-((2-((N-(benzyloxy)formamido)methyl)heptanamido)methyl)-5-(2,5-dimethoxyphenyl)furan-2-carboxamide |
| 54 | (R)-5-(5-(((2-((N-hydroxyformamido)methyl)heptanamido)methyl)carbamoyl)furan-2-yl)-2-methylbenzoic acid | 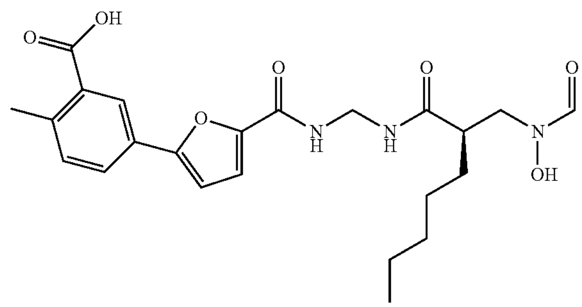 [SMILES: CCCCC[C@H](CN(O)C=O)C(=O)NCNC(=O)c1ccc(-c2ccc(C)c(C(=O)O)c2)o1] | (R)-5-(5-(((2-((N-(benzyloxy)formamido)methyl)heptanamido)methyl)carbamoyl)furan-2-yl)-2-methylbenzoic acid |
| 55 | (R)-3-(5-(((2-((N-hydroxyformamido)methyl)heptanamido)methyl)carbamoyl)furan-2-yl)-2-methoxybenzoic acid | 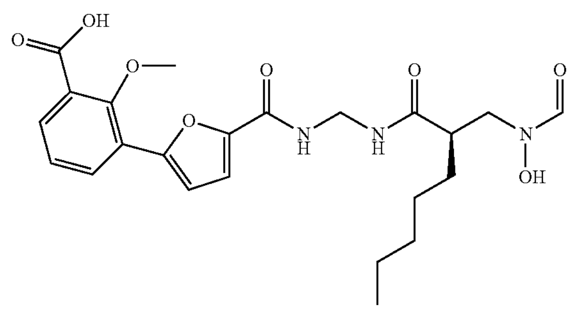 [SMILES: CCCCC[C@H](CN(O)C=O)C(=O)NCNC(=O)c1ccc(-c2cccc(C(=O)O)c2OC)o1] | (R)-3-(5-(((2-((N-(benzyloxy)formamido)methyl)heptanamido)methyl)carbamoyl)furan-2-yl)-2-methoxybenzoic acid |
| 56 | (R)-5-(5-(((2-((N-hydroxyformamido)methyl)heptanamido)methyl)carbamoyl)furan-2-yl)-2-methoxybenzoic acid | 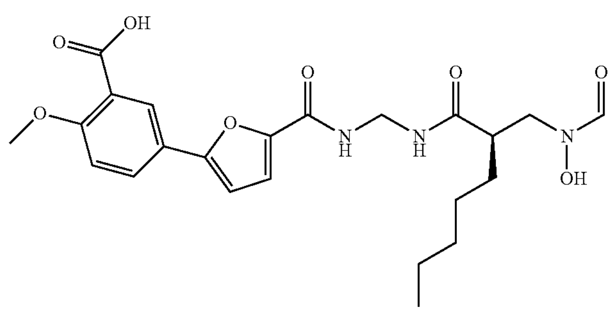 [SMILES: CCCCC[C@H](CN(O)C=O)C(=O)NCNC(=O)c1ccc(-c2ccc(OC)c(C(=O)O)c2)o1] | (R)-5-(5-(((2-((N-(benzyloxy)formamido)methyl)heptanamido)methyl)carbamoyl)furan-2-yl)-2-methoxybenzoic acid |
| 57 | (R)-methyl 2-(5-(((2-((N-hydroxyformamido)methyl)heptanamido)methyl)carbamoyl)furan-2-yl)benzoate | 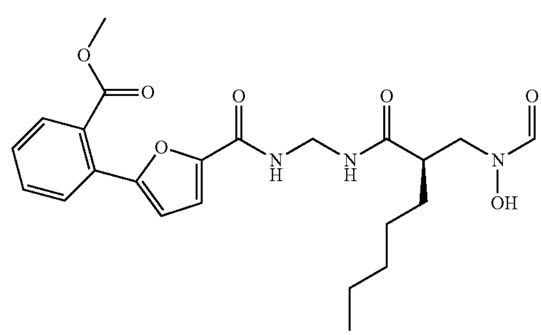 [SMILES: CCCCC[C@H](CN(O)C=O)C(=O)NCNC(=O)c1ccc(-c2ccccc2C(=O)OC)o1] | (R)-methyl 2-(5-(((2-((N-(benzyloxy)formamido)methyl)heptanamido)methyl)carbamoyl)furan-2-yl)benzoate |

-continued

| Ex. | Name | Structure | Intermediate |
|---|---|---|---|
| 58 | (R)-methyl 4-(5-(((2-((N-hydroxyformamido)methyl)heptanamido)methyl)carbamoyl)furan-2-yl)benzoate | 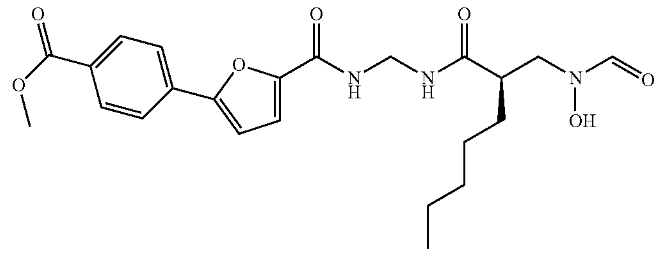 [SMILES: CCCCC[C@H](CN(O)C=O)C(=O)NCNC(=O)c1ccc(-c2ccc(C(=O)OC)cc2)o1] | (R)-methyl 4-(5-(((2-((N-(benzyloxy)formamido)methyl)heptanamido)methyl)carbamoyl)furan-2-yl)benzoate |
| 59 | (R)-2-fluoro-3-(5-(((2-((N-hydroxyformamido)methyl)heptanamido)methyl)carbamoyl)furan-2-yl)benzoic acid | 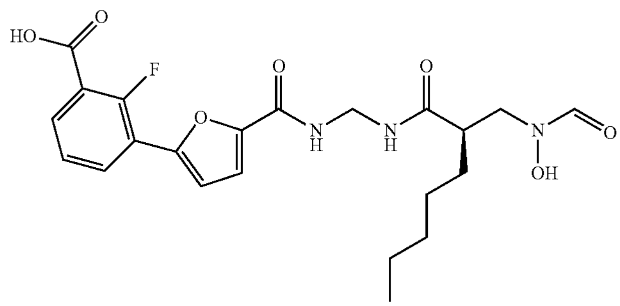 [SMILES: CCCCC[C@H](CN(O)C=O)C(=O)NCNC(=O)c1ccc(-c2cccc(C(=O)O)c2F)o1] | (R)-3-(5-(((2-((N-(benzyloxy)formamido)methyl)heptanamido)methyl)carbamoyl)furan-2-yl)-2-fluorobenzoic acid |
| 60 | (R)-2-(3-(5-(((2-((N-hydroxyformamido)methyl)heptanamido)methyl)carbamoyl)furan-2-yl)phenyl)acetic acid | 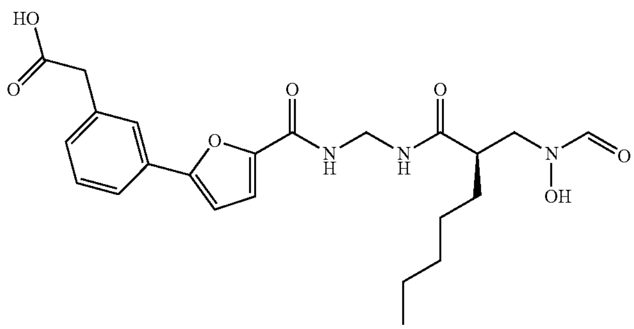 [SMILES: CCCCC[C@H](CN(O)C=O)C(=O)NCNC(=O)c1ccc(-c2cccc(CC(=O)O)c2)o1] | (R)-2-(3-(5-(((2-((N-(benzyloxy)formamido)methyl)heptanamido)methyl)carbamoyl)furan-2-yl)phenyl)acetic acid |
| 61 | (R)-3-(5-(((2-((N-hydroxyformamido)methyl)heptanamido)methyl)carbamoyl)furan-2-yl)-2-methylbenzoic acid | 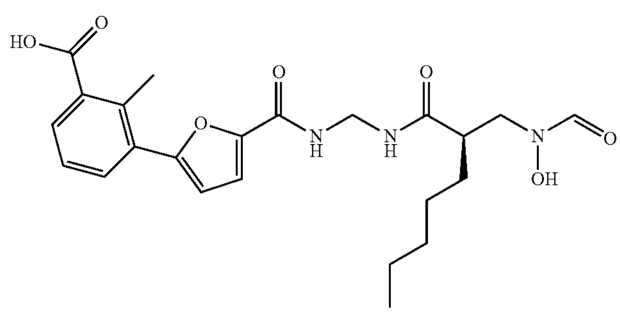 [SMILES: CCCCC[C@H](CN(O)C=O)C(=O)NCNC(=O)c1ccc(-c2cccc(C(=O)O)c2C)o1] | (R)-3-(5-(((2-((N-(benzyloxy)formamido)methyl)heptanamido)methyl)carbamoyl)furan-2-yl)-2-methylbenzoic acid |
| 62 | (R)-2-hydroxy-5-(5-(((2-((N-hydroxyformamido)methyl)heptanamido)methyl)carbamoyl)furan-2-yl)benzoic acid | 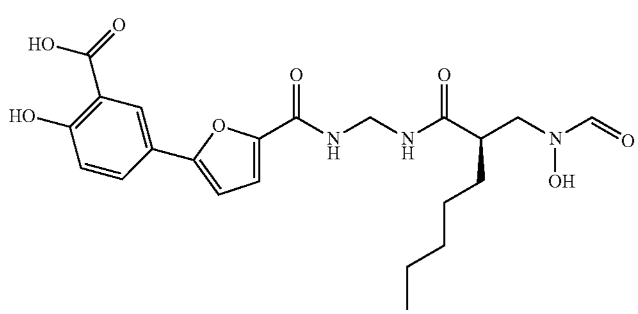 [SMILES: CCCCC[C@H](CN(O)C=O)C(=O)NCNC(=O)c1ccc(-c2ccc(O)c(C(=O)O)c2)o1] | (R)-5-(5-(((2-((N-(benzyloxy)formamido)methyl)heptanamido)methyl)carbamoyl)furan-2-yl)-2-hydroxybenzoic acid |

-continued

| Ex. | Name | Structure | Intermediate |
|---|---|---|---|
| 63 | (R)-tert-butyl 3-(5-(((2-((N-hydroxyformamido)methyl)heptanamido)methyl)carbamoyl)furan-2-yl)benzoate | 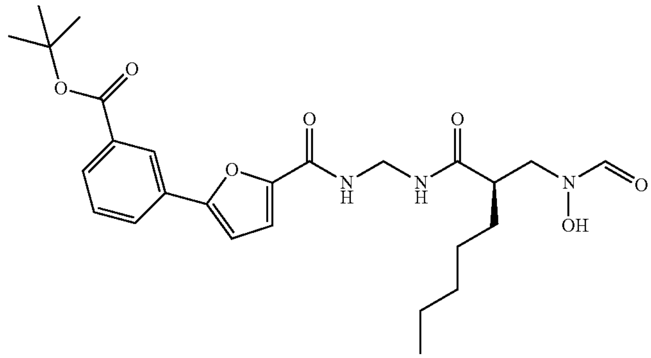 [SMILES: CCCCC[C@H](CN(O)C=O)C(=O)NCNC(=O)c1ccc(-c2cccc(C(=O)OC(C)(C)C)c2)o1] | (R)-tert-butyl 3-(5-(((2-((N-(benzyloxy)formamido)methyl)heptanamido)methyl)carbamoyl)furan-2-yl)benzoate |
| 64 | (R)-2-amino-5-(5-(((2-((N-hydroxyformamido)methyl)heptanamido)methyl)carbamoyl)furan-2-yl)benzoic acid | 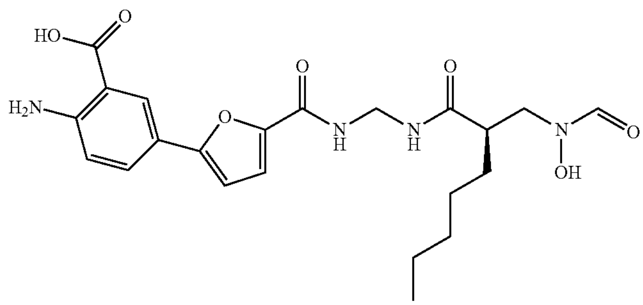 [SMILES: CCCCC[C@H](CN(O)C=O)C(=O)NCNC(=O)c1ccc(-c2ccc(N)c(C(=O)O)c2)o1] | (R)-2-amino-5-(5-(((2-((N-(benzyloxy)formamido)methyl)heptanamido)methyl)carbamoyl)furan-2-yl)benzoic acid |
| 65 | 2-(3-ethoxy-5-(5-((((R)-2-((R)-1-(N-hydroxyformamido)propyl)heptanamido)methyl)carbamoyl)furan-2-yl)benzamido)-N,N,N-trimethylethanaminium hydroxide | 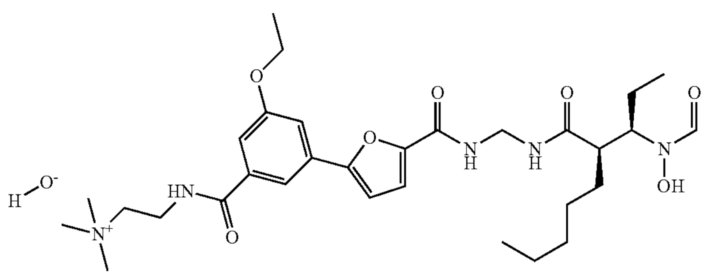 | 2-(3-(5-((((R)-2-((R)-1-(N-(benzyloxy)formamido)propyl)heptanamido)methyl)carbamoyl)furan-2-yl)-5-ethoxybenzamido)-N,N,N-trimethylethanaminium |
| 66 | 5-(5-((((R)-2-((R)-1-(N-hydroxyformamido)propyl)heptanamido)methyl)carbamoyl)furan-2-yl)-2-methoxybenzoic acid | 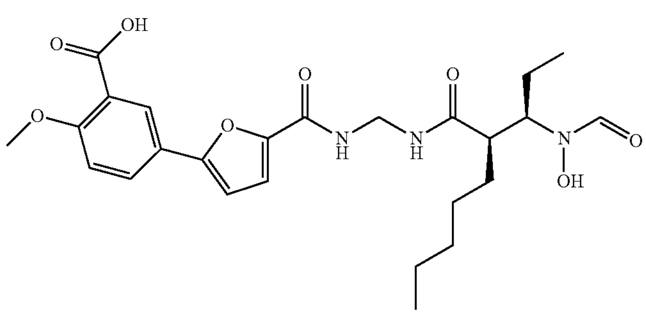 [SMILES: CCCCC[C@@H](C(=O)NCNC(=O)c1ccc(-c2ccc(OC)c(C(=O)O)c2)o1)[C@@H](CC)N(O)C=O] | 5-(5-((((R)-2-((R)-1-(N-(benzyloxy)formamido)propyl)heptanamido)methyl)carbamoyl)furan-2-yl)-2-methoxybenzoic acid |
| 67 | 2-(3-(5-((((R)-2-((R)-1-(N-hydroxyformamido)propyl)heptanamido)methyl)carbamoyl)furan-2-yl)phenyl)-2-methylpropanoic acid | 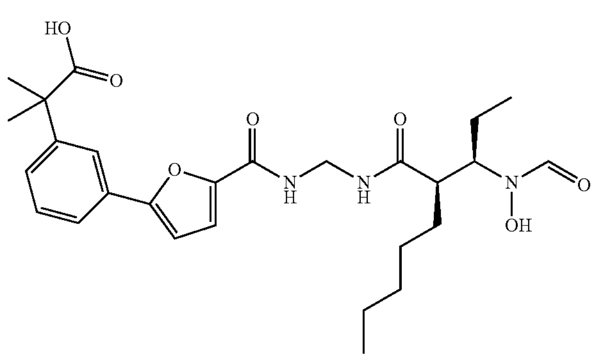 [SMILES: CCCCC[C@@H](C(=O)NCNC(=O)c1ccc(-c2cccc(C(C)(C)C(=O)O)c2)o1)[C@@H](CC)N(O)C=O] | 2-(3-(5-((((R)-2-((R)-1-(N-(benzyloxy)formamido)propyl)heptanamido)methyl)carbamoyl)furan-2-yl)phenyl)-2-methylpropanoic acid |

-continued

| Ex. | Name | Structure | Intermediate |
|---|---|---|---|
| 68 | 5-(5-((((R)-2-((R)-1-(N-hydroxyformamido)propyl)heptanamido)methyl)carbamoyl)furan-2-yl)-2-methylbenzoic acid | 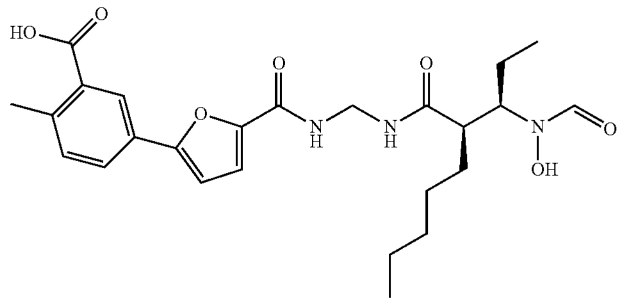 [SMILES: CCCCC[C@@H](C(=O)NCNC(=O)c1ccc(-c2ccc(C)c(C(=O)O)c2)o1)[C@@H](CC)N(O)C=O] | 5-(5-((((R)-2-((R)-1-(N-(benzyloxy)formamido)propyl)heptanamido)methyl)carbamoyl)furan-2-yl)-2-methylbenzoic acid |
| 69 | N-(((R)-2-((R)-1-(N-hydroxyformamido)propyl)heptanamido)methyl)-5-(3-propoxyphenyl)furan-2-carboxamide | 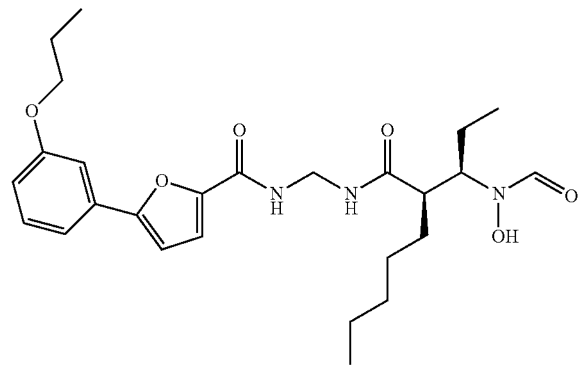 [SMILES: CCCCC[C@@H](C(=O)NCNC(=O)c1ccc(-c2cccc(OCCC)c2)o1)[C@@H](CC)N(O)C=O] | N-(((R)-2-((R)-1-(N-(benzyloxy)formamido)propyl)heptanamido)methyl)-5-(3-propoxyphenyl)furan-2-carboxamide |
| 70 | 2-(2-fluoro-5-(5-((((R)-2-((R)-1-(N-hydroxyformamido)propyl)heptanamido)methyl)carbamoyl)furan-2-yl)phenyl)acetic acid | 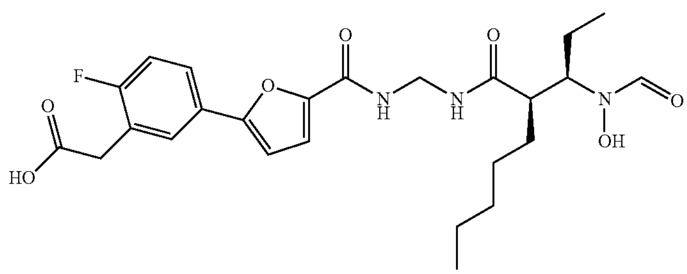 [SMILES: CCCCC[C@@H](C(=O)NCNC(=O)c1ccc(-c2ccc(F)c(CC(=O)O)c2)o1)[C@@H](CC)N(O)C=O] | 2-(5-(5-((((R)-2-((R)-1-(N-(benzyloxy)formamido)propyl)heptanamido)methyl)carbamoyl)furan-2-yl)-2-fluorophenyl)acetic acid |
| 71 | 4-(5-((((R)-2-((R)-1-(N-hydroxyformamido)propyl)heptanamido)methyl)carbamoyl)furan-2-yl)benzoic acid | 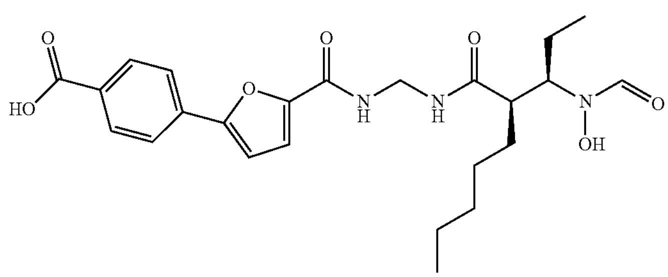 [SMILES: CCCCC[C@@H](C(=O)NCNC(=O)c1ccc(-c2ccc(C(=O)O)cc2)o1)[C@@H](CC)N(O)C=O] | 4-(5-((((R)-2-((R)-1-(N-(benzyloxy)formamido)propyl)heptanamido)methyl)carbamoyl)furan-2-yl)benzoic acid |
| 72 | 2-(3-ethoxy-5-(5-((((R)-2-((R)-1-(N-hydroxyformamido)propyl)heptanamido)methyl)carbamoyl)furan-2-yl)phenyl)acetic acid | 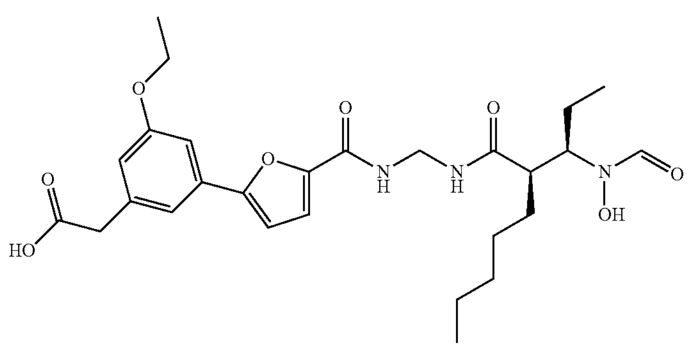 [SMILES: CCCCC[C@@H](C(=O)NCNC(=O)c1ccc(-c2cc(CC(=O)O)cc(OCC)c2)o1)[C@@H](CC)N(O)C=O] | 2-(3-(5-((((R)-2-((R)-1-(N-(benzyloxy)formamido)propyl)heptanamido)methyl)carbamoyl)furan-2-yl)-5-ethoxyphenyl)acetic acid |

| Ex. | Name | Structure | Intermediate |
|---|---|---|---|
| 73 | 5-(3-ethoxy-5-hydroxyphenyl)-N-(((R)-2-((R)-1-(N-hydroxyformamido)propyl)heptanamido)methyl)furan-2-carboxamide | 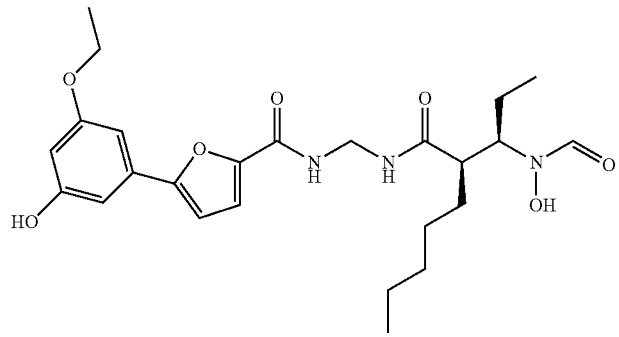 [SMILES: CCCCC[C@@H](C(=O)NCNC(=O)c1ccc(-c2cc(O)cc(OCC)c2)o1)[C@@H](CC)N(O)C=O] | N-(((R)-2-((R)-1-(N-(benzyloxy)formamido)propyl)heptanamido)methyl)-5-(3-ethoxy-5-hydroxyphenyl)furan-2-carboxamide |

Example 74

(S)-2-(2-ethoxy-4-(5-((((R)-2-((R)-1-(N-hydroxyformamido)propyl)heptanamido)methyl)carbamoyl)furan-2-yl)benzamido)succinic acid

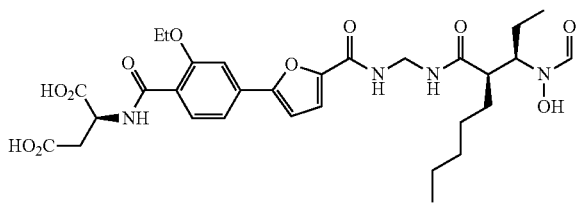 [SMILES: CCCCC[C@@H](C(=O)NCNC(=O)c1ccc(-c2ccc(C(=O)N[C@@H](CC(=O)O)C(=O)O)c(OCC)c2)o1)[C@@H](CC)N(O)C=O]

Step 1: (S)-dimethyl 2-(2-ethoxy-4-(5-((((R)-2-((R)-1-(N-hydroxyformamido)propyl)heptanamido)methyl)carbamoyl)furan-2-yl)benzamido)succinate

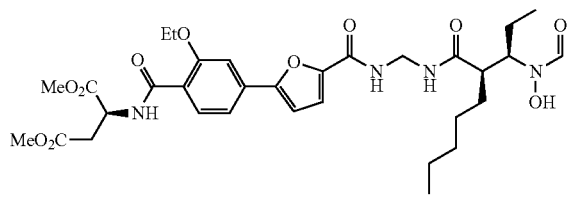 [SMILES: CCCCC[C@@H](C(=O)NCNC(=O)c1ccc(-c2ccc(C(=O)N[C@@H](CC(=O)OC)C(=O)OC)c(OCC)c2)o1)[C@@H](CC)N(O)C=O]

(S)-dimethyl 2-(4-(5-((((R)-2-((R)-1-(N-(benzyloxy)formamido)propyl)heptanamido)methyl)carbamoyl)furan-2-yl)-2-ethoxybenzamido)succinate (418 mg, 0.56 mmol), was dissolved in ethanol (20 ml) and the reaction flushed with nitrogen. Pd/C (118 mg, 0.11 mmol) was then added followed by methanol (20 ml) and the reaction placed under hydrogen atmosphere and stirred at room temperature. After 2 hours, additional Pd/C (148 mg, 0.14 mmol) was added and the mixture stirred for another 2 hours. The reaction was then filtered through a PTFE frit and the filtrate concentrated. The residue was purified by flash chromatography (ISCO Rf, 80 g column, 0-100% EtOAc/DCM over 20 minutes) to give the title compound (301 mg, 82% yield). MS (m/z) 661.3 (M+H+).

Step 2: (S)-2-(2-ethoxy-4-(5-((((R)-2-((R)-1-(N-hydroxyformamido)propyl)heptanamido)methyl)carbamoyl)furan-2-yl)benzamido)succinic acid To a 20 ml vial was added (S)-dimethyl 2-(2-ethoxy-4-(5-((((R)-2-((R)-1-(N-hydroxyformamido)propyl)heptanamido)methyl)carbamoyl)furan-2-yl)benzamido)succinate (301 mg, 0.46 mmol), methanol (6 ml) and water (2 ml) followed by LiOH (70.3 mg, 2.93 mmol). The mixture was stirred at room temperature for 4 hours. The reaction volume was then reduced to ~5 ml and then extracted with EtOAc. The aqueous was then adjusted to acidic pH via dropwise addition of 6 N HCl and extracted twice with EtOAc. The organic layer was concentrated and the resultant solid suspended in EtOAc and stirred at room temperature for 1 hour and then collected by filtration to give the title compound as a light brown/orange solid (200 mg, 70% yield).

Example 75 was prepared from (S)-dimethyl 2-(2-(4-(5-((((R)-2-((R)-1-(N-(benzyloxy)formamido)propyl)heptanamido)methyl)carbamoyl)furan-2-yl)-2-ethoxyphenyl)acetamido)succinate by methods analogous to those described for Example 74.

| Ex. | Name | Structure | Name Step 1 | MS (m/z) (M + H+) Step 1 |
|---|---|---|---|---|
| 75 | (S)-2-(2-(2-ethoxy-4-(5-((((R)-2-((R)-1-(N-hydroxyformamido)propyl)heptanamido)methyl)carbamoyl)furan-2-yl)phenyl)acetamido)succinic acid | 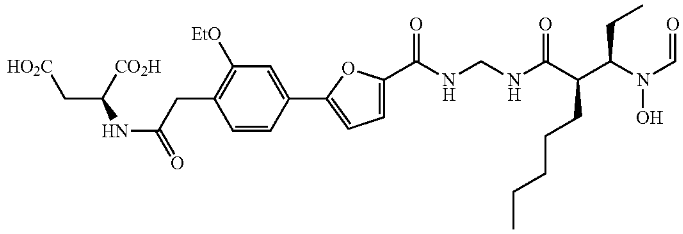 [SMILES: CCCCC[C@@H](C(=O)NCNC(=O)c1ccc(-c2ccc(CC(=O)N[C@@H](CC(=O)O)C(=O)O)c(OCC)c2)o1)[C@@H](CC)N(O)C=O] | (S)-dimethyl 2-(2-(2-ethoxy-4-(5-((((R)-2-((R)-1-(N-hydroxyformamido)propyl)heptanamido)methyl)carbamoyl)furan-2-yl)phenyl)acetamido)succinate | 675.3 |

Example 76

2-(3-(5-((((R)-2-((N-hydroxyformamido)methyl) heptanamido)methyl)carbamoyl)furan-2-yl)phenyl) propanoic acid

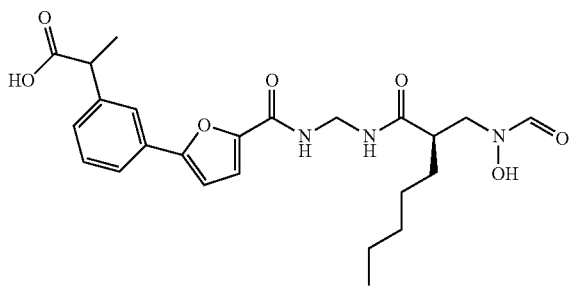 [SMILES: CCCCC[C@H](CN(O)C=O)C(=O)NCNC(=O)c1ccc(-c2cccc(C(C)C(=O)O)c2)o1]

Step 1: methyl 2-(3-(5-((((R)-2-((N-hydroxyformamido)methyl)heptanamido)methyl)carbamoyl)furan-2-yl)phenyl)propanoate

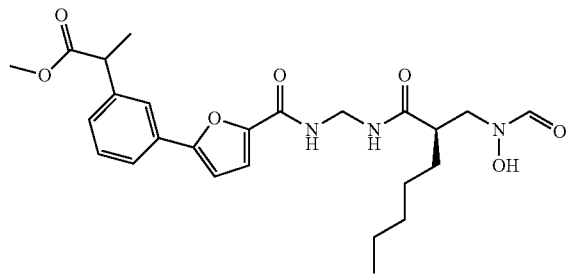 [SMILES: CCCCC[C@H](CN(O)C=O)C(=O)NCNC(=O)c1ccc(-c2cccc(C(C)C(=O)OC)c2)o1]

To a nitrogen purged vial was added Pd/C (7.53 mg, 7.08 µmol) and dichloromethane (0.25 ml). Methyl 2-(3-(5-((((R)-2-((N-(benzyloxy)formamido)methyl)heptanamido) methyl)carbamoyl)furan-2-yl)phenyl)propanoate (161 mg, 0.28 mmol) in methanol (2 ml) was added followed by ammonium formate (44.6 mg, 0.71 mmol). The reaction was stirred at room temperature for 6 hours. Additional Pd/C (7.53 mg, 7.08 µmol) and ammonium formate (44.6 mg, 0.71 mmol) were added and the reaction stirred at room temperature overnight. The reaction mixture was filtered through a plug of Celite®, which was washed with methanol (10 ml). The filtrate was concentrated and the residue was purified via flash chromatography (ISCO Combiflash Rf, 25 g column, 0-15% methanol/DCM) to give impure product which was purified via flash chromatography (ISCO Combiflash Rf, 12 g column, 0-10% methanol/DCM) to give the title compound (64 mg). MS (m/z) 488.2 (M+H$^+$).

Step 2: 2-(3-(5-((((R)-2-((N-hydroxyformamido) methyl)heptanamido)methyl)carbamoyl)furan-2-yl) phenyl)propanoic acid Methyl 2-(3-(5-((((R)-2-((N-hydroxyformamido)methyl) heptanamido)methyl)carbamoyl)furan-2-yl)phenyl)propanoate (64 mg, 0.13 mmol) and lithium hydroxide (9.43 mg, 0.39 mmol) were combined in ethanol (1 ml) and water (0.33 ml) and the reaction stirred at room temperature for 3 hours. The ethanol was removed in vacuu and the residual solution extracted with DCM. The aqueous layer was then adjusted to ~pH 3 via addition of 1 N HCl and extracted with EtOAc (2×5 ml). The organic was passed through a phase separator and concentrated. The residue was purified via flash chromatography (ISCO Combiflash Rf, 12 g column, 0-100% ethyl acetate/DCM) to give the title compound (25 mg, 36.2% yield).

Example 77 was prepared from (S)-dimethyl 2-(3-(5-((((R)-2-((R)-1-(N-(benzyloxy)formamido)propyl)heptanamido)methyl)carbamoyl)furan-2-yl)-5-ethoxybenzamido) succinate by methods analogous to those described for Example 76.

| Ex. | Name | Structure | Name Step | MS (m/z) (M + H$^+$) Step 1 |
|---|---|---|---|---|
| 77 | (S)-2-(3-ethoxy-5-(5-((((R)-2-((R)-1-(N-hydroxyformamido)propyl)heptanamido)methyl)carbamoyl)furan-2-yl)benzamido)succinic acid | 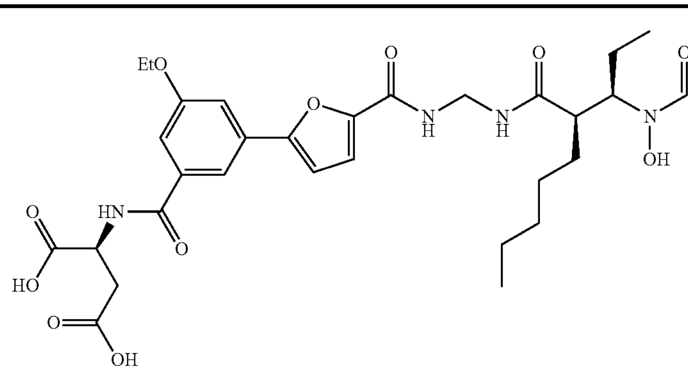 | (S)-dimethyl 2-(3-ethoxy-5-(5-((((R)-2-((R)-1-(N-hydroxyformamido)propyl)heptanamido)methyl)carbamoyl)furan-2-yl)benzamido)succinate | 661.2 |

Example 78 was prepared from (R)-methyl 3-(5-(((2-((N-(benzyloxy)formamido)methyl)heptanamido)methyl)carbamoyl)furan-2-yl)-2,6-difluorobenzoate by methods analogous to those described for Example 76.

| Ex. | Name | Structure | Name Step 1 | MS (m/z) (M + H+) Step 1 |
|---|---|---|---|---|
| 78 | R)-2,6-difluoro-3-(5-(((2-((N-hydroxyformamido)methyl)heptanamido)methyl)carbamoyl)furan-2-yl)benzoic acid | 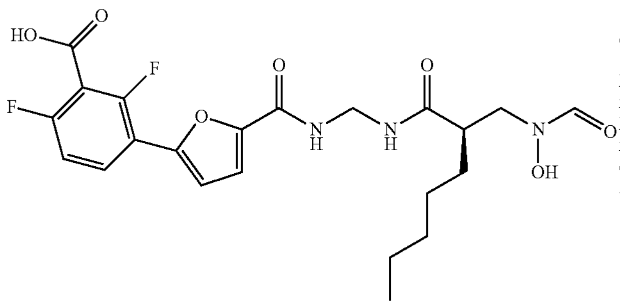 | (R)-methyl 2,6-difluoro-3-(5-(((2-((N-hydroxyformamido)methyl)heptanamido)methyl)carbamoyl)furan-2-yl)benzoate | 496.1 |

Example 79 was prepared from methyl 3-(5-(((3-(N-(benzyloxy)formamido)propanamido)methyl)carbamoyl)furan-2-yl)-5-ethoxybenzoate by methods analogous to those described for Example 76.

| Ex. | Name | Structure | Name Step 1 | MS (m/z) (M + H+) Step 1 |
|---|---|---|---|---|
| 79 | 3-ethoxy-5-(5-(((3-(N-hydroxyformamido)propanamido)methyl)carbamoyl)furan-2-yl)benzoic acid | 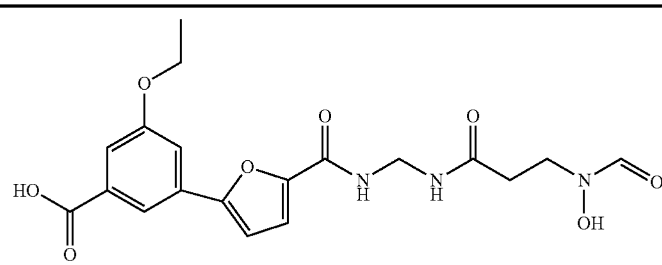 | methyl 3-ethoxy-5-(5-(((3-(N-hydroxyformamido)propanamido)methyl)carbamoyl)furan-2-yl)benzoate | 434.1 |

Example 80 was prepared from methyl 1-(3-(5-((((R)-2-((R)-1-(N-(benzyloxy)formamido)propyl)heptanamido)methyl)carbamoyl)furan-2-yl)phenyl)cyclopropanecarboxylate by methods analogous to those described for Example 76. In Step 2 a mixture of methanol and water was used as the solvent instead of a mixture of ethanol and water.

| Ex. | Name | Structure | Name Step 1 | MS (m/z) (M + H+) Step 1 |
|---|---|---|---|---|
| 80 | 1-(3-(5-((((R)-2-((R)-1-(N-hydroxyformamido)propyl)heptanamido)methyl)carbamoyl)furan-2-yl)phenyl)cyclopropanecarboxylic acid | 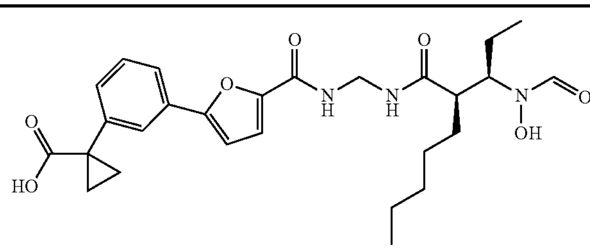 | methyl 1-(3-(5-((((R)-2-((R)-1-(N-hydroxyformamido)propyl)heptanamido)methyl)carbamoyl)furan-2-yl)phenyl)cyclopropanecarboxylate | 528.2 |

Example 81 was prepared from ethyl 3-(5-((((R)-2-((R)-1-(N-(benzyloxy)formamido)propyl)heptanamido)methyl)carbamoyl)furan-2-yl)-5-ethoxy-2-hydroxybenzoate by methods analogous to those described for Example 76. In Step 2 a mixture of methanol, THF and water was used as the solvent instead of a mixture of ethanol and water.

| Ex. | Name | Structure | Name Step 1 | MS (m/z) (M + H$^+$) Step 1 |
|---|---|---|---|---|
| 81 | 5-ethoxy-2-hydroxy-3-(5-((((R)-2-((R)-1-(N-hydroxy-formamido)propyl)heptanamido)methyl)carbamoyl)furan-2-yl)benzoic acid | 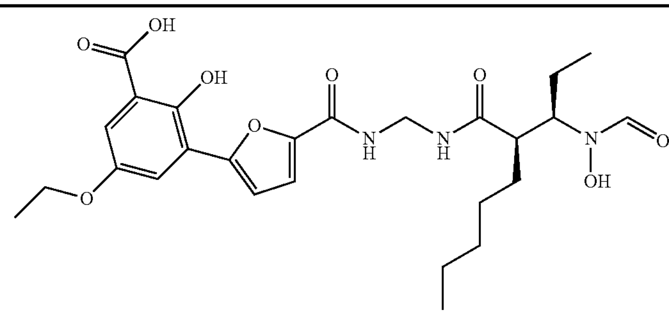 | ethyl 5-ethoxy-2-hydroxy-3-(5-((((R)-2-((R)-1-(N-hydroxy-formamido)propyl)heptanamido)methyl)carbamoyl)furan-2-yl) benzoate | 562.2 |

Example 82 was prepared from methyl 3-(5-((((R)-2-((R)-1-(N-(benzyloxy)formamido)propyl)heptanamido)methyl)carbamoyl)furan-2-yl)-5-propoxybenzoate by methods analogous to those described for Example 76. In Step 2 a mixture of THF and water was used as the solvent instead of a mixture of ethanol and water.

| Ex. | Name | Structure | Name Step 1 | MS (m/z) (M + H$^+$) Step 1 |
|---|---|---|---|---|
| 82 | 3-5-((((R)-2-((R)-1-(N-hydroxy-formamido)propyl)heptanamido)methyl)carbamoyl)furan-2-yl)-5-propoxybenzoic acid | 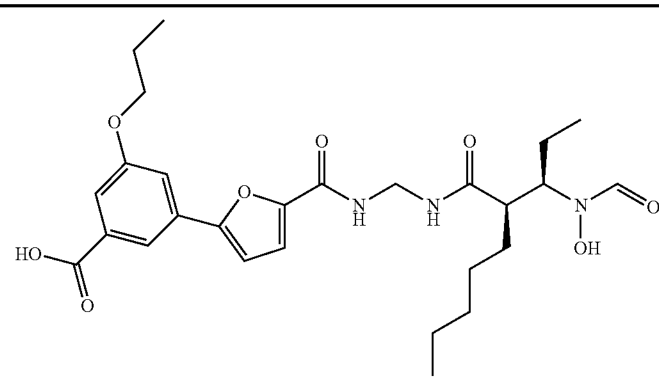 | methyl 3-(5-((((R)-2-((R)-1-(N-hydroxy-formamido)propyl)heptanamido)methyl)carbamoyl)furan-2-yl)-5-propoxybenzoate | 546.3 |

Example 83 was prepared from (S)-dimethyl 2-(3-(5-((((R)-2-((R)-1-(N-(benzyloxy)formamido)propyl)heptanamido)methyl)carbamoyl)furan-2-yl)benzamido)succinate by methods analogous to those described for Example 76. In Step 2 a mixture of THF and water was used as the solvent instead of a mixture of ethanol and water.

| Ex. | Name | Structure | Name Step 1 | MS (m/z) (M + H+) Step 1 |
|---|---|---|---|---|
| 83 | (S)-2-(3-(5-((((R)-2-((R)-1-(N-hydroxyformamido)propyl)heptanamido)methyl)carbamoyl)furan-2-yl)benzamido)succinic acid | 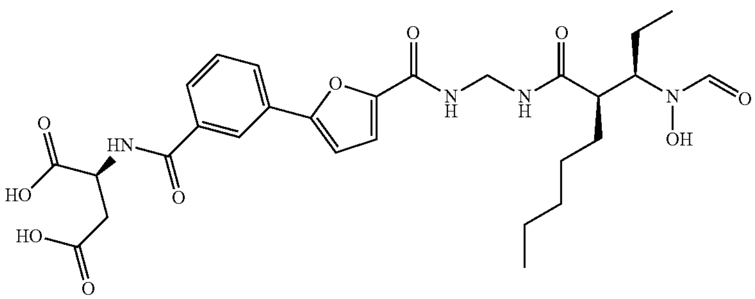 [SMILES: CCCCC[C@@H](C(=O)NCNC(=O)c1ccc(-c2cccc(C(=O)N[C@@H](CC(=O)O)C(=O)O)c2)o1)[C@@H](CC)N(O)C=O] | (S)-dimethyl 2-(3-(5-((((R)-2-((R)-1-(N-hydroxyformamido)propyl)heptanamido)methyl)carbamoyl)furan-2-yl)benzamido)succinate | 617.3 |

Example 84 was prepared from (R)-dimethyl 2-(3-(5-((((R)-2-((R)-1-(N-(benzyloxy)formamido)propyl)heptanamido)methyl)carbamoyl)furan-2-yl)-5-ethoxybenzamido)succinate by methods analogous to those described for Example 76.

| Ex. | Name | Structure | Name Step 1 | MS (m/z) (M + H+) Step 1 |
|---|---|---|---|---|
| 84 | (R)-2-(3-ethoxy-5-(5-((((R)-2-((R)-1-(N-hydroxyformamido)propyl)heptanamido)methyl)carbamoyl)furan-2-yl)benzamido)succinic acid | 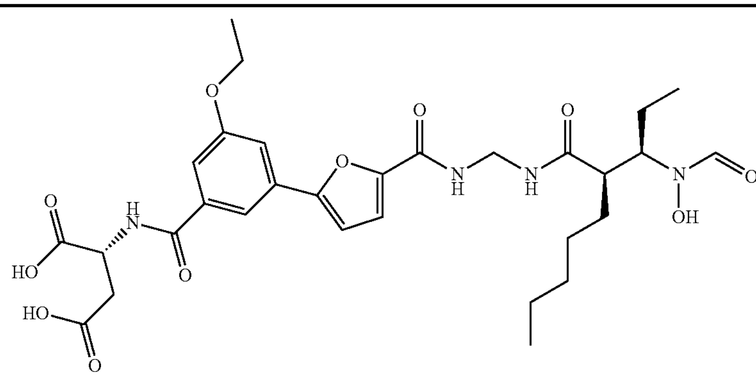 | (R)-dimethyl 2-(3-ethoxy-5-(5-((((R)-2-((R)-1-(N-hydroxyformamido)propyl)heptanamido)methyl)carbamoyl)furan-2-yl)benzamido)succinate | 661.2 |

Example 85 was prepared from methyl 2-(3-(5-((((R)-2-((R)-1-(N-(benzyloxy)formamido)propyl)heptanamido)methyl)carbamoyl)furan-2-yl)-5-ethoxybenzamido)acetate in procedures analogous to those exemplified in Example 76. In Step 2 a mixture of THF and water was used as the solvent instead of a mixture of ethanol and water.

| Ex. | Name | Structure | Name Step 1 | MS (m/z) (M + H+) Step 1 |
|---|---|---|---|---|
| 85 | 2-(3-ethoxy-5-(5-((((R)-2-((R)-1-(N-hydroxyformamido)propyl)heptanamido)methyl)carbamoyl)furan-2-yl)benzamido)acetic acid | 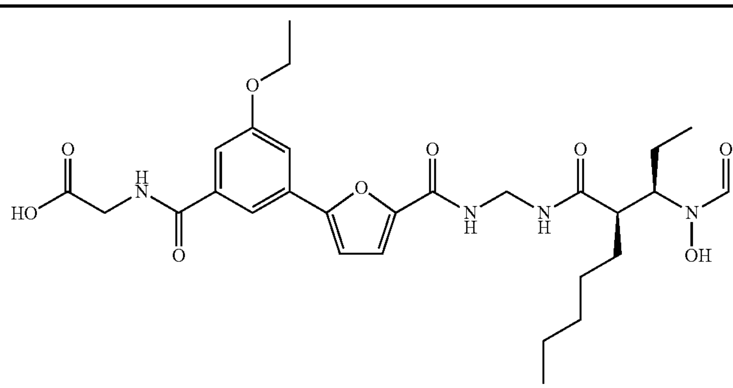 | methyl 2-(3-ethoxy-5-(5-((((R)-2-((R)-1-(N-hydroxyformamido)propyl)heptanamido)methyl)carbamoyl)furan-2-yl)benzamido)acetate | 589.2 |

Example 86 was prepared from dimethyl 2,2'-((4-(5-((((R)-2-((R)-1-(N-(benzyloxy)formamido)propyl)heptanamido)methyl)carbamoyl)furan-2-yl)-2-ethoxybenzoyl)azanediyl)diacetate by methods analogous to those described for Example 76. In Step 2 a mixture of THF and water was used as the solvent instead of a mixture of ethanol and water.

| Ex. | Name | Structure | Name Step 1 | MS (m/z) (M + H⁺) Step 1 |
|---|---|---|---|---|
| 86 | 2,2'-((2-ethoxy-4-(5-((((R)-2-((R)-1-(N-hydroxyformamido)propyl)heptanamido)methyl)carbamoyl)furan-2-yl)benzoyl)azanediyl)diacetic acid | 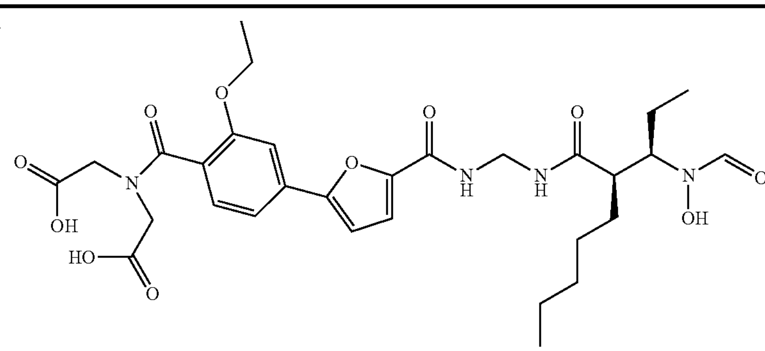 | dimethyl 2,2'-((2-ethoxy-4-(5-((((R)-2-((R)-1-(N-hydroxyformamido)propyl)heptanamido)methyl)carbamoyl)furan-2-yl)benzoyl)azanediyl)diacetate | 661.3 |

Example 87 was prepared from dimethyl 2,2'-((3-(5-((((R)-2-((R)-1-(N-(benzyloxy)formamido)propyl)heptanamido)methyl)carbamoyl)furan-2-yl)-5-ethoxybenzoyl)azanediyl)diacetate by methods analogous to those described for Example 76. In Step 2 a mixture of methanol and water was used as the solvent instead of a mixture of ethanol and water.

| Ex. | Name | Structure | Name Step 1 | MS (m/z) (M + H⁺) Step 1 |
|---|---|---|---|---|
| 87 | 2,2'-((3-ethoxy-5-(5-((((R)-2-((R)-1-(N-hydroxyformamido)propyl)heptanamido)methyl)carbamoyl)furan-2-yl)benzoyl)azanediyl)diacetic acid | 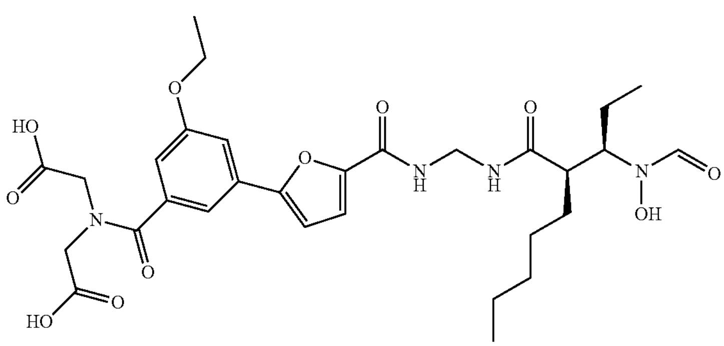 [SMILES: CCCCC[C@@H](C(=O)NCNC(=O)c1ccc(-c2cc(OCC)cc(C(=O)N(CC(=O)O)CC(=O)O)c2)o1)[C@@H](CC)N(O)C=O] | dimethyl 2,2'-((3-ethoxy-5-(5-((((R)-2-((R)-1-(N-hydroxyformamido)propyl)heptanamido)methyl)carbamoyl)furan-2-yl)benzoyl)azanediyl)diacetate | 661.2 |

Example 88

5-(3-((1,3-dihydroxy-2-(hydroxymethyl)propan-2-yl)carbamoyl)-5-ethoxyphenyl)-N—(((R)-2-((R)-1-(N-hydroxyformamido)propyl)heptanamido)methyl)furan-2-carboxamide

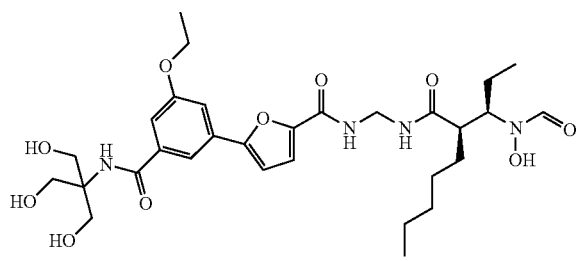 [SMILES: CCCCC[C@@H](C(=O)NCNC(=O)c1ccc(-c2cc(OCC)cc(C(=O)NC(CO)(CO)CO)c2)o1)[C@@H](CC)N(O)C=O]

Step 1: 5-(3-ethoxy-5-((6-(hydroxymethyl)-2,2,3,3,9,9,10,10-octamethyl-4,8-dioxa-3,9-disilaundecan-6-yl)carbamoyl)phenyl)-N—(((R)-2-((R)-1-(N-hydroxyformamido)propyl)heptanamido)methyl)furan-2-carboxamide

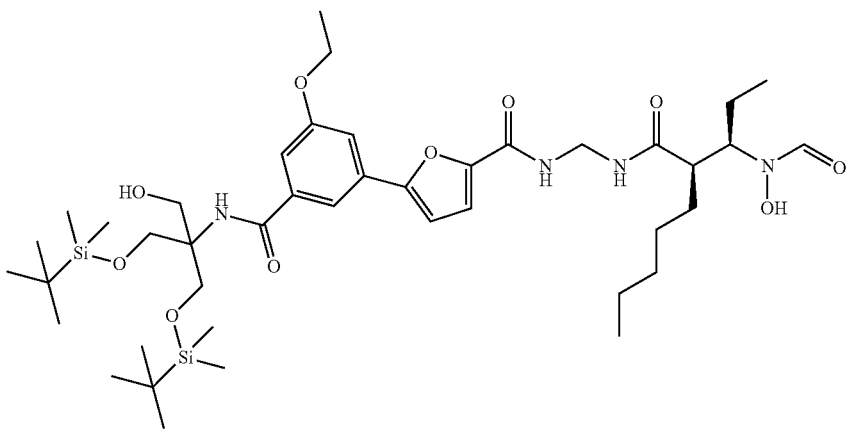 [SMILES: CCCCC[C@@H](C(=O)NCNC(=O)c1ccc(-c2cc(OCC)cc(C(=O)NC(CO)(CO[Si](C)(C)C(C)(C)C)CO[Si](C)(C)C(C)(C)C)c2)o1)[C@@H](CC)N(O)C=O]

Dichloromethane (0.25 ml) was added to Pd/C (10% wt, 8.76 mg, 8.23 µmol) in a nitrogen purged vial. A solution of N—(((R)-2-((R)-1-(N-(benzyloxy)formamido)propyl)heptanamido)methyl)-5-(3-ethoxy-5-((6-(hydroxymethyl)-2,2,3,3,9,9,10,10-octamethyl-4,8-dioxa-3,9-disilaundecan-6-yl)carbamoyl)phenyl)furan-2-carboxamide (173 mg, 0.18 mmol) in methanol (1 ml) was added followed by ammonium formate (51.9 mg, 0.82 mmol) and the reaction mixture stirred at room temperature for 6 hours. Additional Pd/C, (10% wt, 8.76 mg, 8.23 µmol) and ammonium formate (51.9 mg, 0.82 mmol) were added and the reaction stirred at room temperature overnight. The reaction was then filtered through a plug of Celite® which was washed with MeOH (10 ml). The filtrate was concentrated and the residue dissolved in DCM, filtered and then purified by flash chromatography (ISCO Combiflash Rf, 25 g column, 0-20% methanol/DCM) to give the title compound as an orange oil (116 mg, 83% yield). MS (m/z) 849.5 (M+H$^+$).

Step 2: 5-(3-((1,3-dihydroxy-2-(hydroxymethyl)propan-2-yl)carbamoyl)-5-ethoxyphenyl)-N—(((R)-2-((R)-1-(N-hydroxyformamido)propyl)heptanamido)methyl)furan-2-carboxamide To a solution of 5-(3-ethoxy-5-((6-(hydroxymethyl)-2,2,3,3,9,9,10,10-octamethyl-4,8-dioxa-3,9-disilaundecan-6-yl)carbamoyl)phenyl)-N—(((R)-2-((R)-1-(N-hydroxyformamido)propyl)heptanamido)methyl)furan-2-carboxamide (116 mg, 0.14 mmol) in THF (1 ml) cooled to 0° C. was added dropwise a solution of TBAF (1 M in THF, 0.82 ml, 0.82 mmol). The reaction was warmed to room temperature and stirred for 1 hour. Hexanes was then added to the reaction mixture, the hexanes were decanted from the resultant yellow oil. The oil was then dissolved in DCM and washed with water. The organic was collected via hydrophobic frit and concentrated. The residue was purified using reverse phase HPLC (Waters, XBridge Prep Shield RP C$_{18}$ 5 µm OBD 30×150 mm column, 50-90% CH$_3$CN/water+ 0.1% NH$_4$OH over 15 minutes) to give the title compound as a yellow solid (36 mg, 32% yield).

Example 89

(R)-3-(5-(((2-((N-hydroxyformamido)methyl)heptanamido)methyl)carbamoyl)furan-2-yl)benzoic acid

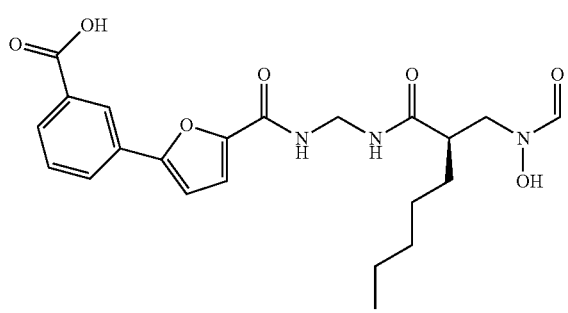 [SMILES: CCCCC[C@H](CN(O)C=O)C(=O)NCNC(=O)c1ccc(-c2cccc(C(=O)O)c2)o1]

(R)-methyl 3-(5-(((2-((N-hydroxyformamido)methyl)heptanamido)methyl)carbamoyl)furan-2-yl)benzoate (50 mg, 0.11 mmol) in methanol (1 ml) and water (0.3 ml) was treated with lithium hydroxide (7.82 mg, 0.33 mmol) for 3 days. The reaction was concentrated and acidified to ~pH 3 via addition of 1 N HCl. The reaction was extracted with EtOAc (3×) and then with DCM (2×). The combined organic extracts were dried over $Na_2SO_4$, filtered and concentrated. The residue was purified via flash chromatography (ISCO, 4 g silica gel column, 0-100% EtOAC/DCM: 5 minutes, 100% EtOAC: 5 minutes, 5% MeOH/DCM: 5 minutes, 5-10% MeOH/DCM: 5 minutes, 10% MeOH/DCM: 5 minutes) to give the title compound as a tan solid (41 mg, 95% yield).

Examples 90-93 were prepared from the indicated ester by methods analogous to those described for Example 89. For Examples 90-92 a mixture of ethanol and water was used as the solvent instead of a mixture of methanol and water.

| Ex. | Name | Structure | Ester |
|---|---|---|---|
| 90 | (R)-2-(5-(((2-((N-hydroxyformamido)methyl)heptanamido)methyl)carbamoyl)furan-2-yl)benzoic acid | 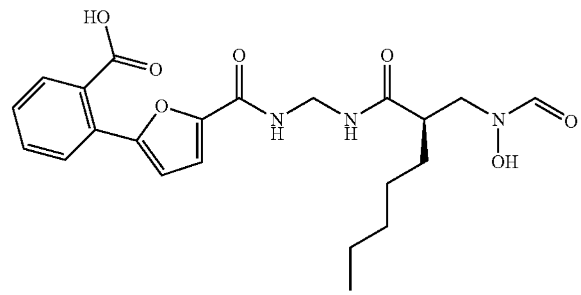 [SMILES: CCCCC[C@H](CN(O)C=O)C(=O)NCNC(=O)c1ccc(-c2ccccc2C(=O)O)o1] | (R)-methyl 2-(5-(((2-((N-hydroxyformamido)methyl)heptanamido)methyl)carbamoyl)furan-2-yl)benzoate |
| 91 | (R)-2-fluoro-5-(5-(((2-((N-hydroxyformamido)methyl)heptanamido)methyl)carbamoyl)furan-2-yl)benzoic acid | 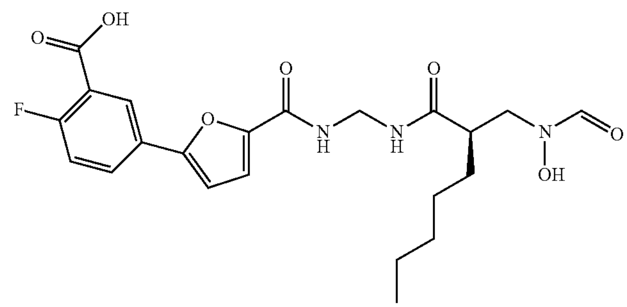 [SMILES: CCCCC[C@H](CN(O)C=O)C(=O)NCNC(=O)c1ccc(-c2ccc(F)c(C(=O)O)c2)o1] | (R)-methyl 2-fluoro-5-(5-(((2-((N-hydroxyformamido)methyl)heptanamido)methyl)carbamoyl)furan-2-yl)benzoate |
| 92 | (R)-4-(5-(((2-((N-hydroxyformamido)methyl)heptanamido)methyl)carbamoyl)furan-2-yl)benzoic acid | 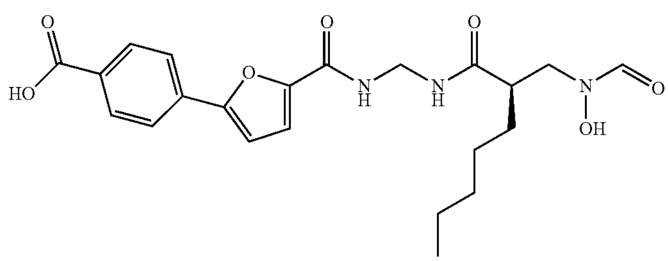 [SMILES: CCCCC[C@H](CN(O)C=O)C(=O)NCNC(=O)c1ccc(-c2ccc(C(=O)O)cc2)o1] | (R)-methyl 4-(5-(((2-((N-hydroxyformamido)methyl)heptanamido)methyl)carbamoyl)furan-2-yl)benzoate |
| 93 | (S)-2-(3-ethoxy-5-(5-((((R)-2-((R)-1-(N-hydroxyformamido)propyl)heptanamido)methyl)carbamoyl)furan-2-yl)benzamido)pentanedioic acid | 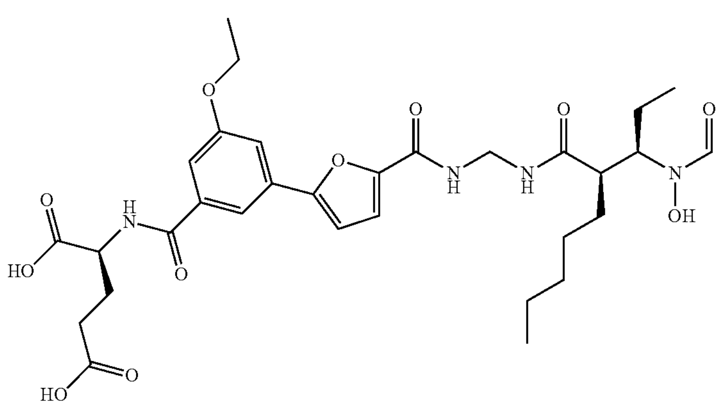 [SMILES: CCCCC[C@@H](C(=O)NCNC(=O)c1ccc(-c2cc(OCC)cc(C(=O)N[C@@H](CCC(=O)O)C(=O)O)c2)o1)[C@@H](CC)N(O)C=O] | (S)-dimethyl 2-(3-ethoxy-5-(5-((((R)-2-((R)-1-(N-hydroxyformamido)propyl)heptanamido)methyl)carbamoyl)furan-2-yl)benzamido)pentanedioate |

Example 94

(3-(5-((((R)-2-((N-hydroxyformamido)methyl)heptanamido)methyl)carbamoyl)furan-2-yl)phenyl)(methyl)phosphinic acid

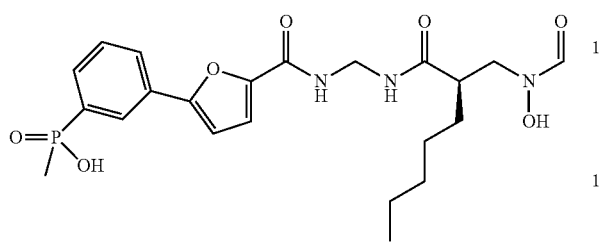

To a solution of ethyl (3-(5-((((R)-2-((N-hydroxyformamido)methyl)heptanamido)methyl)carbamoyl)furan-2-yl)phenyl)(methyl)phosphinate (100 mg, 0.20 mmol) in THF (5 ml) and water (1 ml) was added LiOH monohydrate (12 mg, 0.30 mmol) at 0° C. The reaction was stirred for 2 hours at 0° C. The reaction mixture was then allowed to warm to room temperature and stirred overnight. Additional LiOH monohydrate (6 mg, 0.15 mmol) was added and the reaction mixture stirred for a further 3 hours. The reaction mixture was then cooled to 0° C. and adjusted to pH 3 by addition of 1 M HCl solution (~0.4 ml). The reaction mixture was evaporated under reduced pressure. The residue was chromatographed (12 g, $C_{18}$ SNAP reversed phase silica gel column, 0-50% $CH_3CN$ in water modified with 0.2% formic acid) to give the title compound as a colorless oil (79 mg, 74% yield).

Example 95 methyl hydrogen (3-(5-((((R)-2-((N-hydroxyformamido)methyl)heptanamido)methyl)carbamoyl)furan-2-yl)phenyl)phosphonate

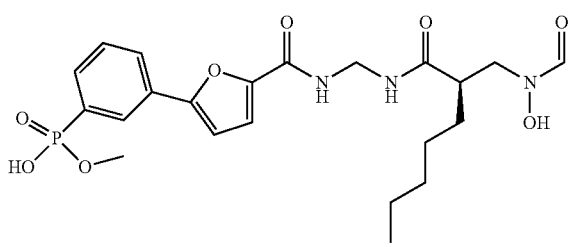 [SMILES: CCCCC[C@H](CN(O)C=O)C(=O)NCNC(=O)c1ccc(-c2cccc(P(=O)(O)OC)c2)o1]

A solution of (R)-dimethyl (3-(5-(((2-((N-hydroxyformamido)methyl)heptanamido)methyl)carbamoyl)furan-2-yl)phenyl)phosphonate (86 mg, 0.17 mmol) in THF (1 ml) and water (1 ml) was treated with LiOH monohydrate (15 mg, 0.36 mmol) and stirred at room temperature for 3 hours. Additional LiOH monohydrate (15 mg, 0.36 mmol) was added and the reaction stirred overnight. The reaction was then diluted with DCM and acidified with 1 N HCl to pH 2. The aqueous was extracted with DCM (3x). The combined organics were washed with brine, dried over $Na_2SO_4$, filtered and concentrated to give the title compound as a white solid (75 mg, 89.7% yield).

Example 96

(3-ethoxy-5-(5-((((R)-2-((R)-1-(N-hydroxyformamido)propyl)heptanamido)methyl)carbamoyl)furan-2-yl)phenyl)phosphonic acid

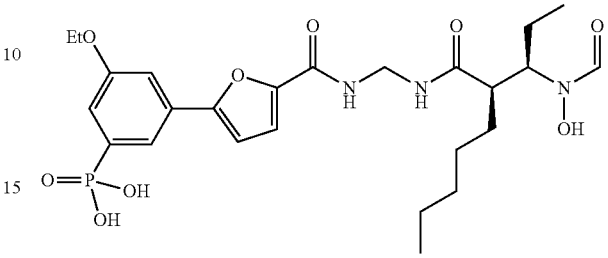

Preparation 1

Step 1: dimethyl (3-ethoxy-5-(5-((((R)-2-((R)-1-(N-hydroxyformamido)propyl)heptanamido)methyl)carbamoyl)furan-2-yl)phenyl)phosphonate

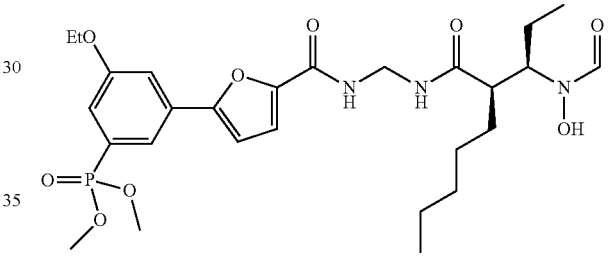

Dimethyl (3-(5-((((R)-2-((R)-1-(N-(benzyloxy)formamido)propyl)heptanamido)methyl)carbamoyl)furan-2-yl)-5-ethoxyphenyl)phosphonate (7.65 g, 11.39 mmol), was dissolved in ethanol (207 ml) and flushed with nitrogen. Pd/C (2.42 g, 2.28 mmol) was then added followed by methanol (20.71 ml) and the reaction then placed under hydrogen atmosphere (balloon). The mixture was stirred at room temperature for 1 hour and then filtered through Celite®, the Celite® was washed with MeOH and EtOAc. Concentration of the filtrates gave an orange residue which was azeotroped with EtOAc and then DCM to give the title compound as an orange residue (6.62 g) which was used without further purification. MS (m/z) 582.3 $(M+H^+)$.

Step 2: (3-ethoxy-5-(5-((((R)-2-((R)-1-(N-hydroxyformamido)propyl)heptanamido)methyl)carbamoyl)furan-2-yl)phenyl)phosphonic acid Dimethyl (3-ethoxy-5-(5-((((R)-2-((R)-1-(N-hydroxyformamido)propyl)heptanamido)methyl)carbamoyl)furan-2-yl)phenyl)phosphonate (6.62 g, 11.38 mmol) was dissolved in dichloromethane (224 ml). The mixture was cooled to 0° C. and then TMSBr (3.32 ml, 25.6 mmol) was added and the mixture was allowed to warm to room temperature and stirred for 1 hour. The reaction was then concentrated and azeotroped with DCM, and then MeOH/EtOAc. The residue was dried under high vacuum and then diluted with ~250 ml of EtOAc and a minimal amount of MeOH to help dissolve the solids. To this solution was added ~200 ml water+0.1% TFA. The solution was shaken and the layers separated. The aqueous layer was extracted twice with EtOAc. The combined EtOAc extracts were concentrated to dryness and the residue suspended with ~200 ml EtOAc, sonicated and spun on a rotary vaporator in a water bath at 60° C. The resulting suspension was cooled to room temperature and allowed to stir. At this time 400 mg of material similarly prepared was added. The light pink suspension was stirred for 1 hour at room temperature and then filtered. The solids were dried to give ~6 g of a light pink solid. This was then stirred in CH$_3$CN and heated to 60° C., then cooled to room temperature and stirred for 1 hour before being filtered. The resulting solids were suspended in EtOAc/hexanes, stirred at room temperature for 1 hour and then filtered. The resulting light pink solids were dried under reduced pressure to give the title compound (5.52 g, 85% yield). The filtrate was utilised to isolate Example 97.

Preparation 2

Step 1: dimethyl (3-ethoxy-5-(5-((((R)-2-((R)-1-(N-hydroxyformamido)propyl)heptanamido)methyl)carbamoyl)furan-2-yl)phenyl)phosphonate

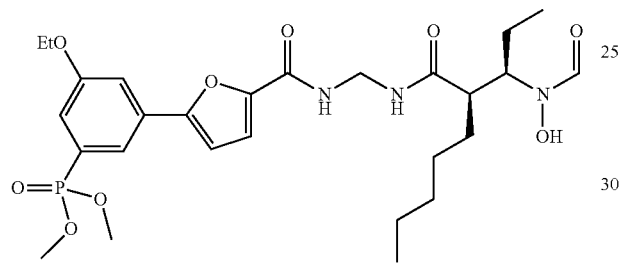

To a 4 neck 1 L round bottom flask, 5-(3-(dimethoxyphosphoryl)-5-ethoxyphenyl)furan-2-carboxylic acid (10 g, 29.4 mmol) and acetonitrile (200 ml) was added and the reaction mixture was cooled to 0-5° C. To the reaction mixture, triethylamine (5.74 ml, 41.2 mmol) and then HATU (10 g, 28.6 mmol) was added and the reaction mixture was warmed to 23-25° C. and stirred for 1 hour to form the HATU-acid adduct. To a separate round bottom flask, (R)—N-(aminomethyl)-2-((R)-1-(N-hydroxyformamido)propyl)heptanamide (7.6 g, 29.3 mmol) and acetonitrile (200 ml) was combined. This mixture was cooled to 0-5° C. and then triethylamine (5.74 ml, 41.2 mmol) and TMS-Cl (7.5 ml, 59.1 mmol) was added and the mixture was stirred at 0-5° C. for 1 hour. After 1 hour, the HATU-acid adduct was added to the second reaction mixture and the mixture was warmed to 23-25° C. over 1 hour. The reaction mixture was concentrated under reduced vacuum at 35-40° C. and the residue was diluted with ethyl acetate (100 ml) and water (50 ml). The layers were separated and the organic layer was washed with 5% sodium bicarbonate solution and then water. The organic layer was collected, dried over sodium sulfate, filtered, and concentrated under reduced pressure. The crude residue was purified by flash chromatography (1-3% MeOH/DCM). The pure fractions were combined and concentrated under reduced pressure to give the title compound (14 g, 82%) as a brown foam.

Step 2: (3-ethoxy-5-(5-((((R)-2-((R)-1-(N-hydroxyformamido)propyl)heptanamido)methyl)carbamoyl)furan-2-yl)phenyl)phosphonic acid Dimethyl (3-ethoxy-5-(5-((((R)-2-((R)-1-(N-hydroxyformamido)propyl)heptanamido)methyl)carbamoyl)furan-2-yl)phenyl)phosphonate (6.62 g, 11.38 mmol) was dissolved in dichloromethane (224 ml). The mixture was cooled to 0° C. and then TMSBr (3.32 ml, 25.6 mmol) was added and the mixture was allowed to warm to room temperature and stirred for 1 hour. The reaction was then concentrated and azeotroped with DCM, and then MeOH/EtOAc. The residue was dried under high vacuum and then diluted with ~250 ml of EtOAc and a minimal amount of MeOH to help dissolve the solids. To this solution was added ~200 ml water+0.1% TFA. The solution was shaken and the layers separated. The aqueous layer was extracted twice with EtOAc. The combined EtOAc extracts were concentrated to dryness and the residue suspended with ~200 ml EtOAc, sonicated and spun on a rotary vaporator in a water bath at 60° C. The resulting suspension was cooled to room temperature and allowed to stir. At this time 400 mg of material that was similarly prepared was added. The light pink suspension was stirred for 1 hour at room temperature and then filtered. The solids were dried to give ~6 g of a light pink solid. This was then stirred in CH$_3$CN and heated to 60° C., then cooled to room temperature and stirred for 1 hour before being filtered. The resulting solids were suspended in EtOAc/hexanes, stirred at room temperature for 1 hour and then filtered. The resulting light pink solids were dried under reduced pressure to give the title compound (5.52 g, 85% yield).

Example 97

(3-ethoxy-5-(5-((((R)-2-((R)-1-(N-hydroxyformamido)propyl)heptanamido)methyl)carbamoyl)tetrahydrofuran-2-yl)phenyl)phosphonic acid

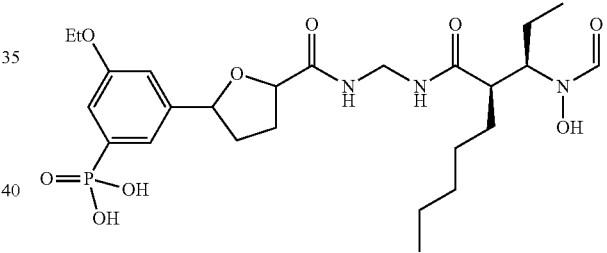

The filtrate from Example 96 was concentrated and purified by reverse phase HPLC (Waters, Starise, 30×150 mm, 20-60% CH$_3$CN/water (+0.1% TFA) over 14 minutes). The fractions were extracted with EtOAc and concentrated to give the title compound (30 mg).

Example 98

(2-ethoxy-4-(5-((((R)-2-((R)-1-(N-hydroxyformamido)propyl)heptanamido)methyl)carbamoyl)furan-2-yl)phenyl)phosphonic acid

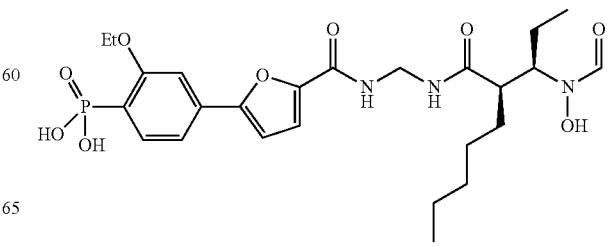

Step 1: (4-(5-((((R)-2-((R)-1-(N-(benzyloxy)formamido)propyl)heptanamido)methyl)carbamoyl)furan-2-yl)-2-ethoxyphenyl)phosphonic acid

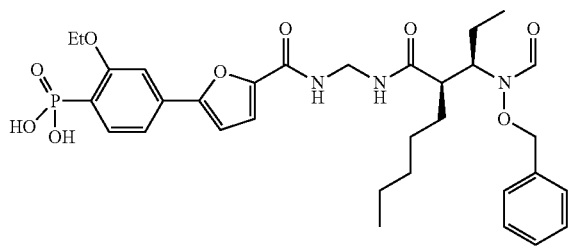 [SMILES: CCCCC[C@@H](C(=O)NCNC(=O)c1ccc(-c2ccc(P(=O)(O)O)c(OCC)c2)o1)[C@@H](CC)N(C=O)OCc1ccccc1]

Dimethyl (4-(5-((((R)-2-((R)-1-(N-(benzyloxy)formamido)propyl)heptanamido)methyl)carbamoyl)furan-2-yl)-2-ethoxyphenyl)phosphonate (600 mg, 0.89 mmol) was dissolved in dichloromethane (8.6 ml). The mixture was cooled to 0° C. and then bromotrimethylsilane (290 μl, 2.23 mmol) was added. The mixture was allowed to warm to room temperature, stirred for 1 hour and then concentrated. The residue was azeotroped twice with DCM to give the title compound as a dark residue which was used without further purification. MS (m/z) 672.3 (M+H$^+$).

Step 2: (2-ethoxy-4-(5-((((R)-2-((R)-1-(N-hydroxyformamido)propyl)heptanamido)methyl)carbamoyl)furan-2-yl)phenyl)phosphonic acid (4-(5-((((R)-2-((R)-1-(N-(benzyloxy)formamido)propyl)heptanamido)methyl)carbamoyl)furan-2-yl)-2-ethoxyphenyl)phosphonic acid (575 mg, 0.89 mmol), was dissolved in ethanol (20 ml) and the reaction flushed with nitrogen. Pd/C (238 mg, 0.22 mmol) was then added followed by methanol (20 ml) and the reaction was then placed under a hydrogen atmosphere (balloon). The mixture was stirred at room temperature for 1.5 hours then filtered through a PTFE filter, the filtrate was concentrated and purified via reverse phase HPLC (Waters, SunfirePrep C$_{18}$ OBD, 5 μM 30×150 mm, 20-60% CH$_3$CN/water (+0.1% TFA) over 14 minutes). Fractions containing product were combined, diluted with EtOAc and the solution extracted with EtOAc (3×). The combined EtOAc extracts were concentrated to give the title compound as an off white solid (245 mg, 50% yield).

Example 99 was prepared from dimethyl 3-(5-((((R)-2-((R)-1-(N-(benzyloxy)formamido)propyl)heptanamido)methyl)carbamoyl)furan-2-yl)-5-ethoxybenzylphosphonate by methods analogous to those described in Example 98. In Step 2 methanol was used as the solvent instead of a mixture of methanol and ethanol.

| Ex. | Name | Structure | Name Step 1 | MS (m/z) (M + H$^+$) Step 1 |
|---|---|---|---|---|
| 99 | (3-ethoxy-5-(5-((((R)-2-((R)-1-(N-hydroxyformamido)propyl)heptanamido)methyl)carbamoyl)furan-2-yl)benzyl)phosphonic acid | 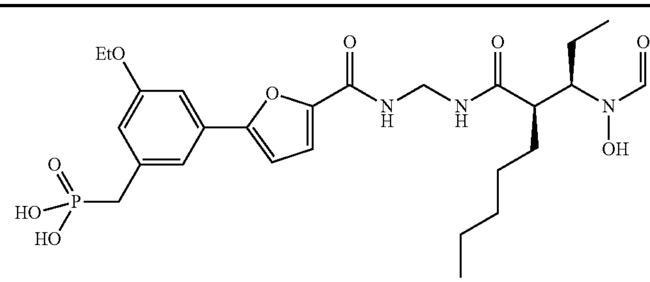 | (3-(5-((((R)-2-((R)-1-(N-(benzyloxy)formamido)propyl)heptanamido)methyl)carbamoyl)furan2-yl)-5-ethoxybenzyl)phosphonic acid | 659.4 |

Example 100 was prepared from diethyl ((3-(5-((((R)-2-((R)-1-(N-(benzyloxy)formamido)propyl)heptanamido)methyl)carbamoyl)furan-2-yl)-5-ethoxybenzamido)methyl)phosphonate by methods analogous to those described in Example 98.

| Ex. | Name | Structure | Name Step 1 | MS (m/z) (M + H$^+$) Step 1 |
|---|---|---|---|---|
| 100 | ((3-ethoxy-5-(5-((((R)-2-((R)-1-(N-hydroxyformamido)propyl)heptanamido)methyl)carbamoyl)furan-2-yl)benzamido)methyl)phosphonic acid | 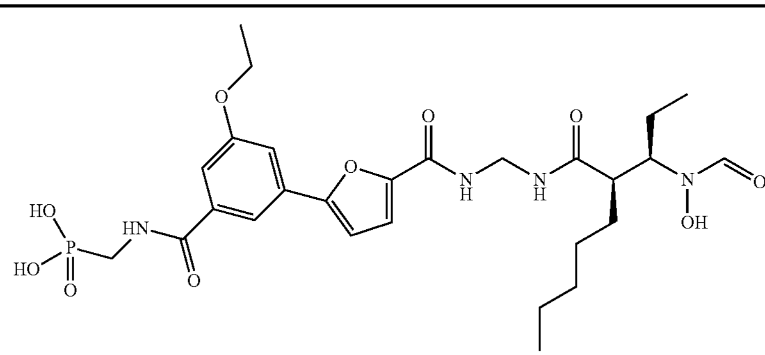 | ((3-(5-((((R)-2-((R)-1-(N-((benzyloxy)formamido)propyl)heptanamido)methyl)carbamoyl)furan-2-yl)-5-ethoxybenzamido)methyl)phosphonic acid | 701.2 |

Example 101 methyl hydrogen (3-ethoxy-5-(5-((((R)-2-((R)-1-(N-hydroxyformamido)propyl)heptanamido)methyl)carbamoyl)furan-2-yl)phenyl)phosphonate

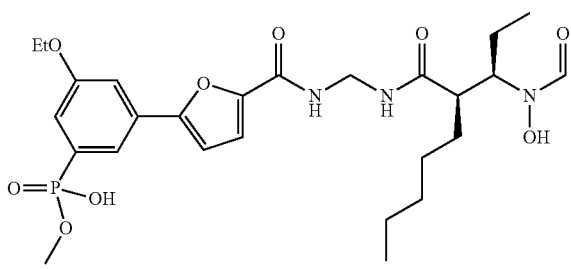 [SMILES: CCCCC[C@@H](C(=O)NCNC(=O)c1ccc(-c2cc(OCC)cc(P(=O)(O)OC)c2)o1)[C@@H](CC)N(O)C=O]

Dimethyl (3-ethoxy-5-(5-((((R)-2-((R)-1-(N-hydroxyformamido)propyl)heptanamido)methyl)carbamoyl)furan-2-yl)phenyl)phosphonate (115 mg, 0.2 mmol) was dissolved in dichloromethane (1.95 ml). The mixture was cooled to 0° C. and then bromotrimethylsilane (25.7 μl, 0.2 mmol) was added and the mixture was allowed to warm to room temperature and stirred for 1 hour and then concentrated. The residue was purified by reverse phase HPLC (Waters, Starise 30×1 50 mm, 20-60% CH$_3$CN/water (+0.1% TFA)). The fractions containing product were passed through a StratoSpheres PL-HCO$_3$ MP SPE cartridge (500 mg/6 ml) and then concentrated to dryness via nitrogen blowdown at 50° C. The residue was then dissolved in acetonitrile (250 μl) and water (600 μl) and lyophilized overnight to yield the title compound (19 mg, 17% yield)

Example 102

(R)-5-(3-(2,2-difluoroethoxy)phenyl)-N-((2-((N-hydroxyformamido)methyl)heptanamido)methyl)furan-2-carboxamide

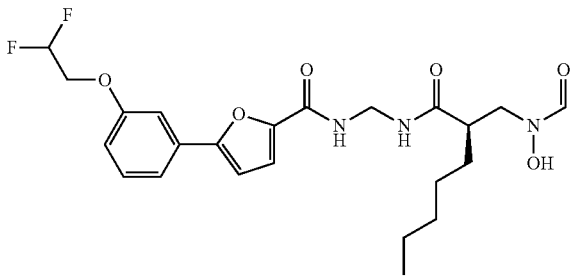 [SMILES: CCCCC[C@H](CN(O)C=O)C(=O)NCNC(=O)c1ccc(-c2cccc(OCC(F)F)c2)o1]

Step 1: (R)-5-(3-(2,2-difluoroethoxy)phenyl)-N-((2-((N-hydroxyformamido)methyl)heptanamido)methyl)furan-2-carboxamide and (R)-5-(3-(2,2-difluoroethoxy)phenyl)-N-((2(hydroxyamino)methyl)heptanamido)methyl)furan-2-carboxamide

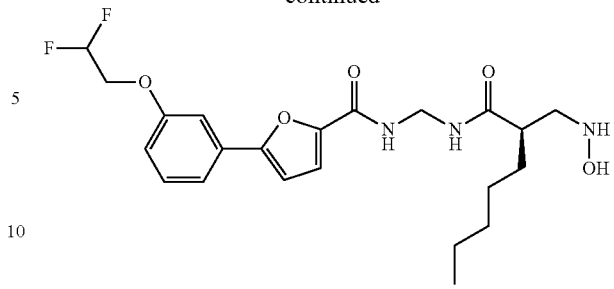

(R)—N-((2-((N-(benzyloxy)formamido)methyl)heptanamido)methyl)-5-(3-(2,2-difluoroethoxy)phenyl)furan-2-carboxamide (103.54 mg, 0.18 mmol) was dissolved in methanol (0.91 ml) under nitrogen. Pd/C (19.28 mg, 0.18 mmol) was added and the reaction placed under hydrogen atmosphere. The reaction was stirred for 4 hours and then filtered and concentrated. The residue was dissolved in DMF and purified by reverse phase HPLC (Gilson, Sunfire Prep C$_{18}$ column, 5 μM, 30×150 mm, 20-80% CH$_3$CN/water (+0.1% TFA) over a 30 minute gradient) to give a mixture of the title compounds (180 mg) which was used without further purification. MS (m/z) 482.1 (M+H$^+$) and 454.2 (M+H$^+$).

Step 2: (R)-5-(3-(2,2-difluoroethoxy)phenyl)-N-((2-((N-hydroxyformamido)methyl)heptanamido)methyl)furan-2-carboxamide CDI (96 mg, 0.6 mmol) was dissolved in DCM and formic acid (22.80 μl, 0.6 mmol) was added. The mixture was stirred for 45 minutes before being added to a solution of (R)-5-(3-(2,2-difluoroethoxy)phenyl)-N-((2-((hydroxyamino)methyl)heptanamido)methyl)furan-2-carboxamide and (R)-5-(3-(2,2-difluoroethoxy)phenyl)-N-((2-((hydroxyamino)methyl)heptanamido)methyl)furan-2-carboxamide (180 mg, 0.4 mmol) in DCM. The reaction mixture was then washed quickly with 0.6 N HCl. The aqueous layer was extracted with DCM. The combined organic layers were washed with H$_2$O, dried over Na$_2$SO$_4$ and concentrated to give the title compound (76.8 mg, 46.3% yield).

Example 103

(R)-5-(3-(ethylthio)phenyl)-N-((2-((N-hydroxyformamido)methyl)heptanamido)methyl)furan-2-carboxamide

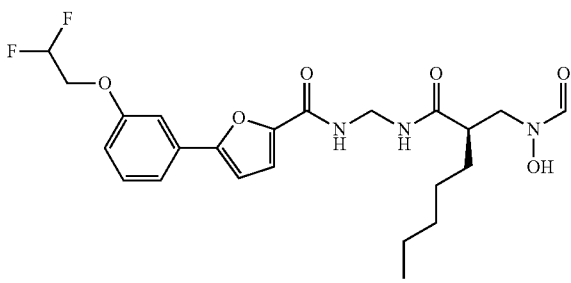

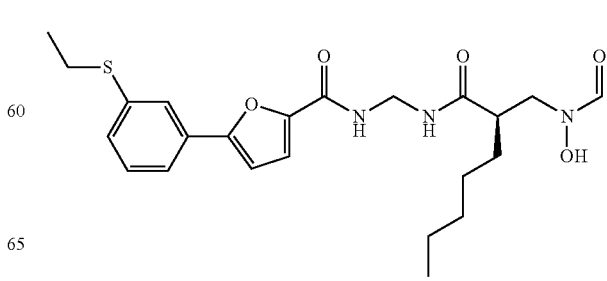

(R)—N-((2-((N-(benzyloxy)formamido)methyl)heptanamido)methyl)-5-(3-(ethylthio)phenyl)furan-2-carboxamide (152.4 mg, 0.28 mmol) was dissolved in dichloromethane (0.55 ml) and boron trichloride (1 M, 0.83 ml, 0.83 mmol) was added and the reaction was stirred for 4 hours. The reaction was then quenched by addition of methanol. After stirring for 5 minutes the reaction was concentrated. Formic acid (20.57 µl, 0.54 mmol) was added to a solution of CDI (87 mg, 0.54 mmol) in dichloromethane (1.77 ml) and the reaction was stirred for 45 minutes before being added to the isolated residue. The reaction was allowed to stir overnight. The reaction was then washed quickly with 0.6 N HCl. The aqueous layer was extracted with DCM. The combined organic layers were washed with $H_2O$, dried over $Na_2SO_4$ and concentrated. The residue was purified by mass directed reverse phase HPLC (Waters, Sunfire 30×150 mm, 30-70% $CH_3CN$/water (+0.1% TFA)). The fractions containing product were passed through a StratoSpheres PL-HCO$_3$ MP SPE cartridge (500 mg/6 ml) and then concentrated to dryness via nitrogen blowdown at 50° C. The residue was then dissolved in acetonitrile (250 µl) and water (600 µl) and lyopholized overnight to yield the title compound (12.1 mg, 9.49% yield).

Example 104 was prepared from the indicated intermediate by methods analogous to those described for Example 103.

A solution of (R)—N-((2-((N-(benzyloxy)formamido)methyl)heptanamido)methyl)-5-(3-nitrophenyl)furan-2-carboxamide (150 mg, 0.28 mmol) in dichloromethane (0.28 ml) was cooled to 0° C. and then treated with boron trichloride (1 M in DCM, 0.84 ml, 0.84 mmol). The reaction was then allowed to warm to room temperature and stirred for 4 hours. The reaction was diluted by the addition of water and the organic collected via hydrophobic frit and concentrated. The residue was then dissolved in dichloromethane (0.28 ml) and treated with 5-methyl-2-thioxo-1,3,4-thiadiazole-3(2H)-carbaldehyde Yazawa, H., et al., Tetrahedron Letters, 1985, 26 (31), 3703-3706 (44.8 mg, 0.28 mmol) and the reaction stirred at room temperature overnight. The reaction was then diluted by the addition of water and the organic collected via hydrophobic frit and concentrated. The residue was purified by flash chromatography (10 g Si SPE, DCM, ether, ethyl acetate, acetone). Fractions containing desired product were concentrated and the residue was dissolved in the minimum amount of DCM and ether added dropwise to achieve precipitate formation. The solid was then collected to yield the title compound as a yellow solid (26 mg, 19.8% yield).

Example 106

(R)—N-((2-((N-hydroxyformamido)methyl)heptanamido)methyl)-5-(1-methyl-1H-indazol-6-yl)furan-2-carboxamide

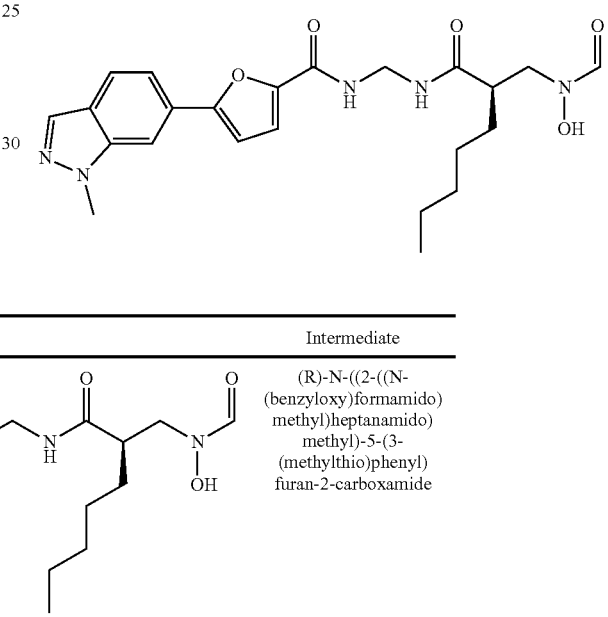

| Ex. | Name | Structure | Intermediate |
|---|---|---|---|
| 104 | (R)-N-((2-((N-hydroxyformamido)methyl)heptanamido)methyl)-5-(3-(methylthio)phenyl)furan-2-carboxamide | 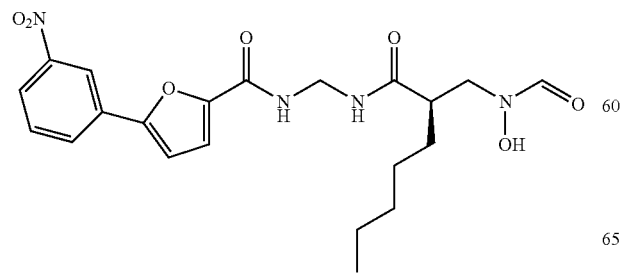 | (R)-N-((2-((N-(benzyloxy)formamido)methyl)heptanamido)methyl)-5-(3-(methylthio)phenyl)furan-2-carboxamide |

Example 105

(R)—N-((2-((N-hydroxyformamido)methyl)heptanamido)methyl)-5-(3-nitrophenyl)furan-2-carboxamide Step 1: (R)—N-((2-((hydroxyamino)methyl)heptanamido)methyl)-5-(1-methyl-1H-indazol-6-yl)furan-2-carboxamide

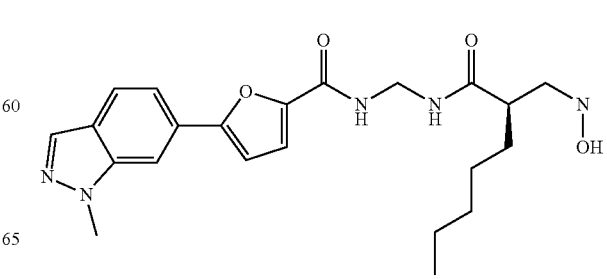

(R)—N-((2-((N-(benzyloxy)formamido)methyl)heptanamido)methyl)-5-(1-methyl-1H-indazol-6-yl)furan-2-carboxamide (208.6 mg, 0.38 mmol) was dissolved in methanol (0.38 ml) under nitrogen. Pd/C (2.03 mg, 0.02 mmol) was added and the reaction placed under H$_2$ atmosphere. The reaction was stirred for 6 hours however LCMS indicated no formation of desired mass. The reaction mixture was filtered and concentrated. Dichloromethane (0.38 ml) was added to the residue followed by boron trichloride (1 M, 1.15 ml, 1.15 mmol). The reaction was stirred for 3 hours then quenched by the addition of MeOH and concentrated to give the title compound (191.3 mg) which was used without further purification. MS (m/z) 428.2 (M+H$^+$).

Step 2: (R)—N-((2-((N-hydroxyformamido)methyl) heptanamido)methyl)-5-(1-methyl-1H-indazol-6-yl) furan-2-carboxamide Formic acid (17.16 µl, 0.45 mmol) was added to a solution of CDI (72.6 mg, 0.45 mmol) in DCM (2.22 ml) and the reaction was stirred for 45 minutes before a solution of (R)—N-((2-((hydroxyamino)methyl)heptanamido)methyl)-5-(1-methyl-1H-indazol-6-yl)furan-2-carboxamide (191.3 mg, 0.45 mmol) in DCM was added. The reaction was stirred overnight. The reaction mixture was then washed quickly with 0.6 N HCl. The aqueous layer was extracted with DCM. The combined organic layers were washed with H$_2$O, dried over Na$_2$SO$_4$ and concentrated. The residue was dissolved in DMF and purified by reverse phase HPLC (Gilson, Sunfire Prep C$_{18}$ column, 5 µM, 30×150 mm, 20-60% CH$_3$CN/water (+0.1% TFA) 45 ml/min over a 30 minute gradient) to yield the title compound (22.7 mg, 11.1% yield).

Example 107

(R)—N-((2-((N-hydroxyformamido)methyl)heptanamido)methyl)-5-(2-methyl-2H-indazol-6-yl)furan-2-carboxamide

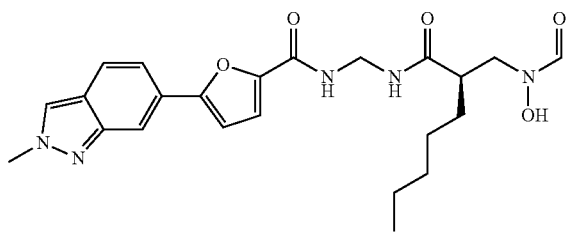 [SMILES: CCCCC[C@H](CN(O)C=O)C(=O)NCNC(=O)c1ccc(-c2ccc3cn(C)nc3c2)o1]

Step 1: (R)—N-((2-((hydroxyamino)methyl)heptanamido)methyl)-5-(2-methyl-2H-indazol-6-yl) furan-2-carboxamide

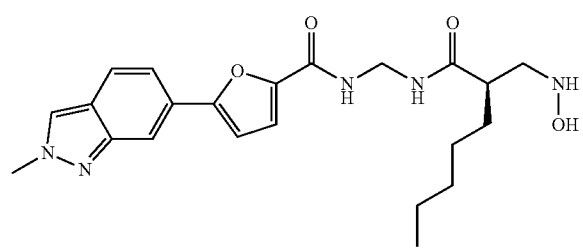 [SMILES: CCCCC[C@H](CNO)C(=O)NCNC(=O)c1ccc(-c2ccc3cn(C)nc3c2)o1]

(R)—N-((2-((N-(benzyloxy)formamido)methyl)heptanamido)methyl)-5-(2-methyl-2H-indazol-6-yl)furan-2-carboxamide (276.3 mg, 0.51 mmol) was dissolved in dichloromethane (0.51 ml) and then boron trichloride (1 M, 1.52 ml, 1.52 mmol) was added and the reaction was stirred for 7 hours. Additional boron trichloride (1 M, 1.01 ml, 1.01 mmol) was added and the reaction was stirred overnight. LCMS indicated no formation of desired mass. The reaction mixture was quenched with MeOH and concentrated. The residue was dissolved in methanol (0.51 ml) and placed under nitrogen atmosphere. Pd/C (53.9 mg, 0.51 mmol) was added and the reaction placed under hydrogen atmosphere and stirred for 6 hours. The reaction was then filtered and concentrated. The residue was dissolved in DMF and purified by reverse phase HPLC (Gilson, Sunfire Prep C$_{18}$ column, 5 µM, 30×150 mm, 0-60% CH$_3$CN/water (+0.1% TFA) over a 30 minute gradient) to give the title compound (75.1 mg, 32.6% yield). MS (m/z) 428.2 (M+H$^+$).

Step 2: (R)—N-((2-((N-hydroxyformamido)methyl) heptanamido)methyl)-5-(2-methyl-2H-indazol-6-yl) furan-2-carboxamide CDI (42.7 mg, 0.26 mmol) was dissolved in DCM and formic acid (10.11 µl, 0.26 mmol) was added. The mixture was stirred for 45 minutes before being added to a solution of (R)—N-((2-((hydroxyamino)methyl)heptanamido) methyl)-5-(2-methyl-2H-indazol-6-yl)furan-2-carboxamide (75.1 mg, 0.18 mmol) in DCM. The reaction was stirred overnight. The reaction mixture was then washed quickly with 0.6 N HCl. The aqueous layer was extracted with DCM. The combined organic layers were washed with H$_2$O, dried over Na$_2$SO$_4$, filtered and concentrated. The residue was purified by mass directed reverse phase HPLC (Waters, Sunfire, 30×150 mm, 20-60% CH$_3$CN/water (+0.1% TFA)). The fractions containing product were passed through a StratoSpheres PL-HCO$_3$ MP SPE cartridge (500 mg/6 ml) and then concentrated to dryness via nitrogen blowdown at 50° C. The residue was then dissolved in acetonitrile (250 µl) and water (600 µl) and lyopholized overnight to give the title compound (5.6 mg, 7% yield).

Example 108

(R)-(3-(5-(((2-((N-hydroxyformamido)methyl)heptanamido)methyl)carbamoyl)furan-2-yl)phenyl) phosphonic acid

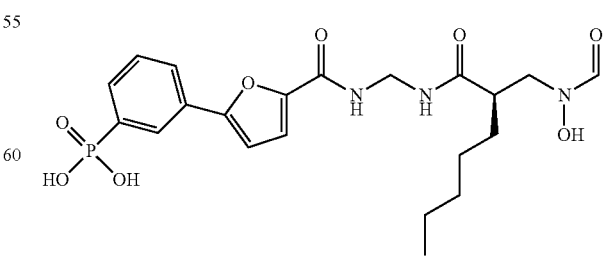

To a mixture of 5-(3-phosphonophenyl)furan-2-carboxylic acid (176 mg, 0.66 mmol), DIPEA (0.23 ml, 1.32 mmol), HOBt (116 mg, 0.86 mmol) in dichloromethane (3 ml) and NMP (3 ml) was added EDC (164 mg, 0.86 mmol) and the reaction mixture stirred for 10 minutes. A solution of (R)—N-(aminomethyl)-2-((N-hydroxyformamido)methyl) heptanamide (152 mg, 0.66 mmol) in dichloromethane (3 ml) and NMP (3 ml) was then added and the reaction stirred for 4 nights. The reaction mixture was diluted with dichloromethane (25 ml) and water (25 ml), an emulsion formed, NaOH (100 mg) was added and the phases separated. The organic phase was washed with aqueous NaOH (100 mg in 20 ml of water). The aqueous phase was then washed with dichloromethane (7×50 ml) then treated with 1 M HCl (2.5 ml). The aqueous phase was loaded directly onto a 30 g SNAP $C_{18}$ column and eluted with water containing 0.1% formic acid and then 0-95% $CH_3CN$ in water containing 0.1% formic acid. Product containing fractions were concentrated to give 14 mg and 59 mg of impure product which were then recombined and purified by mass directed reverse phase HPLC (Waters, Phenomenex Luna $C_{18}$, 10 μm, 250× 21.2 mm, 15-80% $CH_3CN$/water+0.1% HCOOH) to give the title compound as a pale pink glass (27 mg, 8% yield, containing 13% of (R)-(3-(5-(((2-((hydroxyamino)methyl) heptanamido)methyl)carbamoyl)furan-2-yl)phenyl)phosphonic acid).

Example 109

5-(3-((Z)—N'-hydroxycarbamimidoyl)phenyl)-N—(((R)-2-((R)-1-(N-hydroxyformamido)propyl)heptanamido)methyl)furan-2-carboxamide

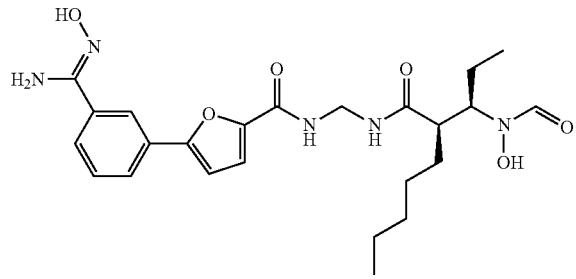 [SMILES: CCCCC[C@@H](C(=O)NCNC(=O)c1ccc(-c2cccc(/C(N)=N/O)c2)o1)[C@@H](CC)N(O)C=O]

5-(3-cyanophenyl)-N—(((R)-2-((R)-1-(N-hydroxyformamido)propyl)heptanamido)methyl)furan-2-carboxamide (132 mg, 0.29 mmol) was dissolved in ethanol (1.45 ml) and treated with hydroxylamine (50 mg, 0.76 mmol) and the reaction mixture heated at 75° C. for 2 hours. The reaction was then cooled to room temperature, filtered through a syringe filter, and purified by reverse phase HPLC (Waters, Starise 30×150 mm, 10-50% $CH_3CN$/water (+0.1% TFA), 50 ml/min). The fractions containing product were passed through a StratoSpheres PL-HCO$_3$ MP SPE cartridge (500 mg/6 ml) and then concentrated to dryness via nitrogen blowdown at 50° C. The residue was then dissolved in acetonitrile (250 μl) and water (600 μl) and lyopholized overnight to give the title compound as an off white solid (76 mg, 54% yield).

Example 110

N—(((R)-2-((R)-1-(N-hydroxyformamido)propyl) heptanamido)methyl)-5-phenyltetrahydrofuran-2-carboxamide

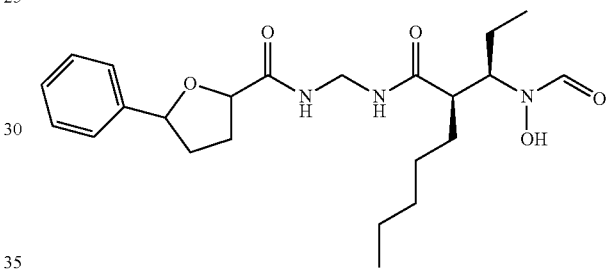

The title compound (400 mg) was isolated as a hydrogenation by-product following column chromatography of N—(((R)-2-((R)-1-(N-hydroxyformamido)propyl)heptanamido)methyl)-5-phenylfuran-2-carboxamide.

Example 111 was prepared from methyl 5-(5-((((R)-2-((R)-1-(N-(benzyloxy)formamido)propyl)heptanamido) methyl)carbamoyl)furan-2-yl)-3-ethoxy-2-fluorobenzoate by methods analogous to those described for Example 74 using a 4:1 ratio of methanol:ethanol in Step 1 and a 3:1:1 ratio of THF:MeOH:H$_2$O in Step 2.

| Ex. | Name | Structure | Name Step 1 | MS (m/z) (M + H$^+$) Step 1 |
|---|---|---|---|---|
| 111 | 3-ethoxy-2-fluoro-5-(5-((((R)-2-((R)-1-(N-hydroxy-formamido)propyl) heptanamido) methyl) carbamoyl)furan-2-yl)benzoic acid | 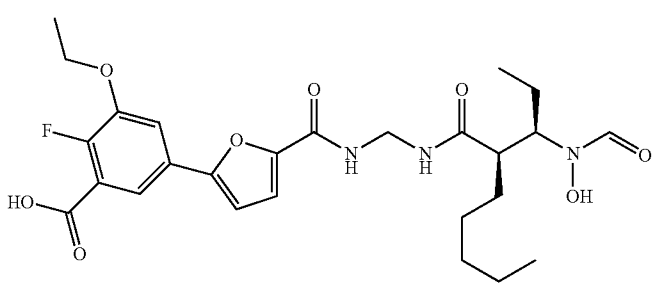 [SMILES: CCCCC[C@@H](C(=O)NCNC(=O)c1ccc(-c2cc(OCC)c(F)c(C(=O)O)c2)o1)[C@@H](CC)N(O)C=O] | methyl 3-ethoxy-2-fluoro-5-(5-((((R)-2-((R)-1-(N-hydroxy-formamido)propyl) heptanamido)methyl) carbamoyl)furan-2-yl) benzoate | 551.2 |

Example 112 was prepared from methyl 3-(5-((((R)-2-((R)-1-(N-(benzyloxy)formamido)propyl)heptanamido)methyl)carbamoyl)furan-2-yl)-5-hydroxybenzoate by methods analogous to those described for Example 74 using Pd(OH)$_2$ instead of Pd/C in Step 1.

| Ex. | Name | Structure | Name Step 1 | MS (m/z) (M + H$^+$) Step 1 |
|---|---|---|---|---|
| 112 | 3-hydroxy-5-(5-((((R)-2((R)-1-(N-hydroxyformamido)propyl)heptanamido)methyl)carbamoyl)furan-2-yl)benzoic acid | 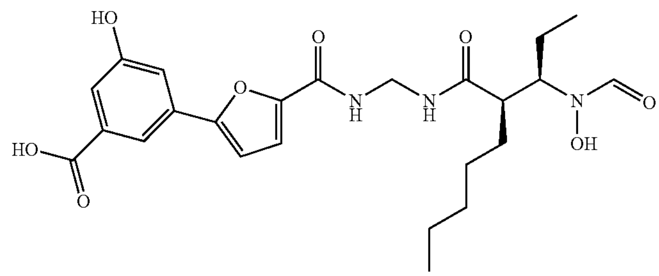 [SMILES: CCCCC[C@@H](C(=O)NCNC(=O)c1ccc(-c2cc(O)cc(C(=O)O)c2)o1)[C@@H](CC)N(O)C=O] | methyl 3-hydroxy-(5-((((R)-2-((R)-1-(N-hydroxy-formamido)propyl)heptanamido)methyl)carbamoyl)furan-2-yl-5-benzoate | 504.1 |

Example 113 was prepared from (methyl 3-(5-((((R)-2-((R)-1-(N-(benzyloxy)formamido)propyl)heptanamido)methyl)carbamoyl)furan-2-yl)-5-(2-methoxy-2-oxoethoxy)benzoate by methods analogous to those described for Example 74 using Pd(OH)$_2$ instead of Pd/C in Step 1.

| Ex. | Name | Structure | Name Step 1 | MS (m/z) (M + H$^+$) Step 1 |
|---|---|---|---|---|
| 113 | 3-(carboxymethoxy)-5-(5-((((R)-2-((R)-1-(N-hydroxformamido)propyl)heptanamido)methyl)carbamoyl)furan-2-yl)benzoic acid | 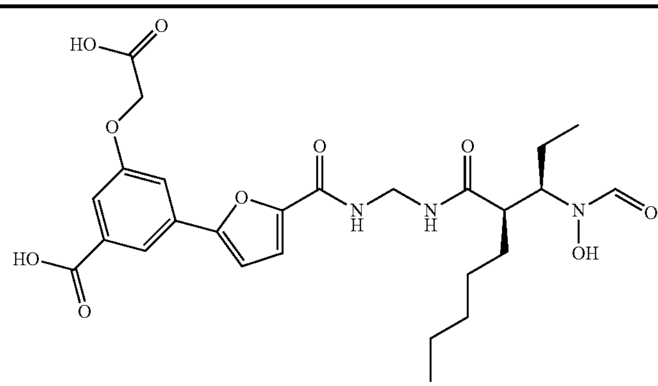 | methyl 3-(5-((((R)-2-((R)-1-(N-hydroxy-formamido)propyl)heptananamido)methyl)carbamoyl)furan-2-yl)-5-(2-methoxy-2-oxoethoxy)benzoate | 576.3 |

Example 114 was prepared from methyl 4-(5-((((R)-2-((R)-1-(N-(benzyloxy)formamido)propyl)heptanamido)methyl)carbamoyl)furan-2-yl)-2-(2-methoxy-2-oxoethyl)benzoate by methods analogous to those described for Example 76 using CH$_3$CN instead of ethanol and water in Step 2. Additionally, reaction times and amount of Pd/C may vary slightly in the Examples 114-132.

| Ex. | Name | Structure | Name Step 1 | MS (m/z) (M + H+) Step 1 |
|---|---|---|---|---|
| 114 | 2-carboxymethyl)-4-(5-((((R)-2-((R)-1-(N-hydroxy-formamido)propyl)heptanamido)methyl)carbamoyl)furan-2-yl)benzoic acid | 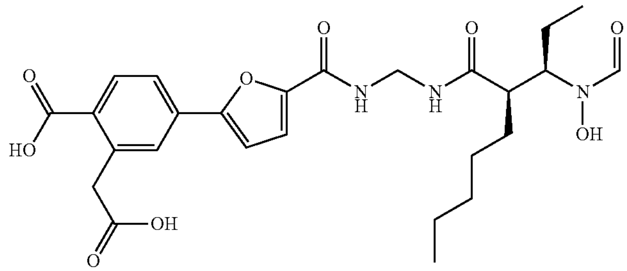 [SMILES: CCCCC[C@@H](C(=O)NCNC(=O)c1ccc(-c2ccc(C(=O)O)c(CC(=O)O)c2)o1)[C@@H](CC)N(O)C=O] | methyl 4-(5-((((R)-2-((R)-1-(N-hydroxyformamido)propyl)heptanamido)methyl)carbamoyl)furan-2-yl)-2-(2-methoxy-2-oxoethyl)benzoate | 560.2 |

Example 115 was prepared from ethyl 3-(5-((((2R,3R)-3-(N-(benzyloxy)formamido)-2-phenethylpentanamido)methyl)carbamoyl)furan-2-yl)-5-ethoxy-2-hydroxybenzoate by methods analogous to those described for Example 76.

| Ex. | Name | Structure | Name Step 1 | MS (m/z) (M + H+) Step 1 |
|---|---|---|---|---|
| 115 | 5-ethoxy-2-hydroxy-3-(5-((((2R,3R)-3-(N-hydroxyformamido)-2-phenethylpentanamido)methyl)carbamoyl)furan-2-yl)benzoic acid | 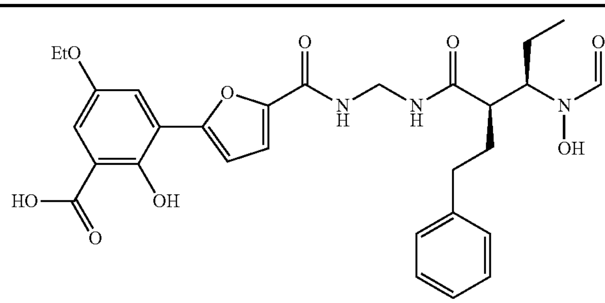 | ethyl 5-ethoxy-2-hydroxy-3-(5-((((2R,3R)-3-(N-hydroxyformamido)-2-phenethylpentanamido)methyl)carbamoyl)furan-2-yl)benzoate | 596.4 |

Example 117 was prepared from (S)-dimethyl 2-(4-(5-((((2R,3R)-3-(N-(benzyloxy)formamido)-2-(2-(naphthalen-2-yl)ethyl)pentanamido)methyl)carbamoyl)furan-2-yl)-2-ethoxybenzamido)succinate by methods analogous to those described for Example 76 using THF and water instead of ethanol and water in Step 2.

| Ex. | Name | Structure | Name Step 1 | MS (m/z) (M + H+) Step 1 |
|---|---|---|---|---|
| 117 | (S)-2-(2-ethoxy-4-(5-((((2R,3R)-3-(N-hydroxyformamido)-2-(2-(naphthalen-2-yl)ethyl)pentanamido)methyl)carbamoyl)furan-2-yl)benzamido)succinic acid | 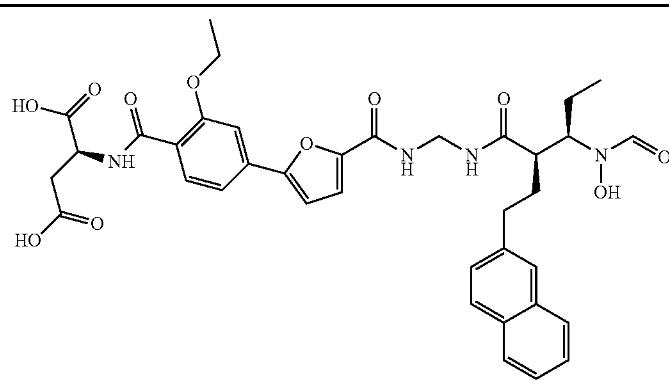 | (S)-dimethyl 2-(2-ethoxy-4-(5-((((2R,3R)-3-(N-hydroxyformamido)-2-(naphthalen-2-yl)ethyl)pentanamido)methyl)carbamoyl)furan-2-yl)benzamido)succinate | 745.2 |

Example 118 was prepared from methyl 3-(5-(((((2R,3R)-3-(N-(benzyloxy)formamido)-2-(2,4-difluorophenethyl)pentanamido)methyl)carbamoyl)furan-2-yl)-2-hydroxy-5-(2-methoxy-2-oxoethoxy) by methods analogous to those described for Example 76 using THF and water instead of ethanol and water in Step 2.

| Ex. | Name | Structure | Name Step 1 | MS (m/z) (M + H+) Step 1 |
|---|---|---|---|---|
| 118 | 5-(carboxymethoxy)-3-(5-((((2R,3R)-2-(2,4-difluorophenethyl)-3-(N-hydroxyformamido)pentanamido)methyl)carbamoyl)furan-2-yl)-2-hydroxybenzoic acid | 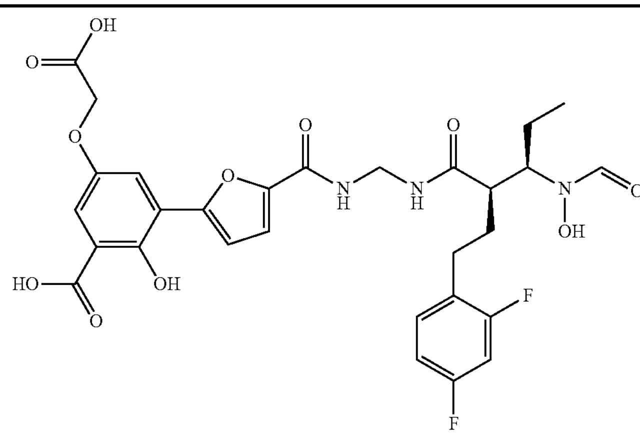 | methyl 3-(5-((((2R,3R)-2-(2,4-difluorophenethyl)-3-(N-hydroxyformamido)pentanamido)methyl)carbamoyl)furan-2-yl)-2-hydroxy-5-(2-methoxy-2-oxoethoxy)benzoate | 662.2 |

Example 119 was prepared from (S)-dimethyl 2-(4-(5-((((R)-2-((R)-1-(N-(benzyloxy)formamido)propyl)heptanamido)methyl)carbamoyl)furan-2-yl)benzamido)succinate by methods analogous to those described for Example 76 using MeOH instead of MeOH and DCM in Step 1.

| Ex. | Name | Structure | Name Step 1 | MS (m/z) (M + H+) Step 1 |
|---|---|---|---|---|
| 119 | (S)-2-(4-(5-((((R)-2-((R)-1-(N-hydroxyformamido)propyl)heptanamido)methyl)carbamoyl)furan-2-yl)benzamido)succinic acid | 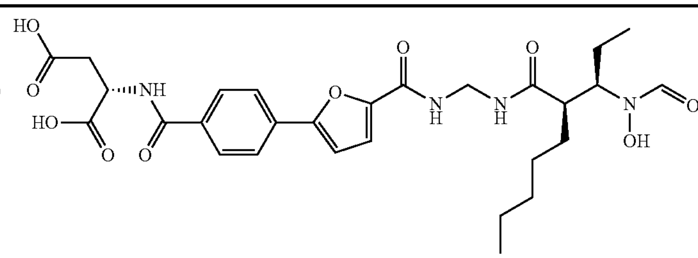 | (S)-dimethyl 2-(4-(5-((((R)-2-((R)-1-(N-hydroxyformamido)propyl)heptanamido)methyl)carbamoyl)furan-2-yl)benzamido)succinate | 617.3 |

Example 120 was prepared from (S)-dimethyl 2-(4-(5-((((R)-2-((R)-1-(N-(benzyloxy)formamido)propyl)heptanamido)methyl)carbamoyl)furan-2-yl)-2-methylbenzamido)succinate by methods analogous to those described for Example 76 using MeOH and water instead of ethanol and water in Step 2.

| Ex. | Name | Structure | Name Step 1 | MS (m/z) (M + H+) Step 1 |
|---|---|---|---|---|
| 120 | (S)-2-(4-(5-((((R)-2-((R)-1-(N-hydroxyformamido)propyl)heptanamido)methyl)carbamoyl)furan-2-yl)-2-methylbenzamido)succinic acid | 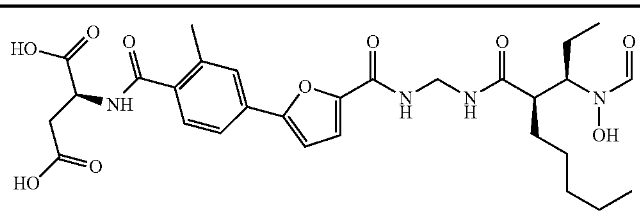 | (S)-dimethyl 2-(4-(5-((((R)-2-((R)-1-(N-hydroxyformamido)propyl)heptanamido)methyl)carbamoyl)furan-2-yl)-2-methylbenzamid)succinate | 631.8 |

Example 121 was prepared from methyl 3-(5-((((R)-2-((R)-1-(N-(benzyloxy)formamido)propyl)heptanamido)methyl)carbamoyl)furan-2-yl)-2-hydroxy-5-(2-methoxy-2-oxoethoxy)benzoate by methods analogous to those described for Example 76 using MeOH and water instead of ethanol and water in Step 2.

| Ex. | Name | Structure | Name Step 1 | MS (m/z) (M + H⁺) Step 1 |
|---|---|---|---|---|
| 121 | 5-(carboxymethoxy)-2-hydroxy-3-(5-((((R)-2-((R)-1-(N-hydroxyformamido)propyl)heptanamido)methyl)carbamoyl)furan-2-yl)benzoic acid | 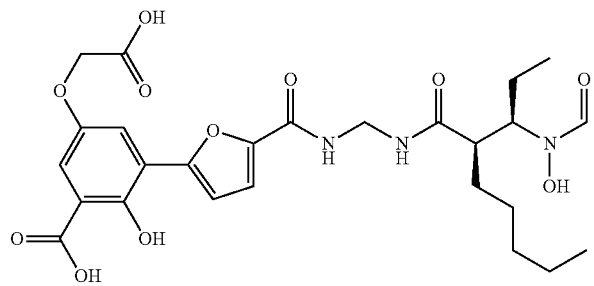 [SMILES: CCCCC[C@@H](C(=O)NCNC(=O)c1ccc(-c2cc(OCC(=O)O)cc(C(=O)O)c2O)o1)[C@@H](CC)N(O)C=O] | methyl 2-hydroxy-3-(5-((((R)-2-((R)-1-(N-hydroxyformamido)propyl)heptanamido)methyl)carbamoyl)furan-2-yl)-5-(2-methoxy-2-oxoethoxy)benzoate | 592.2 |

Example 122 was prepared from dimethyl 2,2'-((3-(5-((((2R,3R)-3-(N-(benzyloxy)formamido)-2-(2,4-difluorophenethyl)pentanamido)methyl)carbamoyl)furan-2-yl)-5-ethoxybenzoyl)azanediyl)diacetate by methods analogous to those described for Example 76 using THF and water instead of ethanol and water in Step 2.

| Ex. | Name | Structure | Name Step 1 | MS (m/z) (M + H⁺) Step 1 |
|---|---|---|---|---|
| 122 | 2,2'-((3-(5-((((2R,3R)-2-(2,4-difluorophenethyl)-3-(N-hydroxyformamido)pentanamido)methyl)carbamoyl)furan-2-yl)-5-ethoxybenzoyl)azanediyl)diacetic acid | 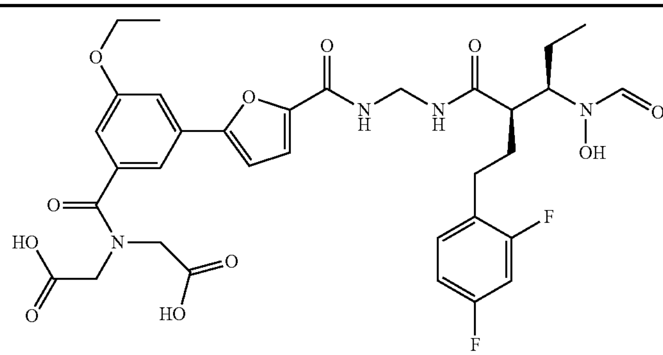 | dimethyl 2,2'-((3-(5-((((2R,3R)-2-(2,4-difluorophenethyl)-3-(N-hydroxyformamido)pentanamido)methyl)carbamoyl)furan-2-yl)-5-ethoxybenzoyl)azanediyl)diacetate | 731.3 |

Example 123 was prepared from (S)-dimethyl 2-(4-(5-((((2R,3R)-3-(N-(benzyloxy)formamido)-2-(2,4-difluorophenethyl)pentanamido)methyl)carbamoyl)furan-2-yl)-2-ethoxybenzamido)succinate by methods analogous to those described for Example 76 using THF and water instead of ethanol and water in Step 2.

| Ex. | Name | Structure | Name Step 1 | MS (m/z) (M + H+) Step 1 |
|---|---|---|---|---|
| 123 | (S)-2-(4-(5-((((2R,3R)-2-(2,4-difluorophenethyl)-3-(N-hydroxyformamido)pentanamido)methyl)carbamoyl)furan-2-yl)-2-ethoxybenzamido)succinic acid | 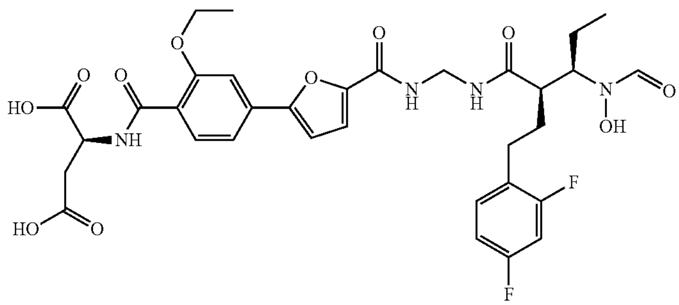 [SMILES: CCOc1cc(-c2ccc(C(=O)NCNC(=O)[C@H](CCc3ccc(F)cc3F)[C@@H](CC)N(O)C=O)o2)ccc1C(=O)N[C@@H](CC(=O)O)C(=O)O] | (S)-dimethyl 2-(4-(5-((((2R,3R)-2-(2,4-difluorophenethyl)-3-(N-hydroxyformamido)pentanamido)methyl)carbamoyl)furan-2-yl)-2-ethoxybenzamido)succinate | 731.3 |

Example 124 was prepared from dimethyl 2,2'-((4-(5-(((((2R,3R)-3-(N-(benzyloxy)formamido)-2-phenethylpentanamido)methyl)carbamoyl)furan-2-yl)-2-ethoxybenzoyl)azanediyl)diacetate by methods analogous to those described for Example 76.

| Ex. | Name | Structure | Name Step 1 | MS (m/z) (M + H+) Step 1 |
|---|---|---|---|---|
| 124 | 2,2'-((2-ethoxy-4-(5-((((2R,3R)-3-(N-hydroxyformamido)-2-phenethylpentanamido)methyl)carbamoyl)furan-2-yl)benzoyl)azanediyl)diacetic acid | 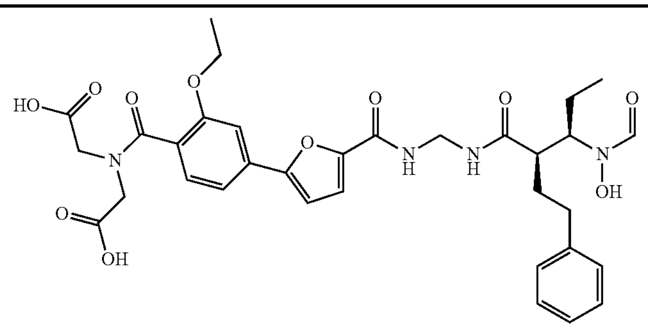 | 2,2'-((2-ethoxy-4-(5-((((2R,3R)-3-(N-hydroxyformamido)-2-phenethylpentanamido)methyl)carbamoyl)furan-2-yl)benzoyl)azanediyl)diacetic acid | 667.2 |

Example 125 was prepared from (S)-dimethyl 2-(3-(5-((((R)-2-((R)-1-(N-(benzyloxy)formamido)propyl)heptanamido)methyl)carbamoyl)furan-2-yl)-5-(2-methoxy-2-oxoethoxy)benzamido)succinate by methods analogous to those described for Example 76 using MeOH and water instead of ethanol and water in Step 2.

| Ex. | Name | Structure | Name Step 1 | MS (m/z) (M + H+) Step 1 |
|---|---|---|---|---|
| 125 | (S)-2-(3-(carboxymethoxy)-5-(5-((((R)-2-((R)-1-(N-hydroxyformamido)propyl)heptanamido)methyl)carbamoyl)furan-2-yl)benzamido)succinic acid | 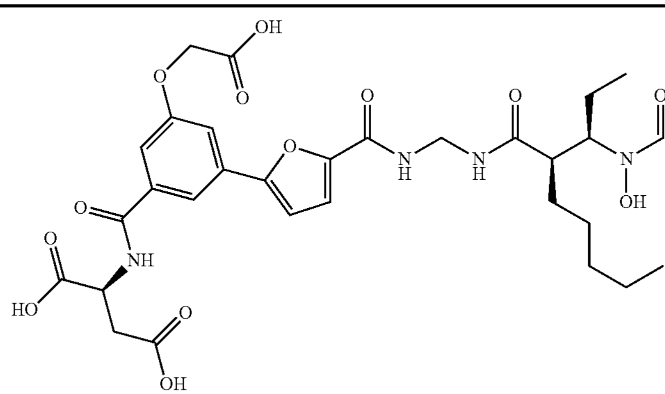 | (S)-dimethyl 2-(3-(5-((((R)-2-((R)-1-(N-hydroxyformamido)propyl)heptanamido)methyl)carbamoyl)furan-2-yl)-5-(2-methoxy-2-oxoethoxy)benzamido)succinate | 705.3 |

Example 126 was prepared from (S)-dimethyl 2-(4-(5-((((R)-2-((R)-1-(N-(benzyloxy)formamido)propyl)heptanamido)methyl)carbamoyl)furan-2-yl)-2-(2-methoxy-2-oxoethoxy)benzamido)succinate by methods analogous to those described for Example 76 using MeOH and water instead of ethanol and water in Step 2.

| Ex. | Name | Structure | Name Step 1 | MS (m/z) (M + H+) Step 1 |
|---|---|---|---|---|
| 126 | (S)-2-(2-(carboxymethoxy)-4-(5-((((R)-2-((R)-1-(N-hydroxyformamido)propyl)heptanamido)methyl)carbamoyl)furan-2-yl)benzamido)succinic acid | 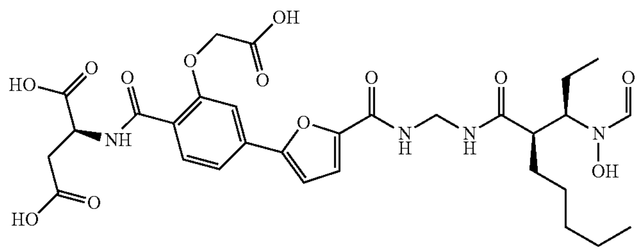 [SMILES: CCCCC[C@@H](C(=O)NCNC(=O)c1ccc(-c2ccc(C(=O)N[C@@H](CC(=O)O)C(=O)O)c(OCC(=O)O)c2)o1)[C@@H](CC)N(O)C=O] | (S)-dimethyl 2-(4-(5-((((R)-2-((R)-1-(N-hydroxyformamido)propyl)heptanamido)methyl)carbamoyl)furan-2-yl)-2-(2-methoxy-2-oxoethoxy)benzamido)succinate | 705.3 |

Example 127 was prepared from (R)-dimethyl 2-(4-(5-(((((2R,3R)-3-(N-(benzyloxy)formamido)-2-phenethylpentanamido)methyl)carbamoyl)furan-2-yl)-2-ethoxybenzamido)succinate by methods analogous to those described for Example 76 using MeOH and water instead of ethanol and water in Step 2.

| Ex. | Name | Structure | Name Step 1 | MS (m/z) (M + H+) Step 1 |
|---|---|---|---|---|
| 127 | (S)-2-(2-ethoxy-4-(5-(((((2R,3R)-3-(N-hydroxyformamido)-2-phenethylpentanamido)methyl)carbamoyl)furan-2-yl)benzamido)succinic acid | 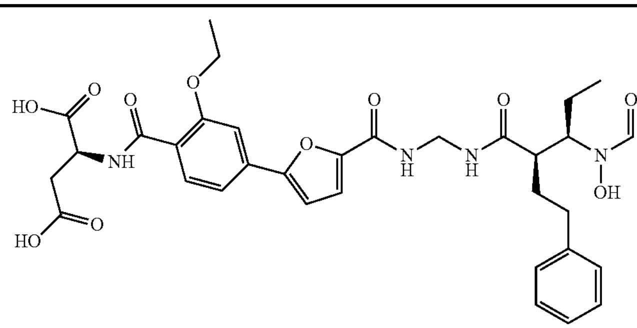 | (S)-dimethyl 2-(2-ethoxy-4-(5-(((((2R,3R)-3-(N-hydroxyformamido)-2-phenethyl-pentanamido)methyl)carbamoyl)furan-2-yl)benzamido)succinate | 695.3 |

Example 128 was prepared from methyl 4-(5-((((R)-2-((R)-1-(N-(benzyloxy)formamido)propyl)heptanamido)methyl)carbamoyl)furan-2-yl)-2-ethoxy-6-hydroxybenzoate by methods analogous to those described for Example 76 using DCM and methanol instead of ethanol and water in Step 1.

| Ex. | Name | Structure | Name Step 1 | MS (m/z) (M + H+) Step 1 |
|---|---|---|---|---|
| 128 | 2-ethoxy-6-hydroxy-4-(5-((((R)-2-((R)-1-(N-hydroxyformamido)propyl)heptanamido)methyl)carbamoyl)furan-2-yl)benzoic acid | 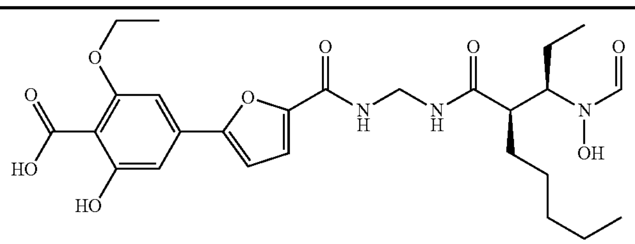 | methyl 2-ethoxy-6-hydroxy-4-(5-((((R)-2-((R)-1-(N-hydroxyformamido)propyl)heptanamido)methyl)carbamoyl)furan-2-yl)benzoate | 548.3 |

Example 129 was prepared from dimethyl 4-(5-((((R)-2-((R)-1-(N-(benzyloxy)formamido)propyl)heptanamido)methyl)carbamoyl)furan-2-yl)phthalate by methods analogous to those described for Example 76 using MeOH instead of MeOH and DCM in Step 1 and using acetonitrile and water instead of ethanol and water in Step 2.

| Ex. | Name | Structure | Name Step 1 | MS (m/z) (M + H$^+$) Step 1 |
|---|---|---|---|---|
| 129 | 4-(5-((((R)-1-(N-hydroxyformamido)propyl)heptanamido)methyl)carbamoyl)furan-2-yl)phthalic acid | 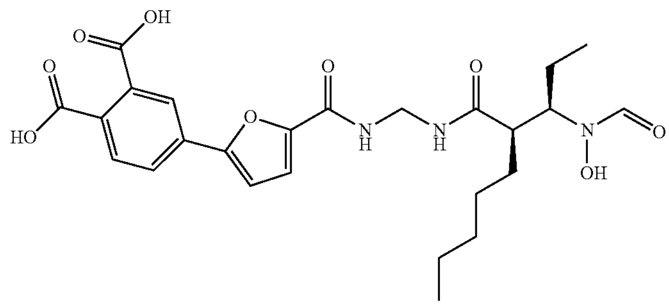 [SMILES: CCCCC[C@@H](C(=O)NCNC(=O)c1ccc(-c2ccc(C(=O)O)c(C(=O)O)c2)o1)[C@@H](CC)N(O)C=O] | dimethyl 4-(5-((((R)-2-((R)-1-(N-hydroxyformamido)propyl)heptanamido)methyl)carbamoyl)furan-2-yl)phthalate | 546.1 |

Example 130 was prepared from methyl 2-((3-(5-((((R)-2-((R)-1-(N-(benzyloxy)formamido)propyl)heptanamido)methyl)carbamoyl)furan-2-yl)-5-ethoxybenzyl)(methyl)amino)acetate by methods analogous to those described for Example 76 using MeOH instead of MeOH and DCM in Step 1.

| Ex. | Name | Structure | Name Step 1 | MS (m/z) (M + H$^+$) Step 1 |
|---|---|---|---|---|
| 130 | 2-((3-ethoxy-5-(5-((((R)-2-((R)-1-(N-hydroxyformamido)propyl)heptanamido)methyl)carbamoyl)furan-2-yl)benzyl)(methyl)amino)acetic acid | 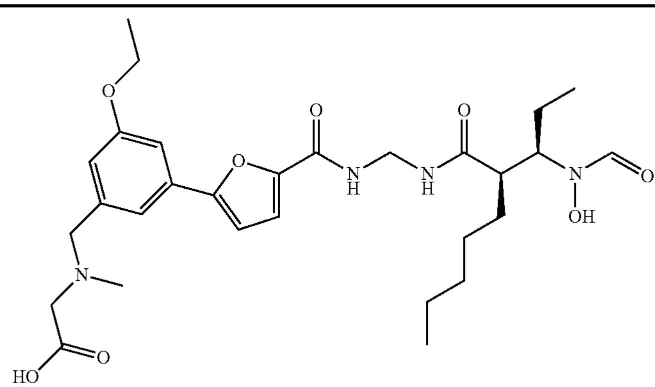 | methyl 2-((3-ethoxy-5-(5-((((R)-2-((R)-1-(N-hydroxyformamido)propyl)heptanamido)methyl)carbamoyl)furan-2-yl)benzyl)(methyl)amino)acetate | 589.2 |

Example 131 was prepared from methyl 3-(2-amino-2-oxoethoxy)-5-(5-((((R)-2-((R)-1-(N-(benzyloxy)formamido)propyl)heptanamido)methyl)carbamoyl)furan-2-yl)benzoate by methods analogous to those described for Example 76.

| Ex. | Name | Structure | Name Step 1 | MS (m/z) (M + H+) Step 1 |
|---|---|---|---|---|
| 131 | 3-(2-amino-2-oxoethoxy)-5-(5-((((R)-2-((R)-1-(N-hydroxyformamido)propyl)heptanamido)methyl)carbamoyl)furan-2-yl)benzoic acid | 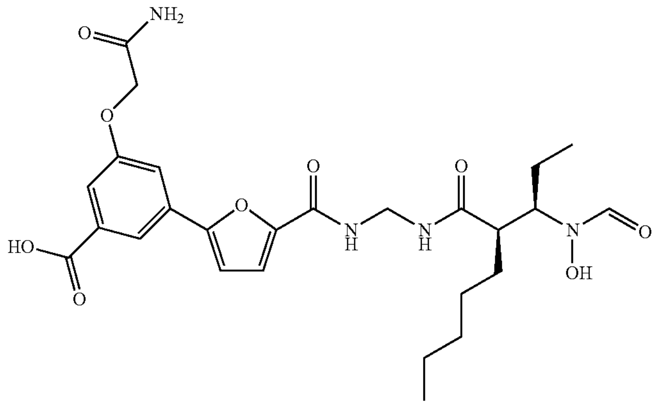 [SMILES: CCCCC[C@@H](C(=O)NCNC(=O)c1ccc(-c2cc(OCC(N)=O)cc(C(=O)O)c2)o1)[C@@H](CC)N(O)C=O] | methyl 3-(2-amino-2-oxoethoxy)-5-(5-((((R)-2-((R)-1-(N-hydroxyformamido)propyl)heptanamido)methyl)carbamoyl)furan-2-yl)benzoate | 561.2 |

Example 132 was prepared from R)-dimethyl 2-(4-(5-((((R)-2-((R)-1-(N-(benzyloxy)formamido)propyl)heptanamido)methyl)carbamoyl)furan-2-yl)-2-ethoxybenzamido)succinate by methods analogous to those described for Example 76 using THF and water instead of ethanol and water in Step 2.

| Ex. | Name | Structure | Name Step 1 | MS (m/z) (M + H+) Step 1 |
|---|---|---|---|---|
| 132 | (R)-2-(2-ethoxy-4-(5-((((R)-2-((R)-1-(N-hydroxyformamido)propyl)heptanamido)methyl)carbamoyl)furan-2-yl)benzamido)succinic acid | 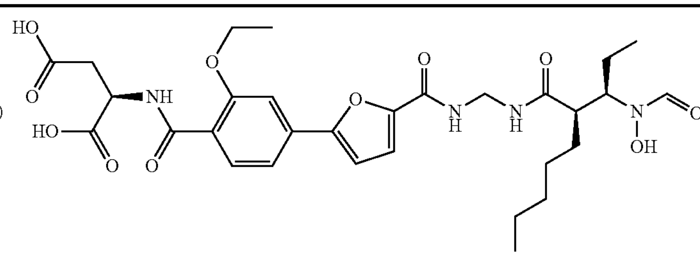 | (R)-dimethyl 2-(2-ethoxy-4-(5-((((R)-2-((R)-1-(N-hydroxyformamido)propyl)heptanamido)methyl)carbamoyl)furan-2-yl)benzamido)succinate | 561.2 |

Example 133 was prepared from (R)-dimethyl 2-(4-(5-((((R)-2-((R)-1-(N-(benzyloxy)formamido)propyl)heptanamido)methyl)carbamoyl)furan-2-yl)benzamido)succinate by methods analogous to those described for Example 76 using THF and a 1M solution of LiOH instead of ethanol/water mixture and solid LiOH in step 2.

| Ex. | Name | Structure | Name Step 1 | MS (m/z) (M + H+) Step 1 |
|---|---|---|---|---|
| 133 | ((R)-2-(4-(5-((((R)-2-((R)-1-(N-hydroxyformamido)propyl)heptanamido)methyl)carbamoyl)furan-2-yl)benzamido)succinic acid | 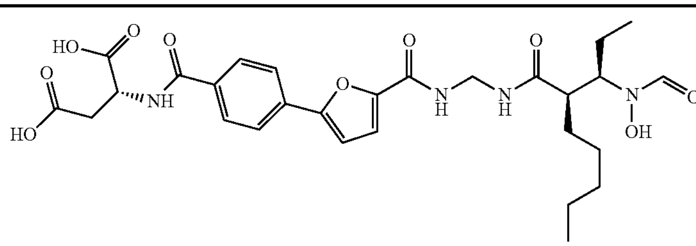 | (R)-dimethyl 2-(4-(5-((((R)-2-((R)-1-(N-hydroxyformamido)propyl)heptanamido)methyl)carbamoyl)furan-2-yl)benzamido)succinate | 617.3 |

Example 134 was prepared from (S)-dimethyl 2-(4-(5-((((R)-2-((R)-1-(N-(benzyloxy)formamido)propyl)heptanamido)methyl)carbamoyl)furan-2-yl)benzamido)pentanedioate by methods analogous to those described for Example 76 using MeOH/water mixture and a 1M solution of LiOH instead of ethanol/water mixture and solid LiOH in step 2.

| Ex. | Name | Structure | Name Step 1 | MS (m/z) (M + H+) Step 1 |
|---|---|---|---|---|
| 134 | (S)-2-(4-(5-((((R)-2-((R)-1-(N-hydroxyformamido)propyl)heptanamido)methyl)carbamoyl)furan-2-yl)benzamido)pentanedioic acid | 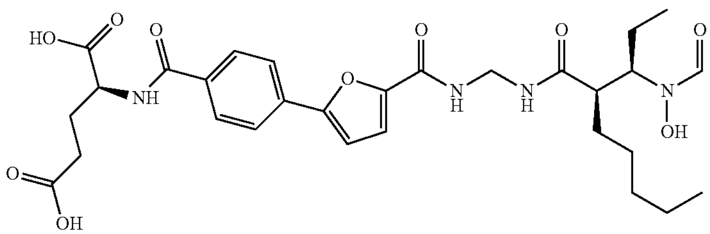 [SMILES: CCCCC[C@@H](C(=O)NCNC(=O)c1ccc(-c2ccc(C(=O)N[C@@H](CCC(=O)O)C(=O)O)cc2)o1)[C@@H](CC)N(O)C=O] | (S)-dimethyl 2-(4-(5-((((R)-2-((R)-1-(N-hydroxyformamido)propyl)heptanamido)methyl)carbamoyl)furan-2-yl)benzamido)pentanedioate | 631.8 |

Example 135 was prepared from (S)-dimethyl 2-(4-(5-((((R)-2-((R)-1-(N-(benzyloxy)formamido)propyl)heptanamido)methyl)carbamoyl)furan-2-yl)-2-ethoxybenzamido)pentanedioate by methods analogous to those described for Example 76 using MeOH/water mixture and a 1M solution of LiOH instead of ethanol/water mixture and solid LiOH in step 2.

| Ex. | Name | Structure | Name Step 1 | MS (m/z) (M + H+) Step 1 |
|---|---|---|---|---|
| 135 | (S)-2-(2-ethoxy-4-(5-((((R)-2-((R)-1-(N-hydroxyformamido)propyl)heptanamido)methyl)carbamoyl)furan-2-yl)benzamido)pentanedioic acid | 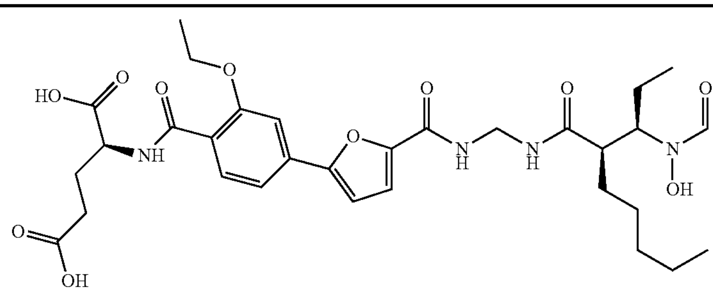 | (S)-dimethyl 2-(2-ethoxy-4-(5-((((R)-2-((R)-1-(N-hydroxyformamido)propyl)heptanamido)methyl)carbamoyl)furan-2-yl)benzamido)pentanedioate | 675.7 |

Example 136 was prepared from dimethyl 2,2'-((4-(5-((((R)-2-((R)-1-(N-(benzyloxy)formamido)propyl)heptanamido)methyl)carbamoyl)furan-2-yl)benzoyl)azanediyl)diacetate by methods analogous to those described for Example 76 using methanol and water instead of ethanol and water in step 2.

| Ex. | Name | Structure | Name Step 1 | MS (m/z) (M + H+) Step 1 |
|---|---|---|---|---|
| 136 | 2,2'-((4-(5-((((R)-2-((R)-1-(N-hydroxyformamido)propyl)heptanamido)methyl)carbamoyl)furan-2-yl)benzoyl)azanediyl)diacetic acid | 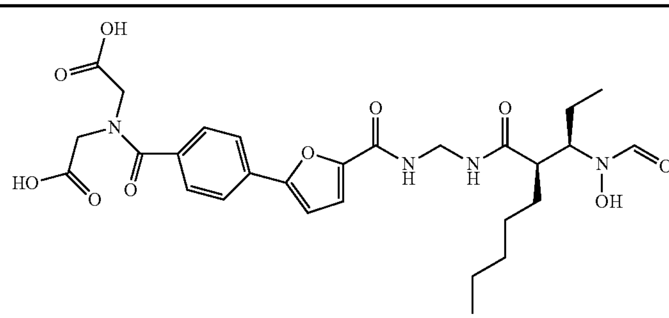 | dimethyl 2,2'-((4-(5-((((R)-2-((R)-1-(N-hydroxyformamido)propyl)heptanamido)methyl)carbamoyl)furan-2-yl)benzoyl)azanediyl)diacetate | 617.4 |

Example 137

(((3-ethoxy-5-(5-((((R)-2-((R)-1-(N-hydroxyformamido) propyl)heptanamido)methyl)carbamoyl)furan-2-yl)benzyl)amino)methyl)phosphonic acid, trifluoroacetic acid salt

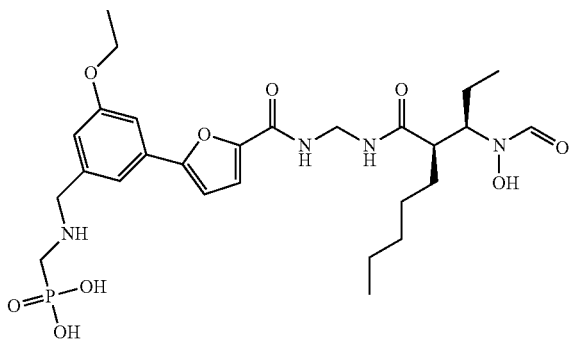 [SMILES: CCCCC[C@@H](C(=O)NCNC(=O)c1ccc(-c2cc(CNCP(=O)(O)O)cc(OCC)c2)o1)[C@@H](CC)N(O)C=O]

Step 1: Diethyl (((3-ethoxy-5-(5-((((R)-2-((R)-1-(N-hydroxyformamido)propyl)heptanamido)methyl)carbamoyl)furan-2-yl)benzyl)amino)methyl)phosphonate

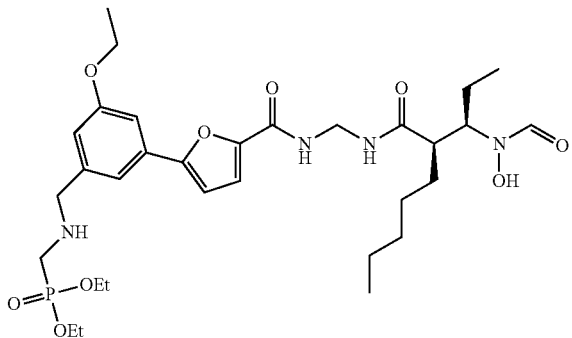

Diethyl (((3-(5-((((R)-2-((R)-1-(N-(benzyloxy)formamido)propyl)hexanamido)methyl)carbamoyl)furan-2-yl)-5-ethoxybenzyl)amino)methyl)phosphonate (0.6 g, 0.8 mmol) was dissolved in MeOH. 10% Pd/C (0.09 g, 0.08 mmol) followed by ammonium formate (0.26 g, 4.12 mmol) were added. The reaction was stirred for 2 h then Pd/C (0.09 g, 0.08 mmol and ammonium formate (0.26 g, 4.12 mmol) were added. The reaction mixture was filtered through celite, and the filtrate was concentrated, suspended in DCM and filtered. After the filtrate was concentrated, it was redissolved in MeOH and resubjected to the same conditions. The reaction mixture was filtered through celite and the filtrate was concentrated to obtain the title compound (0.25 g, 46%) as a yellow oil. MS (m/z) 653.2 (M+H+).

Step 2: (((3-ethoxy-5-(5-((((R)-2-((R)-1-(N-hydroxyformamido)propyl)heptanamido)methyl)carbamoyl)furan-2-yl)benzyl)amino)methyl)phosphonic acid, trifluoroacetic acid salt Diethyl (((3-ethoxy-5-(5-((((R)-2-((R)-1-(N-hydroxyformamido)propyl)heptanamido)methyl)carbamoyl)furan-2-yl)benzyl)amino)methyl)phosphonate (0.26 g, 0.4 mmol) was dissolved in DCM and treated with TMS-Br (154 ul, 1.2 mmol). The reaction stirred for 4 hours and 3 more eq of TMS-Br was added and the reaction was stirred for another 8 hours. The material was then purified via reverse phase HPLC (Sunfire 30×150 mm Acetonitrile: Water TFA 20-60%, flow rate 50 ml/min, gradient 16 min) to obtain the title compound as a white solid (0.035 g, 12%). MS (m/z) 597.2 (M+H+).

Example 138 was prepared from dimethyl (3-(benzyloxy)-5-(5-((((R)-2-((R)-1-(N-(benzyloxy)formamido)propyl)heptanamido)methyl)carbamoyl)furan-2-yl)phenyl) phosphonate by methods analogous to those described in Example 137.

| Ex. | Name | Structure | Name Step 1 | MS (m/z) (M + H+) Step 1 |
|---|---|---|---|---|
| 138 | (3-hydroxy-5-(5-((((R)-2-((R)-1-(N-hydroxyformamido) propyl)heptanamido) methyl) carbamoyl)furan-2-yl)phenyl) phosphonic acid | 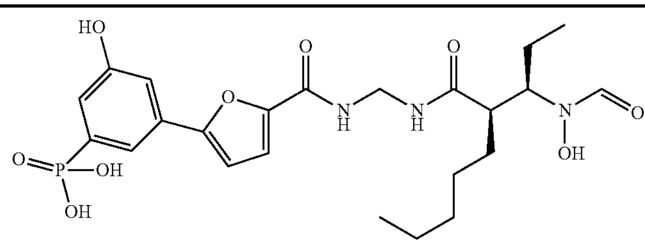 | dimethyl (3-hydroxy-5-(5-((((R)-2-((R)-1-(N-hydroxyformamido) propyl)heptanamido) methyl)carbamoyl) furan-2-yl)phenyl) phosphonate | 554.2 |

Example 139 was prepared from diethyl ((4-(5-((((R)-2-((R)-1-(N-(benzyloxy)formamido)propyl)heptanamido)methyl)carbamoyl)furan-2-yl)-2-ethoxybenzamido)methyl) phosphonate by methods analogous to those described in Example 137 using DCM and MeOH instead of MeOH in Step 1.

| Ex. | Name | Structure | Name Step 1 | MS (m/z) (M + H+) Step 1 |
|---|---|---|---|---|
| 139 | ((2-ethoxy-4-(5-((((R)-2-((R)-1-(N-hydroxyformamido)propyl)heptanamido)methyl)carbamoyl)furan-2-yl)benzamido)methyl)phosphonic acid | 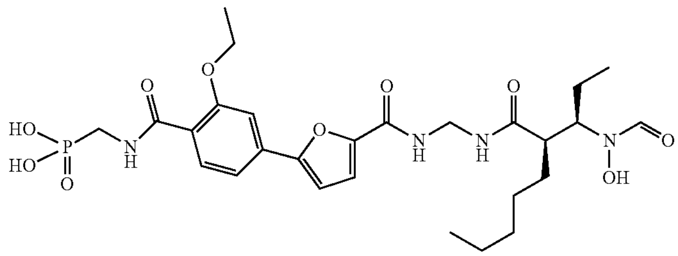 | diethyl ((2-ethoxy-4-(5-((((R)-2-((R)-1-(N-hydroxyformamido)propyl)heptanamido)methyl)carbamoyl)furan-2-yl)benzamido)methyl)phosphonate | 667.5 (M + H) |

Example 140 was prepared from dimethyl (3-(5-((((2R,3R)-3-(N-(benzyloxy)formamido)-2-phenethylpentanamido)methyl)carbamoyl)furan-2-yl)-5-ethoxyphenyl)phosphonate by methods analogous to those described in Example 137 using DCM and MeOH instead of MeOH in Step 1 and using acetonitrile instead of DCM in Step 2.

| Ex. | Name | Structure | Name Step 1 | MS (m/z) (M + H+) Step 1 |
|---|---|---|---|---|
| 140 | (3-ethoxy-5-(5-((((2R,3R)-3-(N-hydroxyformamido)-2-phenethylpentamido)methyl)carbamoyl)furan-2-yl)phenyl)phosphonic acid | 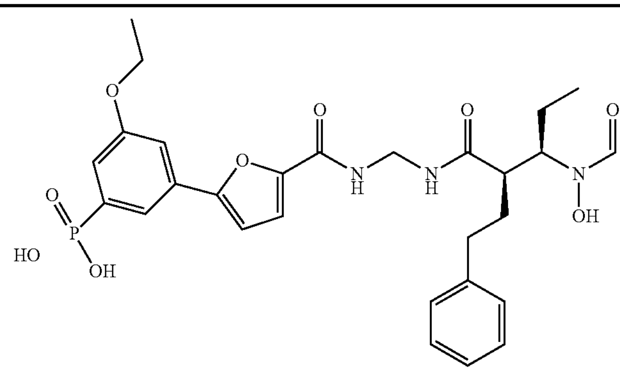 | dimethyl (3-ethoxy-5-(5-((((2R,3R)-3-(N-hydroxyformamido)-2-phenethylpentanamido)methyl)carbamoyl)furan-2-yl)phenyl)phosphonate | 616.3 |

Example 141 was prepared from dimethyl (3-(5-((((2R,3R)-3-(N-(benzyloxy)formamido)-2-(2-(naphthalen-2-yl)ethyl)pentanamido)methyl)carbamoyl)furan-2-yl)-5-ethoxyphenyl)phosphonate by methods analogous to those described in Example 137 using DCM and MeOH instead of MeOH in Step 1.

| Ex. | Name | Structure | Name Step 1 | MS (m/z) (M + H+) Step 1 |
|---|---|---|---|---|
| 141 | (3-ethoxy-5-(5-((((2R,3R)-3-(N-hydroxyformamido)-2-(2-(naphthalen-2-yl)ethyl)pentanamido)methyl)carbamoyl)furan-2-yl)phenyl)phosphonic acid | 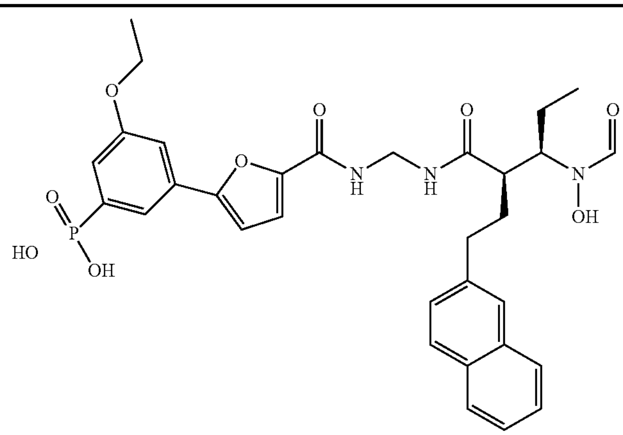 | dimethyl (3-ethoxy-5-(5-((((2R,3R)-3-(N-hydroxyformamido)-2-(2-(naphthalen-2-yl)ethyl)pentanamido)methyl)carbamoyl)furan-2-yl)phenyl)phosphonate | 666.1 |

Example 142 was prepared from diethyl ((2-(benzyloxy)-4-(5-((((R)-2-((R)-1-(N-(benzyloxy)formamido)propyl)heptanamido)methyl)carbamoyl)furan-2-yl)benzamido)methyl)phosphonate by methods analogous to those described in Example 137 using DCM and MeOH instead of MeOH in Step 1.

| Ex. | Name | Structure | Name Step 1 | MS (m/z) (M + H⁺) Step 1 |
|---|---|---|---|---|
| 142 | ((2-hydroxy-4-(5-((((R)-2-((R)-1-(N-hydroxyformamido)propyl)heptanamido)methyl)carbamoyl)furan-2-yl)benzamido)methyl)phosphonic acid | 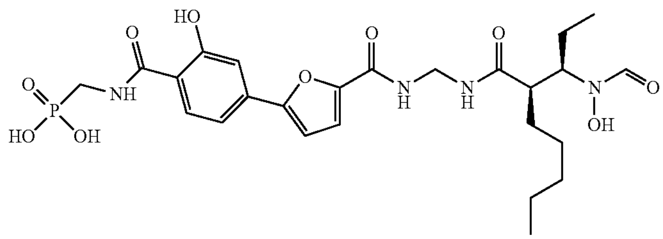 [SMILES: CCCCC[C@@H](C(=O)NCNC(=O)c1ccc(-c2ccc(C(=O)NCP(=O)(O)O)c(O)c2)o1)[C@@H](CC)N(O)C=O] | diethyl ((2-hydroxy-4-(5-((((R)-2-((R)-1-(N-hydroxyformamido)propyl)heptanamido)methyl)carbamoyl)furan-2-yl)benzamido)methyl)phosphonate | 639.3 |

Example 143 was prepared from diethyl ((4-(5-((((R)-2-((R)-1-(N-(benzyloxy)formamido)propyl)heptanamido)methyl)carbamoyl)furan-2-yl)benzamido)methyl)phosphonate by methods analogous to those described in Example 137 using DCM and MeOH instead of MeOH in Step 1.

| Ex. | Name | Structure | Name Step 1 | MS (m/z) (M + H⁺) Step 1 |
|---|---|---|---|---|
| 143 | ((4-(5-((((R)-2-((R)-1-(N-hydroxyformamido)propyl)heptanamido)methyl)carbamoyl)furan-2-yl)benzamido)methyl)phosphonic acid | 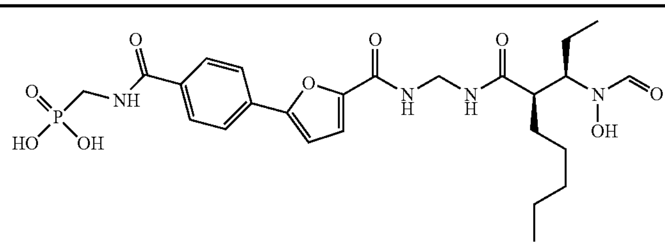 | diethyl ((4-(5-((((R)-2-((R)-1-(N-hydroxyformamido)propyl)heptanamido)methyl)carbamoyl)furan-2-yl)benzamido)methyl)phosphonate | 623.3 |

Example 144 was prepared from diethyl ((4-(5-((((R)-2-((R)-1-(N-(benzyloxy)formamido)propyl)heptanamido)methyl)carbamoyl)furan-2-yl)-2-methylbenzamido)methyl)phosphonate by methods analogous to those described in Example 137 using DCM and MeOH instead of MeOH in Step 1.

| Ex. | Name | Structure | Name Step 1 | MS (m/z) (M + H⁺) Step 1 |
|---|---|---|---|---|
| 144 | ((4-(5-((((R)-2-((R)-1-(N-hydroxyformamido)propyl)heptanamido)methyl)carbamoyl)furan-2-yl)-2-methylbenzamido)methyl)phosphonic acid | 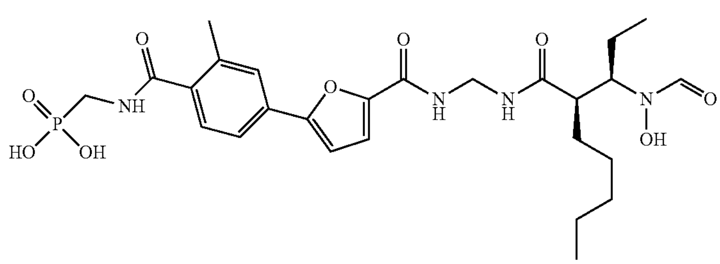 [SMILES: CCCCC[C@@H](C(=O)NCNC(=O)c1ccc(-c2ccc(C(=O)NCP(=O)(O)O)c(C)c2)o1)[C@@H](CC)N(O)C=O] | diethyl ((4-(5-((((R)-2-((R)-1-(N-hydroxyformamido)propyl)heptanamido)methyl)carbamoyl)furan-2-yl)-2-methylbenzamido)methyl)phosphonate | 637.3 |

Example 145 was prepared from 2-(3-(5-((((R)-2-((R)-1-(N-(benzyloxy)formamido)propyl)heptanamido)methyl)carbamoyl)furan-2-yl)-5-(dimethoxyphosphoryl)phenoxy)acetic acid by methods analogous to those described in Example 98 using Pd(OH)$_2$ instead of Pd/C and ethanol instead of an ethanol/methanol mixture in Step 2 and a DCM and acetonitrile mixture instead of DCM in Step 1.

| Ex. | Name | Structure | Name Step 1 | MS (m/z) (M + H$^+$) Step 1 |
|---|---|---|---|---|
| 145 | 2-(3-(5-((((R)-2-((R)-1-(N-hydroxyformamido)propyl)heptanamido)methyl)carbamoyl)furan-2-yl)-5-phosphonophenoxy)acetic acid | 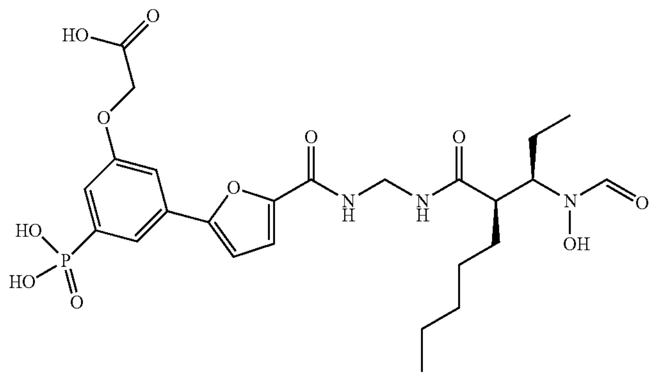 [SMILES: CCCCC[C@@H](C(=O)NCNC(=O)c1ccc(-c2cc(OCC(=O)O)cc(P(=O)(O)O)c2)o1)[C@@H](CC)N(O)C=O] | 2-(3-(5-((((R)-2-((R)-1-(N-(benzyloxy)formamido)propyl)heptanamido)methyl)carbamoyl)furan-2-yl)-5-phosphonophenoxy)acetic acid | 674.1 |

Example 146

2-hydroxy-4-(5-((((R)-2-((R)-1-(N-hydroxyformamido)propyl)heptanamido)methyl)carbamoyl)furan-2-yl)benzoic acid

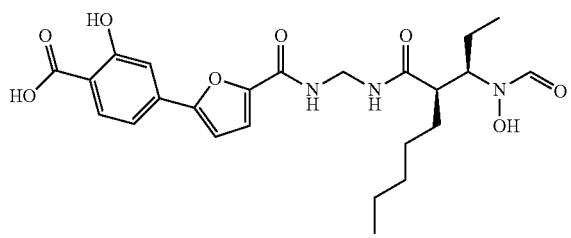 [SMILES: CCCCC[C@@H](C(=O)NCNC(=O)c1ccc(-c2ccc(C(=O)O)c(O)c2)o1)[C@@H](CC)N(O)C=O]

Step 1: 4-(5-((((R)-2-((R)-1-(N-(benzyloxy)formamido)propyl)heptanamido)methyl)carbamoyl)furan-2-yl)-2-hydroxybenzoic acid

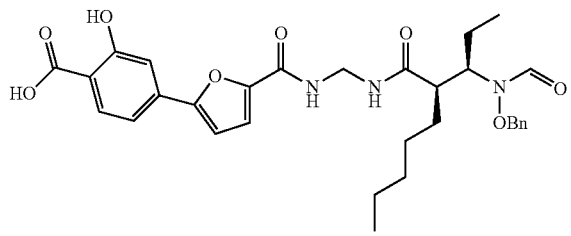 [SMILES: CCCCC[C@@H](C(=O)NCNC(=O)c1ccc(-c2ccc(C(=O)O)c(O)c2)o1)[C@@H](CC)N(C=O)OCc1ccccc1]

To a 20 ml microwave vial equipped with a teflon stir bar was added methyl 4-(5-((((R)-2-((R)-1-(N-(benzyloxy)formamido)propyl)heptanamido)methyl)carbamoyl)furan-2-yl)-2-hydroxybenzoate (300 mg, 0.51 mmol), 1,1,1-trifluoro-2-iodoethane (125 µl, 1.26 mmol), and K$_2$CO$_3$ (349 mg, 2.53 mmol), sequentially at 25° C. Acetonitrile (2402 µl) was added and the reaction heated in the microwave at 150° C. for ½ hour. The material was then redissolved in DCM and the material was cooled at −20° C. for 5 days. The organic solvents were evaporated in vacuo. The organic layer was extracted with 2M NaOH (2×10 mL). The aq layers were combined, cooled to 0° C. with ice, then quenched with HCl (2.0 M) to pH<4. The organic layer was dried over Na$_2$SO$_4$, filtered, and solvents removed in vacuo. The crude material (300 mg) was collected and purified by HPLC (Waters Sunfire 30×150 mm Acetonitrile: Water TFA 50-100%) to give the title compound as a white solid (55 mg, 0.090 mmol, 17.84% yield). MS (m/z) 580.2 (M+H+).

Step 2: 2-hydroxy-4-(5-((((R)-2-((R)-1-(N-hydroxyformamido)propyl)heptanamido)methyl)carbamoyl)furan-2-yl)benzoic acid To a 250 mL round-bottomed-flask equipped with a teflon stir bar was added Pd(OH)$_2$ (6.66 mg, 9.49 µmol). A solution of 4-(5-((((R)-2-((R)-1-(N-(benzyloxy)formamido)propyl)heptanamido)methyl)carbamoyl)furan-2-yl)-2-hydroxybenzoic acid (55 mg, 0.095 mmol) in ethanol (1.9 ml) was added. An atmosphere of H$_2$ was applied and the reaction stirred vigorously at 25° C. for 5 h. The reaction mixture was filtered through a plug of Celite®, eluting with DCM. The filtrate was concentrated in vacuo to provide a crude material which was placed in the freezer ~48 h. The semi-pure solid was dissolved in 20 ml EtOAc. 20 ml 2N NaOH was added with ca. 1 ml MeOH to aid in dissolution. After the solid was fully dissolved, the organic solvents were removed by rotary evaporation. The aq layer was extracted with DCM (3×5 ml). The aq. layer was separated, cooled to 0° C., and brought to a pH of <4.0, and the aq. layer was extracted with 20 ml EtOAc. The layers were separated, the organic layer was dried with Na$_2$SO$_4$, filtered and solvents evaporated to provide the title compound (30 mg, 0.058 mmol, 61.4% yield) as an off-white solid.

Example 147

(3-ethoxy-5-(5-((((R)-2-((R)-1-(N-hydroxyformamido)propyl)heptanamido)methyl)carbamoyl)furan-2-yl)phenyl)phosphonic acid, (−)-1-Deoxy-1-(methylamino)-D-glucitol salt

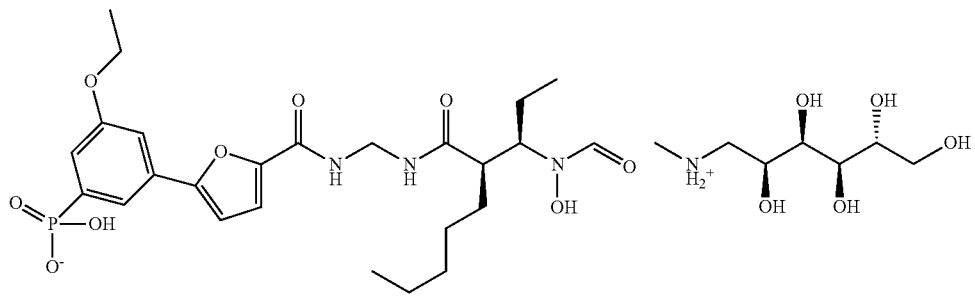 [SMILES: CCCCC[C@@H](C(=O)NCNC(=O)c1ccc(-c2cc(OCC)cc(P(=O)([O-])O)c2)o1)[C@@H](CC)N(O)C=O ; C[NH2+]C[C@H](O)[C@@H](O)[C@H](O)[C@H](O)CO]

Step 1: (3-ethoxy-5-(5-((((R)-2-((R)-1-(N-hydroxyformamido)propyl)heptanamido)methyl)carbamoyl)furan-2-yl)phenyl)phosphonic acid, (−)-1-Deoxy-1-(methylamino)-D-glucitol salt (3-ethoxy-5-(5-((((R)-2-((R)-1-(N-hydroxyformamido)propyl)heptanamido)methyl)carbamoyl)furan-2-yl)phenyl)phosphonic acid (265 mg, 0.479 mmol) was slurried in ethyl acetate (2.65 ml) and tetrahydrofuran (27 ml). (2R,3R,4R,5S)-6-(methylamino)hexane-1,2,3,4,5-pentaol (93 mg, 0.48 mmol) was added. The resulting slurry was stirred at 23° C. for 15 minutes and the slurry was seeded with seed crystals of title compound and then temperature cycled from 40° C. to 5° C. at 1 hour increments for 6 hours, followed by 18 hours at 23° C. The slurry was then temperature cycled from 40° C. to 5° C. at 1 hour increments for 6 hours, followed by 18 hours at 23° C., followed by temperature cycling from 45° C. to 5° C. at 1 hour increments for 6 hours, followed by 18 hours at 23° C., followed by temperature cycling from 45° C. to 5° C. at 1 hour increments for 6 hours, followed by 18 hours at 23° C., followed by temperature cycling from 45° C. to 5° C. at 1 hour increments for 6 hours. After the last 5° C. cycle, the slurry was filtered, rinsed with ethyl acetate, and the solid collected and dried under vacuum for 72 hours to the title compound (330 mg, 0.44 mmol, 92% yield) as a white solid.

Example 148

(3-ethoxy-5-(5-((((R)-2-((R)-1-(N-hydroxyformamido)propyl)heptanamido)methyl)carbamoyl)furan-2-yl)phenyl)phosphonic acid, 2-amino-2-(hydroxymethyl)-1,3-propanediol salt

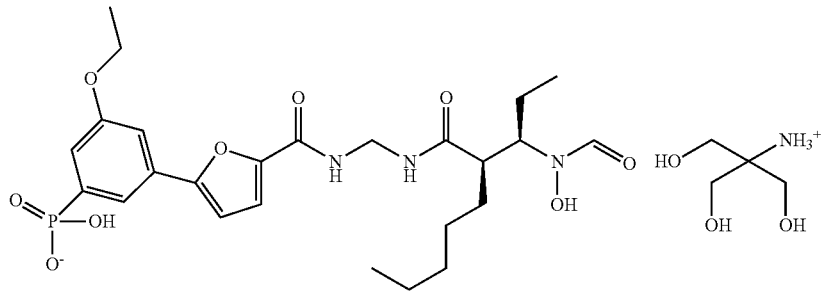 [SMILES: CCCCC[C@@H](C(=O)NCNC(=O)c1ccc(-c2cc(OCC)cc(P(=O)([O-])O)c2)o1)[C@@H](CC)N(O)C=O ; [NH3+]C(CO)(CO)CO]

Step 1: (3-ethoxy-5-(5-((((R)-2-((R)-1-(N-hydroxyformamido)propyl)heptanamido)methyl)carbamoyl)furan-2-yl)phenyl)phosphonic acid, 2-amino-2-(hydroxymethyl)-1,3-propanediol salt (3-ethoxy-5-(5-((((R)-2-((R)-1-(N-hydroxyformamido)propyl)heptanamido)methyl)carbamoyl)furan-2-yl)phenyl)phosphonic acid (390 mg, 0.71 mmol) was slurried in ethyl acetate (7.82 ml). 2-amino-2-(hydroxymethyl)propane-1,3-diol (86 mg, 0.71 mmol) was added. The resulting slurry was stirred at 23° C. for 15 minutes and the slurry was seeded with seed crystals of title compound and then temperature cycled from 40° C. to 5° C. at 1 hour increments for 6 hours, followed by 18 hours at 23° C. The slurry was then temperature cycled from 40° C. to 5° C. at 1 hour increments for 6 hours, followed by 18 hours at 23° C., followed by temperature cycling from 45° C. to 5° C. at 1 hour increments for 6 hours, followed by 18 hours at 23° C., followed by temperature cycling from 45° C. to 5° C. at 1 hour increments for 6 hours, followed by 18 hours at 23° C., followed by temperature cycling from 45° C. to 5° C. at 1 hour increments for 6 hours. After the last 5° C. cycle, the slurry was filtered, rinsed with ethyl acetate, and the solid collected and dried under vacuum for 72 hours to obtain the title compound (375 mg, 0.56 mmol, 79% yield) as a white solid.

Example 149

(3-ethoxy-5-(5-((((R)-2-((R)-1-(N-hydroxyforma-mido)propyl)heptanamido)methyl)carbamoyl)furan-2-yl)phenyl)phosphonic acid, calcium salt

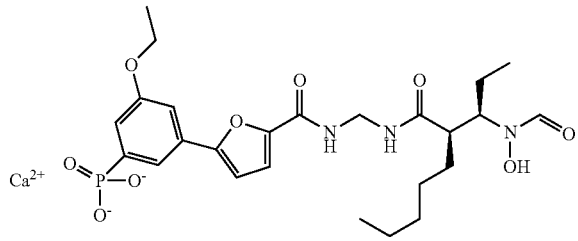 [SMILES: [Ca+2] ; CCCCC[C@@H](C(=O)NCNC(=O)c1ccc(-c2cc(OCC)cc(P(=O)([O-])[O-])c2)o1)[C@@H](CC)N(O)C=O]

Step 1: (3-ethoxy-5-(5-((((R)-2-((R)-1-(N-hydroxy-formamido)propyl)heptanamido)methyl)carbamoyl)furan-2-yl)phenyl)phosphonic acid, calcium salt (3-ethoxy-5-(5-((((R)-2-((R)-1-(N-hydroxyformamido)propyl)heptanamido)methyl)carbamoyl)furan-2-yl)phenyl)phosphonic acid (381 mg, 0.688 mmol) was slurried in ethyl acetate (7.6 ml). Calcium acetate (110 mg, 0.69 mmol) was added. The resulting slurry was stirred at 23° C. for 15 minutes and then temperature cycled from 45° C. to 5° C. at 1 hour increments for 6 hours, followed by 88 hours at −20° C. The slurry was then temperature cycled from 45° C. to 5° C. at 1 hour increments for 6 hours, followed by 18 hours at −20° C., followed by temperature cycling from 45° C. to 5° C. at 1 hour increments for 6 hours, followed by 18 hours at −20° C., followed by temperature cycling from 45° C. to 5° C. at 1 hour increments for 6 hours, followed by 186 hours at −20° C., followed by temperature cycling from 45° C. to 5° C. at 1 hour increments for 6 hours, followed by 18 hours at 23° C. The slurry was filtered, rinsed with ethyl acetate, and the solid collected and dried under vacuum for 72 hours to obtain the title compound (478 mg, 0.77 mmol) as a white solid.

Tabulated spectroscopic data for Examples 1-149:

| Ex. | $^1$H NMR | tR (min) | MS (m/z) |
|---|---|---|---|
| 1 | $^1$H NMR (400 MHz, DMSO-d6) δ ppm: 12.64 (br. s., 1H), 9.60 (s, 0.3H), 9.28 (s, 0.7H), 9.11-9.22 (m, 0.3H), 8.98-9.09 (m, 0.7H), 8.71-8.83 (m, 0.3H), 8.46-8.59 (m, 0.7H), 8.29 (s, 0.3H), 7.76 (s, 0.7H), 7.71 (d, J = 8.0 Hz, 1H), 7.56 (s, 2H), 7.28 (br. s., 2H), 4.47-4.79 (m, 2H), 4.13-4.30 (m, J = 6.8, 6.8, 6.8 Hz, 2.3H), 3.48-3.66 (m, 0.7H), 2.55-2.67 (m, 1H), 1.46-1.60 (m, 2H), 1.30-1.46 (m, 5H), 1.15 (d, J = 6.0 Hz, 6H), 0.78 (br. s., 6H) | 6.23 $^a$ | 518.3 (M + H$^+$) |
| 2 | $^1$H NMR (400 MHz, DMSO-d6) δ ppm: 9.96 (br. s., 0.4H), 9.56 (br. s., 0.6H), 9.08 (br. s., 1H), 8.63 (br. s., 1H), 8.23 (s, 0.4H), 7.92 (d, J = 7.3 Hz, 2H), 7.82(s, 0.6H), 7.44-7.51 (m, 2H), 7.37 (d, J = 8.8 Hz, 1H), 7.25 (d, J = 3.5 Hz, 1H), 7.11 (d, J = 3.5 Hz, 1H), 4.63 (m, 2H), 3.47-3.64 (m, 2H), 2.63-2.79 (m, 1H), 1.20-1.80 (m, 9H), 1.00 (br. s., 2H). | 6.42 $^a$ | 414.0 (M + H$^+$) |
| 3 | $^1$H NMR (400 MHz, DMSO-d6) δ ppm: 9.11 (br. s., 1H), 8.81 (br. s., 1H), 8.19 (s, 0.4H), 7.93 (d, J = 7.0 Hz, 2H), 7.77 (s, 0.6H), 7.44-7.51 (m, 2H), 7.34-7.42 (m, 1H), 7.25 (d, J = 3.5 Hz, 1H), 7.04-7.18 (m, 7H), 4.52-4.74 (m, 2H), 3.43-3.65 (m, 2H), 3.22-3.31 (m, 1H), 2.64-2.87 (m, 1H), 2.41-2.48 (m, 1H), 1.21-1.60 (m, 4H) | 7.38 $^a$ | 450.2 (M + H$^+$) |
| 4 | $^1$H NMR (400 MHz, DMSO-d6) δ ppm: 9.15 (br. s., 1H), 8.83 (br. s., 1H), 8.20 (s, 0.5H), 7.93 (d, J = 6.8 Hz, 2H), 7.80 (s, 0.5H), 7.42-7.52 (m, 2H), 7.34-7.40(m, 1H), 7.26(d, J = 3.5 Hz, 1H), 7.16-7.23 (m, 2H), 7.07-7.15 (m, 4H), 4.54-4.80 (m, 2H), 3.48-3.70 (m, 2H), 3.36-3.47 (m, 1H), 2.64-2.92 (m, 1H), 2.39-2.48 (m, 1H), 1.53-1.80 (m, 2H) | 6.37 $^a$ | 436.1 (M + H$^+$) |
| 5 | $^1$H NMR (400 MHz, DMSO-d6) δ ppm: 9.95 (br.s., 0.3H), 9.50-9.57 (m, 0.5H), 9.04-9.13 (m, 1H), 8.55-8.62 (m, 1H), 8.23 (s, 0.3H), 7.93 (d, J = 7.3 Hz, 2H), 7.83 (s, 0.6H), 7.44-7.50 (m, 2H), 7.35-7.41 (m, 1H), 7.25 (d, J = 3.8 Hz, 1H), 7.11 (d, J = 3.8 Hz, 1H), 4.52-4.70 (m, 2H), 3.52-3.68 (m, 1H), 3.34 (1H excluded by solvent), 2.59-2.76 (m, 1H), 1.27-1.45 (m, 2H), 1.07-1.25 (m, 6H), 0.69-0.81 (m, 3H) | 2.48$^b$ | 402.1 (M + H$^+$) |
| 6 | $^1$H NMR (400 MHz, methanol-d4) δ ppm: 8.13 (s, 0.4H), 7.96 (d, J = 7.5 Hz, 1H), 7.78 (s, 0.6H), 7.50-7.59 (m, 0.6H), 7.47 (dd, J = 6.9, 2.9 Hz, 0.4H), 7.21-7.29 (m, 1H), 7.12 (d, J = 3.5 Hz, 1H), 7.01 (d, J = 8.3 Hz, 1H), 6.92-6.98 (m, 2H), 4.62-4.70 (m, 1H), 3.86 (s, 3H), 3.67 (dd, J = 14.2, 8.9 Hz, 1H), 3.56-3.62 (m, 1H), 3.34 (dd, J = 14.2, 4.9 Hz, 1H), 2.73 (dt, J = 9.0, 4.4 Hz, 0.6H), 2.57 (d, J = 8.0 Hz, 0.4H), 1.39-1.54 (m, 1H), 1.28-1.39 (m, 1H), 1.06-1.26 (m, 6H), 0.68 (d, J = 4.3 Hz, 3H) | 2.54$^b$ | 432.2 (M + H$^+$) |
| 7 | $^1$H NMR (400 MHz, methanol-d4) δ ppm: 8.22-8.32 (m, 0.5H), 8.03 (s, 0.5H), 7.82-7.92 (m, 1H), 7.45 (d, J = 12.8 Hz, 2H), 7.33-7.40 (m, 1H), 7.24 (d, J = 3.5 Hz, 1H), 6.95 (d, J = 4.0 Hz, 2H), 4.74-4.82 (m, 2H), 4.63 (br. s., 1H), 3.88 (s, 3H), 3.62-3.81 (m, 1H), 3.46 (dd, J = 14.1, 5.0 Hz, 1H), 2.76-2.90 (m, 1H), 2.62-2.75 (m, 0.5H), 2.10-2.23 (m, 0.5H), 1.50-1.68 (m, 1H), 1.39-1.51 (m, 1H), 1.28 (m, 6H), 0.73-0.98 (m, 3H) | 2.53$^b$ | 432.2 (M + H$^+$) |

| Ex. | ¹H NMR | tR (min) | MS (m/z) |
|---|---|---|---|
| 8 | ¹H NMR (400 MHz, DMSO-d6) δ ppm: 9.56 (br. s., 1H), 9.17 (br. s., 1H), 8.40-8.51 (m, 1H), 8.17-8.29 (m, 1H), 7.80 (d, J = 7.5 Hz, 1H), 7.62-7.70 (m, 1H), 7.60 (s, 1H), 7.20-7.29 (m, 2H), 4.52-4.76 (m, 2H), 3.22-3.58 (m, 2H), 2.61-2.89 (m, 1H), 1.34-1.55 (m, 2H), 0.99-1.32 (m, 6H), 0.65-0.82 (m, 3H) | 6.89[a] | 427.2 (M + H⁺) |
| 9 | ¹H NMR (400 MHz, DMSO-d6) δ ppm: 8.86 (br. s., 1H), 8.71 (br. s., 1H), 8.20 (s, 0.5H), 7.81-7.95 (m, 1H), 7.78 (s, 0.5H), 7.08-7.24 (m, 2H), 6.99-7.08 (m, 1H), 6.77-6.88 (m, 1H), 6.54-6.67 (m, 1H), 4.47-4.73 (m, 2H), 3.43-3.62 (m, 1H), 3.26-3.38 (m, 1H), 2.62-2.84 (m, 1H), 1.26-1.52 (m, 2H), 1.00-1.26 (m, 6H), 0.66-0.87 (m, 3H) | 6.30[a] | 418.2 (M + H⁺) |
| 10 | ¹H NMR (400 MHz, methanol-d4) δ ppm: 8.66 (br. s., 1H), 8.27 (s, 0.6H), 8.21 (s, 1H), 7.95 (s, 1H), 7.88 (s, 0.4H), 7.29 (br. s., 1H), 7.16 (br. s., 1H), 4.72-4.87 (m, 2H), 3.98 (s, 3H), 3.39-3.87 (m, 2H), 2.62-2.96 (m, 1H), 1.36-1.68 (m, 2H), 1.14-1.35 (m, 6H), 0.81 (m, 3H) | 2.03[b] | 433.3 (M + H⁺) |
| 11 | ¹H NMR (400 MHz, DMSO-d6) δ ppm: 9.28-9.35 (m, 0.5H) 9.17-9.27 (m, 0.5H), 8.84-8.93 (m, 0.5H), 8.74-8.84 (m, 0.5H), 8.19 (s, 0.5H), 8.14 (d, J = 7.5 Hz, 2H), 7.95 (d, J = 8.3 Hz, 2H), 7.80 (s, 0.5H), 7.36 (d, J = 3.8 Hz, 1H), 7.29 (d, J = 3.5 Hz, 1H), 4.52-4.76 (m, 2H), 3.43-3.64 (m, 2H), 2.61-2.80 (m, 1H), 1.25-1.52 (m, 2H), 1.05-1.25 (m, 6H), 0.65-0.81 (m, 3H) | 6.83[a] | 449.1 (M + 23) (M + H⁺) |
| 12 | ¹H NMR (400 MHz, DMSO-d6) δ ppm: 9.10 (br. s., 1H), 8.90 (br. s., 1H), 8.23-8.31 (m, 1H), 8.15 (s, 0.4H), 8.08 (d, J = 7.0 Hz, 1H), 7.72-7.81 (m, 1.6H), 7.59-7.67 (m, 1H), 7.29 (d, J = 3.0 Hz, 1H), 7.15-7.22 (m, 1H), 4.51-4.71 (m, 2H), 3.23-3.65 (m, 2H), 2.55-2.83 (m, 1H), 1.22-1.52 (m, 2H), 0.98-1.22 (m, 6H), 0.60-0.88 (m, 3H) | 5.93[a] | 961.3 (2M + H⁺) |
| 13 | ¹H NMR (400 MHz, DMSO-d6) δ ppm: 8.90-9.37 (m, 2H), 8.14 (s, 0.4H), 7.90-8.03 (m, 2H), 7.70 (s, 0.6H), 7.59 (t, J = 7.9 Hz, 1H), 7.36 (d, J = 8.0 Hz, 1H), 7.21-7.30 (m, 2H), 4.52-4.75 (m, 2H), 3.20-3.64 (m, 2H), 2.60-2.84 (m, 1H), 1.22-1.52 (m, 2H), 0.94-1.22 (m, 6H), 0.63-0.85 (m, 3H) | 8.09[a] | 486.2 (M + H⁺) |
| 14 | ¹H NMR (400 MHz, DMSO-d6) δ ppm: 8.99-9.26 (m, 1H), 8.66-8.87 (m, 1H), 8.19 (s, 0.4H), 7.79 (s, 0.6H), 7.43-7.53 (m, 2H), 7.36 (t, J = 7.9 Hz, 1H), 7.22 (d, J = 3.5 Hz, 1H), 7.11 (d, J = 3.5 Hz, 1H), 6.93 (dd, J = 8.2, 1.6 Hz, 1H), 4.62 (m, 2H), 4.10 (q, J = 6.9 Hz, 2H), 3.45-3.63 (m, 1H), 3.19-3.33 (m, 1H), 2.58-2.80 (m, 1H), 1.36 (t, J = 7.03 Hz, 3H), 1.25-1.49 (m, 2H), 1.06-1.26 (m, 6H), 0.65-0.89 (m, 3H) | 7.67[a] | 446.2 (M + H⁺) |
| 15 | ¹H NMR (400 MHz, DMSO-d6) δ ppm: 9.25 (br. s., 1H), 9.05 (br. s., 1H), 8.10 (s, 0.4H), 7.82 (m, 0.6H), 7.76-7.85 (m, 1H), 7.63-7.69 (m, 1H), 7.60 (d, J = 7.5 Hz, 1H), 7.23-7.30 (m, 1H), 7.07-7.15 (m, 1H), 6.78 (d, J = 8.0 Hz, 1H), 4.52-4.75 (m, 2H), 3.91 (s, 3H), 3.43-3.30 (m, 2H), 2.59-2.85 (m, 1H), 1.33-1.55 (m, 1H), 1.01-1.31 (m, 7H), 0.68-0.89 (m, 3H) | 7.09[a] | 433.2 (M + H⁺) |
| 16 | ¹H NMR (400 MHz, DMSO-d6) δ ppm: 9.03-9.29 (m, 1H), 8.69-9.01 (m, 1H), 8.33-8.47 (m, 1H), 8.10-8.27 (m,1.3H), 7.90-8.02 (m, 1H), 7.71-7.81 (m, 0.7H), 7.56-7.66 (m, 1H), 7.25-7.35 (m, 1H), 7.19-7.25 (m, 1H), 4.52-4.80 (m, 2H), 3.91 (s, 3H), 3.22-3.61 (m, 2H), 2.55-2.85 (m, 1H), 1.23-1.52 (m, 1H), 1.01-1.23 (m, 7H), 0.75 (d, J = 3.5 Hz, 3H) | 7.14[a] | 460.2 (M + H⁺) |
| 17 | ¹H NMR (400 MHz, DMSO-d6) δ ppm: 8.79-9.22 (m, 2H), 8.15 (s, 0.4H), 7.72 (s, 0.6H), 7.57-7.69 (m, 1H), 7.46-7.57 (m, 1H), 7.27-7.36 (m, 1H), 7.23 (d, J = 3.5 Hz, 1H), 7.09-7.14(m, 1H), 4.52-4.73 (m, 2H), 3.93 (s, 3H), 3.47-3.60 (m, 1H), 3.22-3.47 (m, 1H), 2.58-2.83 (m, 1H), 1.34-1.55 (m, 1H), 1.05-1.34 (m, 7H), 0.76 (m, 3H) | 7.31[a] | 472.2 (M + 23) |
| 18 | ¹H NMR (400 MHz, DMSO-d6) δ ppm: 9.85 (br. s., 1H), 9.16 (br. s., 1H), 8.33-8.47 (m, 1H), 8.04 (s, 0.5H), 7.71 (s, 0.5H), 7.60-7.67 (m, 1H), 7.57 (br. s., 1H), 7.21-7.32 (m, 1H), 7.11-7.20 (m, 1H), 6.88-7.01 (m, 1H), 4.45-4.80 (m, 2H), 3.90 (s, 3H), 3.20-3.52 (m, 2H), 2.59-2.87 (m, 1H), 1.34-1.55 (m, 1H), 0.99-1.31 (m, 7H), 0.61-0.88 (m, 3H) | 5.15[a] | 433.2 (M + H⁺) |
| 19 | ¹H NMR (400 MHz, methanol-d4) δ ppm: 8.34-8.39 (m, 1H), 8.15 (s, 0.3H), 8.00-8.08 (m, 1H), 7.79-7.87 (m, 1H), 7.69 (s, 0.7H), 7.57 (t, J = 7.8 Hz, 1H), 7.24-7.30 (m, 1H), 7.01-7.06 (m, 1H), 4.74-4.88 (m, 2H), 3.35-3.86 (m, 2H), 2.96-3.00 (m, 3H), 2.88-2.96 (m, 1H), 1.35-1.71 (m, 2H), 1.11-1.35 (m, 6H), 0.81 (m, 3H) | 5.52[a] | 459.2 (M + H⁺) |
| 20 | ¹H NMR (400 MHz, DMSO-d6) δ ppm: 9.75 (br. s., 1H), 9.24 (br. s., 1H), 8.35-8.44 (m, 1H), 8.21-8.32 (m, 1H), 8.09 (s, 0.3H), 7.89 (d, J = 8.0 Hz, 1H), 7.69-7.77 (m, 1H), 7.64 (s, 0.7H), 7.24-7.35 (m, 2H), 7.15-7.24 (m, 2H), 7.03-7.15 (m, 3H), 4.67 (m, 2H), 3.2-3.75 (m, 3H), 3.28 (s, 3H), 2.71-2.98 (m, 1H), 2.39-2.49 (m, 1H), 1.48-1.85(m, 2H) | 6.29[a] | 514.2 (M + H⁺) |

| Ex. | ¹H NMR | tR (min) | MS (m/z) |
|---|---|---|---|
| 21 | ¹H NMR (400 MHz, DMSO-d6) δ ppm: 9.20 (br. s., 1H), 8.83 (br. s., 1H), 8.22-8.30 (m, 1H), 8.16 (d, J = 8.8 Hz, 1.6H), 7.69-7.79 (m, 3H), 7.29-7.37 (m, 2.3H), 4.53-4.74 (m, 2H), 3.40-3.62 (m, 2H), 2.71-2.80 (m, 1H), 2.65 (s, 6H), 1.34-1.50 (m, 1H), 1.22-1.34 (m, 1H), 1.09-1.22 (m, 6H), 0.74 (m, 3H) | 6.87$^a$ | 509.2 (M + H⁺) |
| 22 | ¹H NMR (400 MHz, DMSO-d6) δ ppm: 9.16 (br. s., 1H), 8.81 (br. s., 1H), 8.12-8.26 (m, 2.4H), 7.66-7.78 (m, 2.6H), 7.21-7.36 (m, 2H), 4.50-4.77 (m, 2H), 3.24-3.64 (m, 2H), 2.57-2.83 (m, 1H), 2.44 (s, 3H), 1.24-1.51 (m, 2H), 1.08-1.24 (m, 6H), 0.75 (d, J = 5.0 Hz, 3H) | 6.35$^a$ | 495.2 (M + H⁺) |
| 23 | ¹H NMR (400 MHz, DMSO-d6) δ ppm: 9.96 (br. s., 0.4H), 9.55 (br. s., 0.6H), 9.10-9.20 (m, 1H), 8.55-8.64 (m, 1H), 8.23 (s, 0.4H), 7.82 (br. s., 0.6H), 7.57-7.67 (m, 2H), 7.44 (t, J = 8.0 Hz, 1H), 7.24 (d, J = 3.5 Hz, 1H), 7.18 (d, J = 3.5 Hz, 1H), 7.08 (dd, J = 8.3, 1.8 Hz, 1H), 4.85 (q, J = 8.8 Hz, 2H), 4.62 (dd, J = 15.8, 5.5 Hz, 2H), 4.36-4.50 (m, 1H), 3.49-3.67 (m, 1H), 2.72 (br. s., 1H), 1.27-1.46 (m, 2H), 1.10-1.26 (m, 6H), 0.67-0.88 (m, 3H) | 2.73$^b$ | 500.2 (M + H⁺) |
| 24 | ¹H NMR (400 MHz, DMSO-d6) δ ppm: 9.61 (s, 0.3H), 9.30 (s, 0.7H), 9.15 (t, J = 5.9 Hz, 0.3H), 9.00 (t, J = 5.9 Hz, 0.7H), 8.79 (t, J = 5.5 Hz, 0.3H), 8.53 (t, J = 5.6 Hz, 0.7H), 8.30 (s, 0.3H), 7.92 (d, J = 8.0 Hz, 2H), 7.76 (s, 0.7H), 7.44-7.50 (m, 2H), 7.35-7.41 (m, 1H), 7.23-7.27 (m, 1H), 7.07-7.14 (m, 1H), 4.47-4.73 (m, 0.2H), 4.22 (q, J = 7.3 Hz, 0.3H), 3.58 (td, J = 9.3, 4.8 Hz, 0.7H), 3.41-3.49 (m, 0.2H), 2.55-2.64 (m, 1H), 1.46-1.57 (m, 2H), 1.35-1.44 (m, 2H), 1.08-1.23 (m, 6H), 0.66-0.82 (m, 6H) | 7.79$^a$ | 430.2 (M + H⁺) |
| 25 | ¹H NMR (400 MHz, methanol-d4) δ ppm: 8.26 (s, 0.4H), 7.90 (s, 0.6H), 7.38-7.48 (m, 2H), 7.34 (t, J = 7.8 Hz, 1H), 7.24 (d, J = 2.3 Hz, 1H), 6.87-6.98 (m, 2H), 4.61-4.85 (m, 3H), 3.39-3.89 (m, 2H), 2.62-2.97 (m, 1H), 1.40-1.70 (m, 2H), 1.35 (d, J = 5.8 Hz, 6H), 1.15-1.33 (m, 6H), 0.72-0.88 (m, 3H) | 7.98$^a$ | 460.2 (M + H⁺) |
| 26 | ¹H NMR (400 MHz, DMSO-d6) δ ppm: 9.94-9.98 (m, 0.3H), 9.53-9.58 (m, 0.5H), 9.19-9.27 (m, 1H), 8.56-8.62 (m, 1H), 8.23-8.25 (m, 0.4H), 8.00-8.03 (m, 1H), 7.83-7.85 (m, 0.6H), 7.78-7.80 (m, 1H), 7.43 (br. s., 1H), 7.29 (d, J = 3.5 Hz, 1H), 7.26 (d, J = 3.8 Hz, 1H), 4.54-4.69 (m, 2H), 4.14-4.20 (m, 2H), 3.90 (s, 3H), 3.54-3.67 (m, 1H), 3.4 (1H excluded by solvent), 1.38 (t, J = 6.9 Hz, 3H), 1.29-1.35 (m, 2H), 1.13-1.21 (m, 6H), 0.72-0.77 (m, 3H) | 2.64$^b$ | 504.2 (M + H⁺) |
| 27 | ¹H NMR (400 MHz, DMSO-d6) δ ppm: 9.95 (s, 0.4H), 8.94-9.06 (m, 1H), 8.23 (s, 0.4H), 8.57 (d, J = 5.5 Hz, 1H), 7.83 (s, 0.6H), 7.25-7.30 (m, 2H), 7.18-7.25 (m, 3H), 7.07 (d, J = 3.5 Hz, 1H), 6.76 (d, J = 7.8 Hz, 1H), 4.62-4.72 (m, 1H), 4.51-4.62 (m, 1H), 3.53-3.67 (m, 1H), 3.28-3.44 (m, 1H), 2.59-2.77 (m, 1H), 1.26-1.46 (m, 2H), 1.17 (br. s., 6H), 0.67-0.84 (m, 3H) | 1.42$^c$ | 445.3 (M + H⁺) |
| 28 | ¹H NMR (400 MHz, methanol-d4) δ ppm: 8.40 (br. s., 1H), 8.24 (s, 0.3H), 7.99 (d, J = 7.5 Hz, 1H), 7.89 (d, J = 7.8 Hz, 1H), 7.83 (s, 0.7H), 7.54 (t, J = 7.7 Hz, 1H), 7.26 (d, J = 3.0 Hz, 1H), 7.03 (d, J = 2.8 Hz, 1H), 4.72-4.88 (m, 2H), 3.40-3.88 (m, 2H), 2.61-2.99 (m, 1H), 2.17 (q, J = 7.5 Hz, 2H), 1.37-1.70 (m, 2H), 1.21-1.37 (m, 6H), 1.03 (t, J = 7.5 Hz, 3H), 0.69-0.86 (m, 3H) | 6.45$^a$ | 537.3 (M + H⁺) |
| 29 | ¹H NMR (400 MHz, DMSO-d6) δ ppm: 9.54 (br. s., 0.3H), 9.14-9.24 (m, 1H), 8.53-8.62 (m, 1H), 8.23 (s, 0.3H), 8.02 (s, 1H), 7.83 (s, 0.5H), 7.70-7.75 (m, 1H), 7.40-7.46 (m, 1H), 7.26 (s, 2H), 4.53-4.71 (m, 2H), 3.89 (s, 3H), 3.54-3.67 (m, 1H), 3.4 (1H excluded by solvent) 2.59-2.76 (m, 1H), 1.27-1.45 (m, 2H), 1.11-1.25 (m, 6H), 0.71-0.79 (m, 3H) | 1.74$^c$ | 476.2 (M + H⁺) |
| 30 | ¹H NMR (400 MHz, DMSO-d6) δ ppm: 9.12 (m, 0.5H), 8.91-8.98 (m, 0.3H), 8.62 (m, 1H), 8.22 (s, 0.3H), 7.93 (s, 1H), 7.83 (s, 0.5H), 7.55 (br. s., 1H), 7.40 (s, 1H), 7.23 (s, 1H), 7.13 (s, 1H), 4.62 (br. s., 2H), 4.11 (q, J = 6.8 Hz, 2H), 3.53-3.68 (m, 1H), 3.4 (1H excluded by solvent) 2.61-2.76 (m, 1H), 1.28-1.42 (m, 5H), 1.13-1.22 (m, 6H), 0.72-0.79 (m, 3H) | 2.36$^b$ | 490.1 (M + H⁺) |
| 31 | ¹H NMR (CHLOROFORM-d) δ ppm: 8.33-8.56 (m, 1H), 8.07-8.18 (m, 1H), 7.63-7.76 (m, 1H), 7.57 (m, 1H), 7.50 (m, 1H), 6.81 (m, 1H), 6.61 (br. s., 0.4H), 6.47 (br. s., 0.6H), 5.07 (m, 1H), 4.65-4.95 (m, 1H), 3.67-4.29 (m, 4H), 3.50 (dt, 3.5, 14.5 Hz, 1H), 2.87 (m, 0.6H), 2.59 (m, 0.4H), 2.05 (d, 1H, J = 14.5 Hz), 1.65-1.80 (m, 3H), 1.43 (t, J = 14.5 Hz, 1.5H), 1.27-1.37 (m, 6H), 1.22 (t, J = 14.5 Hz, 1.5H), 0.90 (m, 3H) | 0.77$^d$ | 508.1 (M + H⁺) |
| 32 | ¹H NMR (CHLOROFORM-d) δ ppm: 9.58 (br.s., 0.5H), 9.07-9.12 (t, 0.1 H), 8.98-9.04 (t, J = 2 Hz, 0.9H), 8.67-8.72 (t, J = 2 Hz, 0.2 H), 8.50-8.56 (t, J = 2 Hz, 0.8H), 8.28 (s, 0.2H), 7.90-7.95 (d, J = 4 Hz, 2 H), 7.76 (s, 0.8H), 7.45-7.51 (t, J = 4 Hz, 2H), 7.36-7.41 (m, 1H), 7.24-7.26 (d, J = 1 Hz, 1H), 7.09-7.12 (d, J = 1.5 Hz, 1H), 4.61-4.73 (m, 2H), 4.50-4.58 (m, 0.7H), 4.32-4.39 (m, 0.3H), 3.63-3.70 (m, 1 H), 3.48-3.54 (m, 2H), 2.60-2.67 (m, 1 H), 1.37-1.46 (m, 6H), 1.08-1.22 (m, 6H), 0.69-0.77 (m, 3H) | 0.86$^d$ | 432.2 (M + H⁺) |

| Ex. | $^1$H NMR | tR (min) | MS (m/z) |
|---|---|---|---|
| 33 | $^1$H NMR (400 MHz, DMSO-d6) δ ppm: 9.07-9.15 (m, 1H), 8.60 (br. s., 1H), 8.54 (br. s., 1H), 8.21-8.25 (m, 0.4H), 7.91 (s, 1H), 7.81-7.85 (m, 0.5H), 7.64 (s, 1H), 7.38 (s, 1H), 7.26 (d, J = 3.5 Hz, 1H), 7.18 (d, J = 3.5 Hz, 1H), 4.55-4.71 (m, 2H), 3.88 (s, 3H), 3.54-3.67 (m, 1H), 3.4 (3H excluded by solvent), 2.72 (t, J = 6.4 Hz, 2H), 2.59-2.68 (m, 1H), 1.28-1.44 (m, 2H), 1.13-1.23 (m, 6H), 0.72-0.80 (m, 3H) | 1.89$^b$ | 518.2 (M + H$^+$) |
| 34 | $^1$H NMR (400 MHz, DMSO-d6) δ ppm: 9.14 (br. s., 1H), 8.55-8.63 (m, 1H), 8.46-8.53 (m, 1H), 8.24 (s, 0.3H), 7.89 (s, 1H), 7.83 (s, 0.5H), 7.65 (s, 1H), 7.37 (s, 1H), 7.26 (d, J = 3.3 Hz, 1H), 7.18 (d, J = 3.0 Hz, 1H), 4.55-4.70 (m, 2H), 4.16 (q, J = 6.4 Hz, 2H), 3.54-3.67 (m, 1H), 3.4 (3H excluded by solvent), 2.71 (t, J = 6.1 Hz, 2H), 2.60-2.67 (m, 1H), 1.29-1.44 (m, 5H), 1.18 (br. s., 6H), 0.70-0.81 (m, 3H) | 1.95$^b$ | 532.3 (M + H$^+$) |
| 35 | $^1$H NMR (400 MHz, methanol-d4) δ ppm: 8.85-8.93 (m, 1H), 8.72-8.65 (m, 1H), 8.13 (s, 0.4H), 7.78 (s, 0.6H), 7.62 (d, J = 7.5 Hz, 1H), 7.58 (br. s., 1H), 7.37 (t, J = 7.8 Hz, 1H), 7.13 (br. s., 1H), 7.04 (d, J = 7.5 Hz, 1H), 6.90 (br. s., 1H), 6.82 (t, J = 74.0 Hz, 1H), 4.66 (br. s., 2H), 3.56-3.70 (m, 1.4H), 3.34 (d, J = 10.3 Hz, 0.6H), 2.75 (m, 0.6H), 2.58 (m, 0.4H), 1.28-1.56 (m, 2H), 1.09-1.22 (m, 6H), 0.54-0.74 (m, 3H) | 2.58$^b$ | 468.1 (M + H$^+$) |
| 36 | $^1$H NMR (CHLOROFORM-d) δ ppm: 8.23-8.37 (m, 2H), 7.99 (s, 0.7H), 7.80-7.90 (m, 1H), 7.67 (m, 1H), 7.52 (m, 1H), 7.44 (s, 0.3H), 7.23 (d, J = 3.5 Hz, 0.3H), 7.03 (d, J = 3.5 Hz, 0.7H), 6.81 (d, J = 3.5 HZ, 0.3H), 6.68 (d, J = 3.5 Hz, 0.7H), 4.77-5.03 (m, 2H), 3.89 (d, J = 11.0 Hz, 3H), 3.80 (m, 1H), 3.76 (d, J = 11.0 Hz, 3H), 3.50 (m, 1H), 2.83 (m, 0.7H), 2.64 (m, 0.3H), 1.71 (m, 2H), 1.29 (m, 6H), 0.87 (m, 3H) | 0.77$^d$ | 510.0 (M + H$^+$) |
| 37 | $^1$H NMR (400 MHz, methanol-d4) δ ppm: 8.35 (d, J = 5.6 Hz, 1H), 8.26 (s, 0.4H), 8.15 (dd, J = 1.6, 8.8 Hz, 1H), 7.89 (s, 0.6H), 7.61 (d, J = 8.0 Hz, 1H), 7.27 (d, J = 5.0 Hz, 1H), 7.12 (d, J = 5.0 Hz, 1H), 4.78 (m, 2H), 4.49 (s, 2H), 3.69-3.82 (m, 1.4H), 3.45 (dd, J = 4.8, 14.0 Hz, 0.6H), 2.84 (m, 0.6H), 2.68 (m, 0.4H), 1.58 (m, 1H), 1.45 (m, 1H), 1.21-1.34 (m, 6H), 0.80 (m, 3H) | 0.72$^d$ | 493.0 (M + H$^+$) |
| 38 | $^1$H NMR (400 MHz, methanol-d4) δ ppm: 8.26 (s, 0.4H), 7.90 (s, 0.6H), 7.50-7.55 (m, 1H), 7.47 (d, J = 7.8 Hz, 1H), 7.38 (t, J = 8.0 Hz, 1H), 7.24 (d, J = 3.5 Hz, 1H), 6.97-7.02 (m, 1H), 6.96 (d, J = 3.5 Hz, 1H), 4.70-4.84 (m, 2H), 4.15-4.40 (m, 2H), 3.41-3.87 (m, 2H), 3.18 (t, J = 5.3 Hz, 2H), 2.89-3.03 (m, 4H), 2.64-2.91 (m, 1H), 1.80-2.05 (m, 4H), 1.37-1.64 (m, 2H), 1.12-1.35 (m, 6H), 0.71-0.91 (m, 3H) | 5.69$^a$ | 515.3 (M + H$^+$) |
| 39 | $^1$H NMR (400 MHz, DMSO-d6) δ ppm: 13.24 (br. s., 1H), 9.62 (s, 0.3H), 9.23-9.32 (m, 1H), 9.14 (t, J = 5.9 Hz, 0.7H), 8.78 (d, J = 5.3 Hz, 0.3H), 8.52 (t, J = 5.5 Hz, 0.7H), 8.30 (s, 0.3H), 8.00 (s, 1H), 7.75 (d, J = 5.8 Hz, 1.7H), 7.41 (br. s., 1H), 7.22-7.28 (m, 2H), 4.47-4.74 (m, 2H), 4.09-4.27 (m, 2.3H), 3.53-3.63 (m, 0.7H), 2.54-2.64 (m, 1H), 1.46-1.57 (m, 2H), 1.38 (t, J = 6.9 Hz, 5H), 1.07-1.22 (m, 6H), 0.66-0.82 (m, 6H) | 7.29$^a$ | 518.3 (M + H$^+$) |
| 40 | $^1$H NMR (400 MHz, DMSO-d6) δ ppm: 9.20 (br. s., 0.3H), 8.99 (br. s., 1H), 8.75-8.82 (m, 0.3H), 8.51 (br. s., 2H), 8.29 (s, 0.3H), 7.90 (br. s., 1H), 7.77 (s, 0.6H), 7.64 (br. s., 1H), 7.37 (br. s., 1H), 7.26 (d, J = 2.5 Hz, 1H), 7.18 (s, 1H), 4.49-4.73 (m, 2H), 4.09-4.22 (m, J = 6.5 Hz, 2H), 3.48-3.63 (m, 1H), 3.4 (2H excluded by solvent) 2.66-2.76 (m, 2H), 2.55-2.64 (m, 1H), 1.46-1.58 (m, 2H), 1.34-1.44 (m, 5H), 1.07-1.23 (m, 6H), 0.67-0.83 (m, 6H) | 2.05$^b$ | 560.2 (M + H$^+$) |
| 41 | $^1$H NMR (400 MHz, DMSO-d6) δ ppm: 12.19 (s, 1H), 9.61 (s, 0.3H), 9.29 (s, 0.7H), 9.03-9.14 (m, 0.3H), 8.88-9.00 (m, 0.7H), 8.70-8.82 (m, 0.3H), 8.45-8.57 (m, 0.7H), 8.30 (s, 0.3H), 7.77 (s, 0.7H), 7.38-7.52 (m, 2H), 7.20-7.33 (m, 2H), 7.11 (d, J = 3.3 Hz, 1H), 4.47-4.80 (m, 2H), 4.19-4.30 (m, 0.5H), 4.13 (q, J = 6.8 Hz, 2H), 3.57-3.71 (m, 0.9H), 2.54-2.76 (m, 1.5H), 1.34 (t, J = 6.8 Hz, 8H), 1.15 (d, J = 5.8 Hz, 6H), 0.59-0.93 (m, 6H) | 6.29$^a$ | 532.3 (M + H$^+$) |
| 42 | $^1$H NMR (400 MHz, DMSO-d6) δ ppm: 12.39 (br. s., 1H), 9.61 (s, 0.3H), 9.29 (br. s., 0.7H), 9.07-9.18 (m, 0.3H), 8.91-9.03 (m, 0.7H), 8.74-8.83 (m, 0.3H), 8.45-8.57 (m, 0.7H), 8.30 (s, 0.3H), 7.86 (d, J = 7.8 Hz, 2H), 7.77 (s, 0.7H), 7.36 (d, J = 8.0 Hz, 2H), 7.24 (d, J = 3.0 Hz, 1H), 7.07 (d, J = 3.3 Hz, 1H), 4.45-4.76 (m, 2H), 4.14-4.29 (m, 0.3H), 3.60-3.71 (1H, concealed under solvent peak), 3.53-3.59 (m, 0.7H), 3.37 (none, 0.3H), 2.56-2.64 (m, 1H), 2.53-2.56 (m, 0.3H), 1.28-1.62 (m, 4H), 1.01-1.28 (m, 6H), 0.57-0.89 (m, 6H) | 5.90$^a$ | 488.3 (M + H$^+$) |

| Ex. | ¹H NMR | tR (min) | MS (m/z) |
|---|---|---|---|
| 43 | ¹H NMR (400 MHz, DMSO-d6) δ ppm: 12.39 (br. s., 1H), 9.61 (s, 0.3H), 9.29 (s, 0.7H), 9.04-9.18 (m, 0.3H), 8.89-9.03 (m, 0.7H), 8.72-8.84 (m, 0.3H), 8.46-8.60 (m, 0.7H), 8.29 (s, 0.3H), 7.86 (d, J = 8.0 Hz, 2H), 7.76 (s, 0.7H), 7.43 (d, J = 8.3 Hz, 2H), 7.25 (d, J = 3.0 Hz, 1H), 7.06 (d, J = 3.5 Hz, 1H), 4.45-4.77 (m, 2H), 4.15-4.29 (m, 0.3H), 3.96-4.11 (m, 0.8H), 3.51-3.67 (m, 0.7H), 2.53-2.66 (m, 1.4H), 2.00 (s, 1H), 1.50 (s, 6H), 1.29-1.45 (m, 2H), 1.17 (d, J = 7.0 Hz, 6H), 0.78 (br. s., 6H) | 6.47ᵃ | 516.3 (M + H⁺) |
| 44 | ¹H NMR (400 MHz, DMSO-d6) δ ppm: 9.51-9.73 (m, 0.2H), 9.07-9.20 (m, 0.3H), 8.91-9.06 (m, 0.7H), 8.71-8.84 (m, 0.3H), 8.45-8.60 (m, 0.7H), 8.29 (s, 0.3H), 7.83 (d, J = 8.0 Hz, 2H), 7.76 (s, 0.7H), 7.41 (d, J = 8.0 Hz, 2H), 7.25 (br. s., 1H), 7.07 (d, J = 3.3 Hz, 1H), 4.44-4.79 (m, 2H), 4.14-4.31 (m, 0.3H), 3.46-3.67 (m, 0.7H), 3.21-3.29 (m, 0.2H), 2.53-2.67 (m, 1.5H), 1.47 (br. s., 6H), 1.18 (br. s., 7H), 0.55-0.92 (m, 6H) | 6.31ᵃ | 514.3 (M + H⁺) |
| 45 | ¹H NMR (400 MHz, DMSO-d6) δ ppm: 12.04-12.21 (m, 0.5H), 9.35-9.49 (m, 0.4H), 9.17 (t, J = 5.1 Hz, 0.3H), 9.07 (t, J = 5.8 Hz, 0.7H), 8.83-8.99 (m, 0.7H), 8.57-8.68 (m, 0.5H), 8.27-8.31 (m, 0.3H), 7.93-7.99 (m, 1H), 7.76 (s, 0.6H), 7.67 (s, 1H), 7.41 (s, 1H), 7.26 (d, J = 3.3 Hz, 1H), 7.17-7.21 (m, 1H), 4.68-4.80 (m, 1H), 4.45-4.61 (m, 1H), 4.32-4.40 (m, 1H), 4.17 (q, J = 7.0 Hz, 2H), 3.53-3.61 (m, 1H), 2.54-2.62 (m, 1H), 2.38 (m, 2H), 2.04-2.15 (m, 1H), 1.91-2.02 (m, 1H), 1.48-1.57 (m, 2H), 1.43 (s, 9H), 1.39 (t, J = 6.9 Hz, 5H), 1.10-1.21 (m, 6H), 0.69-0.81 (m, 6H) | 2.78ᵇ | 703.3 (M + H⁺) |
| 46 | ¹H NMR (400 MHz, DMSO-d6) δ ppm: 9.60-9.72 (m, 0.3H), 9.34-9.51 (m, 1.7H), 9.27 (q, J = 6.0 Hz, 1H), 9.08 (s, 1H), 8.80-8.86 (m, 0.3H), 8.78 (s, 1H), 8.57 (t, J = 5.8 Hz, 0.7H), 8.35 (s, 0.3H), 7.82 (s, 0.7H), 7.43-7.51 (m, 1H), 7.30-7.38 (m, 1H), 4.50-4.82 (m, 2H), 4.21-4.34 (m, 0.3H), 3.57-3.72 (m, 0.7H), 2.59-2.71 (m, 1H), 1.51-1.65 (m, 2H), 1.37-1.51 (m, 2H), 1.10-1.27 (m, 6H), 0.80-0.87 (m, 3H), 0.70-0.80 (m, 3H) | 5.88ᵃ | 475.0 (M + H⁺) |
| 47 | ¹H NMR (400 MHz, DMSO-d6) δ ppm: 12.45 (br. s., 0.7H), 9.58-9.65 (m, 0.2H), 9.25-9.33 (m, 0.5H), 9.17-9.22 (m, 0.3H), 9.02-9.08 (m, 0.6H), 8.84 (d, J = 7.5 Hz, 1H), 8.75-8.80 (m, 0.3H), 8.48-8.55 (m, 0.6H), 8.29-8.33 (m, 0.3H), 7.88 (s, 1H), 7.77 (s, 0.6H), 7.68 (s, 1H), 7.38 (s, 1H), 7.25-7.30 (m, 1H), 7.15-7.20 (m, 1H), 4.64-4.76 (m, 2H), 4.50-4.59 (m, 1H), 4.17 (q, J = 6.8 Hz, 2H), 3.54-3.62 (m, 1H), 2.80-2.89 (m, 1H), 2.67-2.77 (m, 1H), 2.56-2.64 (m, 1H), 1.49-1.58 (m, 2H), 1.36-1.47 (m, 14H), 1.10-1.23 (m, 6H), 0.67-0.84 (m, 6H) | 2.69ᵇ | 689.3 (M + H⁺) |
| 48 | ¹H NMR (400 MHz, DMSO-d6) δ ppm: 9.60 (s, 0.3H), 9.28 (s, 0.7H), 9.20 (d, J = 12.5 Hz, 0.3H), 9.05 (t, J = 5.6 Hz, 0.6H), 8.84 (d, J = 7.3 Hz, 1H), 8.73-8.79 (m, 0.3H), 8.50 (t, J = 5.6 Hz, 0.7H), 8.30 (s, 0.3H), 7.90 (s, 1H), 7.77 (s, 0.6H), 7.69 (s, 1H), 7.42 (s, 1H), 7.25-7.29 (m, 1H), 7.17-7.21 (m, 1H), 4.64-4.73 (m, 1H), 4.46-4.58 (m, 2H), 4.18 (q, J = 6.8 Hz, 2H), 3.67 (s, 3H), 3.53-3.64 (m, 4H), 2.56-2.64 (m, 1H), 2.5 (2H excluded by solvent) 2.10-2.21 (m, 1H), 1.99-2.10 (m, 1H), 1.47-1.58 (m, 2H), 1.35-1.44 (m, 5H), 1.11-1.22 (m, 6H), 0.68-0.83 (m, 6H) | 2.65ᵇ | 675.3 (M + H⁺) |
| 49 | ¹H NMR (400 MHz, methanol-d4) δ ppm: 8.98-9.23 (m, 0.3H), 8.72-8.95 (m, 0.7H), 8.26-8.37 (m, 0.3H), 7.81-7.93 (m, 0.7H), 7.63-7.71 (m, 1H), 7.56-7.63 (m, 1H), 7.22-7.31 (m, 1H), 7.08-7.16 (m, 1H), 6.94-7.08 (m, 1H), 4.63-4.87 (m, 2H), 4.15-4.22 (q, J = 8 Hz, 2H), 3.51-3.75 (m, 1H), 2.51-2.82 (m, 1H), 1.49-1.77 (m, 4H), 1.47 (t, J = 8.0 Hz, 3H), 1.13-1.34 (m, 6H), 0.84-0.97 (m, 3H), 0.78 (m, 3H) | 7.43ᵃ | 568.0 (M + H⁺) |
| 50 | ¹H NMR (400 MHz, DMSO-d6) δ ppm: 9.60 (s, 0.3H), 9.27 (s, 0.7H), 9.20-9.26 (m, 0.3H), 9.10 (t, J = 6.0 Hz, 0.7H), 8.76 (t, J = 5.9 Hz, 0.3H), 8.50 (t, J = 5.6 Hz, 0.7H), 8.30 (s, 0.3H), 7.70-7.79 (m, J = 5.3 Hz, 2.7H), 7.28-7.33 (m, 1H), 7.24-7.28 (m, 1H), 7.16 (d, J = 14.3 Hz, 1H), 4.47-4.78 (m, 2H), 4.21-4.27 (m, 0.3H), 4.17 (q, J = 7.0 Hz, 2H), 3.72 (s, 3H), 3.69 (s, 3H), 3.53-3.63 (m, 0.8H), 2.54-2.66 (m, 1H), 1.47-1.59 (m, 2H), 1.38 (t, 5H), 1.04-1.27 (m, 6H), 0.64-0.85 (m, 6H) | 6.55ᵃ | 582.3 (M + H⁺) |
| 51 | ¹H NMR (400 MHz, DMSO-d6) δ ppm: 9.99 (br. s., 0.4H), 9.55 (br. s., 0.5H), 9.09-9.30 (m, 1H), 8.51-8.70 (m, 1H), 8.35 (dd, J = 6.8, 2.3 Hz, 1H), 8.17-8.27 (m, 1.3H), 7.83 (s, 0.6H), 7.51 (dd, J = 10.5, 8.8 Hz, 1H), 7.26 (d, J = 3.5 Hz, 1H), 7.21 (d, J = 3.8 Hz, 1H), 4.50-4.76 (m, 2H), 3.91 (s, 3H), 3.47-3.72 (m, 1H), 3.29-3.45 (1H, excluded by solvent), 2.59-2.82 (m, 1H), 1.26-1.49 (m, 2H), 1.07-1.25 (m, 6H), 0.69-0.80 (m, 3H) | 2.46ᵇ | 478.1 (M + H⁺) |

| Ex. | $^1$H NMR | tR (min) | MS (m/z) |
|---|---|---|---|
| 52 | $^1$H NMR (400 MHz, DMSO-d6) δ ppm: 9.99 (br. s., 0.3H), 9.55 (br. s., 0.5H), 8.97-9.20 (m, 1H), 8.58 (t, J = 4.3 Hz, 1H), 8.23 (s, 0.4H), 7.83 (s, 0.6H), 7.23 (d, J = 3.5 Hz, 1H), 7.15 (d, J = 3.8 Hz, 1H), 7.09 (d, J = 2.3 Hz, 2H), 6.53 (t, J = 2.3 Hz, 1H), 4.49-4.75 (m, 2H), 3.82 (s, 6H), 3.48-3.70 (m, 1H), 3.29-3.46 (1H, excluded by solvent), 2.59-2.78 (m, 1H), 1.26-1.53 (m, 2H), 1.11-1.22 (6H, excluded by ethyl acetate), 0.71-0.80 (m, 3H) | 2.52$^b$ | 462.2 (M + H$^+$) |
| 53 | $^1$H NMR (400 MHz, DMSO-d6) δ ppm: 10.01 (s, 0.4H), 9.56 (br. s., 0.6H), 8.99-9.28 (m, J = 6.3, 6.3 Hz, 1H), 8.58 (t, J = 5.0 Hz, 1H), 8.23 (s, 0.4H), 7.83 (s, 0.6H), 7.68 (d, J = 3.0 Hz, 1H), 7.22 (d, J = 3.5 Hz, 1H), 7.08 (d, J = 9.0 Hz, 1H), 7.04 (d, J = 3.5 Hz, 1H), 6.97 (d, J = 3.0 Hz, 0.6H), 6.95 (d, J = 3.3 Hz, 0.4H), 4.48-4.76 (m, 2H), 3.88 (s, 3H), 3.80 (s, 3H), 3.49-3.68 (m, 1H), 3.28-3.45 (1H, excluded by solvent), 2.57-2.79 (m, 1H), 1.25-1.47 (m, 2H), 1.08-1.25 (m, 6H), 0.68-0.81 (m, J = 2.3 Hz, 3H) | 2.52$^b$ | 462.1 (M + H$^+$) |
| 54 | $^1$H NMR (400 MHz, DMSO-d6) δ ppm: 9.11 (t, J = 6.5 Hz, 0.6H), 9.04 (t, J = 6.7 Hz, 0.4H), 8.61 (t, J = 5.8 Hz, 1H), 8.29 (s, 0.5H), 8.22 (s, 0.4H), 8.19 (d, J = 1.5 Hz, 1H), 7.90 (dd, J = 7.8, 1.5 Hz, 1H), 7.83 (s, 0.7H), 7.34 (d, J = 8.0 Hz, 1H), 7.25 (d, J = 3.5 Hz, 1H), 7.09 (d, J = 3.5 Hz, 1H), 4.45-4.75 (m, 2H), 3.28-3.67 (2H, excluded by solvent), 3.17 (s, 3H), 2.58-2.79 (m, 1H), 1.27-1.48 (m, 2H), 1.08-1.22 (m, 6H), 0.75 (t, J = 5.5 Hz, 3H) | 2.29$^b$ | 460.2 (M + H$^+$) |
| 55 | $^1$H NMR (400 MHz, DMSO-d6) δ ppm: 13.05-13.82 (m, 1H), 10.00 (s, 0.2H), 9.55 (br. s., 0.4H), 9.06-9.23 (m, 1H), 8.48-8.67 (m, 1H), 8.20-8.31 (m, J = 8.0 Hz, 1H), 7.92-8.02 (m, 0.5H), 7.79-7.86 (m, 0.5H), 7.67 (dd, J = 7.5, 1.5 Hz, 1H), 7.26-7.33 (m, 2H), 7.08 (d, J = 3.8 Hz, 1H), 4.45-4.75 (m, 2H), 3.79 (s, 3H), 3.50-3.69 (m, 1H), 3.07-3.45 (1H, excluded by solvent), 2.58-2.80 (m, 1H), 1.26-1.47 (m, 2H), 1.07-1.23 (m, 6H), 0.69-0.80 (m, 3H) | 2.16$^b$ | 476.2 (M + H$^+$) |
| 56 | $^1$H NMR (400 MHz, DMSO-d6) δ ppm: 9.10 (t, J = 6.0 Hz, 0.6H), 8.99-9.07 (m, J = 5.8 Hz, 0.4H), 8.59 (t, J = 5.6 Hz, 1H), 8.19-8.30 (m, 1H), 8.03 (d, J = 2.3 Hz, 1H), 7.99 (br. s., 0.3H), 7.96 (dd, J = 8.5, 2.0 Hz, 1H), 7.83 (s, 0.5H), 7.22 (d, J = 3.5 Hz, 1H), 7.17 (d, J = 8.8 Hz, 1H), 7.00 (d, J = 3.8 Hz, 1H), 4.45-4.74 (m, 2H), 3.85 (s, 3H), 3.28-3.68 (2H, excluded by solvent), 2.58-2.80 (m, 1H), 1.26-1.50 (m, 2H), 1.17 (br. s., 6H), 0.75 (t, J = 5.5 Hz, 3H) | 2.16$^b$ | 476.1 (M + H$^+$) |
| 57 | $^1$H NMR (400 MHz, DMSO-d6) δ ppm: 9.99 (br. s., 0.4H), 9.55 (br. s., 0.6H), 8.79-9.00 (m, 1H), 8.56-8.73 (m, 1H), 8.23 (s, 0.4H), 7.86 (d, J = 7.5 Hz, 1H), 7.83 (s, 0.6H), 7.61-7.70 (m, J = 7.5 Hz, 2H), 7.46-7.56 (m, J = 8.0 Hz, 1H), 7.30 (d, J = 3.5 Hz, 1H), 6.86 (d, J = 3.5 Hz, 1H), 4.45-4.70 (m, 2H), 3.81 (s, 3H), 3.49-3.70 (m, 1H), 3.29-3.44 (1H, excluded by solvent), 2.58-2.78 (m, 1H), 1.26-1.49 (m, 2H), 1.08-1.23 (m, 6H), 0.76 (t, 3H) | 2.42$^b$ | 460.1 (M + H$^+$) |
| 58 | $^1$H NMR (400 MHz, DMSO-d6) δ ppm: 10.01 (m, 0.3H), 9.52-9.60 (m, 0.5H), 9.17-9.27 (m, 1H), 8.58-8.66 (m, 1H), 8.24 (s, 0.4H), 8.01-8.10 (m, 4H), 7.83 (s, 0.5H), 7.27-7.32 (m, 2H), 4.55-4.71 (m, 2H), 3.88 (s, 3H), 3.54-3.67 (m, 1H), 3.37-3.45 (m, 1H), 2.60-2.75 (m, 1H), 1.28-1.44 (m, 2H), 1.11-1.25 (m, 6H), 0.70-0.79 (m, 3H) | 2.49$^b$ | 460.2 (M + H$^+$) |
| 59 | $^1$H NMR (400 MHz, DMSO-d6) δ ppm: 9.15-9.23 (m, 0.5H), 9.12 (t, J = 6.0 Hz, 0.5H), 8.59-8.72 (m, 1H), 8.35 (s, 1H), 8.22 (s, 0.4H), 8.04 (t, J = 6.5 Hz, 1H), 7.82 (s, 0.6H), 7.48-7.59 (m, 1H), 7.26 (br. s., 1H), 7.19 (t, J = 7.8 Hz, 1H), 6.92 (br. s., 1H), 4.50-4.76 (m, 2H), 3.29-3.63 (2H, excluded by solvent), 2.60-2.81 (m, 1H), 1.27-1.53 (m, 2H), 1.17 (br. s., 6H), 0.75 (t, 3H) | 2.17$^b$ | 464.2 (M + H$^+$) |
| 60 | $^1$H NMR (400 MHz, DMSO-d6) δ ppm: 12.48 (s, 0.9H), 9.57 (br. s., 0.5H), 8.97-9.21 (m, 1H), 8.50-8.65 (m, 1H), 8.23 (s, 0.4H), 7.82 (d, J = 8.0 Hz, 1H), 7.80 (s, 1.6H), 7.42 (t, J = 7.8 Hz, 1H), 7.22-7.31 (m, 2H), 7.08 (d, J = 3.5 Hz, 1H), 4.48-4.75 (m, 2H), 3.62-3.69 (m, 2H), 3.51-3.62 (m, 1H), 3.29-3.44 (1H, excluded by solvent), 2.58-2.80 (m, 1H), 1.26-1.49 (m, 2H), 1.08-1.26 (m, 6H), 0.76 (t, 3H) | 2.22$^b$ | 460.2 (M + H$^+$) |
| 61 | $^1$H NMR (400 MHz, DMSO-d6) δ ppm: 13.10 (br. s., 0.7H), 10.00 (s, 0.2H), 9.56 (br. s., 0.5H), 8.91-9.12 (m, J = 5.5 Hz, 1H), 8.52-8.67 (m, 1H), 8.23 (s, 0.4H), 7.89 (d, J = 7.8 Hz, 1H), 7.69 (d, J = 7.5 Hz, 1H), 7.83 (s, 0.6H), 7.38 (t, J = 7.7 Hz, 1H), 7.30 (d, J = 3.5 Hz, 1H), 6.87 (d, J = 3.5 Hz, 1H), 4.45-4.74 (m, 2H), 3.49-3.72 (m, 1H), 3.28-3.44 (1H, excluded by solvent), 2.58-2.77 (m, 1H), 2.55 (s, 3H), 1.26-1.48 (m, 2H), 1.16 (br. s., 6H), 0.70-0.81 (m, 3H) | 2.21$^b$ | 460.1 (M + H$^+$) |
| 62 | $^1$H NMR (400 MHz, DMSO-d6) δ ppm: 9.99 (s, 0.4H), 9.56 (s, 0.6H), 8.84-8.99 (m, 1H), 8.45-8.62 (m, 1H), 8.24 (s, 0.4H), 8.14 (d, J = 2.5 Hz, 1H), 7.83 (s, 0.6H), 7.74 (dd, J = 8.3, 1.8 Hz, 1H), 7.20 (d, J = 3.5 Hz, 1H), 6.78 (d, J = 3.5 Hz, 1H), 6.74 (d, J = 8.5 Hz, 1H), 4.46-4.73 (m, 2H), 3.49-3.74 (m, 1H), 3.23-3.44 (1H, excluded by solvent), 2.58-2.78 (m, 1H), 1.26-1.48 (m, 2H), 1.08-1.23 (m, 6H), 0.76 (t, 3H) | 2.27$^b$ | 462.1 (M + H$^+$) |

| Ex. | ¹H NMR | tR (min) | MS (m/z) |
|---|---|---|---|
| 63 | ¹H NMR (400 MHz, DMSO-d6) δ ppm: 9.97 (br. s., 0.4H), 9.55 (br. s., 0.6H), 9.17 (dt, J = 12.5, 6.0 Hz, 1H), 8.61 (d, J = 4.5 Hz, 1H), 8.34 (s, 1H), 8.20-8.27 (m, 0.5H), 8.17 (d, J = 8.0 Hz, 1H), 7.88 (d, J = 8.0 Hz, 1H), 7.83 (s, 0.6H), 7.60 (t, J = 7.8 Hz, 1H), 7.29 (d, J = 3.5 Hz, 1H), 7.23 (d, J = 3.5 Hz, 1H), 4.49-4.73 (m, 2H), 3.51-3.70 (m, 1H), 3.30-3.40 (1H, excluded by solvent), 2.59-2.79 (m, 1H), 1.58 (s, 9H), 1.26-1.48 (m, 2H), 1.09-1.25 (m, 6H), 0.69-0.79 (m, 3H) | 2.82$^b$ | 502.2 (M + H⁺) |
| 64 | ¹H NMR (400 MHz, DMSO-d6) δ ppm: 10.08 (s, 0.1H), 9.38-9.77 (m, 0.6H), 8.89-8.98 (m, J = 5.3, 5.3 Hz, 0.6H), 8.82-8.90 (m, 0.4H), 8.56 (t, J = 5.5 Hz, 1H), 8.23 (s, 0.4H), 8.16 (d, J = 2.3 Hz, 1H), 7.83 (s, 0.6H), 7.74 (d, J = 8.8 Hz, 1H), 7.19 (d, J = 3.5 Hz, 1H), 6.81 (d, J = 8.8 Hz, 1H), 6.77 (d, J = 3.5 Hz, 1H), 4.46-4.73 (m, 2H), 3.50-3.73 (m, 1H), 3.24-3.45 (1H, excluded by solvent), 2.58-2.79 (m, 1H), 1.26-1.48 (m, 2H), 1.09-1.23 (m, 6H), 0.76 (t, 3H) | 2.14$^b$ | 461.1 (M + H⁺) |
| 65 | ¹H NMR (400 MHz, DMSO-d6) δ ppm: 9.35-9.82 (m, 0.9H), 8.49-8.76 (m, 0.6H), 8.13-8.29 (m, 0.6H), 7.63 (s, 1H), 7.58 (br. s., 0.7H), 7.40 (br. s., 1H), 7.17 (d, J = 12.8 Hz, 2H), 4.33-4.86 (m, 2H), 4.12 (d, J = 6.8 Hz, 2H), 3.66-3.87 (m, 2H), 3.59 (br. s., 2H), 3.23-3.49 (m, 2H), 3.17 (br. s., 9H), 2.56-2.70 (m, 0.8H), 1.53-1.84 (m, 1H), 1.36 (t, J = 6.8 Hz, 5H), 0.94-1.29 (m, 6H), 0.55-0.89 (m, 6H) | 2.07$^b$ | 602.3 (M⁺) |
| 66 | ¹H NMR (400 MHz, DMSO-d6) δ ppm: 9.02-9.10 (m, 0.3H), 8.91-8.99 (m, 0.7H), 8.84-8.91 (m, 0.3H), 8.52-8.66 (m, 0.7H), 8.23-8.33 (m, 0.3H), 7.87 (d, J = 2.0 Hz, 1H), 7.80 (d, J = 8.8 Hz, 1H), 7.76 (s, 0.7H), 7.21 (d, J = 3.5 Hz, 1H), 7.04 (d, J = 8.8 Hz, 1H), 6.89-6.99 (m, J = 3.5 Hz, 1H), 4.45-4.73 (m, 2H), 3.79 (s, 3H), 3.53-3.64 (m, 1H), 2.55-2.66 (m, 1H), 1.30-1.61 (m, 4H), 1.03-1.28 (m, 6H), 0.65-0.85 (m, 6H) | 2.32$^b$ | 504.1 (M + H⁺) |
| 67 | ¹H NMR (400 MHz, methanol-d4) δ ppm: 8.33 (s, 0.2H), 7.90 (s, 1H), 7.87 (s, 0.7H), 7.73 (d, J = 5.0 Hz, 1H), 7.35-7.48 (m, 2H), 7.25 (d, J = 3.5 Hz, 1H), 6.93 (d, J = 3.3 Hz, 1H), 4.67-4.87 (m, 2H), 4.29-4.41 (m, 0.3H), 3.57-3.72 (m, 0.7H), 2.57-2.79 (m, 1H), 1.66-1.78 (m, 2H), 1.61 (s, 6H), 1.45-1.57 (m, 2H), 1.14-1.37 (m, 6H), 0.84-1.00 (m, 3H), 0.77 (none, 3H) | 2.56$^b$ | 516.2 (M + H⁺) |
| 68 | ¹H NMR (400 MHz, methanol-d4) δ ppm: 8.33 (s, 0.3H), 8.15 (br. s., 1H), 7.87 (s, 0.7H), 7.82 (d, J = 7.5 Hz, 1H), 7.32 (d, J = 8.0 Hz, 1H), 7.25 (d, J = 3.5 Hz, 1H), 6.92 (br. s., 1H), 4.67-4.86 (m, J = 13.1 Hz, 2H), 4.27-4.42 (m, 0.3H), 3.56-3.72 (m, 0.8H), 2.60-2.78 (m, 1H), 2.56 (s, 3H), 1.43-1.79 (m, 4H), 1.27 (br. s., 6H), 0.69-0.97 (m, 6H) | 2.46$^b$ | 488.2 (M + H⁺) |
| 69 | ¹H NMR (400 MHz, DMSO-d6) δ ppm: 9.23-9.80 (m, 0.8H), 9.11-9.24 (m, 0.3H), 9.03 (br. s., 0.6H), 8.73-8.89 (m, 0.2H), 8.43-8.69 (m, 0.6H), 8.29 (s, 0.3H), 7.76 (br. s., 0.7H), 7.43-7.57 (m, 2H), 7.31-7.42 (m, 1H), 7.23 (d, J = 1.3 Hz, 1H), 7.13 (br. s., 1H), 6.90-7.00 (m, J = 7.3 Hz, 1H), 4.42-4.78 (m, 2H), 4.14-4.31 (m, 0.3H), 4.00 (t, J = 5.8 Hz, 2H), 3.49-3.66 (m, 0.7H), 2.55-2.65 (m, 1H), 1.68-1.86 (m, 2H), 1.51 (br. s., 2H), 1.39 (br. s., 2H), 1.06-1.27 (m, J = 6.0 Hz, 6H), 1.01 (t, J = 7.2 Hz, 3H), 0.62-0.84 (m, 6H) | 2.99$^b$ | 488.3 (M + H⁺) |
| 70 | ¹H NMR (400 MHz, methanol-d4) δ ppm: 8.20 (s, 0.3H), 7.71-7.80 (m, J = 2.0 Hz, 1.7H), 7.57-7.68 (m, 1H), 7.11 (d, J = 3.8 Hz, 1H), 7.01 (t, J = 9.0 Hz, 1H), 6.69-6.80 (m, 1H), 4.55-4.72 (m, J = 10.8 Hz, 2H), 4.15-4.30 (m, 0.3H), 3.44-3.58 (m, 2.7H), 2.44-2.66 (m, 1H), 1.33-1.67 (m, 4H), 1.04-1.23 (m, 6H), 0.73-0.85 (m, 3H), 0.60-0.72 (m, 3H) | 2.50$^b$ | 506.2 (M + H⁺) |
| 71 | ¹H NMR (400 MHz, methanol-d4) δ ppm: 8.40-8.41 (m, 0.1H), 8.20-8.22 (m, 0.2H), 8.00-8.05 (m, 0.1H), 7.94 (d, J = 8.0 Hz, 2H), 7.80 (d, J = 8.0 Hz, 2H), 7.76 (s, 0.5H), 7.15 (d, J = 3.3 Hz, 1H), 6.89-6.95 (m, 1H), 4.58-4.72 (m, J = 9.0 Hz, 2H), 4.18-4.27 (m, 0.2H), 3.86-3.93 (m, 0.11H), 3.48-3.57 (m, 0.6H), 2.56-2.65 (m, 0.7H), 2.48-2.55 (m, 0.3H), 2.33 (m, 0.2H), 1.35-1.63 (m, 4H), 1.06-1.20 (m, 6H), 0.75-0.83 (m, 3H), 0.59-0.72 (m, 3H) | 2.42$^b$ | 474.2 (M + H⁺) |
| 72 | ¹H NMR (400 MHz, methanol-d4) δ ppm: 8.20 (s, 0.3H), 7.74 (s, 0.7H), 7.26 (s, 1H), 7.22 (s, 1H), 7.11 (d, J = 3.5 Hz, 1H), 6.78-6.83 (m, 1H), 6.76 (s, 1H), 4.53-4.72 (m, 2H), 4.00 (q, J = 7.1 Hz, 2H), 3.44-3.56 (m, 3H), 2.42-2.64 (m, 1H), 1.33-1.64 (m, 4H), 1.30 (t, J = 7.0 Hz, 3H), 1.01-1.21 (m, 6H), 0.71-0.82 (m, J = 7.0, 7.0 Hz, 3H), 0.60-0.71 (m, 3H) | 2.57$^b$ | 532.3 (M + H⁺) |

| Ex. | ¹H NMR | tR (min) | MS (m/z) |
|---|---|---|---|
| 73 | ¹H NMR (400 MHz, DMSO-d6) δ ppm: 9.64 (s, 1H), 9.61 (s, 0.3H), 9.29 (s, 0.7H), 9.12 (t, J = 5.9 Hz, 0.3H), 8.98 (t, J = 6.0 Hz, 0.7H), 8.77 (t, J = 5.6 Hz, 0.3H), 8.51 (t, J = 5.8 Hz, 0.7H), 8.29 (s, 0.3H), 7.76 (s, 0.7H), 7.19-7.25 (m, J = 3.8 Hz, 1H), 6.98-7.04 (m, 1H), 6.91-6.97 (m, 1H), 6.84-6.89 (m, J = 1.5 Hz, 1H), 6.34 (q, J = 2.2 Hz, 1H), 4.44-4.72 (m, J = 11.9, 11.9, 5.8 Hz, 2H), 4.16-4.28 (m, 0.3H), 3.95-4.10 (m, 2H), 3.57 (td, J = 9.3, 5.0 Hz, 0.7H), 2.53-2.64 (m, 1H), 1.36-1.59 (m, 4H), 1.33 (t, J = 6.9 Hz, 3H), 1.05-1.23 (m, 6H), 0.67-0.83 (m, 6H) | 2.54[b] | 490.0 (M + H⁺) |
| 74 | ¹H NMR (400 MHz, DMSO-d6) δ ppm: 12.32-13.17 (m, 1H), 9.60 (s, 0.3H), 9.20-9.40 (m, 0.6H), 9.10-9.19 (m, 0.3H), 8.95-9.06 (m, 0.7H), 8.87 (d, J = 7.8 Hz, 1H), 8.72-8.80 (m, 0.3H), 8.46-8.57 (m, 0.7H), 8.30 (s, 0.3H), 8.01 (d, J = 8.0 Hz, 1H), 7.77 (s, 0.7H), 7.56-7.70 (m, 2H), 7.23-7.38 (m, 2H), 4.77-4.92 (m, 1H), 4.49-4.77 (m, 2H), 4.33 (q, J = 6.9 Hz, 2H), 4.17-4.28 (m, 0.3H), 3.52-3.66 (m, 0.7H), 2.74-3.01 (m, 2H), 2.54-2.67 (m, 1H), 1.49 (t, J = 6.9 Hz, 6H), 1.19 (s, 7H), 0.62-0.85 (m, 6H) | 5.56[a] | 633.3 (M + H⁺) |
| 75 | ¹H NMR (400 MHz, methanol-d4) δ ppm: 8.21 (s, 0.2H), 7.94 (d, J = 8.0 Hz, 2H), 7.80 (d, J = 8.0 Hz, 2H), 7.75 (s, 0.7H), 7.15 (d, J = 3.5 Hz, 1H), 6.92 (d, J = 2.8 Hz, 1H), 4.57-4.72 (m, J = 9.0 Hz, 2H), 4.16-4.30 (m, 0.3H), 3.46-3.59 (m, 0.7H), 2.47-2.66 (m, 1H), 1.34-1.64 (m, J = 7.3 Hz, 4H), 1.03-1.22 (m, 6H), 0.73-0.85 (m, 3H), 0.60-0.72 (m, 3H) | 5.66[a] | 647.3 (M + H⁺) |
| 76 | ¹H NMR (400 MHz, DMSO-d6) δ ppm: 12.39 (br. s., 1H), 9.97 (s, 0.2H), 9.55 (br. s., 0.6H), 8.96-9.16 (m, 1H), 8.51-8.66 (m, 1H), 8.23 (s, 0.4H), 7.82 (d, J = 7.3 Hz, 1H), 7.80 (s, 1.6H), 7.43 (t, J = 7.8 Hz, 1H), 7.29 (d, J = 7.0 Hz, 1H), 7.25 (d, J = 3.5 Hz, 1H), 7.11 (d, J = 3.5 Hz, 1H), 4.49-4.76 (m, 2H), 3.69-3.81 (m, 1H), 3.50-3.69 (m, 1H), 3.27-3.45 (1H, excluded by solvent), 2.57-2.79 (m, 1H), 1.43 (d, J = 7.0 Hz, 3H), 1.27-1.39 (m, 2H), 1.17 (d, J = 7.0 Hz, 6H), 0.76 (t, 3H) | 2.31[b] | 474.1 (M + H⁺) |
| 77 | ¹H NMR (400 MHz, Deuteriumoxide) δ ppm: 7.83 (s, 0.1H), 7.75 (s, 1H), 7.49 (s, 1H), 7.41 (s, 0.9H), 7.27 (s, 1H), 7.18 (d, J = 3.8 Hz, 1H), 7.00 (d, J = 3.8 Hz, 1H), 4.74-4.83 (1H, concealed under solvent peak), 4.44-4.56 (m, 2H), 4.13 (q, J = 6.9 Hz, 2H), 3.26-3.37 (m, 1H), 2.46-2.73 (m, 3H), 1.36-1.63 (m, 3H), 1.31 (t, J = 7.0 Hz, 4H), 0.80-1.12 (m, 6H), 0.68 (t, J = 7.2 Hz, 3H), 0.37-0.49 (m, 3H) | 2.33[b] | 633.3 (M + H⁺) |
| 78 | ¹H NMR (400 MHz, DMSO-d6) δ ppm: 10.02 (s, 0.4H), 9.56 (s, 0.6H), 9.08-9.23 (m, 1H), 8.59 (q, J = 5.4 Hz, 1H), 8.23 (s, 0.4H), 7.86-7.98 (m, 1H), 7.83 (s, 0.6H), 7.25 (d, J = 3.8 Hz, 1H), 7.06 (t, J = 8.3 Hz, 1H), 6.86 (t, J = 3.6 Hz, 1H), 4.46-4.77 (m, 2H), 3.50-3.73 (m, 1H), 3.26-3.44 (1H, excluded by solvent), 2.59-2.82 (m, 1H), 1.26-1.48 (m, 2H), 1.09-1.26 (m, 6H), 0.75 (t, 3H) | 2.20[b] | 482.1 (M + H⁺) |
| 79 | ¹H NMR (400 MHz, DMSO-d6) δ ppm: 13.18 (br. s., 1H), 10.02 (br. s., 0.3H), 9.54 (br. s., 0.5H), 9.14-9.31 (m, 1H), 8.50-8.65 (m, 1H), 8.21 (s, 0.4H), 8.01 (s, 1H), 7.90 (s, 0.6H), 7.75 (s, 1H), 7.42 (s, 1H), 7.26 (s, 2H), 4.63 (t, J = 5.6 Hz, 2H), 4.16 (q, J = 6.8 Hz, 2H), 3.65 (dt, J = 14.2, 6.8 Hz, 2H), 2.37-2.48 (m, 2H), 1.38 (t, J = 6.9 Hz, 3H) | 2.23[b] | 420.1 |
| 80 | ¹H NMR (400 MHz, DMSO-d6) δ ppm: 8.86 (br. s., 1H), 7.69-7.94 (m, 1H), 7.60 (br. s., 2H), 7.21 (br. s., 3H), 6.98 (br. s., 1H), 4.61 (br. s., 2H), 4.13 (br. s., 1H), 1.61-1.89 (m, 1H), 1.30-1.59 (m, 4H), 1.20 (d, J = 13.8 Hz, 8H), 0.77 (br. s., 8H) | 2.50[b] | 514.2 (M + H⁺) |
| 81 | ¹H NMR (400 MHz, methanol-d4) δ ppm: 8.47 (s, 0.3H), 8.34 (s, 0.2H), 7.87 (s, 0.8H), 7.72 (d, J = 2.3 Hz, 1H), 7.50 (d, J = 2.5 Hz, 1H), 7.25-7.29 (m, 1H), 7.24 (br. s., 0.8H), 4.68-4.87 (m, 2H), 4.29-4.41 (m, 0.3H), 4.09 (q, J = 6.9 Hz, 2H), 3.56-3.74 (m, 0.8H), 3.37 (s, 0.8H), 2.58-2.78 (m, 1H), 1.46-1.81 (m, 4H), 1.41 (t, J = 6.9 Hz, 3H), 1.14-1.35 (m, 6H), 0.85-1.00 (m, J = 7.2, 7.2 Hz, 3H), 0.72-0.85 (m, 3H) | 2.57[b] | 534.2 (M + H⁺) |
| 82 | ¹H NMR (400 MHz, DMSO-d6) δ ppm: 11.06-11.71 (m, 0.6H), 8.70-8.96 (m, 1H), 7.90 (br. s., 1H), 7.58 (br. s., 1H), 7.40 (d, J = 12.3 Hz, 2H), 7.21 (d, J = 2.5 Hz, 1H), 7.01 (br. s., 1H), 4.62 (br. s., 2H), 3.98 (t, J = 6.1 Hz, 2H), 3.18 (br. s., 1H), 2.38-2.48 (m, 1H), 1.71-1.85 (m, J = 6.0 Hz, 2H), 1.31-1.64 (m, 4H), 1.21 (br. s., 6H), 0.96-1.09 (m, J = 7.0 Hz, 3H), 0.78 (d, J = 7.3 Hz, 6H) | 2.72[b] | 532.2 (M + H⁺) |
| 83 | ¹H NMR (400 MHz, Deuteriumoxide) δ ppm: 8.17 (s, 1H), 7.95 (d, J = 7.5 Hz, 1H), 7.69-7.79 (m, 2H), 7.49-7.59 (m, 1H), 7.23 (d, J = 3.5 Hz, 1H), 7.00 (d, J = 3.5 Hz, 1H), 4.79 (d, J = 13.8 Hz, 1H), 4.53-4.63 (m, 2H), 4.09-4.28 (m, 0.2H), 3.56 (t, J = 8.7 Hz, 0.8H), 2.53-2.83 (m, 3H), 1.31-1.75 (m, 4H), 0.99-1.19 (m, 4H), 0.86-0.99 (m, 2H), 0.69-0.82 (m, 3H), 0.50 (t, 3H) | 2.27[b] | 589.2 (M + H⁺) |

| Ex. | ¹H NMR | tR (min) | MS (m/z) |
|---|---|---|---|
| 84 | ¹H NMR (400 MHz, DMSO-d6) δ ppm: 12.17-12.93 (m, 2H), 9.59 (s, 0.3H), 9.25 (s, 0.7H), 9.17 (t, J = 5.5 Hz, 0.3H), 9.02 (t, J = 5.6 Hz, 0.7H), 8.83 (d, J = 8.0 Hz, 1H), 8.74 (t, J = 5.5 Hz, 0.3H), 8.47 (t, J = 5.6 Hz, 0.7H), 8.27 (s, 0.3H), 7.87 (s, 1H), 7.74 (s, 0.7H), 7.65 (s, 1H), 7.36 (s, 1H), 7.23 (d, J = 3.0 Hz, 1H), 7.14 (d, J = 3.3 Hz, 1H), 4.75 (q, J = 7.4 Hz, 1H), 4.44-4.70 (m, 2H), 4.17-4.25 (m, 0.3H), 4.14 (q, J = 7.0 Hz, 2H), 3.55 (td, J = 9.0, 5.5 Hz, 0.7H), 2.79-2.91 (m, J = 5.8 Hz, 1H), 2.69 (dd, J = 16.6, 8.3 Hz, 1H), 2.51-2.62 (m, 1H), 1.42-1.58 (m, 3H), 1.36 (t, J = 6.9 Hz, 4H), 1.03-1.23 (m, J = 13.1, 7.3 Hz, 6H), 0.63-0.81 (m, 6H) | 2.33[b] | 633.2 (M + H⁺) |
| 85 | ¹H NMR (400 MHz, methanol-d4) δ ppm: 8.32 (s, 0.2H), 7.91-8.00 (m, 1H), 7.88 (s, 0.7H), 7.65 (s, 1H), 7.43 (s, 1H), 7.27 (d, J = 3.8 Hz, 1H), 7.00-7.08 (m, 1H), 4.72-4.82 (m, 2H), 4.20 (q, J = 7.5 Hz, 2H), 4.15 (s, 2H), 2.51-2.80 (m, 1H), 1.50-1.77 (m, 4H), 1.46 (t, J = 6.9 Hz, 4H), 1.15-1.35 (m, 6H), 0.85-0.97 (m, 3H), 0.74-0.85 (m, 3H) | 2.38[b] | 575.2 (M + H⁺) |
| 86 | ¹H NMR (400 MHz, DMSO-d6) δ ppm: 12.68 (br. s., 2H), 9.22-9.75 (m, 0.6H), 9.11-9.21 (m, 0.4H), 9.02 (t, J = 5.8 Hz, 0.7H), 8.73-8.86 (m, 0.3H), 8.55 (t, J = 5.5 Hz, 0.7H), 8.35 (s, 0.3H), 7.82 (s, 0.7H), 7.51-7.66 (m, 2H), 7.31 (d, J = 3.3 Hz, 1H), 7.27 (t, J = 3.5 Hz, 1H), 7.22 (d, J = 7.5 Hz, 1H), 4.50-4.85 (m, 2H), 4.14-4.43 (m, 4H), 4.04-4.14 (m, 0.3H), 3.96 (s, 2H), 3.54-3.73 (m, 0.5H), 2.60-2.75 (m, 1H), 1.52-1.67 (m, 2H), 1.42-1.51 (m, 2H), 1.38 (s, 3H), 1.10-1.28 (m, 6H), 0.68-0.89 (m, 6H) | 2.26[b] | 633.3 (M + H⁺) |
| 87 | ¹H NMR (400 MHz, methanol-d4) δ ppm: 8.19 (s, 0.3H), 7.75 (s, 0.7H), 7.44-7.50 (m, 1H), 7.39 (t, J = 1.3 Hz, 1H), 7.13 (d, J = 3.5 Hz, 1H), 6.82-6.90 (m, 2H), 4.56-4.73 (m, 2H), 4.21 (s, 2H), 4.01-4.07 (m, 4H), 3.97-4.01 (m, 0.3H), 3.46-3.59 (m, 0.8H), 2.44-2.66 (m, 1H), 1.37-1.67 (m, 4H), 1.33 (s, 3H), 1.01-1.22 (m, 6H), 0.73-0.85 (m, 3H), 0.65 (s, 3H) | 2.30[b] | 633.3 (M + H⁺) |
| 88 | ¹H NMR (400 MHz, DMSO-d6) δ ppm: 9.17-9.26 (m, 0.4H), 8.99-9.15 (m, 0.7H), 8.72-8.88 (m, 0.3H), 8.55 (br. s., 0.7H), 8.29 (s, 0.2H), 7.82 (s, 1H), 7.76 (s, 0.8H), 7.66 (br. s., 1H), 7.41 (br. s., 1H), 7.32 (br. s., 1H), 7.26 (br. s., 1H), 7.19 (br. s., 1H), 4.75 (br. s., 2H), 4.45-4.72 (m, 1H), 4.17 (br. s., 2H), 3.72 (br. s., 6H), 3.49-3.64 (m, 1H), 2.55-2.69 (m, 1H), 1.46-1.63 (m, 2H), 1.39 (br. s., 4H), 1.16 (br. s., 6H), 0.61-0.90 (m, 6H) | 2.28[b] | 621.3 (M + H⁺) |
| 89 | ¹H NMR (400 MHz, DMSO-d6) δ ppm: 9.03-9.14 (m, 0.5H), 8.87-8.98 (m, 0.5H), 8.66-8.80 (m, 1H), 8.29-8.38 (m, 1H), 8.22 (s, 0.4H), 7.92 (d, J = 7.8 Hz, 1H), 7.87 (d, J = 7.8 Hz, 1H), 7.82 (s, 0.6H), 7.42 (t, J = 7.5 Hz, 1H), 7.26 (d, J = 3.3 Hz, 1H), 7.08 (d, J = 3.0 Hz, 1H), 4.48-4.81 (m, 2H), 3.19-3.70 (m, 2H), 2.53-2.80 (m, 1H), 1.26-1.49 (m, 2H), 0.90-1.26 (m, 6H), 0.63-0.79 (m, 3H) | 6.17[a] | 446.1 (M + H⁺) |
| 90 | ¹H NMR (400 MHz, DMSO-d6) δ ppm: 8.83 (br. s., 0.4H), 8.54-8.69 (m, 1H), 8.47 (br. s., 0.5H), 8.20 (s, 0.5H), 7.73-7.88 (m, 1.6H), 7.26-7.45 (m, 3.4H), 7.18 (dd, J = 8.4, 3.4 Hz, 1.3H), 6.87-6.99 (m, 1H), 4.47-4.73 (m, 2H), 3.51-3.77 (m, 1H), 3.29-3.49 (1H, excluded by solvent), 2.54-2.76 (m, 1H), 1.28-1.55 (m, 2H), 1.12-1.23 (m, 6H), 0.78 (q, 3H) | 2.27[b] | 446.3 (M + H⁺) |
| 91 | ¹H NMR (400 MHz, DMSO-d6) δ ppm: 10.18 (br. s., 0.3H), 9.60 (br. s., 0.5H), 9.11 (d, J = 1.3 Hz, 0.5H), 9.03 (t, J = 5.8 Hz, 0.5H), 8.61 (t, J = 5.6 Hz, 1H), 8.19-8.27 (m, 0.4H), 8.14 (br. s., 1H), 7.93 (br. s., 1H), 7.83 (s, 0.6H), 7.19-7.29 (m, J = 3.5 Hz, 2H), 7.07 (d, J = 3.5 Hz, 1H), 4.44-4.74 (m, 2H), 3.50-3.70 (m, 1H), 3.24-3.45 (1H, excluded by solvent), 2.58-2.81 (m, 1H), 1.27-1.48 (m, 2H), 1.08-1.22 (m, 6H), 0.74 (t, 3H) | 2.22[b] | 464.1 (M + H⁺) |
| 92 | ¹H NMR (400 MHz, DMSO-d6) δ ppm: 13.10 (br. s., 1H), 9.96 (br. s., 0.3H), 9.55 (br. s., 0.6H), 9.11-9.27 (m, 1H), 8.54-8.66 (m, 1H), 8.23 (s, 0.4H), 8.03 (q, J = 8.5 Hz, 4H), 7.84 (s, 0.6H), 7.23-7.32 (m, 2H), 4.51-4.76 (m, 2H), 3.49-3.71 (m, 1H), 3.28-3.44 (1H, excluded by solvent), 2.59-2.78 (m, 1H), 1.26-1.47 (m, 2H), 1.10-1.23 (m, 6H), 0.75 (t, 3H) | 2.22[b] | 446.2 (M + H⁺) |
| 93 | ¹H NMR (400 MHz, DMSO-d6) δ ppm: 12.45 (br.s., 1.6H), 9.58-9.64 (m, 0.3H), 9.28 (s, 0.6H), 9.17-9.23 (m, 0.3H), 9.02-9.09 (m, 0.6H), 8.75-8.80 (m, 0.3H), 8.70 (d, J = 7.3 Hz, 1H), 8.47-8.54 (m, 0.6H), 8.28-8.33 (m, 0.3H), 7.91 (s, 1H), 7.77 (s, 0.6H), 7.69 (s, 1H), 7.43 (s, 1H), 7.27 (s, 1H), 7.19 (s, 1H), 4.49-4.74 (m, 2H), 4.40-4.49 (m, 1H), 4.13-4.24 (m, 2H), 3.53-3.63 (m, 1H), 2.56-2.64 (m, 1H), 2.39 (t, J = 7.3 Hz, 2H), 2.07-2.19 (m, 1H), 1.94-2.04 (m, 1H), 1.47-1.59 (m, 2H), 1.34-1.46 (m, 5H), 1.11-1.23 (m, 6H), 0.67-0.84 (m, 6H) | 2.42[b] | 647.3 (M + H⁺) |

| Ex. | ¹H NMR | tR (min) | MS (m/z) |
|---|---|---|---|
| 94 | ¹H NMR (400 MHz, DMSO-d6) δ ppm: 9.11 (m, 1H), 8.59 (m, 1H), 8.20 (m, 1.4H), 8.09 (d, J = 8.0 Hz, 1H), 7.84 (s, 0.6H), 7.72 (m, 1H), 7.61 (dt, J = 3.0, 8.0 Hz, 1H), 7.29 (d, J = 3.0 Hz, 1H), 7.20 (d, J = 3.0 Hz, 1H), 4.63 (m, 2H), 3.60 (m, 1H), 3.42 (m, 1H), 2.62-2.74 (m, 1H), 1.57 (d, J = 14.5 Hz, 3H), 1.41 (m, 1H), 1.33 (m, 1H), 1.14-1.24 (m, 6H), 0.77 (m, 3H) | 0.65[d] | 480.1 (M + H⁺) |
| 95 | ¹H NMR (400 MHz, methanol-d4) δ ppm: 8.26 (s, 0.4H), 8.23 (d, J = 13.0 Hz, 1H), 7.96 (d, J = 13.0 Hz, 1H), 7.89 (s, 0.6H), 7.76 (dd, J = 7.4, 12.6 Hz, 1H), 7.50 (dt, J = 4.8, 8.0 Hz, 1H), 7.25 (d, J = 2.8 Hz, 1H), 6.98 (d, J = 2.8 Hz, 1H), 4.79 (m, 2H), 3.69-3.81 (m, 1.4H), 3.50 (d, J = 10.4 Hz, 3H), 3.46 (m, 0.6H), 2.84 (m, 0.6H), 2.69 (m, 0.4H), 1.57 (m, 1H), 1.45 (m, 1H), 1.21-1.34 (m, 6H), 0.81 (m, 3H) | 0.61[d] | 496.0 (M + H⁺) |
| 96 | ¹H NMR (400 MHz, DMSO-d6) δ ppm: 11.18 (br. s., 1.7H), 9.57 (br. s., 0.2H), 9.26 (br. s., 0.5H), 9.09-9.18 (m, 0.3H), 8.98 (t, J = 6.0 Hz, 0.7H), 8.72 (t, J = 5.4 Hz, 0.3H), 8.47 (t, J = 5.6 Hz, 0.7H), 8.26 (s, 0.3H), 7.72 (s, 0.7H), 7.65 (d, J = 13.3 Hz, 1H), 7.57 (s, 1H), 7.22 (d, J = 3.5 Hz, 1H), 7.06-7.17 (m, 2H), 4.43-4.70 (m, 2H), 4.14-4.24 (m, 0.3H), 4.09 (q, J = 6.8 Hz, 2H), 3.48-3.59 (m, 0.8H), 2.50-2.61 (m, 1H), 1.42-1.55 (m, 2H), 1.28-1.41 (m, 5H), 1.01-1.21 (m, 6H), 0.63-0.81 (m, 6H) | 6.04[a] | 554.0 (M + H⁺) |
| 97 | ¹H NMR (400 MHz, DMSO-d6) δ ppm: 9.75 (br. s., 0.3H), 9.44 (br. s., 0.4H), 8.96-9.11 (m, 0.3H), 8.73-8.88 (m, 0.7H), 8.40-8.54 (m, 0.5H), 8.32 (t, J = 6.3 Hz, 0.7H), 7.88-7.93 (m, 0.7H), 7.37-7.51 (m, 2H), 7.26 (d, J = 14.6 Hz, 1H), 5.05-5.16 (m, 1H), 4.49-4.74 (m, 3H), 4.35-4.45 (m, 0.3H), 4.26 (q, J = 6.8 Hz, 2H), 3.63-3.80 (m, 0.8H), 2.72-2.79 (m, 1H), 2.35-2.54 (m, 2H), 2.10-2.26 (m, 1H), 1.77-1.92 (m, 1H), 1.63-1.78 (m, 2H), 1.53 (s, 5H), 1.24-1.45 (m, 6H), 0.82-1.04 (m, 6H) | 1.70[c] | 558.0 (M + H⁺) |
| 98 | ¹H NMR (400 MHz, DMSO-d6) δ ppm: 9.60 (s, 0.3H), 9.27 (br. s., 0.5H), 9.12 (t, J = 6.3 Hz, 0.3H), 8.98 (t, J = 5.9 Hz, 0.7H), 8.76 (t, J = 5.4 Hz, 0.3H), 8.51 (t, J = 5.4 Hz, 0.7H), 8.30 (s, 0.3H), 7.77 (s, 0.7H), 7.71 (dd, J = 14.2, 7.9 Hz, 1H), 7.47-7.56 (m, J = 5.3 Hz, 2H), 7.21-7.30 (m, 2H), 4.47-4.79 (m, 2H), 4.20 (q, J = 6.9 Hz, 2.2H), 3.51-3.65 (m, 0.7H), 2.55-2.67 (m, 1H), 1.47-1.61 (m, 2H), 1.38 (t, J = 5H), 1.07-1.29 (m, 6H), 0.64-0.85 (m, 6H) | 5.62[a] | 554.3 (M + H⁺) |
| 99 | ¹H NMR (400 MHz, methanol-d4) δ ppm: 8.19 (s, 0.3H), 7.75 (s, 0.7H), 7.29 (br. s., 1H), 7.22 (br. s., 1H), 7.12 (d, J = 3.5 Hz, 1H), 6.75-6.87 (m, J = 3.5 Hz, 2H), 4.56-4.72 (m, 2H), 4.16-4.28 (m, 0.3H), 4.02 (q, J = 6.9 Hz, 2H), 3.44-3.58 (m, 0.7H), 3.07 (s, 1H), 3.02 (s, 1H), 2.54-2.66 (m, 0.7H), 2.44-2.54 (m, 0.3H), 1.35-1.65 (m, 4H), 1.31 (t, J = 6.9 Hz, 3H), 1.02-1.22 (m, 6H), 0.72-0.84 (m, J = 7.2, 7.2 Hz, 3H), 0.61-0.72 (m, 3H) | 2.41[b] | 568.2 |
| 100 | ¹H NMR (400 MHz, DMSO-d6) δ ppm: 9.16-9.35 (m, 0.7H), 9.03-9.16 (m, 0.3H), 8.84-8.94 (m, 0.6H), 8.64-8.72 (m, 0.4H), 8.55-8.64 (m, 1H), 8.39-8.48 (m, 0.7H), 8.22 (s, 0.3H), 7.82-7.90 (m, 1H), 7.70 (s, 1H), 7.59 (d, J = 1.5 Hz, 1H), 7.35 (d, J = 1.0 Hz, 1H), 7.18 (d, J = 3.5 Hz, 1H), 7.09 (d, J = 3.0 Hz, 1H), 4.42-4.66 (m, 2H), 4.04-4.13 (m, 2H), 3.44-3.59 (m, 3H), 2.47-2.57 (m, 1H), 1.36-1.51 (m, 3H), 1.31 (t, J = 6.7 Hz, 4H), 1.01-1.15 (m, 6H), 0.60-0.75 (m, 6H) | 6.06[a] | 610.8 (M + H⁺) |
| 101 | ¹H NMR (400 MHz, DMSO-d6) δ ppm: 9.62 (br. s., 0.3H), 9.30 (br. s., 0.5H), 9.21 (t, J = 5.9 Hz, 0.3H), 9.05 (t, J = 5.6 Hz, 0.7H), 8.76 (t, J = 5.6 Hz, 0.3H), 8.51 (t, J = 5.5 Hz, 0.7H), 8.30 (s, 0.3H), 7.77 (s, 0.7H), 7.65-7.75 (m, J = 13.6 Hz, 2H), 7.26 (d, J = 2.5 Hz, 1H), 7.21-7.25 (m, 1H), 7.15 (d, J = 14.3 Hz, 1H), 4.47-4.77 (m, 2H), 4.19-4.28 (m, 0.4H), 4.15 (q, J = 6.8 Hz, 2H), 3.52-3.62 (m, J = 11.0 Hz, 3.7H), 2.55-2.66 (m, 1H), 1.48-1.59 (m, 2H), 1.38 (t, J = 6.9 Hz, 5H), 1.05-1.25 (m, 6H), 0.66-0.84 (m, 6H) | 1.84[c] | 568.0 (M + H⁺) |
| 102 | ¹H NMR (400 MHz, methanol-d4) δ ppm: 8.14 (s, 0.4H), 7.78 (s, 0.6H), 7.41 (br. s., 1H), 7.37 (d, J = 7.8 Hz, 1H), 7.26 (t, J = 7.9 Hz, 1H), 7.12 (d, J = 3.3 Hz, 1H), 6.87 (d, J = 8.0 Hz, 1H), 6.83 (br. s., 1H), 6.10 (tt, J = 3.6, 56.0 Hz, 1H), 4.58-4.72 (m, 2H), 4.21 (td, J = 13.6, 3.3 Hz, 2H), 3.52-3.74 (m, 1.4H), 3.34 (dd, J = 14.2, 4.9 Hz, 0.6H), 2.73 (m, 0.6H), 2.58 (m, 0.4H), 1.38-1.54 (m, 1H), 1.26-1.38 (m, 1H), 1.00-1.26 (m, 6H), 0.68 (br. s., 3H) | 2.57[b] | 482.1 (M + H⁺) |
| 103 | ¹H NMR (400 MHz, DMSO-d6) δ ppm: 9.95 (s, 0.4H), 9.55 (s, 0.6H), 9.08-9.20 (m, 1H), 8.51-8.64 (m, 1H), 8.24 (s, 0.4H), 7.86 (s, 1H), 7.83 (s, 0.6H), 7.73 (d, J = 7.8 Hz, 1H), 7.42 (t, J = 7.8 Hz, 1H), 7.32 (d, J = 8.5 Hz, 1H), 7.24 (d, J = 3.5 Hz, 1H), 7.15-7.19 (m, 1H), 4.52-4.71 (m, 2H), 3.52-3.68 (m, 2H), 2.72 (br. s., 0.6H), 2.64 (br. s., 0.4H), 1.30-1.46 (m, 2H), 1.17 (br. s., 6H), 0.69-0.81 (m, 3H) | 2.17[b] | 462.2 (M + H⁺) |

| Ex. | ¹H NMR | tR (min) | MS (m/z) |
|---|---|---|---|
| 104 | ¹H NMR (400 MHz, methanol-d4) δ ppm: 8.14 (s, 0.4H), 7.78 (s, 0.6H), 7.67 (s, 1H), 7.50 (d, J = 7.8 Hz, 1H), 7.21-7.32 (m, 1H), 7.15 (d, J = 8.3 Hz, 1H), 7.13 (d, J = 3.3 Hz, 1H), 6.85 (d, J = 3.0 Hz, 1H), 4.60-4.69 (m, 2H), 3.53-3.72 (m, 1.4H), 3.34 (dd, J = 14.1, 4.8 Hz, 0.6H), 2.65-2.79 (m, 0.4H), 2.52-2.65 (m, 0.6H), 2.44 (s, 3H), 1.25-1.50 (m, 2H), 1.11-1.18 (m, 6H), 0.68 (d, J = 2.0 Hz, 3H) | 2.61[b] | 448.2 (M + H⁺) |
| 105 | ¹H NMR (400 MHz, DMSO-d6) δ ppm: 9.95 (br.s., 0.3H), 9.50-9.57 (m, 0.5H), 9.26-9.36 (m, 1H), 8.75 (s, 1H), 8.57-8.65 (m, 1H), 8.38 (d, J = 7.8 Hz, 1H), 8.18-8.26 (m, 1.4H), 7.84 (s, 0.6H), 7.78 (t, J = 8.0 Hz, 1H), 7.40 (d, J = 3.8 Hz, 1H), 7.30 (d, J = 3.5 Hz, 1H), 4.55-4.72 (m, 2H), 3.54-3.67 (m, 1H), 3.4 (1H excluded by solvent), 2.60-2.76 (m, 1H), 1.28-1.44 (m, 2H), 1.13-1.23 (m, 6H), 0.70-0.77 (m, 3H) | 2.47[b] | 447.1 (M + H⁺) |
| 106 | ¹H NMR (CHLOROFORM-d) δ ppm: 8.22 (br. s., 0.6H), 7.97 (s, 0.4H), 7.94 (br. s., 1H), 7.85 (br. s., 0.6H), 7.65-7.82 (m, 3H), 7.35-7.47 (m, 1H), 6.75 (br. s., 1H), 4.80 (m, 2H), 3.67-3.82 (m, 1H), 3.26-3.46 (m, 1H), 2.70-2.81 (m, 1H), 2.63 (s, 3H), 1.65 (br. s., 2H), 1.17 (br. s., 6H), 0.82 (br. s., 3H) | 2.34[b] | 456.1 (M + H⁺) |
| 107 | ¹H NMR (400 MHz, methanol-d4) δ ppm: 8.27 (s, 0.4H), 8.21 (s, 1H), 8.15 (s, 1H), 7.90 (s, 0.6H), 7.77 (d, J = 8.8 Hz, 1H), 7.56 (d, J = 8.8 Hz, 1H), 7.27 (d, J = 3.5 Hz, 1H), 6.99 (d, J = 3.5 Hz, 1H), 4.72-4.87 (m, 2H), 4.24 (s, 3H), 3.70-3.84 (m, 1.4H), 3.47 (dd, J = 14.2, 5.1 Hz, 0.6H), 2.81-2.92 (m, 0.6H), 2.70 (m, 0.4H), 1.51-1.67 (m, 1H), 1.38-1.51 (m, 1H), 1.18-1.38 (m, 6H), 0.64-0.86 (m, 3H) | 1.70[c] | 456.3 (M + H⁺) |
| 108 | ¹H NMR (400 MHz, methanol-d4) δ ppm: 8.26 (m, 1.5H), 8.06 (m, 1.5H), 7.91 (s, 0.5H), 7.80 (m, 1H), 7.58 (m, 1H), 7.27 (d, J = 3.5 Hz, 1H), 7.01 (d, J = 3.5 Hz, 0.5H), 4.80 (m, 2H), 3.70-3.83 (m, 1.5H), 3.47 (dd, J = 5.2, 14.5 Hz, 0.5H), 2.86 (m, 0.5H), 2.71 (m, 0.5H), 1.58 (m, 1H), 1.47 (m, 1H), 1.21-1.36 (m, 6H), 0.82 (m, 3H) | 0.58[d] | 482.0 (M + H⁺) |
| 109 | ¹H NMR (400 MHz, methanol-d4) δ ppm: 8.25 (s, 1H), 8.15 (d, J = 6.8 Hz, 1H), 7.95-8.06 (m, 1H), 7.86 (s, 1H), 7.61-7.70 (m, 2H), 7.42-7.50 (m, 1H), 7.27 (d, J = 3.5 Hz, 1H), 7.05-7.13 (m, 1H), 4.69-4.81 (m, 2H), 3.57-3.67 (m, 1H), 2.65-2.76 (m, 1H), 1.44-1.74 (m, 6H), 1.13-1.33(m, 4H), 0.89 (t, J = 7.4 Hz, 3H), 0.81 (t, J = 6.5 Hz, 3H) | 5.60[a] | 488.0 (M + H⁺) |
| 110 | ¹H NMR (400 MHz, DMSO-d6) δ ppm: 9.54-9.64 (m, 0.3H), 9.24-9.32 (m, 0.7H), 8.81-8.95 (m, 0.3H), 8.64 (t, J = 5.8 Hz, 0.7H), 8.27-8.33 (m, 0.3H), 8.22 (t, J = 6.0 Hz, 0.3H), 8.08 (t, J = 6.3 Hz, 0.7H), 7.64-7.78 (m, 0.7H), 7.14-7.52 (m, 5H), 4.80-4.98 (m, 1H), 4.27-4.59 (m, 3H), 4.15-4.27 (m, 0.3H), 3.47-3.63 (m, 0.7H), 2.18-2.36 (m, 2H), 1.92-2.08 (m, 1H), 1.28-1.76 (m, 5.2H), 0.94-1.28 (m, 6.4H), 0.51-0.92 (m, 6.4H) | 2.64[b] | 434.2 |
| 111 | ¹H NMR (METHANOL-d4) Shift: 8.32 (s, 0.3H), 7.90 (d, J = 5.5 Hz, 1H), 7.87 (s, 0.7H), 7.82 (d, J = 7.3 Hz, 1H), 7.26 (d, J = 3.5 Hz, 1H), 7.00 (d, J = 3.3 Hz, 1H), 4.69-4.84 (m, 2H), 4.35 (br. s., 0.3H), 4.21-4.31 (m, 2H), 3.56-3.69 (m, 0.7H), 2.67-2.77 (m, 0.7H), 2.62 (br. s., 0.3H), 1.63-1.73 (m, 2H), 1.50 (t, J = 6.9 Hz, 5H), 1.13-1.36 (m, 6H), 0.84-0.97 (m, 3H), 0.71-0.84 (m, 3H) | 7.15[a] | 536.0 (M + H⁺) |
| 112 | ¹H NMR (DMSO-d6) Shift: 10.01 (br. s., 0.1H), 9.67 (br. s., 0.1H), 9.33 (br. s., 0.5H), 9.14-9.23 (m, 0.3H), 9.05 (t, J = 5.9 Hz, 0.7H), 8.79 (t, J = 5.5 Hz, 0.3H), 8.53 (t, J = 5.6 Hz, 0.7H), 8.29 (s, 0.3H), 7.85 (s, 1H), 7.76 (s, 0.7H), 7.51 (br. s., 1H), 7.35 (d, J = 1.3 Hz, 1H), 7.21-7.29 (m, 1H), 7.09-7.17 (m, 1H), 4.43-4.75 (m, 2H), 4.22 (q, J = 7.8 Hz, 0.3H), 3.57 (td, J = 9.2, 4.9 Hz, 0.7H), 2.54-2.70 (m, 1H), 1.31-1.62 (m, 4H), 1.03-1.28 (m, 6H), 0.59-0.87 (m, 6H) | 5.41[g] | 490.2 (M + H⁺) |
| 113 | ¹H NMR (DMSO-d6) Shift: 9.61 (s, 0.2H), 9.22-9.37 (m, 0.7H), 9.13 (t, J = 5.9 Hz, 0.6H), 8.78 (t, J = 5.9 Hz, 0.3H), 8.52 (t, J = 5.9 Hz, 0.6H), 8.30 (s, 0.3H), 7.99-8.09 (m, 1H), 7.70-7.82 (m, 1.7H), 7.38 (t, J = 2.0 Hz, 1H), 7.21-7.29 (m, 2H), 4.84 (s, 2H), 4.43-4.74 (m, 2H), 4.15-4.29 (m, 0.3H), 3.57 (td, J = 9.4, 4.8 Hz, 0.7H), 2.54-2.67 (m, 1H), 1.32-1.62 (m, 4H), 1.00-1.29 (m, 6H), 0.59-0.84 (m, 6H) | 5.39[g] | 548.3 (M + H⁺) |
| 114 | ¹H NMR (DMSO-d6) Shift: 9.61 (s, 0.3H), 9.29 (s, 0.7H), 9.20 (t, J = 5.9 Hz, 0.3H), 9.06 (t, J = 6.1 Hz, 0.7H), 8.79 (t, J = 5.8 Hz, 0.3H), 8.54 (t, J = 5.9 Hz, 0.7H), 8.29 (s, 0.3H), 7.95-8.02 (m, 1H), 7.85-7.94 (m, 2H), 7.76 (s, 0.7H), 7.26-7.32 (m, 1H), 7.20-7.25 (m, 1H), 4.47-4.78 (m, 2H), 4.22 (q, J = 7.3 Hz, 0.3H), 3.99 (s, 2H), 3.58 (td, J = 9.5, 4.6 Hz, 0.7H), 2.54-2.67 (m, 1H), 1.30-1.60 (m, 4H), 1.05-1.21 (m, 6H), 0.59-0.86 (m, 6H) | 2.26[b] | 532.1 (M + H⁺) |

| Ex. | ¹H NMR | tR (min) | MS (m/z) |
|---|---|---|---|
| 115 | ¹H NMR (DMSO-d6) Shift: 9.61 (s, 0.3H), 9.26-9.43 (m, 0.8H), 8.76 (t, J = 5.6 Hz, 0.2H), 8.53 (t, J = 5.8 Hz, 0.7H), 8.30 (s, 0.3H), 7.96-8.08 (m, 1H), 7.79 (s, 0.7H), 7.29-7.38 (m, 1H), 7.23-7.28 (m, 1H), 7.04-7.21 (m, 6H), 4.50-4.88 (m, 2H), 4.29 (d, J = 6.8 Hz, 0.1H), 4.06 (q, J = 6.9 Hz, 2H), 3.49-3.76 (m, 0.6H), 2.58-2.75 (m, 1H), 2.39-2.54 (2H, under solvent peak), 1.63-1.87 (m, 2H), 1.45-1.59 (m, 2H), 1.25-1.39 (m, 3H), 0.58-0.87 (m, 3H) | 0.89$^e$ | 568.5 (M + H⁺) |
| 117 | ¹H NMR (DMSO-d6) Shift: 9.58 (s, 0.3H), 9.28 (s, 0.7H), 9.21 (t, J = 5.8 Hz, 0.5H), 8.83 (d, J = 7.8 Hz, 1H), 8.58 (t, J = 5.9 Hz, 0.6H), 8.30 (s, 0.3H), 7.96 (d, J = 8.0 Hz, 1.4H), 7.51-7.86 (m, 7H), 7.24-7.46 (m, 5H), 4.97 (dt, J = 7.7, 5.3 Hz, 1.2H), 4.28 (dd, J = 7.2, 2.1 Hz, 0.6H), 4.11 (q, J = 5.1 Hz, 0.7H), 3.69 (s, 4H), 3.62 (s, 2H), 3.17 (d, J = 5.0 Hz, 2H), 2.97 (dd, J = 8.0, 5.3 Hz, 2H), 2.58-2.75 (m, 2H), 1.32-1.51 (m, 3H), 0.64-0.86 (m, 3H) | 1.21$^h$ | 717.2 (M + H⁺) |
| 118 | ¹H NMR (METHANOL-d4) Shift: 8.27 (s, 0.3H), 7.82-8.00 (m, 1.6H), 7.44 (d, J = 3.3 Hz, 1H), 7.10-7.33 (m, 3H), 6.72-6.88 (m, 2H), 4.60-4.88 (m, 4H), 4.35-4.50 (m, 0.3H), 3.63-3.82 (m, 0.7H), 2.69-2.92 (m, 1H), 2.47-2.66 (m, 2H), 1.56-2.00 (m, 4H), 0.69-1.03 (m, 3H) | 6.57$^a$ | 634.2 (M + H⁺) |
| 119 | ¹H NMR (METHANOL-d4) Shift: 9.11 (t, J = 6.0 Hz, 0.2H), 9.01 (t, J = 6.0 Hz, 0.5H), 8.91 (t, J = 5.9 Hz, 0.2H), 8.84 (t, J = 6.0 Hz, 0.5H), 8.74 (d, J = 7.8 Hz, 0.3H), 8.32 (s, 0.2H), 7.91-8.05 (m, 4H), 7.87 (s, 0.7H), 7.28 (d, J = 3.5 Hz, 1H), 7.03-7.14 (m, 1H), 4.97-5.06 (m, 1H), 4.66-4.88 (m, 2H), 4.35 (ddd, J = 10.0, 7.2, 5.1 Hz, 0.2H), 3.55-3.75 (m, 0.8H), 2.86-3.13 (m, 2H), 2.52-2.81 (m, 1H), 1.43-1.81 (m, 4H), 1.11-1.37 (m, 6H), 0.66-1.01 (m, 6H) | 5.40$^a$ | 589.3 (M + H⁺) |
| 120 | ¹H NMR (DMSO-d6) Shift: 9.61 (s, 0.3H), 9.29 (s, 0.7H), 9.17 (t, J = 6.0 Hz, 0.2H), 9.03 (t, J = 6.0 Hz, 0.7H), 8.78 (t, J = 5.5 Hz, 0.2H), 8.64 (br. s., 0.6H), 8.53 (t, J = 6.0 Hz, 0.7H), 8.29 (s, 0.3H), 7.72-7.86 (m, 2.8H), 7.39 (d, J = 8.0 Hz, 1H), 7.23-7.30 (m, 1H), 7.13-7.20 (m, 1H), 4.46-4.78 (m, 3H), 4.22 (q, J = 7.4 Hz, 0.2H), 3.58 (td, J = 9.5, 4.8 Hz, 0.7H), 2.77-2.89 (m, 1H), 2.55-2.73 (m, 2H), 2.41 (s, 3H), 1.33-1.62 (m, 4H), 1.05-1.25 (m, 6H), 0.60-0.85 (m, 6H) | 5.46$^a$ | 603.3 (M + H⁺) |
| 121 | ¹H NMR (DMSO-d6) Shift: 9.62 (s, 0.3H), 9.26-9.41 (m, 0.7H), 9.21 (t, J = 6.0 Hz, 0.6H), 8.79 (t, J = 5.6 Hz, 0.3H), 8.52 (t, J = 5.9 Hz, 0.7H), 8.30 (s, 0.3H), 7.97-8.07 (m, 1H), 7.76 (s, 0.7H), 7.27-7.34 (m, 1H), 7.22-7.26 (m, 1H), 7.15-7.19 (m, 1H), 4.73 (s, 2H), 4.45-4.71 (m, 2H), 4.14-4.29 (m, 0.2H), 3.58 (td, J = 9.5, 5.1 Hz, 0.7H), 2.54-2.68 (m, 1H), 1.31-1.63 (m, 4H), 1.03-1.26 (m, 6H), 0.57-0.86 (m, 6H) | 5.29$^i$ | 564.1 (M + H⁺) |
| 122 | ¹H NMR (METHANOL-d4) Shift: 8.32 (s, 0.3H), 7.89 (s, 0.6H), 7.52 (d, J = 18.3 Hz, 2H), 7.24 (d, J = 3.5 Hz, 1H), 7.12-7.21 (m, 1H), 6.90-7.02 (m, 2H), 6.70-6.86 (m, 2H), 4.65-4.89 (m, 2H), 4.28-4.47 (m, 2.2H), 4.03-4.22 (m, 4H), 3.59-3.77 (m, 0.7H), 2.47-2.89 (m, 3H), 1.52-1.97 (m, 4H), 1.42 (t, J = 6.9 Hz, 3H), 0.77-1.00 (m, 3H) | 6.56$^a$ | 703.2 (M + H⁺) |
| 123 | ¹H NMR (METHANOL-d4) Shift: 9.27 (d, J = 7.5 Hz, 0.6H), 9.13 (t, J = 6.0 Hz, 0.1H), 8.27 (s, 0.3H), 8.09 (d, J = 8.3 Hz, 1H), 7.90 (s, 0.6H), 7.58-7.68 (m, 0.6H), 7.52 (d, J = 8.3 Hz, 1H), 7.26-7.37 (m, 1H), 7.15-7.25 (m, 1H), 7.03-7.14 (m, 1H), 6.70-6.89 (m, 2H), 4.66-4.86 (m, 2H), 4.26-4.50 (m, 2.3H), 3.60-3.82 (m, 0.6H), 2.88-3.21 (m, 2H), 2.67-2.86 (m, 1H), 2.50-2.64 (m, 2H), 1.77-1.96 (m, 2H), 1.51-1.76 (m, 5H), 0.76-1.02 (m, 3H) | 6.40$^a$ | 703.2 (M + H⁺) |
| 124 | ¹H NMR (DMSO-d6) Shift: 9.63 (s, 0.3H), 9.31 (s, 0.6H), 9.20 (t, J = 6.1 Hz, 0.3H), 9.12 (t, J = 6.0 Hz, 0.6H), 8.78 (t, J = 5.8 Hz, 0.3H), 8.56 (t, J = 5.8 Hz, 0.6H), 8.30 (s, 0.3H), 7.79 (s, 0.7H), 7.49-7.62 (m, 2H), 7.26-7.31 (m, 1H), 7.22-7.25 (m, 1H), 7.07-7.20 (m, 6H), 4.48-4.87 (m, 2H), 4.28 (d, J = 6.3 Hz, 0.1H), 4.13 (br. s., 2H), 3.89 (s, 2H), 3.57-3.73 (m, 0.7H), 3.26-3.46 (2H, under solvent peak), 2.56-2.76 (m, 1H), 2.40-2.54 (2H, under solvent peak), 1.63-1.83 (m, 2H), 1.43-1.60 (m, 2H), 1.17-1.38 (m, 3H), 0.65-0.85 (m, 3H) | 5.47$^a$ | 667.4 (M + H⁺) |
| 125 | ¹H NMR (DMSO-d6) Shift: 9.62 (s, 0.2H), 9.21-9.40 (m, 0.4H), 9.07 (br. s., 0.6H), 8.72-8.89 (m, 0.3H), 8.53 (t, J = 5.6 Hz, 0.7H), 8.30 (s, 0.3H), 7.93 (s, 1H), 7.76 (s, 0.7H), 7.67-7.72 (m, 1H), 7.39 (s, 1H), 7.24-7.31 (m, 1H), 7.14-7.22 (m, 1H), 4.83 (s, 2H), 4.46-4.78 (m, 2H), 4.13-4.31 (m, 0.2H), 3.58 (td, J = 9.5, 4.6 Hz, 0.7H), 3.28-3.42 (2H, under solvent peak), 2.79-2.96 (m, 1H), 2.56-2.75 (m, 0.8H), 1.33-1.62 (m, 4H), 0.96-1.26 (m, 6H), 0.61-0.85 (m, 6H) | 5.27$^a$ | 663.3 (M + H⁺) |
| 126 | ¹H NMR (DMSO-d6) Shift: 9.63 (br. s., 0.1H), 9.13-9.26 (m, 1H), 8.99 (t, J = 6.0 Hz, 0.7H), 8.78 (t, J = 5.8 Hz, 0.2H), 8.54 (t, J = 5.9 Hz, 0.7H), 8.29 (s, 0.3H), 7.90-8.07 (m, 1H), 7.77 (s, 0.7H), 7.64-7.72 (m, 1H), 7.53-7.63 (m, 1H), 7.17-7.37 (m, 2H), 4.88-5.06 (m, 2H), 4.49-4.84 (m, 3H), 4.22 (q, J = 7.4 Hz, 0.2H), 3.57 (td, J = 9.6, 4.4 Hz, 0.7H), 2.71-2.92 (m, 2H), 2.54-2.65 (m, 1H), 1.32-1.64 (m, 4H), 1.00-1.24 (m, 6H), 0.64-0.83 (m, 6H) | 5.38$^a$ | 663.3 (M + H⁺) |

| Ex. | ¹H NMR | tR (min) | MS (m/z) |
|---|---|---|---|
| 127 | ¹H NMR (DMSO-d6) Shift: 9.62 (s, 0.3H), 9.31 (s, 0.7H), 9.24 (t, J = 5.8 Hz, 0.3H), 9.15 (t, J = 6.1 Hz, 0.6H), 8.90 (d, J = 7.3 Hz, 1H), 8.77 (t, J = 5.5 Hz, 0.2H), 8.56 (t, J = 5.8 Hz, 0.7H), 8.30 (s, 0.3H), 8.01 (d, J = 8.3 Hz, 1H), 7.79 (s, 0.7H), 7.59-7.68 (m, 2H), 7.28-7.35 (m, 2H), 7.07-7.24 (m, 5H), 4.51-4.89 (m, 3H), 4.17-4.40 (m, 2.5H), 3.56-3.73 (m, 0.7H), 2.59-2.96 (m, 2H), 2.40-2.57 (2H, under solvent peak), 1.33-1.91 (m, 7H), 0.65-0.87 (m, 3H) | 0.79$^e$ | 667.6 (M + H⁺) |
| 128 | ¹H NMR (METHANOL-d4) d: 8.29-8.34 (m, 0.2H), 7.87 (s, 0.8H), 7.27 (d, J = 3.8 Hz, 1H), 7.08-7.17 (m, J = 17.1, 1.5 Hz, 3H), 4.69-4.85 m, 2H), 4.37 (q, J = 7.0 Hz, 2H), 4.20-4.33 (m, J = 5.8, 5.8 Hz, 3.57-3.69 (m, 0.7H), 2.72 (td, J = 9.8, 4.8 Hz, 0.7H), 2.62 (ddd, 0.2H), J = 10.4, 7.2, 4.5 Hz, 0.3H), 1.43-1.77 (m, 7H), 1.12-1.36 (m, 6H), 0.85-0.97 (m, J = 7.2, 7.2 Hz, 3H), 0.73-0.84 (m, 3H) | 0.97$^e$ | 534.1 (M + H⁺) |
| 129 | ¹H NMR (DMSO-d6) Shift: 9.61 (s, 0.3H), 9.26-9.36 (m, 0.6H), 9.20 (t, J = 5.9 Hz, 0.6H), 8.72-8.82 (m, 0.1H), 8.53 (t, J = 5.8 Hz, 0.7H), 8.29 (s, 0.3H), 8.17 (s, 1H), 8.10 (dd, J = 8.3, 1.8 Hz, 1H), 7.83 (d, J = 8.0 Hz, 1H), 7.76 (s, 0.7H), 7.31-7.38 (m, 1H), 7.25-7.30 (m, 1H), 4.45-4.77 (m, 2H), 4.14-4.29 (m, 0.1H), 3.58 (td, J = 9.3, 4.9 Hz, 0.5H), 2.53-2.67 (m, 1H), 1.31-1.61 (m, 4H), 1.02-1.23 (m, 6H), 0.56-0.83 (m, 6H) | 2.23$^b$ | 519.0 (M + H⁺) |
| 130 | ¹H NMR (METHANOL-d4) Shift: 9.06 (t, J = 5.9 Hz, 0.1H), 8.89 (dt, J = 16.5, 5.9 Hz, 0.7H), 8.29 (s, 0.3H), 8.10 (s, 0.1H), 7.83-7.93 (m, 0.8H), 7.61-7.69 (m, 1H), 7.54-7.59 (m, 1H), 7.27 (d, J = 3.8 Hz, 1H), 7.13 (d, J = 1.5 Hz, 1H), 7.00-7.08 (m, 1H), 4.71-4.85 (m, 2H), 4.42 (s, 2H), 3.92 (s, 2H), 3.56-3.73 (m, 0.8H), 2.93 (s, 3H), 2.55-2.81 (m, 1H), 1.37-1.80 (m, 4H), 1.12-1.35 (m, 6H), 0.65-1.03 (m, 6H) | 5.87$^a$ | 575.2 (M + H⁺) |
| 131 | ¹H NMR (METHANOL-d4) Shift: 8.32 (s, 0.2H), 8.13-8.17 (m, 0.8H), 8.08-8.12 (m, 0.1H), 7.87 (s, 0.7H), 7.72-7.82 (m, 0.8H), 7.64 (t, J = 1.9 Hz, 0.8H), 7.55-7.60 (m, 0.2H), 7.25-7.31 (m, 1H), 7.01-7.11 (m, 1H), 4.70-4.81 (m, 2H), 4.65-4.68 (m, 2H), 4.26-4.42 (m, 0.2H), 3.56-3.73 (m, 0.7H), 2.55-2.80 (m, 1H), 1.46-1.83 (m, 3H), 1.14-1.36 (m, 7H), 0.63-1.00 (m, 6H) | 5.65$^a$ | 547.3 (M + H⁺) |
| 132 | ¹H NMR (METHANOL-d4) Shift: 8.31 (s, 0.3H), 8.06 (d, J = 8.3 Hz, 1H), 7.89 (s, 0.7H), 7.54-7.61 (m, 1H), 7.48 (d, J = 8.0 Hz, 1H), 7.23-7.30 (m, 1H), 7.01-7.11 (m, 1H), 4.64-4.86 (m, 2H), 4.19-4.45 (m, 2.5H), 3.86-4.00 (m, 0.2H), 3.59-3.78 (m, 0.8H), 3.41-3.54 (m, 0.2H), 3.13 (dd, J = 17.2, 4.4 Hz, 1H), 2.87-3.02 (m, 1H), 2.55-2.80 (m, 1H), 1.45-1.85 (m, 7H), 1.08-1.37 (m, 6H), 0.62-0.98 (m, 6H) | 5.80$^a$ | 633.4 (M + H⁺) |
| 133 | ¹H NMR (DMSO-d6) Shift: 12.82 (br. s., 1H), 12.42 (br. s., 1H), 9.61 (s, 0.3H), 9.30 (br. s., 0.6H), 9.24 (t, J = 6.5 Hz, 0.3H), 9.09 (t, J = 5.9 Hz, 0.7H), 8.86 (d, J = 7.8 Hz, 1H), 8.79 (s, 0.3H), 8.54 (t, J = 5.4 Hz, 0.7H), 8.29 (s, 0.3H), 7.93-8.06 (m, 4H), 7.77 (s, 0.7H), 7.24-7.30 (m, 2H), 4.74-4.80 (m, 1H), 4.49-4.72 (m, 2H), 4.19-4.26 (m, 0.3H), 3.54-3.68 (m, 0.7H), 2.87 (dd, J = 16.4, 5.6 Hz, 1H), 2.73 (dd, J = 16.8, 7.8 Hz, 1H), 2.54-2.64 (m, 1H), 1.34-1.56 (m, 4H), 1.04-1.22 (m, 6H), 0.63-0.81 (m, 6H) | 2.15$^b$ | 589.2 |
| 134 | ¹H NMR (DMSO-d6) Shift: 12.50 (br. s., 1H), 9.61 (s, 0.3H), 9.30 (s, 0.7H), 9.24 (t, J = 6.1 Hz, 0.3H), 9.09 (t, J = 6.0 Hz, 0.7H), 8.79 (t, J = 5.5 Hz, 0.3H), 8.70 (d, J = 7.5 Hz, 1H), 8.54 (t, J = 5.8 Hz, 0.7H), 8.29 (s, 0.3H), 7.96-8.06 (m, 4H), 7.77 (s, 0.7H), 7.24-7.31 (m, 2H), 4.49-4.72 (m, 2H), 4.43 (ddd, J = 9.7, 7.8, 5.1 Hz, 1H), 4.22 (d, J = 7.5 Hz, 0.3H), 3.58 (td, J = 9.6, 4.6 Hz, 0.7H), 2.54-2.67 (m, 1H), 2.32-2.43 (m, 2H), 2.06-2.16 (m, 1H), 1.91-2.02 (m, 1H), 1.34-1.56 (m, 4H), 1.06-1.23 (m, 6H), 0.66-0.82 (m, 6H) | 0.84$^f$ | 603.3 |
| 135 | ¹H NMR (DMSO-d6) Shift: 12.90 (br. s., 1H), 12.23 (br. s., 1H), 9.61 (s, 0.3H), 9.29 (s, 0.7H), 9.18 (t, J = 5.9 Hz, 0.3H), 9.04 (t, J = 6.0 Hz, 0.7H), 8.77 (t, J = 5.6 Hz, 0.3H), 8.50-8.59 (m, 1.7H), 8.29 (s, 0.3H), 7.88 (d, J = 8.0 Hz, 1H), 7.76 (s, 0.7H), 7.59-7.65 (m, 2H), 7.27-7.33 (m, 2H), 4.50-4.73 (m, 3H), 4.27-4.37 (m, 2H), 4.22 (q, J = 6.6 Hz, 0.3H), 3.57 (td, J = 9.6, 4.6 Hz, 0.7H), 2.53-2.63 (m, 1H), 2.26-2.40 (m, 2H), 2.09-2.18 (m, 1H), 1.89-1.99 (m, 1H), 1.35-1.56 (m, 7H), 1.07-1.23 (m, 6H), 0.66-0.82 (m, 6H) | 5.773$^a$ | 647.4 |
| 136 | ¹H NMR (DMSO-d6) Shift: 12.77 (br. s., 2H), 9.61 (s, 0.3H), 9.29 (s, 0.7H), 9.24 (t, J = 5.9 Hz, 0.3H), 9.09 (t, J = 5.8 Hz, 0.7H), 8.79 (br. s., 0.3H), 8.54 (t, J = 5.6 Hz, 0.7H), 8.29 (s, 0.3H), 7.93-8.06 (m, 2H), 7.76 (s, 0.7H), 7.41 (d, J = 8.3 Hz, 2H), 7.18-7.32 (m, 2H), 4.48-4.72 (m, 2H), 4.18-4.27 (m, 0.4H), 4.15 (s, 2H), 4.00-4.08 (m, 2H), 3.58 (td, J = 9.3, 4.8 Hz, 0.7H), 2.55-2.65 (m, 1H), 1.33-1.56 (m, 4H), 1.07-1.26 (m, 6H), 0.66-0.86 (m, 6H) | 5.283$^a$ | 589.3 |
| 137 | ¹H NMR (DEUTERIUM OXIDE) Shift: 7.75 (s, 0.7H), 7.42 (s, 0.9H), 7.33 (s, 1H), 7.11-7.19 (m, 1H), 6.98 (s, 1H), 6.85-6.92 (m, 1H), 4.48-4.63 (m, 1H), 4.23 (s, 2H), 4.08 (q, J = 7.0 Hz, 2.5H), 3.01 (d, J = 12.5 Hz, 2H), 1.30 (t, J = 7.0 Hz, 3.4H), 0.92-1.14 (m, 0.6H), 0.64-0.81 (m, 3H), 0.37-0.53 (m, 2H) | 5.64$^a$ | 597.2 (M + H⁺) |

-continued

| Ex. | ¹H NMR | tR (min) | MS (m/z) |
|---|---|---|---|
| 138 | ¹H NMR (DMSO-d6) Shift: 9.93 (br. s., 0.8H), 9.62 (br. s., 0.2H), 9.17 (t, J = 6.0 Hz, 0.3H), 9.00 (t, J = 6.0 Hz, 0.7H), 8.79 (t, J = 5.9 Hz, 0.3H), 8.54 (t, J = 5.9 Hz, 0.7H), 8.29 (s, 0.3H), 7.76 (s, 0.7H), 7.55 (dd, J = 13.4, 1.1 Hz, 1H), 7.38-7.46 (m, 1H), 7.22-7.32 (m, 1H), 7.01-7.18 (m, 2H), 4.44-4.76 (m, 2H), 4.15-4.29 (m, 0.3H), 3.57 (td, J = 9.5, 4.6 Hz, 0.7H), 2.53-2.68 (m, 1H), 1.31-1.61 (m, 4H), 1.04-1.26 (m, 6H), 0.62-0.86 (m, 6H) | 4.93$^a$ | 526.3 (M + H$^+$) |
| 139 | ¹H NMR (DMSO-d6) Shift: 9.61 (s, 0.2H), 9.29 (br. s., 0.6H), 9.17 (t, J = 5.9 Hz, 0.3H), 9.03 (t, J = 5.9 Hz, 0.7H), 8.77 (t, J = 5.6 Hz, 0.3H), 8.53 (t, J = 5.8 Hz, 0.7H), 8.38 (q, J = 5.2 Hz, 1H), 8.29 (s, 0.3H), 8.02 (d, J = 8.3 Hz, 1H), 7.76 (s, 0.7H), 7.57-7.68 (m, 2H), 7.22-7.36 (m, 2H), 4.48-4.79 (m, 2H), 4.32 (q, J = 6.9 Hz, 2H), 4.22 (q, J = 7.4 Hz, 0.3H), 3.50-3.66 (m, 2.8H), 2.54-2.68 (m, 1H), 1.31-1.65 (m, 7H), 1.12 (dt, J = 17.8, 6.7 Hz, 6H), 0.61-0.83 (m, 6H) | 0.76$^f$ | 611.2 (M + H$^+$) |
| 140 | ¹H NMR (DMSO-d6) Shift: 9.62 (s, 0.2H), 9.27 (t, J = 5.9 Hz, 0.2H), 9.17 (t, J = 6.0 Hz, 0.6H), 8.77 (t, J = 5.8 Hz, 0.3H), 8.55 (t, J = 5.8 Hz, 0.7H), 8.30 (s, 0.3H), 7.79 (s, 0.7H), 7.56-7.75 (m, 2H), 7.29 (d, J = 3.5 Hz, 1H), 7.02-7.24 (m, 7.4H), 4.50-4.88 (m, 2H), 4.22-4.36 (m, 0.2H), 4.12 (q, J = 6.9 Hz, 2H), 3.65 (td, J = 9.9, 3.9 Hz, 0.7H), 2.59-2.73 (m, 1H), 2.40-2.55 (2H, under solvent peak), 1.64-1.81 (m, 2H), 1.44-1.61 (m, 2H), 1.28-1.41 (m, 3H), 0.69-0.83 (m, 3H) | 5.61$^a$ | 588.2 (M + H$^+$) |
| 141 | ¹H NMR (DMSO-d6) Shift: 9.58 (s, 0.3H), 9.21-9.35 (m, 1.5H), 8.74 (s, 0.2H), 8.57 (t, J = 5.5 Hz, 0.6H), 8.30 (s, 0.3H), 7.68-7.88 (m, 5.6H), 7.65 (s, 1H), 7.56 (s, 1H), 7.38-7.50 (m, 2H), 7.28-7.33 (m, 2H), 7.13-7.21 (m, 2H), 4.71-4.82 (m, 1H), 4.54-4.65 (m, 1H), 4.31 (br. s., 0.3H), 4.11 (q, J = 6.9 Hz, 2H), 3.64-3.71 (m, 0.8H), 2.60-2.71 (m, 3H), 1.74-1.92 (m, 2H), 1.47-1.67 (m, 2H), 1.25-1.38 (m, 3H), 0.71-0.81 (m, 3H) | 6.17$^a$ | 638.3 (M + H$^+$) |
| 142 | ¹H NMR (DMSO-d6) Shift: 11.70 (s, 1H), 9.04-9.20 (m, 1.7H), 8.79 (s, 0.3H), 8.55 (br. s., 0.7H), 8.27 (s, 0.3H), 8.01 (d, J = 8.3 Hz, 1H), 7.76 (s, 0.7H), 7.59 (br. s., 0.7H), 7.40 (d, J = 8.5 Hz, 1H), 7.02-7.25 (m, 4H), 4.58-4.73 (m, 1H), 4.44-4.55 (m, 1H), 4.17-4.23 (m, 0.3H), 3.48-3.59 (m, 2.7H), 2.53-2.62 (m, 1H), 1.34-1.56 (m, 4H), 1.05-1.24 (m, 6H), 0.59-0.83 (m, 6H) | 5.279$^a$ | 583.2 |
| 143 | ¹H NMR (DMSO-d6) Shift: 11.01 (s, 0.6H), 9.24 (s, 0.3H), 9.10 (t, J = 6.0 Hz, 0.7H), 8.80 (s, 0.3H), 8.63 (br. s., 1H), 8.54 (t, J = 5.6 Hz, 0.7H), 8.29 (s, 0.3H), 7.99 (s, 3.7H), 7.73-7.78 (m, 1H), 7.20-7.29 (m, 2H), 7.13 (d, J = 3.5 Hz, 2H), 4.49-4.72 (m, 2H), 4.18-4.25 (m, 0.3H), 3.46-3.61 (m, 2.7H), 2.53-2.63 (m, 1H), 1.34-1.56 (m, 4H), 1.04-1.24 (m, 6H), 0.62-0.83 (m, 6H) | 5.129$^a$ | 567.3 |
| 144 | ¹H NMR (DMSO-d6) Shift: 11.04 (s, 0.8H), 9.17 (t, J = 5.9 Hz, 0.3H), 9.03 (t, J = 5.8 Hz, 0.7H), 8.77-8.81 (m, 0.3H), 8.53 (t, J = 5.6 Hz, 0.7H), 8.39 (s, 0.3H), 8.29 (s, 1H), 7.73-7.79 (m, 2.7H), 7.43 (d, J = 8.0 Hz, 1H), 7.02-7.26 (m, 4H), 4.48-4.72 (m, 2H), 4.19-4.25 (m, 0.3H), 3.54-3.61 (m, 0.7H), 3.47 (dd, J = 12.3, 5.8 Hz, 2H), 2.53-2.64 (m, 1H), 2.41 (s, 3H), 1.34-1.56 (m, 4H), 1.05-1.23 (m, 6H), 0.64-0.83 (m, 6H) | 5.173$^a$ | 581.3 |
| 145 | ¹H NMR (DMSO-d6) Shift: 7.99-8.12 (m, 0.4H), 7.53 (br. s., 0.3H), 6.99-7.14 (m, 2H), 6.90 (br. s., 1H), 6.40-6.62 (m, 2.5H), 6.23 (br. s., 1H), 3.86-4.08 (m, 4H), 3.56 (br. s., 0.3H), 2.84 (br. s., 0.9H), 1.79-1.97 (m, 1H), 0.70-0.94 (m, 4H), 0.35-0.56 (m, 6H), −0.06-0.16 (m, 6H) | 4.95$^a$ | 584.1 (M + H$^+$) |
| 146 | ¹H NMR (DMSO-d6) Shift: 9.62 (s, 0.3H), 9.22-9.36 (m, 1H), 9.14 (t, J = 6.0 Hz, 0.7H), 8.78 (t, J = 5.4 Hz, 0.3H), 8.52 (t, J = 5.9 Hz, 0.7H), 8.29 (s, 0.3H), 7.71-7.85 (m, 1.7H), 7.49 (s, 1H), 7.36 (d, J = 8.3 Hz, 1H), 7.15-7.28 (m, 2H), 4.43-4.78 (m, 2H), 4.14-4.29 (m, 0.3H), 3.58 (td, J = 9.3, 4.6 Hz, 0.7H), 2.53-2.66 (m, 1H), 1.30-1.64 (m, 4H), 1.01-1.28 (m, 6H), 0.59-0.88 (m, 6H) | 2.43$^b$ | 488.0 (M + H$^+$) |
| 147 | ¹H NMR (DMSO-d6) Shift: 7.68-8.16 (m, 1H), 7.62 (d, J = 12.5 Hz, 1H), 7.34 (s, 1H), 7.09-7.20 (m, 2H), 6.97 (d, J = 3.5 Hz, 1H), 4.68 (d, J = 13.3 Hz, 1H), 4.41-4.55 (1H, under solvent peak), 4.06 (q, J = 6.6 Hz, 2H), 3.87 (d, J = 5.3 Hz, 1H), 3.38-3.66 (m, 8H), 2.89-3.06 (m, 3H), 2.50-2.60 (1H, under solvent peak), 1.29 (t, J = 7.0 Hz, 3H), 0.90-1.08 (m, 1H), 0.64-0.77 (m, 3H), 0.46-0.60 (m, 3H) | 5.68$^a$ | 554.2 |
| 148 | ¹H NMR (DMSO-d6) Shift: 7.69-8.18 (m, 1H), 7.62 (d, J = 12.3 Hz, 1H), 7.35 (d, J = 1.8 Hz, 1H), 7.11-7.21 (m, 2H), 6.92-7.00 (m, 1H), 4.67 (d, J = 13.3 Hz, 1H), 4.41-4.55 (1H, under solvent peak), 4.06 (q, J = 7.0 Hz, 2H), 3.38-3.58 (7H, under solvent peak), 2.53-2.59 (m, 1H), 1.23-1.62 (m, 7H), 0.88-1.16 (m, 6H), 0.71 (t, J = 7.3 Hz, 3H), 0.45-0.63 (m, 3H) | 5.67$^a$ | 554.3 |

-continued

| Ex. | $^1$H NMR | tR (min) | MS (m/z) |
|---|---|---|---|
| 149 | $^1$H NMR (DMSO-d6) Shift: 7.68-8.18 (m, 1H), 7.62 (d, J = 13.1 Hz, 1H), 7.36 (s, 1H), 7.08-7.22 (m, 2H), 6.97 (d, J = 3.5 Hz, 1H), 4.67 (d, J = 13.6 Hz, 1H), 4.39-4.58 (1H, under solvent peak), 4.07 (d, J = 7.0 Hz, 2H), 2.39-2.50 (1H, under solvent peak), 1.29 (t, J = 6.9 Hz, 6H), 0.64-0.77 (m, 3H), 0.52 (t, J = 7.0 Hz, 4H) | 5.63[a] | 554.3 |

Analytical methods:

[a]LCMS Method: Agilent 1100 Series LC/MSD SL or VL using electrospray positive [ES + ve to give M + H$^+$] equipped with a Xorbax Eclipse XDB-C8 5.0 μm column (4.6 mm × 150 mm, i.d.), eluting with 0.05% TFA in water (solvent A) and 0.05% TFA in CH$_3$CN (solvent B), using the following elution gradient 10-100% (solvent B) over 10.0 min and holding at 100% for 1.6 min at a flow rate of 1.0 ml/min.

[b]LCMS Method: Agilent 1100 Series LC/MSD SL or VL using electrospray positive [ES + ve to give M + H$^+$] equipped with a Sunfire C18 5.0 μm column (3.0 mm × 50 mm, i.d.), eluting with 0.05% TFA in water (solvent A) and 0.05% TFA in CH$_3$CN (solvent B), using the following elution gradient: 10-100% (solvent B) over 2.5 min and holding at 100% for 1.7 min at a flow rate of 1.0 ml/min.

[c]LCMS Method: Agilent 1200 Series LC/MSD SL or VL using electrospray positive [ES + ve to give M + H$^+$] equipped with a Sunfire C18 5.0 μm column (3.0 mm × 50 mm, i.d.), eluting with 0.1% TFA in water (solvent A) and 0.1% TFA in CH$_3$CN (solvent B), using the following elution gradient: 10-100% (solvent B) over 2.5 min and holding at 100% for 1.7 min at a flow rate of 1.0 ml/min.

[d]UPLC Method: Acquity UPLC with SQD MSD using electrospray positive [ES + ve to give M + H$^+$] equipped with a BEH C18 1.7 μm column (2.1 mm × 50 mm i.d.) eluting with 0.1% formic acid in water (solvent A) and 0.1% formic acid in CH$_3$CN (solvent B), using the following elution gradient: 3-100% (solvent B) over 1.5 min and holding at 100% for 0.4 min at a flow rate of 1.0 ml/min.

[e]LCMS Method: Shimadzu 10 Avp with Sedere Sedex 75C and PE Sciex Single Quadrupole 150 EX using electrospray positive [ES + ve to give M + H$^+$] equipped with a Thermo Hypersil Gold C18 1.9 μm column (2.1 mm × 20 mm i.d.) eluting with 0.02% TFA in water (solvent A) and 0.02% TFA in CH$_3$CN (solvent B), using the following elution gradient: 4-95% (solvent B) over 1.88 min and holding at 4% for 0.9 min at a flow rate of 1.4 ml/min.

[f]LCMS Method: Shimadzu 10 Avp with Sedere Sedex 75C and Waters ZQ Single Quadrupole using electrospray positive [ES + ve to give M + H$^+$] equipped with a Thermo Hypersil Gold C18 1.9 μm column (2.1 mm × 20 mm i.d.) eluting with 0.02% TFA in water (solvent A) and 0.02% TFA in CH$_3$CN (solvent B), using the following elution gradient: 4-95% (solvent B) over 1.88 min and holding at 4% for 0.9 min at a flow rate of 1.4 ml/min.

[g]LCMS Method: Agilent 1200 Series LC/MSD SL or VL using electrospray positive [ES + ve to give M + H$^+$] equipped with a Zorbax C18 5.0 μm column (4.6 mm × 150 mm, i.d.), eluting with 0.1% TFA in water (solvent A) and 0.1% TFA in CH$_3$CN (solvent B), using the following elution gradient: 10-100% (solvent B) over 12.5 min and holding at 100% for 1.8 min at a flow rate of 1.0 ml/min.

[h]LCMS Method: Agilent 1200 Series LC/MSD SL or VL using electrospray positive [ES + ve to give M + H$^+$] equipped with a Sunfire C18 2.5 μm column (2.1 mm × 20 mm, i.d.), eluting with 0.05% TFA in water (solvent A) and 0.05% TFA in CH$_3$CN (solvent B), using the following elution gradient: 10-100% (solvent B) over 2.5 min and holding at 100% for 0.2 min at a flow rate of 1.3 ml/min.

[i]LCMS Method: Agilent 1200 Series LC/MSD SL or VL using electrospray positive [ES + ve to give M + H$^+$] equipped with an Agilent Eclipse XBD-C18 5.0 μm column (4.6 mm × 250 mm, i.d.), eluting with 0.05% TFA in water (solvent A) and 0.05% TFA in CH$_3$CN (solvent B), using the following elution gradient: 1-99% (solvent B) over 10 min at a flow rate of 1.0 ml/min.

Pharmaceutical Compositions

Example A

Tablets are prepared using conventional methods and are formulated as follows:

| Ingredient | Amount per tablet |
|---|---|
| Compound of the invention | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
|---|---|
| Compound of the invention | 15 mg |
| Dried starch | 178 mg |
| Magnesium stearate | 2 mg |
| Total | 195 mg |

Example C

Nanosuspensions are prepared using conventional aqueous bead milling methods and are formulated as follows:

| Ingredient | Amount per nanosuspension |
|---|---|
| Compound of the invention | 50 mg |
| Polysorbate 20 | 10 mg |
| Polyethylene Glycol 4000 | 20 mg |
| Mannitol | 30 mg |
| Purified Water | qs |
| Total | 110 mg |

Example D

Melt Extrudates are prepared using conventional melt extrusion techniques and cryomilling to achieve adequate particle size as follows:

| Ingredient | Amount per Melt Extrudate |
|---|---|
| Compound of the invention | 67 mg |
| 75:25 Poly(lactic-co-glycolic acid) | 34 mg |
| Total | 100 mg |

Example E

A lyophilized product is prepared by conventional methods formulated as follows:

| Ingredient | Amount per Lyophilized Formulation |
| --- | --- |
| Compound of the invention | 20 mg |
| Sodium Hydroxide | qs |
| Glycine | 30 mg |
| Polyethylene Glycol | 50 mg |
| Polysorbate | 2.5 mg |

Biological Assays

Materials:

Buffer components were purchased from Sigma-Aldrich (St. Louis, Mo.) or an equivalent supplier. The promyostatin peptide substrate was custom synthesized by American Peptide Company (Sunnyvale, Calif.) using the myostatin protein sequence (Uniprot accession number O14793) surrounding the cleavage site reviewed in Hopkins, D. R., et al., 2007 Matrix Biology, 26, 508-523. The procollagen peptide substrate used in the high enzyme BMP1 cleavage assay was custom synthesized by 21$^{st}$ Century Biochemicals (Marlboro, Mass.) using the procollagen Iα protein sequence (Uniprot accession number P02452) surrounding the cleavage site reviewed in Hopkins, D. R., et al., 2007 Matrix Biology, 26, 508-523.

Preparation of Human BMP1 Protein:

The DNA sequence encoding amino acids 23-721 of human BMP1 (NM_001190) with the human RAGE signal sequence (aa1-22 of NM_001136) at the N-terminus and FLAG-6×His epitope tags at the C-terminus was amplified using PCR technology. The resultant Rgss-BMP1(23-721)-FLAG-6×His fragment was subcloned into pCDN, a mammalian expression vector driven by the CMV promoter and containing the DHFR gene to allow selection in nucleoside-free cell culture media. This construct was electroporated into CHOE1a cells. After selection, conditioned media from individual clones were analyzed using a BMP1 assay for promyostatin-derived peptidase activity (see assay below). Conditioned media from several clones with the highest activity were analyzed via western blot to confirm expression. The clone with the highest expression and peptidase activity was used for protein expression.

The mature form of human BMP1 (121-721), secreted from the stably transfected CHO cell line, was purified. All purification steps were carried out at 4° C. 10 l of conditioned medium was concentrated to 1.2 l with a Watson Marlow diafiltration system (A/G Technology Corporation, Model # UFP-10-C-55) using a 10 kDa cut off cartridge. A subsequent buffer exchange was carried out on the same system with 5 l of 50 mM Tris buffer, pH 8.0, containing 0.5 M NaCl, 20% glycerol, 1 mM CHAPS, 5 mM CaCl$_2$, 10 µM ZnCl$_2$, and 20 mM imidazole. The diafiltrated medium was subjected to successive nickel NTA superflow chromatography (Qiagen, Valencia, Calif.) using 50 ml, 30 ml, and 15 ml resin volumes, each overnight at 4° C., and the unbound fraction containing most of the BMP1 was retained. 100 ml of this unbound fraction was diluted into 1000 ml of 50 mM Tris buffer, pH 8.0, containing 20% glycerol, 10 mM NaCl, 5 mM CaCl$_2$, 10 µM ZnCl$_2$, and 1 mM CHAPS and applied to 20 ml of Q Sepharose Fast Flow (GE Healthcare Life Sciences). The Q Sepharose unbound fraction, which contains BMP1, was further concentrated on a Viva Spin, 10 kDa cut off cartridge (Viviproducts, Littleton, Mass.).

Preparation of Human TLL1 Protein:

The DNA sequence encoding a natural variant of full length native human TLL1 (BD165892.1) containing three amino acid substitutions I156V, N221S, V284A was amplified from human heart and brain cDNA and subcloned into the pCDN expression vector. The plasmid was electroporated into CHOE1A cells. After selection, a clone expressing high levels of TLL1 was scaled and used for protein purification.

All purification steps were carried out at 4° C. CHO conditioned medium was diluted 3-fold with 5 mM Tris buffer, pH 8.4, and human TLL1 was captured by Source 30 Q resin (GE Healthcare Life Sciences). After an extensive wash with 50 mM Tris buffer, pH 8.0, human TLL1 was eluted with a linear gradient of 0 to 0.5 M NaCl in 50 mM Tris buffer, pH 8.0. Following a 3.6-fold dilution into 20 mM Tris buffer, pH 7.4, human TLL1 from the Source 30Q pool was then captured onto a Macro-prep ceramic hydroxyapatite (HA) type I 40 µm resin (BioRad, Hercules, Calif.). The HA resin was washed with 20 mM Tris buffer, pH 7.4, and human TLL1 was eluted with 0.5 M potassium phosphate buffer, pH 7.4, in a linear gradient from wash buffer. Human TLL1 from the HA pool was salt fractionated with 40% ammonium sulfate saturation and resolubilized with 20 mM Tris buffer, pH 7.0, containing 0.25 M NaCl and 7 mM CaCl$_2$.

Preparation of Human TLL2 Protein:

The DNA sequence encoding amino acids 26-1015 of human TLL2 (NM_0124565) was PCR amplified from DNA template with the human RAGE signal sequence at the N-terminus and Avi-6×His epitope tags at the C-terminus (GGLNDIFEAQKIEWHEHHHHHH). The Rgss-TLL2 Avi-6×His fragment was subcloned into a pCDN expression vector by Gateway™ recombination (Life Technologies, Grand Island, N.Y.). DHFR deficient CHOE1a cells were maintained in MR1 media (Life Technologies) supplemented with nucleosides at 37° C. in 5% CO2. Linearized plasmid DNA was electroporated into the cells and clones were generated in media without nucleosides. Clones were screened for TLL2 activity in the promyostatin-derived peptidase assay (see below) which allowed identification of clones that expressed optimal levels of the active form of TLL2.

Stably expressing TLL2 CHO cell conditioned medium was concentrated by diafiltration as described for BMP1. 325 ml of concentrated medium was purified by nickel NTA superflow chromatography (20 ml Ni-NTA SF, overnight at 4° C.). The resin was washed with a 15 mM to 100 mM imidazole linear gradient, and protein was eluted with 0.3 M imidazole in buffer A (50 mM Tris, pH 8.0, 0.5 M NaCl, 20% glycerol, 1 mM CHAPS, 5 mM CaCl$_2$, 10 µM ZnCl$_2$).

Enzyme Inhibition Assay for Human BMP1:

(i) Low Enzyme Concentration

Inhibition of BMP1 peptidase activity by test compounds of the invention was measured by monitoring cleavage of a promyostatin peptide substrate by recombinant, mature BMP1 protein (BMP1(121-721)-Flag-His). FRET quenching of dual-labeled peptide ((5-FAM)-ELIDQYD-VQRDDSSDGSLED-K(5,6 TAMRA)-CONH$_2$) is relieved by BMP1-catalyzed cleavage. This assay was run as a 10 µl endpoint assay in 384-well format where the reaction contains 0.5 nM BMP1 and 0.8 µM promyostatin peptide substrate in 25 mM HEPES buffer, pH 7.5, containing 0.01% Brij-35 detergent, 5 mM CaCl$_2$, and 1 µM ZnCl$_2$. The assay was run by adding 5 µl enzyme solution to a black, low volume assay plate (Greiner 784076) pre-dispensed with 100 nl test compound solutions in DMSO. After 10 minutes, 5 µl substrate were added and the reaction was incubated at ambient temperature for an additional 60 minutes. The reaction was quenched with 5 µl of 0.5 M EDTA and the plate was read on a ViewLux (PerkinElmer) multilabel plate reader using a 480 nm excitation filter and 540 nm emission filter. The test compounds were prepared in neat DMSO at a concentration of 10 mM. For inhibition curves, compounds were diluted in DMSO using a three-fold serial dilution and tested at 11 concentrations (100 µM-1.7 nM, final 1% DMSO). Responses were normalized to the uninhibited and no-enzyme controls within each plate. Dose-response curves were analyzed using a four-parameter logistic fit in ActivityBase and results are expressed as $pIC_{50}$ values.

The compounds of Examples 1-115 and 117-149 were tested and exhibited a $pIC_{50}$>6.9 according to this assay.

(ii) High Enzyme Concentration

Use of a high enzyme concentration assay may be useful, e.g., as discussed in Habig, M., et al., Journal of Biomolecular Screening, 2009, 14, 679-689.

This assay was run as a 10 µl endpoint assay in 384-well format where the reaction contains 50 nM BMP1 enzyme and 6 µM procollagen I peptide substrate ((5-FAM)-DG-GRYYRADDANVVRD-K(5,6-TAMRA)-CONH$_2$) in 25 mM HEPES buffer, pH 7.5, containing 0.01% Brij-35 detergent, 5 mM CaCl$_2$, and 1 µM ZnCl$_2$. The assay was run by adding 5 µl enzyme solution to a black, low volume assay plate (Greiner 784076) pre-dispensed with 100 nl test compound solutions in DMSO. After 10 minutes, 5 µl substrate were added and the reaction was incubated at ambient temperature for an additional 30 minutes. The reaction was quenched with 5 µl of 0.5 M EDTA and the plate was read on a ViewLux (Perkin Elmer) multilabel plate reader using a 480 nm excitation filter and 540 nm emission filter. Data fitting and compound preparations were performed as described above for the low enzyme concentration.

The compounds of Examples 1-115, 117-146 and 149 were tested and exhibited a $pIC_{50}$>6.7 according to this assay.

Enzyme Inhibition Assay for Human TLL1 and TLL2:

Inhibition of human TLL1 and TLL2 recombinant enzymes was measured in 10 ul endpoint assays in 384-well format using the same promyostatin peptide substrate employed in the above Enzyme Inhibition Assay for human BMP1. The TLL1 reaction contained 2 nM TLL1 and 0.8 µM promyostatin peptide substrate in 25 mM HEPES buffer, pH 7.5, containing 0.01% Brij-35 detergent, 5 mM CaCl$_2$, and 1 µM ZnCl$_2$. The TLL1 assay was run by adding 5 µl enzyme solution to a black, low volume assay plate (Greiner 784076) pre-dispensed with 100 nl test compound solutions in DMSO. Following a 10 minute preincubation of enzyme with inhibitor, 5 µl of substrate solution were added. TLL1 reactions were incubated at ambient temperature for an additional 60 minutes. The TLL2 reaction contained 18 nM TLL2 and 5 µM promyostatin peptide substrate in 25 mM HEPES buffer, pH 7.5, containing 0.01% Brij-35 detergent, 5 mM CaCl$_2$, and 1 µM ZnCl$_2$. The TLL2 assay was run without an enzyme-inhibitor preincubation by adding 5 µl enzyme and 5 µl substrate solutions to a black, low volume assay plate (Greiner 784076) pre-dispensed with 100 nl compound solutions in DMSO. TLL2 reactions were incubated at ambient temperature for 60 minutes. TLL1 and TLL2 reactions were quenched with 5 µl of 0.5 M EDTA and plates were read on a ViewLux (Perkin Elmer) multilabel plate reader using a 480 nm excitation filter and 540 nm emission filter. Data fitting and compound preparations were performed as described above for the Enzyme Inhibition Assay for human BMP1.

The compounds of Examples 1-33, 35-71, 73-84, 86-115, 117-140, and 142-146 were tested in the TLL1 enzyme inhibition assay and exhibited a $pIC_{50}$>6.4 according to this assay.

The compounds of Examples 1-24, 26-33, 35-71, 73-78, 80-84, 86-115, 117-140, and 142-146 were tested in the TLL2 enzyme inhibition assay and exhibited a $pIC_{50}$>6.1 according to this assay.

The above enzyme assay results indicate that the tested compounds are potent inhibitors of one or more of BMP1, TLL1 and TLL2 enzymatic activity. The tested compounds inhibited one or more of these metalloproteases in biochemical assays using isolated enzymes and peptide substrates.

Cell-Based Inhibition Assay of Generation of Procollagen I C-Terminal Propeptide (PICP) and Mature Collagen:

An adaptation of the collagen deposition assay described by Chen, C. Z. C., et al., British Journal of Pharmacology, 2009, 158, 1196-1209 was used to examine effect of compounds on procollagen I processing and collagen deposition. In the adapted assay, human cardiac fibroblasts were utilized. Processing of procollagen I was determined by a PICP ELISA assay and deposition of mature collagen was determined by immunostaining.

Human cardiac fibroblasts were cultured and maintained until passage 6 in FGM-3 media (Lonza, #CC-3132) in a 37° C. humidified incubator with 5% CO$_2$. They were then seeded in 96-well black wall, clear bottom plates at 10,000 to 15,000 cells per well in eagle's minimum essential media (EMEM, ATCC #30-2003) containing 10% fetal bovine serum (FBS, Life Technologies #10082147), 1% Glutamax (Life Technologies #35050061) and 1% Penicillin and Streptomycin (Life Technologies #15070063). These cultures were placed in 37° C. incubator. The next day, media were removed by aspiration and cells were rinsed with phosphate buffered saline. Crowding media (also called ficoll media) was prepared by adding 112.5 mg/ml of ficoll70 and 75 mg/ml ficoll400 (GE healthcare #17-0310-10 and 17-0300-10, respectively), 100 µM ascorbic acid, 1% Glutamax and 1% Penicillin and Streptomycin to EMEM media. Test compounds (dissolved in DMSO) were diluted into crowding media and then added to the cells. Final concentration of DMSO in crowding media was less than 0.3%. Cells were treated for 24 to 48 hr in a 37° C. incubator. At the end of the treatment period, cell media were collected. The level of PICP in the media were determined by a PICP ELISA assay (Quidel #8003) following the manufacturer's protocol. Potencies of test compounds were calculated by fitting PICP levels, relative to untreated controls, to log (inhibitor) vs. response equation using Graphpad Prism software 5.0 and expressed as $pIC_{50}$.

For some compounds, deposition of mature collagen was measured by immunostaining in addition to PICP levels. At the end of the treatment period, cells on culture plate were fixed with 100% methanol (prechilled to −20° C.) for 10 min. Then the cells were immunostained with mouse anti-mature collagen I antibody (1:500 dilution, Sigma#C2456), anti-mouse secondary antibody Alexa647 (1:500 dilution, Invitrogen#A21236) and Hoechst (for nuclei, 2 µg/ml, Invitrogen#H3596). Fluorescent image acquisition was done using the Operetta High Content Imaging system (Perkin Elmer). For each image field, the intensity of mature collagen staining was normalized with the number of nuclei. Normalized collagen levels were used to calculate the potency of test compounds with Graphpad Prism software, as described above.

The compounds of Examples 1, 5, 12-14, 16, 18, 22-30, 33-35, 39-45, 47-53, 55, 59-62, 64, 65, 67, 70-78, 80-89, 91-106, 108, 111-115, and 117-146 were tested in the PICP cellular inhibition assay and exhibited a $pIC_{50}$>5.4 in this assay.

The compounds of Examples 5, 24, 39, 47, 74, 75, 77, 80-82, 86, 93, 96, 98, 99, 111-113, 121-124, 126-128, 132, and 139 were tested in the mature collagen cellular inhibition assay and exhibited a $pIC_{50}>6.0$ in this assay.

The above cellular assay results demonstrate that the tested compounds inhibit the processing of procollagen substrate by native enzyme produced by the fibroblast, the cell type that drives fibrosis in vivo.

In view of the above, compounds of the invention should have benefit as anti-fibrotic agents across a wide variety of diseases driven by pathological fibrosis, and diseases related to other in vivo substrates for these enzymes, e.g., where muscle function or muscle mass is diminished.

What is claimed is:
1. A compound of Formula (I):

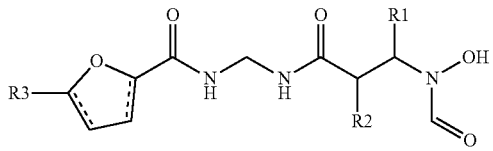

or a salt thereof,
wherein:
R1 is selected from the group consisting of H, $(C_1-C_4)$ straight chain alkyl, and $(C_1-C_4)$ straight chain alkyl substituted with a hydroxy group;
R2 is selected from H, $(C_1-C_{11})$alkyl, $(C_1-C_3)$alkyl-$(C_3-C_6)$cycloalkyl, $(C_1-C_3)$alkyl-phenyl, $(C_1-C_3)$alkyl-naphthyl and $(C_1-C_3)$alkyl-heterocyclyl, wherein heterocyclyl is a monocyclic ring having 5-6 ring atoms wherein 1-2 of the ring atoms are selected from nitrogen, oxygen and sulfur, and wherein said $(C_1-C_{11})$ alkyl, cycloalkyl, phenyl, naphthyl and heterocyclyl are optionally substituted with 1-2 groups independently selected from $(C_1-C_4)$alkyl, $(C_1-C_4)$alkoxy, halo, and cyano; and
R3 is selected from:
  a) phenyl, optionally substituted with 1-3 groups independently selected from:
    $(C_1-C_6)$alkyl, optionally substituted with 1-3 groups independently selected from: fluoro; —$CO_2H$; —$P(O)R^fR^g$; $NR^aR^b$ wherein $R^a$ is selected from H and $(C_1-C_4)$alkyl and $R^b$ is selected from $(C_1-C_4)$alkyl substituted with —$CO_2H$ or —$P(O)R^fR^g$, and —$C(O)NR^aR^b$ wherein $R^a$ and $R^b$ are independently selected from H and $(C_1-C_4)$alkyl, wherein the $(C_1-C_4)$alkyl is optionally substituted with 1-3 groups independently selected from hydroxy, —$CO_2H$, —$C(O)O(C_1-C_4)$alkyl and —$P(O)R^fR^g$;
    cyclopropyl, optionally substituted with 1 —$CO_2H$;
    —$C(O)NR^aR^b$ wherein $R^a$ and $R^b$ are independently selected from H and $(C_1-C_4)$alkyl, wherein the $(C_1-C_4)$ alkyl is optionally substituted with 1-3 groups independently selected from hydroxy, —$CO_2H$, —$C(O)O(C_1-C_4)$alkyl, —$P(O)R^fR^g$, $NR^cR^d$ and $N^+R^cR^dR^e$;
    $(C_1-C_6)$alkoxy, optionally substituted with 1-3 substituents independently selected from halo, hydroxy, —$CO_2H$, $(C_3-C_6)$cycloalkyl, —$C(O)NH_2$ and pyrrolidinyl;
    $(C_3-C_6)$cycloalkoxy, optionally substituted with 1-3 substituents independently selected from halo, hydroxy, and —$CO_2H$;
    —$NR^aR^b$ wherein $R^a$ and $R^b$ are independently selected from H and $(C_1-C_4)$alkyl, wherein the $(C_1-C_4)$alkyl is optionally substituted with 1-3 groups independently selected from oxo and —$CO_2H$;
    —$SR^a$ wherein $R^a$ is selected from H and $(C_1-C_4)$alkyl;
    —$CO_2H$; —$C(NOH)NH_2$, cyano; —$C(O)O(C_1-C_4)$alkyl; —$C(O)CO_2H$; —$P(O)R^fR^g$; —$OP(O)R^fR^g$; halo; hydroxy; nitro; —$NHSO_2(C_1-C_2)$alkyl; —$SO_3H$; —$SO_2(C_1-C_2)$alkyl; —$SO_2NR^cR^d$; —$SO_2NHC(O)(C_1-C_2)$alkyl; and —$B(OH)_2$;
    and
  b) heteroaryl, optionally substituted with 1-2 groups independently selected from: $(C_1-C_4)$alkyl, $(C_1-C_4)$ alkoxy, oxo, —$CO_2H$, —$P(O)R^fR^g$, and —$OP(O)R^fR^g$;
    wherein in each occurrence: $R^c$, $R^d$ and $R^e$ are independently selected from H and $(C_1-C_2)$alkyl; and $R^f$ and $R^g$ are independently selected from hydroxy, $(C_1-C_2)$alkyl and $(C_1-C_2)$alkoxy.

2. The compound or salt thereof according to claim 1, wherein the compound of Formula (I):
R1 is selected from the group consisting of H, $(C_1-C_4)$ straight chain alkyl, and $(C_1-C_4)$ straight chain alkyl substituted with a hydroxy group;
R2 is selected from H, $(C_1-C_{11})$alkyl, $(C_1-C_3)$alkyl-$(C_3-C_6)$cycloalkyl, $(C_1-C_3)$alkyl-phenyl, and $(C_1-C_3)$alkyl-heterocyclyl, wherein heterocyclyl is a monocyclic ring having 5-6 ring atoms wherein 1-2 of the ring atoms are selected from nitrogen, oxygen and sulfur, and wherein said $(C_1-C_{11})$alkyl, cycloalkyl, phenyl, and heterocyclyl are optionally substituted with 1-2 groups independently selected from $(C_1-C_4)$alkyl, $(C_1-C_4)$alkoxy, halo, and cyano; and
R3 is selected from:
  c) phenyl, optionally substituted with 1-3 groups independently selected from:
    $(C_1-C_6)$alkyl, optionally substituted with 1-3 groups independently selected from: fluoro; —$CO_2H$; —$P(O)R^fR^g$; and —$C(O)NR^aR^b$ wherein $R^a$ and $R^b$ are independently selected from H and $(C_1-C_4)$alkyl, wherein the $(C_1-C_4)$alkyl is optionally substituted with 1-3 groups independently selected from hydroxy, —$CO_2H$, —$C(O)O(C_1-C_4)$alkyl and —$P(O)R^fR^g$;
    cyclopropyl, optionally substituted with 1 —$CO_2H$;
    —$C(O)NR^aR^b$ wherein $R^a$ and $R^b$ are independently selected from H and $(C_1-C_4)$alkyl, wherein the $(C_1-C_4)$ alkyl is optionally substituted with 1-3 groups independently selected from hydroxy, —$CO_2H$, —$C(O)O(C_1-C_4)$alkyl, —$P(O)R^fR^g$, $NR^cR^d$ and $N^+R^cR^dR^e$;
    $(C_1-C_6)$alkoxy, optionally substituted with 1-3 substituents independently selected from halo, hydroxy, —$CO_2H$, $(C_3-C_6)$cycloalkyl, and pyrrolidinyl;
    $(C_3-C_6)$cycloalkoxy, optionally substituted with 1-3 substituents independently selected from halo, hydroxy, and —$CO_2H$;
    —$NR^aR^b$ wherein $R^a$ and $R^b$ are independently selected from H and $(C_1-C_4)$alkyl, wherein the $(C_1-C_4)$alkyl is optionally substituted with 1-3 groups independently selected from oxo and —$CO_2H$;
    —$SR^a$ wherein $R^a$ is selected from H and $(C_1-C_4)$alkyl;
    —$CO_2H$; —$C(NOH)NH_2$, cyano; —$C(O)O(C_1-C_4)$alkyl; —$C(O)CO_2H$; —$P(O)R^fR^g$; —$OP(O)R^fR^g$; halo; hydroxy; nitro; —$NHSO_2(C_1-C_2)$alkyl; —$SO_3H$; —$SO_2(C_1-C_2)$alkyl; —$SO_2NR^cR^d$; —$SO_2NHC(O)(C_1-C_2)$alkyl; and —$B(OH)_2$;
    and
  d) heteroaryl, optionally substituted with 1-2 groups independently selected from: $(C_1-C_4)$alkyl, $(C_1-C_4)$ alkoxy, oxo, —$CO_2H$, —$P(O)R^fR^g$, and —$OP(O)R^fR^g$;

wherein in each occurrence: $R^c$, $R^d$ and $R^e$ are independently selected from H and ($C_1$-$C_2$)alkyl; and $R^f$ and $R^g$ are independently selected from hydroxy, ($C_1$-$C_2$)alkyl and ($C_1$-$C_2$)alkoxy.

3. The compound or salt thereof according to claim 1, wherein the compound according to Formula (I) has the Formula (I)(a):

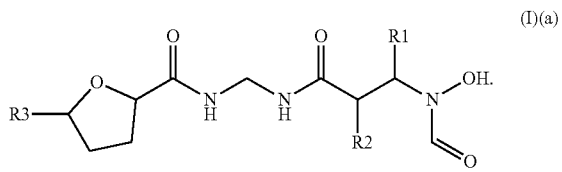

(I)(a)

4. The compound or salt thereof according to claim 1 wherein the compound according to Formula (I) has the Formula (I)(b):

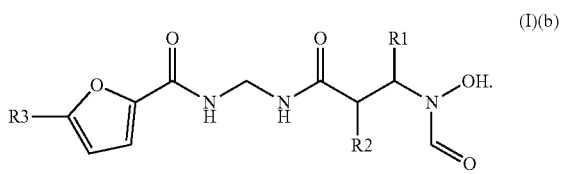

(I)(b)

5. The compound or salt thereof according to claim 1, wherein R1 is H, methyl, ethyl or —CH$_2$OH.

6. The compound or salt thereof according to claim 1, wherein R2 is H or optionally substituted n-pentyl, 2-ethylbutyl, (cyclopentyl)methyl, benzyl, 2-phenylethyl, 3-phenylpropyl, or 2-naphthylethyl.

7. The compound or salt thereof according to claim 1, wherein R1 and R2 have (R) stereochemistry.

8. The compound or salt thereof according to claim 1, wherein R3 is optionally substituted phenyl.

9. The compound or salt thereof according to claim 1, wherein R3 is disubstituted phenyl wherein the substituents are ethoxy in the 3-position and —P(O)(OH)$_2$, —CO$_2$H, —OCH$_2$CO$_2$H, or C(O)NHCH(CO$_2$H)(CH$_2$CO$_2$H) in the 4- or 5-position.

10. The compound or salt thereof according to claim 1, wherein R3 is phenyl optionally substituted with 1-3 groups selected from: —OCH$_3$, —OC$_2$H$_5$, —OC$_3$H$_7$, —OCH(CH$_3$)$_2$, —OCF$_3$, —OCHF$_2$, —OCH$_2$CF$_3$, —OCH$_2$CHF$_2$, —OC$_2$H$_4$-pyrrolidine, —OCH$_2$CO$_2$H, —OCH$_2$C(O)NH$_2$, —CO$_2$H, —CH$_3$, cyclopropane-1-carboxylic acid, —CH$_2$CO$_2$H, —C(CH$_3$)$_2$CO$_2$H, —CH(CH$_3$)CO$_2$H, —CF$_2$CO$_2$H, —CH$_2$C(O)NHCH(CO$_2$H)(CH$_2$CO$_2$H), —CH$_2$P(O)(OH)$_2$, —CH$_2$N(CH$_3$)(CH$_2$CO$_2$H), —CH$_2$NHCH$_2$P(O)(OH)$_2$, —C(NH$_2$)(NOH), cyano, nitro, hydroxy, —SO$_2$NH$_2$, —SO$_2$N(CH$_3$)$_2$, —SO$_2$NH(CH$_3$), —SO$_2$CH$_3$, —SO$_2$NHC(O)C$_2$H$_5$, —SCH$_3$, —SC$_2$H$_5$, —C(O)OCH$_3$, —C(O)OC(CH$_3$)$_3$, —C(O)NHCH$_3$, —C(O)NH(C$_2$H$_4$NH$_2$), —C(O)NHC$_2$H$_4$N$^+$(CH$_3$)$_3$, —C(O)NHCH(CO$_2$H)(CH$_2$CO$_2$H), —C(O)NHCH(CO$_2$H)(C$_2$H$_4$CO$_2$H), —C(O)NHCH$_2$CO$_2$H, —C(O)N(CH$_2$CO$_2$H)$_2$, —C(O)NHCH$_2$P(O)(OH)$_2$, —C(O)NHC(CH$_2$OH)$_3$ fluoro, —NH$_2$, —N(CH$_3$)$_2$, —P(O)(CH$_3$)(OC$_2$H$_5$), —P(O)(OCH$_3$)$_2$, —P(O)(CH$_3$)(OH), —P(O)(OH)(OCH$_3$), and —P(O)(OH)$_2$.

11. The compound or salt thereof according to claim 10, wherein R3 is phenyl substituted with 1-3 groups selected from: —OC$_2$H$_5$, hydroxy, —CO$_2$H, —OCH$_2$CO$_2$H, —P(O)(OH)$_2$, —C(O)NHCH(CO$_2$H)(CH$_2$CO$_2$H) and —C(O)NHCH$_2$P(O)(OH)$_2$.

12. The compound or salt thereof according to claim 1, wherein R3 is optionally substituted pyridyl, pyridazinyl, pyrimidinyl, oxazolyl, tetrazolyl, pyrazolyl, indazolyl, or 1,1-dioxido-2,3-dihydrobenzo[d]isothiazolyl.

13. The compound or salt thereof according to claim 1, wherein the compound of Formula (I) is selected from the group consisting of:
2-ethoxy-4-(5-((((R)-2-((R)-1-(N-hydroxyformamido)propyl)heptanamido)methyl)carbamoyl)furan-2-yl)benzoic acid,
(R)—N-((3-cyclopentyl-2-((N-hydroxyformamido)methyl)propanamido)methyl)-5-phenylfuran-2-carboxamide,
(R)—N-((2-((N-hydroxyformamido)methyl)-5-phenylpentanamido)methyl)-5-phenylfuran-2-carboxamide,
(R)—N-((2-((N-hydroxyformamido)methyl)-4-phenylbutanamido)methyl)-5-phenylfuran-2-carboxamide,
(R)—N-((2-((N-hydroxyformamido)methyl)heptanamido)methyl)-5-phenylfuran-2-carboxamide,
(R)—N-((2-((N-hydroxyformamido)methyl)heptanamido)methyl)-5-(2-methoxyphenyl)furan-2-carboxamide,
(R)—N-((2-((N-hydroxyformamido)methyl)heptanamido)methyl)-5-(3-methoxyphenyl)furan-2-carboxamide,
(R)-5-(3-cyanophenyl)-N-((2-((N-hydroxyformamido)methyl)heptanamido)methyl)furan-2-carboxamide,
(R)—N-((2-((N-hydroxyformami,do)methyl)heptanamido)methyl)-5-(2-hydroxyphenyl)furan-2-carboxamide,
(R)—N-((2-((N-hydroxyformamido)methyl)heptanamido)methyl)-5-(5-methoxypyridin-3-yl)furan-2-carboxamide,
(R)-5-(4-cyanophenyl)-N-((2-((N-hydroxyformamido)methyl)heptanamido)methyl)furan-2-carboxamide,
(R)—N-((2-((N-hydroxyformamido)methyl)heptanamido)methyl)-5-(3-sulfamoylphenyl)furan-2-carboxamide,
(R)—N-((2-((N-hydroxyformamido)methyl)heptanamido)methyl)-5-(3-(trifluoromethoxy)phenyl)furan-2-carboxamide,
(R)-5-(3-ethoxyphenyl)-N-((2-((N-hydroxyformamido)methyl)heptanamido)methyl)furan-2-carboxamide,
(R)—N-((2-((N-hydroxyformamido)methyl)heptanamido)methyl)-5-(6-methoxypyridin-2-yl)furan-2-carboxamide,
(R)-methyl 3-(5-(((2-((N-hydroxyformamido)methyl)heptanamido)methyl)carbamoyl)furan-2-yl)benzoate,
(R)-5-(4-fluoro-3-methoxyphenyl)-N-((2-((N-hydroxyformamido)methyl)heptanamido)methyl)furan-2-carboxamide,
(R)—N-((2-((N-hydroxyformamido)methyl)heptanamido)methyl)-5-(4-methoxypyridin-2-yl)furan-2-carboxamide,
(R)—N-((2-((N-hydroxyformamido)methyl)heptanamido)methyl)-5-(3-(methylcarbamoyl)phenyl)furan-2-carboxamide,
(R)—N-((2-((N-hydroxyformamido)methyl)-4-phenylbutanamido)methyl)-5-(3-(methylsulfonyl)phenyl)furan-2-carboxamide,
(R)-5-(3-(N,N-dimethylsulfamoyl)phenyl)-N-((2-((N-hydroxyformamido)methyl)heptanamido)methyl)furan-2-carboxamide, (R)—N-((2-((N-hydroxyformamido)methyl)heptanamido)methyl)-5-(3-(N-methylsulfamoyl)phenyl)furan-2-carboxamide,
(R)—N-((2-((N-hydroxyformamido)methyl)heptanamido)methyl)-5-(3-(2,2,2-trifluoroethoxy)phenyl)furan-2-carboxamide,
N—(((R)-2-((R)-1-(N-hydroxyformamido)propyl)heptanamido)methyl)-5-phenylfuran-2-carboxamide,
(R)—N-((2-((N-hydroxyformamido)methyl)heptanamido)methyl)-5-(3-isopropoxyphenyl)furan-2-carboxamide,
(R)-methyl 3-ethoxy-5-(5-(((2-((N-hydroxyformamido)methyl)heptanamido)methyl)carbamoyl)furan-2-yl)benzoate,
(R)-5-(3-(dimethylamino)phenyl)-N-((2-((N-hydroxyformamido)methyl)heptanamido)methyl)furan-2-carboxamide,
(R)—N-((2-((N-hydroxyformamido)methyl)heptanamido)methyl)-5-(3-(N-propionylsulfamoyl)phenyl)furan-2-carboxamide,
(R)-3-(5-(((2-((N-hydroxyformamido)methyl)heptanamido)methyl)carbamoyl)furan-2-yl)-5-methoxybenzoic acid,
(R)-3-ethoxy-5-(5-(((2-((N-hydroxyformamido)methyl)heptanamido)methyl)carbamoyl)furan-2-yl)benzoic acid, ethyl(3-(5-((((R)-2-((N-hydroxyformamido)methyl)heptanamido)methyl)carbamoyl)furan-2-yl)phenyl)(methyl)phosphinate,
N—(((R)-2-((S)-2-hydroxy-1-(N-hydroxyformamido)ethyl)heptanamido)methyl)-5-phenylfuran-2-carboxamide,
(R)-5-(3-((2-aminoethyl)carbamoyl)-5-methoxyphenyl)-N-((2-((N-hydroxyformamido)methyl)heptanamido)methyl)furan-2-carboxamide,
(R)-5-(3-((2-aminoethyl)carbamoyl)-5-ethoxyphenyl)-N-((2-((N-hydroxyformamido)methyl)heptanamido)methyl)furan-2-carboxamide,
(R)-5-(3-(difluoromethoxy)phenyl)-N-((2-((N-hydroxyformamido)methyl)heptanamido)methyl)furan-2-carboxamide,
(R)-dimethyl (3-(5-(((2-((N-hydroxyformamido)methyl)heptanamido)methyl)carbamoyl)furan-2-yl)phenyl)phosphonate,
(R)-5-(1,1-dioxido-2,3-dihydrobenzo[d]isothiazol-6-yl)-N-((2-((N-hydroxyformamido)heptanamido)methyl)furan-2-carboxamide,
(R)—N-((2-((N-hydroxyformamido)methyl)heptanamido)methyl)-5-(3-(2-(pyrrolidin-1-yl)ethoxy)phenyl)furan-2-carboxamide,
3-ethoxy-5-(5-((((R)-2-((R)-1-(N-hydroxyformamido)propyl)heptanamido)methyl)carbamoyl)furan-2-yl)benzoic acid,
5-(3-((2-aminoethyl)carbamoyl)-5-ethoxyphenyl)-N—(((R)-2-((R)-1-(N-hydroxyformamido)propyl)heptanamido)methyl)furan-2-carboxamide,
2-(2-ethoxy-4-(5-((((R)-2-((R)-1-(N-hydroxyformamido)propyl)heptanamido)methyl)carbamoyl)furan-2-yl)phenyl)acetic acid,
2-(4-(5-((((R)-2-((R)-1-(N-hydroxyformamido)propyl)heptanamido)methyl)carbamoyl)furan-2-yl)phenyl)acetic acid,
2-(4-(5-((((R)-2-((R)-1-(N-hydroxyformamido)propyl)heptanamido)methyl)carbamoyl)furan-2-yl)phenyl)-2-methylpropanoic acid,
1-(4-(5-((((R)-2-((R)-1-(N-hydroxyformamido)propyl)heptanamido)methyl)carbamoyl)furan-2-yl)phenyl)cyclopropanecarboxylic acid,
(S)-5-(tert-butoxy)-4-(3-ethoxy-5-(5-((((R)-2-((R)-1-(N-hydroxyformamido)propyl)heptanamido)methyl)carbamoyl)furan-2-yl)benzamido)-5-oxopentanoic acid,
5-(5-((((R)-2-((R)-1-(N-hydroxyformamido)propyl)heptanamido)methyl)carbamoyl)furan-2-yl)nicotinic acid,
(S)-4-(tert-butoxy)-3-(3-ethoxy-5-(5-((((R)-2-((R)-1-(N-hydroxyformamido)propyl)heptanamido)methyl)carbamoyl)furan-2-yl)benzamido)-4-oxobutanoic acid,
(S)-dimethyl 2-(3-ethoxy-5-(5-((((R)-2-((R)-1-(N-hydroxyformamido)propyl)heptanamido)methyl)carbamoyl)furan-2-yl)benzamido)pentanedioate,
2-(3-ethoxy-5-(5-((((R)-2-((R)-1-(N-hydroxyformamido)propyl)heptanamido)methyl)carbamoyl)furan-2-yl)phenyl)-2,2-difluoroacetic acid,
dimethyl (3-ethoxy-5-(5-((((R)-2-((((R)-1-(N-hydroxyformamido)propyl)heptanamido)methyl)carbamoyl)furan-2-yl)phenyl)phosphonate,
(R)-methyl 2-fluoro-5-(5-(((2-((N-hydroxyformamido)methyl)heptanamido)methyl)carbamoyl)furan-2-yl)benzoate,
(R)-5-(3,5-dimethoxyphenyl)-N-((2-((N-hydroxyformamido)methyl)heptanamido)methyl)furan-2-carboxamide,
(R)-5-(2,5-dimethoxyphenyl)-N-((2-((N-hydroxyformamido)methyl)heptanamido)methyl)furan-2-carboxamide,
(R)-5-(5-(((2-((N-hydroxyformamido)methyl)heptanamido)methyl)carbamoyl)furan-2-yl)-2-methylbenzoic acid,
(R)-3-(5-(((2-((N-hydroxyformamido)methyl)heptanamido)methyl)carbamoyl)furan-2-yl)-2-methoxybenzoic acid,
(R)-5-(5-(((2-((N-hydroxyformamido)methyl)heptanamido)methyl)carbamoyl)furan-2-yl)-2-methoxybenzoic acid,
(R)-methyl 2-(5-(((2-((N-hydroxyformamido)methyl)heptanamido)methyl)carbamoyl)furan-2-yl)benzoate,
(R)-methyl 4-(5-(((2-((N-hydroxyformamido)methyl)heptanamido)methyl)carbamoyl)furan-2-yl)benzoate,
(R)-2-fluoro-3-(5-(((2-((N-hydroxyformamido)methyl)heptanamido)methyl)carbamoyl)furan-2-yl)benzoic acid,
(R)-2-(3-(5-(((2-((N-hydroxyformamido)methyl)heptanamido)methyl)carbamoyl)furan-2-yl)phenyl)acetic acid,
(R)-3-(5-(((2-((N-hydroxyformamido)methyl)heptanamido) methyl)carbamoyl)furan-2-yl)-2-methylbenzoic acid,
(R)-2-hydroxy-5-(5-(((2-((N-hydroxyformamido)methyl)heptanamido)methyl)carbamoyl)furan-2-yl)benzoic acid,
(R)-tert-butyl 3-(5-(((2-((N-hydroxyformamido)methyl)heptanamido)methyl)carbamoyl)furan-2-yl)benzoate,
(R)-2-amino-5-(5-(((2-((N-hydroxyformamido)methyl)heptanamido)methyl)carbamoyl)furan-2-yl)benzoic acid,
2-(3-ethoxy-5-(5-((((R)-2-((R)-1-(N-hydroxyformamido)propyl)heptanamido)methyl)carbamoyl)furan-2-yl)benzamido)-N,N,N-trimethylethanaminium hydroxide,
5-(5-((((R)-2-((R)-1-(N-hydroxyformamido)propyl)heptanamido)methyl)carbamoyl)furan-2-yl)-2-methoxybenzoic acid,
2-(3-(5-((((R)-2-((R)-1-(N-hydroxyformamido)propyl)heptanamido)methyl)carbamoyl)furan-2-yl)phenyl)-2-methylpropanoic acid, 5-(5-((((R)-2-((R)-1-(N-hydroxyformamido)propyl)heptanamido)methyl)carbamoyl)furan-2-yl)-2-methylbenzoic acid,
N—(((R)-2-((R)-1-(N-hydroxyformamido)propyl)heptanamido)methyl)-5-(3-propoxyphenyl)furan-2-carboxamide,
2-(2-fluoro-5-(5-((((R)-2-((R)-1-(N-hydroxyformamido)propyl)heptanamido)methyl)carbamoyl)furan-2-yl)phenyl)acetic acid,
4-(5-((((R)-2-((R)-1-(N-hydroxyformamido)propyl)heptanamido)methyl)carbamoyl)furan-2-yl)benzoic acid,
2-(3-ethoxy-5-(5-((((R)-2-((R)-1-(N-hydroxyformamido)propyl)heptanamido)methyl)carbamoyl)furan-2-yl)phenyl)acetic acid,
5-(3-ethoxy-5-hydroxyphenyl)-N—(((R)-2-(((R)-1-(N-hydroxyformamido)propyl)heptanamido)methyl)furan-2-carboxamide,
(S)-2-(2-ethoxy-4-(5-((((R)-2-((R)-1-(N-hydroxyformamido)propyl)heptanamido)methyl)carbamoyl)furan-2-yl)benzamido)succinic acid,
(S)-2-(2-(2-ethoxy-4-(5-((((R)-2-((R)-1-(N-hydroxyformamido)propyl)heptanamido)methyl)carbamoyl)furan-2-yl)phenyl)acetamido)succinic acid,
2-(3-(5-((((R)-2-((N-hydroxyformamido)methyl)heptanamido)methyl)carbamoyl)furan-2-yl)phenyl)propanoic acid,
(S)-2-(3-ethoxy-5-(5-((((R)-2-((((R)-1-(N-hydroxyformamido)propyl)heptanamido)methyl)carbamoyl)furan-2-yl)benzamido)succinic acid,
(R)-2,6-difluoro-3-(5-(((2-((N-hydroxyformamido)methyl)heptanamido)methyl)carbamoyl)furan-2-yl)benzoic acid,
3-ethoxy-5-(5-(((3-(N-hydroxyformamido)propanamido)methyl)carbamoyl)furan-2-yl)benzoic acid,
1-(3-(5-((((R)-2-((R)-1-(N-hydroxyformamido)propyl)heptanamido)methyl)carbamoyl)furan-2-yl)phenyl)cyclopropanecarboxylic acid,
5-ethoxy-2-hydroxy-3-(5-((((R)-2-((R)-1-(N-hydroxyformamido)propyl)heptanamido)methyl)carbamoyl)furan-2-yl)benzoic acid,
3-(5-((((R)-2-((R)-1-(N-hydroxyformamido)propyl)heptanamido)methyl)carbamoyl)furan-2-yl)-5-propoxybenzoic acid,
(S)-2-(3-(5-((((R)-2-((R)-1-(N-hydroxyformamido)propyl)heptanamido)methyl)carbamoyl)furan-2-yl)benzamido)succinic acid,
(R)-2-(3-ethoxy-5-(5-((((R)-2-((R)-1-(N-hydroxyformamido)propyl)heptanamido)methyl)carbamoyl)furan-2-yl)benzamido)succinic acid,
2-(3-ethoxy-5-(5-((((R)-2-((R)-1-(N-hydroxyformamido)propyl)heptanamido)methyl)carbamoyl)furan-2-yl)benzamido)acetic acid,
2,2'-((2-ethoxy-4-(5-((((R)-2-((R)-1-(N-hydroxyformamido)propyl)heptanamido)methyl)carbamoyl)furan-2-yl)benzoyl)azanediyl)diacetic acid,
2,2'-((3-ethoxy-5-(5-((((R)-2-((R)-1-(N-hydroxyformamido)propyl)heptanamido)methyl)carbamoyl)furan-2-yl)benzoyl)azanediyl)diacetic acid,
5-(3-((1,3-dihydroxy-2-(hydroxymethyl)propan-2-yl)carbamoyl)-5-ethoxyphenyl)-N—(((R)-2-((R)-1-(N-hydroxyformamido)propyl)heptanamido)methyl)furan-2-carboxamide,
(R)-3-(5-(((2-((N-hydroxyformamido)methyl)heptanamido)methyl)carbamoyl)furan-2-yl)benzoic acid,
(R)-2-(5-(((2-((N-hydroxyformamido)methyl)heptanamido)methyl)carbamoyl)furan-2-yl)benzoic acid,
(R)-2-fluoro-5-(5-(((2-((N-hydroxyformamido)methyl)heptanamido)methyl)carbamoyl)furan-2-yl)benzoic acid,
(R)-4-(5-(((2-((N-hydroxyformamido)methyl)heptanamido)methyl)carbamoyl)furan-2-yl)benzoic acid,
(S)-2-(3-ethoxy-5-(5-((((R)-2-((R)-1-(N-hydroxyformamido)propyl)heptanamido)methyl)carbamoyl)furan-2-yl)benzamido)pentanedioic acid,
(3-(5-((((R)-2-((N-hydroxyformamido)methyl)heptanamido)methyl)carbamoyl)furan-2-yl)phenyl)(methyl)phosphinic acid,
methyl hydrogen (3-(5-((((R)-2-((N-hydroxyformamido)methyl)heptanamido)methyl)carbamoyl)furan-2-yl)phenyl)phosphonate,
(3-ethoxy-5-(5-((((R)-2-((R)-1-(N-hydroxyformamido)propyl)heptanamido)methyl)carbamoyl)furan-2-yl)phenyl)phosphonic acid,
(3-ethoxy-5-(5-((((R)-2-((R)-1-(N-hydroxyformamido)propyl)heptanamido)methyl)carbamoyl)tetrahydrofuran-2-yl)phenyl)phosphonic acid,
(2-ethoxy-4-(5-((((R)-2-((R)-1-(N-hydroxyformamido)propyl)heptanamido)methyl)carbamoyl)furan-2-yl)phenyl)phosphonic acid,
(3-ethoxy-5-(5-((((R)-2-((R)-1-(N-hydroxyformamido)propyl)heptanamido)methyl)carbamoyl)furan-2-yl)benzyl)phosphonic acid,
((3-ethoxy-5-(5-((((R)-2-((R)-1-(N-hydroxyformamido)propyl)heptanamido)methyl)carbamoyl)furan-2-yl)benzamido)methyl)phosphonic acid,
methyl hydrogen (3-ethoxy-5-(5-((((R)-2-((R)-1-(N-hydroxyformamido)propyl)heptanamido)methyl)carbamoyl)furan-2-yl)phenyl)phosphonate,
(R)-5-(3-(2,2-difluoroethoxy)phenyl)-N-((2-((N-hydroxyformamido)methyl)heptanamido)methyl)furan-2-carboxamide,
(R)-5-(3-(ethylthio)phenyl)-N-((2-((N-hydroxyformamido)methyl)heptanamido)methyl)furan-2-carboxamide,
(R)—N-((2-((N-hydroxyformamido)methyl)heptanamido)methyl)-5-(3-(methylthio)phenyl)furan-2-carboxamide,
(R)—N-((2-((N-hydroxyformamido)methyl)heptanamido)methyl)-5-(3-nitrophenyl)furan-2-carboxamide,
(R)—N-((2-((N-hydroxyformamido)methyl)heptanamido)methyl)-5-(1-methyl-1H-indazol-6-yl)furan-2-carboxamide,
(R)—N-((2-((N-hydroxyformamido)methyl)heptanamido)methyl)-5-(2-methyl-2H-indazol-6-yl)furan-2-carboxamide,
(R)-(3-(5-(((2-((N-hydroxyformamido)methyl)heptanamido)methyl)carbamoyl)furan-2-yl)phenyl)phosphonic acid,
5-(3-((Z)—N'-hydroxycarbamimidoyl)phenyl)-N—(((R)-2-((R)-1-(N-hydroxyformamido)propyl)heptanamido)methyl)furan-2-carboxamide, and
N—(((R)-2-((R)-1-(N-hydroxyformamido)propyl)heptanamido)methyl)-5-phenyltetrahydrofuran-2-carboxamide.

14. The compound or salt thereof according to claim 1, wherein the compound of Formula (I) is selected from the group consisting of:
(3-ethoxy-2-fluoro-5-(5-((((R)-2-((R)-1-(N-hydroxyformamido)propyl)heptanamido)methyl)carbamoyl)furan-2-yl)benzoic acid,
3-hydroxy-5-(5-((((R)-2-((R)-1-(N-hydroxyformamido)propyl)heptanamido)methyl)carbamoyl)furan-2-yl)benzoic acid, 3-(carboxymethoxy)-5-(5-((((R)-2-((R)-1-(N-hydroxyformamido)propyl)heptanamido)methyl)carbamoyl)furan-2-yl)benzoic acid, 2-(carboxymethyl)-4-(5-((((R)-2-((R)-1-(N-hydroxyformamido)propyl)heptanamido)methyl)carbamoyl)furan-2-yl)benzoic acid, 5-ethoxy-2-hydroxy-3-(5-((((2R,3R)-3-(N-hydroxyformamido)-2-phenethylpentanamido)methyl)carbamoyl)furan-2-yl)benzoic acid, (S)-2-(2-ethoxy-4-(5-((((2R,3R)-3-(N-hydroxyformamido)-2-(2-(naphthalen-2-yl)ethyl)pentanamido)methyl)carbamoyl)furan-2-yl)benzamido)succinic acid, 5-(carboxymethoxy)-3-(5-((((2R,3R)-2-(2,4-difluorophenethyl)-3-(N-hydroxyformamido)pentanamido)methyl)carbamoyl)furan-2-yl)-2-hydroxybenzoic acid, (S)-2-(4-(5-((((R)-2-((R)-1-(N-hydroxyformamido)propyl)heptanamido)methyl)carbamoyl)furan-2-yl)benzamido)succinic acid, (S)-2-(4-(5-((((R)-2-((R)-1-(N-hydroxyformamido)propyl)heptanamido)methyl)carbamoyl)furan-2-yl)-2-methylbenzamido)succinic acid, 5-(carboxymethoxy)-2-hydroxy-3-(5-((((R)-2-((R)-1-(N-hydroxyformamido)propyl)heptanamido)methyl)carbamoyl)furan-2-yl)benzoic acid, 2,2'-((3-(5-((((2R,3R)-2-(2,4-difluorophenethyl)-3-(N-hydroxyformamido)pentanamido)methyl)carbamoyl)furan-2-yl)-5-ethoxybenzoyl)azanediyl)diacetic acid, (S)-2-(4-(5-((((2R,3R)-2-(2,4-difluorophenethyl)-3-(N-hydroxyformamido)pentanamido)methyl)carbamoyl)furan-2-yl)-2-ethoxybenzamido)succinic acid, 2,2'-((2-ethoxy-4-(5-((((2R,3R)-3-(N-hydroxyformamido)-2-phenethylpentanamido)methyl)carbamoyl)furan-2-yl)benzoyl)azanediyl)diacetic acid, (S)-2-(3-(carboxymethoxy)-5-(5-((((R)-2-((R)-1-(N-hydroxyformamido)propyl)heptanamido)methyl)carbamoyl)furan-2-yl)benzamido)succinic acid, (S)-2-(2-(carboxymethoxy)-4-(5-((((R)-2-((R)-1-(N-hydroxyformamido)propyl)heptanamido)methyl)carbamoyl)furan-2-yl)benzamido)succinic acid, (S)-2-(2-ethoxy-4-(5-((((2R,3R)-3-(N-hydroxyformamido)-2-phenethylpentanamido)methyl)carbamoyl)furan-2-yl)benzamido)succinic acid, 2-ethoxy-6-hydroxy-4-(5-((((R)-2-((R)-1-(N-hydroxyformamido)propyl)heptanamido)methyl)carbamoyl)furan-2-yl)benzoic acid, 4-(5-((((R)-2-((R)-1-(N-hydroxyformamido)propyl)heptanamido)methyl)carbamoyl)furan-2-yl)phthalic acid, 2-((3-ethoxy-5-(5-((((R)-2-((R)-1-(N-hydroxyformamido)propyl)heptanamido)methyl)carbamoyl)furan-2-yl)benzyl)(methyl)amino)acetic acid, 3-(2-amino-2-oxoethoxy)-5-(5-((((R)-2-((R)-1-(N-hydroxyformamido)propyl)heptanamido)methyl)carbamoyl)furan-2-yl)benzoic acid, (R)-2-(2-ethoxy-4-(5-((((R)-2-((R)-1-(N-hydroxyformamido)propyl)heptanamido)methyl)carbamoyl)furan-2-yl)benzamido)succinic acid, ((R)-2-(4-(5-((((R)-2-((R)-1-(N-hydroxyformamido)propyl)heptanamido)methyl)carbamoyl)furan-2-yl)benzamido)succinic acid, (S)-2-(4-(5-((((R)-2-((R)-1-(N-hydroxyformamido)propyl)heptanamido)methyl)carbamoyl)furan-2-yl)benzamido)pentanedioic acid, (S)-2-(2-ethoxy-4-(5-((((R)-2-((R)-1-(N-hydroxyformamido)propyl)heptanamido)methyl)carbamoyl)furan-2-yl)benzamido)pentanedioic acid, 2,2'-((4-(5-((((R)-2-((R)-1-(N-hydroxyformamido)propyl)heptanamido)methyl)carbamoyl)furan-2-yl)benzoyl)azanediyl)diacetic acid, (((3-ethoxy-5-(5-((((R)-2-((R)-1-(N-hydroxyformamido)propyl)heptanamido)methyl)carbamoyl)furan-2-yl)benzyl)amino)methyl)phosphonic acid, (3-hydroxy-5-(5-((((R)-2-((R)-1-(N-hydroxyformamido)propyl)heptanamido)methyl)carbamoyl)furan-2-yl)phenyl)phosphonic acid, ((2-ethoxy-4-(5-((((R)-2-((R)-1-(N-hydroxyformamido)propyl)heptanamido)methyl)carbamoyl)furan-2-yl)benzamido)methyl)phosphonic acid, (3-ethoxy-5-(5-((((2R,3R)-3-(N-hydroxyformamido)-2-phenethylpentanamido)methyl)carbamoyl)furan-2-yl)phenyl)phosphonic acid, (3-ethoxy-5-(5-((((2R,3R)-3-(N-hydroxyformamido)-2-(2-(naphthalen-2-yl)ethyl)pentanamido)methyl)carbamoyl)furan-2-yl)phenyl)phosphonic acid, ((2-hydroxy-4-(5-((((R)-2-((R)-1-(N-hydroxyformamido)propyl)heptanamido)methyl)carbamoyl)furan-2-yl)benzamido)methyl)phosphonic acid, ((4-(5-((((R)-2-((R)-1-(N-hydroxyformamido)propyl)heptanamido)methyl)carbamoyl)furan-2-yl)benzamido)methyl)phosphonic acid, ((4-(5-((((R)-2-((R)-1-(N-hydroxyformamido)propyl)heptanamido)methyl)carbamoyl)furan-2-yl)-2-methylbenzamido)methyl)phosphonic acid, 2-(3-(5-((((R)-2-((R)-1-(N-hydroxyformamido)propyl)heptanamido)methyl)carbamoyl)furan-2-yl)-5-phosphonophenoxy)acetic acid, and 2-hydroxy-4-(5-((((R)-2-((R)-1-(N-hydroxyformamido)propyl)heptanamido)methyl)carbamoyl)furan-2-yl)benzoic acid.

15. The compound or salt thereof according to claim 1, wherein the compound of Formula (I) is selected from the group consisting of:

2-ethoxy-4-(5-((((R)-2-((R)-1-(N-hydroxyformamido)propyl)heptanamido)methyl)carbamoyl)furan-2-yl)benzoic acid, 3-ethoxy-5-(5-((((R)-2-((R)-1-(N-hydroxyformamido)propyl)heptanamido)methyl)carbamoyl)furan-2-yl)benzoic acid, (S)-2-(2-ethoxy-4-(5-((((R)-2-((R)-1-(N-hydroxyformamido)propyl)heptanamido)methyl)carbamoyl)furan-2-yl)benzamido)succinic acid, (S)-2-(3-ethoxy-5-(5-((((R)-2-((R)-1-(N-hydroxyformamido)propyl)heptanamido)methyl)carbamoyl)furan-2-yl)benzamido)succinic acid, 5-ethoxy-2-hydroxy-3-(5-((((R)-2-((R)-1-(N-hydroxyformamido)propyl)heptanamido)methyl)carbamoyl)furan-2-yl)benzoic acid, (3-ethoxy-5-(5-((((R)-2-((R)-1-(N-hydroxyformamido)propyl)heptanamido)methyl)carbamoyl)furan-2-yl)phenyl)phosphonic acid, (2-ethoxy-4-(5-((((R)-2-((R)-1-(N-hydroxyformamido)propyl)heptanamido)methyl)carbamoyl)furan-2-yl)phenyl)phosphonic acid, 3-(carboxymethoxy)-5-(5-((((R)-2-((R)-1-(N-hydroxyformamido)propyl)heptanamido)methyl)carbamoyl)furan-2-yl)benzoic acid, (S)-2-(4-(5-((((R)-2-((R)-1-(N-hydroxyformamido)propyl)heptanamido)methyl)carbamoyl)furan-2-yl)benzamido)succinic acid, (S)-2-(2-(carboxymethoxy)-4-(5-((((R)-2-((R)-1-(N-hydroxyformamido)propyl)heptanamido)methyl)carbamoyl)furan-2-yl)benzamido)succinic acid, 4-(5-((((R)-2-((R)-1-(N-hydroxyformamido)propyl)heptanamido)methyl)carbamoyl)furan-2-yl)phthalic acid, (3-hydroxy-5-(5-((((R)-2-((R)-1-(N-hydroxyformamido)propyl)heptanamido)methyl)carbamoyl)furan-2-yl)phenyl)phosphonic acid, ((2-ethoxy-4-(5-((((R)-2-((R)-1-(N-hydroxyformamido)propyl)heptanamido)methyl)carbamoyl)furan-2-yl)benzamido)methyl)phosphonic acid, and (3-ethoxy-5-(5-((((2R,3R)-3-(N-hydroxyformamido)-2-phenethylpentanamido)methyl)carbamoyl)furan-2-yl)phenyl)phosphonic acid.

16. The compound or salt thereof according to claim 1, wherein the salt is a pharmaceutically acceptable salt of said compound.

17. A compound which is selected from:
(3-ethoxy-5-(5-((((R)-2-((R)-1-(N-hydroxyformamido)propyl)heptanamido)methyl)carbamoyl)furan-2-yl)phenyl)phosphonic acid of formula:

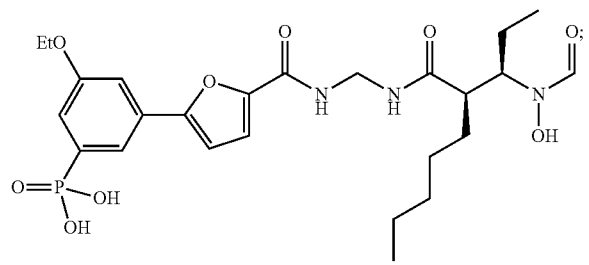 [SMILES: CCCCC[C@@H](C(=O)NCNC(=O)c1ccc(-c2cc(OCC)cc(P(=O)(O)O)c2)o1)[C@@H](CC)N(O)C=O]

(S)-2-(2-ethoxy-4-(5-((((R)-2-((R)-1-(N-hydroxyformamido)propyl)heptanamido)methyl)carbamoyl)furan-2-yl)benzamido)succinic acid of formula:

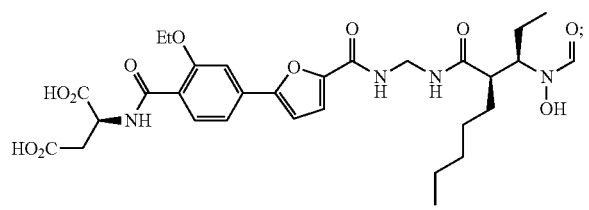 [SMILES: CCCCC[C@@H](C(=O)NCNC(=O)c1ccc(-c2ccc(C(=O)N[C@@H](CC(=O)O)C(=O)O)c(OCC)c2)o1)[C@@H](CC)N(O)C=O]

and
(S)-2-(2-(carboxymethoxy)-4-(5-((((R)-2-((R)-1-(N-hydroxyformamido)propyl)heptanamido)methyl)carbamoyl)furan-2-yl)benzamido)succinic acid of formula:

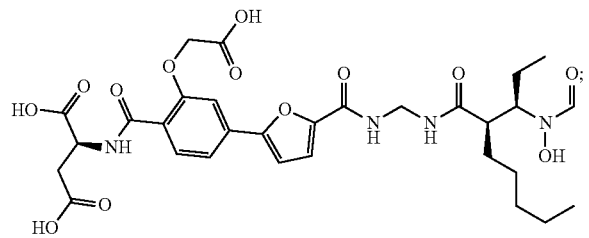 [SMILES: CCCCC[C@@H](C(=O)NCNC(=O)c1ccc(-c2ccc(C(=O)N[C@@H](CC(=O)O)C(=O)O)c(OCC(=O)O)c2)o1)[C@@H](CC)N(O)C=O]

or a salt thereof.

18. A pharmaceutical composition comprising the compound or pharmaceutically acceptable salt thereof according to claim 16, and one or more pharmaceutically acceptable excipients.

19. A composition comprising a) the compound of formula (I) or a pharmaceutically acceptable salt thereof according to claim 16; and b) another therapeutically active agent selected from: anticoagulants, angiotensin-converting-enzyme inhibitors, angiotensin II receptor blockers, beta-blockers, aldosterone antagonists, diuretics, vasodilators, cholesterol-lowering drugs, platelet antagonists, anti-arrhythmics, calcium channel blockers, erythropoiesis-stimulating agents, iron, beta agonists, inhaled or oral steroids, anticholinergics, theophylline, PDE4 inhibitors, antibiotics, other antifibrotic agents, PDE5 inhibitors, immune modulators, neprilysin inhibitors, *digitalis* preparations, and combinations thereof.

20. A combination of a) the compound of formula (I) or a pharmaceutically acceptable salt thereof according to claim 16; and b) another therapeutically active agent selected from: anticoagulants, angiotensin-converting-enzyme inhibitors, angiotensin II receptor blockers, beta-blockers, aldosterone antagonists, diuretics, vasodilators, cholesterol-lowering drugs, platelet antagonists, anti-arrhythmics, calcium channel blockers, erythropoiesis-stimulating agents, iron, beta agonists, inhaled or oral steroids, anticholinergics, theophylline, PDE4 inhibitors, antibiotics, other antifibrotic agents, PDE5 inhibitors, immune modulators, neprilysin inhibitors, *digitalis* preparations, and combinations thereof.

21. The compound or salt thereof according to claim 1, wherein R1 is methyl, ethyl or —CH$_2$OH.

22. The compound or salt thereof according to claim 1, wherein R1 is ethyl.

23. The compound or salt thereof according to claim 1 wherein R2 is n-pentyl.

24. A compound of Formula (I)(b):

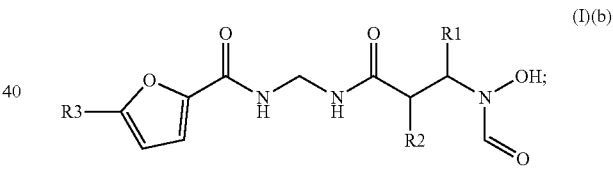

or a pharmaceutically acceptable salt thereof, wherein:
R1 is H, methyl, ethyl or —CH$_2$OH;
R2 is H or optionally substituted n-pentyl, 2-ethylbutyl, (cyclopentyl)methyl, benzyl, 2- phenylethyl, 3-phenylpropyl, or 2-naphthylethyl;
R$^1$ and R$^2$ have (R) stereochemistry; and
R3 is selected from:
a) phenyl, optionally substituted with 1-3 groups independently selected from:
(C$_1$-C$_6$)alkyl, optionally substituted with 1-3 groups independently selected from: fluoro; —CO$_2$H; —P(O)R$^f$R$^g$; NR$^a$R$^b$ wherein R$^a$ is selected from H and (C$_1$-C$_4$)alkyl and R$^b$ is selected from (C$_1$-C$_4$)alkyl substituted with —CO$_2$H or —P(O)R$^f$R$^g$, and —C(O)NR$^a$R$^b$ wherein R$^a$ and R$^b$ are independently selected from H and (C$_1$-C$_4$)alkyl, wherein the (C$_1$-C$_4$)alkyl is optionally substituted with 1-3 groups independently selected from hydroxy, —CO$_2$H, —C(O)O(C$_1$-C$_4$)alkyl and —P(O)R$^f$R$^g$;
cyclopropyl, optionally substituted with 1 —CO$_2$H;
—C(O)NR$^a$R$^b$ wherein R$^a$ and R$^b$ are independently selected from H and (C$_1$-C$_4$)alkyl, wherein the (C$_1$-C$_4$) alkyl is optionally substituted with 1-3 groups independently selected from hydroxy, —CO₂H, —C(O)O(C₁-C₄)alkyl, —P(O)R$^f$R$^g$, NR$^c$R$^d$ and N$^+$R$^c$R$^d$R$^e$;

(C₁-C₆)alkoxy, optionally substituted with 1-3 substituents independently selected from halo, hydroxy, —CO₂H, (C₃-C₆)cycloalkyl, —C(O)NH₂ and pyrrolidinyl;

(C₃-C₆)cycloalkoxy, optionally substituted with 1-3 substituents independently selected from halo, hydroxy, and —CO₂H;

—NR$^a$R$^b$ wherein R$^a$ and R$^b$ are independently selected from H and (C₁-C₄)alkyl, wherein the (C₁-C₄)alkyl is optionally substituted with 1-3 groups independently selected from oxo and —CO₂H;

—SR$^a$ wherein R$^a$ is selected from H and (C₁-C₄)alkyl;

—CO₂H; —C(NOH)NH₂; cyano; —C(O)O(C₁-C₄)alkyl; —C(O)CO₂H; —P(O)R$^f$R$^g$; —OP(O)R$^f$R$^g$; halo; hydroxy; nitro; —NHSO₂(C₁-C₂)alkyl; —SO₃H; —SO₂(C₁-C₂)alkyl; —SO₂NR$^c$R$^d$; —SO₂NHC(O)(C₁-C₂)alkyl; and —B(OH)₂;

and b) heteroaryl, optionally substituted with 1-2 groups independently selected from: (C₁-C₄)alkyl, (C₁-C₄)alkoxy, oxo, —CO₂H, —P(O)R$^f$R$^g$, and —OP(O)R$^f$R$^g$;

wherein in each occurrence:

R$^c$, R$^d$ and R$^e$ are independently selected from H and (C₁-C₂)alkyl; and

R$^f$ and R$^g$ are independently selected from hydroxy, (C₁-C₂)alkyl and (C₁-C₂)alkoxy.

25. The compound or pharmaceutically acceptable salt according to claim 24, wherein R3 is said optionally substituted phenyl.

26. The compound or pharmaceutically acceptable salt according to claim 25, wherein R3 is phenyl substituted with 1-3 groups selected from: -OCH₃, —OC₂H₅, —OC₃H₇, —OCH(CH₃)₂, —OCF₃, —OCHF₂, —OCH₂CF₃, —OCH₂CHF₂, —OC₂H₄-pyrrolidine, —OCH₂CO₂H, —OCH₂C(O)NH₂, —CO₂H, —CH₃, cyclopropane-1-carboxylic acid, —CH₂CO₂H, —C(CH₃)₂CO₂H, —CH(CH₃)CO₂H, —CF₂CO₂H, —CH₂C(O)NHCH(CO₂H)(CH₂CO₂H), —CH₂P(O)(OH)₂, —CH₂N(CH₃)(CH₂CO₂H), —CH₂NHCH₂P(O)(OH)₂, —C(NH2)(NOH), cyano, nitro, hydroxy, —SO₂NH₂, —SO₂N(CH₃)₂, —SO₂NH(CH₃), —SO₂CH₃, —SO₂NHC(O)C₂H₅, —SCH₃, —SC₂H₅, —C(O)OCH₃, —C(O)OC(CH₃)₃, —C(O)NHCH₃, —C(O)NH(C₂H₄NH₂), —C(O)NHC₂H₄N$^+$(CH₃)₃, —C(O)NHCH(CO₂H)(CH₂CO₂H), —C(O)NHCH(CO₂H)(C₂H₄CO₂H), —C(O)NHCH₂CO₂H, —C(O)N(CH₂CO₂H)₂, —C(O)NHCH₂P(O)(OH)₂, —C(O)NHC(CH₂OH)₃, fluoro, —NH₂, —N(CH₃)₂, —P(O)(CH₃)(OC₂H₅), —P(O)(OCH3)₂, —P(O)(CH₃)(OH), —P(O)(OH)(OCH₃), and —P(O)(OH)₂.

27. The compound or pharmaceutically acceptable salt according to claim 25, wherein R3 is phenyl substituted with 1-3 groups selected from: —OC₂H₅, hydroxy, —CO₂H, —OCH₂CO₂H, —P(O)(OH)₂, —C(O)NHCH(CO₂H)(CH₂CO₂H) and —C(O)NHCH₂P(O)(OH)₂.

28. The compound or pharmaceutically acceptable salt according to claim 27, wherein: R1 is ethyl and R2 is n-pentyl.

29. The compound or pharmaceutically acceptable salt according to claim 24, wherein: R1 is methyl, ethyl or —CH₂OH.

30. The compound or pharmaceutically acceptable salt according to claim 24, wherein: R1 is ethyl.

31. A compound which is (3-ethoxy-5-(5-((((R)-2-((R)-1-(N-hydroxyformamido)propyl)heptanamido)methyl)carbamoyl)furan-2-yl)phenyl)phosphonic acid of formula:

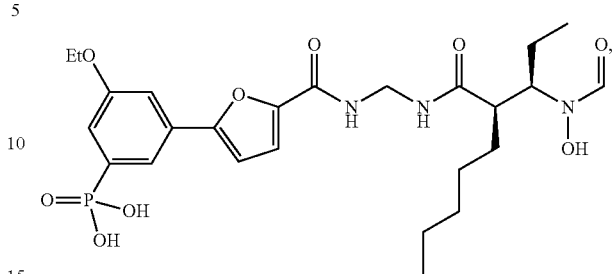

or a pharmaceutically acceptable salt thereof.

32. The compound (3-ethoxy-5-(5-((((R)-2-((R)-1-(N-hydroxyformamido)propyl)heptanamido)methyl)carbamoyl)furan-2-yl)phenyl)phosphonic acid according to claim 31.

33. The pharmaceutically acceptable salt of (3-ethoxy-5-(5-((((R)-2-((R)-1-(N-hydroxyformamido)propyl)heptanamido)methyl)carbamoyl)furan-2-yl)phenyl)phosphonic acid according to claim 31.

34. The pharmaceutically acceptable salt according to claim 33, wherein the salt is a meglumine salt, Tris salt, or calcium salt.

35. A compound which is (S)-2-(2-ethoxy-4-(5-((((R)-2-((R)-1-(N-hydroxyformamido)propyl)heptanamido)methyl)carbamoyl)furan-2-yl)benzamido)succinic acid of formula:

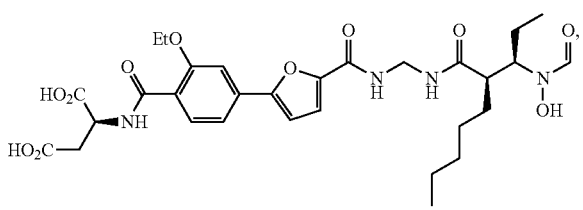 [SMILES: CCCCC[C@@H](C(=O)NCNC(=O)c1ccc(-c2ccc(C(=O)N[C@@H](CC(=O)O)C(=O)O)c(OCC)c2)o1)[C@@H](CC)N(O)C=O]

or a pharmaceutically acceptable salt thereof.

36. The compound (S)-2-(2-ethoxy-4-(5-((((R)-2-((R)-1-(N-hydroxyformamido)propyl)heptanamido)methyl)carbamoyl)furan-2-yl)benzamido)succinic acid according to claim 35.

37. The pharmaceutically acceptable salt of (S)-2-(2-ethoxy-4-(5-((((R)-2-((R)-1-(N-hydroxyformamido)propyl)heptanamido)methyl)carbamoyl)furan-2-yl)benzamido)succinic acid according to claim 35.

38. A compound which is (S)-2-(2-(carboxymethoxy)-4-(5-((((R)-2-((R)-1-(N-hydroxyformamido)propyl)heptanamido)methyl)carbamoyl)furan-2-yl)benzamido)succinic acid of formula:

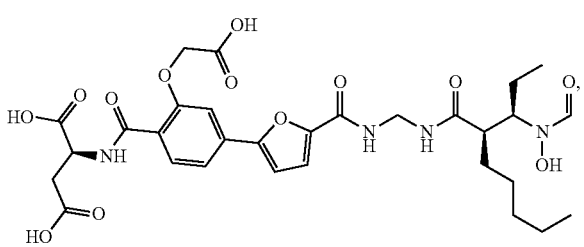 [SMILES: CCCCC[C@@H](C(=O)NCNC(=O)c1ccc(-c2ccc(C(=O)N[C@@H](CC(=O)O)C(=O)O)c(OCC(=O)O)c2)o1)[C@@H](CC)N(O)C=O]

or a pharmaceutically acceptable salt thereof.

39. The compound (S)-2-(2-(carboxymethoxy)-4-(5-((((R)-2-((R)-1-(N-hydroxyformamido)propyl)heptanamido)methyl)carbamoyl)furan-2-yl)benzamido)succinic acid according to claim 38.

40. The pharmaceutically acceptable salt of (S)-2-(2-(carboxymethoxy)-4-(5-((((R)-2-((R)-1-(N-hydroxyformamido)propyl)heptanamido)methyl)carbamoyl)furan-2-yl)benzamido)succinic acid according to claim 38.

* * * * *